(12) United States Patent
Yang et al.

(10) Patent No.: US 12,201,617 B2
(45) Date of Patent: *Jan. 21, 2025

(54) HDAC6 INHIBITORS FOR TREATMENT OF METABOLIC DISEASE AND HFPEF

(71) Applicant: Tenaya Therapeutics, Inc., South San Francisco, CA (US)

(72) Inventors: Jin Yang, Lexington, MA (US); Mohammad A. Mandegar, San Francisco, CA (US); Timothy C. Hoey, Hillsborough, CA (US)

(73) Assignee: Tenaya Therapeutics, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/360,752

(22) Filed: Jul. 27, 2023

(65) Prior Publication Data

US 2023/0381148 A1 Nov. 30, 2023

Related U.S. Application Data

(63) Continuation of application No. PCT/US2022/027725, filed on May 4, 2022.

(60) Provisional application No. 63/210,690, filed on Jun. 15, 2021, provisional application No. 63/210,676, filed on Jun. 15, 2021, provisional application No. 63/183,914, filed on May 4, 2021.

(51) Int. Cl.
| | |
|---|---|
| *A61K 31/427* | (2006.01) |
| *A61K 31/17* | (2006.01) |
| *A61K 31/42* | (2006.01) |
| *A61K 31/437* | (2006.01) |
| *A61K 31/4439* | (2006.01) |
| *A61K 31/505* | (2006.01) |
| *A61K 31/5377* | (2006.01) |
| *A61P 3/04* | (2006.01) |
| *A61P 3/10* | (2006.01) |
| *A61P 9/04* | (2006.01) |

(52) U.S. Cl.
CPC ............ *A61K 31/427* (2013.01); *A61K 31/17* (2013.01); *A61K 31/42* (2013.01); *A61K 31/437* (2013.01); *A61K 31/4439* (2013.01); *A61K 31/505* (2013.01); *A61K 31/5377* (2013.01); *A61P 3/04* (2018.01); *A61P 3/10* (2018.01); *A61P 9/04* (2018.01)

(58) Field of Classification Search
CPC ............ A61K 31/427; A61K 31/4439; A61K 31/5377; A61K 31/4245; A61K 31/444; A61P 9/04; A61P 3/00; A61P 3/10; A61P 9/00; A61P 9/12

See application file for complete search history.

(56) References Cited

U.S. PATENT DOCUMENTS

| | | | |
|---|---|---|---|
| 6,509,110 B1 | 1/2003 | Salbeck et al. |
| 6,706,686 B2 | 3/2004 | Long et al. |
| 6,946,441 B2 | 9/2005 | Long et al. |
| 7,863,414 B2 | 1/2011 | Backs et al. |
| 8,217,076 B2 | 7/2012 | Williams et al. |
| 8,222,423 B2 | 7/2012 | Bradner et al. |
| 8,227,516 B2 | 7/2012 | Maurer et al. |
| 8,431,538 B2 | 4/2013 | Kozikowski et al. |
| 8,440,716 B2 | 5/2013 | Tang et al. |
| 8,471,026 B2 | 6/2013 | Blackburn et al. |
| 8,513,421 B2 | 8/2013 | Gould et al. |
| 8,546,588 B2 | 10/2013 | Blackburn et al. |
| 8,624,040 B2 | 1/2014 | Blackburn et al. |
| 8,673,911 B2 | 3/2014 | Mallais et al. |
| 8,765,773 B2 | 7/2014 | England et al. |
| 8,889,742 B2 | 11/2014 | Gruber et al. |
| 9,096,518 B2 | 8/2015 | Blackburn et al. |
| 9,238,028 B2 | 1/2016 | Van Den Bosch et al. |
| 9,345,905 B2 | 5/2016 | Wang et al. |
| 9,409,858 B2 | 8/2016 | Sotomayor et al. |
| 9,512,083 B2 | 12/2016 | Raje et al. |
| 9,586,973 B2 | 3/2017 | Bracke et al. |
| 9,663,825 B2 | 5/2017 | Yang et al. |
| 9,670,193 B2 | 6/2017 | Hebach et al. |
| 9,751,832 B2 | 9/2017 | Sotomayor et al. |
| 9,884,031 B2 | 2/2018 | Patel et al. |
| 9,890,136 B2 | 2/2018 | Breslow et al. |

(Continued)

FOREIGN PATENT DOCUMENTS

| | | |
|---|---|---|
| CA | 3109419 A1 | 2/2020 |
| CN | 112794860 A | 5/2021 |

(Continued)

OTHER PUBLICATIONS

Jeong et al. (Science. Translational Medicine 10, eaao0144 (2018), pp. 1-10). (Year: 2018).*
Muhammad Saad et al ("Patient Management in the telemetry/cardiac step-down unit" A case-based approach, McGraw Hill, 2020) (Year: 2020).*
ProbeChem, https://www.probechem.com/products_TYA-018.html, accessed on May 22, 2024 (Year: 2024).*
Tenaya Therapeutics ("Tenaya Therapeutics Announces Publication of Preclinical HDAC6 Inhibitor Data for Heart Failure with Preserved Ejection Fraction in Nature Communications" Feb. 26, 2024) (Year: 2024).*
Anna Courant (Cardiology Advisor, Nov. 18, 2022) (Year: 2022).*
Coenraad Withaar et al (European Heart Journal (2021) 42, 4420-4430) (Year: 2021).*

(Continued)

*Primary Examiner* — Jean P Cornet
(74) *Attorney, Agent, or Firm* — COOLEY LLP

(57) ABSTRACT

Provided herein are methods of treating or preventing metabolic disease with an HDAC6 inhibitor. Also provided herein are methods of treating or preventing heart failure with preserved ejection fraction with an HDAC6 inhibitor. A variety of HDAC6 inhibitors are described herein for use in treating or preventing metabolic disease or heart failure with preserved ejection fraction. In one aspect, described herein are methods of treating a human patient by orally administering an HDAC6 inhibitor, such as an inhibitor of Formula (I) or Formula (II).

29 Claims, 60 Drawing Sheets

(56) References Cited

U.S. PATENT DOCUMENTS

| | | |
|---|---|---|
| 9,987,258 B2 | 6/2018 | Villagra et al. |
| 9,993,459 B2 | 6/2018 | De Vreese et al. |
| 10,011,611 B2 | 7/2018 | Ma et al. |
| 10,016,421 B2 | 7/2018 | Sotomayor et al. |
| RE47,009 E | 8/2018 | Kozikowski et al. |
| 10,040,769 B2 | 8/2018 | Golonzhka et al. |
| 10,041,046 B2 | 8/2018 | Karp et al. |
| 10,106,540 B2 | 10/2018 | Mahboobi et al. |
| 10,112,915 B2 | 10/2018 | Zheng et al. |
| 10,183,934 B2 | 1/2019 | Zheng et al. |
| 10,239,845 B2 | 3/2019 | Zheng et al. |
| 10,266,489 B2 | 4/2019 | Li et al. |
| 10,287,255 B2 | 5/2019 | Song et al. |
| 10,357,493 B2 | 7/2019 | Yates |
| 10,377,726 B2 | 8/2019 | Zheng et al. |
| 10,435,399 B2 | 10/2019 | Ito et al. |
| 10,464,911 B2 | 11/2019 | Lee et al. |
| 10,472,337 B2 | 11/2019 | Zheng et al. |
| 10,479,772 B2 | 11/2019 | Zheng et al. |
| 10,494,353 B2 | 12/2019 | Zheng et al. |
| 10,494,354 B2 | 12/2019 | Zheng et al. |
| 10,494,355 B2 | 12/2019 | Kim et al. |
| 10,538,498 B2 | 1/2020 | Lee et al. |
| 10,568,854 B2 | 2/2020 | Bjornsson et al. |
| 10,584,117 B2 | 3/2020 | Lee et al. |
| 10,654,814 B2 | 5/2020 | Hammer et al. |
| 10,660,890 B2 | 5/2020 | Gradilone et al. |
| 10,717,716 B2 | 7/2020 | Lee et al. |
| 10,745,389 B2 | 8/2020 | Wu et al. |
| 10,829,461 B2 | 11/2020 | Zheng et al. |
| 10,829,462 B2 | 11/2020 | Zheng et al. |
| 10,858,323 B2 | 12/2020 | Golonzhka et al. |
| 11,578,066 B1 | 2/2023 | Patel et al. |
| 11,926,622 B2 | 3/2024 | Patel et al. |
| 2004/0167188 A1 | 8/2004 | Xin et al. |
| 2004/0214870 A1 | 10/2004 | Xin et al. |
| 2007/0207950 A1 | 9/2007 | Yao et al. |
| 2008/0262028 A1 | 10/2008 | Kallus et al. |
| 2009/0298924 A1 | 12/2009 | Davidson et al. |
| 2010/0069381 A1 | 3/2010 | Itoh |
| 2010/0093824 A1 | 4/2010 | Frydman et al. |
| 2010/0216796 A1 | 8/2010 | Kattar et al. |
| 2010/0292169 A1 | 11/2010 | Yao et al. |
| 2011/0171196 A1 | 7/2011 | Backs et al. |
| 2011/0195432 A1 | 8/2011 | Alumkal |
| 2011/0288117 A1 | 11/2011 | Gould et al. |
| 2012/0015942 A1 | 1/2012 | Calderwood et al. |
| 2012/0015943 A1 | 1/2012 | Blackburn et al. |
| 2012/0258993 A1 | 10/2012 | Giannini et al. |
| 2013/0225543 A1 | 8/2013 | Jones et al. |
| 2014/0031368 A1 | 1/2014 | Breslow et al. |
| 2014/0243335 A1 | 8/2014 | Blackburn et al. |
| 2014/0294856 A1 | 10/2014 | Aboagye et al. |
| 2014/0357512 A1 | 12/2014 | Yang et al. |
| 2015/0105358 A1 | 4/2015 | Quayle et al. |
| 2015/0119327 A1 | 4/2015 | Muotri et al. |
| 2015/0176076 A1 | 6/2015 | Yang et al. |
| 2015/0250786 A1 | 9/2015 | Berton |
| 2016/0069887 A1 | 3/2016 | La Thangue |
| 2016/0228434 A1 | 8/2016 | Reilly et al. |
| 2016/0271083 A1 | 9/2016 | Chen et al. |
| 2017/0173083 A1 | 6/2017 | Federation et al. |
| 2017/0182127 A1 | 6/2017 | Dschietzig |
| 2018/0028477 A1 | 2/2018 | Chen et al. |
| 2018/0127356 A1 | 5/2018 | Van Duzer et al. |
| 2018/0243317 A1 | 8/2018 | Shuttleworth et al. |
| 2019/0135799 A1 | 5/2019 | Ito et al. |
| 2019/0169127 A1 | 6/2019 | Lin et al. |
| 2019/0185462 A1 | 6/2019 | Walji et al. |
| 2019/0192521 A1 | 6/2019 | Zhang et al. |
| 2019/0209559 A1 | 7/2019 | Jones et al. |
| 2019/0216751 A1 | 7/2019 | Kelber et al. |
| 2019/0262337 A1 | 8/2019 | Moore et al. |
| 2019/0270733 A1 | 9/2019 | Ma et al. |
| 2019/0270744 A1 | 9/2019 | Ma et al. |
| 2019/0282573 A1 | 9/2019 | Quayle et al. |
| 2019/0282574 A1 | 9/2019 | Quayle et al. |
| 2019/0321361 A1 | 10/2019 | Huang et al. |
| 2020/0022966 A1 | 1/2020 | Tang et al. |
| 2020/0046698 A1 | 2/2020 | North et al. |
| 2020/0054773 A1 | 2/2020 | Hooker et al. |
| 2020/0071288 A1 | 3/2020 | Grindrod et al. |
| 2020/0155549 A1 | 5/2020 | Indraccolo et al. |
| 2020/0171028 A1 | 6/2020 | Yates |
| 2020/0179313 A1 | 6/2020 | Haldar et al. |
| 2020/0216563 A1 | 7/2020 | Matthias et al. |
| 2020/0308174 A1 | 10/2020 | Mahboobi et al. |
| 2020/0339569 A1 | 10/2020 | Carceller González et al. |
| 2020/0405716 A1 | 12/2020 | Yang et al. |
| 2021/0009538 A1 | 1/2021 | Zheng et al. |
| 2021/0009539 A1 | 1/2021 | Zheng et al. |
| 2021/0077487 A1 | 3/2021 | Jang et al. |
| 2021/0078963 A1 | 3/2021 | Grindrod et al. |
| 2021/0078999 A1 | 3/2021 | Papaioannou et al. |
| 2021/0088831 A1 | 3/2021 | Nagasawa |
| 2021/0094944 A1 | 4/2021 | Ito et al. |
| 2023/0123856 A1 | 4/2023 | Mandegar et al. |
| 2023/0143804 A1 | 5/2023 | Patel et al. |
| 2024/0182462 A1* | 6/2024 | Patel .................. C07D 487/04 |
| 2024/0252502 A1 | 8/2024 | Yang et al. |
| 2024/0269137 A1 | 8/2024 | Mandegar et al. |

FOREIGN PATENT DOCUMENTS

| | | |
|---|---|---|
| EP | 0625513 A1 | 11/1994 |
| EP | 0826685 A1 | 3/1998 |
| EP | 0950407 A1 | 10/1999 |
| EP | 1297851 B1 | 1/2005 |
| EP | 3272742 A1 | 1/2018 |
| JP | 2011008205 A | 1/2011 |
| WO | WO-9740017 A2 | 10/1997 |
| WO | WO-0021959 A1 | 4/2000 |
| WO | WO-03074038 A1 | 9/2003 |
| WO | WO-2004016221 A2 | 2/2004 |
| WO | WO-2004069812 A1 | 8/2004 |
| WO | WO-2004074266 A1 | 9/2004 |
| WO | WO-2005000300 A1 | 1/2005 |
| WO | WO-2005090328 A1 | 9/2005 |
| WO | WO-2006044958 A1 | 4/2006 |
| WO | WO-2006057922 A2 | 6/2006 |
| WO | WO-2006129199 A1 | 12/2006 |
| WO | WO-2007034846 A1 | 3/2007 |
| WO | WO-2008105607 A1 | 9/2008 |
| WO | WO-2009151529 A1 | 12/2009 |
| WO | WO-2009156336 A1 | 12/2009 |
| WO | WO-2010089303 A1 | 8/2010 |
| WO | WO-2010091310 A1 | 8/2010 |
| WO | WO-2010122151 A1 | 10/2010 |
| WO | WO-2010139966 A1 | 12/2010 |
| WO | WO-2011038185 A2 | 3/2011 |
| WO | WO-2011132048 A1 | 10/2011 |
| WO | WO-2011143466 A1 | 11/2011 |
| WO | WO-2012018499 A2 | 2/2012 |
| WO | WO-2012045710 A1 | 4/2012 |
| WO | WO-2012054510 A1 | 4/2012 |
| WO | WO-2012066330 A1 | 5/2012 |
| WO | WO-2012076898 A1 | 6/2012 |
| WO | WO-2012170867 A1 | 12/2012 |
| WO | WO-2013066831 A1 | 5/2013 |
| WO | WO-2013066835 A2 | 5/2013 |
| WO | WO-2013068552 A1 | 5/2013 |
| WO | WO-2013068554 A1 | 5/2013 |
| WO | WO-2014047662 A2 | 3/2014 |
| WO | WO-2014179144 A1 | 11/2014 |
| WO | WO-2014181137 A1 | 11/2014 |
| WO | WO-2014202582 A1 | 12/2014 |
| WO | WO-2015031824 A1 | 3/2015 |
| WO | WO-2015042418 A1 | 3/2015 |
| WO | WO-2015078081 A1 | 6/2015 |
| WO | WO-2015187088 A1 | 12/2015 |
| WO | WO-2015196071 A1 | 12/2015 |
| WO | WO-2016004318 A1 | 1/2016 |
| WO | WO-2016055786 A1 | 4/2016 |
| WO | WO-2016113273 A1 | 7/2016 |

(56) References Cited

FOREIGN PATENT DOCUMENTS

| | | | |
|---|---|---|---|
| WO | WO-2016174377 A1 | 11/2016 | |
| WO | WO-2017018803 A1 | 2/2017 | |
| WO | WO-2017018804 A1 | 2/2017 | |
| WO | WO-2017018805 A1 | 2/2017 | |
| WO | WO-2017023133 A2 | 2/2017 | |
| WO | WO-2017027357 A1 | 2/2017 | |
| WO | WO-2017049173 A1 | 3/2017 | |
| WO | WO-2017049177 A1 | 3/2017 | |
| WO | WO-2017053706 A1 | 3/2017 | |
| WO | WO-2017065473 A1 | 4/2017 | |
| WO | WO-2017075192 A1 | 5/2017 | |
| WO | WO-2017193030 A1 | 11/2017 | |
| WO | WO-2017222950 A1 * | 12/2017 | ............ A61K 45/06 |
| WO | WO-2017222951 A1 | 12/2017 | |
| WO | WO-2018029602 A1 | 2/2018 | |
| WO | WO-2018154118 A2 | 8/2018 | |
| WO | WO-2018165520 A1 | 9/2018 | |
| WO | WO-2018222795 A1 | 12/2018 | |
| WO | WO-2019027054 A1 | 2/2019 | |
| WO | WO-2019067999 A1 | 4/2019 | |
| WO | WO-2019076986 A1 | 4/2019 | |
| WO | WO-2019099353 A1 | 5/2019 | |
| WO | WO-2019099977 A2 | 5/2019 | |
| WO | WO-2019118528 A1 | 6/2019 | |
| WO | WO-2019155066 A1 | 8/2019 | |
| WO | WO-2019171234 A1 | 9/2019 | |
| WO | WO-2019173790 A1 | 9/2019 | |
| WO | WO-2019211463 A1 | 11/2019 | |
| WO | WO-2019232103 A1 | 12/2019 | |
| WO | WO-2020022794 A1 | 1/2020 | |
| WO | WO-2020036979 A1 | 2/2020 | |
| WO | WO-2020039088 A2 | 2/2020 | |
| WO | WO-2020097511 A2 | 5/2020 | |
| WO | WO-2020207941 A1 | 10/2020 | |
| WO | WO-2020247445 A1 | 12/2020 | |
| WO | WO-2020247447 A1 | 12/2020 | |
| WO | WO-2021048242 A1 | 3/2021 | |
| WO | WO-2021067859 A1 | 4/2021 | |
| WO | WO-2021081337 A1 | 4/2021 | |
| WO | WO-2021113401 A2 | 6/2021 | |
| WO | WO-2021127643 A1 * | 6/2021 | ......... A61K 31/4245 |
| WO | WO-2021183796 A1 | 9/2021 | |
| WO | WO-2021185256 A1 | 9/2021 | |
| WO | WO-2021261562 A1 | 12/2021 | |
| WO | WO-2021261563 A1 | 12/2021 | |
| WO | WO-2022038500 A1 | 2/2022 | |
| WO | WO-2022042591 A1 | 3/2022 | |
| WO | WO-2022226388 A1 | 10/2022 | |
| WO | WO-2022235842 A1 | 11/2022 | |

OTHER PUBLICATIONS

International Preliminary Report on Patentability for International Application No. PCT/US2022/026065 dated Nov. 2, 2023, 11 pages.
International Preliminary Report on Patentability for International Application No. PCT/US2022/027725 dated Nov. 16, 2023, 11 pages.
Partial Supplementary European Search Report for European Application No. EP20903640.9 dated Dec. 1, 2023, 11 pages.
Arber et al., 1997. MLP-Deficient Mice Exhibit a Disruption of Cardiac Cytoarchitectural Organization, Dilated Cardiomyopathy, and Heart Failure. Cell 88, 393-403. https://doi.org/10.1016/S0092-8674(00)81878-4.
Bacon, T., et al., "Histone deacetylase 3 indirectly modulates tubulin acetylation," Biochem. J. 2015, 472, 367-377, doi:10.1042/BJ20150660.
Batchu, S. N., et al., "The therapeutic hope for HDAC6 inhibitors in malignancy and chronic disease," Clinical Science 2016, 130: 987-1003, DOI: 10.1042/CS20160084.
Benjamini, Y. and Y. Hochberg (1995) "Controlling the false discovery rate: A practical and powerful approach to multiple testing" Journal of the Royal Statistical Society. Series B (Methodological), 57:289-300.
Bettica, P., et al., "Histological effects of givinostat in boys with Duchenne muscular dystrophy," Neuromuscular Disorders 26 (2016), pp. 643-649, http://dx.doi.org/10.1016/j.nmd.2016.07.002.
Brindisi, M., et al., "Old but Gold: Tracking the New Guise of Histone Deacetylase 6 (HDAC6) Enzyme as a Biomarker and Therapeutic Target in Rare Diseases," Journal of Medicinal Chemistry 2020, 63, pp. 23-39, published Aug. 15, 2019, DOI: 10.1021/acs.jmedchem.9b00924.
Brix, S., "HDAC6 controls the development and progression of cardiac mal-adaptive hypertrophy," Dissertation, submitted to the Department of Biology, Chemistry and Pharmacy of Freie Universität Berlin, 2017, 116 pages.
Buikema, J. W., et al., "Wnt Activation and Reduced Cell-Cell Contact Synergistically Induce Massive Expansion of Functional Human iPSC-Derived Cardiomyocytes," Cell Stem Cell 27, 50-63. e1-e5, Jul. 2, 2020, https://doi.org/10.1016/j.stem.2020.06.001.
Butler et al. (2010). "Rational Design and Simple Chemistry Yield a Superior, Neuroprotective HDAC Inhibitor, Tubastatin A," J. Am. Chem. Soc., vol. 132: 10842-10846.
Butler, R. E., et al., "Abstract P436: Modeling Genetic Dilated Cardiomyopathy Using Induced Pluripotent Stem Cell-derived Engineered Heart Tissues for Precision Medicine," Circulation Research 2021;129:AP436, originally published Nov. 22, 2021, https://doi.org/10.1161/res.129.suppl_1.P436, 1 page.
Cao, D. J., et al., "Histone deacetylase (HDAC) inhibitors attenuate cardiac hypertrophy by suppressing autophagy," Proc. Natl. Acad. Sci., Mar. 8, 2011, vol. 108, No. 10, pp. 4123-4128, https://doi.org/10.1073/pnas.1015081108.
Chami, N., et al., "Nonsense mutations in BAG3 are associated with early-onset dilated cardiomyopathy in French Canadians," Canadian Journal of Cardiology 30 (2014), pp. 1655-1661, https://dx.doi.org/10.1016/j.cjca.2014.09.030.
Chen, C. Y., et al., "Suppression of detyrosinated microtubules improves cardiomyocyte function in human heart failure," Nature Medicine, vol. 24, Aug. 2018, pp. 1225-1233, including Methods and Reporting Summary, https://doi.org/10.1038/s41591-018-0046-2 (15 total pages).
Choi, S. Y., et al., "Inhibition of class IIa histone deacetylase activity by gallic acid, sulforaphane, TMP269, and panobinostat," Biomedicine & Pharmacotherapy 101 (2018), pp. 145-154, doi: 10.1016/j.biopha.2018.02.071.
Cleland, J.G.F., et al., "The year in cardiology: heart failure," European Heart Journal 2020, 41, 1232-1248, doi:10.1093/eurheartj/ehz949.
Demos-Davies, Kimberly M. et al., "HDAC6 contributes to pathological responses of heart and skeletal muscle to chronic angiotensin-II signaling,", American Journal of Physiology heart and Circulatory Physiology, Jul. 2014, vol. 307, No., 2, pp. H252-H258, DOI: 10.1152/ajpheart.00149.2014.
Dominguez, F., et al., "Dilated Cardiomyopathy Due to BLC2-Associated Athanogene 3 (BAG3) Mutations," Journal of the American College of Cardiology 2018, vol. 72, No. 20, 2471-2481. https://doi.org/10.1016/j.jacc.2018.08.2181.
Everly, M. J., et al., "Cardiac Transplantation in the United States: An Analysis of the UNOS Registry," Chapter 3, Clinical Transplants 2008, pp. 35-43.
Extended European Search Report, dated Aug. 30, 2023, for European Application No. 20870779.4 (8 total pages).
Fang, X., et al., "Loss-of-function mutations in co-chaperone BAG3 destabilize small HSPs and cause cardiomyopathy," The Journal of Clinical Investigation, Aug. 2017, vol. 127, No. 8, pp. 3189-3200, https://doi.org/10.1172/JCI94310.
Feldman, A. M., et al., "Decreased Levels of BAG3 in a Family With a Rare Variant and in Idiopathic Dilated Cardiomyopathy," Journal of Cellular Physiology 229, 1697-1702 (2014), DOI: 10.1002/jcp.24615.
Ferguson, B. S., et al., "Non-Sirtuin Histone Deacetylases in the Control of Cardiac Aging," Journal of Molecular and Cellular Cardiology 83, Jun. 2015, pp. 14-20, http://dx.doi:10.1016/j.yjmcc.2015.03.010.

(56) References Cited

OTHER PUBLICATIONS

Feyen, D. A. M., et al., Metabolic Maturation Media Improve Physiological Function of Human iPSC-Derived Cardiomyocytes. Cell Rep. Jul. 21, 2020;32(3):107925. doi: 10.1016/j.celrep.2020. 107925.
Franceschelli, S., et al., "Bag3 Gene Expression is Regulated by Heat Shock Factor 1," Journal of Cellular Physiology 215: 575-577 (2008), DOI: 10.1002/jcp.21397.
Gallinari, P., et al., "HDACs, histone deacetylation and gene transcription: from molecular biology to cancer therapeutics," Cell Research 2007, 17:195-211, published online Feb. 27, 2007, doi:10.1038/sj.cr.7310149.
Gamerdinger, M., et al., "BAG3 mediates chaperone-based aggresome-targeting and selective autophagy of misfolded proteins," EMBO Reports 2011, vol. 12, No. 2, pp. 149-156, published online Jan. 21, 2011, doi: 10.1038/embor.2010.203.
Gao, X., et al., "Efficacy and toxicity of histone deacetylase inhibitors in relapsed/refractory multiple myeloma: Systematic review and meta-analysis of clinical trials," Experimental and Therapeutic Medicine 18, 1057-1068 (2019), DOI: 10.3892/etm.2019.7704.
Gazewood, J. D. and Turner, P. L., "Heart Failure with Preserved Ejection Fraction: Diagnosis and Management," American Family Physician, Nov. 1, 2017, vol. 96, No. 9, pp. 582-588, including eTable, 2 pages.
Glozak, M. A., et al., "Histone deacetylases and cancer," Oncogene 2007, 26, 5420-5432, doi:10.1038/sj.onc.1210610.
Gräff, J., et al., "The potential of HDAC Inhibitors as Cognitive Enhancers," Annu. Rev. Pharmacol. Toxicol. 2013, 53:311-330, including Contents, doi:10.1146/annurev-pharmtox-011112-140216 (23 total pages).
Haberland, M., et al., "The many roles of histone deacetylases in development and physiology: implications for disease and therapy," Nature Reviews Genetics, vol. 10, Jan. 2009, pp. 32-42, doi:10.1038/nrg2485.
Hass, J., et al., "Atlas of the clinical genetics of human dilated cardiomyopathy," European Heart Journal (2015) 36, 1123-1135 & 1135a, doi:10.1093/eurheartj/ehu301.
Heidersbach, A., et al., "MicroRNA-1 regulates sarcomere formation and suppresses smooth muscle gene expression in the mammalian heart," ELife 2013;2:e01323, DOI: 10.7554/eLife.01323, 22 pages.
Homma, S., et al., "BAG3 Deficiency Results in Fulminant Myopathy and Early Lethality," The American Journal of Pathology, vol. 169, No. 3, Sep. 2006, pp. 761-773. DOI: 10.2353/ajpath.2006.060250.
Hubbert, C., et al., "HDAC6 is a microtubule-associated deacetylase," Nature, vol. 417, May 23, 2002, pp. 455-458, https://doi.org/10.1038/417455a.
International Preliminary Report on Patentability for International Application No. PCT/US2020/054134 dated Apr. 14, 2022, 9 pages.
International Preliminary Report on Patentability for International Application No. PCT/US2020/066439 dated Jun. 30, 2022, 8 pages.
International Search Report and Written Opinion for International Application No. PCT/US2022/026065, mailed Sep. 29, 2022, 18 pages.
International Search Report and Written Opinion for International Application No. PCT/US2022/027725, mailed Jul. 22, 2022, 20 pages.
International Search Report and Written Opinion, mailed Apr. 27, 2021, for International Application No. PCT/US2020/066439 (12 pages).
International Search Report and Written Opinion, mailed Jan. 11, 2021, for International Application No. PCT/US2020/054134 (11 total pages).
International Search Report and Written Opinion, mailed Oct. 8, 2020, for International Application No. PCT/US2020/032943 (12 total pages).
Invitation to Pay Additional Fees and, Where Applicable, Protest Fee, mailed Aug. 3, 2022, for International Application No. PCT/US2022/026065, 10 total pages.
Ito, K., et al., "Orthovanadate-Induced Vasoconstriction of Rat Mesenteric Arteries Is Mediated by Rho Kinase-Dependent Inhibition of Myosin Light Chain Phosphatase," Biological & Pharmaceutical Bulletin, vol. 38, No. 11, pp. 1809-1816 (2015).
Jeong, M. Y., et al., "Histone deacetylase activity governs diastolic dysfunction through a nongenomic mechanism," Science Translational Medicine, 10, eaao0144 (2018), Feb. 7, 2018, https://doi.org/10.1126/scitranslmed.aao0144, 10 pages.
Joshi, P., et al., "The functional interactome landscape of the human histone deacetylase family," Molecular Systems Biology 2013, 9:672, doi:10.1038/msb.2013.26, 21 pages.
Judge, L. M., et al., "A BAG3 chaperone complex maintains cardiomyocyte function during proteotoxic stress," JCI Insight 2017, 2(14):e94623, published Jul. 20, 2017, https://doi.org/10.1172/jci.insight.94623, 18 pages.
Kee, H. J., et al., "HDAC Inhibition Suppresses Cardiac Hypertrophy and Fibrosis in DOCA-Salt Hypertensive Rats via Regulation of HDAC6/HDAC8 Enzyme Activity," Kidney & Blood Pressure Research 2013, 37:229-239, DOI: 10.1159/000350148, Published online Jul. 8, 2013.
Knöll, R., et al., A Common MLP (Muscle LIM Protein) Variant Is Associated With Cardiomyopathy, Circulation Research, Mar. 5, 2010, 695-704, DOI: 10.1161/CIRCRESAHA.109.206243.
Krukowski, K., et al., "HDAC6 inhibition effectively reverses chemotherapy-induced peripheral neuropathy," Pain, Jun. 2017, vol. 158, No. 6, pp. 1126-1137, doi: 10.1097/j.pain.0000000000000893.
Lam, C. S. P., et al., "Heart failure with preserved ejection fraction: from mechanisms to therapies," European Heart Journal 2018, 39, 2780-2792. doi: 10.1093/eurheartj/ehy301.
Lecun, Y., et al., "Deep learning," Nature, vol. 521, May 28, 2015, 436-444, doi: 10.1038/nature14539.
Leoni, F., et al., "The histone deacetylase inhibitor ITF2357 reduces production of pro-inflammatory cytokines in vitro and systemic inflammation in vivo," Molecular Medicine, vol. 11, Nos. 1-2, Jan.-Dec. 2005, doi: 10.2119/2006-00005.Dinarello, 15 pages.
Lewinter, M. M. and Meyer, M., "Mechanisms of Diastolic Dysfuntion in Heart Failure with a Preserved Ejection Fraction, If It's Not One Thing It's Another," Circulation Heart Failure 2013, 6:1112-1115, DOI: 10.1161/CIRCHEARTFAILURE.113.000825.
Lian, X. et al., "Robust cardiomyocyte differentiation from human pluripotent stem cells via temporal modulation of canonical Wnt signaling," PNAS, Published online May 29, 2012, 109(27):E1848-E1857. https://doi.org/10.1073/pnas.1200250109.
Loffredo, F. S., et al., "Heart Failure with Preserved Ejection Fraction, Molecular Pathways of the Aging Myocardium," Circulation Research, Jun. 20, 2014, pp. 97-107, DOI: 10.1161/CIRCRESAHA.115.302929.
Ludwig, T. E., et al., "Feeder-independent culture of human embryonic stem cells," Nature Methods, vol. 3, No. 8, Aug. 2006, pp. 637-646, including Erratum published Oct. 2006, 1 page, DOI:10.1038/NMETH902.
Ma, Z. et al., "Contractile deficits in engineered cardiac microtissues as a result of MYBPC3 deficiency and mechanical overload," Nat Biomed Eng, 2:955-967 (2018). https://doi.org/10.1038/s41551-018-0280- 4, and Supplementary Information, 16 pages.
Maddah, M., et al., "Quantifying drug-induced structural toxicity in hepatocytes and cardiomyocytes derived from hiPSCs using a deep learning method," Journal of Pharmacological and Toxicological Methods 105 (2020) 106895, https://doi.org/10.1016/j.vascn.2020.106895, 13 pages.
Magupalli, V. G., et al., "HDAC6 mediates an aggresome-like mechanism for NLRP3 and pyrin inflammasome activation," Science 2020, 369, eaas8995, Sep. 18, 2020 (18 total pages).
Mariño, G., et al., "Self-consumption: the interplay of autophagy and apoptosis," Nature Reviews Molecular Cell Biology, vol. 15, Feb. 2014, pp. 81-94, doi: 10.1038/nrm3735.
McLendon, P. M., et al., "Tubulin hyperacetylation is adaptive in cardiac proteotoxicity by promoting autophagy," PNAS, Published online Nov. 17, 2014, E5178-E5186, www.pnas.org/cgi/doi/10.1073/pnas.1415589111.
McNally, E. M., et al., Genetic mutations and mechanisms in dilated cardiomyopathy, The Journal of Clinical Investigation, Jan. 2013, vol. 123, No. 1, pp. 19-26, https://doi.org/10.1172/JCI62862.

(56) References Cited

OTHER PUBLICATIONS

Milan, M., et al., "Givinostat reduces adverse cardiac remodeling through regulating fibroblasts activation," Cell Death and Disease 2018, 9:108, DOI 10.1038/s41419-017-0174-5 (17 total pages).
Mohammadi, M. M., et al., "A surgical mouse model of neonatal pressure overload by transverse aortic constriction," Nature Protocols, vol. 16, Feb. 2021, pp. 775-790, including Reporting Summary, https://doi.org/10.1038/s41596-020-00434-9 (19 total pages).
Nagata, S., et al., "Histone Deacetylase Inhibitor SAHA Treatment Prevents the Development of Heart Failure after Myocardial Infarction via an Induction of Heat-Shock Proteins in Rats," Biol. Pharm. Bull. 2019, vol. 42, No. 3, pp. 453-461, https://doi.org/10.1248/bpb.b18-00785.
Nebbioso, A., et al., "c-Myc Modulation and Acetylation Is a Key HDAC Inhibitor Target in Cancer," Clinical Cancer Research 23(10), May 15, 2017, pp. 2542-2555. doi: 10.1158/1078-0432.CCR-15-2388.
Non-Final Office Action for U.S. Appl. No. 18/087,933 dated May 12, 2023, 06 pages.
Norton, N., et al., "Genome-wide Studies of Copy Number Variation and Exome Sequencing Identify Rare Variants in BAG3 as a Cause of Dilated Cardiomyopathy," The American Journal of Human Genetics, 88, 273-282, Mar. 11, 2011, DOI: 10.1016/j.ajhg.2011.01.016.
Notice of Allowance, dated Aug. 22, 2023, for U.S. Appl. No. 18/087,933, 5 pages.
Park, Jin Kyun et al., "Therapeutic potential of CKD-506, a novel selective histone deacetylase 6 inhibitor, in a murine model of rheumatoid arthritis," Arthritis Research & Therapy, 22, 176, https://doi.org/10.1186/s13075-020-02258-0 (Jul. 2020).
Patel, R. B., et al., "Drug Targets for Heart Failure with Preserved Ejection Fraction: A Mechanic Approach and Review of Contemporary Clinical Trials," Annu. Rev. Pharmacol. Toxicol. 2019, 59:41-63, https://doi.org/10.1146/annurev-pharmtox-010818-021136 (26 total pages).
Perez-Salvia, M., et al., "In vitro and in vivo activity of a new small-molecule inhibitor of HDAC6 in mantle cell lymphoma," Haematologica, vol. 103, No. 11: e537-540, doi: 10.3324/haematol.2018.189241 (Nov. 2018).
Portran, D., 2017. Tubulin acetylation protects long-lived microtubules against mechanical ageing. Nat. Cell Biol. 19, 391-398. https://doi.org/10.1038/ncb3481.
"Pubchem CID 50954356"; Create Date: Mar. 29, 2011 (Mar. 29, 2011); Date Accessed: Apr. 12, 2021 (Apr. 12, 2021), 7 pages.
"Pubchem CID 82008729"; Create Date: Oct. 20, 2014 (Oct. 20, 2014); Date Accessed: Apr. 12, 2021 (Apr. 12, 2021), 7 pages.
Rajbhandari, P., et al., "IL-10 Signaling Remodels Adipose Chromatin Architecture to Limit Thermogenesis and Energy Expenditure," Cell 172, 218-233, e1-e7, including Supplemental Figures, Jan. 11, 2018, https://doi.org/10.1016/j.cell.2017.11.019 (34 total pages).
Ranjbarvaziri, S., et al., "HDAC6 Inhibition Reduces Cardiac Fibrosis, Enhances Mitochondrial Function and Demonstrates Comparable Efficacy as Empagliflozin in a Mouse Model of Heart Failure with Preserved Ejection Fraction," 2022 European Society of Cardiology—Heart Failure Congress, May 24, 2022, 1 page.
Ranjbarvaziri, S., et al., "Histone Deacetylase 6 Inhibition Demonstrates Comparable Efficacy as Empagliflozin in a Mouse Model of Heart Failure with Preserved Ejection Fraction," American Heart Association Scientific Sessions 2022, Nov. 5, 2022, 1 page.
Rauch, J. N., et al., "BAG3 is a Modular, Scaffolding Protein that physically Links Heat Shock Protein 70 (Hsp70) to the Small Heat Shock Proteins," J. Mol. Biol. (2017), 429, 128-141. https://doi.org/10.1016/j.jmb.2016.11.013.
Riehle, C., et al., "Key inflammatory mechanisms underlying heart failure," Herz 2019, 44:96-106, https://doi.org/10.1007/s00059-019-4785-8, published online Feb. 4, 2019.
Robison, P., et al., "Detyrosinated microtubules buckle and bear load in contracting cardiomyocytes," Science, vol. 352, Issue 6284, aaf0659 (Apr. 22, 2016), DOI: 10.1126/science.aaf0659, 12 pages.
Ruparelia, A.A., et al., "Zebrafish models of BAG3 myofibrillar myopathy suggest a toxic gain of function leading to BAG3 insufficiency," Acta Neuropathol (2014) 128: 821-833, DOI:10.1007/s00401-014-1344-5.
Santo et al., "Preclinical activity, pharmacodynamic, and pharmacokinetic properties of a selective HDAC6 inhibitor, ACY-1215, in combination with bortezomib in multiple myeloma," Blood, publ. 2012, vol. 119(11), pp. 2579-2589 (2012).
Schiattarella, G.G., et al., "Can HFpEF and HFrEF Coexist?," Circulation 2020, 141: 709-711, Mar. 3, 2020, DOI: 10.1161/CIRCULATIONAHA.119.045171.
Schiattarella, G.G. et al., "Nitrosative stress drives heart failure with preserved ejection fraction," Nature, vol. 568, Apr. 18, 2019, pp. 351-356, including Methods and Extended Data (28 total pages).
Schmittgen, T. D., et al., "Analyzing real-time PCR data by the comparative CT method," Nature Protocols 2008, vol. 3, No. 6, 1101-1108, published online Jun. 5, 2008, doi: 10.1038/nprot.2008.73.
Shen, S., et al., "Bicyclic-Capped Histone Deacetylase 6 Inhibitors with Improved Activity in a Model of Axonal Charcot-Marie-Tooth Disease," ACS Chemical Neuroscience 2016, vol. 7, No. 2, 240-258, https://doi.org/10.1021/acschemneuro.5b00286, 77 pages.
Stürner, E. and Behl, C., "The Role of the Multifunctional BAG3 Protein in Cellular Protein Quality Control and in Disease," Frontiers in Molecular Neuroscience, vol. 10, Article 177, Jun. 2017, doi:10.3389/fnmol.2017.00177, 18 pages.
Subramanian, A. et al. (Oct. 2005), "Gene set enrichment analysis: A knowledge-based approach for interpreting genome-wide expression profiles," Proc Natl Acad Sci USA, vol. 102, No. 43, pp. 15545-15550. www.pnas.orgcgidoi10.1073pnas.0506580102.
Subramanian, S., et al., "Clinical Toxicities of Histone Deacetylase Inhibitors," Pharmaceuticals 2010, 3, 2751-2767, doi:10.3390/ph3092751.
Sukumar, M. et al. (Jan. 12, 2016) "Mitochondrial Membrane Potential Identifies Cells with Enhanced Stemness for Cellular Therapy" Cell Metabolism, 23:63-76.
Tao, H., et al., "HDAC6 Promotes Cardiac Fibrosis Progression through Suppressing RASSF1A Expression," Cardiology 2016, 133:18-26, Published Online Sep. 25, 2015, DOI: 10.1159/000438781.
Tarone, G., et al., "Keep your heart in shape: molecular chaperone networks for treating heart disease," Cardiovascular Research 2014, 102, 346-361, doi:10.1093/cvr/cvu049.
Tong, D. et al., "Female Sex is Protective in a Preclinical Model of Heart Failure with Preserved Ejection Fraction," Circulation, 140, pp. 1769-1771, doi: 10.1161/CIRCULATIONAHA.119.042267 (Nov. 2019).
Tschöpe, C., et al., "New Insights in (Inter)Cellular Mechanisms by Heart Failure with Preserved Ejection Fraction," Curr Heart Fail Rep 2014, 11:436-444, DOI 10.1007/s11897-014-0219-3.
Villard, E., et al., "A genome-wide association study identifies two loci associated with heart failure due to dilated cardiomyopathy," European Heart Journal (2011), 32, 1065-1076, doi:10.1093/eurheartj/ehr105.
Vogl, D. T., et al., "Ricolinostat, the First Selective Histone Deacetylase 6 Inhibitor, in Combination with Bortezomib and Dexamethasone for Relapsed or Refractory Multiple Myeloma," Clinical Cancer Research, 23(13), Jul. 1, 2017, 3307-3315, doi: 10.1158/1078-0432.CCR-16-2526.
Wallner, M., et al., "HDAC inhibition improves cardiopulmonary function in a feline model of diastolic dysfunction," Science Translation Medicine, 12, eaay7205 (2020), Jan. 8, 2020, 14 pages.
Wang, C.-Y., et al., "A Mouse Model of Diet-Induced Obesity and Insulin Resistance," Chapter 27, Methods in Molecular Biology, vol. 821, pp. 421-433 (2012), DOI 10.1007/978-1-61779-430-8_27.
Watanabe, K., et al., "A ROCK inhibitor permits survival of dissociated human embryonic stem cells," Nature Biotechnology, vol. 25, No. 6, Jun. 2007, pp. 681-686, published online May 27, 2007, doi: 10.1038/nbt1310.
Xie, M., et al., "Histone Deacetylase Inhibition Blunts Ischemia/Reperfusion Injury by Inducing Cardiomyocyte Autophagy," Circulation, Mar. 11, 2014, 129: 1139-1151, DOI: 10.1161/CIRCULATIONAHA.113.002416.

(56) References Cited

OTHER PUBLICATIONS

Yang, J., et al., "HDAC6 Inhibition Improves Heart Function in Preclinical Models of Heart Failure with Preserved Ejection Fraction," 2021 European Society of Cardiology—Heart Failure Congress, Jun. 29, 2021, 6 pages.

Yang, J., et al., "Phenotypic screening identifies HDAC6 inhibitors as cardioprotective agents in BAG3 cardiac-knockout mouse model of dilated cardiomyopathy," 2021 European Society of Cardiology—Heart Failure Congress, Jun. 29, 2021, 1 page.

Yang, J., et al., "Phenotypic screening with deep learning identifies HDAC6 inhibitors as cardioprotective in a BAG3 mouse model of dilated cardiomyopathy," Science Translational Medicine, Jul. 6, 2022, vol. 14, Issue 652, including Supplementary Material, DOI: 10.1126/scitranslmed.abl5654, 60 pages.

Yoon, S., et al., "HDAC and HDAC Inhibitor: From Cancer to Cardiovascular Diseases," Chonnam Medical Journal, 2016, 52:1-11, https://dx.doi.org/10.4068/cmj.2016.52.1.1.

Zhang, C. L., et al., "Class II Histone Deacetylases Act as Signal-Responsive Repressors of Cardiac Hypertrophy," Cell, vol. 110, 479-488, Aug. 23, 2002, https://doi.org/10.1016/S0092-8674(02)00861-9.

Zhang, Y., et al., "Mice Lacking Histone Deacetylase 6 Have Hyperacetylated Tubulin but Are Viable and Develop Normally," Molecular and Cellular Biology, Mar. 2008, vol. 28, No. 5, pp. 1688-1701, doi:10.1128/MCB.01154-06.

Extended European Search Report for European Application No. EP20903640.9 dated Feb. 22, 2024, 11 pages.

Granger, A., Abdullah, I., Huebner, F., Stout, A., Wang, T., Huebner, T., Epstein, J.A., Gruber, P.J., 2008. Histone deacetylase inhibition reduces myocardial ischemia-reperfusion injury in mice. FASEB J. 22, 3549-3560. https://doi.org/10.1096/fj.08-108548.

Invitation to Pay Additional Search Fees, mailed Dec. 1, 2023, for EP Application No. EP 20903640.9, 11 pages.

Iyer, A., et al., 2010. Antifibrotic activity of an inhibitor of histone deacetylases in DOCA-salt hypertensive rats. Br. J. Pharmacol. 159, 1408-1417. https://doi.org/10.1111/j.1476-5381.2010.00637.x.

Kee Hae Jin, et al., 2006. Inhibition of Histone Deacetylation Blocks Cardiac Hypertrophy Induced by Angiotensin II Infusion and Aortic Banding. Circulation 113, 51-59. https://doi.org/10.1161/CIRCULATIONAHA.105.559724.

Kong Yongli, et al., 2006. Suppression of Class I and II Histone Deacetylases Blunts Pressure-Overload Cardiac Hypertrophy. Circulation 113, 2579-2588. https://doi.org/10.1161/CIRCULATIONAHA.106.625467.

Kook, H., et al., 2003. Cardiac hypertrophy and histone deacetylase-dependent transcriptional repression mediated by the atypical homeodomain protein Hop. J. Clin. Invest. 112, 863-871. https://doi.org/10.1172/JCI19137.

Leng, Y., et al., 2018. Inhibition of HDAC6 Activity Alleviates Myocardial Ischemia/Reperfusion Injury in Diabetic Rats: Potential Role of Peroxiredoxin 1 Acetylation and Redox Regulation [WWW Document]. Oxid. Med. Cell. Longev, 16 pages. https://doi.org/10.1155/2018/9494052.

Liu, F., et al., 2008. Histone-deacetylase inhibition reverses atrial arrhythmia inducibility and fibrosis in cardiac hypertrophy independent of angiotensin. J. Mol. Cell. Cardiol. 45, 715-723. https://doi.org/10.1016/j.yjmcc.2008.08.015.

Zhao, T.C., et al., 2007. Inhibition of histone deacetylases triggers pharmacologic preconditioning effects against myocardial ischemic injury. Cardiovasc. Res. 76, 473-481. https://doi.org/10.1016/j.cardiores.2007.08.010.

Invitation to Pay Additional Fees dated Mar. 1, 2021, for International Application No. PCT/US2020/066439, 17 pages.

Perez-Bermejo, et al., "Functional analysis of a common BAG3 allele associated with protection from heart failure," bioRxiv preprint doi: https://www.doi.org/10.1101/2021.10.06.463213; this version posted Oct. 6, 2021, 54 pages.

* cited by examiner

HDAC6 INHIBITORS FOR TREATMENT OF METABOLIC DISEASE AND HFPEF

CROSS-REFERENCE TO RELATED APPLICATIONS

This application is a continuation of International Patent Application No. PCT/US2022/027725 filed May 4, 2022, which claims the benefit of U.S. Provisional Patent Application No. 63/183,914 filed May 4, 2021, U.S. Provisional Patent Application No. 63/210,690 filed Jun. 15, 2021, and U.S. Provisional Patent Application No. 63/210,676 filed Jun. 15, 2021, the entire disclosures of each of which are incorporated by reference herein in their entireties.

FIELD

The present disclosure relates to treatment of metabolic disease. The present disclosure also relates to treatment of heart failure with preserved ejection fraction (HFpEF).

BACKGROUND

Metabolic diseases are a major source of health problems, particularly in countries where high calorie diets are typical. In particular, diet-induced obesity (DIO) affects a growing number of people worldwide. Metabolic diseases associated with obesity include diabetes and pre-diabetes, diabetic cardiomyopathy, metabolic syndrome (a termed for heart-related disorders associated with metabolism), hypertension, and hypertriglyceridemia/dyslipidemia.

Heart failure with preserved ejection fraction (HFpEF) is a major health problem without effective therapies. This syndrome is rising in prevalence and is associated with high morbidity and mortality. HFpEF, also known as diastolic heart failure, affects at least 2.5 million persons per year in the United States alone. (Gazewood and Turner. Am Fam Physician. 2017 Nov. 1; 96(9):582-588.) Risk factors include older age, female sex, obesity, hypertension, tobacco use, diabetes mellitus, coronary artery disease (CAD), valvular heart disease, and atrial fibrillation. In 2013, health care expenditures directly attributed to heart failure totaled approximately $30 billion.

Finding effective pharmaceutical treatments for obesity and associated metabolic diseases remains challenging. There is an unmet need for treatments for metabolic disease.

Finding effective pharmaceutical treatments for HFpEF also remains challenging. The most common pharmaceutical treatment for HFpEF remains administration of a diuretic. There is an unmet need for treatments for HFpEF.

The present disclosure addresses these needs.

SUMMARY

In some aspects, the present disclosure relates to methods of treating or preventing metabolic disease by administering an HDAC6 inhibitor.

In some embodiments, the disclosure provides a method of treating a metabolic disease in a subject in need thereof, comprising administering a HDAC6 inhibitor to the subject. In some embodiments, the disclosure provides a method of preventing a metabolic disease in a subject in need thereof, comprising administering a HDAC6 inhibitor to the subject. In some embodiments, the metabolic disease is a metabolic disease associated with obesity, such as diet-induced obesity. In some embodiments, the metabolic disease is not diet-induced. In some embodiments, the metabolic disease is a diabetes, pre-diabetes, diabetic cardiomyopathy, metabolic syndrome, hypertension, hypertriglyceridemia, or dyslipidemia. In some embodiments, the metabolic disease is type 2 diabetes.

In some embodiments, the disclosure provides a method of treating or preventing diabetes in a subject in need thereof, comprising administering a HDAC6 inhibitor. In some embodiments, the disclosure provides a method of treating or preventing diabetes mellitus in a subject in need thereof, comprising administering a HDAC6 inhibitor. In some embodiments, the disclosure provides a method of treating or preventing Type 2 diabetes in a subject in need thereof, comprising administering a HDAC6 inhibitor. In some embodiments, the disclosure provides a method of treating or preventing pre-diabetes in a subject in need thereof, comprising administering a HDAC6 inhibitor. In some embodiments, the disclosure provides a method of treating or preventing diabetic cardiomyopathy in a subject in need thereof, comprising administering a HDAC6 inhibitor. In some embodiments, the disclosure provides a method of treating or preventing metabolic syndrome in a subject in need thereof, comprising administering a HDAC6 inhibitor. In some embodiments, the disclosure provides a method of treating or preventing hypertension in a subject in need thereof, comprising administering a HDAC6 inhibitor. In some embodiments, the disclosure provides a method of treating or preventing metabolic hypertriglyceridemia and/or dyslipidemia in a subject in need thereof, comprising administering a HDAC6 inhibitor. In some embodiments, the subject is obese. In other embodiments, the subject is not obese.

In some aspects, the disclosure provides a method of treating or preventing obesity in a subject in need thereof, comprising administering a HDAC6 inhibitor to the subject. The subject may be an obese subject or a subject at risk for obesity.

In some embodiments, the subject has or is at risk for hypertension. In some embodiments, the subject has or is at risk for diabetes (e.g., diabetes mellitus or Type 2 diabetes). In some embodiments, the subject has or is at risk for diabetic cardiomyopathy. In some embodiments, the subject has or is at risk for metabolic syndrome. In some embodiments, the subject has or is at risk for hyperglyceridemia or dyslipidemia.

In some embodiments, the subject is a human. In some embodiments, the subject is at least 65 years old. In some embodiments, the subject is at least 70 years old.

In some embodiments, the disclosure provides methods of treating metabolic disease (e.g., diabetes, such as diabetes mellitus, or metabolic syndrome) or treating obesity in a subject in need thereof, comprising administering an HDAC6 inhibitor to the subject, wherein the HDAC6 inhibitor is fluoroalkyl-oxadiazole derivative. In some embodiments, the HDAC6 inhibitor is fluoroalkyl-oxadiazole derivative according to the following Formula:

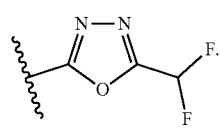 [SMILES: *c1nnc(C(F)F)o1]

In some embodiments, the disclosure provides methods of preventing metabolic disease (e.g., diabetes, such as diabetes mellitus, or metabolic syndrome) in a subject in need thereof, comprising administering an HDAC6 inhibitor to the subject, wherein the HDAC6 inhibitor is fluoroalkyl-oxadiazole derivative. In some embodiments, the HDAC6 inhibitor is fluoroalkyl-oxadiazole derivative according to the following Formula:

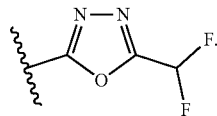 [SMILES: *c1nnc(C(F)F)o1]

In some embodiments, the method treats or prevents at least one symptom of metabolic disease. In some embodiments, the method improves glucose tolerance. In some embodiments, the method improves insulin resistance. In some embodiments, the method reduces glucose level. In some embodiments, the method inhibits inflammatory genes in adipose tissue. In some embodiments, the method reduces body weight of the subject.

In other aspects, the disclosure provides an HDAC6 inhibitor for use in a method for treating metabolic disease.

In other aspects, the disclosure provides a pharmaceutical composition for use in a method for treating metabolic disease, comprising an HDAC6 inhibitor.

In other aspects, the disclosure provides a kit, comprising an HDAC6 inhibitor and instructions for use in a method for treating metabolic disease.

In other aspects, the disclosure provides a use of an HDAC6 inhibitor in treating metabolic disease.

In some aspects, the present disclosure relates to methods of treating or preventing heart failure with preserved ejection fraction (HFpEF) by administering an HDAC6 inhibitor.

In some embodiments, the disclosure provides a method of treating heart failure with preserved ejection fraction (HFpEF) in a subject in need thereof, comprising administering a HDAC6 inhibitor to the subject. In some embodiments, the disclosure provides a method of preventing heart failure with preserved ejection fraction (HFpEF) in a subject in need thereof, comprising administering a HDAC6 inhibitor to the subject.

In some aspects, the disclosure provides a method of treating or preventing cardiac fibrosis (e.g., associated with HFpEF) in a subject in need thereof, comprising administering a HDAC6 inhibitor to the subject.

In some aspects, the disclosure provides a method of treating or preventing diastolic dysfunction (e.g., associated with HFpEF) in a subject in need thereof, comprising administering a HDAC6 inhibitor to the subject.

In some embodiments, the subject has or is at risk of metabolic disease. In some embodiments, the subject has or is at risk for hypertension. In some embodiments, the subject has or is at risk for diabetes (e.g., diabetes mellitus or Type 2 diabetes). In some embodiments, the subject has or is at risk for coronary artery disease (CAD). In some embodiments, the subject has or is at risk for valvular heart disease. In some embodiments, the subject has or is at risk for atrial fibrillation. In some embodiments, the subject has or is at risk of metabolic syndrome. In some embodiments, the subject is obese.

In some embodiments, the subject does not have a metabolic disease. In some embodiments, the subject does not have metabolic syndrome. In some embodiments, the subject does not have diabetes (e.g., does not have diabetes mellitus or Type 2 diabetes). In some embodiments, the subject does not have hypertension. In some embodiments, the subject is not obese.

In some embodiments, the subject is a human. In some embodiments, the subject is at least 65 years old. In some embodiments, the subject is at least 70 years old.

In some embodiments, the method treats or prevents at least one symptom of HFpEF. In some embodiments, the method reduces left ventricular (LV) mass. In some embodiments, the method reduces LV wall thickness. In some embodiments, the method improves LV relaxation. In some embodiments, the method improves LV filling pressure. In some embodiments, the method prevents heart failure in the subject.

In some embodiments, the methods described herein reduce cardiac fibrosis (e.g., associated with HFpEF). In some embodiments, administration of an HDAC6 inhibitor is effective to significantly reduce cardiac fibroblast activation in a cell (e.g., in cell culture or in vivo). In some embodiments, administration of an HDAC6 inhibitor is effective to reduce cardiac fibroblast activation in a cell (e.g., in cell culture or in vivo), e.g., by 10%, 20%, 30%, 40%, 50%, 60%, 80%, 90% or more (relative to before administration or in the absence of administration). In some embodiments, administration of an HDAC6 inhibitor is effective to significantly reduce expression of one or more genes associated with fibrosis (e.g., in cells of a subject after administration of an HDAC6 inhibitor to the subject). In some embodiments, administration of an HDAC6 inhibitor is effective to reduce expression of one or more genes associated with fibrosis (e.g., in cells of a subject after administration of an HDAC6 inhibitor to the subject), e.g., by 10%, 20%, 30%, 40%, 50%, 60%, 80%, 90% or more (relative to before administration or in the absence of administration).

In some embodiments, administration of an HDAC6 inhibitor is effective to significantly reduce TGF-beta receptor signaling (e.g., in cells of a subject after administration of an HDAC6 inhibitor to the subject). In some embodiments, administration of an HDAC6 inhibitor is effective to reduce TGF-beta receptor signaling (e.g., in cells of a subject after administration of an HDAC6 inhibitor to the subject), e.g., by 10%, 20%, 30%, 40%, 50%, 60%, 80%, 90% or more (relative to before administration or in the absence of administration). In some embodiments, administration of an HDAC6 inhibitor is effective to significantly reduce expression of one or more genes associated with TGF-beta receptor signaling (e.g., in cells of a subject after administration of an HDAC6 inhibitor to the subject). In some embodiments, administration of an HDAC6 inhibitor is effective to reduce expression of one or more genes associated with TGF-beta receptor signaling (e.g., in cells of a subject after administration of an HDAC6 inhibitor to the subject), e.g., by 10%, 20%, 30%, 40%, 50%, 60%, 80%, 90% or more (relative to before administration or in the absence of administration).

In some embodiments, the methods described herein reduce cardiac muscle hypertrophy (e.g., associated with HFpEF).

In some embodiments, the methods described herein reduce mitochondrial dysfunction. In some embodiments, administration of an HDAC6 inhibitor is effective to significantly increase expression of genes associated with oxidative phosphorylation and/or mitochondrial complex I (e.g., in cells of a subject after administration of an HDAC6 inhibitor to the subject). In some embodiments, administration of an HDAC6 inhibitor is effective to increase expression of genes associated with oxidative phosphorylation and/or mitochondrial complex I (e.g., in cells of a subject after administration of an HDAC6 inhibitor to the subject), e.g., by 10%, 20%, 30%, 40%, 50%, 60%, 80%, 90% or more (relative to before administration or in the absence of administration). In some embodiments, administration of an HDAC6 inhibitor is effective to increase (e.g., significantly increase) mitochondrial membrane potential in a cell (e.g., in vitro or in vivo). In some embodiments, administration of an HDAC6 inhibitor is effective to increase (e.g., significantly increase) spare respiratory capacity in a cell (e.g., in cell culture or in vivo).

In some embodiments, the disclosure provides methods of treating HFpEF in a subject in need thereof, comprising administering an HDAC6 inhibitor, wherein the HDAC6 inhibitor is fluoroalkyl-oxadiazole derivative. In some embodiments, the HDAC6 inhibitor is fluoroalkyl-oxadiazole derivative according to the following Formula:

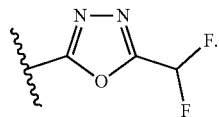 [SMILES: *c1nnc(C(F)F)o1]

In some embodiments, the disclosure provides methods of preventing HFpEF in a subject in need thereof, comprising administering an HDAC6 inhibitor, wherein the HDAC6 inhibitor is fluoroalkyl-oxadiazole derivative. In some embodiments, the HDAC6 inhibitor is fluoroalkyl-oxadiazole derivative according to the following Formula:

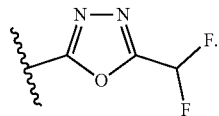 [SMILES: *c1nnc(C(F)F)o1]

In other aspects, the disclosure provides an HDAC6 inhibitor for use in a method for treating heart failure with preserved ejection fraction.

In other aspects, the disclosure provides a pharmaceutical composition for use in a method for treating heart failure with preserved ejection fraction, comprising an HDAC6 inhibitor.

In other aspects, the disclosure provides a kit, comprising an HDAC6 inhibitor and instructions for use in a method for treating heart failure with preserved ejection fraction.

In other aspects, the disclosure provides a use of an HDAC6 inhibitor in treating heart failure with preserved ejection fraction.

In some embodiments of any of the methods described herein, the administering to the subject is oral (e.g., oral administering to a human subject). In some embodiments, the treatment reduces or alleviates (i.e., is effective to reduce or alleviate) one or more symptoms or parameters of the disease being treated.

In some aspects, the method comprises selecting the HDAC6 inhibitor by performing in vitro testing for selective inhibition of HDAC6 on each member of the plurality of candidate compounds, thereby identifying a selected compound for use as the HDAC6 inhibitor.

In some embodiments, the HDAC6 inhibitor is a compound according to Formula (I):

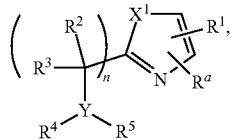

wherein
R$^1$ is selected from the group consisting of:

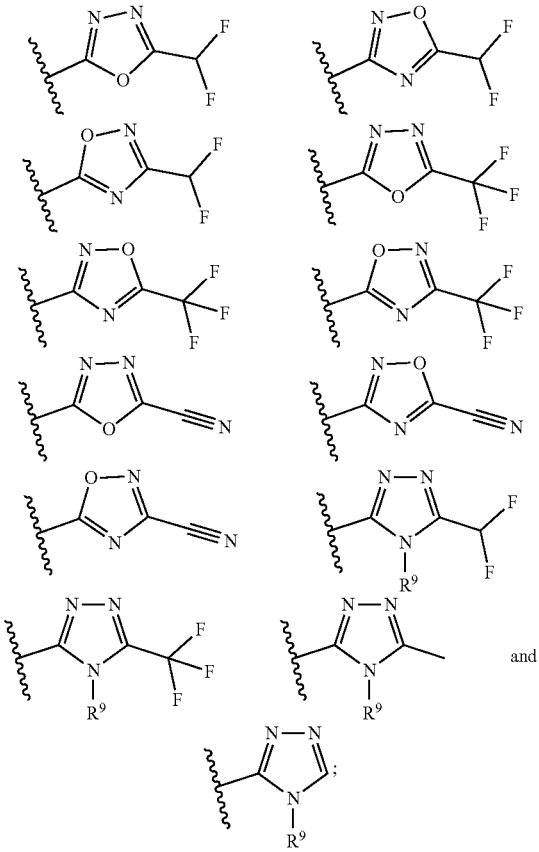

R$^a$ is selected from the group consisting of H, halo, C$_{1-3}$ alkyl, cycloalkyl, haloalkyl, and alkoxy;

R$^2$ and R$^3$ are independently selected from the group consisting of H, halogen, alkoxy, haloalkyl, aryl, heteroaryl, alkyl, and cycloalkyl each of which is optionally substituted, or R$^2$ and R$^3$ together with the atom to which they are attached form a cycloalkyl or heterocyclyl;

R$^4$ and R$^5$ are independently selected from the group consisting of H, —(SO$_2$)R$^2$, —(SO$_2$)NR$^2$R$^3$, —(CO)R$^2$, —(CONR$^2$R$^3$), aryl, arylheteroaryl, alkylenearyl, heteroaryl, cycloalkyl, heterocyclyl, alkyl, haloalkyl, and alkoxy, each of which is optionally substituted, or R$^4$ and R$^5$ together with the atom to which they are attached form a cycloalkyl or heterocyclyl, each of which is optionally substituted;

R$^9$ is selected from the group consisting of H, C$_1$-C$_6$ alkyl, haloalkyl, cycloalkyl and heterocyclyl;

X$^1$ is selected from the group consisting of S, O, NH and NR$^6$, wherein R$^6$ is selected from the group consisting of C$_1$-C$_6$ alkyl, alkoxy, haloalkyl, cycloalkyl and heterocyclyl;

Y is selected from the group consisting of $CR^2$, O, N, S, SO, and $SO_2$, wherein when Y is O, S, SO, or $SO_2$, $R^5$ is not present and when $R^4$ and $R^5$ together with the atom to which they are attached form a cycloalkyl or heterocyclyl, Y is $CR^2$ or N; and n is selected from 0, 1, and 2.

In some embodiments, the HDAC6 inhibitor is a compound according to Formula (Ik):

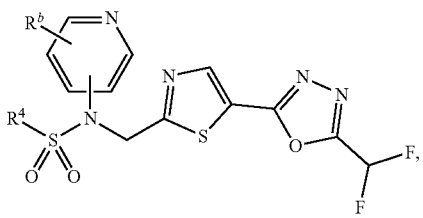

(Ik)

or a pharmaceutically acceptable salt thereof,
wherein:
$R^b$ is H, halogen, alkyl, cycloalkyl, —CN, haloalkyl, or haloalkoxy; and
$R^4$ is alkyl, alkoxy, haloalkyl, or cycloalkyl, each of which is optionally substituted.

In some embodiments of Formula (Ik), $R^b$ is H, halogen, haloalkyl, or haloalkoxy.

In some embodiments of Formula (Ik), $R^4$ is optionally substituted alkyl or cycloalkyl.

In some embodiments, the HDAC6 inhibitor is a compound according to Formula (Ik-1):

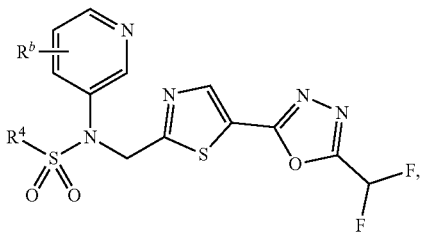

(Ik-1)

or a pharmaceutically acceptable salt thereof,
wherein:
$R^b$ is H, halogen, alkyl, cycloalkyl, —CN, haloalkyl, or haloalkoxy; and
$R^4$ is alkyl, alkoxy, haloalkyl, or cycloalkyl, each of which is optionally substituted.

In some embodiments of Formula (Ik-1), $R^b$ is H, halogen, haloalkyl, or haloalkoxy.

In some embodiments of Formula (Ik-1), $R^4$ is optionally substituted alkyl or cycloalkyl.

In some embodiments of Formula (Ik-1), $R^4$ is alkyl.

In some embodiments, the HDAC6 inhibitor is a compound according to Formula (Ik-2):

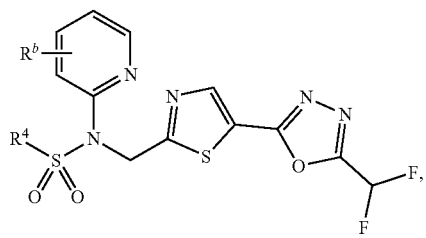

(Ik-2)

or a pharmaceutically acceptable salt thereof,
wherein:
$R^b$ is H, halogen, alkyl, cycloalkyl, —CN, haloalkyl, or haloalkoxy; and
$R^4$ is alkyl, alkoxy, haloalkyl, or cycloalkyl, each of which is optionally substituted.

In some embodiments of Formula (Ik-2), $R^b$ is H, halogen, haloalkyl, or haloalkoxy.

In some embodiments of Formula (Ik-2), $R^4$ is optionally substituted alkyl.

In some embodiments, the HDAC6 inhibitor is a compound is a compound according to Formula I(y):

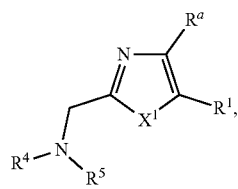

I(y)

or a pharmaceutically acceptable salt thereof,
wherein:
$X^1$ is S;
$R^a$ is selected from the group consisting of H, halogen, and $C_{1-3}$ alkyl;
$R^1$ is

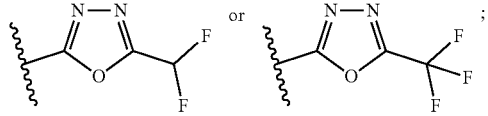 [SMILES: *c1nnc(C(F)F)o1 ; *c1nnc(C(F)(F)F)o1]

$R^2$ is selected from the group consisting of alkyl, alkoxy, and cycloalkyl, each of which is optionally substituted;
$R^3$ is H or alkyl;
$R^4$ is selected from the group consisting of alkyl, —($SO_2$)$R^2$, —($SO_2$)$NR^2R^3$, and —(CO)$R^2$; and
$R^5$ is aryl or heteroaryl; or $R^4$ and $R^5$ together with the atom to which they are attached form a heterocyclyl, each of which is optionally substituted.

In some embodiments of Formula I(y), $R^a$ is H.
In some embodiments of Formula I(y), $R^1$ is

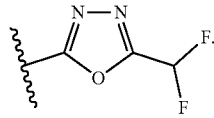 [SMILES: *c1nnc(C(F)F)o1]

In some embodiments of Formula I(y), $R^4$ is —$(SO_2)R^2$.

In some embodiments of Formula I(y), —$(SO_2)R^2$ is —$(SO_2)$alkyl, —$(SO_2)$alkyleneheterocyclyl, —$(SO_2)$haloalkyl, —$(SO_2)$haloalkoxy, or —$(SO_2)$cycloalkyl.

In some embodiments of Formula I(y), $R^5$ is heteroaryl.

In some embodiments of Formula I(y), the heteroaryl is a 5- to 6-membered heteroaryl.

In some embodiments of Formula I(y), the 5- to 6-membered heteroaryl is selected from the group consisting of

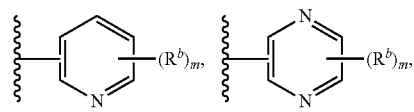

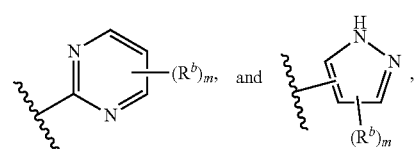

wherein $R^b$ is halogen, alkyl, alkoxy, cycloalkyl, —CN, haloalkyl, or haloalkoxy; and m is 0 or 1.

In some embodiments of Formula I(y), $R^b$ is F, Cl, —$CH_3$, —$CH_2CH_3$, —$CF_3$, —$CHF_2$, —$CF_2CH_3$, —CN, —$OCH_3$, —$OCH_2CH_3$, —$OCH(CH_3)_2$, —$OCF_3$, —$OCHF_2$, —$OCH_2CF_2H$, and cyclopropyl.

In some embodiments of Formula I(y), the aryl is selected from the group consisting of phenyl, 3-chlorophenyl, 3-chloro-4-fluorophenyl, 3-trifluoromethylphenyl, 3,4-difluorophenyl, and 2,6-difluorophenyl.

In some embodiments of Formula I(y), the compound is:

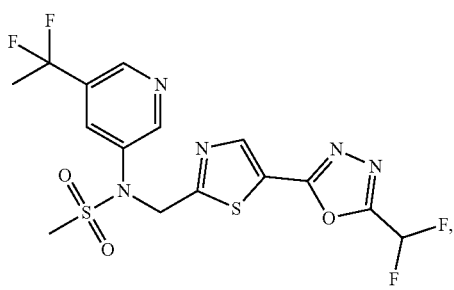 [SMILES: CC(F)(F)c1cncc(N(Cc2ncc(-c3nnc(C(F)F)o3)s2)S(C)(=O)=O)c1]

or a pharmaceutically acceptable salt thereof.

In some embodiments of Formula I(y), the compound is:

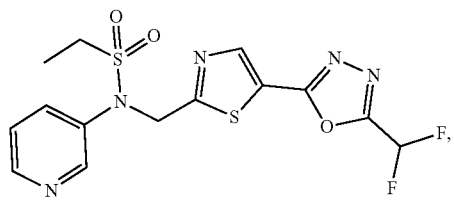 [SMILES: CCS(=O)(=O)N(Cc1ncc(-c2nnc(C(F)F)o2)s1)c1cccnc1]

or a pharmaceutically acceptable salt thereof.

In some embodiments of Formula I(y), the compound is:

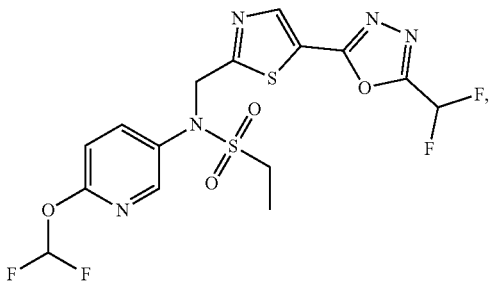 [SMILES: CCS(=O)(=O)N(Cc1ncc(-c2nnc(C(F)F)o2)s1)c1ccc(OC(F)F)nc1]

or a pharmaceutically acceptable salt thereof.

In some embodiments of Formula I(y), the compound is:

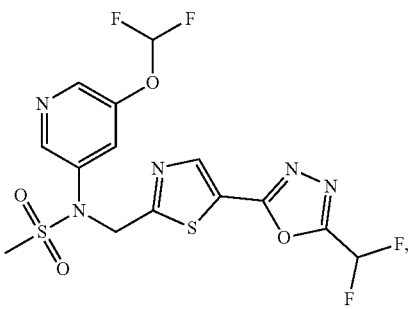 [SMILES: CS(=O)(=O)N(Cc1ncc(-c2nnc(C(F)F)o2)s1)c1cncc(OC(F)F)c1]

or a pharmaceutically acceptable salt thereof.

In some embodiments of Formula I(y), the compound is:

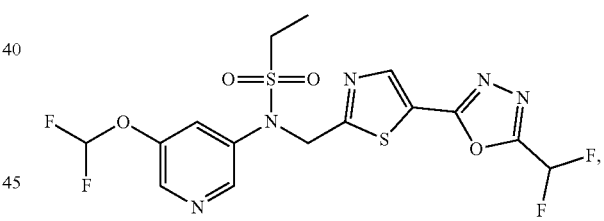

or a pharmaceutically acceptable salt thereof.

In some embodiments of Formula I(y), the compound is:

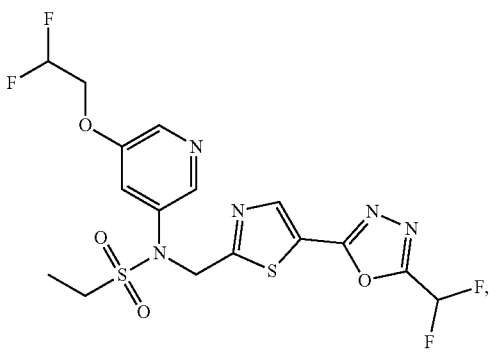 [SMILES: CCS(=O)(=O)N(Cc1ncc(-c2nnc(C(F)F)o2)s1)c1cncc(OCC(F)F)c1]

or a pharmaceutically acceptable salt thereof.

In some embodiments of Formula I(y), the compound is:

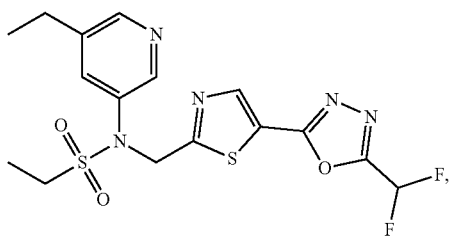 [SMILES: CCc1cncc(N(Cc2ncc(-c3nnc(C(F)F)o3)s2)S(=O)(=O)CC)c1]

or a pharmaceutically acceptable salt thereof.

In some embodiments of Formula I(y), the compound is:

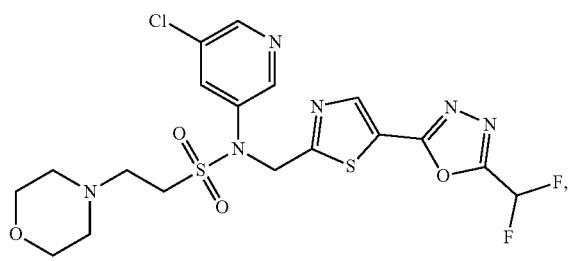 [SMILES: O=S(=O)(CCN1CCOCC1)N(Cc1ncc(-c2nnc(C(F)F)o2)s1)c1cncc(Cl)c1]

or a pharmaceutically acceptable salt thereof.

In some embodiments of Formula I(y), the compound is:

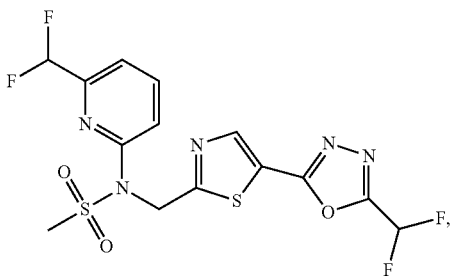 [SMILES: CS(=O)(=O)N(Cc1ncc(-c2nnc(C(F)F)o2)s1)c1cccc(C(F)F)n1]

or a pharmaceutically acceptable salt thereof.

In some embodiments of Formula I(y), the compound is:

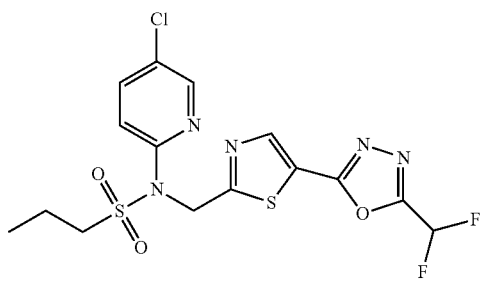 [SMILES: CCCS(=O)(=O)N(Cc1ncc(-c2nnc(C(F)F)o2)s1)c1ccc(Cl)cn1]

or a pharmaceutically acceptable salt thereof.

In some embodiments, the HDAC6 inhibitor is selected from the group consisting of:

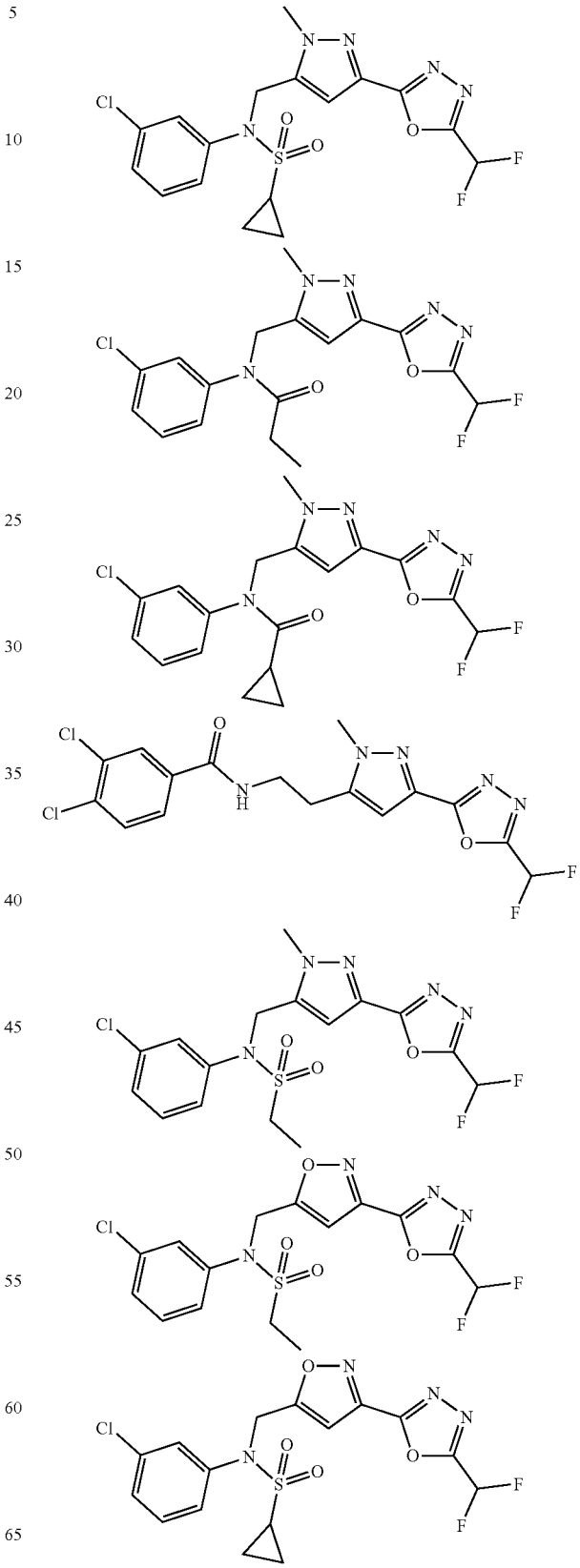

-continued

-continued

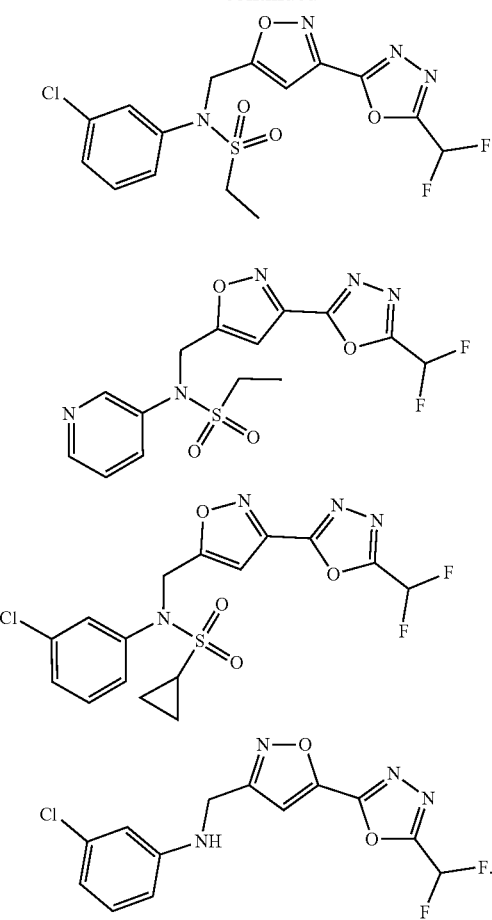

In some embodiments, the HDAC6 inhibitor is

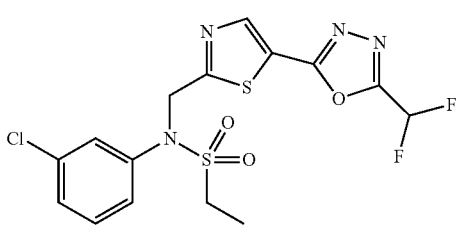 [SMILES: CCS(=O)(=O)N(Cc1ncc(-c2nnc(C(F)F)o2)s1)c1cccc(Cl)c1]

or an analog thereof.

In some embodiments, the HDAC6 inhibitor is

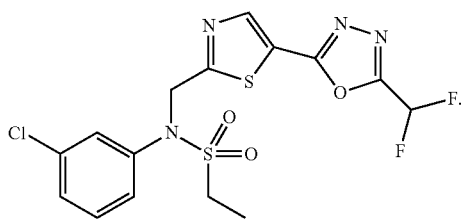 [SMILES: CCS(=O)(=O)N(Cc1ncc(-c2nnc(C(F)F)o2)s1)c1cccc(Cl)c1]

In some embodiments, the HDAC6 inhibitor is a compound of Formula (II):

$$\text{(II)}$$

wherein
n is 0 or 1;
X is O, NR$^4$, or CR$^4$R$^{4'}$;
Y is a bond, CR$^2$R$^3$ or S(O)$_2$;
R$^1$ is selected from the group consisting of H, amido, carbocyclyl, heterocyclyl, aryl, and heteroaryl;
R$^2$ and R$^3$ are independently selected from the group consisting of H, halogen, alkyl, carbocyclyl, heterocyclyl, aryl, heteroaryl, —(CH$_2$)-carbocyclyl, —(CH$_2$)-heterocyclyl, —(CH$_2$)-aryl, and —(CH$_2$)-heteroaryl; or
R$^1$ and R$^2$ taken together with the carbon atom to which they are attached form a carbocyclyl or heterocyclyl; or
R$^2$ and R$^3$ taken together with the carbon atom to which they are attached form a carbocyclyl or heterocyclyl; and
R$^4$ and R$^{4'}$ are each independently selected from the group consisting of H, alkyl, —CO$_2$-alkyl, carbocyclyl, heterocyclyl, aryl, heteroaryl, —(CH$_2$)-carbocyclyl, —(CH$_2$)— heterocyclyl, —(CH$_2$)-aryl, and —(CH$_2$)-heteroaryl; or
R$^4$ and R$^{4'}$ taken together with the carbon atom to which they are attached form a carbocyclyl or heterocyclyl;
wherein each alkyl, carbocyclyl, heterocyclyl, aryl, and heteroaryl is independently optionally substituted with one or more substituents selected from the group consisting of halogen, haloalkyl, oxo, hydroxy, alkoxy, —OCH$_3$, —CO$_2$CH$_3$, —C(O)NH(OH), —CH$_3$, morpholine, and —C(O)N-cyclopropyl.

In some embodiments, the HDAC6 inhibitor is CAY10603, tubacin, rocilinostat (ACY-1215), citarinostat (ACY-241), ACY-738, QTX-125, CKD-506, nexturastat A, tubastatin A, or HPOB. In some embodiments, the HDAC6 inhibitor is tubastatin A. In some embodiments, the HDAC6 inhibitor is ricolinostat. In some embodiments, the HDAC6 inhibitor is CAY10603. In some embodiments, the HDAC6 inhibitor is nexturastat A.

In some embodiments, the HDAC6 inhibitor is at least 100-fold selective against HDAC6 compared to all other isozymes of HDAC.

In some embodiments, the HDAC6 inhibitor reduces HDAC6 activity by at least 30%, at least 40%, at least 50%, at least 60%, at least 70%, at least 75%, at least 80%, at least 90%, at least 95%, or at least 98%. In some embodiments, the HDAC6 inhibitor substantially eliminates HDAC6 activity.

BRIEF DESCRIPTION OF DRAWINGS

FIG. 1A to FIG. 1F show results of intraperitoneal glucose-tolerance tests (GTT) performed by injection of glucose (2 g/kg in saline) after 6 hours fasting. Tail blood glucose levels (mg/dl) were measured with a glucometer before (0 min) and at 15, 30, 45, 60 and 120 min after glucose administration. Diet Induced Obese (DIO) mice at 16 weeks of age developed severe glucose intolerance compared to controls. FIG. 1A shows GTT results in control and DIO mice. Based on glucose AUC level, DIO mice were evenly randomized into four treatment groups to receive Vehicle (n=9) or TYA-11631 at three dosages 3, 10, 30 mg/kg (n=10 each). Control mice were also divided to dose orally with vehicle (n=10) or 30 mg/kg TYA-11631 (n=10). To assess the acute response of TYA-11631 on glucose metabolism, GTT was performed at 6 h after $1^{st}$ dose. FIG. 1B shows GTT results before dose of TYA-11631. FIG. 1C and FIG. 1D show GTT results after a single dose of TYA-11631. A single dose of TYA-11631 at all three dosages significantly reduced glucose level. FIG. 1E and FIG. 1F show GTT results after TYA-11631 treatment for 2 weeks. TYA-11631 treatment for 2 weeks led to a pronounced improvements in glucose tolerance in a dose dependent manner.

FIG. 1G and FIG. 1H show results of intraperitoneal insulin-tolerance tests (ITT) performed by injection of insulin (1 U/kg) after 6 hours fasting. Tail blood glucose levels (mg/dl) were measured with a glucometer before (0 min) and at 15, 30, 45, 60 and 120 min after insulin administration. HDAC6 inhibitor (TYA-11631) treatment for 4 weeks improved insulin resistance in DIO mice. 10 and 30 mg/kg were significantly reduced glucose AUC (ITT) with comparable activities, 3 mg/kg showed a trend of reduction.

FIG. 1I shows effects of TYA-11631 on blood glucose in non-fasting mice. Tail blood samples were collected in the morning and measured with a glucometer. TYA-11631 treatment for 6 wks led to a dose-dependent reduction of non-fasting glucose, consistent with the data of glucose tolerant test after fasting.

FIG. 1J and FIG. 1K show that treatment with TYA-11631 caused a dose dependent reduction of body weight in DIO mice. FIG. 1L shows that no differences in food consumption were observed between groups. Notably, control mice dosed with TYA-11631 30 mg/kg for 6 wks did not show changes on blood glucose levels and body weights. Bars and error bars show means and SEM. *P<0.05, P<0.01, *P<0.001, ****P<0.0001.

FIG. 3A shows TYA-11018 led to a dose-dependent reduction of fasting glucose in db/db mice. FIG. 3B shows both 1.5 and 15 mg/kg significantly decreased blood glucose after 4 hours of dosing/fasting, compared to vehicle treated db/db mice. FIG. 3C shows 15 mg/kg TYA-11018 significantly reduced fasting glucose after 6 hours of dosing. Bars and error bars show means and SEM.

FIG. 4A shows a schematic overview of HFpEF model induction by concomitant metabolic and moderate pressure overload stress in wildtype mice for 12 wks. n=5 mice in control group fed on regular diet without mTAC surgery, n=15 mice in HFpEF model development group induction with HFD/mTAC.

FIG. 4B and FIG. 4C show, respectively, HFD/mTAC induced continuous body weight increase and glucose intolerance compared to the control mice.

FIG. 4D shows left ventricular ejection fraction (LVEF) was preserved in mice with HFD/mTAC evaluated by echocardiography.

Figure 4A:
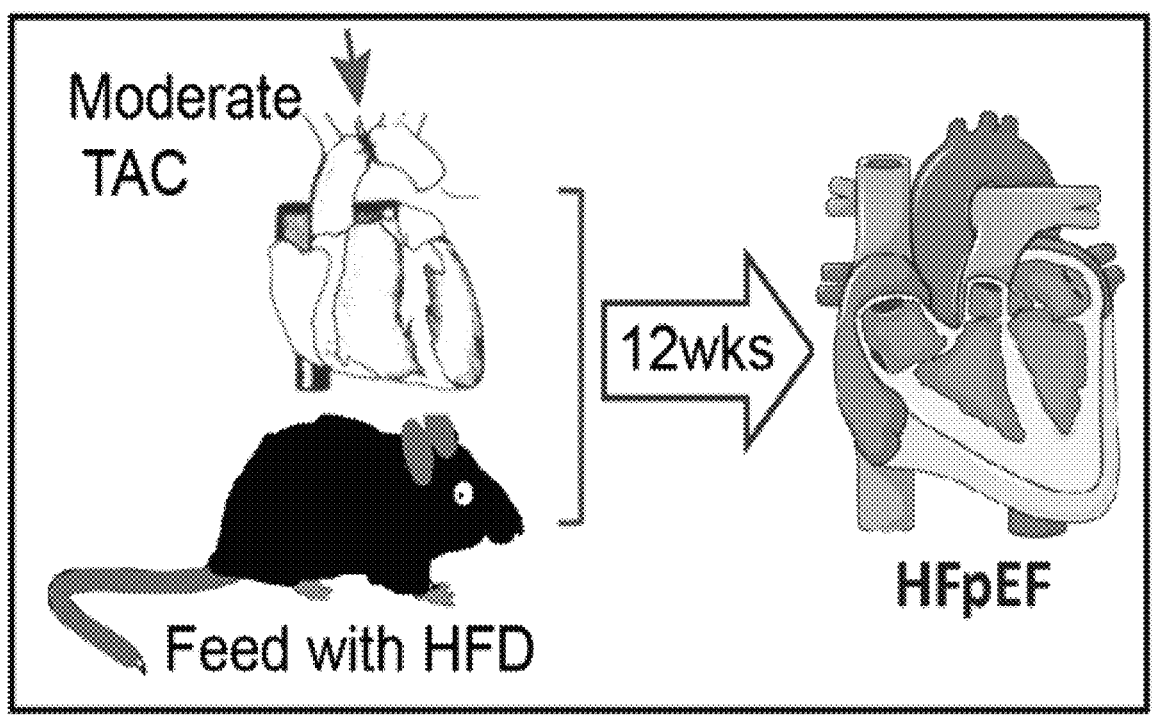
FIGS. 4A-4H show mice fed on HFD in combination with moderate TAC develop a cardio-metabolic heart failure phenotype that recapitulates systemic and cardiovascular features of HFpEF in human.
Figure 4B:
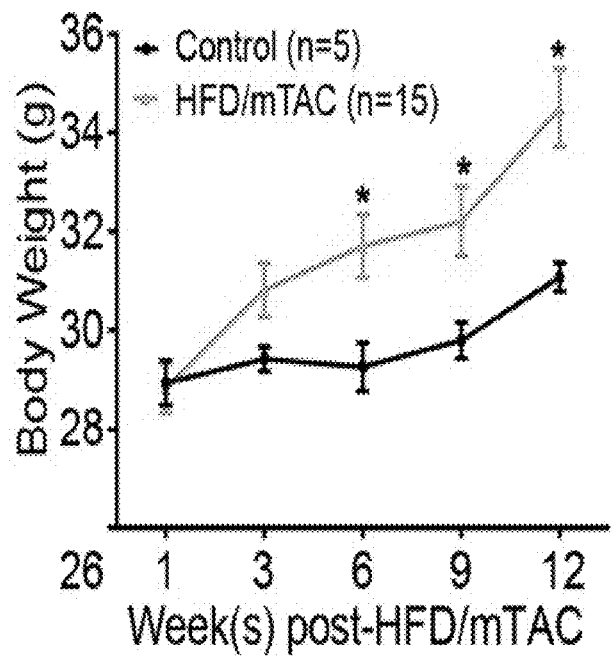
Figure 4C:
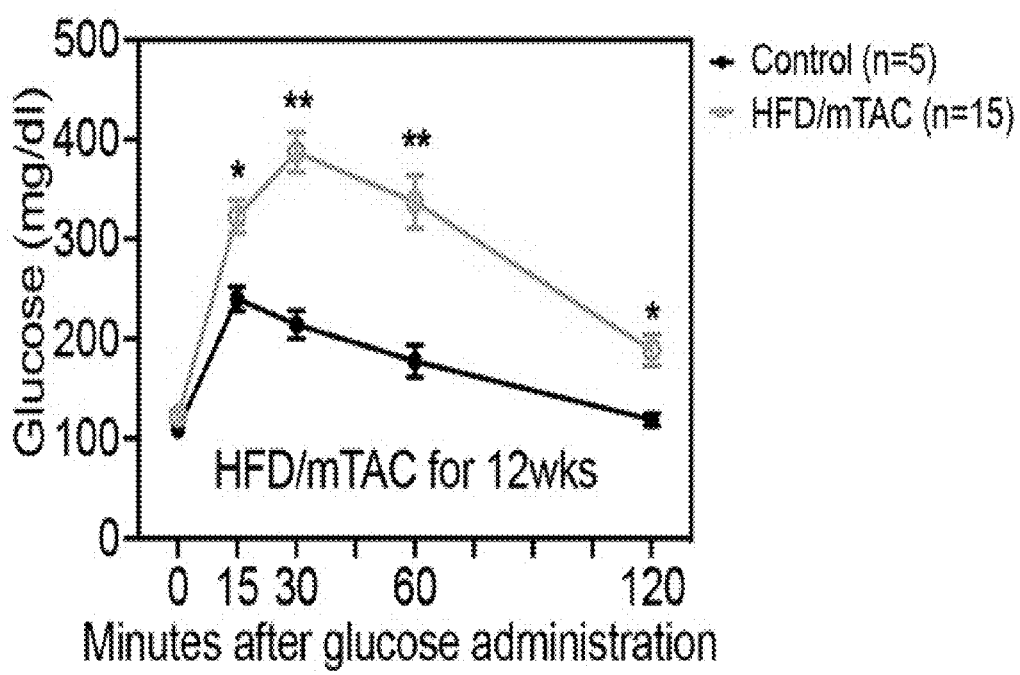
Figure 4D:
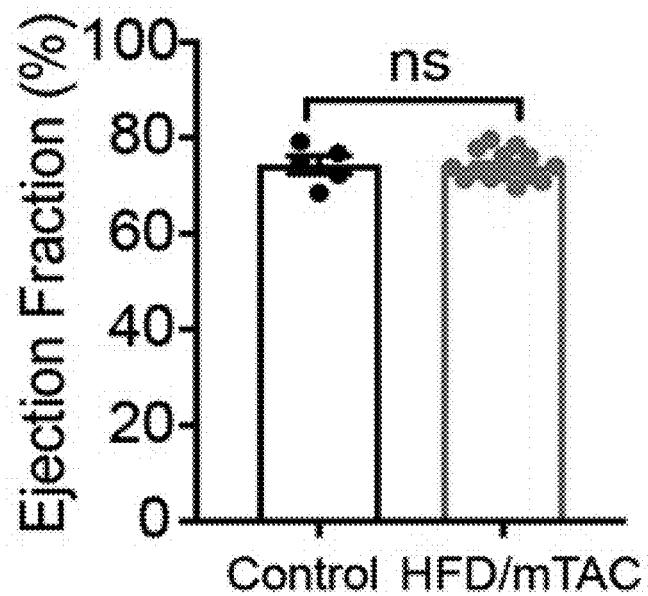
Figure 4E:
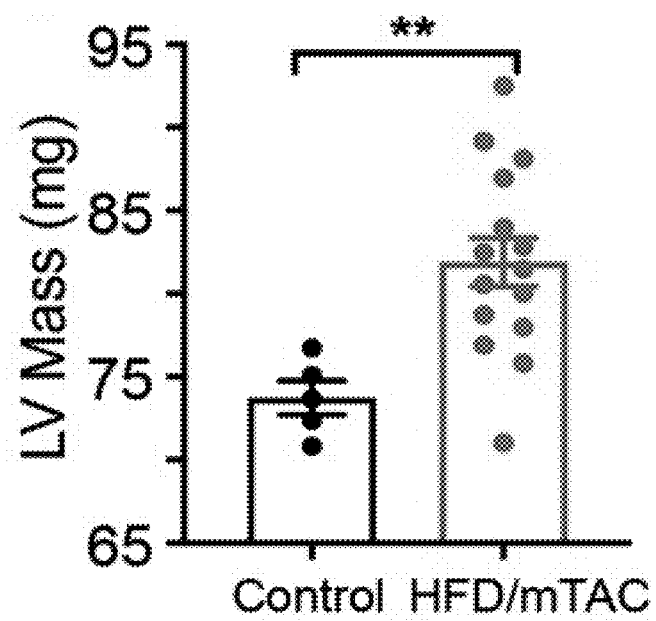
Figure 4F:
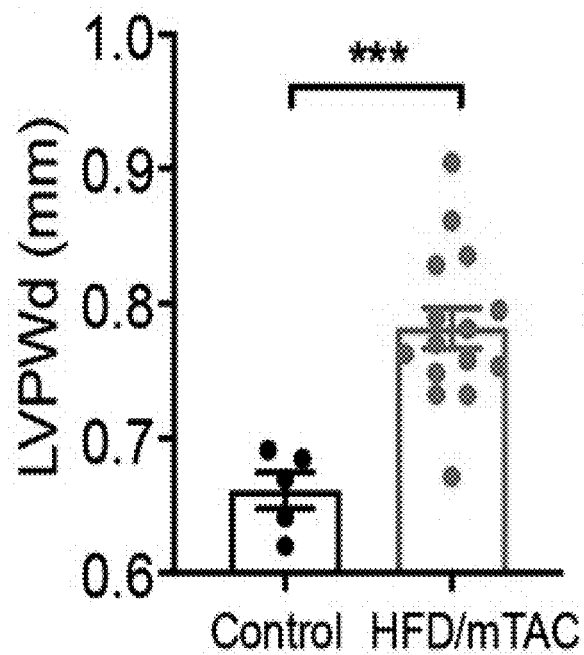

Significant concentric left ventricular (LV) hypertrophy was present in HFD/mTAC animals, as indicated by increases in LV mass (FIG. 4E) and LV diastolic wall thickness (FIG. 4F).

Figure 4G:
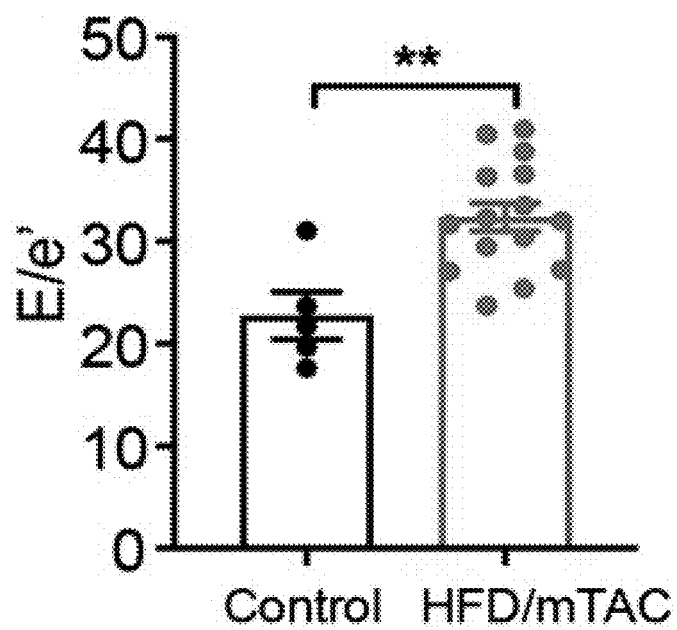
Figure 4H:
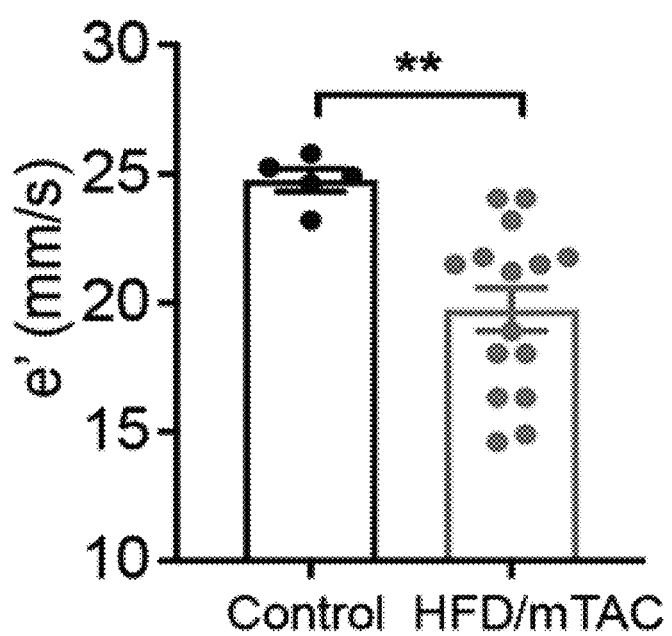

LV diastolic dysfunction with increased left ventricular filling pressure was developed in HFD/mTAC mice as evidenced by decreased e' velocity (FIG. 4H) and increased ratio of E/e' (FIG. 4G), measured by noninvasive Doppler imaging. Bars and error bars show means and SEM. *P<0.05, P<0.01, *p<0.001 Vs. control group.

Figure 5A:
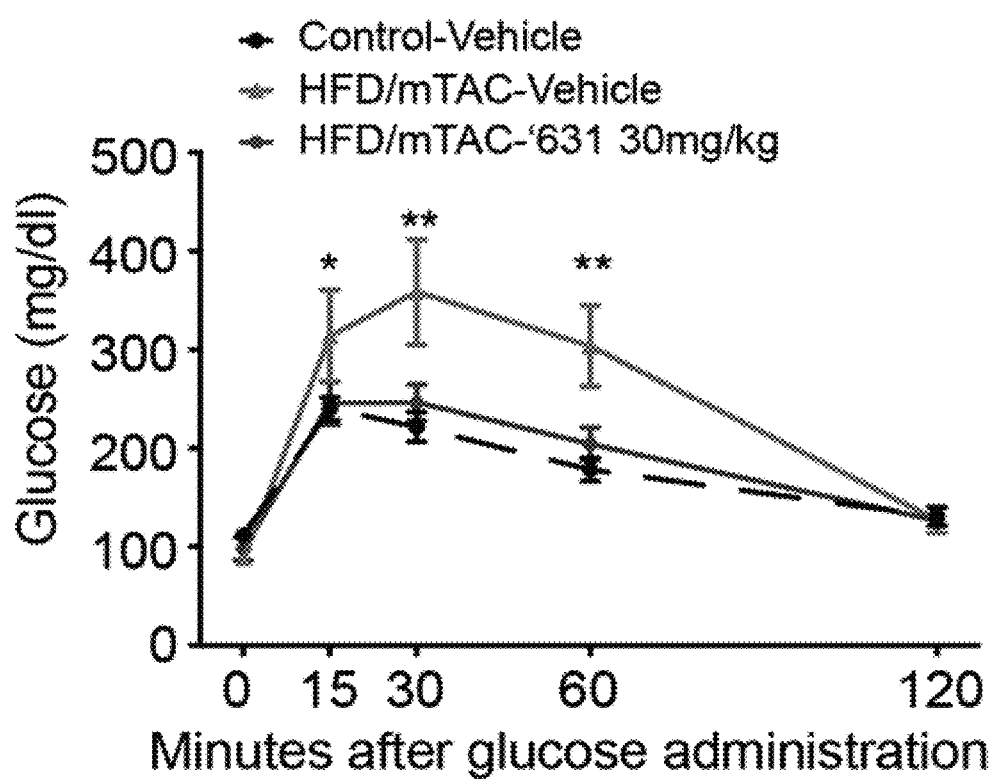
Figure 5B:
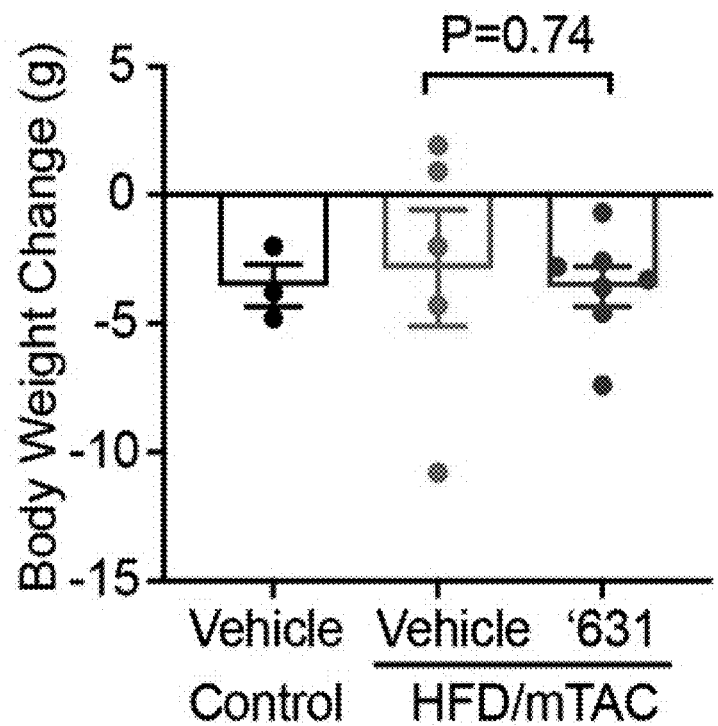
Figure 5C:
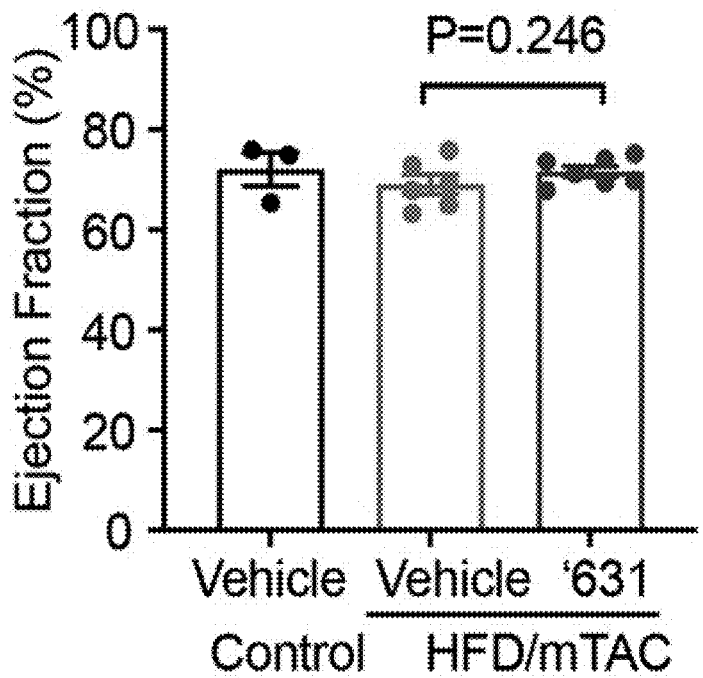
Figure 5D:
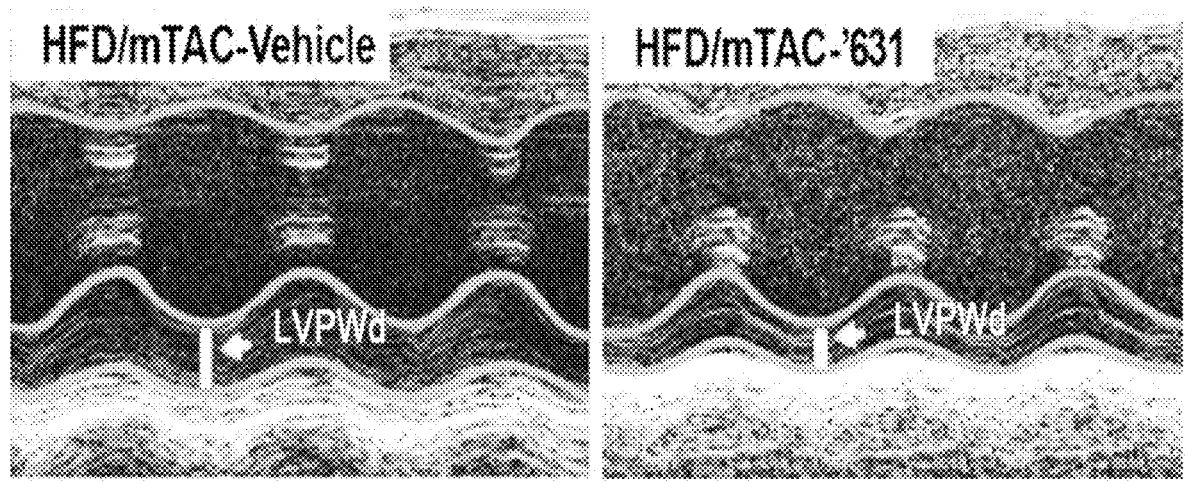
Figure 5E:
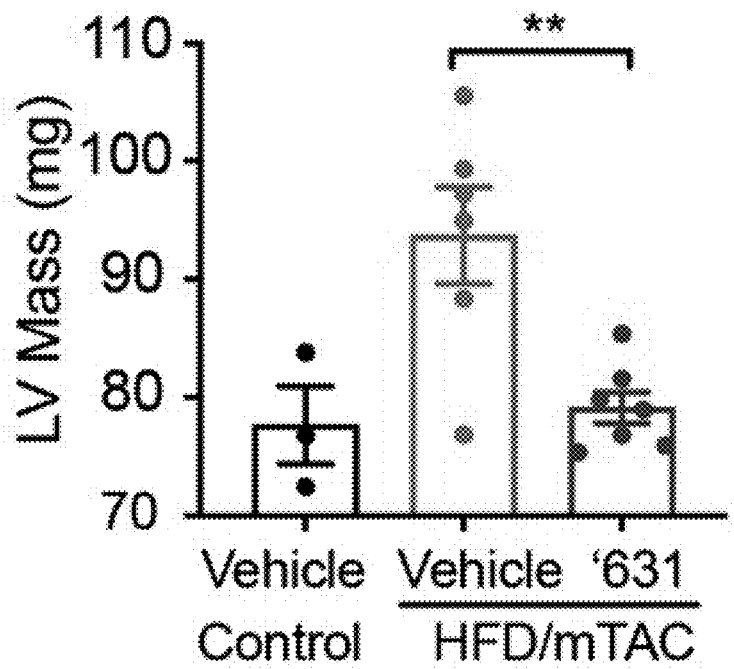
Figure 5F:
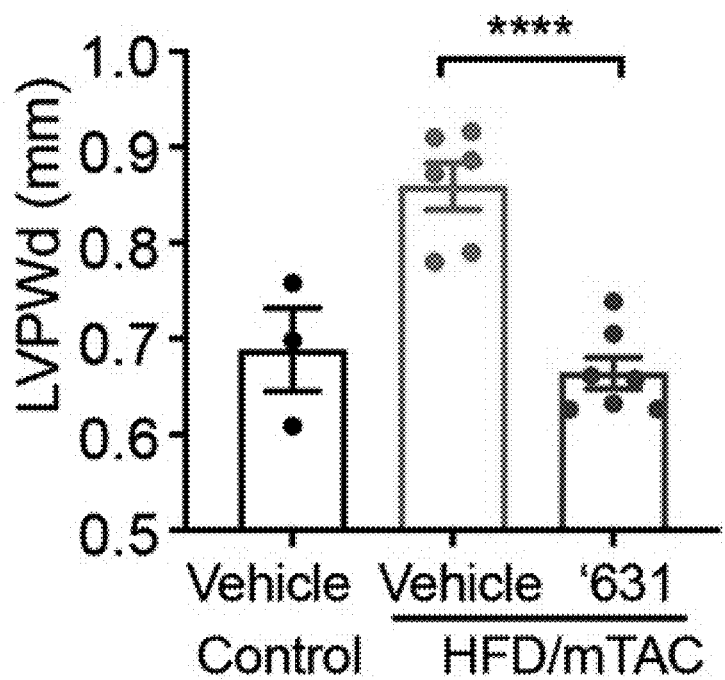
Figure 5G:
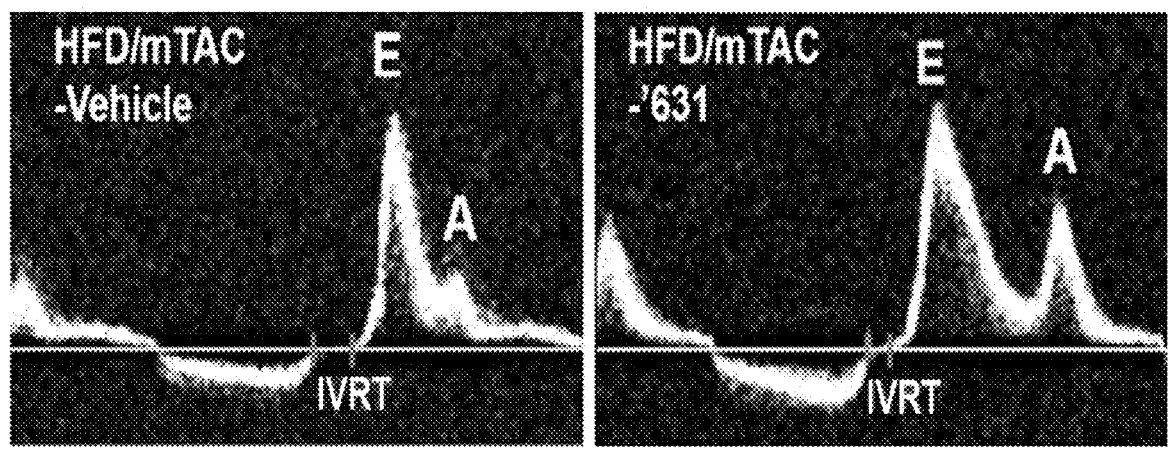
Figure 5H:
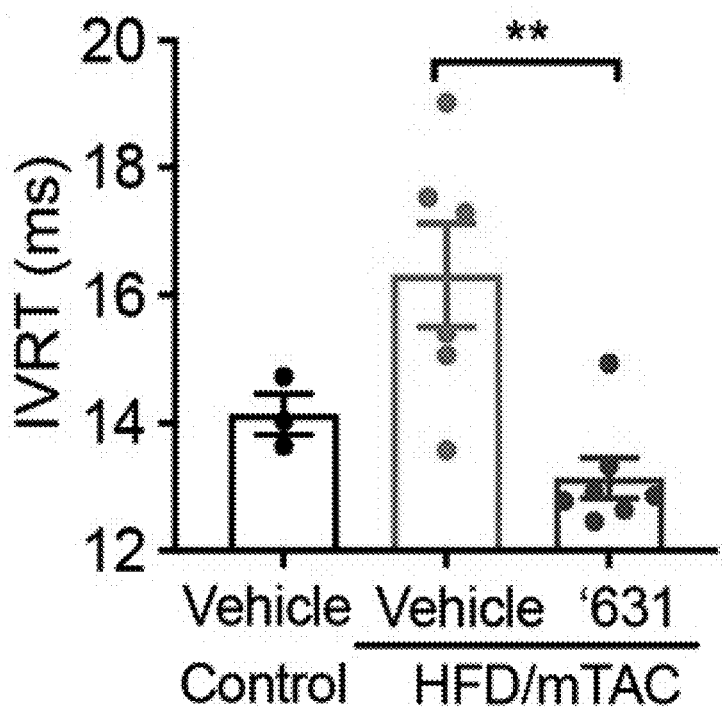
Figure 5I:
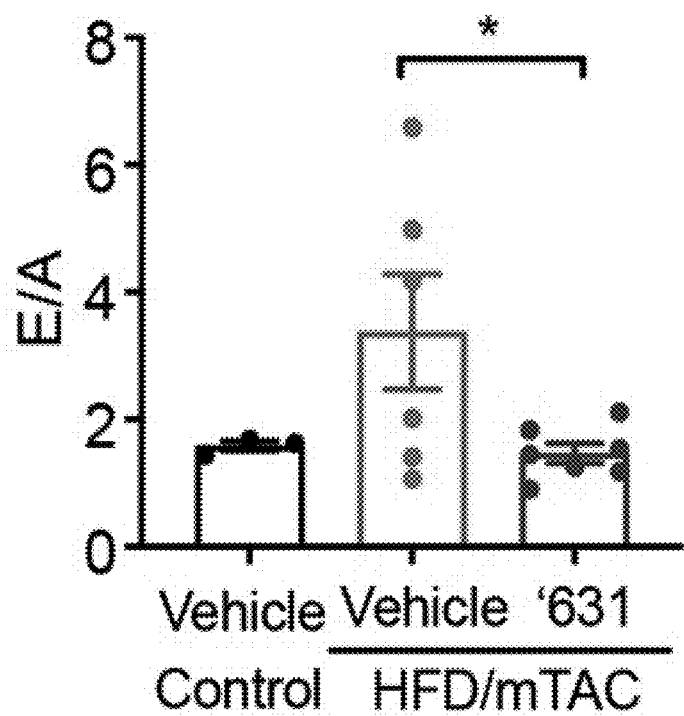
Figure 5J:
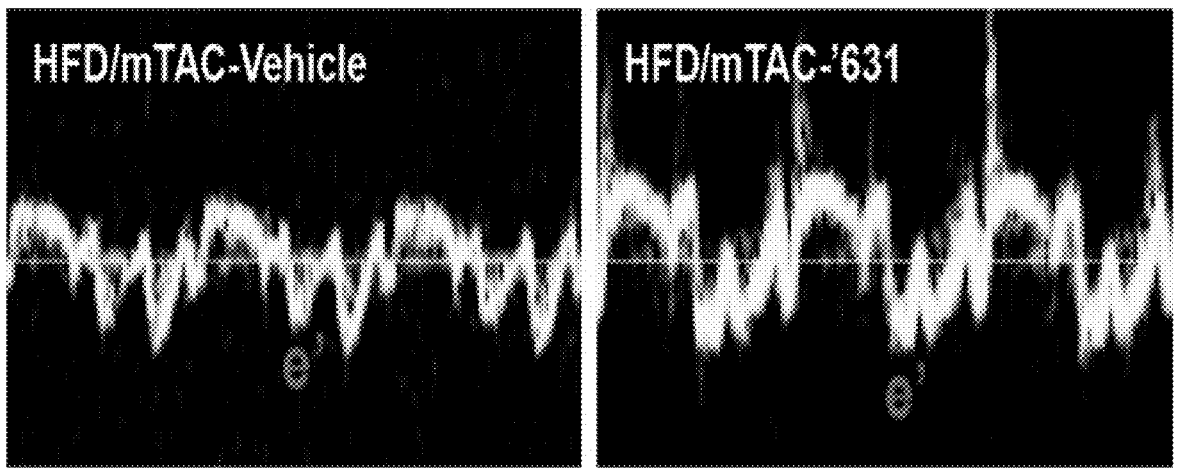
Figure 5K:
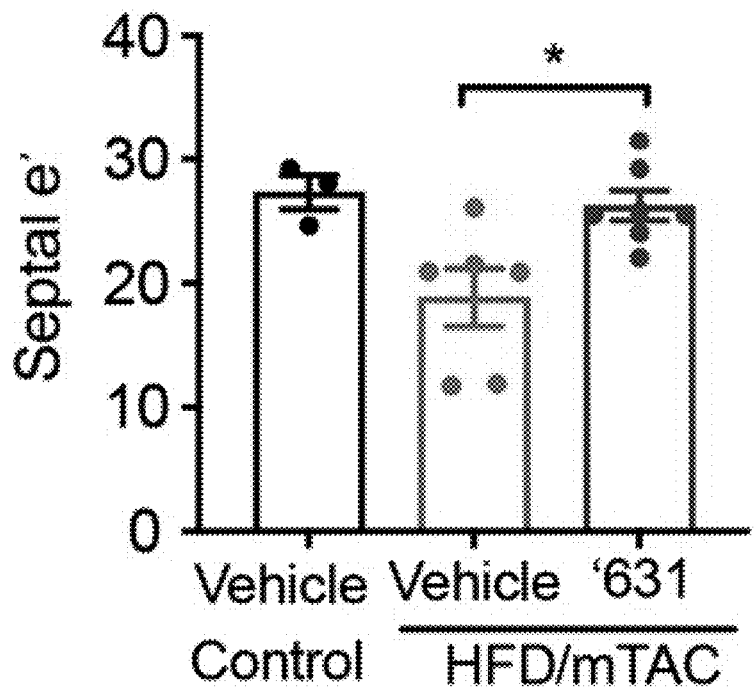
Figure 5L:
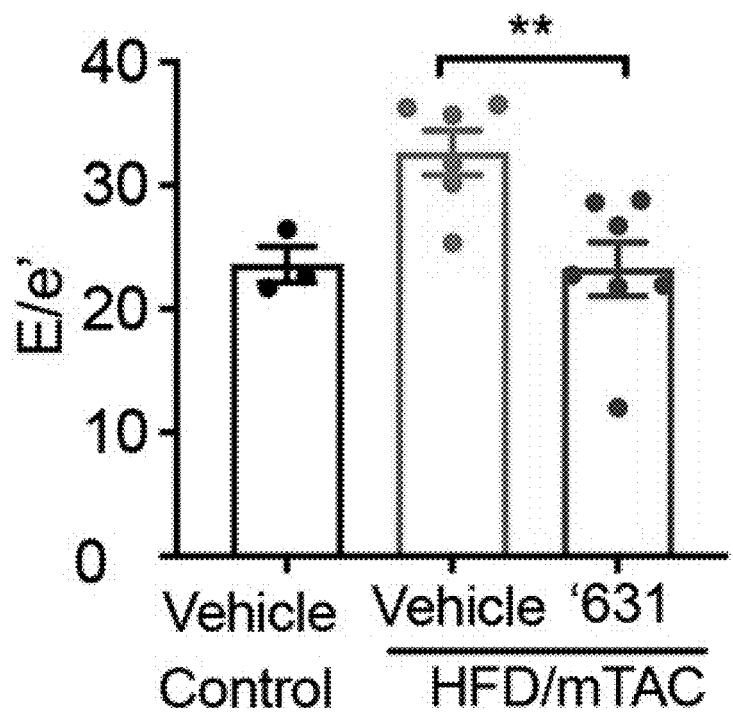
Figure 5M:
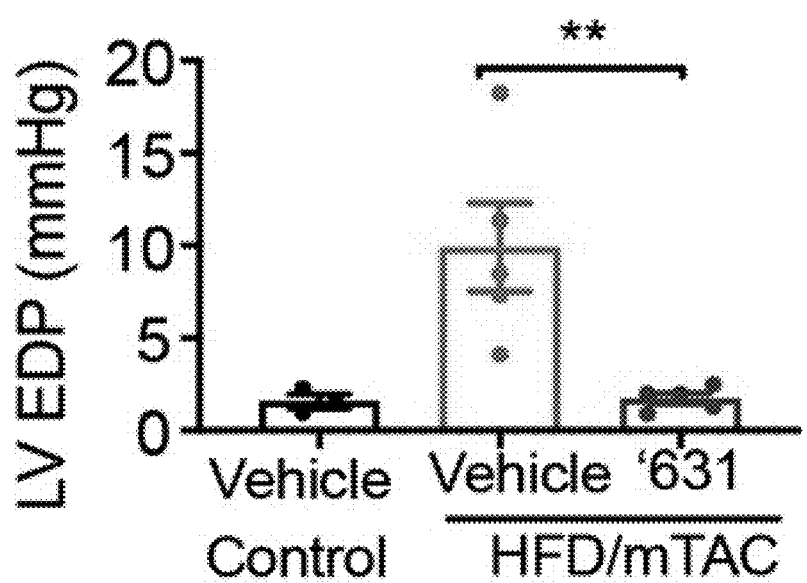
Figure 5N:
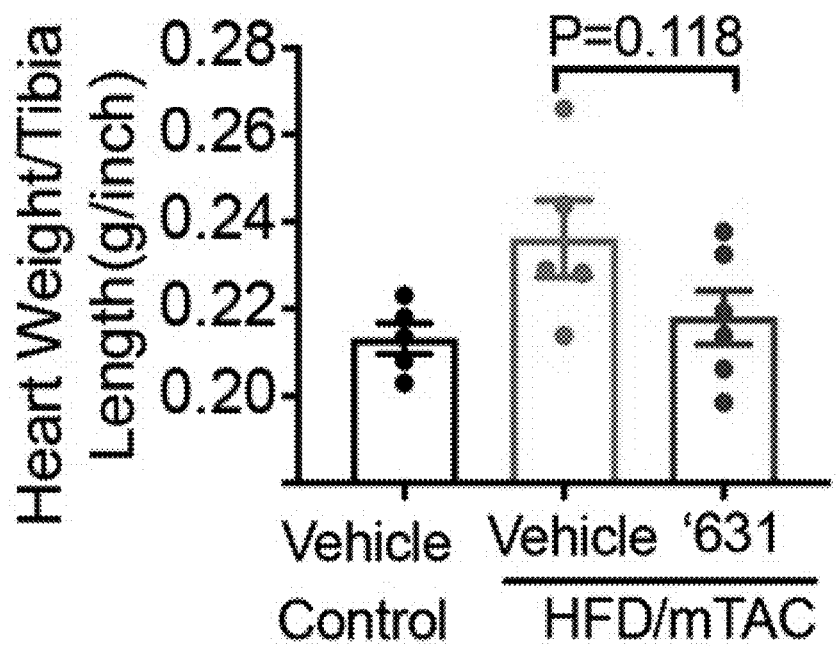
Figure 5O:
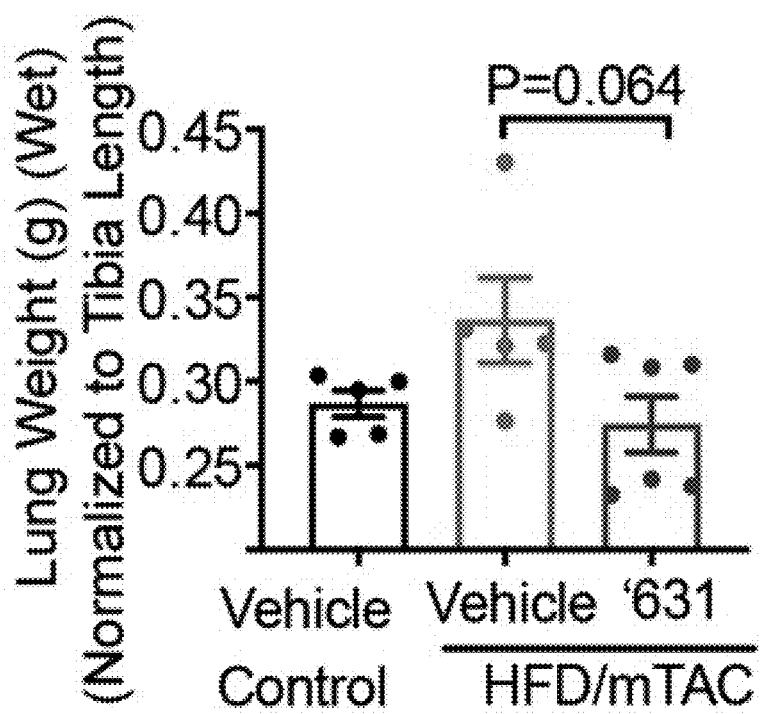
Figure 6A:
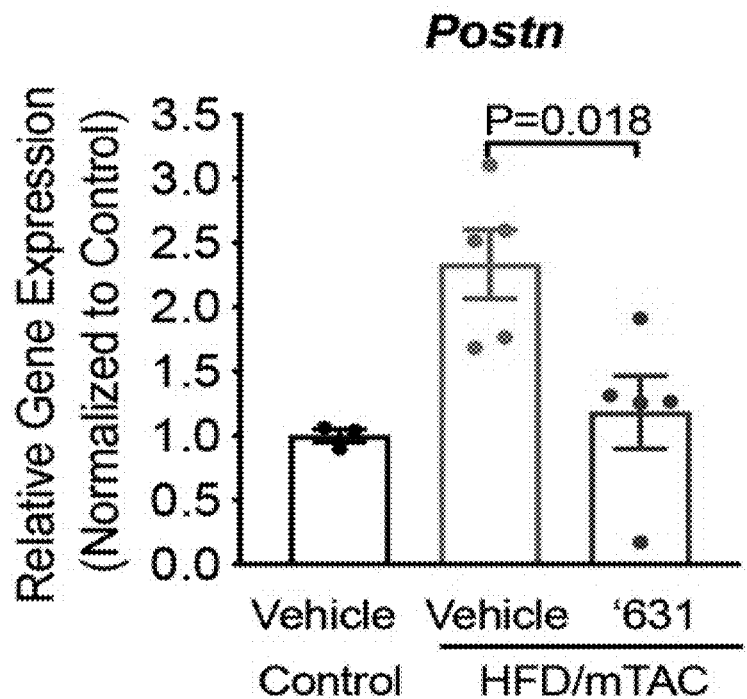
Figure 6B:
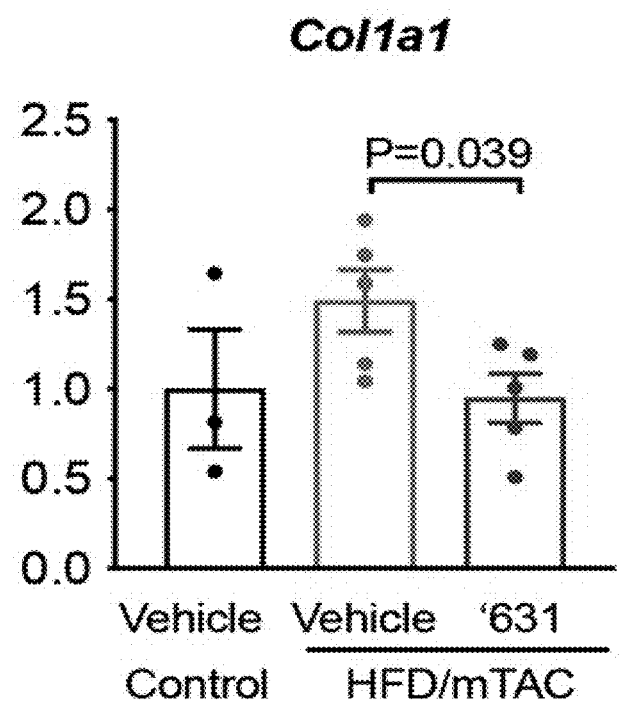
Figure 6C:
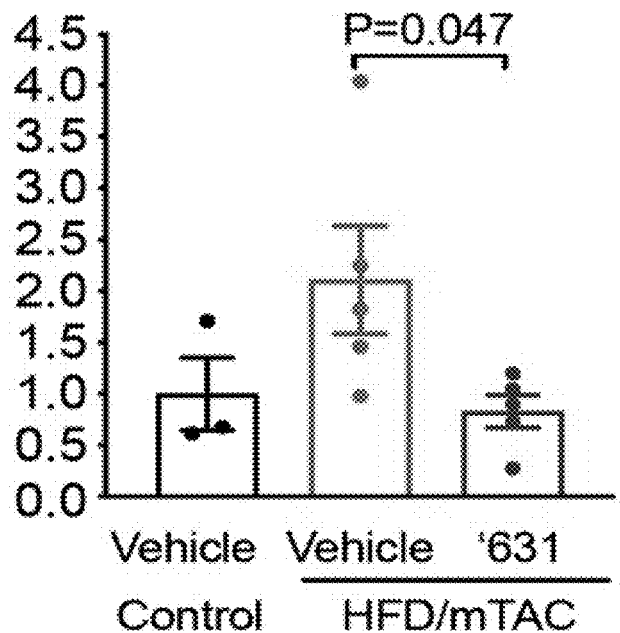
Figure 6D:
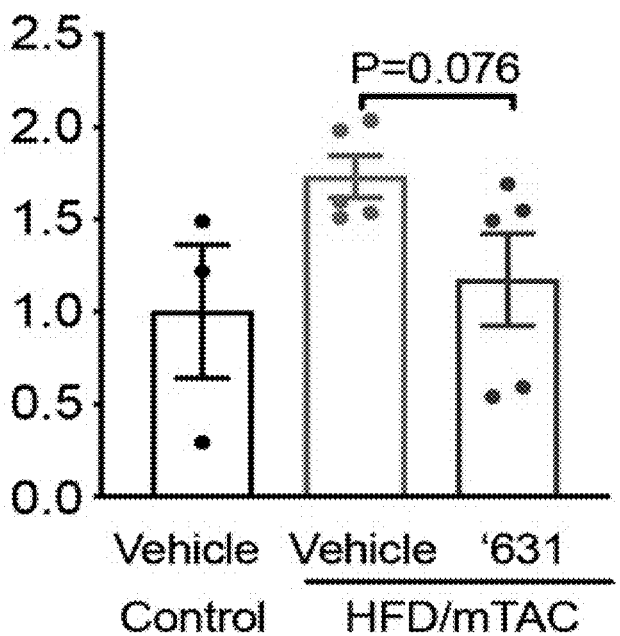
Figure 6E:
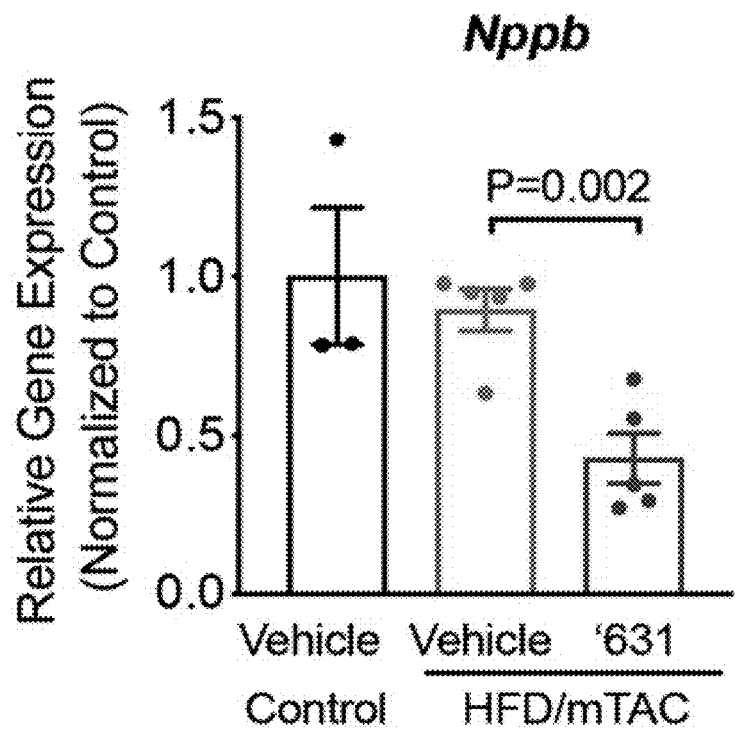
Figure 6F:
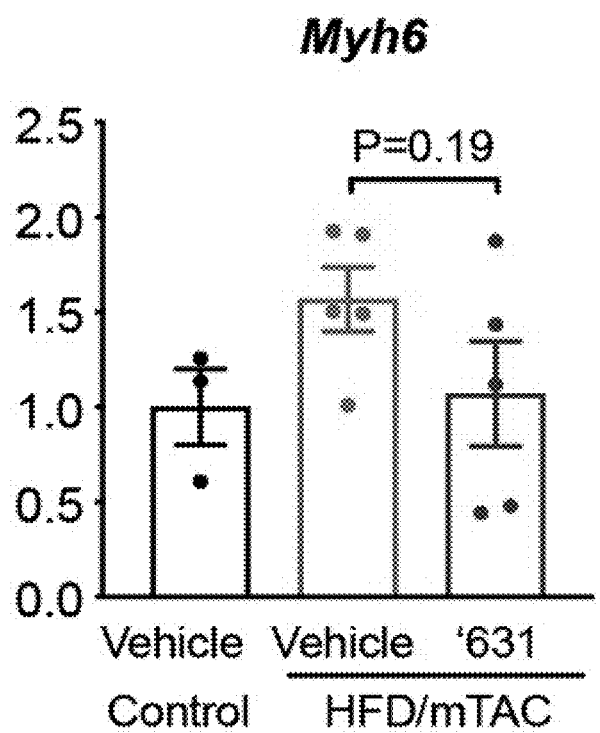
Figure 6G:
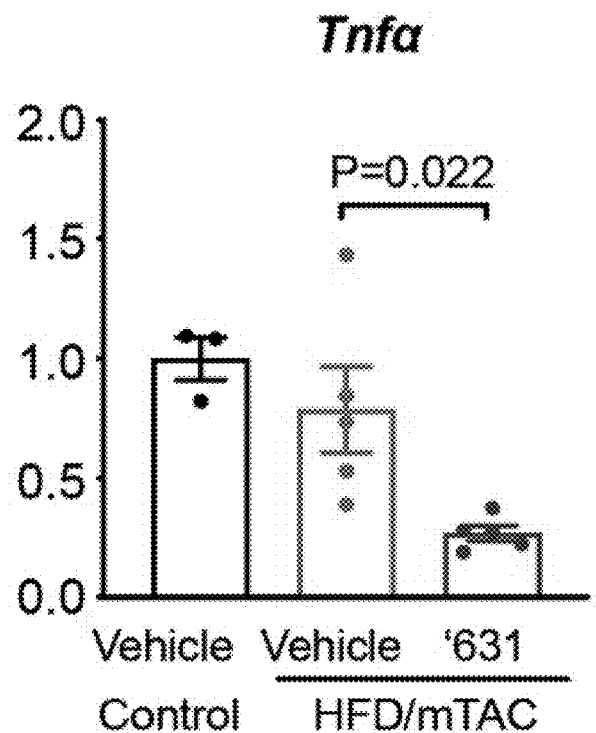
Figure 6H:
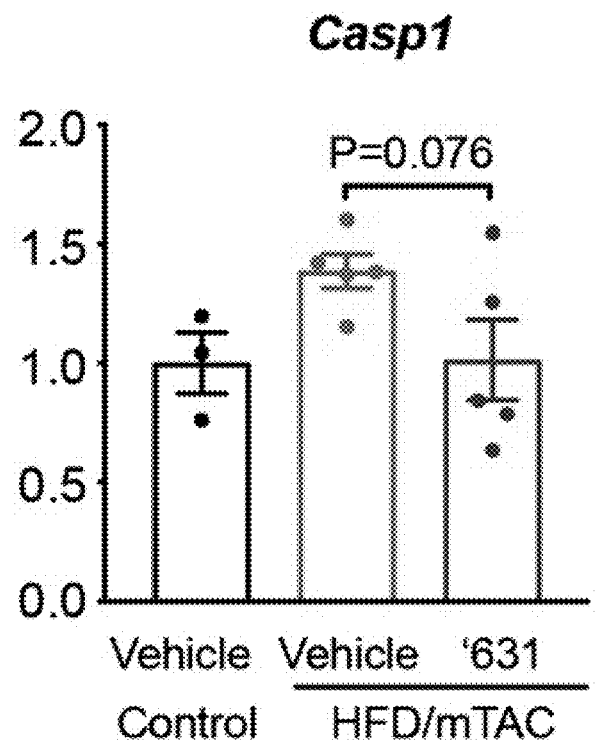

FIGS. 5A-5O show oral dosing of TYA-11631 improved glucose tolerance and diastolic dysfunction in HFD/mTAC mice. After the HFpEF phenotypes were established, animals were randomized to dose orally with 30 mg/kg TYA-11631 (n=8) or vehicle (n=7) once per day for six weeks, respectively. n=3 mice in control group dosed with vehicle. Treatment with TYA-11631 led to markedly improved glucose tolerance (FIG. 5A), with no difference of body weight change (FIG. 5B) compared to vehicle dosed animals. Echocardiographic evaluation (representative echocardiography-derived M-mode tracings, see FIG. 5D) revealed that TYA-11631 treatment unaltered ejection fraction (FIG. 5C), however significantly reduced left ventricular mass (FIG. 5E) and LV wall thickness (FIG. 5F).

In addition, noninvasive Doppler imaging (representative pulsed-wave Doppler (FIG. and tissue Doppler (FIG. 5J) tracings) and invasive catheterization analysis showed that TYA-11631 treatment sustained improved LV relaxation and LV filling pressures as shown by decreased prolongation of isovolumetric relaxation time (FIG. 5H), lower E/A (FIG. 5I) and E/e' ratios (FIG. 5K), improved e' velocity (FIG. 5L), and reduced end diastolic pressure (FIG. 5M). Each of these efficacy parameters were normalized to control levels.

HFD/mTAC mice treated with TYA-11631 showed a trending decrease in heart weight (FIG. 5N) and lung weight (FIG. 5O), indicating improved LV hypertrophy and pulmonary congestion respectively, consistent with reduced filling pressure. Bars and error bars show means and SEM. *P<0.05, P<0.01, **p<0.0001.

TYA-11631 inhibits upregulation genes commonly associated with HFpEF disease as shown in FIGS. 6A-6H. Realtime q-PCR data showed that TYA-11631 significantly inhibited upregulation of genes associated with fibrosis Postn (FIG. 6A), Col1a1 (FIG. 6B), Col3a1 (FIG. 6C) and Col5a2 (FIG. 6D); cardiac stress, Nppb (FIG. 6E) and Myh6 (FIG. 6F); and inflammation Tnfα (FIG. 6G) and Casp1 (FIG. 6H) in heart tissue of HFD/mTAC mice, consistent with the improvements of LV structure and heart function. Bars and error bars show means and SEM.

FIGS. 7A-7L show that wild-type (WT) mice on high-fat diet coupled with inhibition of constitutive nitric oxide synthases with N[w]-nitro-1-arginine methyl ester (HFD/L-NAME) for eight weeks develop obesity, hypertension and diastolic dysfunction, recapitulating HFpEF phenotypes in humans.

Figure 7A:
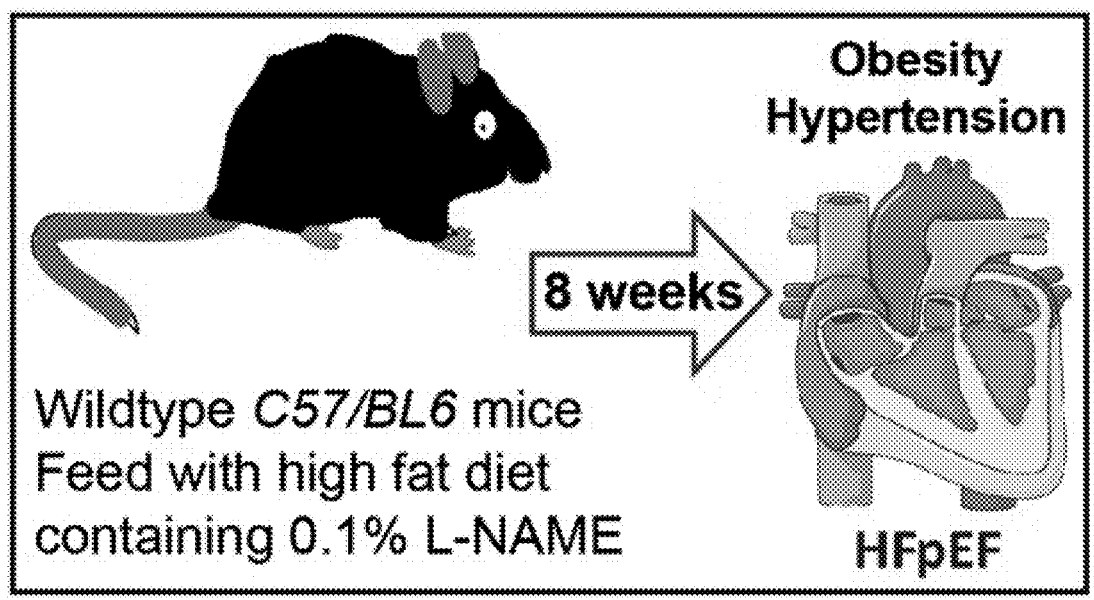
Figure 7B:
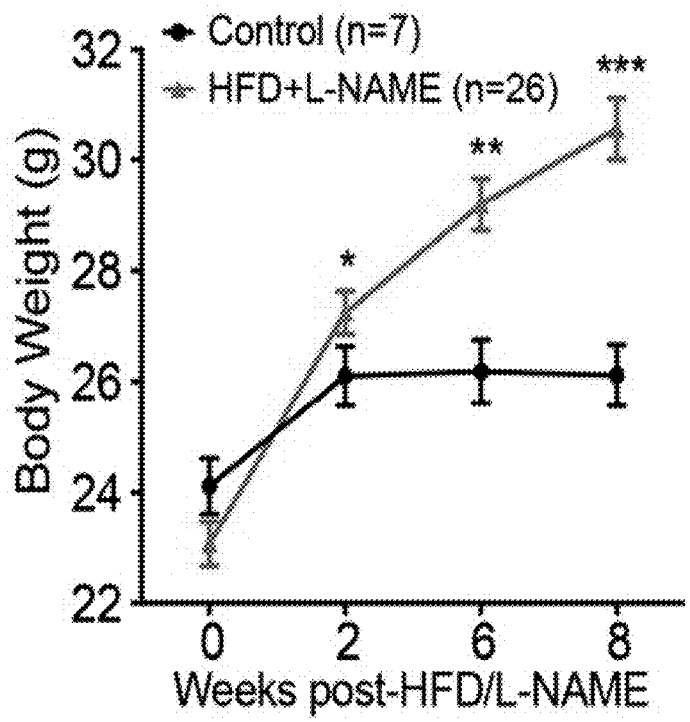
Figure 7C:
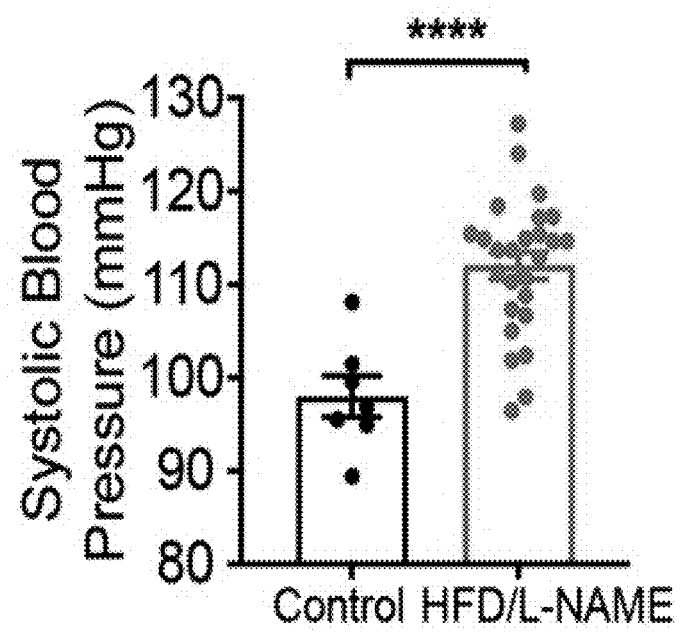
Figure 7D:
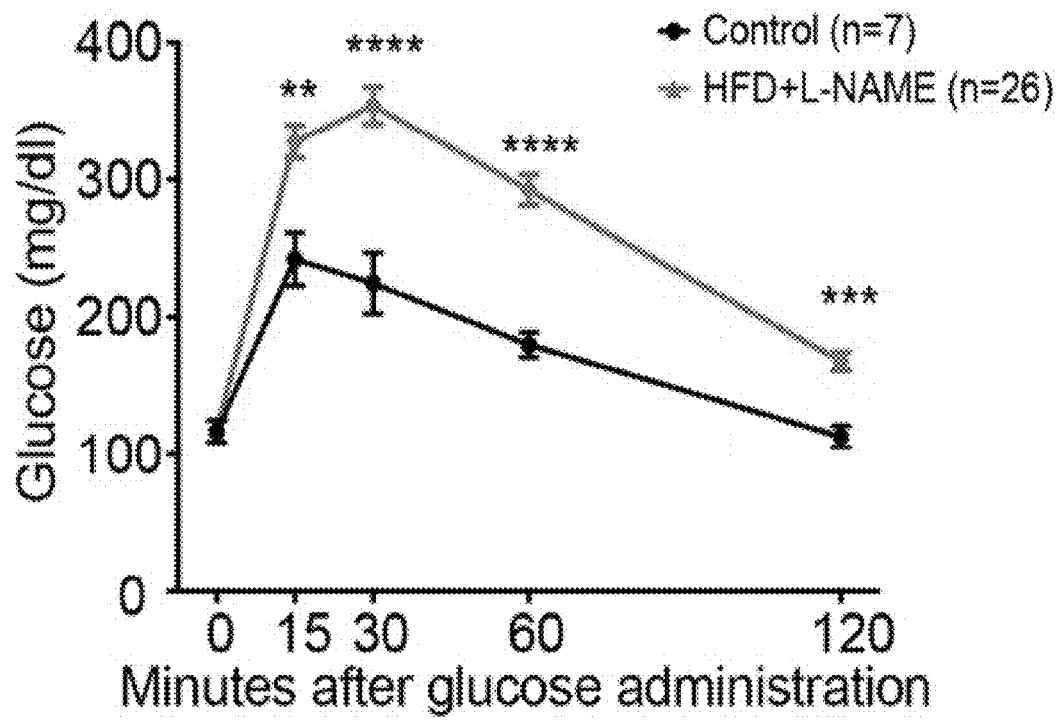

FIG. 7A shows a schematic overview of HFpEF model induction by concomitant metabolic and hypertensive stress in wildtype mice elicited by a combination of high fat diet and inhibition of constitutive nitric oxide synthase using $N^{\omega}$-nitrol-arginine methyl ester (L-NAME). n=7 mice in control group fed on regular diet, n=26 mice in HFpEF model development group induction with HFD/L-NAME.

Figure 7E:
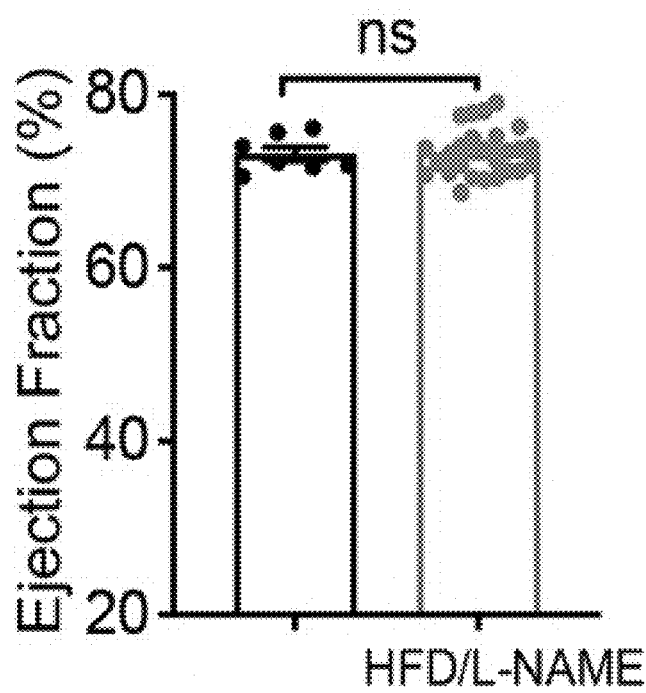
Figure 7F:
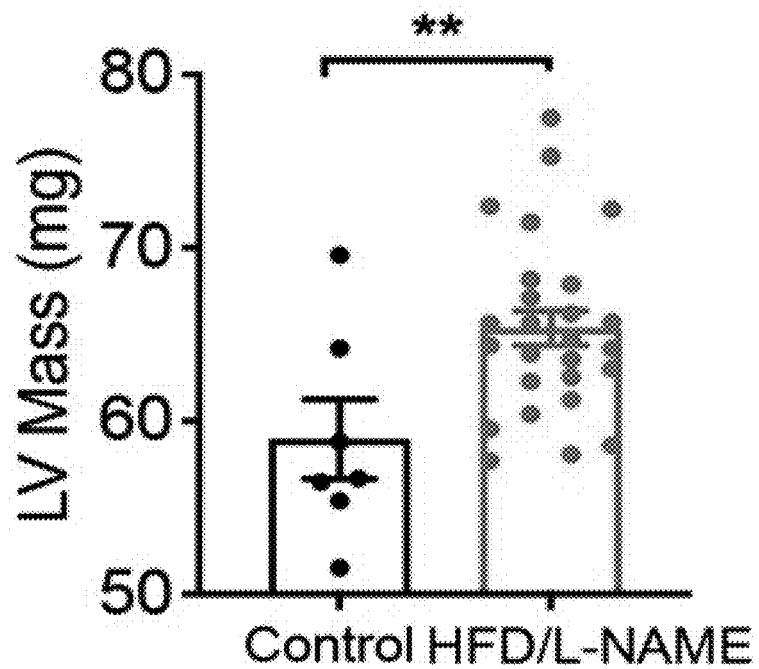
Figure 7G:
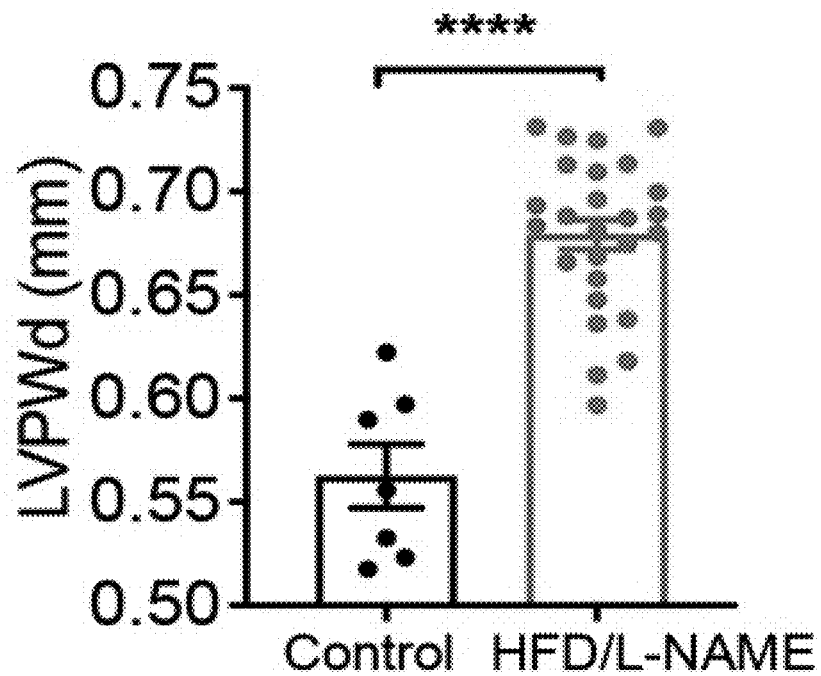
Figure 7H:
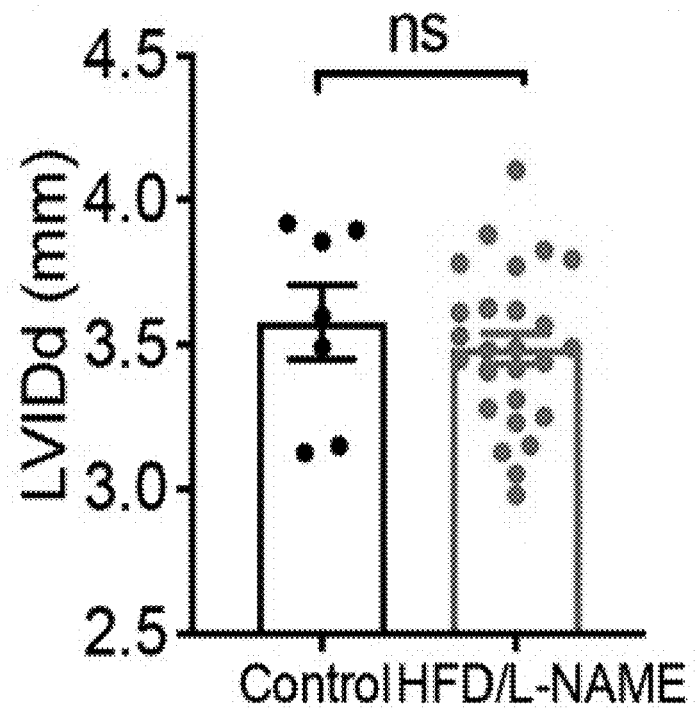
Figure 7I:
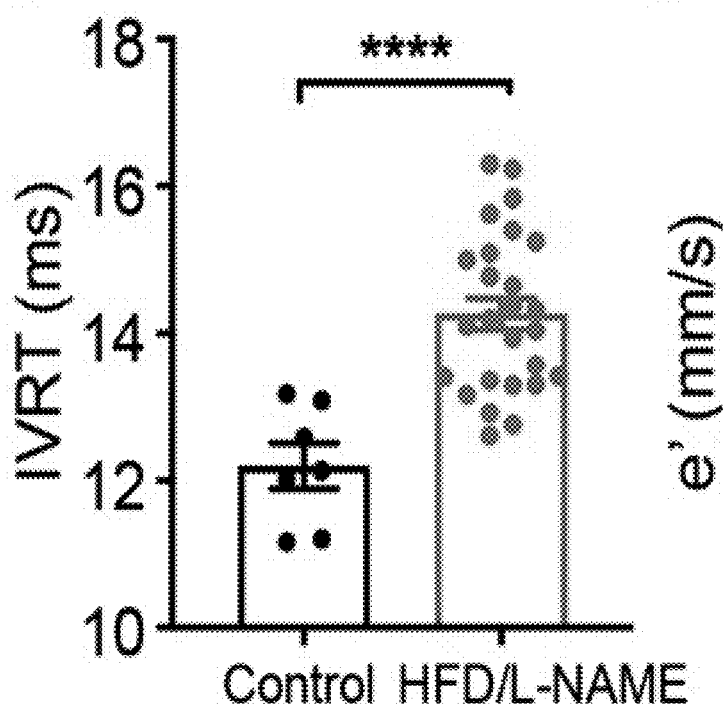
Figure 7J:
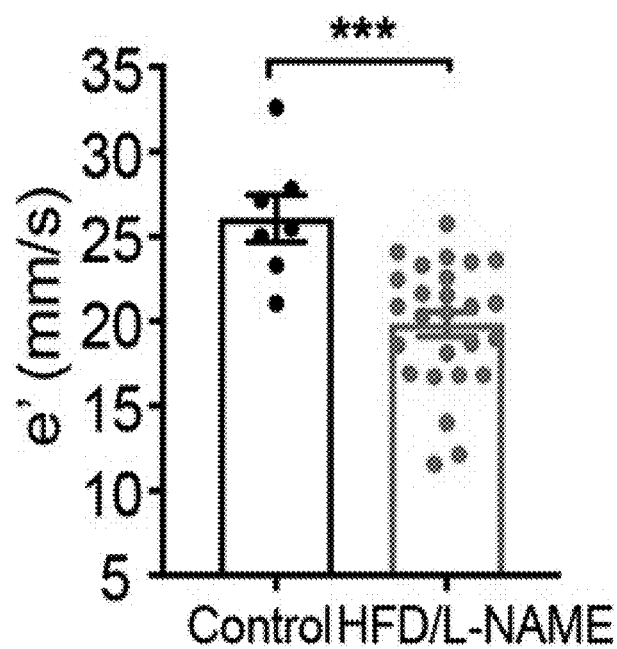
Figure 7K:
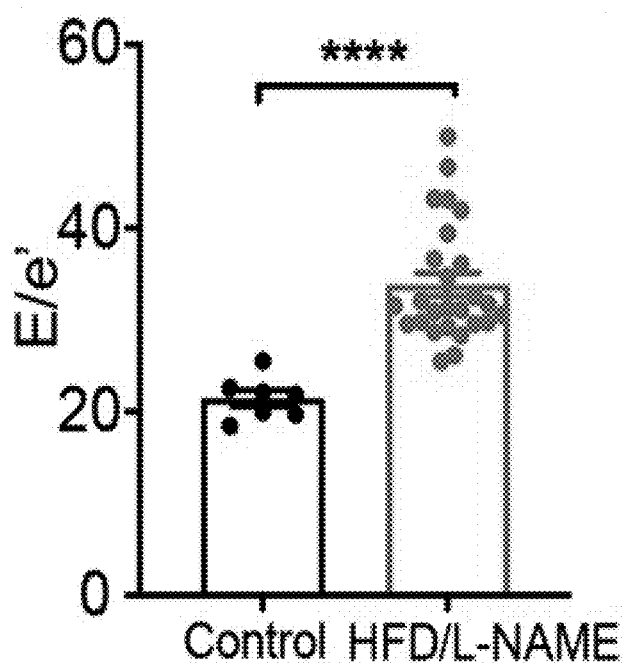
Figure 7L:
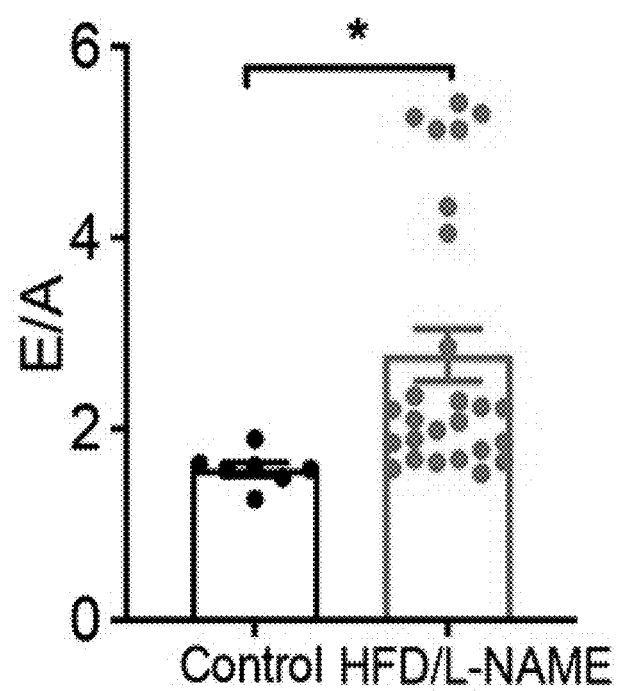

HFD/L-NAME treatment for 8 weeks significantly induced body weight increase (FIG. 7B), hypertension (FIG. 7C) and glucose intolerance (FIG. 7D) compared to the control mice. Echocardiographic evaluation revealed persistent preservation of the left ventricular ejection fraction (LVEF) (FIG. 7E). Significant concentric left ventricular (LV) hypertrophy was present in HFD/L-NAME mice, as indicated by increases in LV mass (FIG. 7F) and LV wall thickness at diastole (FIG. 7G), without LV chamber dilatation (FIG. 7H). In addition, mice concomitantly exposed to HFD/L-NAME exhibited signs of LV diastolic dysfunction with impaired relaxation and increased left ventricular filling pressure, as evidenced by prolonged IVRT (FIG. 7I), decreased e' velocity (FIG. 7J), and increased ratios of E/e' (FIG. 7K), E/A (FIG. 7L), measured by noninvasive Doppler imaging. Bars and error bars show means and SEM. *P<0.05, P<0.01, *P<0.001, ****P<0.0001 Vs. control group.

Figure 8A:
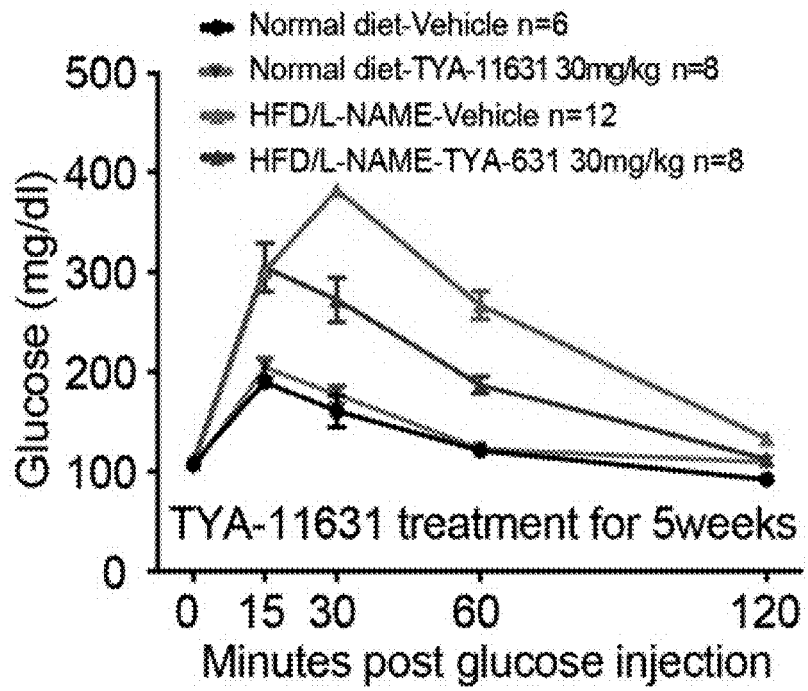
Figure 8B:
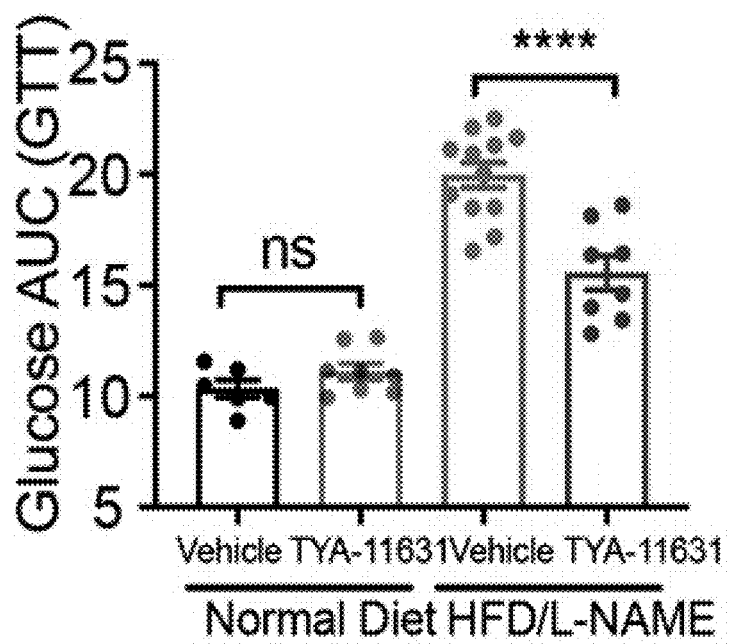
Figure 8C:
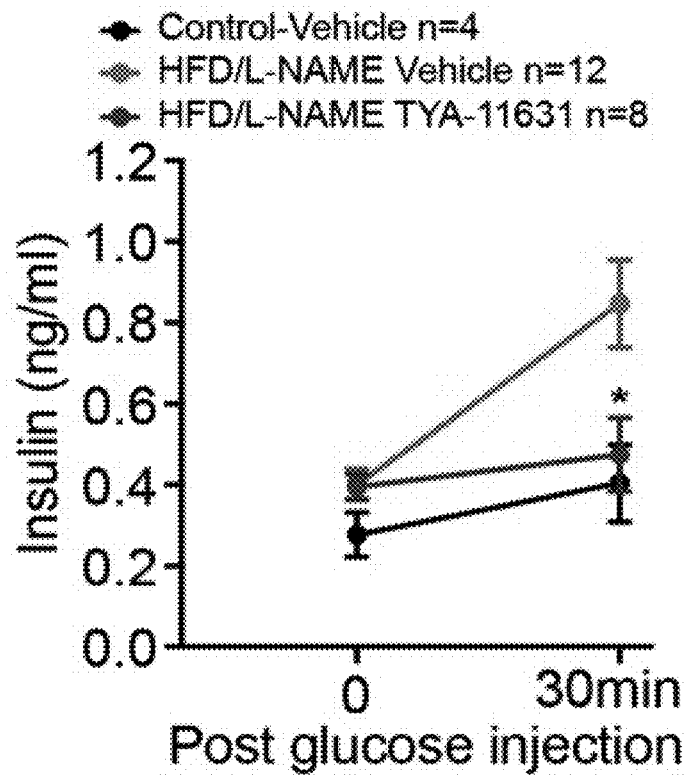
Figure 8D:
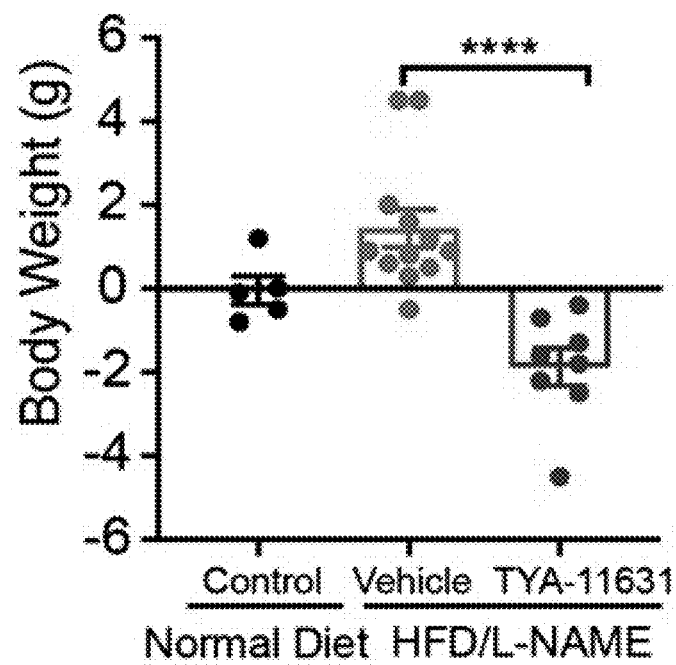
Figure 8E:
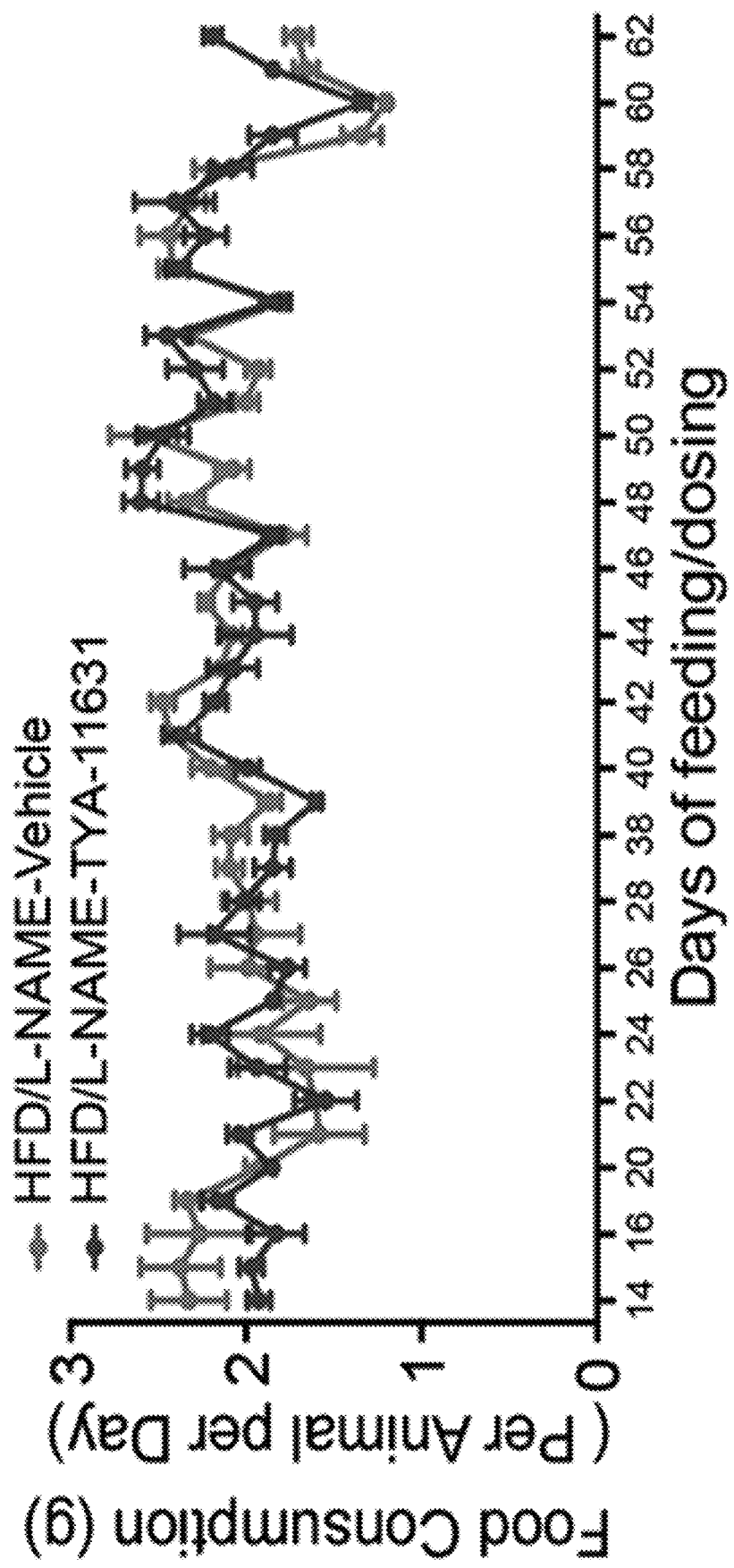
Figure 8F:
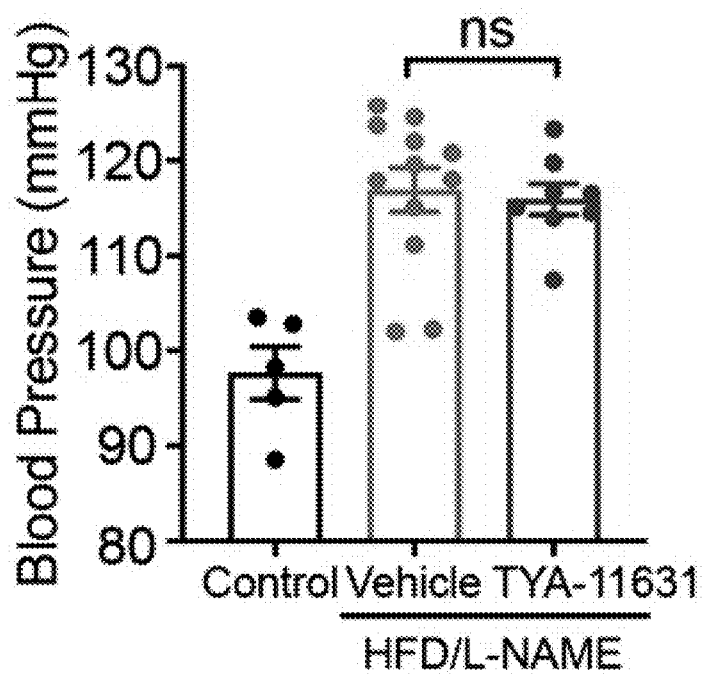
Figure 8G:
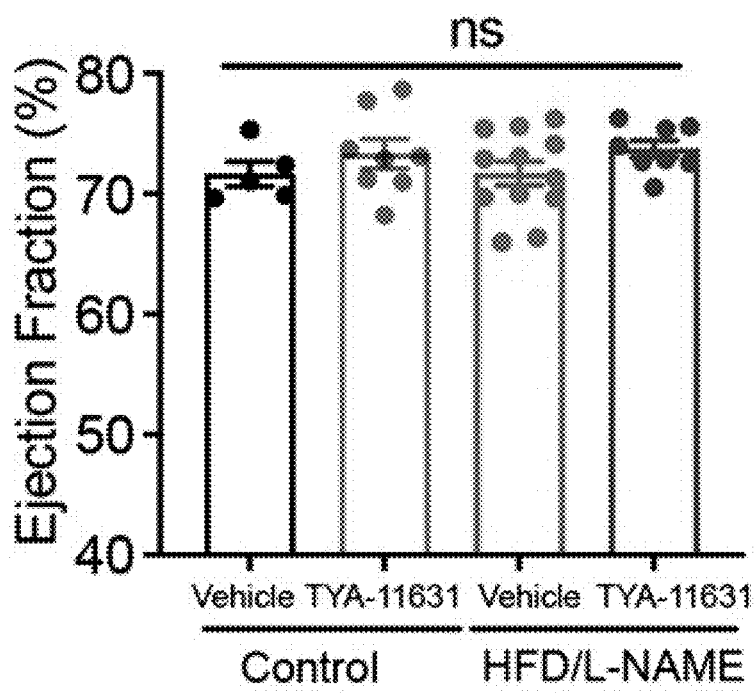
Figure 8H:
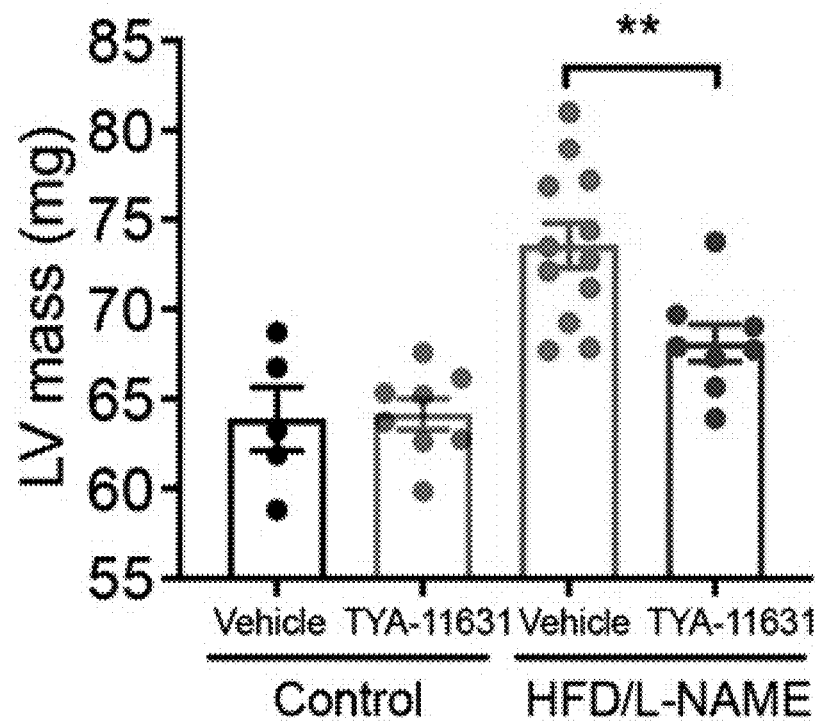
Figure 8I:
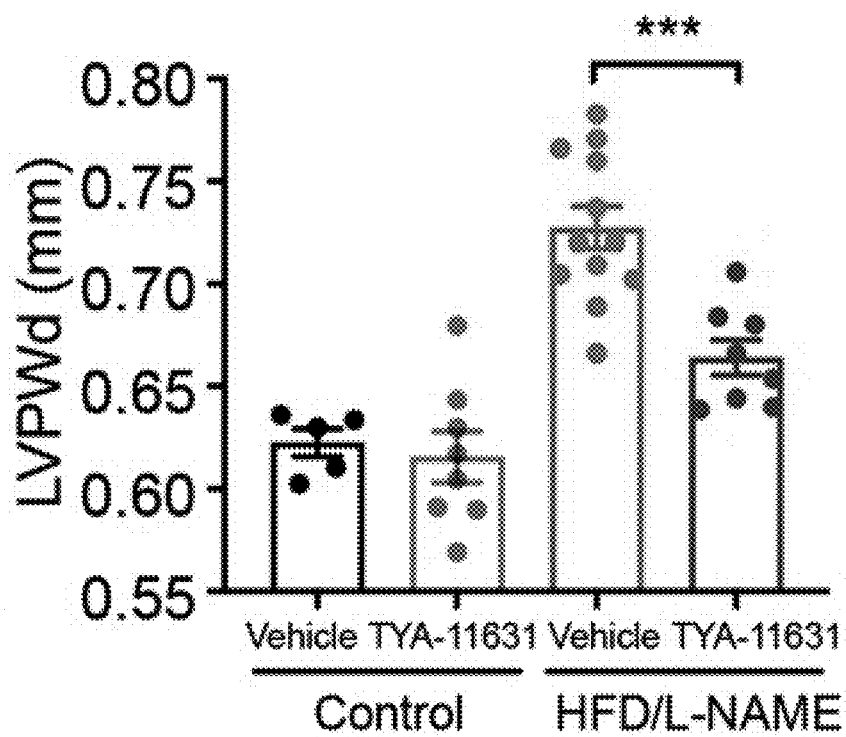
Figure 8J:
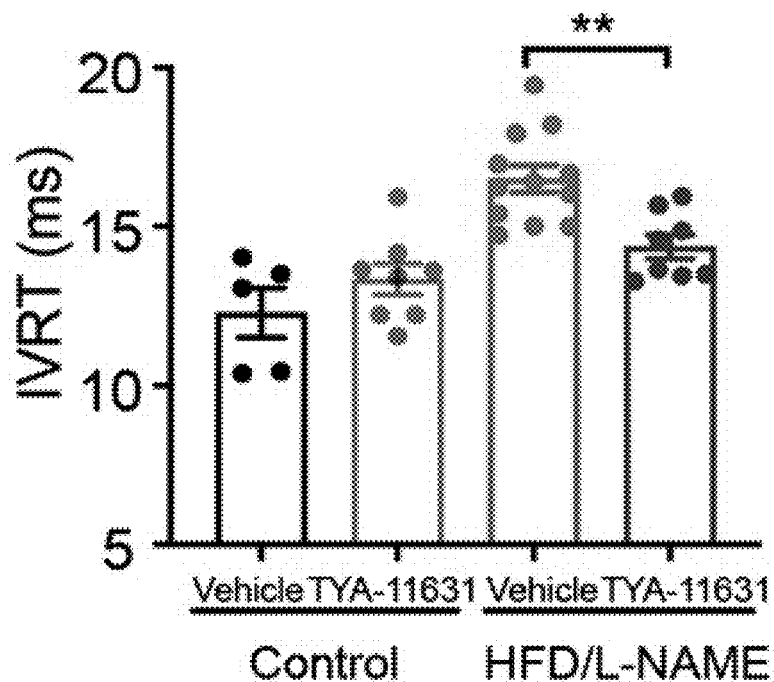
Figure 8K:
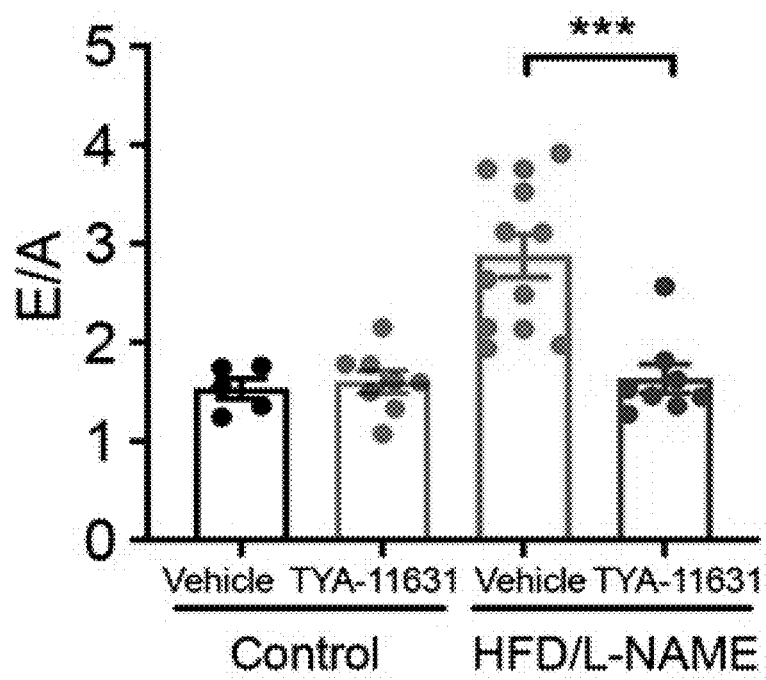
Figure 8L:
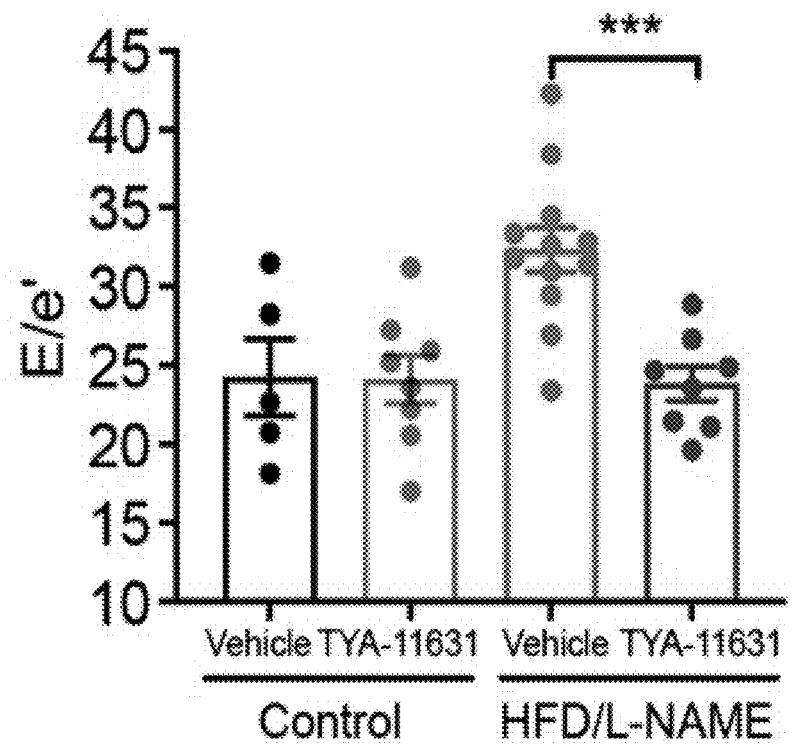
Figure 8M:
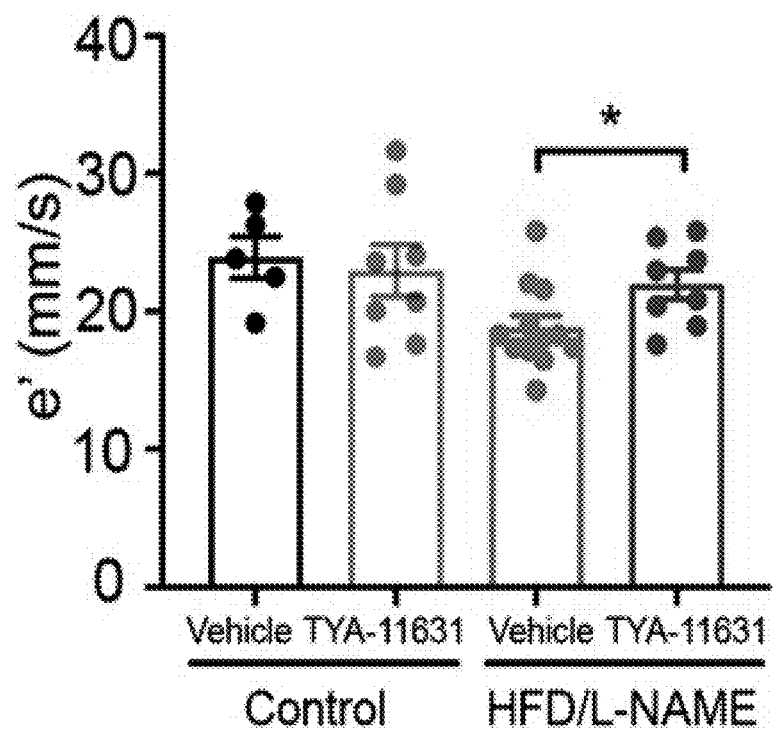
Figure 8N:
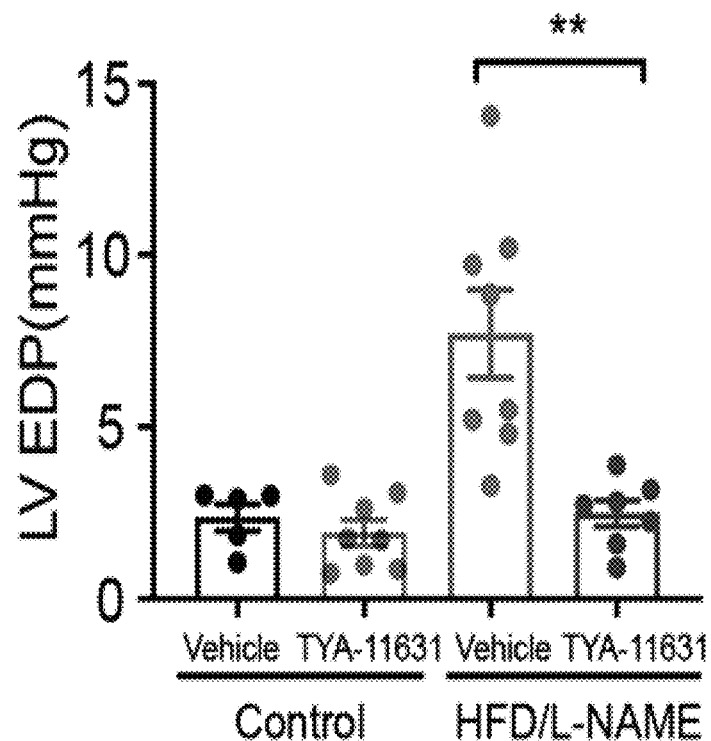
Figure 8O:
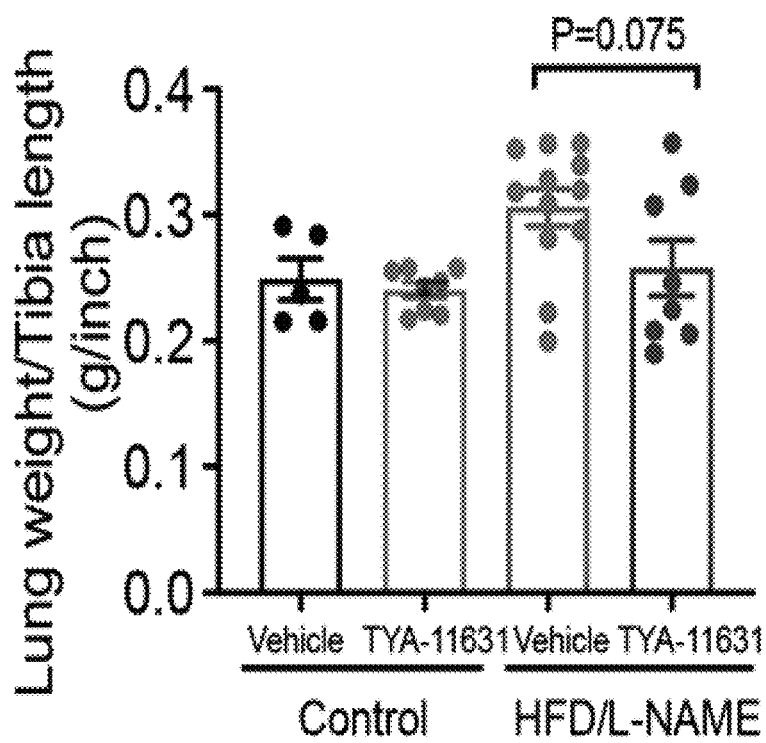
Figure 8P:
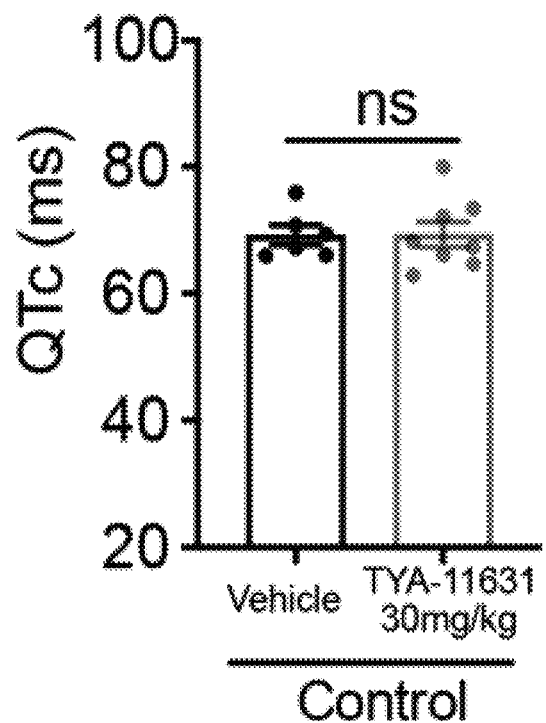
Figure 8Q:
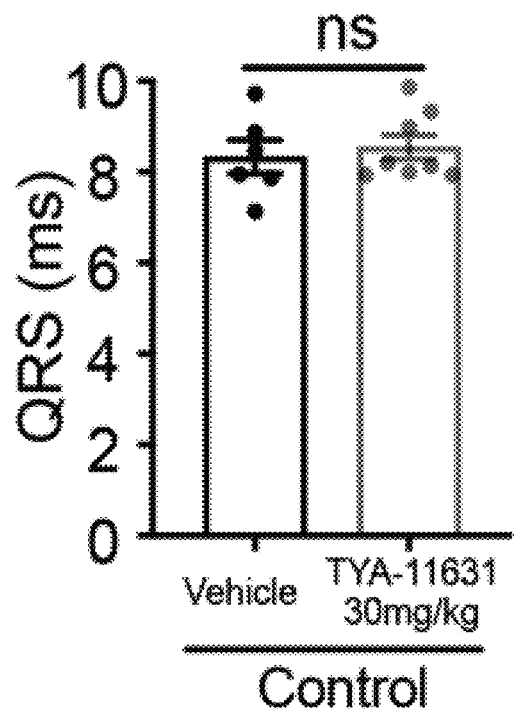
Figure 8R:
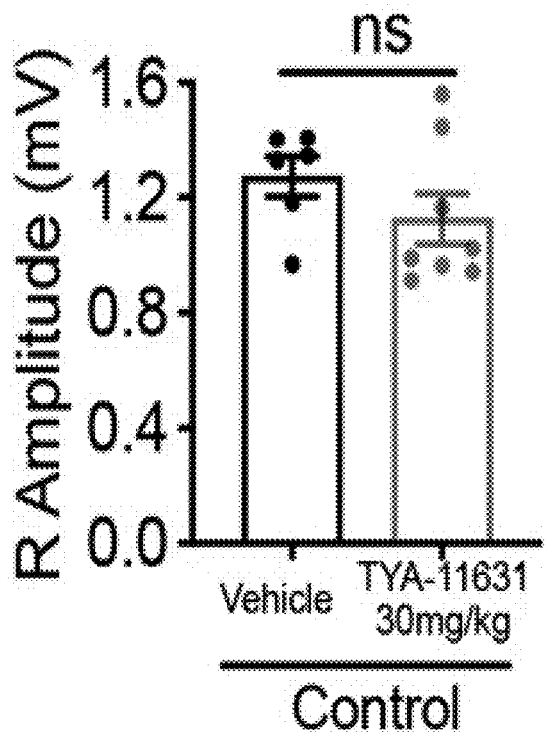
Figure 8S:
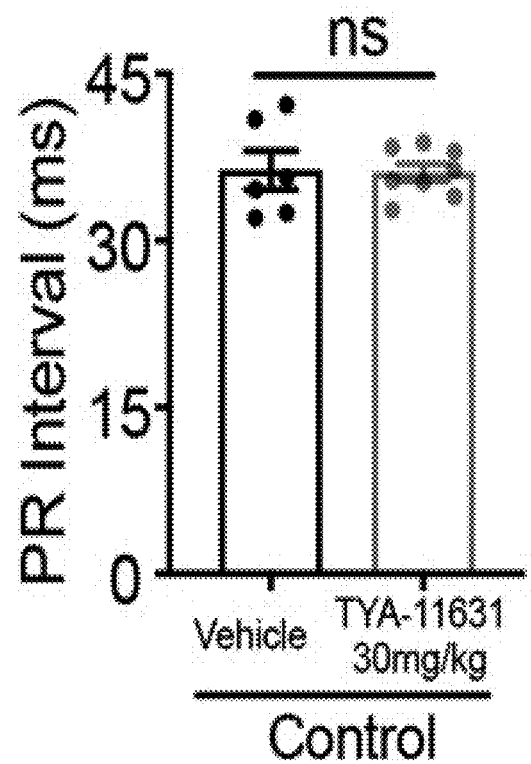

FIGS. 8A-8S show TYA-11631 treatment for 9 weeks improves glucose tolerance and diastolic dysfunction in HFD/L-NAME model.

FIG. 8A and FIG. 8B show results of Glucose tolerance test (GTT) performed after 5 weeks of dosing. Treatment with TYA-11631 markedly improved glucose tolerance in HFD/L-NAME mice, but no changes in control animals.

FIG. 8C shows plasma insulin level during GTT at the indicated time points (0 and 30 minutes after glucose injection) as measured by a sensitive mouse insulin detection kit (Cat. 80-INSMS-E01, ALPCO). TYA-11631 treatment led to decreased insulin secretion, suggesting that the improved glucose tolerance might be due to improved insulin action/sensitivity.

FIG. 8D and FIG. 8E show, respectively, that treatment with TYA-11631 caused a significant reduction of body weight, but no difference of food consumption in mice fed with HFD/L-NAME.

FIG. 8F shows that TYA-11631 did not affect systolic blood pressure in HFD/L-NAME mice measured by noninvasive tail cuff method.

Echocardiography shows that TYA-11631 treatment preserved ejection fraction (FIG. 8G), but significantly reduced left ventricular mass (FIG. 8H) and LV wall thickness (FIG. 8I).

Noninvasive Doppler imaging and terminal invasive catheterization analysis revealed that treatment with TYA-11631 for 9 wks decreased prolongation of isovolumetric relaxation time (FIG. 8J), E/A (FIG. 8K) and E/e' ratios (FIG. 8L), increased e' velocity (FIG. 8M), and reduced end diastolic pressure (FIG. 8N), indicating the improved LV relaxation and filling pressure. In addition, HFD/L-NAME mice treated with TYA-11631 showed a trending decrease in lung weight (FIG. 8O), suggesting an improved pulmonary congestion, consistent with the reduction of filling pressure.

Notably, no adverse effects related to TYA-11631 were observed. Control animals dosed with TYA-11631 had no changes on each of LV structural and functional parameters, as well as ECG signals—QT, QRS, R amplitude and PR intervals (FIG. 8P, FIG. 8Q, FIG. 8R and FIG. 8S, respectively), further supporting an overall favorable safety profile of the compound. Bars and error bars show means and SEM. *P<0.05, P<0.01, *P<0.001, ****P<0.0001.

Figure 9:
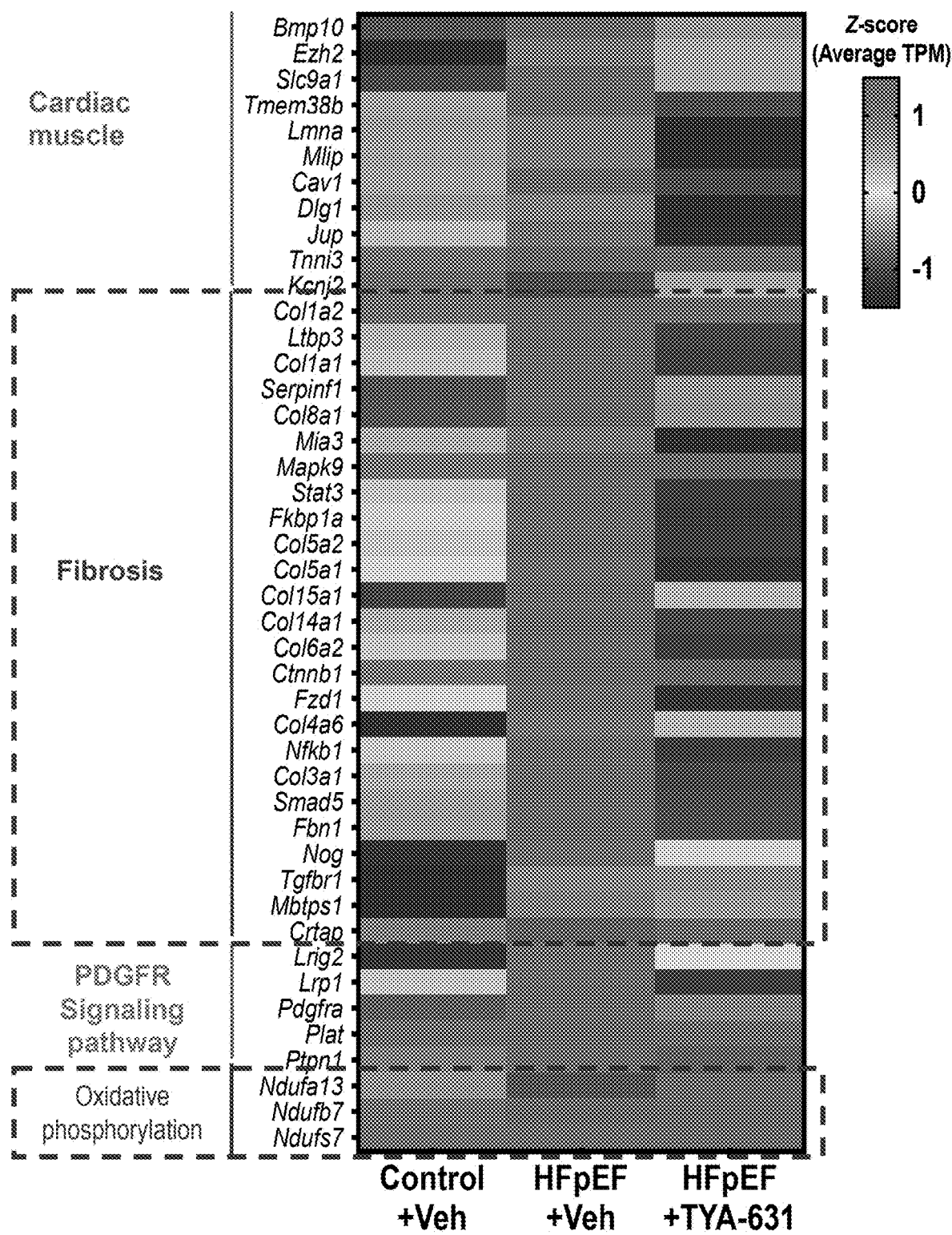

FIG. 9 shows a heatmap of selected genes from significantly altered functional gene sets. Only genes with significant expression differences in each (GO) and WikiPathways (WP) database gene set are shown. Heatmap shows correction of key genes associated with cardiac muscle, fibrosis and mitochondrial function.

Figure 10:
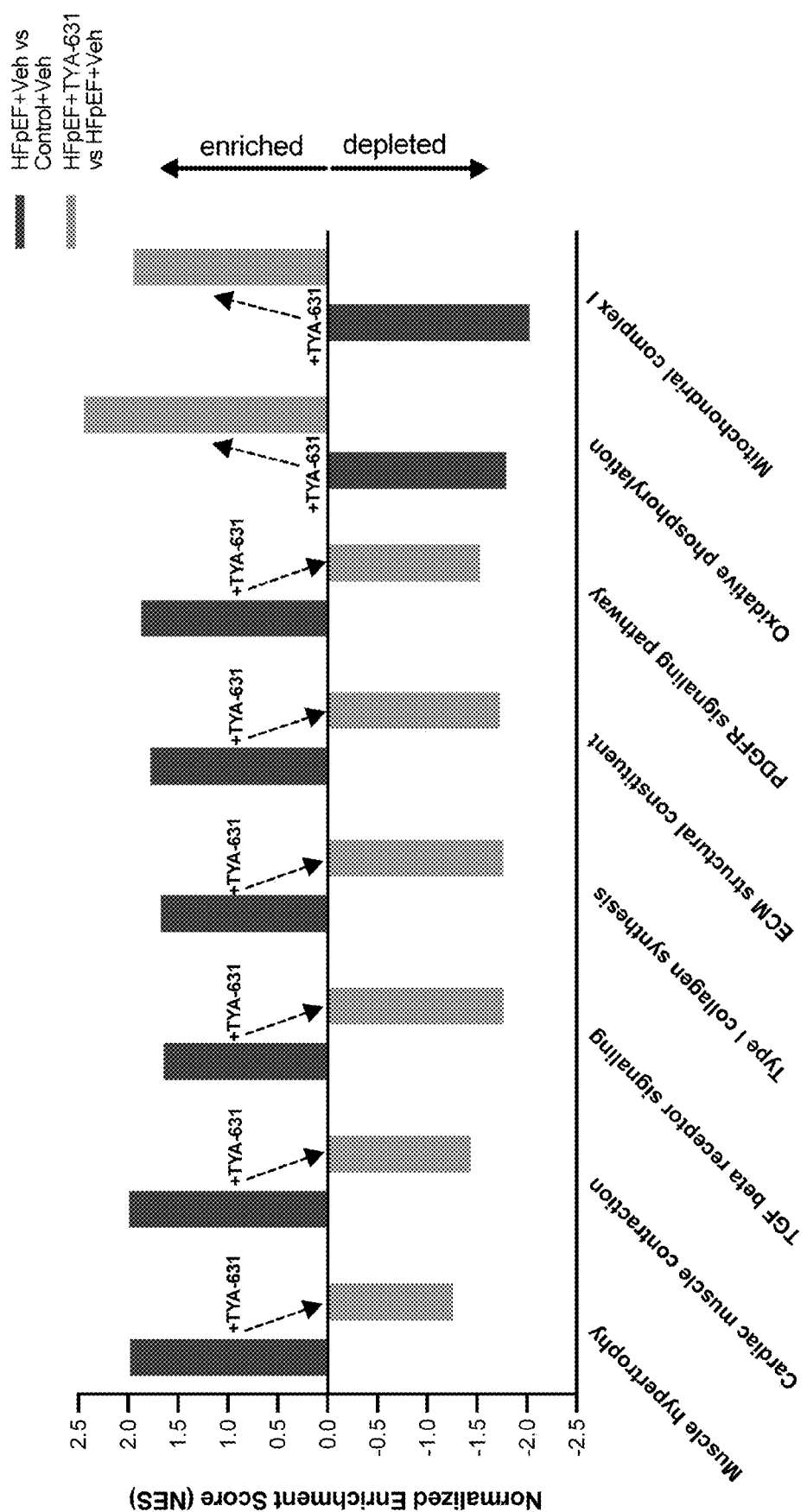

FIG. 10 shows significantly altered gene sets from Gene Ontology (GO) and WikiPathways (WP) databases. Selected categories were based on the normalized enrichment scores (NES) and FDR<0.25. For each condition, bars on the left indicate data for vehicle-treated HFpEF mice relative to healthy controls, and bars on the right indicate data for HFpEF mice treated with TYA-11631 relative to vehicle. TGFβ: transforming growth factor beta, PDGFR: platelet-derived growth factor receptors, OXPHOS: oxidative phosphorylation.

Figure 11A:
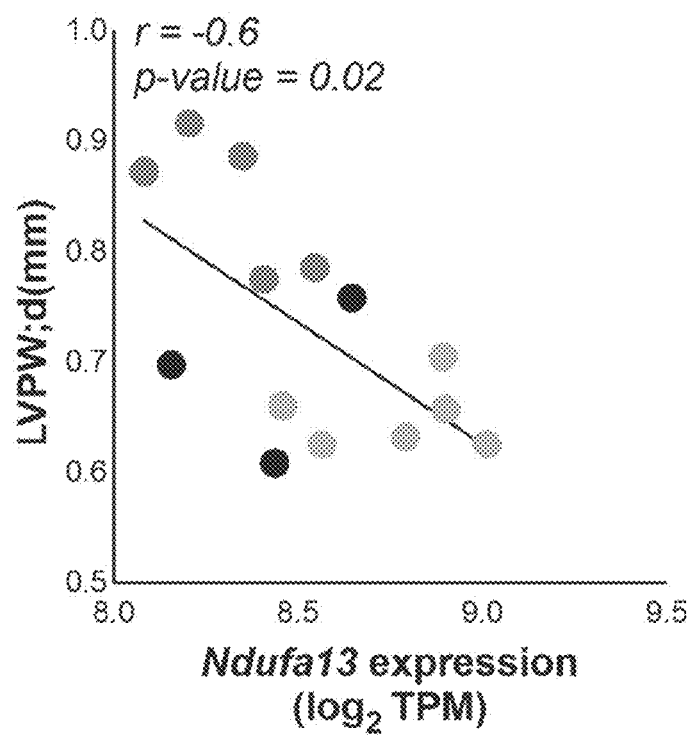
Figure 11B:
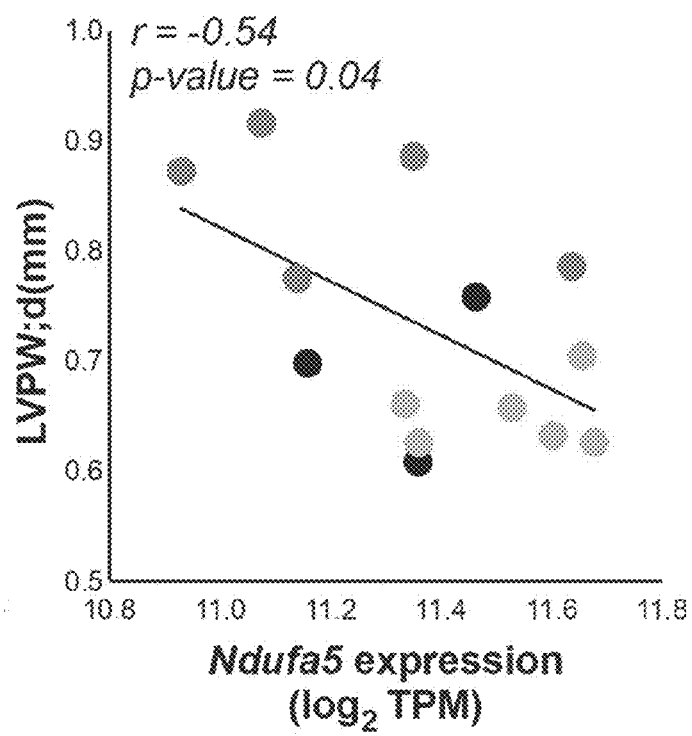
Figure 11C:
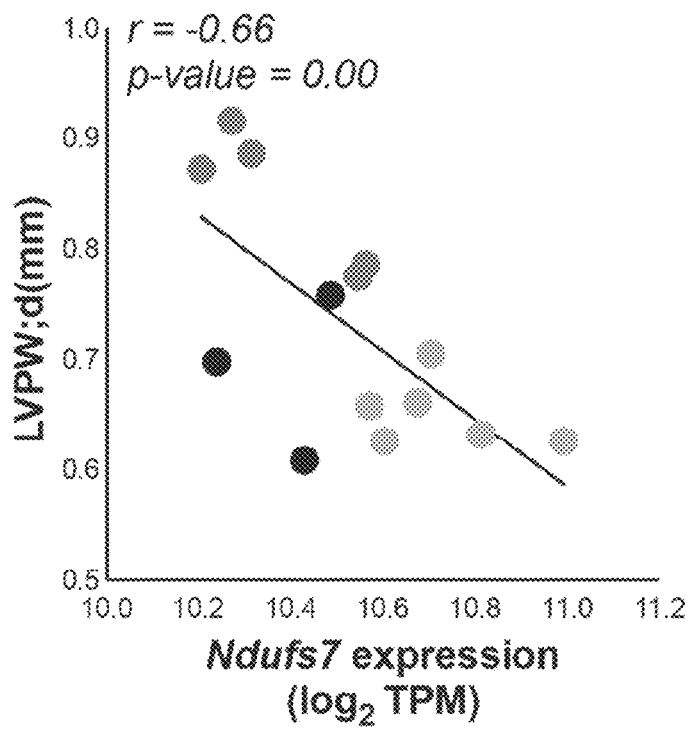
Figure 11D:
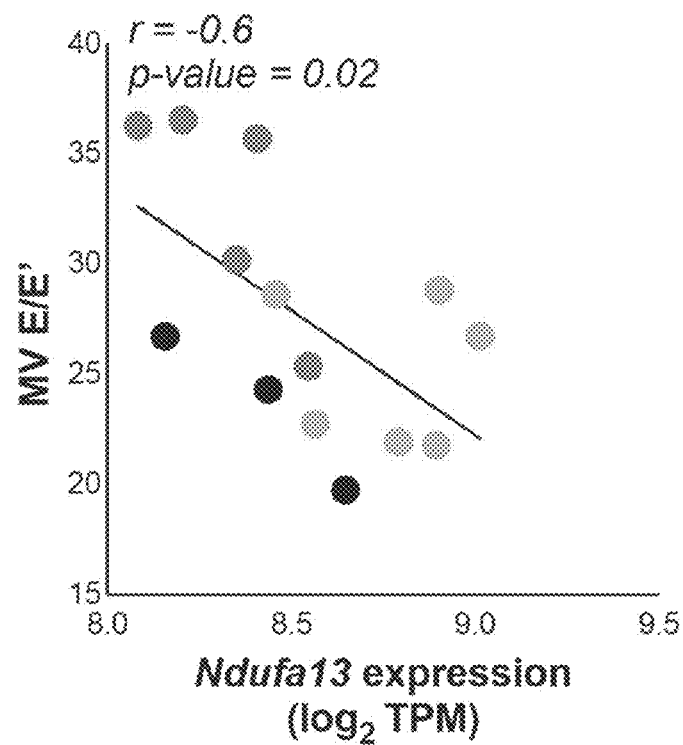
Figure 11E:
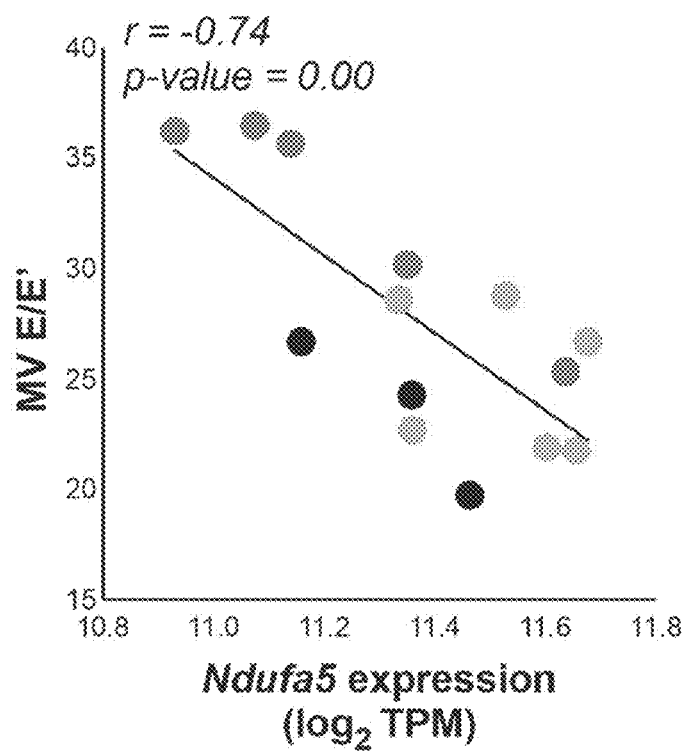
Figure 11F:
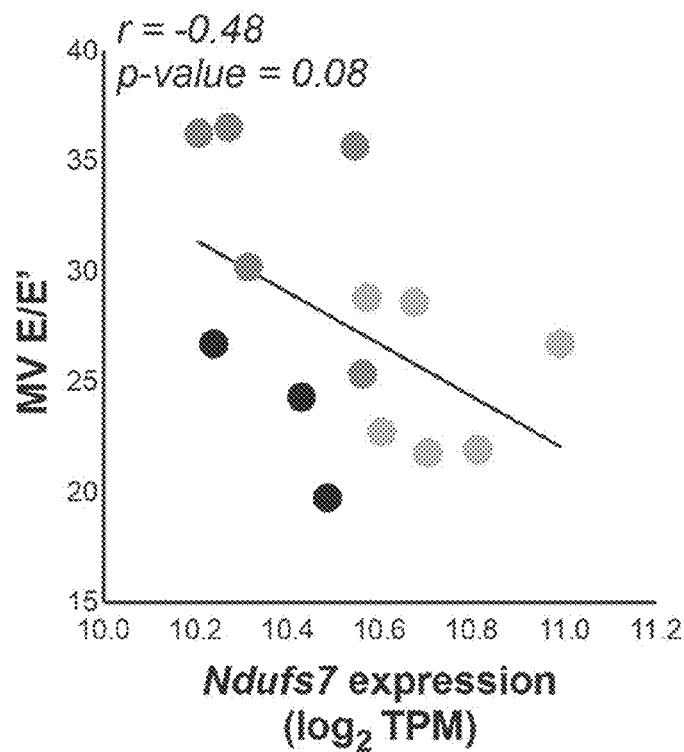
Figure 11H:
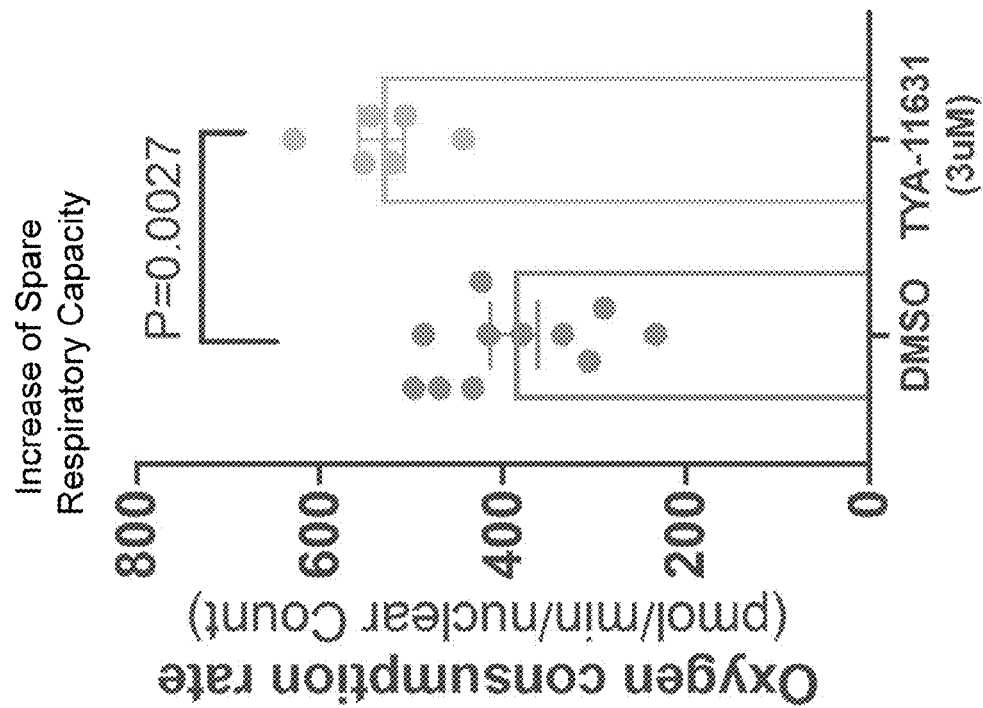
Figure 11G:
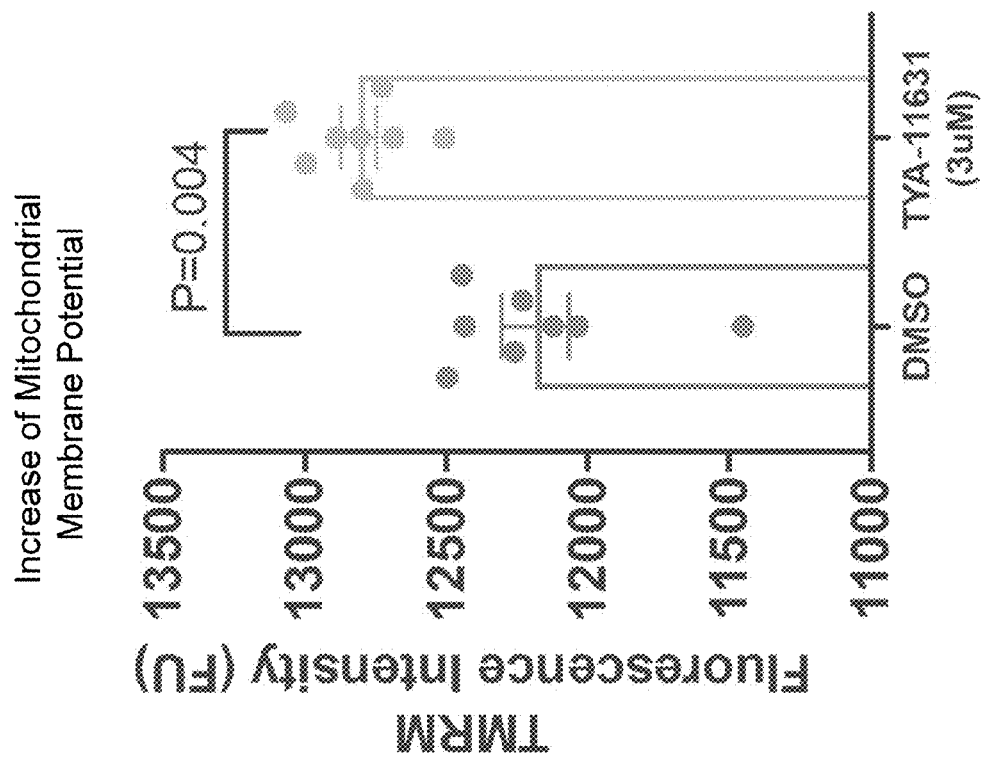

FIGS. 11A-11F show correlation of mitochondrial genes and diastolic function. In FIGS. 11A-11F, the expression level of genes associated with different subunits of mitochondrial respiratory electron transport chain (NADH: Ubiquinone Oxidoreductase subunits) on the x-axis are plotted against markers of diastolic function (LVPWd and MV E/E') on the y-axis. In particular, Ndufa13 (FIG. 11A), Ndufa5 (FIG. 11B), Ndufs7 (FIG. 11C) on the x-axis are plotted against the marker of diastolic function, LVPWd, on the y-axis. Ndufa13 (FIG. 11D), Ndufa5 (FIG. 11E), Ndufs7 (FIG. 11F)) on the x-axis are plotted against the marker of diastolic function, MV E/E', on the y-axis. For better visualization, the expression levels of genes were plotted on logarithmic scale ($\log_2$ TPM). Values are Pearson correlation coefficients. Black circles indicate data for vehicle treated healthy animals. Dark gray and light gray circles show HFpEF mice treated with vehicle or TYA-11631 respectively. FIG. 11G shows increased mitochondrial membrane potential, and FIG. 11H shows enhanced reserve respiratory capacity, in human iPSC-derived CMs treated with TYA-11631 (3 μM) (relative to DMSO control). Oxygen consumption rate values were normalized to nuclear count. Data represent mean values±SEM.

Figure 12A:
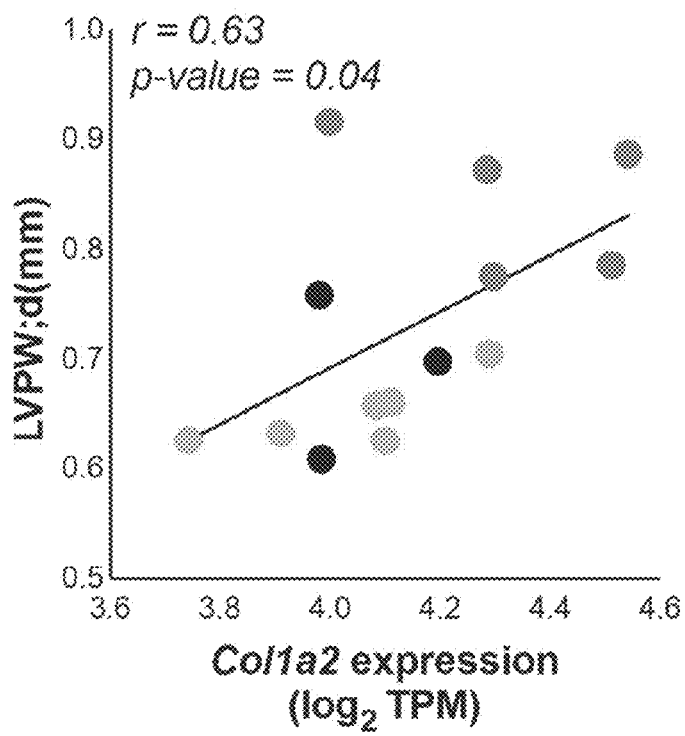
Figure 12B:
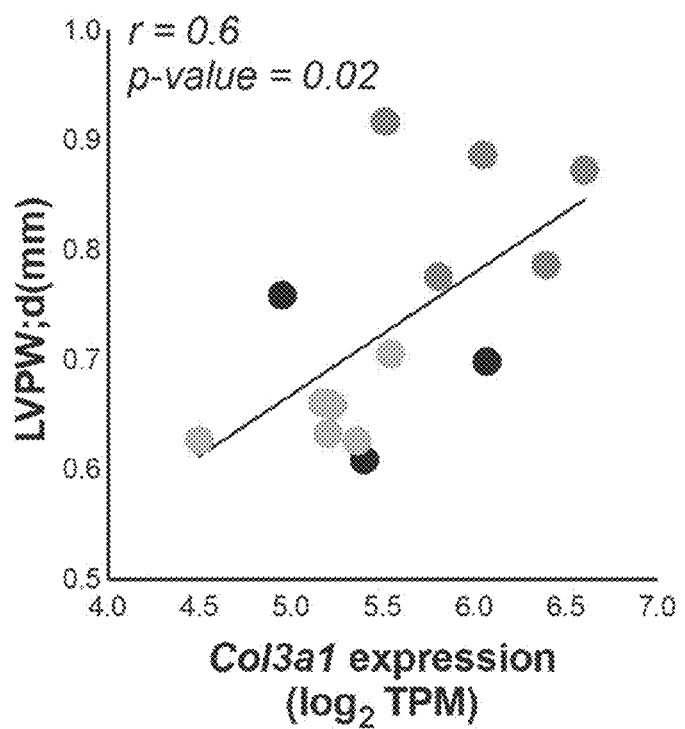
Figure 12C:
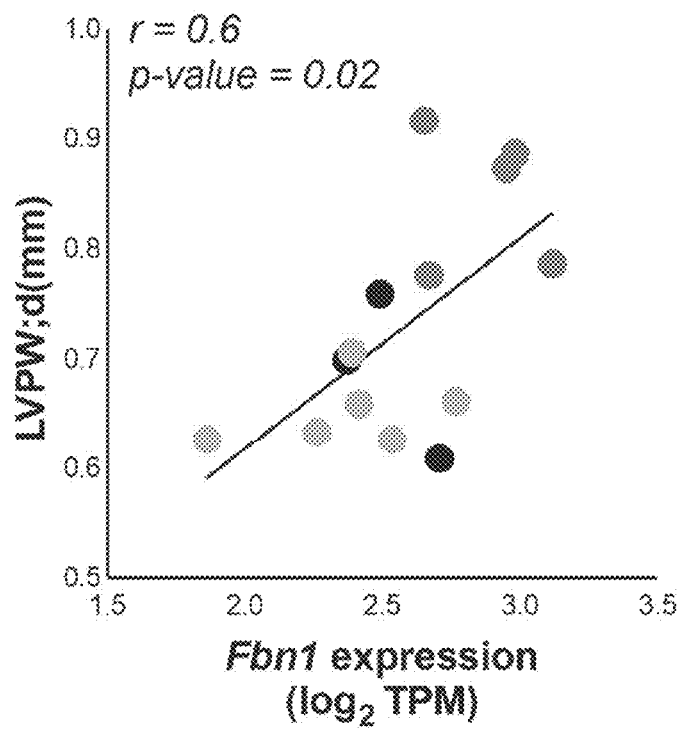
Figure 12D:
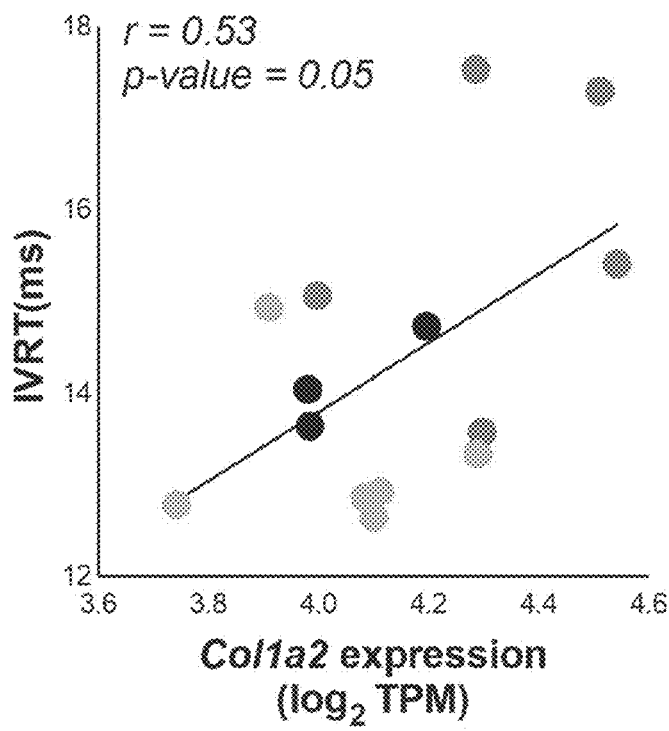
Figure 12E:
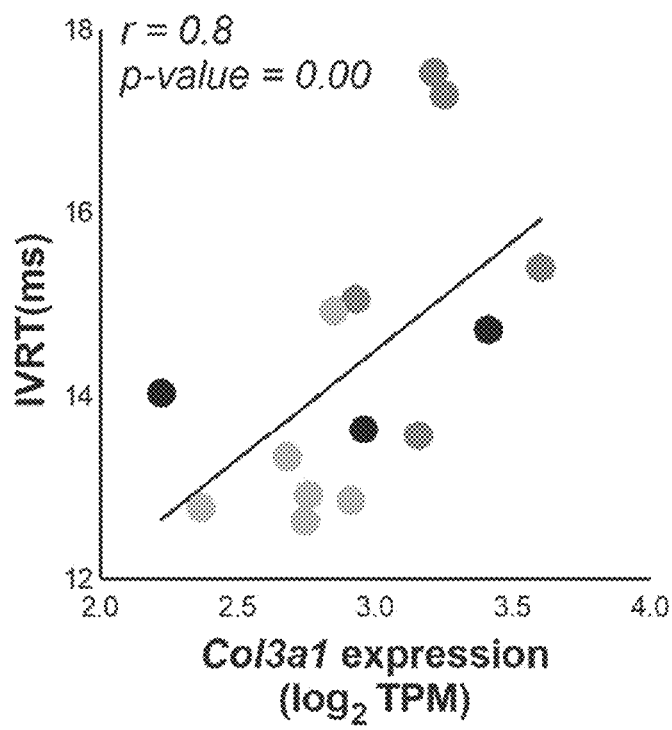
Figure 12F:
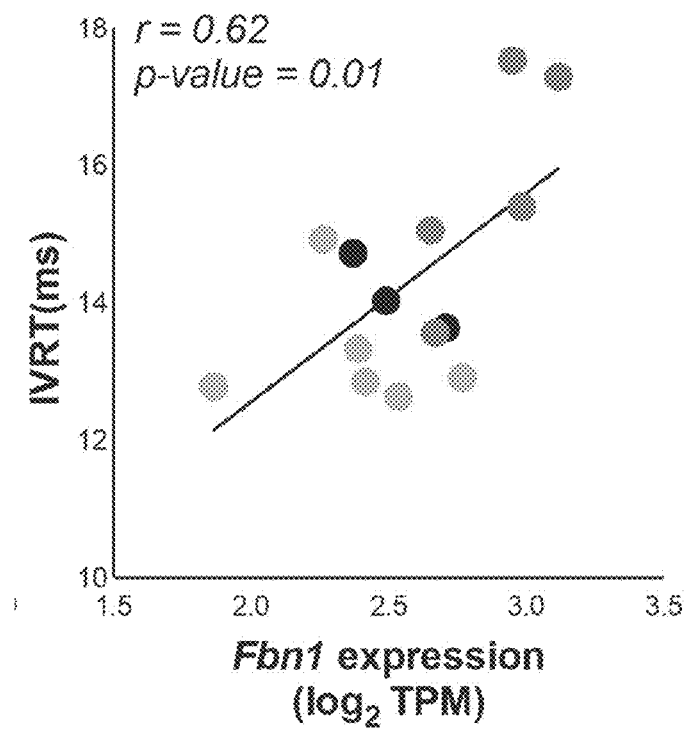

FIGS. 12A-12C show expression levels of genes associated with fibrosis Col1a2 (FIG. 12A), Col3a1 (FIG. 12B), Fbn1 (FIG. 12C) on the x-axis plotted against diastolic function parameter, LVPWd, on the y-axis. FIGS. 12D-12F show expression levels of genes associated with fibrosis Col1a2 (FIG. 12D), Col3a1 (FIG. 12E), Fbn1 (FIG. 12F) on the x-axis plotted against diastolic function parameter, IVRT, on the y-axis.

Figure 13A:
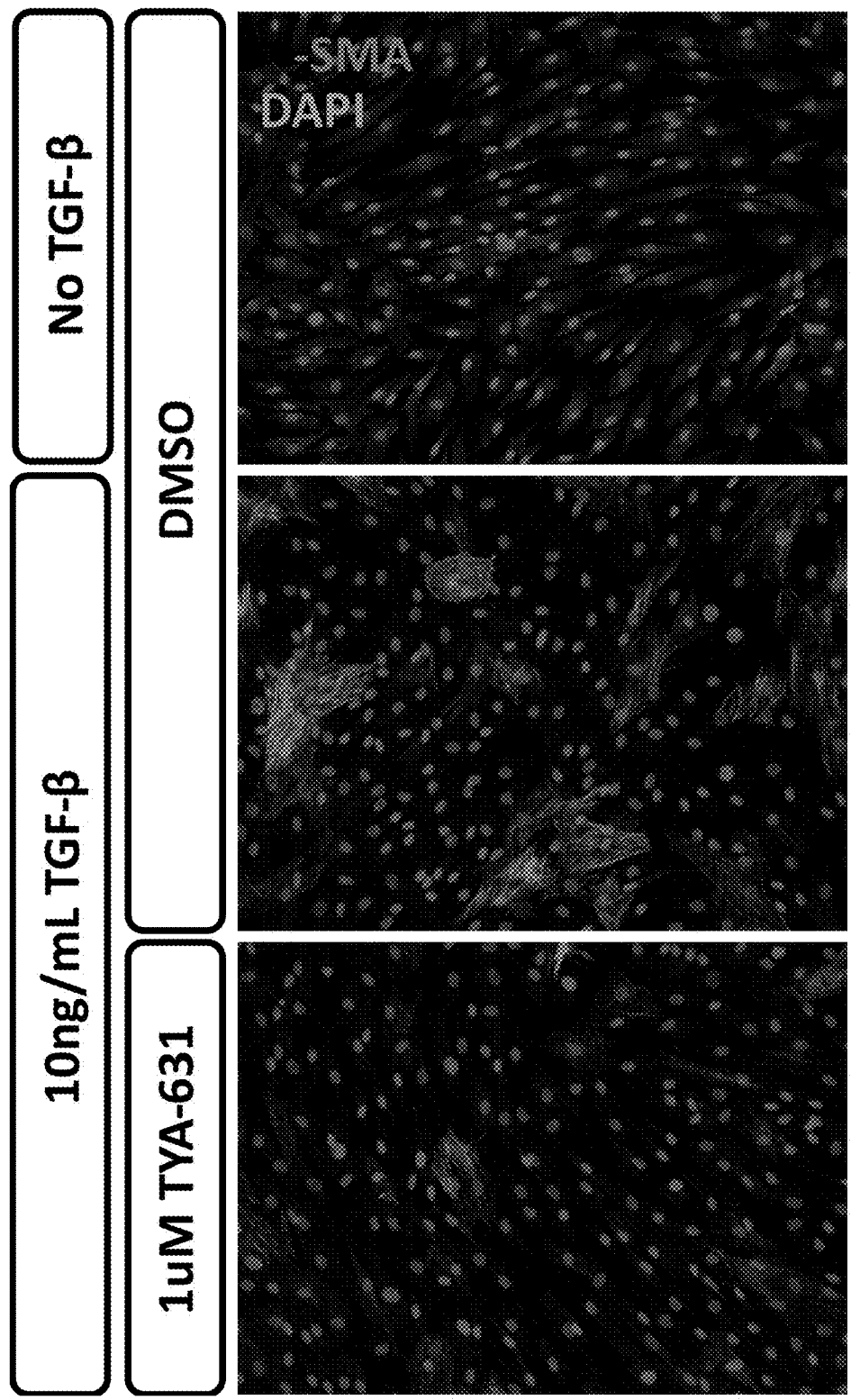
Figure 13B:
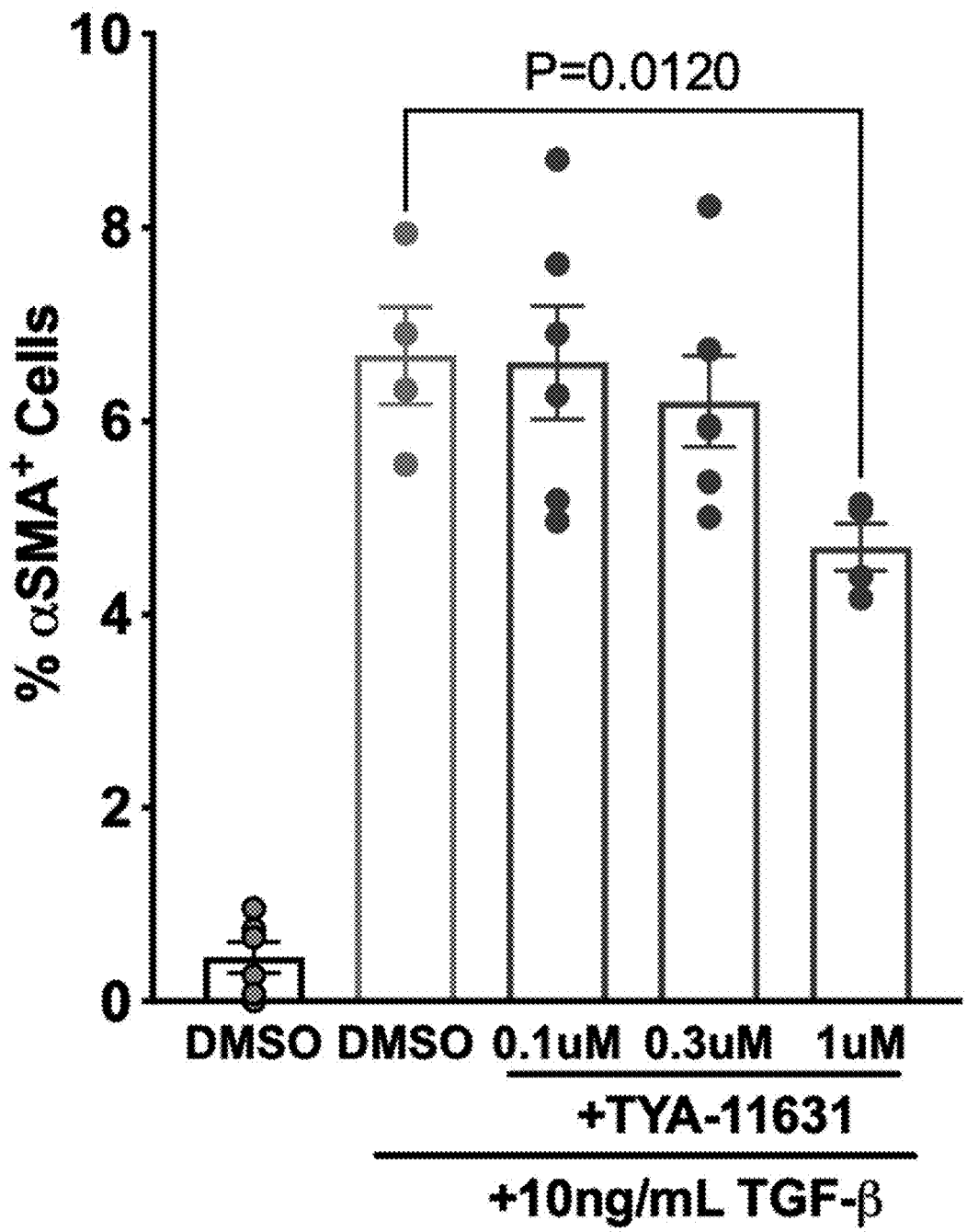

FIGS. 13A-13B show that HDAC6 inhibitors prevent fibroblast activation from TGF-β in human cardiac fibroblasts. FIG. 13A shows immunostaining of alpha-SMA (smooth muscle actin) in human cardiac fibroblasts in control (first panel from the top), treated with vehicle in the presence of TGF-beta (second panel from the top) or 1 uM TYA-11631 in the presence of TGF-beta (third panel from the top). 10 ng/ml TGF-beta was used. Scale bars are μM. FIG. 13B shows that TYA-11631 (1 uM) effectively reduced TGF-beta induced human cardiac fibroblast activation as measured by alpha-SMA+ cells. Alpha-SMA staining count was determined by blinded analyses. Each point represents 9 images per well. Data represent mean values±SEM.

Figure 14A:
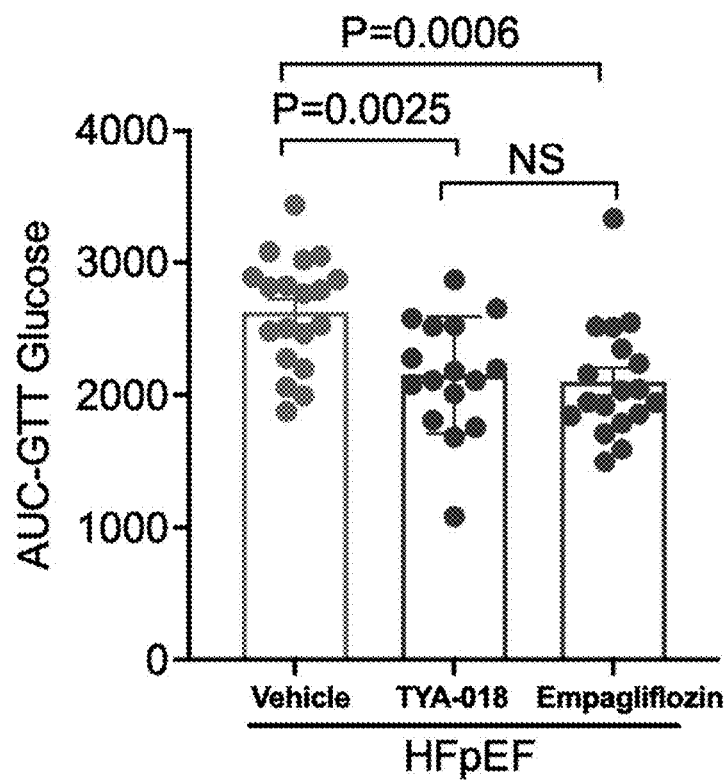
Figure 14B:
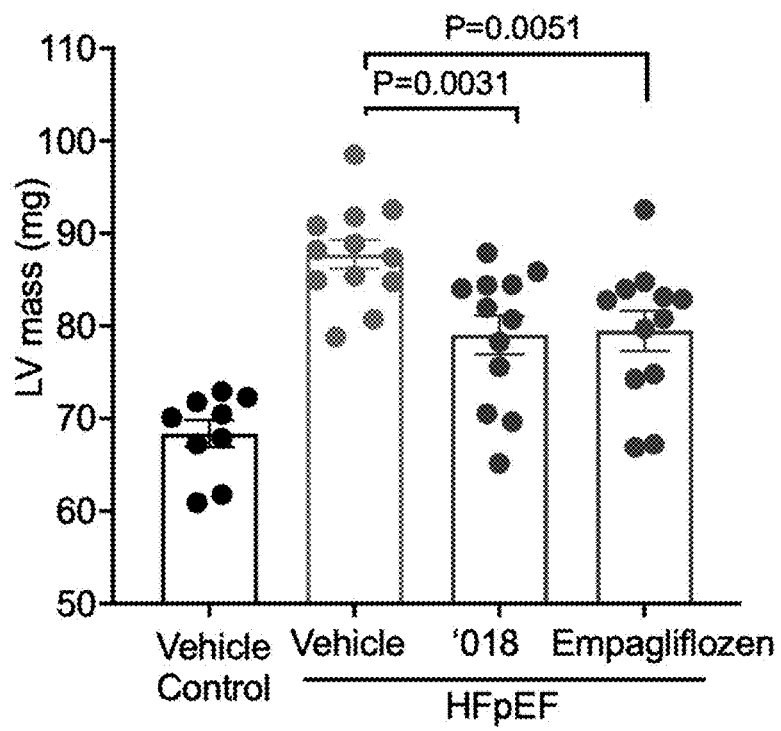
Figure 14C:
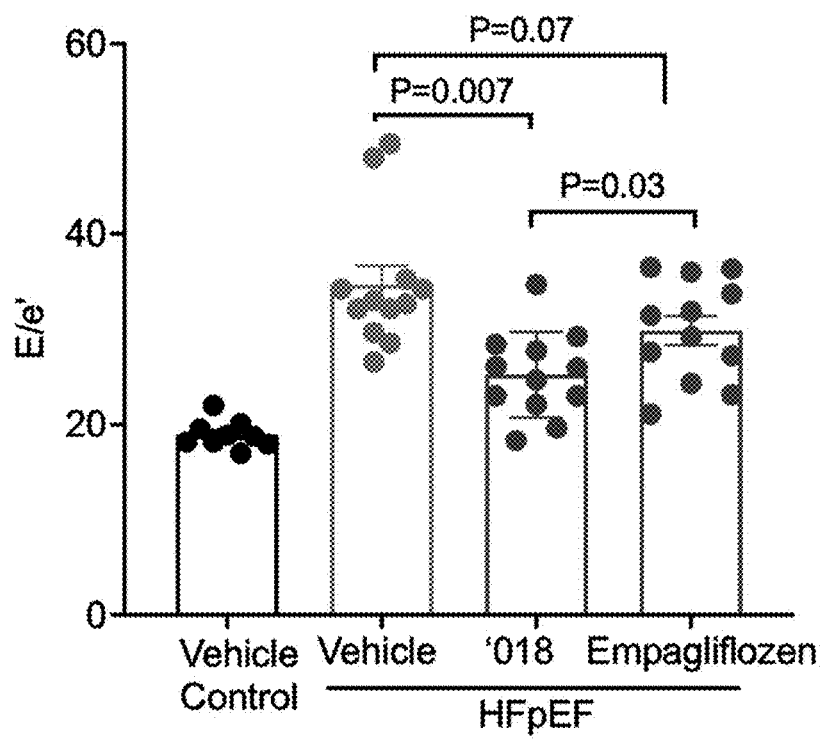
Figure 14D:
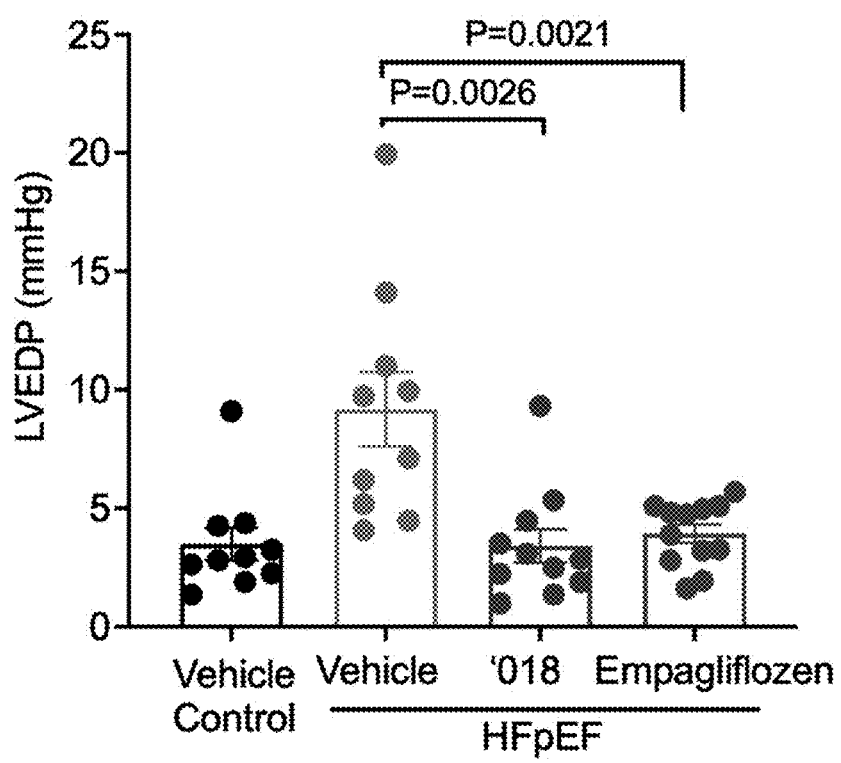

FIG. 14A shows a single dose of TYA-11018 (a HDAC6 selective inhibitor with similar potency to TYA-11631) significantly improved glucose tolerance to similar levels as Empagliflozin (SGLT2 selective inhibitor, 10 mg/kg) in the established mouse HFpEF model. FIGS. 14B-14D show that chronic treatment with TYA-11018 for 9 weeks reduced LV hypertrophy (FIG. 14B), and improved diastolic function as measured by E/e' (FIG. 14C) and end diastolic pressure LVEDP (FIG. 14D).

Figure 14E:
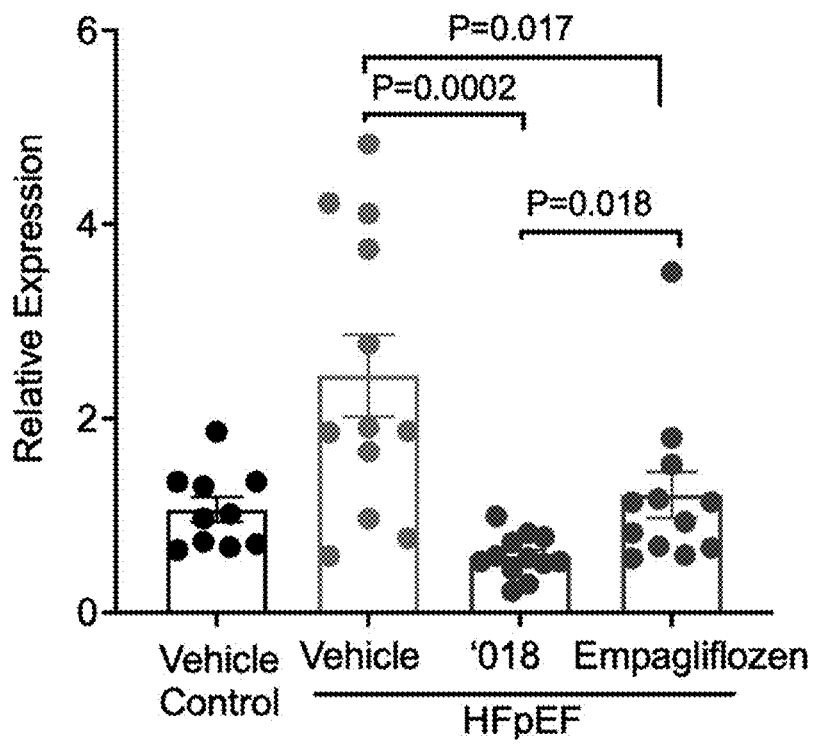
Figure 14F:
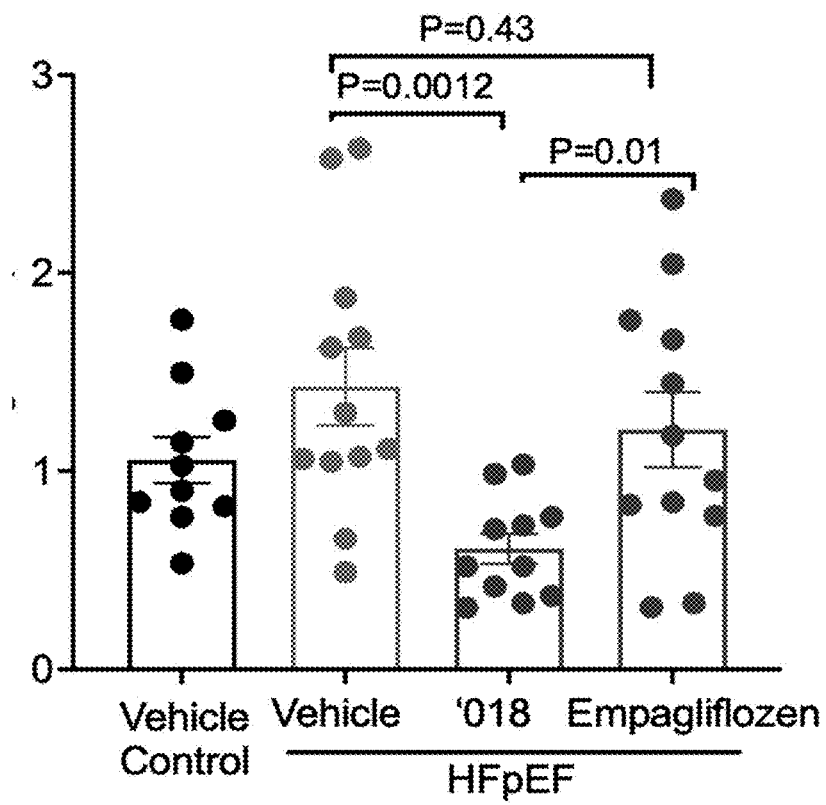

Real time q-PCR data showed that TYA-11018 treatment for 9 wks led to significant inhibitions of Nppb (FIG. 14E) and Col3a1 (FIG. 14F) in heart tissue of HFpEF mice compared to vehicle group. Notably, TYA-11018 showed a superior effect on the inhibition of these genes compared to Empagliflozin. Bars and error bars show means.

DETAILED DESCRIPTION

Overview

The present disclosure relates generally to the demonstration, in vivo, of the efficacy of HDAC6 inhibitors in metabolic disease. In particular, as disclosed herein, various physiological indicators of metabolic disease were improved when an animal model of metabolic disease (including a diet-induced obesity model and a diet-independent diabetes model) was administered an HDAC6 inhibitor. Further, the potency of a large number of various HDAC6 inhibitors against HDAC6 is disclosed herein. Accordingly, the disclosure provides support for use of HDAC6 inhibitors for the treatment of metabolic diseases.

In some aspects, the disclosure provides a method of treating or preventing metabolic disease (such as any metabolic disease described herein) in a subject in need thereof, comprising administering a therapeutically effective amount of a HDAC6 inhibitor. In some aspects, the disclosure provides a method of treating or preventing metabolic syndrome in a subject in need thereof, comprising administering a therapeutically effective amount of a HDAC6 inhibitor. In some aspects, the disclosure provides a method of treating or preventing diabetes (e.g., diabetes mellitus) in a subject in need thereof, comprising administering a therapeutically effective amount of a HDAC6 inhibitor. In some aspects, the disclosure provides a method of treating obesity in a subject in need thereof, comprising administering a therapeutically effective amount of a HDAC6 inhibitor.

In some embodiments, provided herein are methods of treating or preventing metabolic disease (e.g., a metabolic disease, e.g., diabetes or metabolic syndrome, or obesity) in a subject in need thereof, comprising orally administering to a human subject a HDAC6 inhibitor.

In another aspect, the present disclosure relates generally to the demonstration, in vivo, of the efficacy of HDAC6 inhibitors in heart failure with preserved ejection fraction (HFpEF). In particular, as disclosed herein, various physiological indicators of HFpEF were improved when an animal model of HFpEF was administered an HDAC6 inhibitor. Further, the potency of a large number of various HDAC6 inhibitors against HDAC6 is disclosed herein. Accordingly, the disclosure provides support for use of HDAC6 inhibitors for the treatment of HFpEF.

In some aspects, the disclosure provides a method of treating or preventing heart failure with preserved ejection fraction (HFpEF) in a subject in need thereof, comprising administering a therapeutically effective amount of a HDAC6 inhibitor.

In some embodiments, provided herein are methods of treating or preventing HFpEF in a subject in need thereof, comprising orally administering to a human subject a HDAC6 inhibitor.

In some aspects, the disclosure provides a method of treating or preventing cardiac fibrosis in a subject in need thereof, comprising administering a therapeutically effective amount of a HDAC6 inhibitor. In some embodiments, provided herein are methods of treating or preventing cardiac fibrosis associated with HFpEF in a subject in need thereof, comprising administering (e.g., orally) to a subject (e.g., a human) a HDAC6 inhibitor.

In some aspects, the disclosure provides a method of treating or preventing diastolic dysfunction in a subject in need thereof, comprising administering a therapeutically effective amount of a HDAC6 inhibitor. In some embodiments, provided herein are methods of treating or preventing diastolic dysfunction associated with HFpEF in a subject in need thereof, comprising administering (e.g., orally) to a subject (e.g., a human) a HDAC6 inhibitor.

Advantageously, administration of a selective HDAC6 inhibitor may be less toxic than a pan-HDAC inhibitor. Without being bound by theory, an HDAC6 inhibitor may (1) act as an anti-inflammatory agent by inhibiting pro-inflammatory genes in white adipose tissue, the major source of obesity-related inflammation that leads to insulin resistance and metabolic dysfunction, and/or (2) improve mitochondrial activity/function. Without being bound by theory, an HDAC6 inhibitor may also: 1) directly act at the sarcomere level by protecting microtubules against mechanical damage, 2) improve myocyte compliance, and/or 3) promote autophagic flux and clearance of misfolded and damaged proteins. HDAC6 inhibition may directly stabilize and protect microtubules against damage and protect the Z-disk.

Definitions

Unless the context indicates otherwise, it is specifically intended that the various features of the invention described herein can be used in any combination. Moreover, the disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

All numerical designations, e.g., pH, temperature, time, concentration, and molecular weight, including ranges, are approximations which are varied (+) or (−) by increments of 1.0 or 0.1, as appropriate, or alternatively by a variation of +/−15%, or alternatively 10%, or alternatively 5%, or alternatively 2%. It is to be understood, although not always explicitly stated, that all numerical designations are preceded by the term "about". It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth. It also is to be understood, although not always explicitly stated, that the reagents described herein are merely exemplary and that equivalents of such are known in the art.

Also as used herein, "and/or" refers to and encompasses any and all possible combinations of one or more of the associated listed items, as well as the lack of combinations when interpreted in the alternative ("or").

The term "a" or "an" refers to one or more of that entity, i.e. can refer to plural referents. As such, the terms "a," "an," "one or more," and "at least one" are used interchangeably herein. In addition, reference to "an element" by the indefinite article "a" or "an" does not exclude the possibility that more than one of the elements is present, unless the context clearly requires that there is one and only one of the elements.

Throughout this application, the term "about" is used to indicate that a value includes the inherent variation of error for the device or the method being employed to determine the value, or the variation that exists among the samples being measured. Unless otherwise stated or otherwise evident from the context, the term "about" means within 10% above or below the reported numerical value (except where such number would exceed 100% of a possible value or go below 0%). When used in conjunction with a range or series of values, the term "about" applies to the endpoints of the range or each of the values enumerated in the series, unless otherwise indicated. As used in this application, the terms "about" and "approximately" are used as equivalents.

As used herein, the term "HDAC6" refers to the enzyme that in humans is encoded by the HDAC6 gene.

As used herein, the term "HDAC6 inhibitor" refers to a compound that inhibits at least one enzymatic activity of HDAC6.

An HDAC6 inhibitor may be a "selective" HDAC6 inhibitor. The term "selective" as used herein refers to selectivity against other HDACs, known in the art as "isozymes." In some embodiments, the selectivity ratio of HDAC6 over HDAC1 is from about 5 to about 30,0000, e.g., about 5, about 10, about 20, about 30, about 40, about 50, about 60, about 70, about 80, about 90, about 100, about 1000, about 2000, about 3000, about 4000, about 5000, about 6000, about 7000, about 8000, about 9000, about 10,000, about 15,000, about 20,000, about 25,000, or about 30,000, including all values and ranges therebetween.

For example, a HDAC6 inhibitor may be at least 100-fold selective against HDAC6 compared to all other isozymes of HDAC. In some cases, selectivity may be determined by reference of another HDAC inhibitor, such as a pan-HDAC inhibitor—that is an inhibitor that inhibits HDACs other than HDAC6 in addition to HDAC6. Givinostat is an example of a pan-HDAC6 inhibitor. In some embodiments, a selective HDAC6 inhibitor inhibits HDACs other than HDAC6 at least 100-fold less effectively than givinostat.

"Alkyl" or "alkyl group" refers to a fully saturated, straight or branched hydrocarbon chain having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

"Alkylene" or "alkylene chain" refers to a fully saturated, straight or branched divalent hydrocarbon chain radical, and having from one to twelve carbon atoms. Non-limiting examples of $C_1$-$C_{12}$ alkylene include methylene, ethylene, propylene, n-butylene, and the like. The alkylene chain is attached to the rest of the molecule through a single bond and to a radical group (e.g., those described herein) through a single bond. The points of attachment of the alkylene chain to the rest of the molecule and to the radical group can be through one carbon or any two carbons within the chain. Unless stated otherwise specifically in the specification, an alkylene chain can be optionally substituted.

"Alkenyl" or "alkenyl group" refers to a straight or branched hydrocarbon chain having from two to twelve carbon atoms, and having one or more carbon-carbon double bonds. Each alkenyl group is attached to the rest of the molecule by a single bond. Alkenyl group comprising any number of carbon atoms from 2 to 12 are included. An alkenyl group comprising up to 12 carbon atoms is a $C_2$-$C_{12}$ alkenyl, an alkenyl comprising up to 10 carbon atoms is a $C_2$-$C_{10}$ alkenyl, an alkenyl group comprising up to 6 carbon atoms is a $C_2$-$C_6$ alkenyl and an alkenyl comprising up to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_2$-$C_{12}$ alkenyl includes all the foregoing moieties, but also includes Cu and $C_{12}$ alkenyls. Non-limiting examples of $C_2$-$C_{12}$ alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Unless stated otherwise specifically in the specification, an alkyl group can be optionally substituted.

"Alkenylene" or "alkenylene chain" refers to an unsaturated, straight or branched divalent hydrocarbon chain radical having one or more olefins and from two to twelve carbon atoms. Non-limiting examples of $C_2$-$C_{12}$ alkenylene include ethenylene, propenylene, n-butenylene, and the like. The alkenylene chain is attached to the rest of the molecule through a single bond and to a radical group (e.g., those described herein) through a single bond. The points of attachment of the alkenylene chain to the rest of the molecule and to the radical group can be through one carbon or any two carbons within the chain. Unless stated otherwise specifically in the specification, an alkenylene chain can be optionally substituted.

"Alkynyl" or "alkynyl group" refers to a straight or branched hydrocarbon chain having from two to twelve carbon atoms, and having one or more carbon-carbon triple bonds. Each alkynyl group is attached to the rest of the molecule by a single bond. Alkynyl group comprising any number of carbon atoms from 2 to 12 are included. An alkynyl group comprising up to 12 carbon atoms is a $C_2$-$C_{12}$ alkynyl, an alkynyl comprising up to 10 carbon atoms is a $C_2$-$C_{10}$ alkynyl, an alkynyl group comprising up to 6 carbon atoms is a $C_2$-$C_6$ alkynyl and an alkynyl comprising up to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes $C_{11}$ and $C_{12}$ alkynyls. Non-limiting examples of $C_2$-$C_{12}$ alkenyl include ethynyl, propynyl, butynyl, pentynyl and the like. Unless stated otherwise specifically in the specification, an alkyl group can be optionally substituted.

"Alkynylene" or "alkynylene chain" refers to an unsaturated, straight or branched divalent hydrocarbon chain radical having one or more alkynes and from two to twelve carbon atoms. Non-limiting examples of $C_2$-$C_{12}$ alkynylene include ethynylene, propynylene, n-butynylene, and the like. The alkynylene chain is attached to the rest of the molecule through a single bond and to a radical group (e.g., those described herein) through a single bond. The points of attachment of the alkynylene chain to the rest of the molecule and to the radical group can be through any two carbons within the chain having a suitable valency. Unless stated otherwise specifically in the specification, an alkynylene chain can be optionally substituted.

"Alkoxy" refers to a group of the formula —OR$^a$ where R$^a$ is an alkyl, alkenyl or alknyl as defined above containing one to twelve carbon atoms. Unless stated otherwise specifically in the specification, an alkoxy group can be optionally substituted.

"Aryl" refers to a hydrocarbon ring system comprising hydrogen, 6 to 18 carbon atoms and at least one aromatic ring, and which is attached to the rest of the molecule by a single bond. For purposes of this disclosure, the aryl can be a monocyclic, bicyclic, tricyclic or tetracyclic ring system, which can include fused or bridged ring systems. Aryls include, but are not limited to, aryls derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the "aryl" can be optionally substituted.

"Carbocyclyl," "carbocyclic ring" or "carbocycle" refers to a rings structure, wherein the atoms which form the ring are each carbon, and which is attached to the rest of the molecule by a single bond. Carbocyclic rings can comprise from 3 to 20 carbon atoms in the ring. Carbocyclic rings include aryls and cycloalkyl, cycloalkenyl, and cycloalkynyl as defined herein. Unless stated otherwise specifically in the specification, a carbocyclyl group can be optionally substituted.

"Carbocyclylalkyl" refers to a radical of the formula —R$^b$—R$^d$ where R$^b$ is an alkylene, alkenylene, or alkynylene group as defined above and R$^d$ is a carbocyclyl radical as defined above. Unless stated otherwise specifically in the specification, a carbocyclylalkyl group can be optionally substituted.

"Cycloalkyl" refers to a stable non-aromatic monocyclic or polycyclic fully saturated hydrocarbon consisting solely of carbon and hydrogen atoms, which can include fused or bridged ring systems, having from three to twenty carbon atoms (e.g., having from three to ten carbon atoms) and which is attached to the rest of the molecule by a single bond. Monocyclic cycloalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, 7,7-dimethyl-bicyclo [2.2.1]heptanyl, and the like. Unless otherwise stated specifically in the specification, a cycloalkyl group can be optionally substituted.

"Cycloalkenyl" refers to a stable non-aromatic monocyclic or polycyclic hydrocarbon consisting solely of carbon and hydrogen atoms, having one or more carbon-carbon double bonds, which can include fused or bridged ring systems, having from three to twenty carbon atoms, preferably having from three to ten carbon atoms, and which is attached to the rest of the molecule by a single bond. Monocyclic cycloalkenyls include, for example, cyclopentenyl, cyclohexenyl, cycloheptenyl, cyclooctenyl, and the like. Polycyclic cycloalkenyls include, for example, bicyclo [2.2.1]hept-2-enyl and the like. Unless otherwise stated specifically in the specification, a cycloalkenyl group can be optionally substituted.

"Cycloalkynyl" refers to a stable non-aromatic monocyclic or polycyclic hydrocarbon consisting solely of carbon and hydrogen atoms, having one or more carbon-carbon triple bonds, which can include fused or bridged ring systems, having from three to twenty carbon atoms, preferably having from three to ten carbon atoms, and which is attached to the rest of the molecule by a single bond. Monocyclic cycloalkynyl include, for example, cycloheptynyl, cyclooctynyl, and the like. Unless otherwise stated specifically in the specification, a cycloalkynyl group can be optionally substituted.

"Haloalkyl" refers to an alkyl, as defined above, that is substituted by one or more halo radicals, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group can be optionally substituted.

"Heterocyclyl," "heterocyclic ring" or "heterocycle" refers to a stable saturated, unsaturated, or aromatic 3- to 20-membered ring which consists of two to nineteen carbon atoms and from one to six heteroatoms selected from the group consisting of nitrogen, oxygen and sulfur, and which is attached to the rest of the molecule by a single bond. Heterocyclyl or heterocyclic rings include heteroaryls, heterocyclylalkyls, heterocyclylalkenyls, and hetercyclylalkynyls. Unless stated otherwise specifically in the specification, the heterocyclyl can be a monocyclic, bicyclic, tricyclic or tetracyclic ring system, which can include fused or bridged ring systems; and the nitrogen, carbon or sulfur atoms in the heterocyclyl can be optionally oxidized; the nitrogen atom can be optionally quaternized; and the heterocyclyl can be partially or fully saturated. Examples of such heterocyclyl include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group can be optionally substituted.

"Heteroaryl" refers to a 5- to 20-membered ring system comprising hydrogen atoms, one to nineteen carbon atoms, one to six heteroatoms selected from the group consisting of nitrogen, oxygen and sulfur, at least one aromatic ring, and which is attached to the rest of the molecule by a single bond. For purposes of this disclosure, the heteroaryl can be a monocyclic, bicyclic, tricyclic or tetracyclic ring system, which can include fused or bridged ring systems; and the nitrogen, carbon or sulfur atoms in the heteroaryl can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group can be optionally substituted.

"Heterocyclylalkyl" refers to a radical of the formula —$R^b$—$R^e$ where $R^b$ is an alkylene, alkenylene, or alkynylene group as defined above and $R^e$ is a heterocyclyl radical as defined above. Unless stated otherwise specifically in the specification, a heterocycloalkylalkyl group can be optionally substituted.

The term "substituted" used herein means any of the groups described herein (e.g., alkyl, alkenyl, alkynyl, alkoxy, aryl, aralkyl, carbocyclyl, cycloalkyl, cycloalkenyl, cycloalkynyl, haloalkyl, heterocyclyl, and/or heteroaryl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted" also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents.

As used herein, the symbol

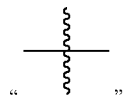

(hereinafter can be referred to as "a point of attachment bond") denotes a bond that is a point of attachment between two chemical entities, one of which is depicted as being attached to the point of attachment bond and the other of which is not depicted as being attached to the point of attachment bond. For example,

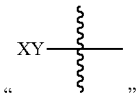

indicates that the chemical entity "XY" is bonded to another chemical entity via the point of attachment bond. Furthermore, the specific point of attachment to the non-depicted chemical entity can be specified by inference. For example, the compound $CH_3$—$R^3$, wherein $R^3$ is H or

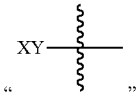

infers that when $R^3$ is "XY", the point of attachment bond is the same bond as the bond by which $R^3$ is depicted as being bonded to $CH_3$.

As used herein, the term "treating" refers to acting upon a disease, disorder, or condition with an agent to reduce or ameliorate harmful or any other undesired effects of the disease, disorder, condition and/or their symptoms.

As used herein, the term "preventing" refers to reducing the incidence or risk of developing, or delaying the development of, harmful or any other undesired effects of the disease, disorder, condition and/or symptoms "Administration," "administering" and the like, refer to administration to a subject by a medical professional or by self-administration by the subject, as well as to indirect administration, which may be the act of prescribing a composition of the invention. Typically, an effective amount is administered, which amount can be determined by one of skill in the art. Any method of administration may be used. Administration to a subject can be achieved by, for example, oral administration, in liquid or solid form, e.g. in capsule or tablet form; intravascular injection; intramyocardial delivery; or other suitable forms of administration.

As used herein, the term "effective amount" and the like refers to an amount that is sufficient to induce a desired physiologic outcome (e.g., increased cardiac function, decreased mortality, or decreased risk/incidence of hospitalization, increased exercise capacity, or reduced expression of one or more biomarkers associated with heart failure—such as BNP). An effective amount can be administered in one or more administrations, applications or dosages. Such delivery is dependent on a number of variables including the time period which the individual dosage unit is to be used, the bioavailability of the composition, the route of administration, etc. It is understood, however, that specific amounts of the compositions for any particular subject depends upon a variety of factors including the activity of the specific agent employed, the age, body weight, general health, sex, and diet of the subject, the time of administration, the rate of excretion, the composition combination, severity of the particular disease being treated and form of administration.

As used herein, the terms "subject" or "patient" refers to any animal, such as a domesticated animal, a zoo animal, or a human. The "subject" or "patient" can be a mammal like a dog, cat, horse, livestock, a zoo animal, or a human. The subject or patient can also be any domesticated animal such as a bird, a pet, or a farm animal. Specific examples of "subjects" and "patients" include, but are not limited to, individuals with a metabolic disease (e.g., obesity), and individuals with metabolic disease-related characteristics or symptoms. Specific examples of "subjects" and "patients" also include, but are not limited to, individuals with a cardiac disease or disorder, and individuals with cardiac disorder-related characteristics or symptoms.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salts" include those obtained by reacting the active compound functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. Those skilled in the art will further recognize that acid addition salts may be prepared by reaction of the compounds with the appropriate inorganic or organic acid via any of a number of known methods.

As used herein, the term "restores" refers to increasing the level of biochemical or physiological parameter to a level observed in the subject prior to development of disease or condition, or to the level observed in a subject not having the disease or condition.

As used herein, the term "reduces" refers to decreasing the level of biochemical or physiological parameter.

As used herein, the term "metabolic disease" refers to a condition causes by either excessive nutrient intake or by the body's failure to properly metabolize nutrients. Metabolic disease includes but is not limited to obesity. It is a cluster of conditions that occur together, associated with heart diseases, type 2 diabetes and stroke. These conditions include hypertension, hyperglycemia, excess body fat and abnormal cholesterol or triglyceride levels.

The term "obesity" refers to a condition of having too much body fat. Obesity may increase the risk of diabetes, heart disease, stroke, and arthritis. Weight that is higher than what is considered healthy for a given height is described as overweight or obesity. Body Mass Index (BMI) is a screening tool for overweight and obesity. BMI is a person's weight in kilograms divided by the square of height in meters. A calculator for BMI is available at www.cdc.gov at obesity/adult/defining.html. In various embodiments, the subject may have a BMI of 25, 30, 35, 40 or higher, such as a BMI of 25-30, 25-30, or 25-40. In some cases, the subject may have severe obesity (also known as class 3 obesity), defined as a BMI of 40 or greater. Obesity is a chronic disease, also a risk factor for other diseases, such as heart disease, hypertension, stroke, diabetes etc.

In some embodiments, the methods of the disclosure decrease, prevent, or ameliorate one or more symptoms of metabolic disease. Symptoms of metabolic disease include glucose intolerance, insulin resistance, high glucose level, and inflammation in adipose tissue.

As used herein, the term "heart failure" refers to a condition in which the heart cannot pump enough blood to meet the body's need.

"Heart failure (HF) is a complex clinical syndrome that can result from any structural or functional cardiovascular disorder causing systemic perfusion inadequate to meet the body's metabolic demands without excessively increasing left ventricular filling pressures. It is characterized by specific symptoms, such as dyspnea and fatigue, and signs, such as fluid retention. As used herein, "chronic heart failure" or "congestive heart failure" or "CHF" refer, interchangeably, to an ongoing or persistent forms of heart failure. Common risk factors for CHF include old age, diabetes, high blood pressure and being overweight. CHF is broadly classified according to the systolic function of the left ventricle as HF with reduced or preserved ejection fraction (HFrEF and HFpEF). The term "heart failure" does not mean that the heart has stopped or is failing completely, but that it is weaker than is normal in a healthy person. In some cases, the condition can be mild, causing symptoms that may only be noticeable when exercising, in others, the condition may be more severe, causing symptoms that may be life-threatening, even while at rest. The most common symptoms of chronic heart failure include shortness of breath, tiredness, swelling of the legs and ankles, chest pain and a cough. In some embodiments, the methods of the disclosure decrease, prevent, or ameliorate one or more symptoms of CHF (e.g., HFpEF) in a subject suffering from or at risk for CHF (e.g., HFpEF). In some embodiments, the disclosure provides methods of treating CHF and conditions that can lead to CHF.

As used herein "acute heart failure" or "decompensated heart failure" refer, interchangeably, to a syndrome of the worsening of signs and symptoms reflecting an inability of the heart to pump blood at a rate commensurate to the needs of the body at normal filling pressure. AHF typically develops gradually over the course of days to weeks and then decompensates requiring urgent or emergent therapy due to the severity of these signs or symptoms. AHF may be the result of a primary disturbance in the systolic or diastolic function of the heart or of abnormal venous or arterial vasoconstriction, but generally represents an interaction of multiple factors, including volume overload. The majority of patients with AHF have decompensation of chronic heart failure (CHF) and consequently much of the discussion of the pathophysiology, presentation, and diagnosis of CHF is directly relevant to an understanding of AHF. In other cases, AHF results from an insult to the heart or an event that impairs heart function, such as an acute myocardial infarction, severe hypertension, damage to a heart valve, abnormal heart rhythms, inflammation or infection of the heart, toxins and medications. In some embodiments, the methods of the disclosure decrease, prevent, or ameliorate one or more symptoms of AHF in a subject suffering from or at risk for AHF. In some embodiments, the disclosure provides methods of treating AHF and conditions that can lead to AHF. AHF may be the result of ischemia associated with myocardial infarction.

In some embodiments, the methods of the disclosure decrease, prevent, or ameliorate one or more symptoms of heart failure in a subject suffering from or at risk for heart failure associated with HFpEF. The terms "heart failure with preserved ejection fraction" or "diastolic heart failure" are used, interchangeably, refers generally to a form of heart failure is characterized by signs and symptoms of heart failure and a left ventricular ejection fraction (LVEF) greater than 50%. The terms may also encompass heart failure associated with intermediate reductions in LVEF (40% to 49%). In some embodiments, HFpEF comprises HFpEF associated with CHF. In some embodiments, HFpEF comprises HFpEF associated with AHF.

HFpEF is more common among older patients and women. Typical symptoms include fatigue, weakness, dyspnea, orthopnea, paroxysmal nocturnal dyspnea, edemal. Signs of HFpEF (e.g., HFpEF associated with CHF) may include S3 heart sound, displaced apical pulse, and jugular venous distension. Echocardiographic findings of normal ejection fraction with impaired diastolic function confirm the diagnosis. Measurement of natriuretic peptides (e.g., BNP or NT-proBNP) is useful in the evaluation of patients with suspected heart failure with preserved ejection fraction in the ambulatory setting.

As used herein, the term "deleterious mutation" refers to a mutation that decreases the function of a gene. Deleterious mutations may include missense mutations, deletions or insertions in coding regions, non-coding mutations that influence gene expression or gene splicing, or others. Deleterious mutations include partial or total deletion of a gene. As used herein, the term may refer to homozygous or heterozygous mutations in a gene, provided the mutation manifests a phenotypic effect upon the carrier.

As used herein, the term "left ventricular internal diameter at diastole" or "LVIDd" refers to left ventricular size at diastole.

As used herein, the term "left ventricular internal diameter at systole" or "LVIDs" refers to left ventricular size at systole.

As used herein, the term "left ventricular mass" refers to the weight of the left ventricle.

As used herein, the term "ejection fraction" refers to the amount of blood being bumped out of the left ventricle each time it contracts, expressed as a percentage to the total amount of blood in left ventricle.

The detailed description of the disclosure is divided into various sections only for the reader's convenience and disclosure found in any section may be combined with that in another section. Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

Treating or Preventing Metabolic Disease

Provided herein are methods of treating or preventing metabolic disease with an HDAC6 inhibitor.

Treating or Preventing Heart Failure with Preserved Ejection Fraction (HFpEF)

Provided herein are methods of treating or preventing Heart Failure with preserved Ejection Fraction (HFpEF) with an HDAC6 inhibitor.

HDAC6 Inhibitors

Histone deacetylases ("HDAC") are a class of enzymes with deacetylase activity with a broad range of genomic and non-genomic substrates. There are eleven Zinc-dependent HDAC enzymes classified based on sequence identity and catalytic activity (Haberland et al., 2009).

Histone deacetylase inhibitors have been described as a therapeutic agents in oncology (Yoon and Eom, 2016), neurodegeneration (Butler et al., 2010) autoimmune disease (Choi et al., 2018), chemotherapy-induced peripheral neuropathy (Krukowski et al., 2017) and cardiac indications (Zhang et al., 2002). Given the role of nuclear HDACs on regulating gene transcription, inhibition of these class of targets is known to have pleiotropic effects in various cell types; most notably resulting in cell toxicities. Therefore, limiting the toxicity of pan-HDAC inhibitors has been a major obstacle in wide-spread utilization for this class of compounds. In addition, significant adverse effects of pan-HDAC inhibitors (e.g. SAHA and Panabinostat) has been observed in the clinic including fatigue, nausea, diarrhea and thrombocytopenia (Subramanian et al., 2010).

In the cardiac-indication space, most studies have utilized pan-HDAC inhibitors (e.g. SAHA, TSA and Givinostat) for the treatment of pressure-overload rodent models with contractile dysfunction including transverse aortic constriction (TAC) (Cao et al., 2011), hypertension in Dahl salt-sensitive rats (Jeong et al., 2018) and myocardial infarction (Nagata et al., 2019). In addition, HDAC6-selective inhibitors have been used to ameliorate the LV systolic dysfunction of pressure overload rodent mode (Demos-Davies et al., 2014) and provide protection against proteotoxicity in a transgenic cardiomyopathy mouse model (McLendon et al., 2014). However, these experiments in pressure overload rodent models that were all accompanied with reduced ejection fraction and exhibited HFrEF phenotypes, are not predictive of treatment for HFpEF. Pressure overload mediated by conventional transverse aortic constriction induces cardiac hypertrophy followed by heart failure with reduced Ejection Fraction (HFrEF) not HFpEF (Mohammadi et al. 2021). HFpEF is distinct from HFrEF. The two forms of heart failure differ fundamentally in the pathophysiological mechanisms, and extent of myocardial loss/dysfunction, the pattern of remodeling at the chamber and ultrastructural level, and the response to therapeutic interventions. (Schiattarella et al., 2020).

HDAC6 belongs to the class IIb enzyme and contains two catalytic domains, a ubiquitin binding domain and a cytoplasmic retention domain (Haberland et al., 2009). HDAC6 is predominately a cytoplasmic enzyme and its best-characterized substrates include tubulin, HSP90 and cortactin (Brindisi et al., 2020).

Pharmacological inhibition of HDAC6 blocks its deacetylase activity, thus resulting in hyperacetylation of its substrates, most notably tubulin (Hubbert et al., 2002).

HDAC6-selective inhibitors are known to have reduced cytotoxicity due to the cytoplasmic nature of HDAC6 substrates and reduced effects on nuclear targets (including H3K9 and c-MYC) and on global transcription (Nebbioso et al., 2017).

Hydroxamic acids are zinc chelators and have been used extensively in the development of pan- and HDAC-selective inhibitors. However, most hydroxamic-acid based HDAC inhibitors either lack the desired selectivity or show poor bioavailability with a poor pharmacokinetic profile (Butler et al., 2010; Santo et al., 2012).

Various selective HDAC6 are known in the art. In addition, using known methods it is routine to screen compounds to identify further selective HDAC6 inhibitors. In particular, given a known HDAC6 inhibitor, a person of skill in the art can identify which analogs of the compound have selective HDAC6 activity.

In some embodiments, the HDAC6 inhibitor is a gene silencing agent, such as an RNA silencing agent (e.g., siRNA). In some embodiments, the HDAC6 inhibitor is not a gene silencing agent. In some embodiments, the HDAC6 is a small molecule HDAC6 inhibitor.

Known HDAC6 Inhibitors

In some embodiments, the HDAC6 inhibitor is CAY10603, tubacin, rocilinostat (ACY-1215), citarinostat (ACY-241), ACY-738, QTX-125, CKD-506, nexturastat A, tubastatin A, or HPOB (listed in Table 1), or an analog thereof.

9,409,858B2, U.S. Pat. No. 9,663,825B2, US20150119327A1, US20150250786A1, U.S. Ser. No. 10/041,046B2, U.S. Pat. No. 9,586,973B2, US20160069887A1, US20140357512A1, U.S. Pat. No. 9,751,832B2, US20160228434A1, US20150105358A1, U.S. Ser. No. 10/660,890B2, US20160271083A1, US20150176076A1, US20200405716A1, U.S. Pat. No. 9,890,136B2, U.S. Ser. No. 10/287,255B2, US20170173083A1, U.S. Ser. No. 10/016,421B2, U.S. Pat. No. 9,987,258B2, U.S. Ser. No. 10/568,854B2, U.S. Ser. No. 10/106,540B2, U.S. Ser. No. 10/266,489B2, U.S. Pat. No. 9,993,459B2, U.S. Ser. No. 10/183,934B2, U.S. Ser. No. 10/494,354B2, U.S. Ser. No. 10/494,353B2, U.S. Ser. No. 10/112,915B2, U.S. Ser. No. 10/377,726B2, U.S. Ser. No. 10/829,462B2, U.S. Ser. No. 10/829,461B2, US20210009539A1, US20210009538A1, U.S. Ser. No. 10/239,845B2, U.S. Ser. No. 10/472,337B2, U.S. Ser. No. 10/479,772B2, U.S. Ser. No. 10/464,911B2, U.S. Ser. No. 10/584,117B2, U.S. Ser. No. 10/538,498B2, U.S. Ser. No. 10/011,611B2, U.S. Ser. No. 10/494,355B2, U.S. Ser. No. 10/040,769B2, U.S. Ser. No. 10/858,323B2, U.S. Ser. No. 10/654,814B2, US20190209559A1, US20190185462A1, US20190192521A1, US20190321361A1, US20200046698A1, US20190262337A1, US20190282573A1, US20190282574A1, US20200071288A1, U.S. Ser. No. 10/745,389B2, U.S. Ser.

TABLE 1

| Compound | Description | IC$_{50}$ |
| --- | --- | --- |
| CAY10603 | CAY10603 is a potent and selective HDAC6 inhibitor with IC50 of 2 pM, >200-fold selectivity over other HDACs. | 2 pM |
| Tubacin | Tubacin is a highly potent and selective, reversible, cell-permeable HDAC6 inhibitor with an IC50 of 4 nM, approximately 350-fold selectivity over HDAC1. | 4 nM |
| Rocilinostat (ACY-1215) | Rocilinostat (ACY-1215) is a selective HDAC6 inhibitor with IC50 of 5 nM. It is >10-fold more selective for HDAC6 than HDAC1/2/3 (class I HDACs) with slight activity against HDAC8, minimal activity against HDAC4/5/7/9/11, Sirtuin1, and Sirtuin2. Phase 2. | 4.7 nM |
| Citarinostat (ACY-241) | Citarinostat (ACY-241, HDAC-IN-2) is an orally available selective HDAC6 inhibitor with IC50 of 2.6 nM and 46 nM for HDAC6 and HDAC3, respectively. It has 13 to 18-fold selectivity towards HDAC6 in comparison to HDAC1-3. | 2.6 nM |
| ACY-738 | ACY-738 inhibits HDAC6 with low nanomolar potency (IC50 = 1.7 nM) and a selectivity of 60- to 1500-fold over class I HDACs. | 1.7 nM |
| QTX-125 | HDAC6 inhibitor with 11-fold selectivity over HDAC1 | 0.6 nM |
| CKD-506 | HDAC6 inhibitor with an 80-fold selectivity over HDAC1 | 2.9 nM |
| Nexturastat A | Nexturastat A is a potent and selective HDAC6 inhibitor with IC50 of 5 nM, >190-fold selectivity over other HDACs. | 5 nM |
| Tubastatin A | Tubastatin A is a potent and selective HDAC6 inhibitor with IC50 of 15 nM. It is selective against all the other isozymes (1000-fold) except HDAC8 (57-fold). | 15 nM |
| HPOB | HPOB is a potent, selective HDAC6 inhibitor with IC50 of 56 nM, >30-fold selectivity over other HDACs. | 56 nM |

Further illustrative HDAC6 inhibitors are provided in U.S. Patent Publications Nos. U.S. Pat. No. 8,227,516B2, US20100292169A1, US20070207950A1, U.S. Pat. No. 8,222,423B2, US20100093824A1, US20100216796A1, U.S. Pat. No. 8,673,911B2, U.S. Pat. No. 8,217,076B2, U.S. Pat. No. 8,440,716B2, US20110195432A1, U.S. Pat. No. 8,624,040B2, U.S. Pat. No. 9,096,518B2, U.S. Pat. No. 8,431,538B2, US20120258993A1, U.S. Pat. No. 8,546,588B2, U.S. Pat. No. 8,513,421B2, US20140031368A1, US20120015943A1, US20120015942A1, US20140243335A1, US20130225543A1, U.S. Pat. No. 8,471,026B2, U.S. Pat. No. 9,238,028B2, U.S. Pat. No. 8,765,773B2, U.S. Pat. No. RE47,009E1, US20140294856A1, U.S. Pat. No. 9,512,083B2, U.S. Pat. No. 9,670,193B2, U.S. Pat. No. 9,345,905B2, U.S. Pat. No. 10/357,493B2, US20200171028A1, US20200054773A1, US20200308174A1, US20200155549A1, U.S. Ser. No. 10/435,399B2, US20200216563A1, US20190216751A1, US20200339569A1, US20210078963A1, US20210077487A1, US20190270733A1, US20190270744A1, US20200022966A1, and US20210094944A1, which are incorporated herein for purposes of identifying HDAC6 inhibitors that may be used in the methods disclosed herein. In some embodiments, the HDAC6 inhibitor is TYA-631 or an analog thereof.

Fluoroalkyl-Oxadiazole Derivatives

In some embodiments, the HDAC6 inhibitor is a fluoroalkyl-oxadiazole derivative. Illustrative fluoroalkyl-oxadiazole derivatives that may be used as HDAC6 inhibitors include those described herein and those described in Int'l Pat. Appl. No. PCT/US2020/066439, published as WO2021127643A1 the content of which is incorporated by reference herein in its entirety. PCT/US2020/066439, published as WO2021127643A1, also describes methods of synthesis of such compounds, which are specifically incorporated by reference herein.

In some embodiments, the HDAC6 inhibitor is a compound of Formula (I):

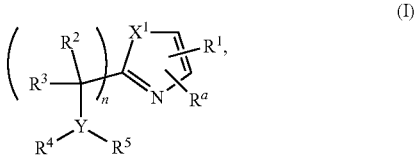

wherein $R^1$ is selected from the group consisting of:

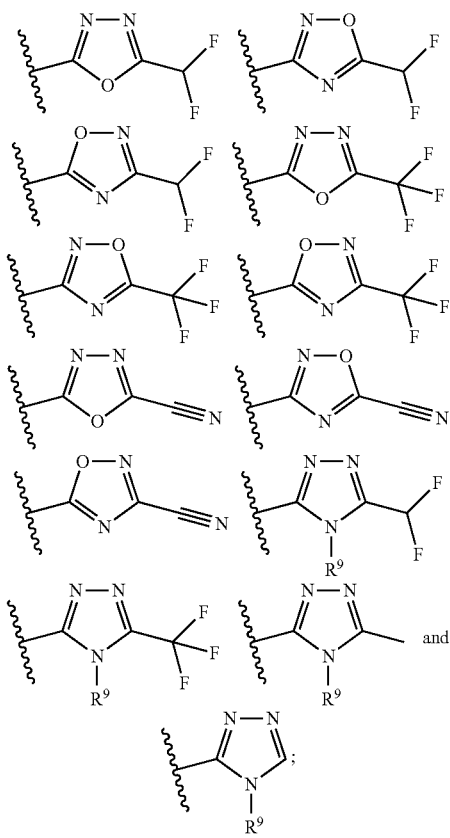

$R^a$ is selected from the group consisting of H, halo, $C_{1-3}$ alkyl, cycloalkyl, haloalkyl, and alkoxy;

$R^2$ and $R^3$ are independently selected from the group consisting of H, halogen, alkoxy, haloalkyl, aryl, heteroaryl, alkyl, and cycloalkyl each of which is optionally substituted, or $R^2$ and $R^3$ together with the atom to which they are attached form a cycloalkyl or heterocyclyl;

$R^4$ and $R^5$ are independently selected from the group consisting of H, —(SO$_2$)R$^2$, —(SO$_2$)NR$^2$R$^3$, —(CO)R$^2$, —(CONR$^2$R$^3$), aryl, arylheteroaryl, alkylenearyl, heteroaryl, cycloalkyl, heterocyclyl, alkyl, haloalkyl, and alkoxy, each of which is optionally substituted, or $R^4$ and $R^5$ together with the atom to which they are attached form a cycloalkyl or heterocyclyl, each of which is optionally substituted;

$R^9$ is selected from the group consisting of H, $C_1$-$C_6$ alkyl, haloalkyl, cycloalkyl and heterocyclyl;

$X^1$ is selected from the group consisting of S, O, NH and NR$^6$, wherein R$^6$ is selected from the group consisting of $C_1$-$C_6$ alkyl, alkoxy, haloalkyl, cycloalkyl and heterocyclyl;

Y is selected from the group consisting of CR$^2$, O, N, S, SO, and SO$_2$, wherein when Y is O, S, SO, or SO$_2$, R$^5$ is not present and when R$^4$ and R$^5$ together with the atom to which they are attached form a cycloalkyl or heterocyclyl, Y is CR$^2$ or N; and n is selected from 0, 1, and 2.

In some embodiments of Formula (I), n is 0. In some embodiments, n is 1. In some embodiments n is 2. In some embodiments, n is 0 or 1. In some embodiments n is 1 or 2. In some embodiments n is 0 or 2.

In some embodiments of Formula (I), $X^1$ is O. In some embodiments, $X^1$ is S. In some embodiments, $X^1$ is NH. In some embodiments, $X^1$ is NR$^6$. In some embodiments, $X^1$ is selected from the group consisting of S, O, and NR$^6$. In some embodiments, $X^1$ is selected from the group consisting of S, O, and NCH$_3$. In some embodiments, $X^1$ is S or O. In some embodiments, $X^1$ is S or NR$^6$. In some embodiments, R$^6$ is $C_1$-$C_6$ alkyl.

In some embodiments of Formula (I), R$^2$ and R$^3$ are H.

In some embodiments of Formula (I), Y is N, CR$^2$, or O. In some embodiments, Y is N or O. In some embodiments, Y is N. In some embodiments, Y is CR$^2$. In some embodiments, Y is O.

In some embodiments, R$^4$ and R$^5$ are independently selected from the group consisting of H, —(SO$_2$)R$^2$, —(SO$_2$)NR$^2$R$^3$, —(CO)R$^2$, —(CONR$^2$R$^3$), aryl, arylheteroaryl, heteroaryl, alkylenearyl, cycloalkyl, alkylenecycloalkyl, heterocyclyl, alkyleneheterocyclyl, alkyl, haloalkyl, and alkoxy, each of which is optionally substituted, or R$^4$ and R$^5$ together with the atom to which they are attached form a cycloalkyl or heterocyclyl, each of which is optionally substituted In some embodiments of Formula (I), R$^4$ is selected from the group consisting of —C(O)—alkyl, —C(O)-cycloalkyl, —C(O)-aryl, —C(O)-heteroaryl, —(SO$_2$)NR$^2$R$^3$, —SO$_2$-alkyl, and —SO$_2$-cycloalkyl, each of which is optionally substituted. In some embodiments, R$^4$ is selected from the group consisting of —C(O)-alkyl, —C(O)-cycloalkyl, —SO$_2$-alkyl, —SO$_2$-haloalkyl, —SO$_2$-cycloalkyl, and —(SO$_2$)NR$^2$R$^3$, each of which is optionally substituted. In some embodiments, aryl is optionally substituted with one or more halogens. In some embodiments of Formula (I), R$^4$ is selected from the group consisting of —SO$_2$ alkyl, —SO$_2$ haloalkyl, or —SO$_2$ cycloalkyl. In some embodiments of Formula (I), R$^4$ is selected from the group consisting of —SO$_2$Me, —SO$_2$Et, and —SO$_2$-cPr. In some embodiments, R$^2$ and R$^3$ are each independently —C$_{1-5}$ alkyl. In some embodiments, R$^2$ and R$^3$ taken together with the nitrogen atom to which they are attached form an optionally substituted heterocyclyl. In some embodiments, the optionally substituted heterocyclyl is morpholine, thiomorpholine, or thiomorpholine 1,1-dioxide.

In some embodiments of Formula (I), R$^5$ is aryl, heteroaryl, or cycloalkyl, each of which is optionally substituted.

In some embodiments, $R^5$ is aryl. In some embodiments, aryl is

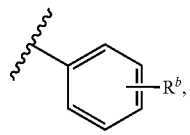

wherein $R^b$ is one or more selected from the group consisting of halogen, haloalkyl, alkyl, Oalkyl, Ohaloalkyl, alkylene-Ohaloalkyl, cycloalkyl, heterocyclyl aryl, heteroaryl, alkylnitrile, or CN. In some embodiments, the haloalkyl is selected from $CF_3$, $CF_2CH_3$, $CHF_2$, or $CH_2F$. In some embodiments, the alkyl is a —$C_{1-5}$ alkyl. In some embodiments, —$C_{1-5}$ alkyl is methyl, ethyl, propyl, i-propyl, butyl, or t-butyl. In some embodiments, methyl, ethyl, propyl, i-propyl, butyl, or t-butyl is optionally substituted with OH. In some embodiments, the cycloalkyl is a $C_{3-6}$ cycloalkyl. In some embodiments, the aryl is a phenyl. In some embodiments, the heteroaryl is 5- or 6-membered heteroaryl having 1, 2, or 3 heteroatoms selected from N, O, and S. In some embodiments, the heterocyclyl is a 4- to 7-member heterocyclyl with 1 or 2 heteroatoms selected from N, O, and S. In some embodiments, the Ohaloalkyl is selected from $OCF_3$, $OCHF_2$, or $OCH_2F$. In some embodiments, the Oalkyl is O-methyl, O-ethyl, O-propyl, O-butyl, or O-t-butyl.

In some embodiments, $R^5$ is heteroaryl. In some embodiments, heteroaryl is an optionally substituted 5- to 14-membered heteroaryl. In some embodiments, heteroaryl is an optionally substituted 5- to 14-membered heteroaryl having 1, 2, or 3 heteroatoms selected from the group consisting of N, O, and S. In some embodiments, the optionally substituted 5- to 14-membered heteroaryl is selected from the group consisting of pyrazolyl, imidazolyl, oxazolyl, thiazolyl, pyridinyl, pyrimidinyl, pyrazinyl, pyridazinyl, quinolinyl, isoquinolinyl, quinoxalinyl, cinnolinyl, indolizinyl, azaindolizinyl, indolyl, azaindolyl, benzoxazolyl, benzthiazolyl, benzfuranyl, benzothiophenyl, imidazopyridinyl, imidazopyrazinyl, and benzimidazolyl. In some embodiments, the optionally substituted 5- to 14-membered heteroaryl is selected from the group consisting of pyrazolyl, pyridinyl, pyrimidinyl, pyrazinyl, pyridazinyl, benzoxazolyl, imidazopyridinyl, and imidazopyrazinyl. In some embodiments, $R^5$

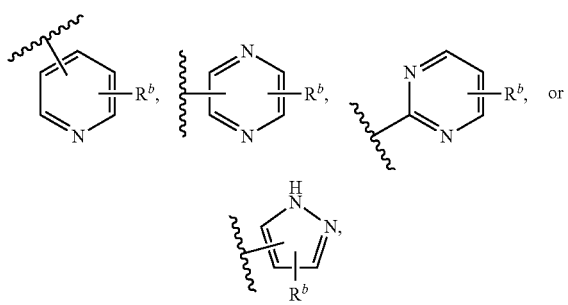

wherein $R^b$ is one or more selected from the group consisting of halogen, haloalkyl, alkyl, Oalkyl, Ohaloalkyl, alkylene-Ohaloalkyl, cycloalkyl, heterocyclyl aryl, heteroaryl, alkylnitrile, or CN. In some embodiments, the haloalkyl is selected from $CF_3$, $CF_2CH_3$, $CHF_2$, or $CH_2F$. In some embodiments, the alkyl is a —$C_{1-5}$ alkyl. In some embodiments, —$C_{1-5}$ alkyl is methyl, ethyl, propyl, i-propyl, butyl, or t-butyl. In some embodiments, methyl, ethyl, propyl, i-propyl, butyl, or t-butyl is optionally substituted with OH. In some embodiments, the cycloalkyl is a $C_{3-6}$ cycloalkyl. In some embodiments, the aryl is a phenyl. In some embodiments, the heteroaryl is 5- or 6-membered heteroaryl having 1, 2, or 3 heteroatoms selected from N, O, and S. In some embodiments, the heterocyclyl is a 4- to 7-member heterocyclyl with 1 or 2 heteroatoms selected from N, O, and S. In some embodiments, the Ohaloalkyl is selected from $OCF_3$, $OCHF_2$, or $OCH_2F$. In some embodiments, the Oalkyl is O-methyl, O-ethyl, O-propyl, O-butyl, or O-t-butyl.

In some embodiments, $R^5$ is cycloalkyl. In some embodiments, cycloalkyl is a cyclopropyl, cyclobutyl, cyclopentyl, or cyclohexyl, each of which is optionally substituted. In some embodiments, the optionally substituted cycloalkyl is

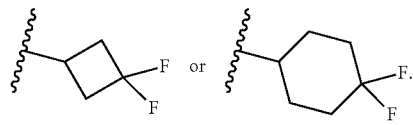 [SMILES: *C1CC(F)(F)C1 ; *C1CCC(F)(F)CC1]

In some embodiments, $R^5$ is selected from the group consisting of phenyl, 3-chlorophenyl, 3-chloro-4-fluorophenyl, 3-trifluoromethylphenyl, 3,4-difluorophenyl, and 2,6-difluorophenyl. In some embodiments, $R^5$ is cyclopropyl. In some embodiments, $R^5$ selected from the group consisting of pyridin-3-yl and 1-methylindazole-6-yl. In some embodiments, $R^5$ is selected from the group consisting of H, phenyl, 3-chlorophenyl, 3-chloro-4-fluorophenyl, 3-trifluoromethylphenyl, 3,4-difluorophenyl, cyclopropyl, pyridin-3-yl, 1-methylindazole-6-yl, 3,3-difluorocyclobutyl, and 4,4-difluorocyclohexyl. In some embodiments, $R^5$ is 3-chlorophenyl. In some embodiments $R^5$ is H. In some embodiments, $R^5$ is

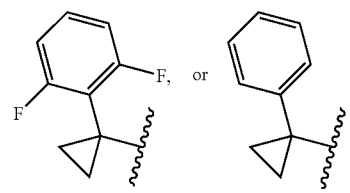

In some embodiments, $R^5$ is —$CH_2CH_2Ph$. In some embodiments, $R^5$ is selected from the group consisting of H, aryl, heteroaryl, alkylenearyl, cycloalkyl, heterocyclyl, alkyl, and haloalkyl, each of which is optionally substituted, or $R^4$ and $R^5$ together with the atom to which they are attached form an optionally substituted heterocyclyl.

In some embodiments of Formula (I), $R^5$ is optionally substituted with one or more halogen, haloalkyl, alkyl, Oalkyl, Ohaloalkyl, cycloalkyl, heterocyclyl aryl, or heteroaryl. In some embodiments, the haloalkyl is selected from $CF_3$, $CHF_2$, or $CH_2F$. In some embodiments, the alkyl is a —$C_{1-5}$ alkyl. In some embodiments, —$C_{1-5}$ alkyl is methyl, ethyl, propyl, i-propyl, butyl, or t-butyl. In some embodiments, the cycloalkyl is a $C_{3-6}$ cycloalkyl. In some embodiments, the aryl is a phenyl. In some embodiments, the heteroaryl is 5- or 6-membered heteroaryl having 1, 2, or 3 heteroatoms selected from N, O, and S. In some embodiments, the heterocyclyl is a 4- to 7-member heterocyclyl with 1 or 2 heteroatoms selected from N, O, and S. In some embodiments, the Ohaloalkyl is selected from $OCF_3$, $OCHF_2$, or $OCH_2F$. In some embodiments, the Oalkyl is O-methyl, O-ethyl, O-propyl, O-i-propyl, O-butyl, or O-t-butyl.

In some embodiments of Formula (I), $R^4$ is H or $-C_{1-5}$ alkyl and $R^5$ is aryl. In some embodiments, $R^4$ is H or $-C_{1-5}$ alkyl and $R^5$ is heteroaryl. In some embodiments, $R^4$ is H or $-C_{1-5}$ alkyl and $R^5$ is cycloalkyl. In some embodiments, the $-C_{1-5}$ alkyl is methyl, ethyl, or propyl. In some embodiments, the $-C_{1-5}$ alkyl is methyl. In some embodiments, the aryl is optionally substituted phenyl. In some embodiments, the heteroaryl is a 5- to 14-membered heteroaryl having 1, 2, or 3 heteroatoms selected from the group consisting of N, O, and S. In some embodiments, the optionally substituted 5- to 14-membered heteroaryl is selected from the group consisting of pyrazolyl, imidazolyl, oxazolyl, thiazolyl, pyridinyl, pyrimidinyl, pyrazinyl, pyridazinyl, quinolinyl, isoquinolinyl, quinoxalinyl, cinnolinyl, indolizinyl, azaindolizinyl, indolyl, azaindolyl, benzoxazolyl, benzthiazolyl, benzfuranyl, benzothiophenyl, imidazopyridinyl, imidazopyrazinyl, and benzimidazolyl. In some embodiments, the heteroaryl is a 5- or 6-membered heteroaryl ring. In some embodiments, the 5-membered heteroaryl is optionally substituted pyrazolyl, imidazolyl, or oxazolyl. In some embodiments, the 6-membered heteroaryl is optionally substituted pyridinyl, pyrimidinyl, pyrazinyl, or pyridazinyl. In some embodiments, cycloalkyl is optionally substituted cyclopropyl, cyclobutyl, cyclopentyl, or cyclohexyl. In some embodiments, aryl is optionally substituted with one or more substituents selected from the group consisting of halogen, $C_{1-6}$ haloalkyl, $C_{1-6}$ alkyl, $O-C_{1-6}$ alkyl, $O-C_{1-6}$ haloalkyl, or $C_{3-6}$ cycloalkyl. In some embodiments, heteroaryl is optionally substituted with one or more substituents selected from the group consisting of halogen, $C_{1-6}$ haloalkyl, $C_{1-6}$ alkyl, $O-C_{1-6}$ alkyl, $O-C_{1-6}$ haloalkyl, or $C_{3-6}$ cycloalkyl.

In some embodiments of Formula (I), $R^4$ is $-(CO)R^2$ and $R^5$ is aryl. In some embodiments, $R^4$ is $-(CO)R^2$ and $R^5$ is heteroaryl. In some embodiments, $R^4$ is $-(CO)R^2$ and $R^5$ is cycloalkyl. In some embodiments, the aryl is optionally substituted phenyl. In some embodiments, the aryl is optionally substituted phenyl. In some embodiments, the heteroaryl is a 5- to 14-membered heteroaryl having 1, 2, or 3 heteroatoms selected from the group consisting of N, O, and S. In some embodiments, the optionally substituted 5- to 14-membered heteroaryl is selected from the group consisting of pyrazolyl, imidazolyl, oxazolyl, thiazolyl, pyridinyl, pyrimidinyl, pyrazinyl, pyridazinyl, quinolinyl, isoquinolinyl, quinoxalinyl, cinnolinyl, indolizinyl, azaindolizinyl, indolyl, azaindolyl, benzoxazolyl, benzthiazolyl, benzfuranyl, benzothiophenyl, imidazopyridinyl, imidazopyrazinyl, and benzimidazolyl. In some embodiments, the heteroaryl is a 5- or 6-membered heteroaryl ring. In some embodiments, the 5-membered heteroaryl is optionally substituted pyrazolyl, imidazolyl, oxazolyl, In some embodiments, the 6-membered heteroaryl is optionally substituted pyridinyl, pyrimidinyl, pyrazinyl, or pyridazinyl. In some embodiments, cycloalkyl is optionally substituted cyclopropyl, cyclobutyl, cyclopentyl, or cyclohexyl. In some embodiments, aryl is optionally substituted with one or more substituents selected from the group consisting of halogen, $C_{1-6}$ haloalkyl, $C_{1-6}$ alkyl, $O-C_{1-6}$ alkyl, $O-C_{1-6}$ haloalkyl, or $C_{3-6}$ cycloalkyl. In some embodiments, heteroaryl is optionally substituted with one or more substituents selected from the group consisting of halogen, $C_{1-6}$ haloalkyl, $C_{1-6}$ alkyl, $O-C_{1-6}$ alkyl, $O-C_{1-6}$ haloalkyl, or $C_{3-6}$ cycloalkyl.

In some embodiments of Formula (I), $R^4$ is $-(SO_2)R^2$ and $R^5$ is aryl. In some embodiments, $R^4$ is $-(SO_2)R^2$ and $R^5$ is heteroaryl. In some embodiments, $R^4$ is $-(SO_2)R^2$ and $R^5$ is cycloalkyl. In some embodiments, the aryl is optionally substituted phenyl. In some embodiments, the heteroaryl is a 5- to 14-membered heteroaryl having 1, 2, or 3 heteroatoms selected from the group consisting of N, O, and S. In some embodiments, the optionally substituted 5- to 14-membered heteroaryl is selected from the group consisting of pyrazolyl, imidazolyl, oxazolyl, thiazolyl, pyridinyl, pyrimidinyl, pyrazinyl, pyridazinyl, quinolinyl, isoquinolinyl, quinoxalinyl, cinnolinyl, indolizinyl, azaindolizinyl, indolyl, azaindolyl, benzoxazolyl, benzthiazolyl, benzfuranyl, benzothiophenyl, imidazopyridinyl, imidazopyrazinyl, and benzimidazolyl. In some embodiments, the heteroaryl is a 5- or 6-membered heteroaryl ring. In some embodiments, the 5-membered heteroaryl is optionally substituted pyrazolyl, imidazolyl, or oxazolyl. In some embodiments, the 6-membered heteroaryl is optionally substituted pyridinyl, pyrimidinyl, pyrazinyl, or pyridazinyl. In some embodiments, cycloalkyl is optionally substituted cyclopropyl, cyclobutyl, cyclopentyl, or cyclohexyl. In some embodiments, aryl is optionally substituted with one or more substituents selected from the group consisting of halogen, $C_{1-6}$ haloalkyl, $C_{1-6}$ alkyl, $O-C_{1-6}$ alkyl, $O-C_{1-6}$ haloalkyl, or $C_{3-6}$ cycloalkyl. In some embodiments, heteroaryl is optionally substituted with one or more substituents selected from the group consisting of halogen, $C_{1-6}$ haloalkyl, $C_{1-6}$ alkyl, $O-C_{1-6}$ alkyl, $O-C_{1-6}$ haloalkyl, or $C_{3-6}$ cycloalkyl. In some embodiments, the $C_{1-6}$ haloalkyl is $CF_3$, $CHF_2$, or $CH_2F$. In some embodiments, the $O-C_{1-6}$ haloalkyl is $OCF_3$, $OCHF_2$, or $OCH_2F$. In some embodiments, cycloalkyl is optionally substituted with halogen, $C_{1-6}$ alkyl, or $O-C_{1-6}$ alkyl.

In some embodiments of Formula (I), $R^4$ and $R^5$ together with the atom to which they are attached form a cycloalkyl or heterocyclyl. In some embodiments, $R^4$ and $R^5$ together with the atom to which they are attached form a cycloalkyl or heterocyclyl, each of which is optionally substituted. In some embodiments, the cycloalkyl or heterocyclyl is optionally substituted with $-NS(O_2)(alkyl)(aryl)$. In some embodiments, the alkyl is $C_{1-5}$ alkyl and the aryl is phenyl optionally substituted with one or more halogen atoms. In some embodiments, the heterocyclyl is a 4- to 10-membered heterocyclyl. In some embodiments the heterocyclyl is a saturated 4- to 7-membered heterocyclyl.

In some embodiments of Formula (I), n is 0 and $R^4$ and $R^5$ together with the atom to which they are attached form an optionally substituted heterocyclyl selected from the group consisting of:

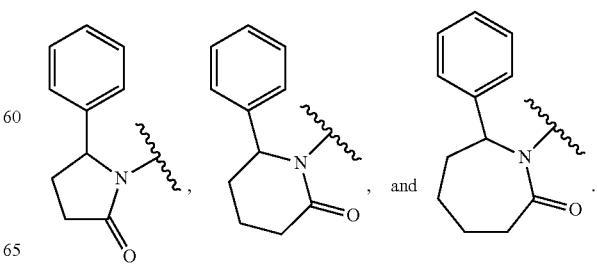

In some embodiments, the optionally substituted heterocyclyl is

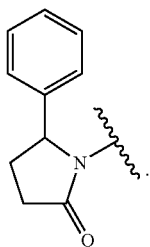 [SMILES: *N1C(=O)CCC1c1ccccc1]

In some embodiments, the optionally substituted heterocyclyl is

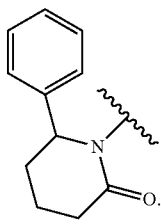 [SMILES: *N1C(=O)CCCC1c1ccccc1]

In some embodiments, the optionally substituted heterocyclyl is

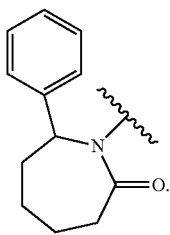 [SMILES: *N1C(=O)CCCCC1c1ccccc1]

In some embodiments of Formula (I) $R^1$ is selected from the group consisting of

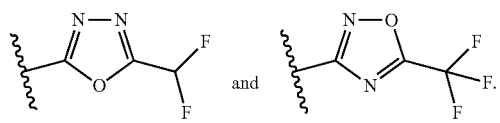 [SMILES: *c1nnc(C(F)F)o1 ; *c1noc(C(F)(F)F)n1]

In some embodiments of Formula (I), $R^1$ is

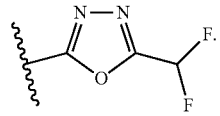 [SMILES: *c1nnc(C(F)F)o1]

In some embodiments, $R^1$ is

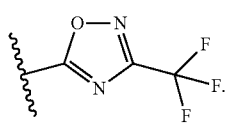

In some embodiments, $R^1$ is

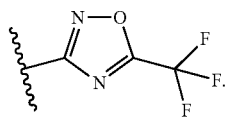 [SMILES: *c1noc(C(F)(F)F)n1]

In some embodiments, $R^1$

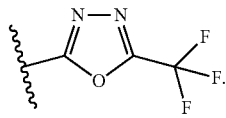 [SMILES: *c1nnc(C(F)(F)F)o1]

In some embodiments of Formula (I), $R^a$ is H, halo, $C_{1-3}$ alkyl, or haloalkyl. In some embodiments, $R^a$ is H. In some embodiments, $R^a$ is $C_{1-3}$ alkyl. In some embodiments, $R^a$ is haloalkyl. In some embodiments, halo is F. In some embodiments, the $C_{1-3}$ alkyl alkyl is methyl, ethyl or isopropyl. In some embodiments, haloalkyl is $CF_3$, $CHF_2$, or $CH_2F$.

In some embodiments of Formula (I), Y is CH and $R^4$ and $R^5$ are H.

In some embodiments of Formula (I), Y is N, $R^4$ is H, and $R^5$ is ethyl optionally substituted with —N(S(O_2)alkyl)(aryl) or —N(S(O_2)cycloalkyl)(aryl). In some embodiments, alkyl is $C_{1-5}$ alkyl, cycloalkyl is $C_{3-6}$ cycloalkyl, and aryl is phenyl optionally substituted with one or more halogen atoms.

In some embodiments of Formula (I), n is 1, $X^1$ is O or N, Y is N, $R^1$ is

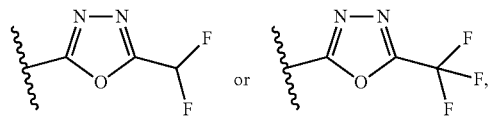 [SMILES: *c1nnc(C(F)F)o1 ; *c1nnc(C(F)(F)F)o1]

$R^2$ and $R^3$ are H, $R^4$ is H, —C(O)alkyl, —C(O)cycloalkyl, —(SO_2)NR^2R^3, —SO_2 alkyl, —SO_2 haloalkyl and —SO_2 cycloalkyl, each of which is optionally substituted, and $R^5$ is aryl, heteroaryl, or cycloalkyl, each of which is optionally substituted.

In some embodiments of Formula (I), n is 1, $X^1$ is O or N, Y is O, $R^1$ is

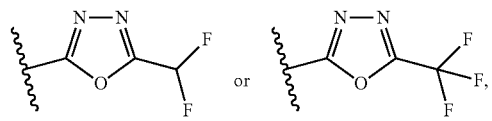 [SMILES: *c1nnc(C(F)F)o1 ; *c1nnc(C(F)(F)F)o1]

$R^2$ and $R^3$ are H, and $R^5$ is aryl, heteroaryl, cycloalkyl, or alkylenecycloalkyl, each of which is optionally substituted.

In some embodiments of Formula (I), n is 0, $X^1$ is O or N, Y is N, $R^1$ is

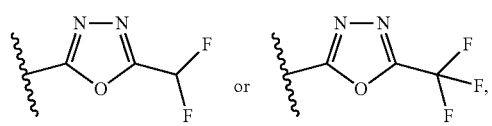 [SMILES: *c1nnc(C(F)F)o1 ; *c1nnc(C(F)(F)F)o1]

and R⁴ and R⁵ taken together with the atom to which they are attached form a cycloalkyl or heterocyclyl, each of which is optionally substituted.

In some embodiments, the present disclosure provides a compound of Formula (Ia) or a pharmaceutically acceptable salt thereof:

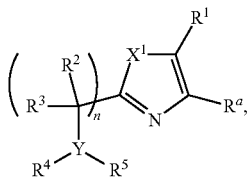

(Ia)

wherein:

R¹, R², R³, R⁴, R⁵, Rᵃ, X¹, n, and Y are as defined above for Formula (I).

In some embodiments of Formula (Ia), R¹ is

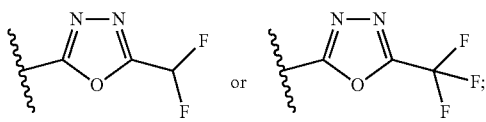 [SMILES: *c1nnc(C(F)F)o1 ; *c1nnc(C(F)(F)F)o1]

n is 1; Y is N; X¹ is S or O; and variables R², R³, R⁴, R⁵, and Rᵃ are as defined above for Formula (I).

In some embodiments of Formula (Ia), n is 1, X¹ is S, Y is N, R¹ is

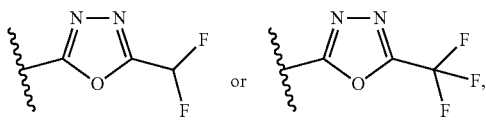 [SMILES: *c1nnc(C(F)F)o1 ; *c1nnc(C(F)(F)F)o1]

R² and R³ are H, R⁴ is —SO₂ alkyl, —SO₂ haloalkyl, or —SO₂ cycloalkyl, each of which is optionally substituted, R⁵ is heteroaryl, each of which is optionally substituted, and Rᵃ is H or F. In some further embodiments, R⁴ is —SO₂C₁₋₅ alkyl, —SO₂ cyclopropyl, —SO₂CF₃ or —SO₂CHF₂, and the heteroaryl is optionally substituted pyridine or pyrazine. In some further embodiments, the heteroaryl is optionally substituted pyridine.

In some embodiments of Formula (Ia), n is 1, X¹ is S, Y is N, R¹ is

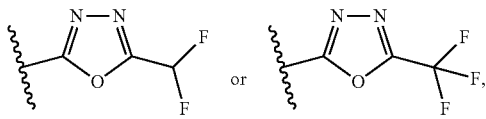 [SMILES: *c1nnc(C(F)F)o1 ; *c1nnc(C(F)(F)F)o1]

R² and R³ are H, R⁴ is —SO₂Me, —SO₂Et, or —SO₂ cyclopropyl, each of which is optionally substituted, R⁵ is pyridine or pyrazine, each of which is optionally substituted, and Rᵃ is H. In some embodiments, R⁵ is optionally substituted pyridine.

In some embodiments of Formula (Ia), n is 1, X¹ is S, Y is N, R¹ is

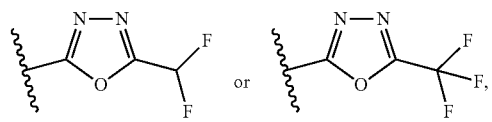 [SMILES: *c1nnc(C(F)F)o1 ; *c1nnc(C(F)(F)F)o1]

R² and R³ are H, R⁴ is —SO₂ alkyl or —SO₂ cycloalkyl, each of which is optionally substituted, R⁵ is

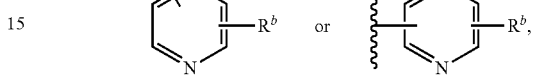

wherein Rᵇ is selected from the group consisting of halogen, —C₁₋₅ alkyl, haloalkyl, —OC₁₋₅ alkyl, —Ohaloalkyl, —CH₂Ohaloalkyl, cyclopropyl, and CN, and Rᵃ is H. In some embodiments, the halogen is F or Cl. In some embodiments, the haloalkyl is CF₃, CHF₂, CH₂CF₃, or CF₂CH₃. In some embodiments, the —C₁₋₅ alkyl is methyl.

In some embodiments of Formula (Ia), n is 1, X¹ is S, Y is N, R¹ is

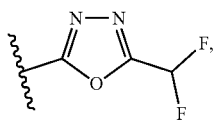

R² and R³ are H, R⁴ is —SO₂Me, —SO₂Et, or —SO₂ cyclopropyl, each of which is optionally substituted, and R⁵ is

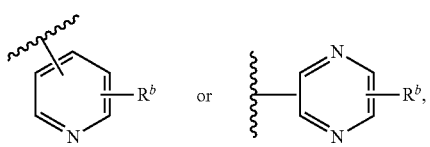

wherein Rᵇ is selected from the group consisting of halogen, —C₁₋₅ alkyl, haloalkyl, —OC₁₋₅ alkyl, —Ohaloalkyl, —CH₂Ohaloalkyl, cyclopropyl, or CN, and Rᵃ is H. In some embodiments, the halogen is F or Cl. In some embodiments, the haloalkyl is CF₃, CHF₂, CH₂CF₃, or CF₂CH₃. In some embodiments, the —C₁₋₅ alkyl is methyl.

In some embodiments of Formula (Ia), n is 1, X¹ is S, Y is N, R¹ is

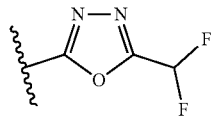 [SMILES: *c1nnc(C(F)F)o1]

R² and R³ are H, R⁴ is —SO₂Me, —SO₂Et, or —SO₂ cyclopropyl, each of which is optionally substituted, and R⁵ is

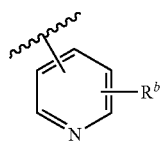

wherein $R^b$ is selected from the group consisting of $C_1$, F, Me, cyclopropyl, $CF_3$, $CHF_2$, $CF_2CH_3$, $OCF_3$, $OCHF_2$, $OCH_2CF_2H$ and CN, and $R^a$ is H.

In some embodiments, the present disclosure provides a compound of Formula (Ib) or a pharmaceutically acceptable salt thereof:

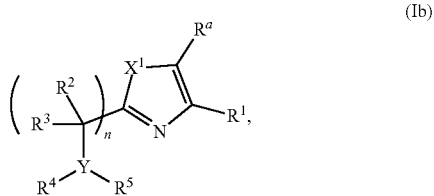

(Ib)

wherein:
$R^1$, $R^2$, $R^3$, $R^4$, $R^5$, $R^a$, $X^1$, n, and Y are as defined above for Formula (I).

In some embodiments of Formulas (I)—(Ib), each optionally substituted alkyl is independently an optionally substituted $C_{1-6}$ alkyl. In some embodiments, the $C_{1-6}$ alkyl is Me or Et.

In some embodiments of Formulas (I)—(Ib), each optionally substituted haloalkyl is independently an optionally substituted $C_{1-6}$ haloalkyl. In some embodiments, the $C_{1-6}$ haloalkyl is $CF_3$, $CHF_2$, or $CH_2F$. In some embodiments, the $C_{1-6}$ haloalkyl is $CF_3$ or $CHF_2$.

In some embodiments of Formulas (I)—(Ib), each optionally substituted cycloalkyl is independently an optionally substituted $C_{3-12}$ cycloalkyl. In some embodiments, the cycloalkyl is a $C_{3-6}$ cycloalkyl. In some embodiments, the cycloalkyl is selected from the group consisting of cyclopropyl, cyclobutyl, cyclopentyl, and cyclohexyl.

In some embodiments of Formulas (I)—(Ib), each optionally substituted heterocyclyl is independently an optionally substituted 3-12 membered heterocycloalkyl having 1 or 2 heteroatoms independently selected from N, O, and S. In some embodiments, each optionally substituted heterocyclyl is independently an optionally substituted 3-6 membered heterocycloalkyl having 1 or 2 heteroatoms independently selected from N, O, and S. In further embodiments, the heterocycloalkyl is an optionally substituted 5-membered or 6-membered heterocycle having 1 or 2 heteroatoms independently selected from N, O, and S. In some embodiments, the heterocyclyl is selected from the group consisting of aziridinyl, azetidinyl, pyrrolidinyl, piperidinyl, and morpholinyl, and thiomorpholinyl.

In some embodiments of Formulas (I)—(Ib), each optionally substituted aryl is independently a $C_{6-12}$ aryl. In further embodiments, the $C_{6-12}$ aryl is an optionally substituted phenyl.

In some embodiments of Formulas (I)—(Ib), each optionally substituted heteroaryl is independently a 5-12 membered heteroaryl having 1, 2, or 3 heteroatoms independently selected from N, O, and S. In some embodiments, each optionally substituted heteroaryl is independently a 5-12 membered heteroaryl having 3 heteroatoms independently selected from N, O, and S. In some embodiments, each optionally substituted heteroaryl is independently a membered heteroaryl having 2 heteroatoms independently selected from N, O, and S. In some embodiments, each optionally substituted heteroaryl is independently a 5-12 membered heteroaryl having 1 heteroatom independently selected from N, O, and S. In further embodiments, each optionally substituted heteroaryl is an optionally substituted 5-membered or 6-membered heteroaryl having 1 heteroatom independently from N, O, and S. In some embodiments, each heteroaryl is independently selected from the group consisting of tetrazole, oxadiazole, thiadiazole, imidazole, pyrazole, thiazole, or oxazole, each of which is optionally substituted.

In some embodiments, the compound of Formula (I) is selected from the group consisting of:

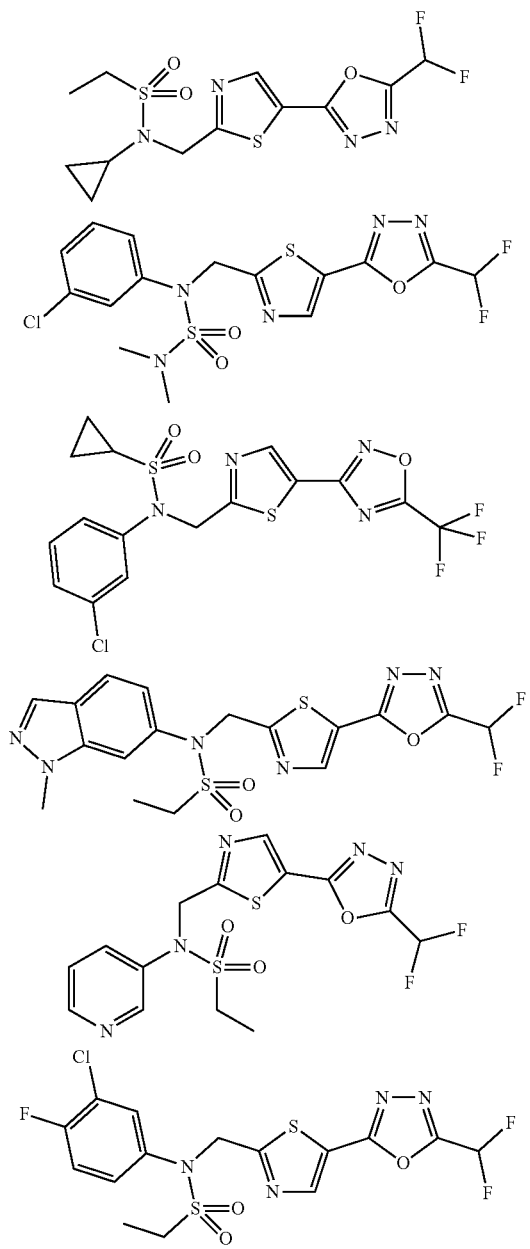

-continued
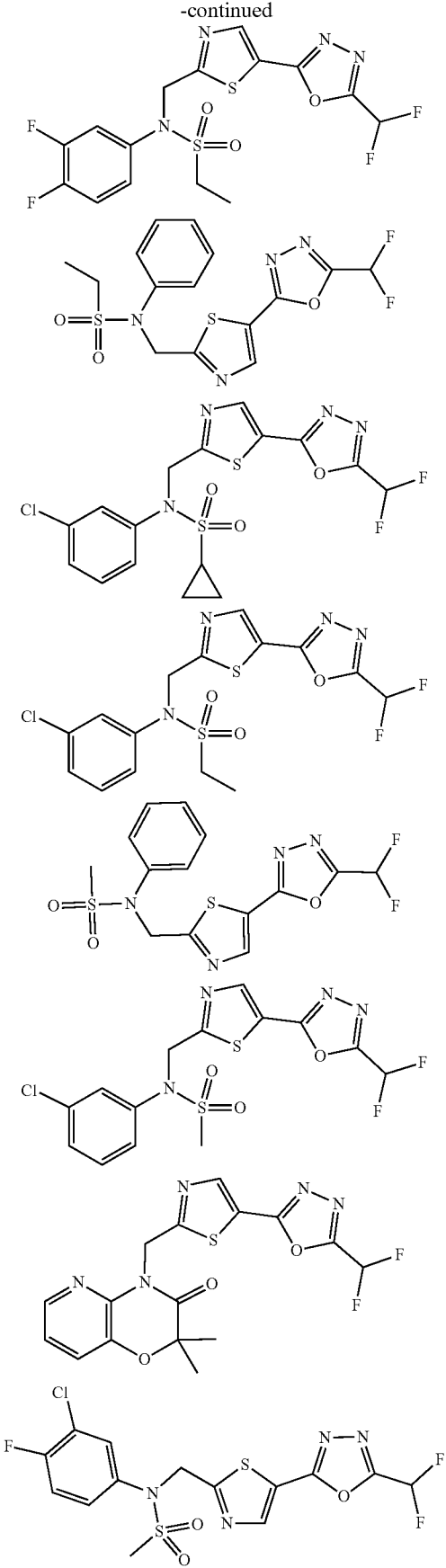
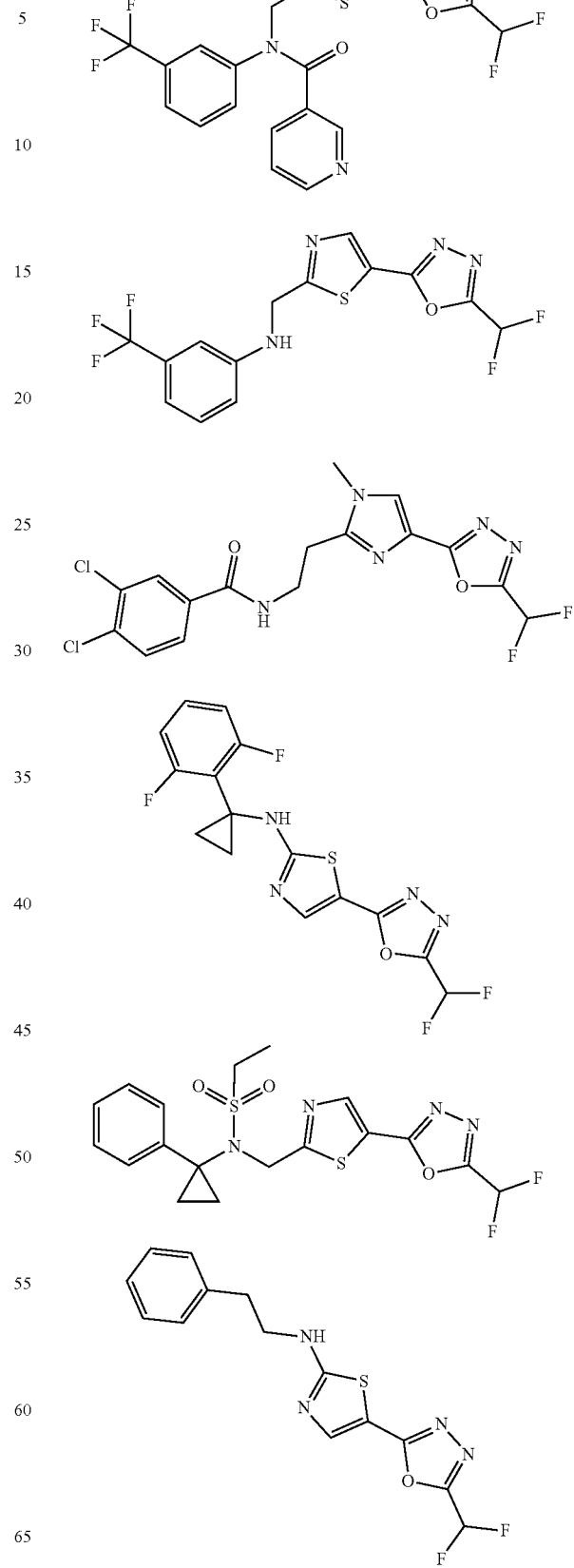

49
-continued
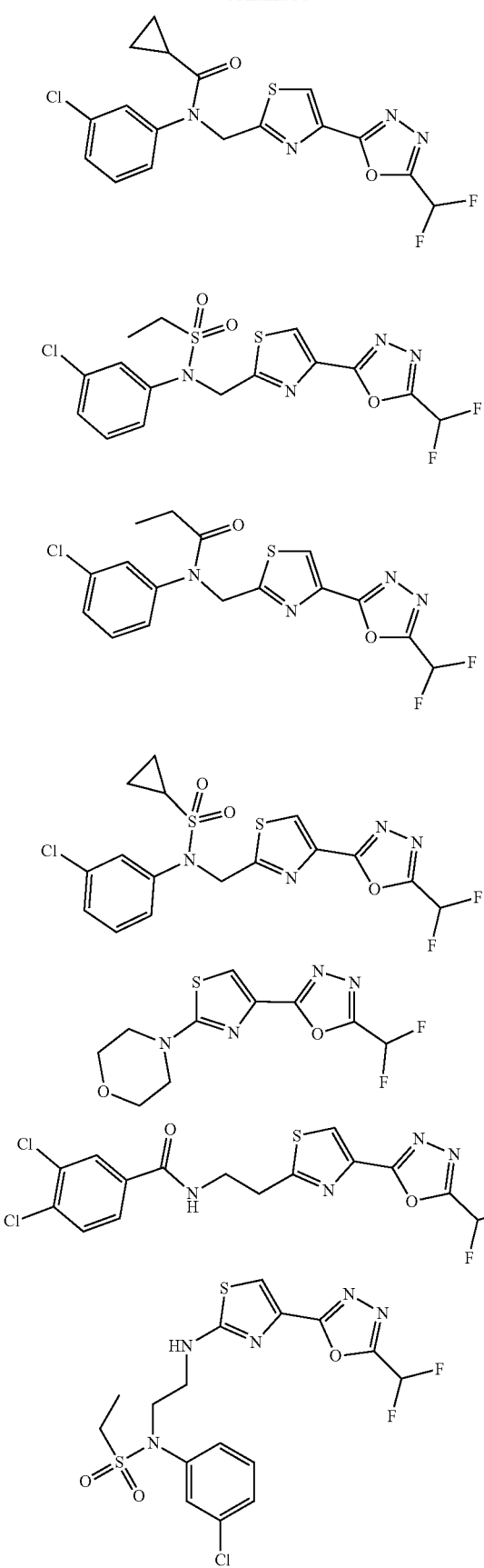
50
-continued
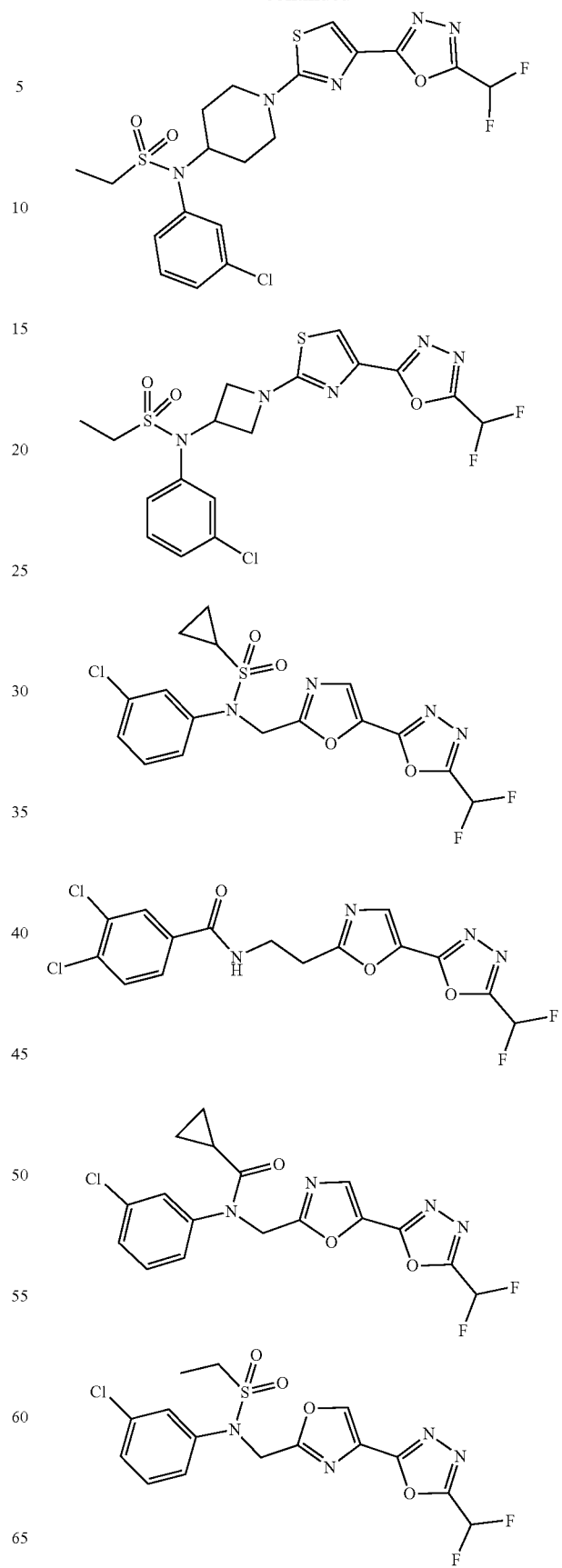

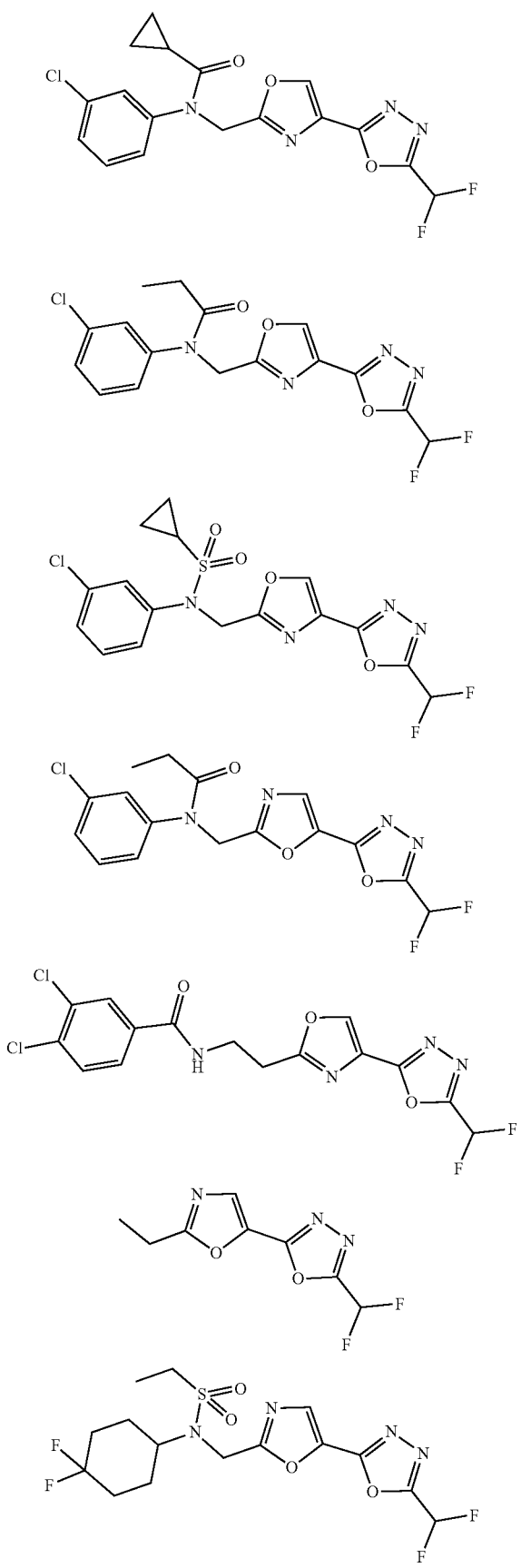
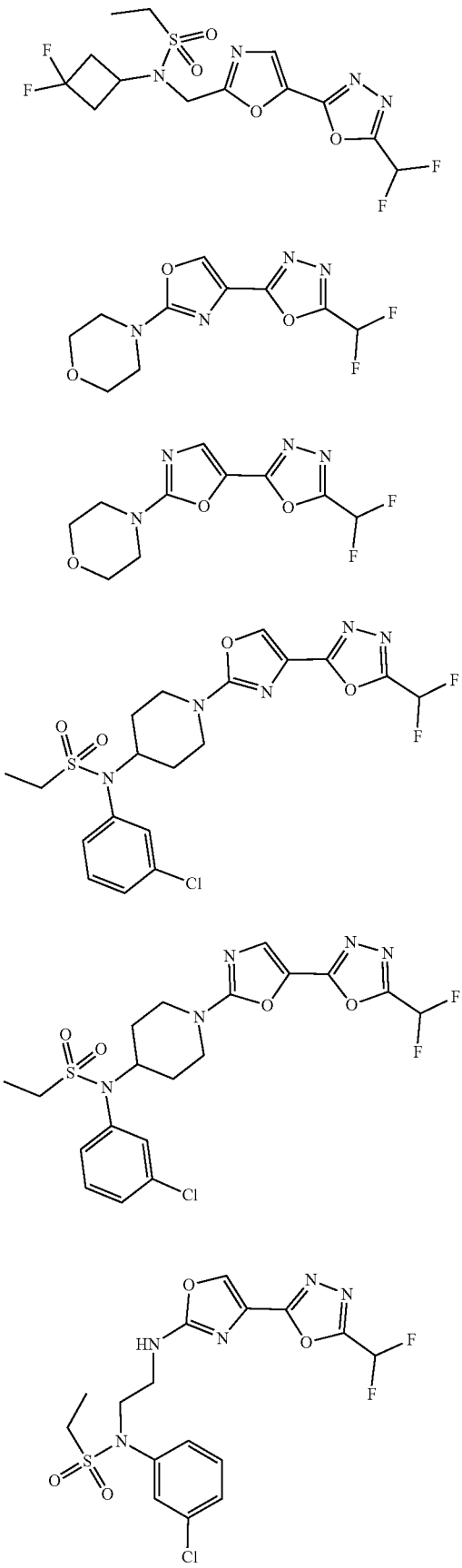

53
-continued
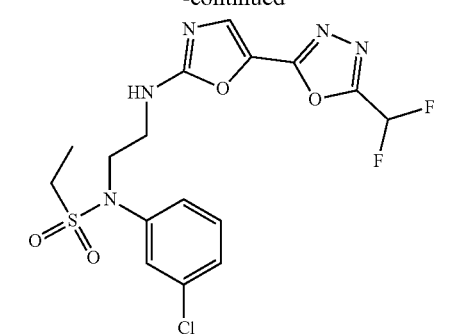
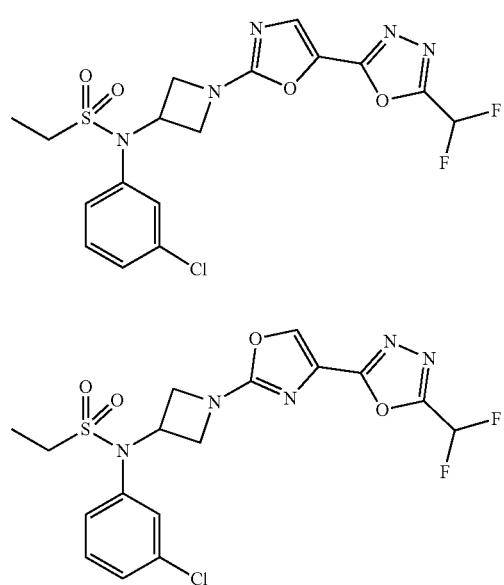
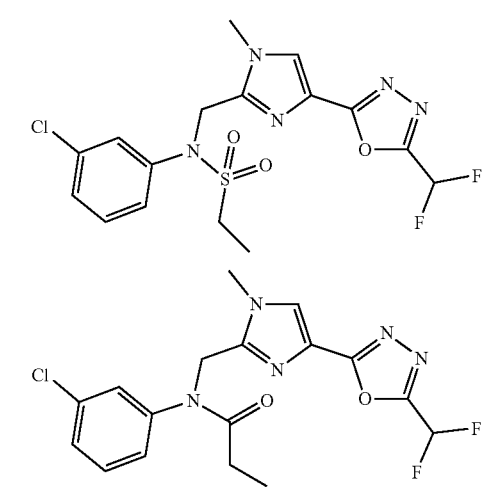
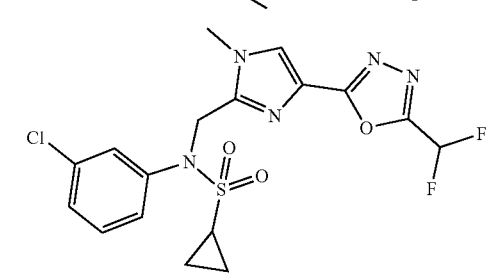
54
-continued
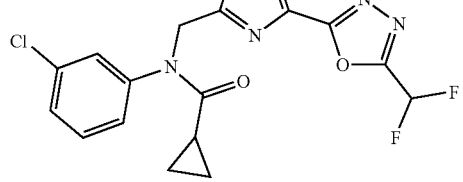
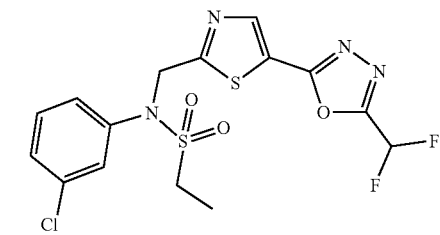
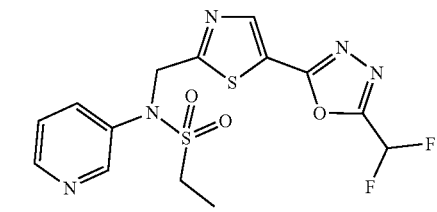
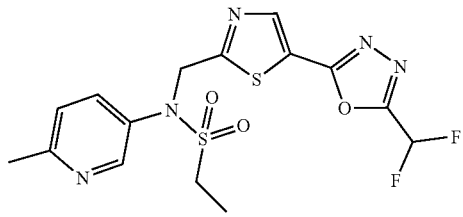
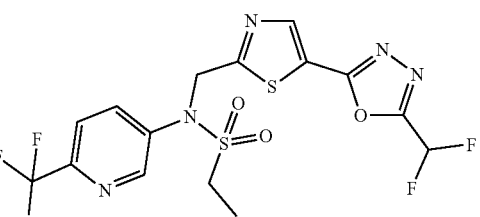
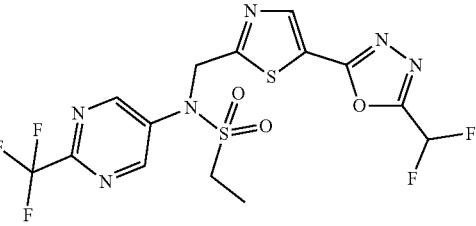
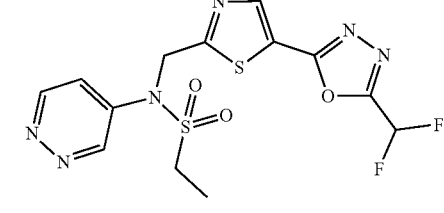

55
-continued
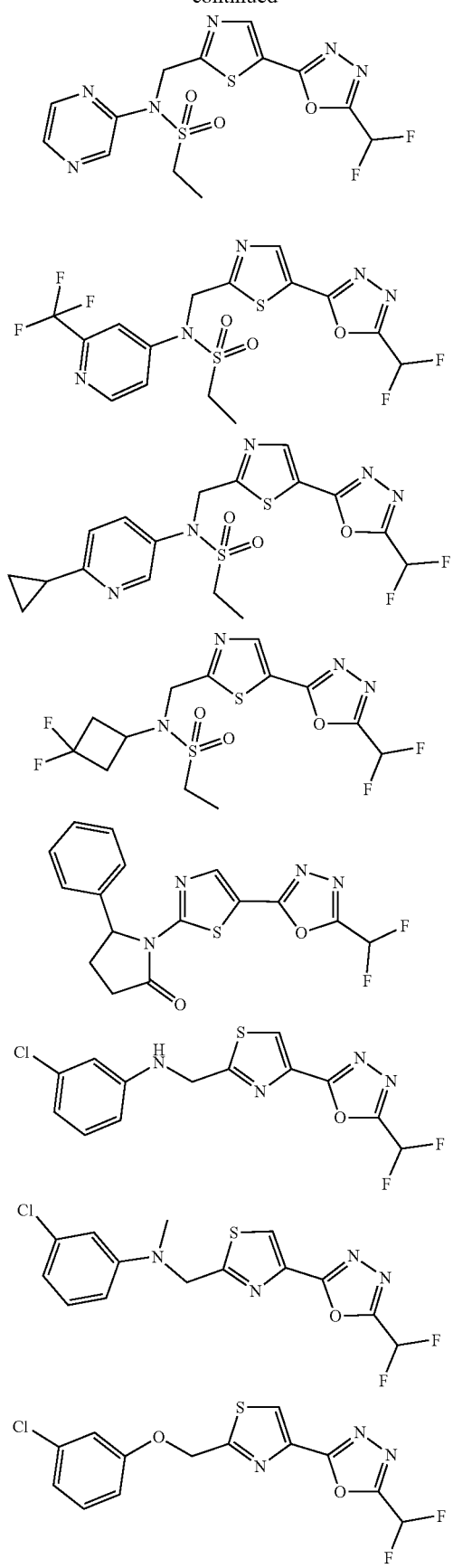
56
-continued
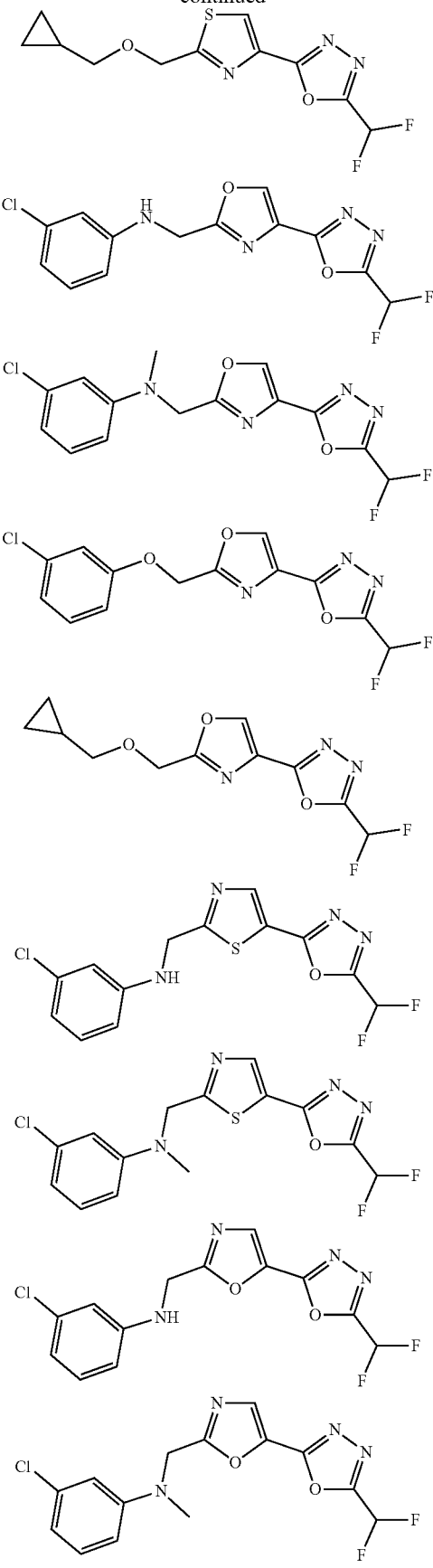

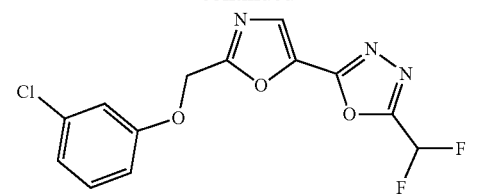
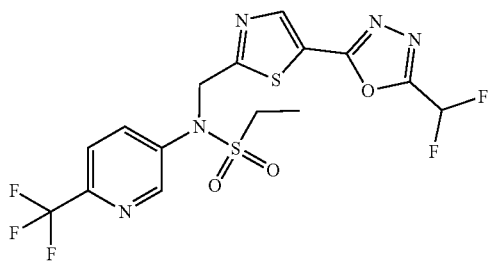
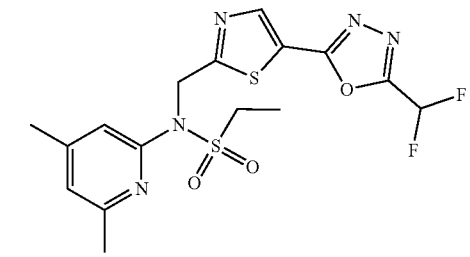
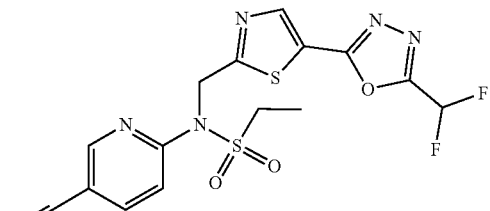
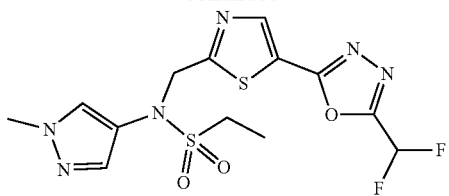
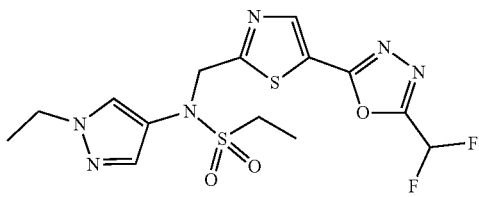
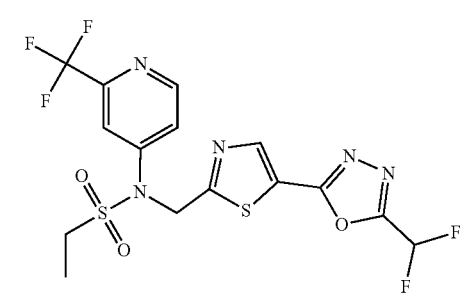
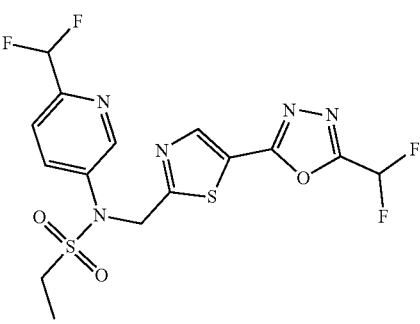
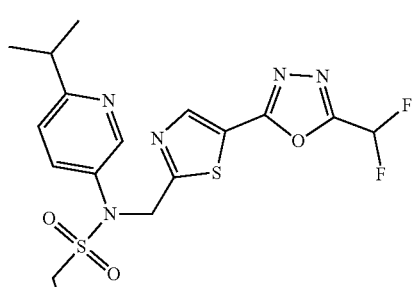
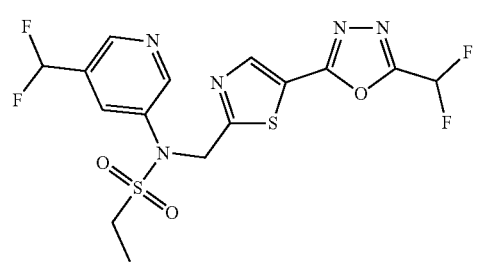

59
-continued
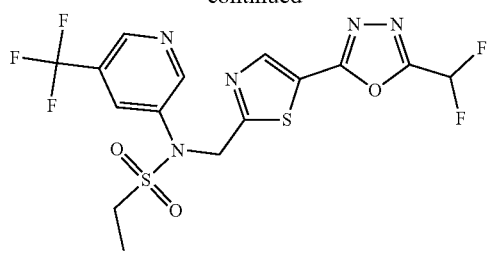
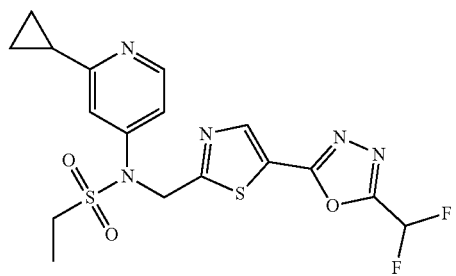
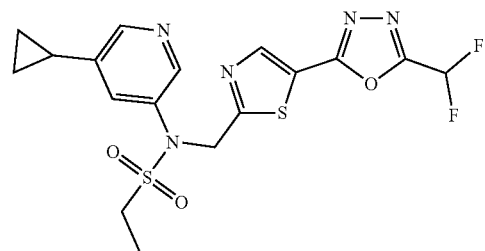
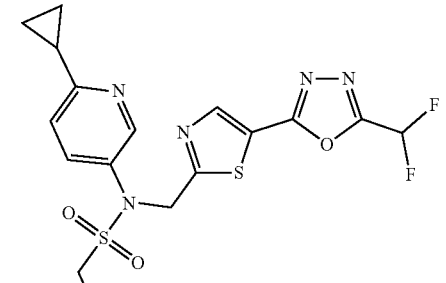
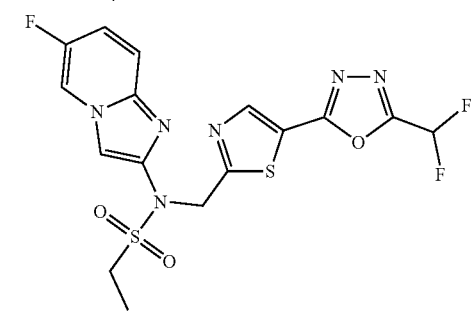
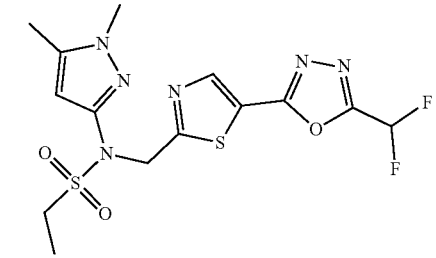
60
-continued
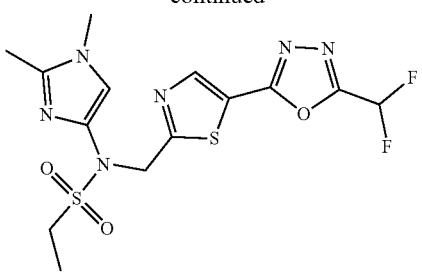
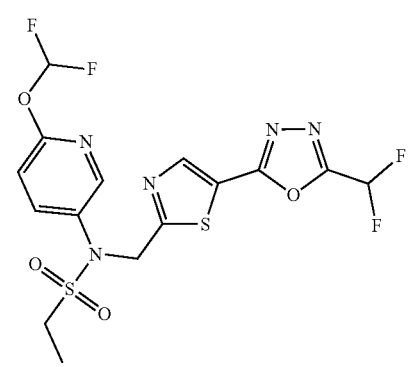
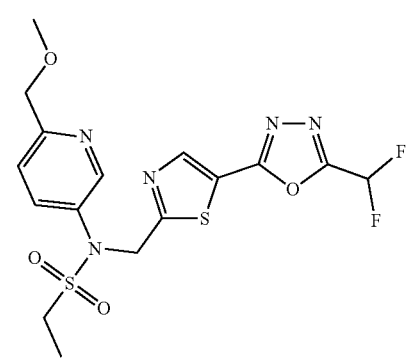
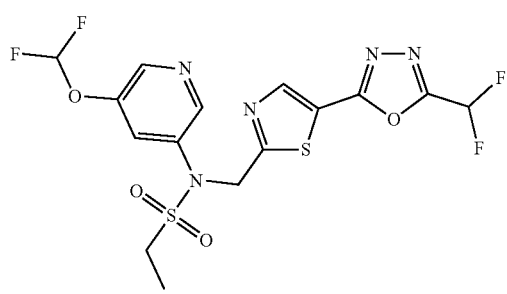
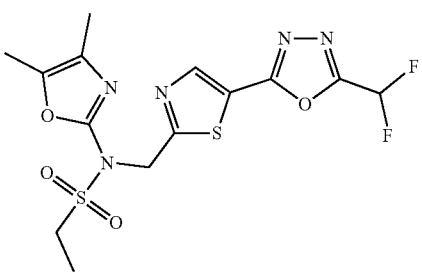

-continued
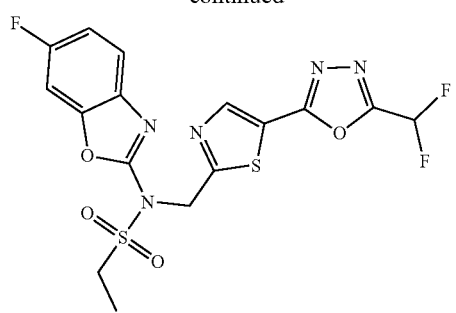
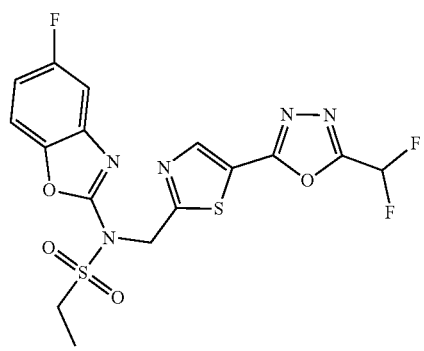
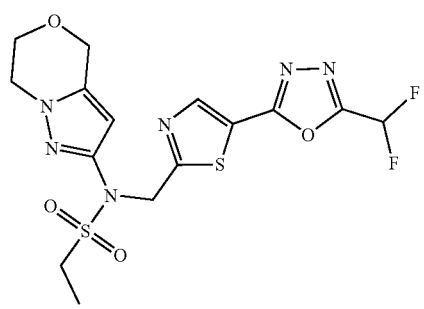
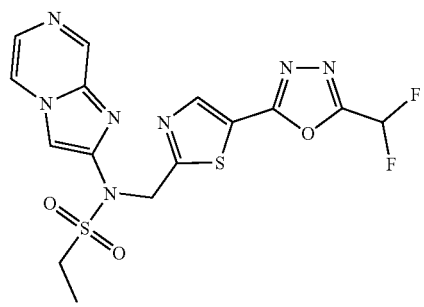
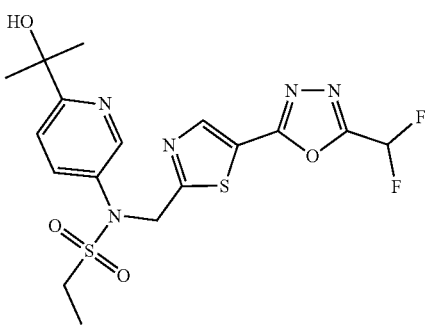
-continued
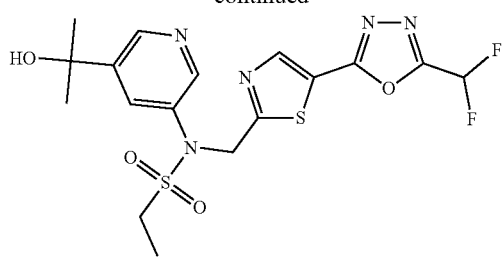
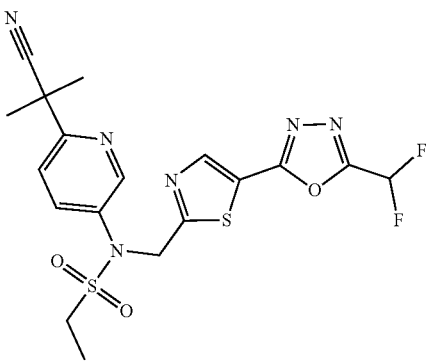
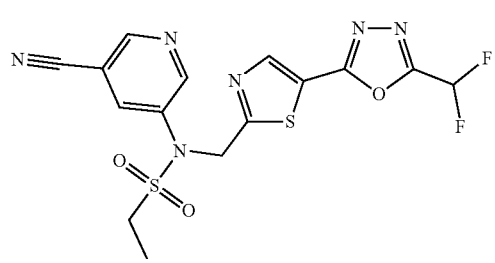
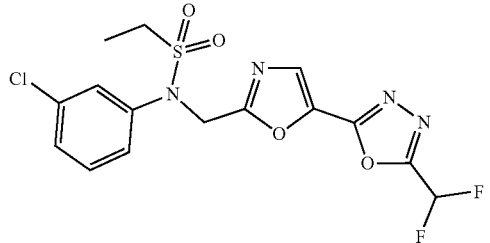
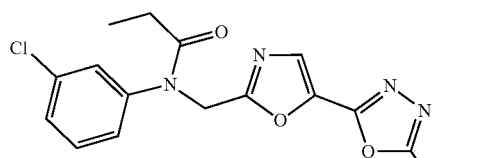
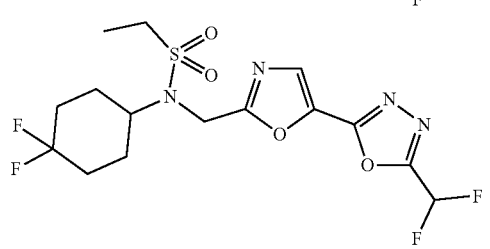

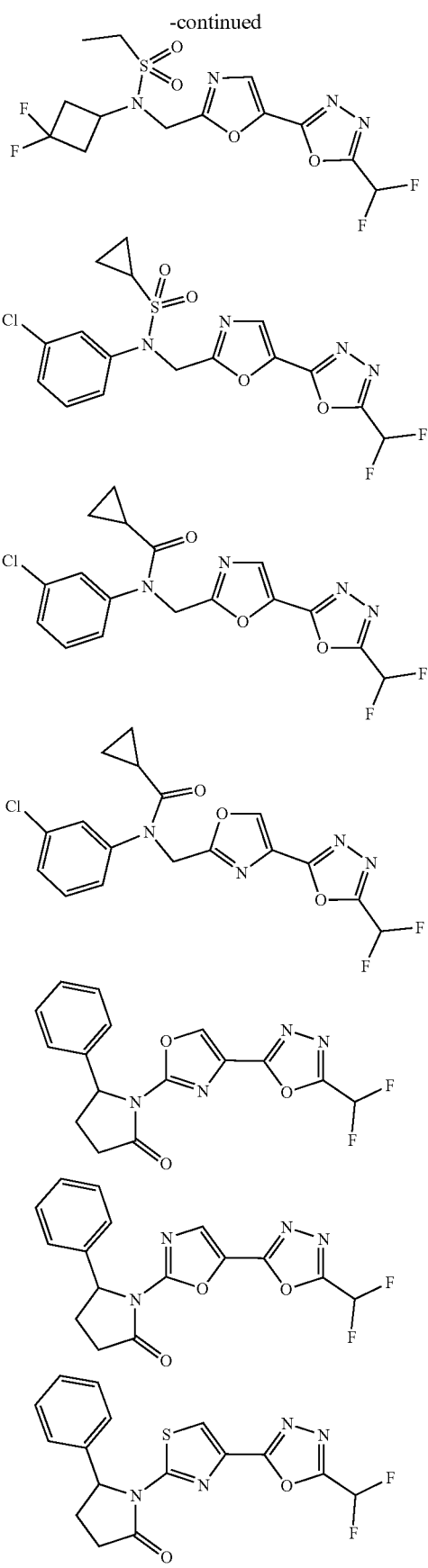
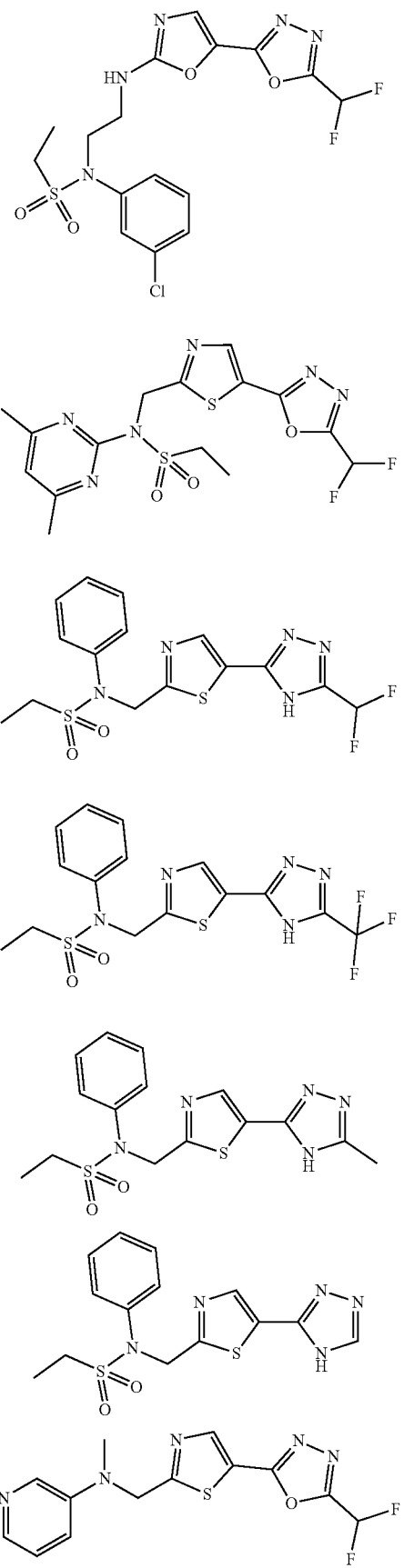

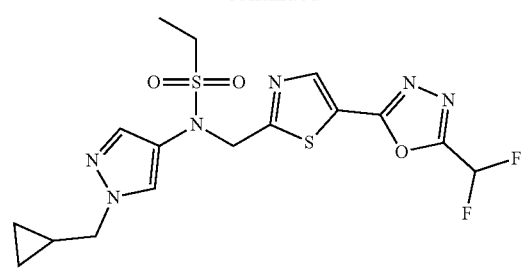
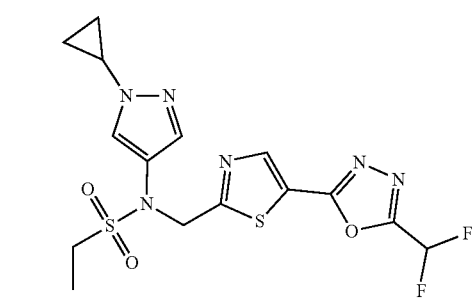
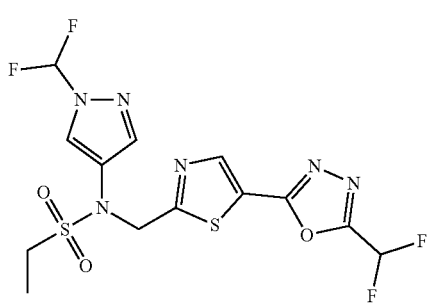
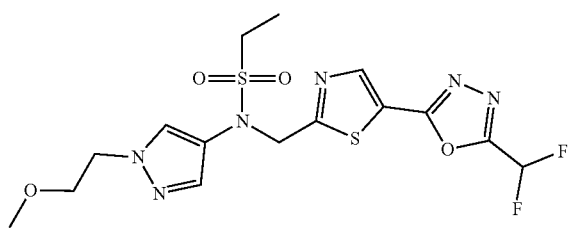
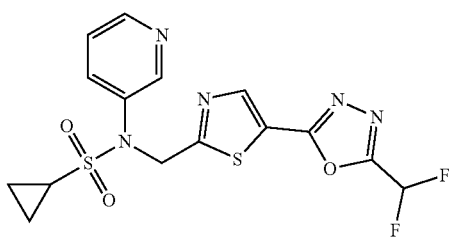
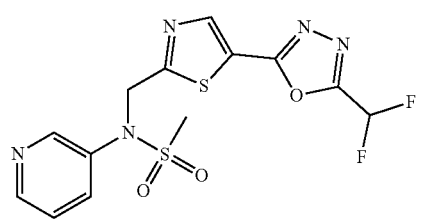
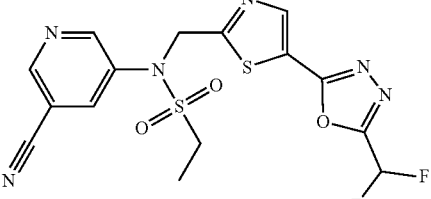
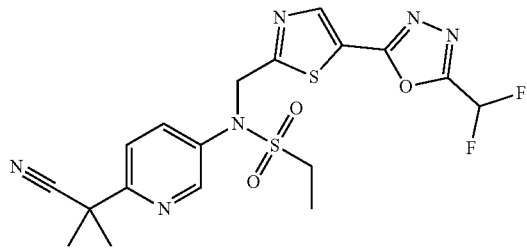
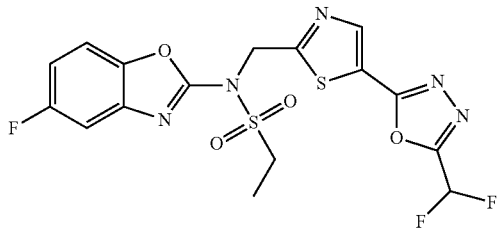
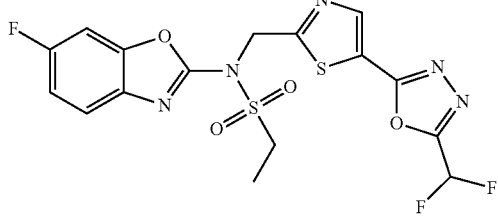
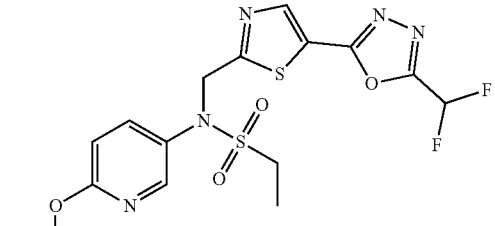

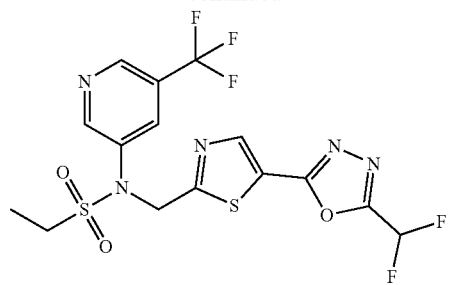
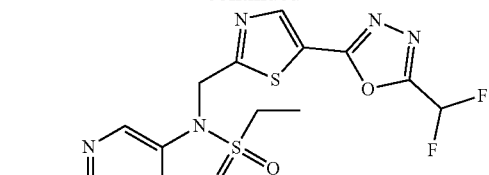
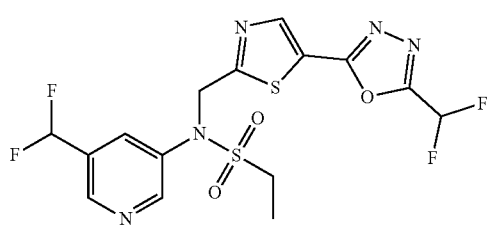
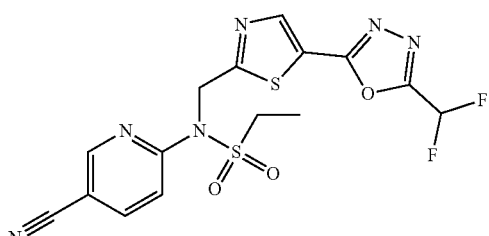
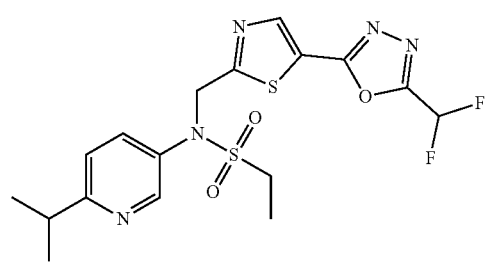
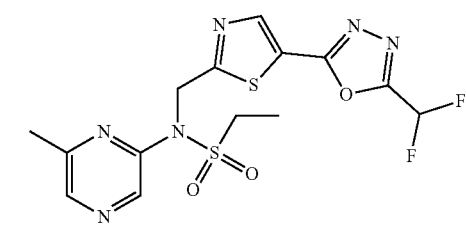
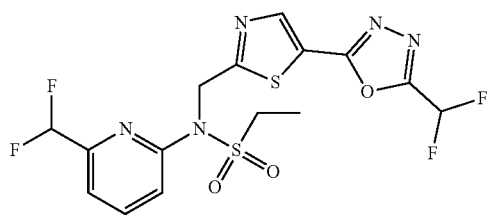
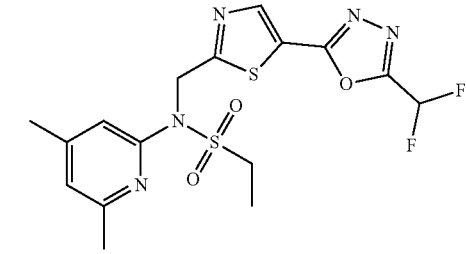
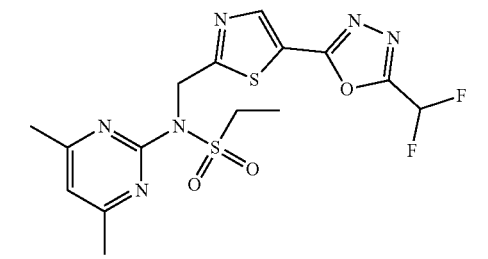
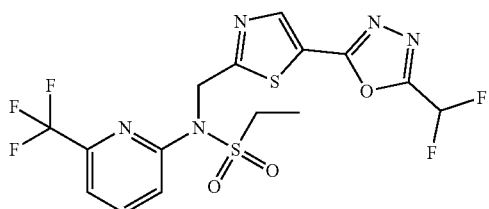
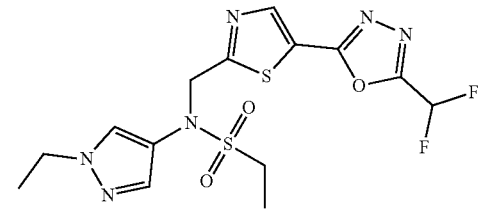
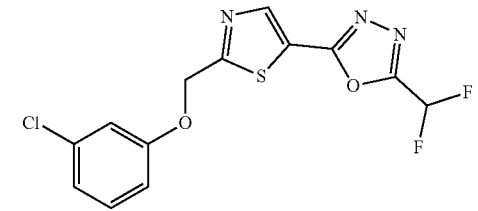
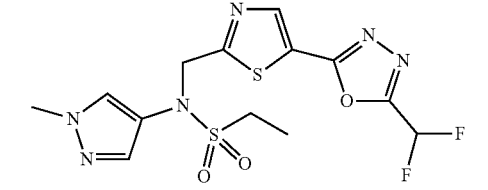
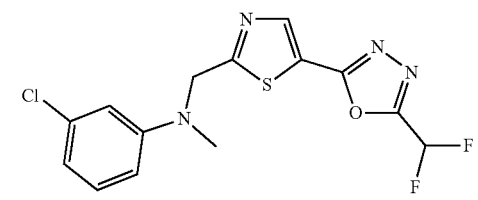

69
-continued
70
-continued
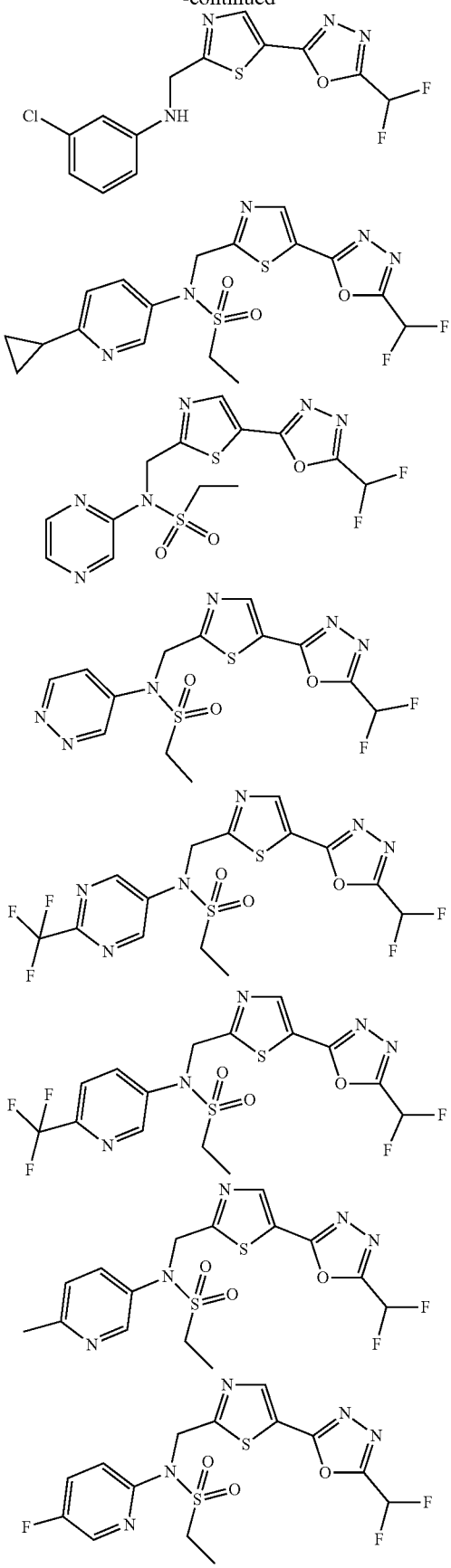
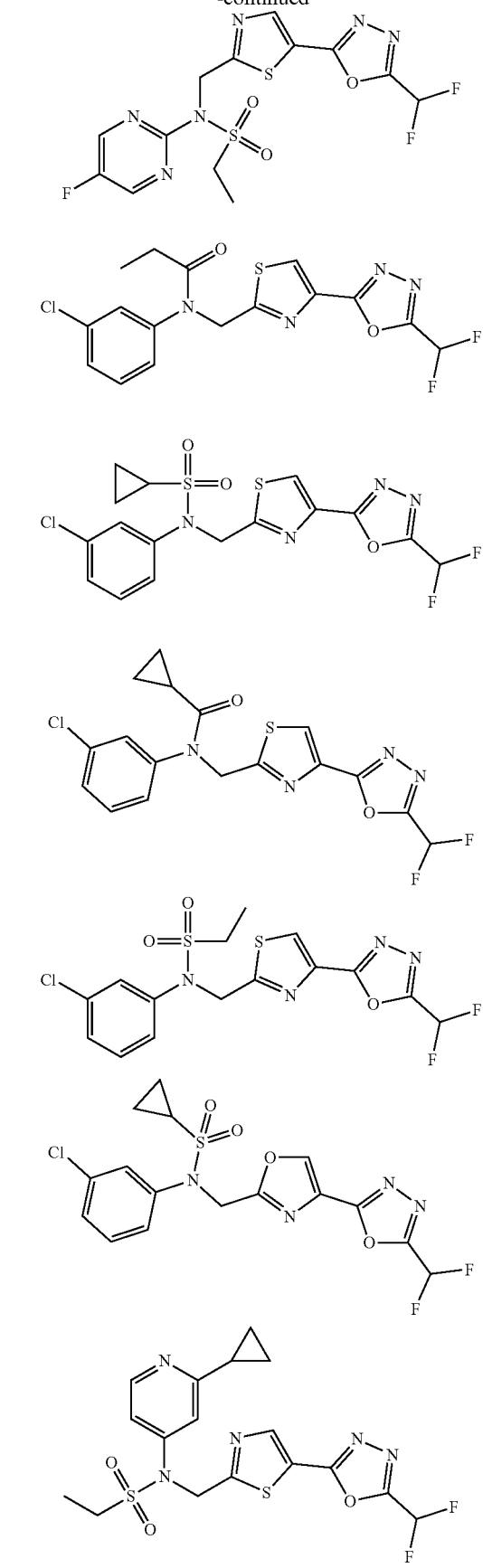

-continued
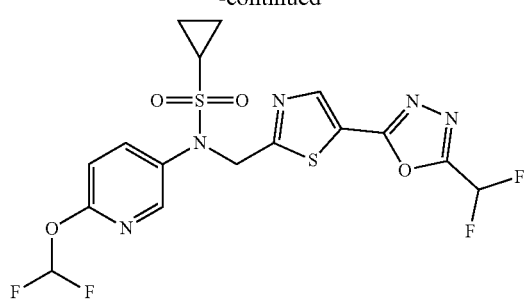
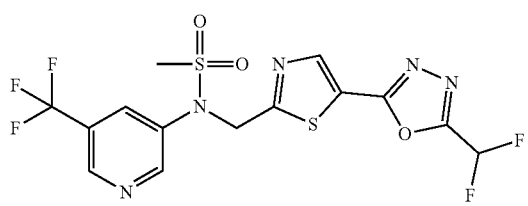
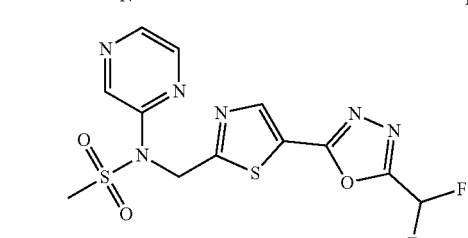
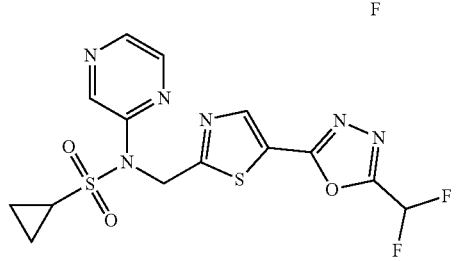
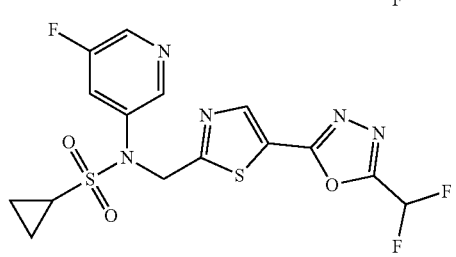
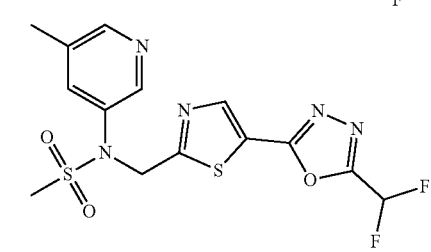
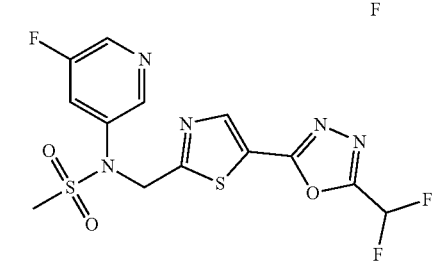
-continued
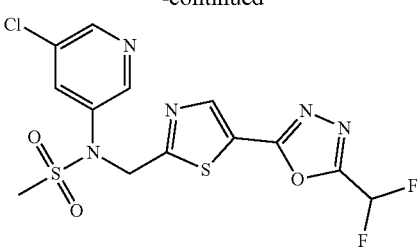
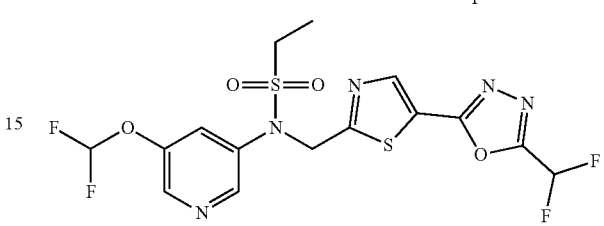
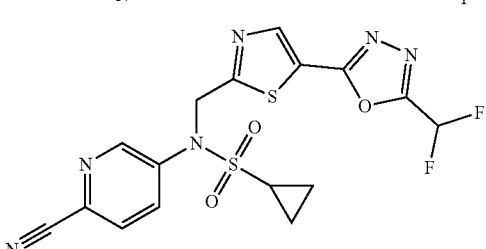
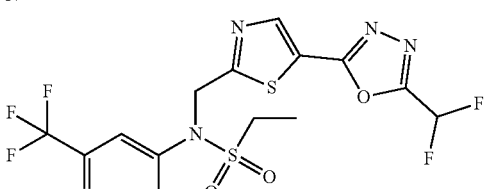
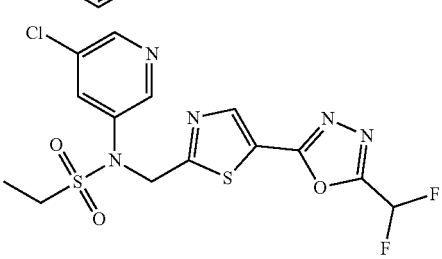
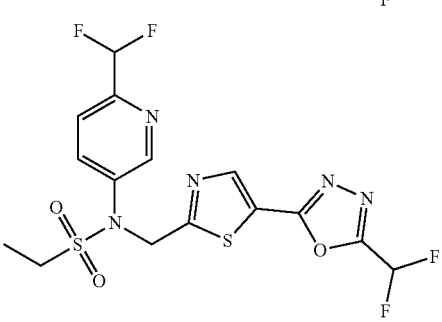
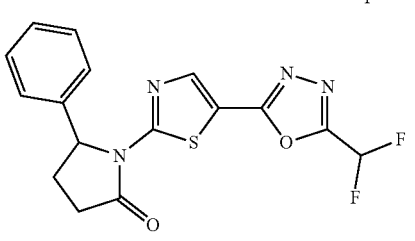

73
-continued
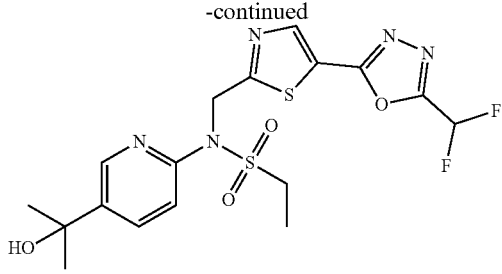
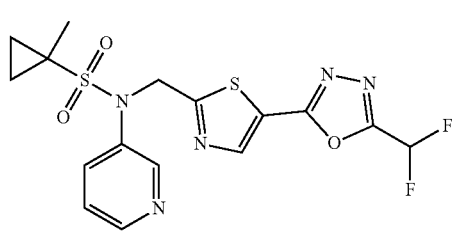
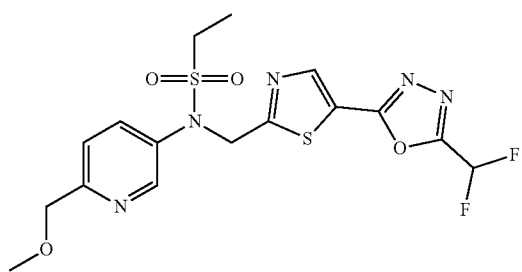
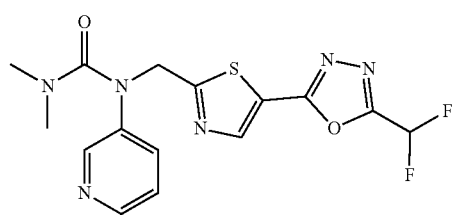
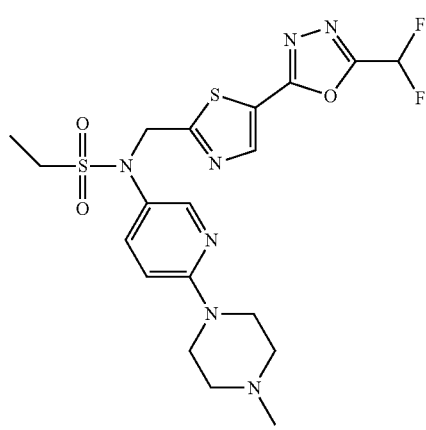
74
-continued
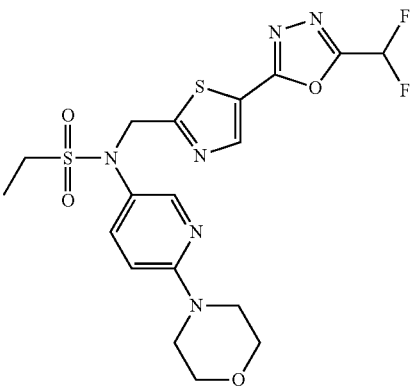
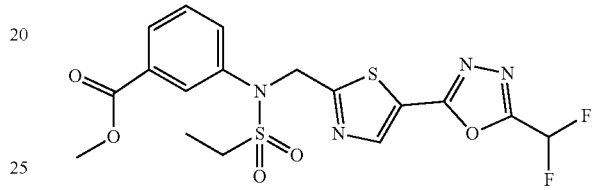
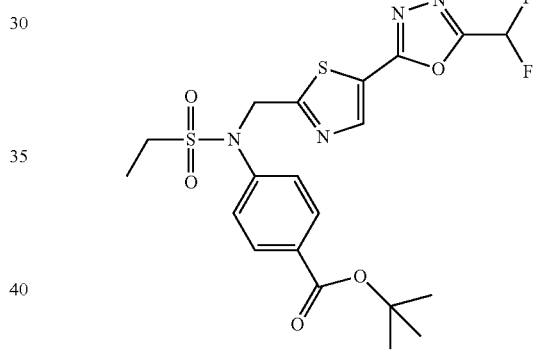
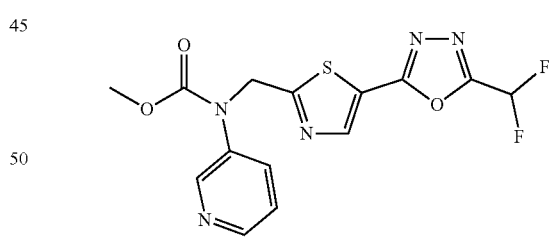
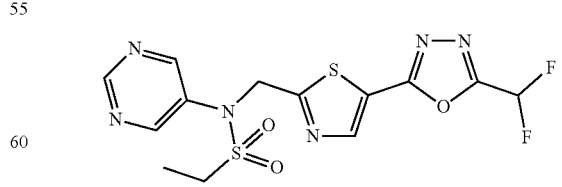
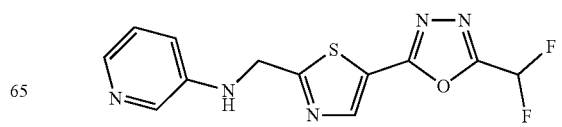

75
-continued
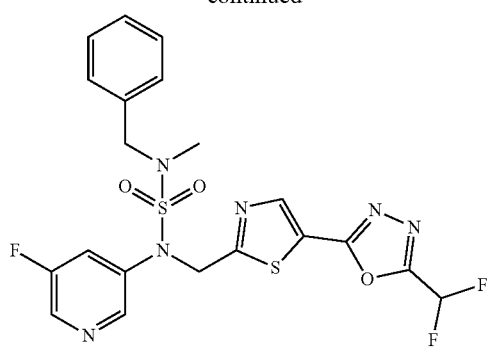
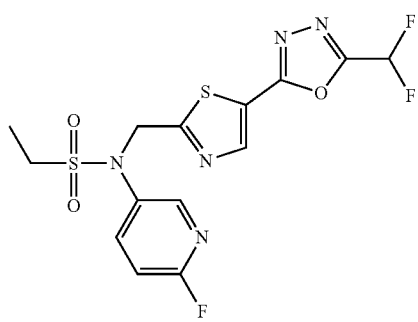
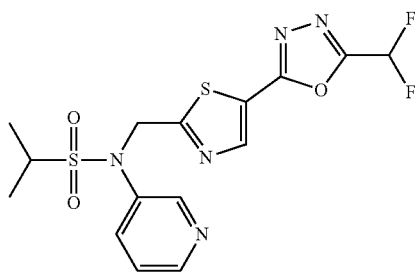
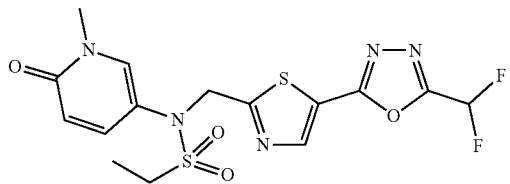
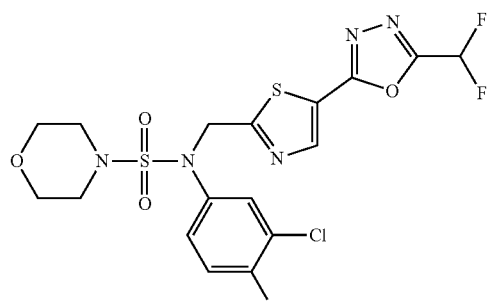
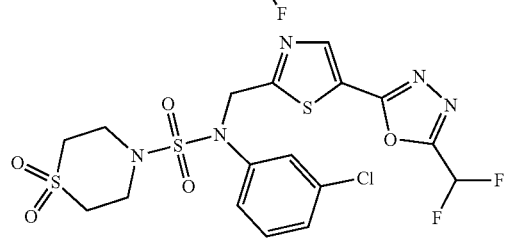
76
-continued
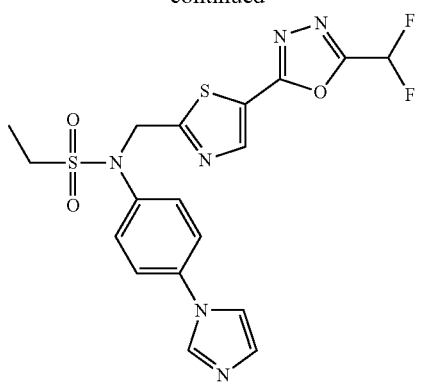
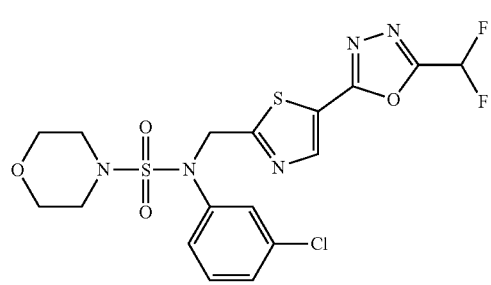
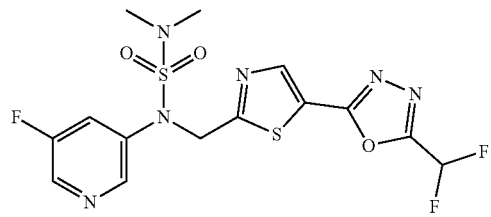
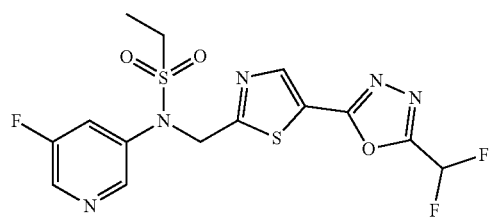
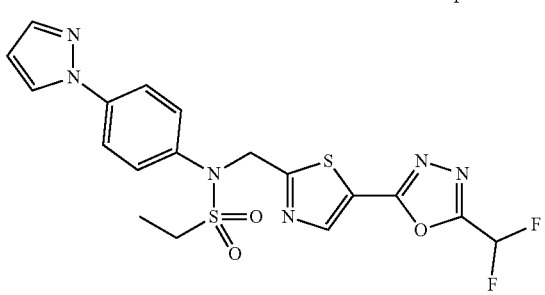
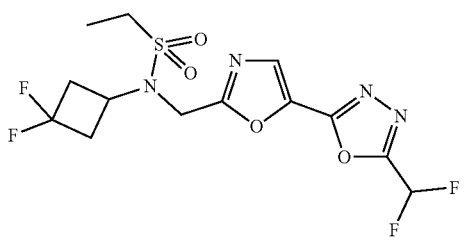

77
-continued
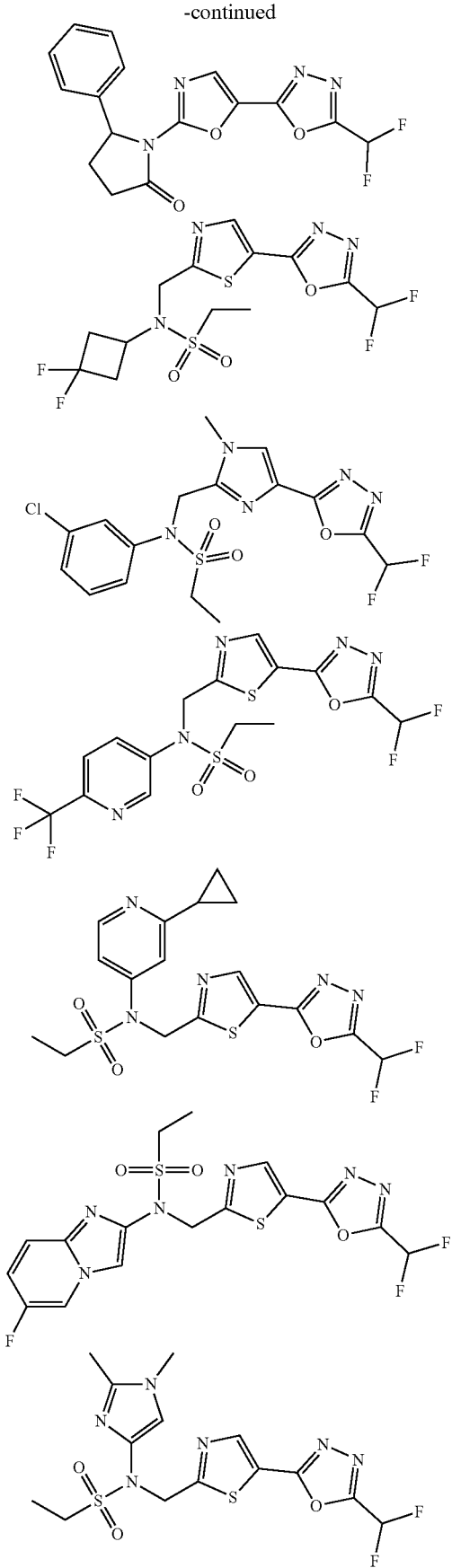
78
-continued
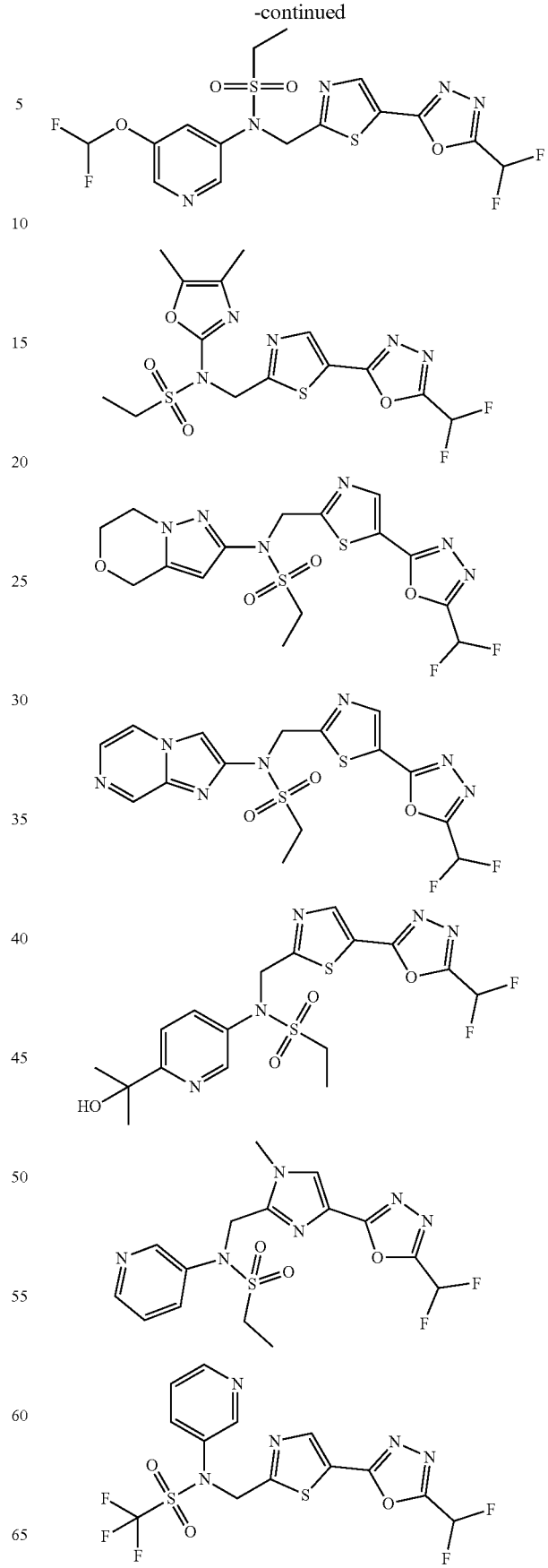

-continued
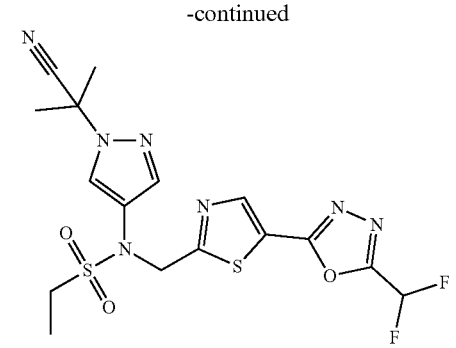
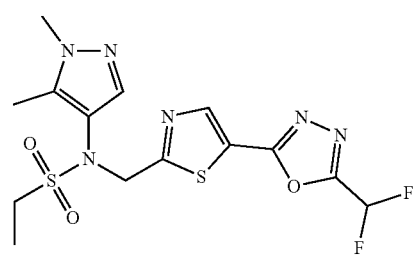
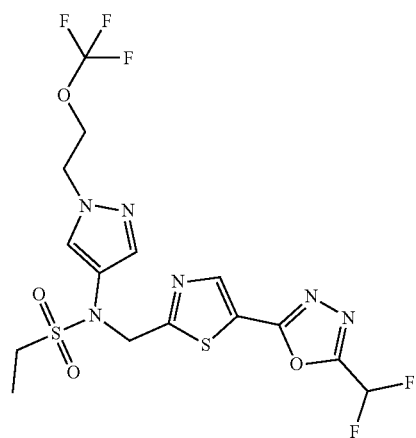
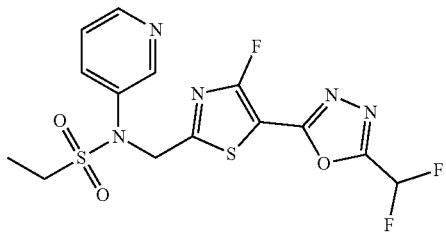
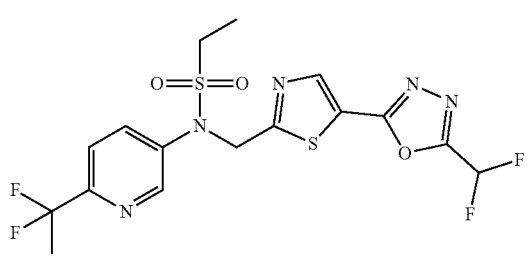
-continued
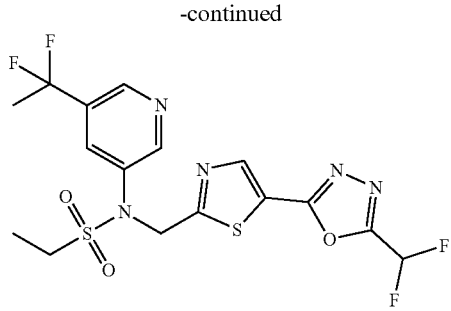
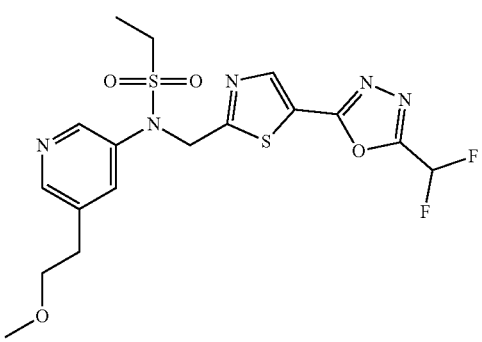
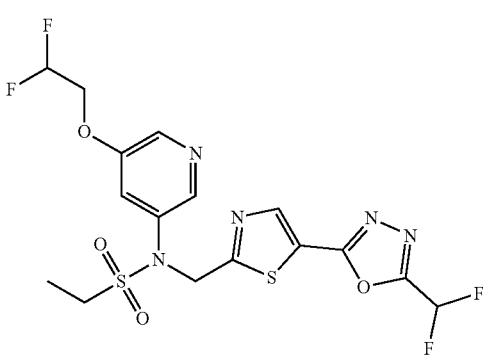
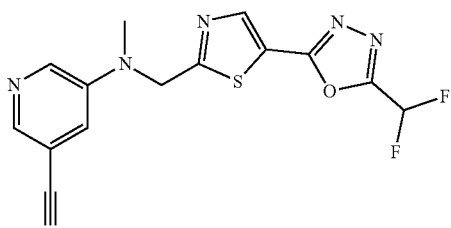
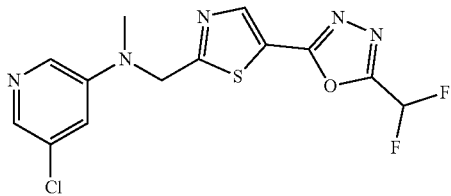
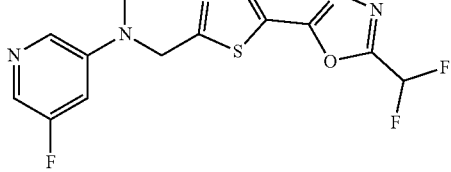

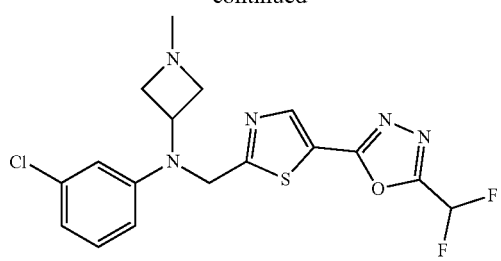
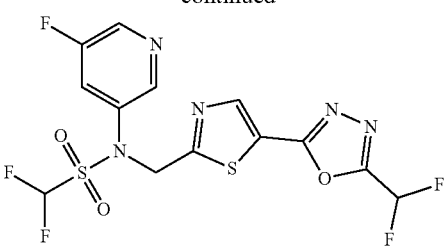
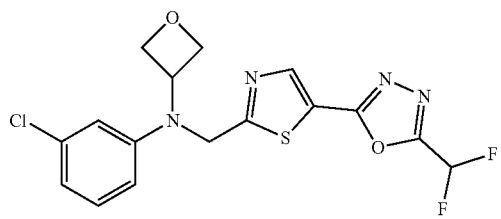
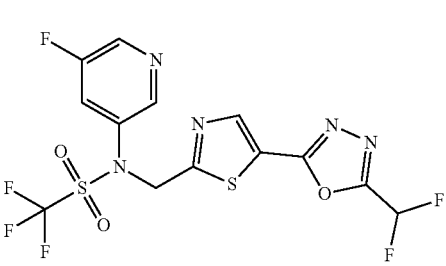
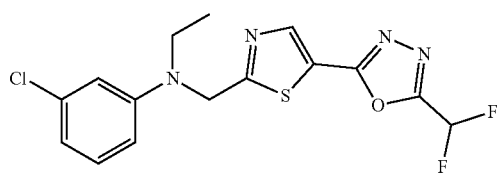
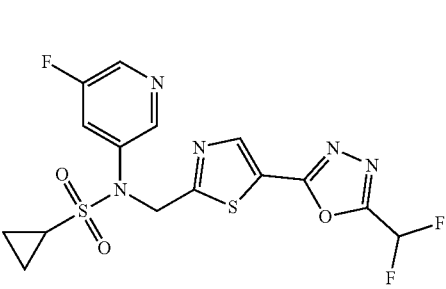
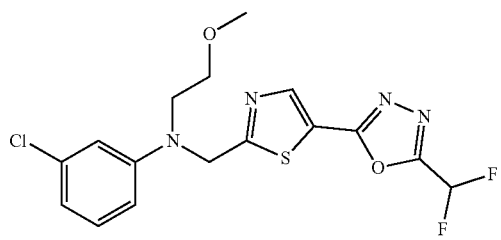
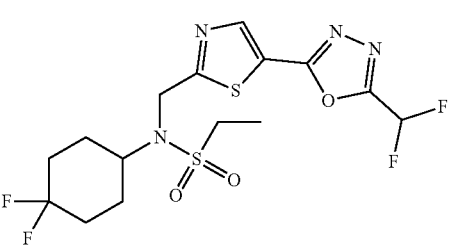
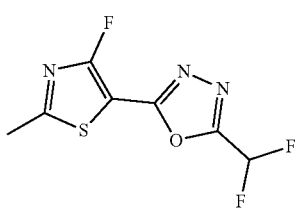
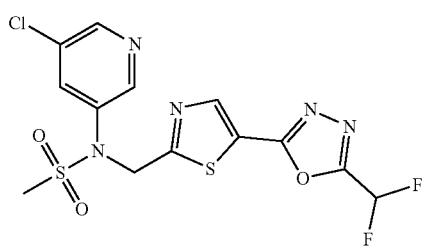
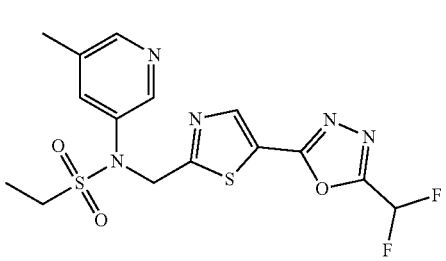
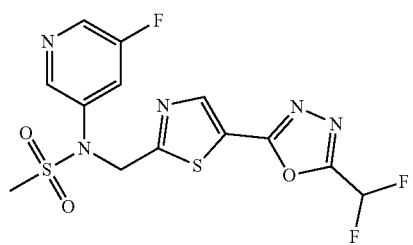
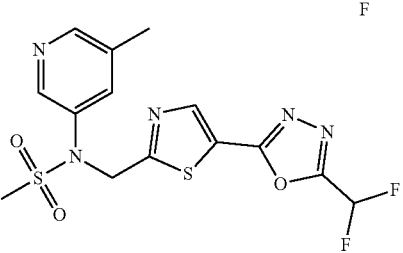

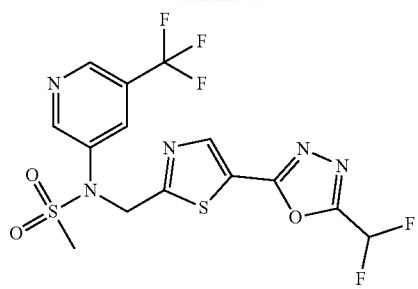
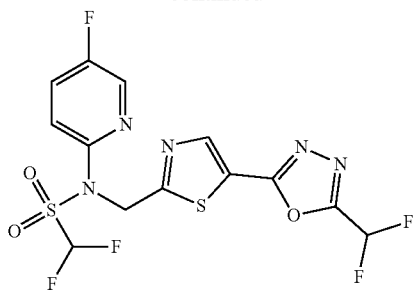
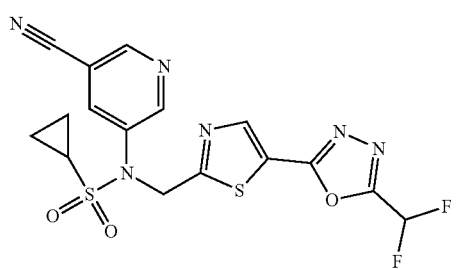
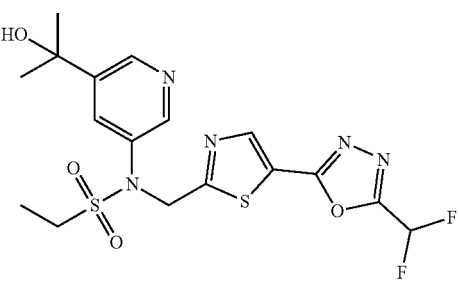
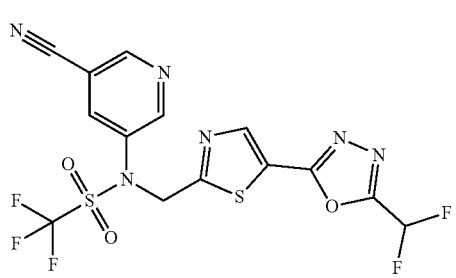
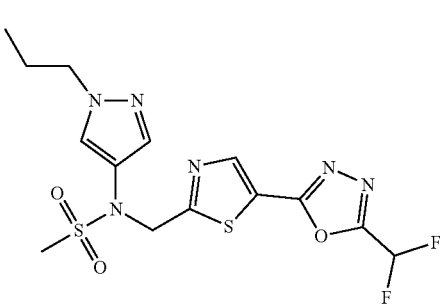
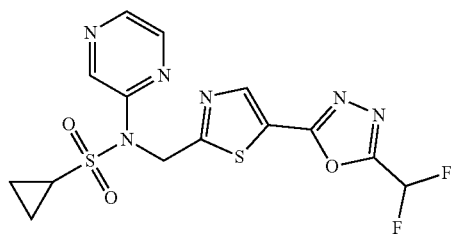
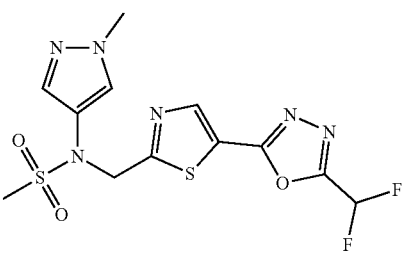
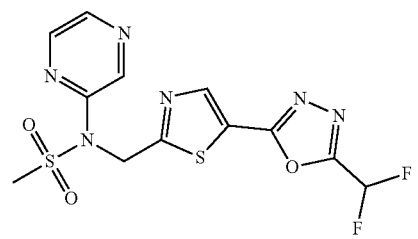
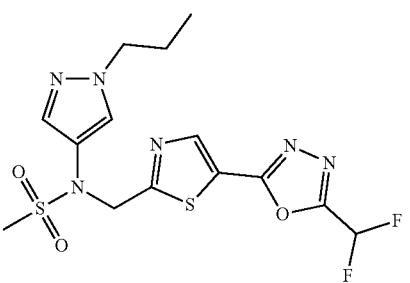
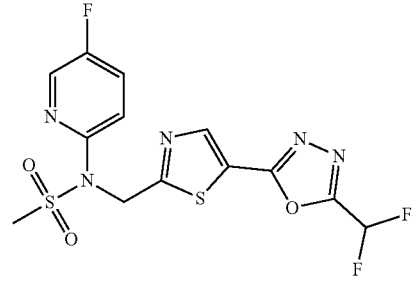
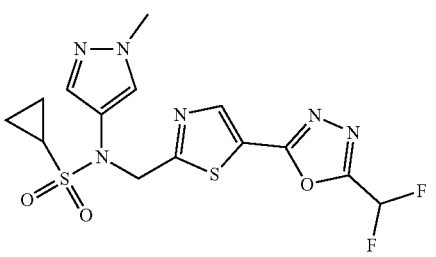

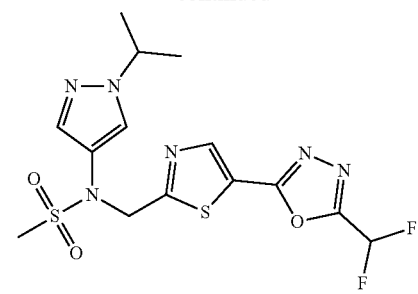
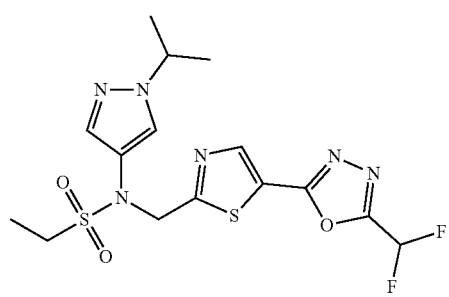
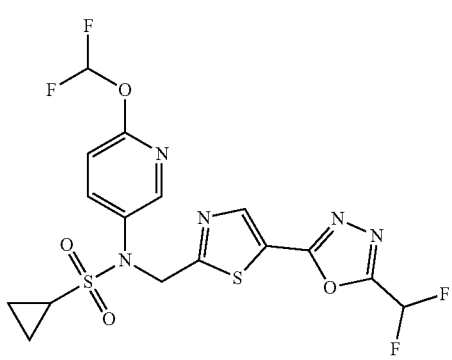
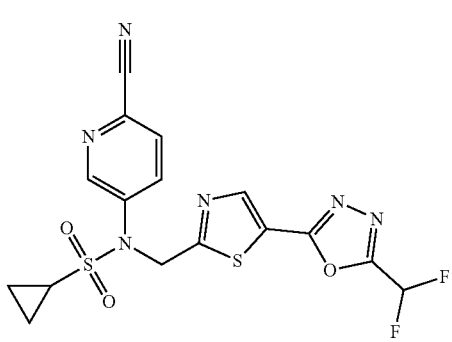
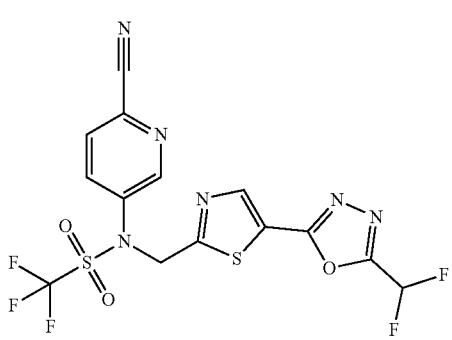
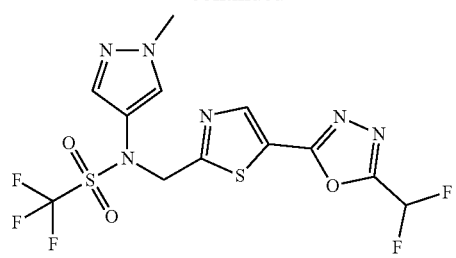
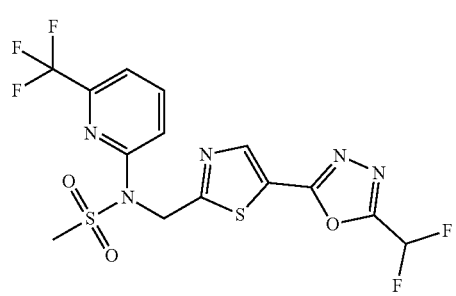
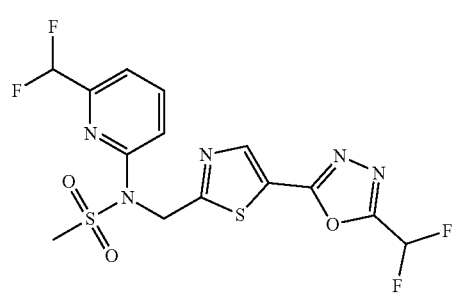
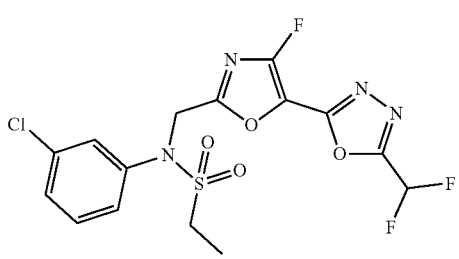
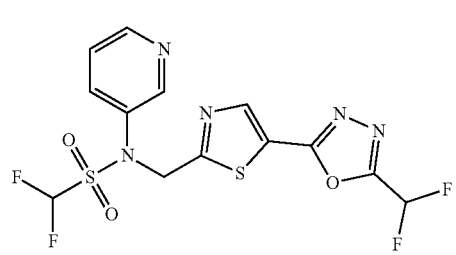
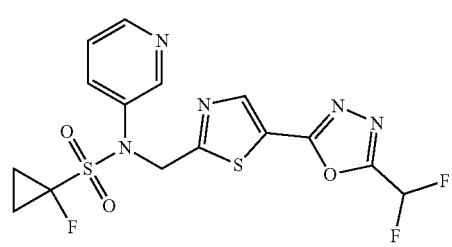

87
-continued
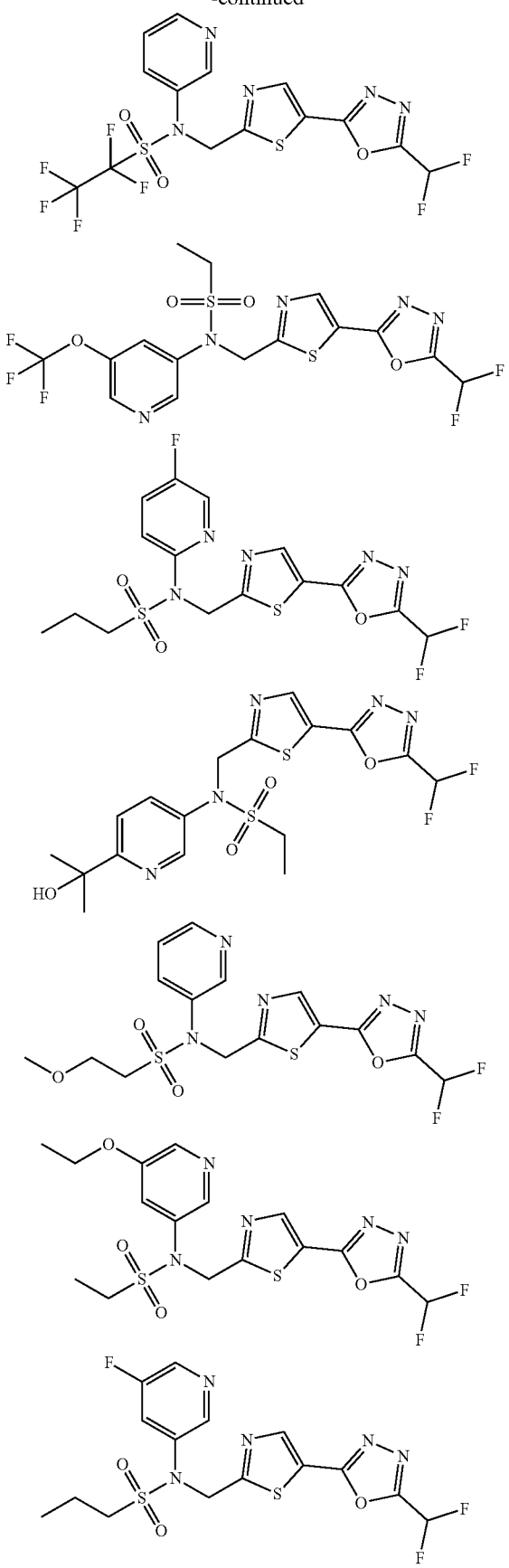
88
-continued
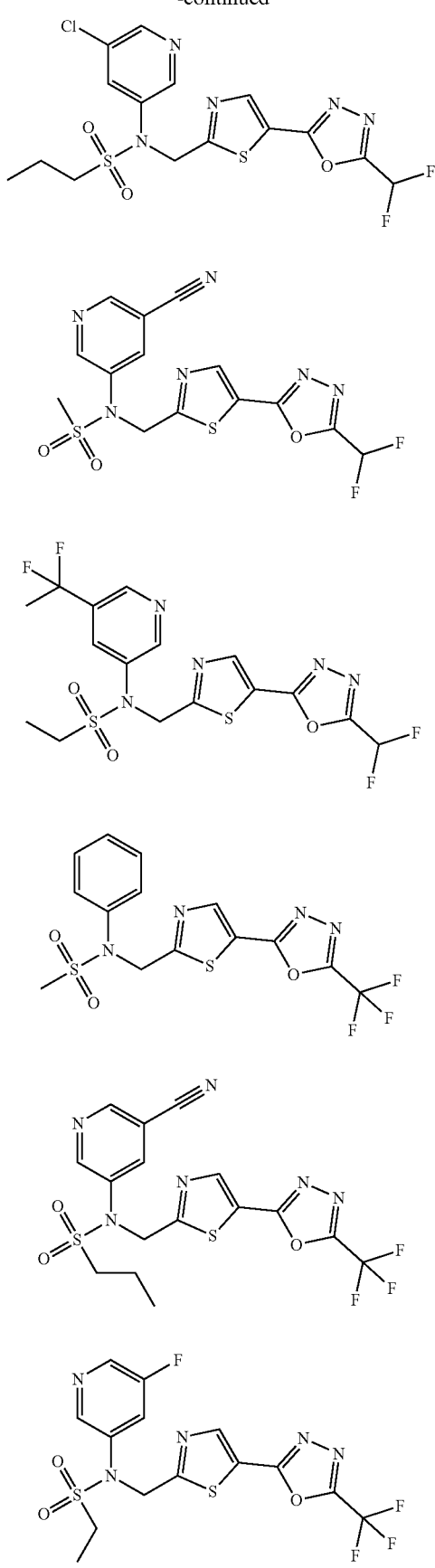

89
-continued
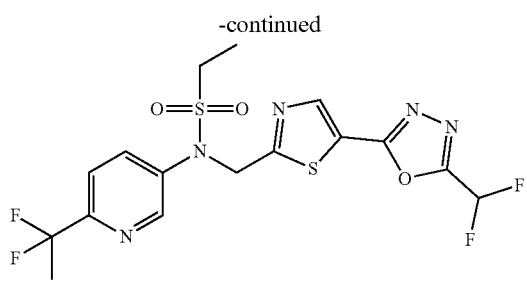
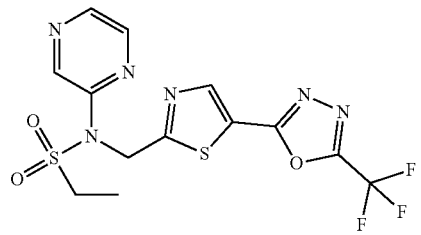
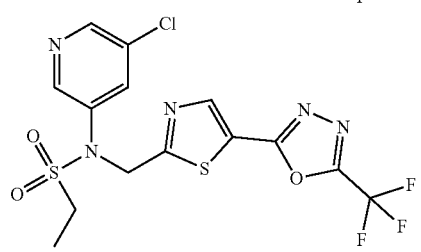
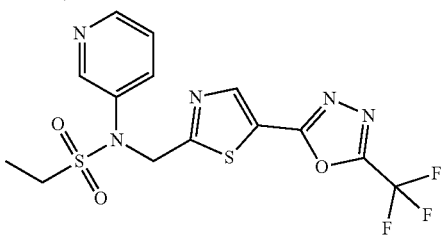
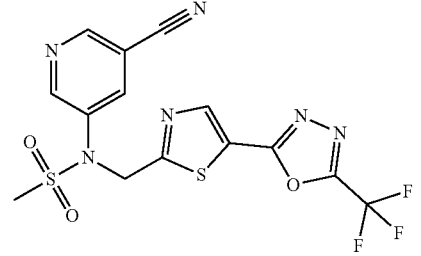
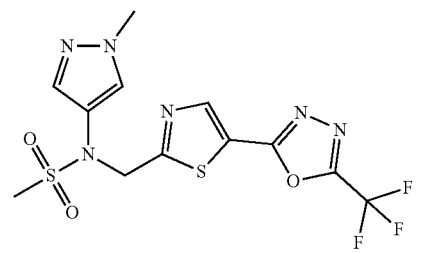
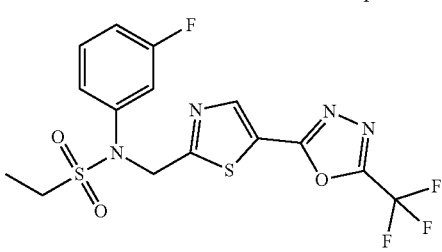
90
-continued
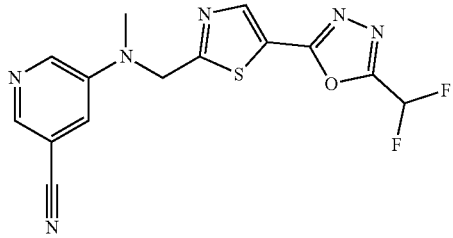
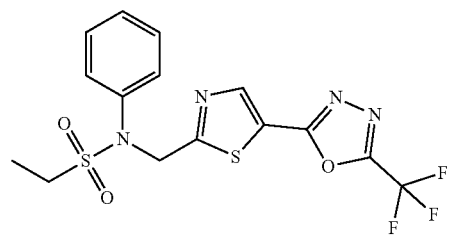
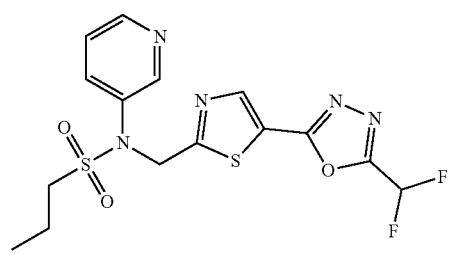
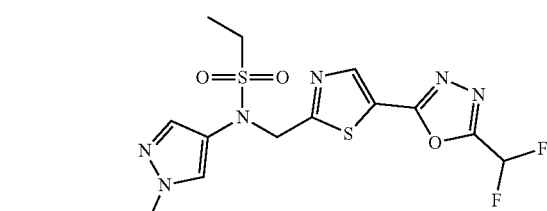
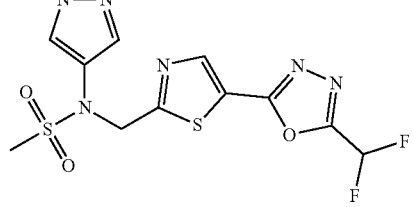
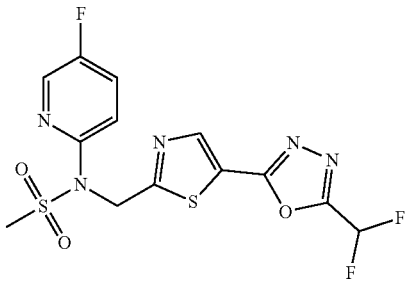

91
-continued
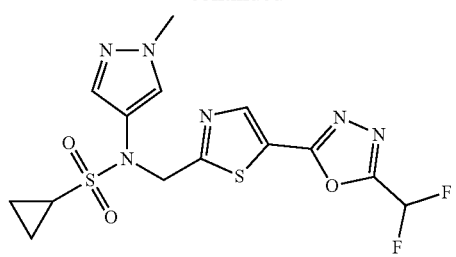
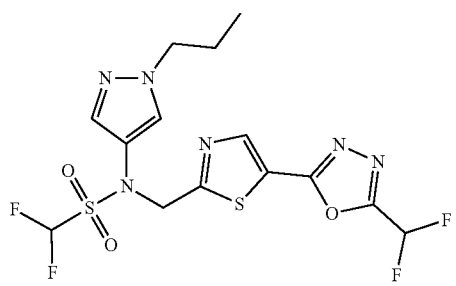
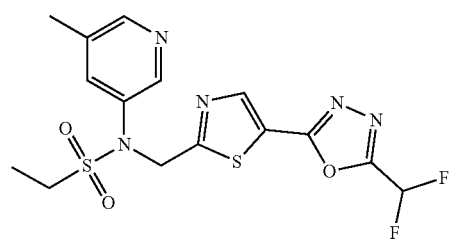
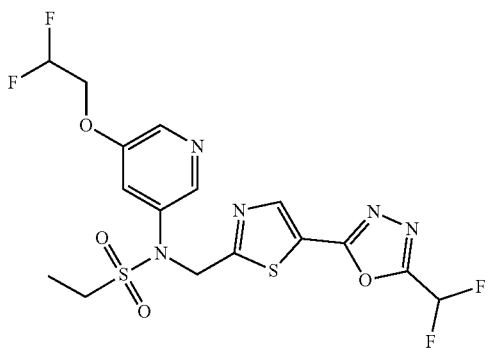
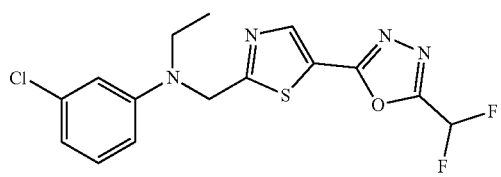
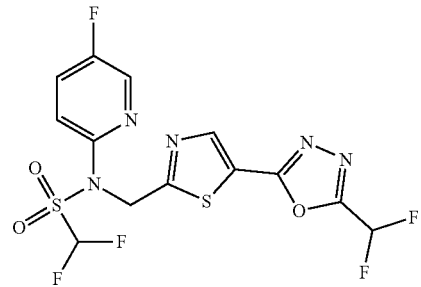
92
-continued
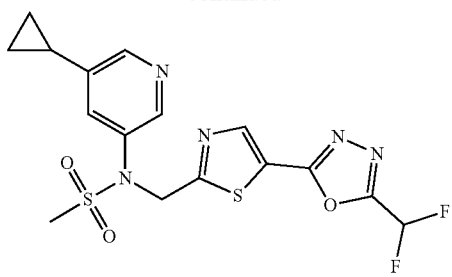
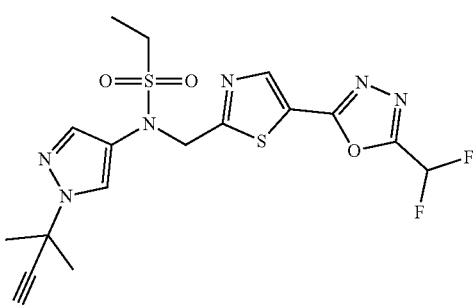
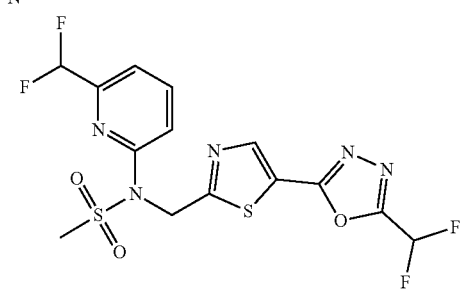
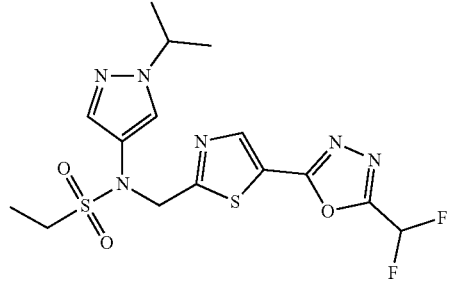
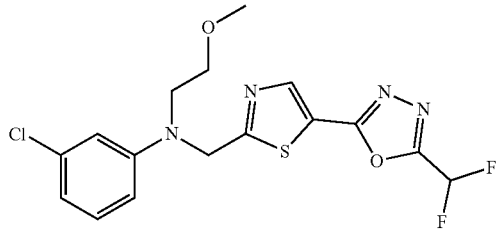
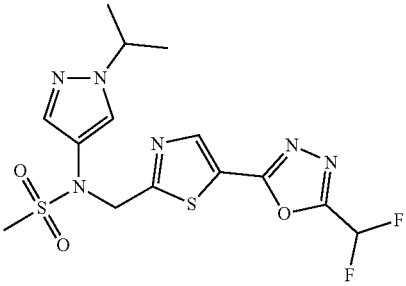

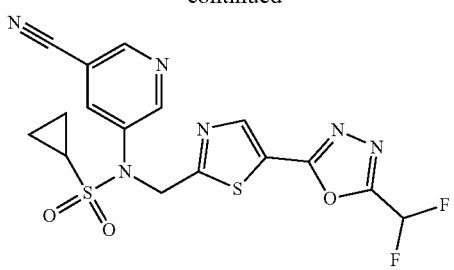
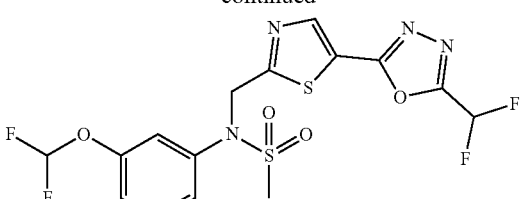

95
-continued
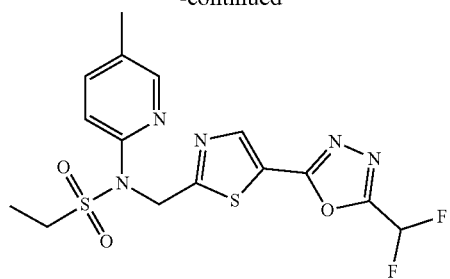
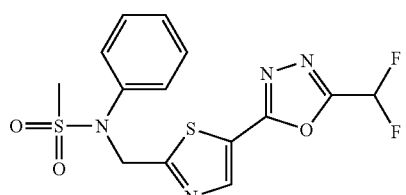
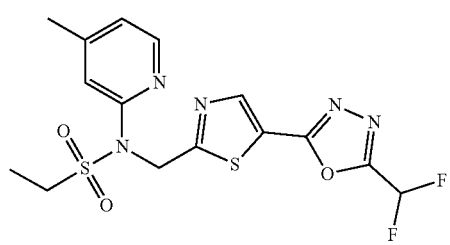
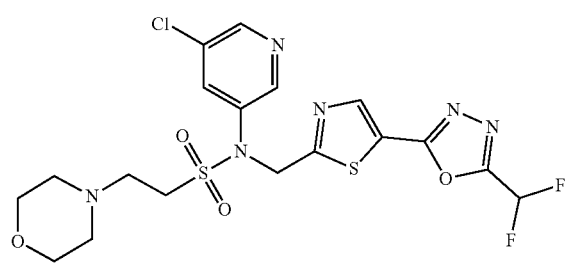
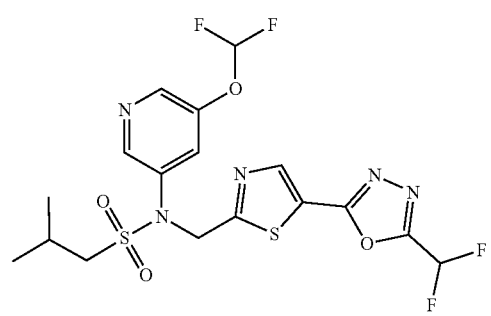
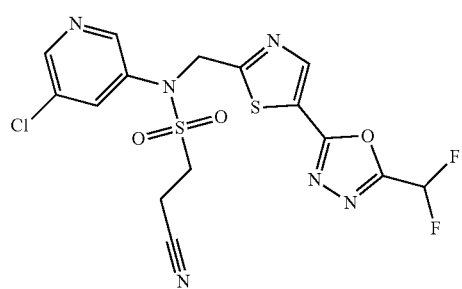
96
-continued
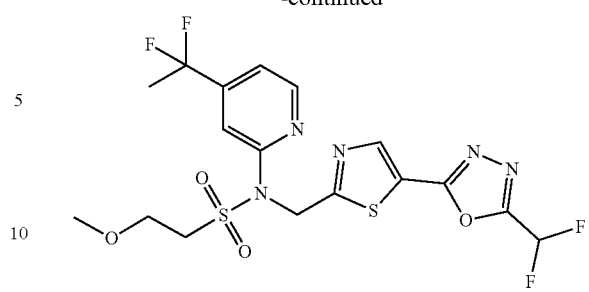
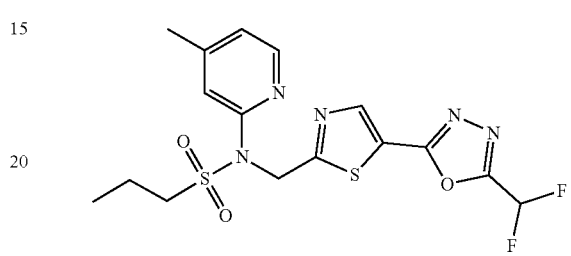
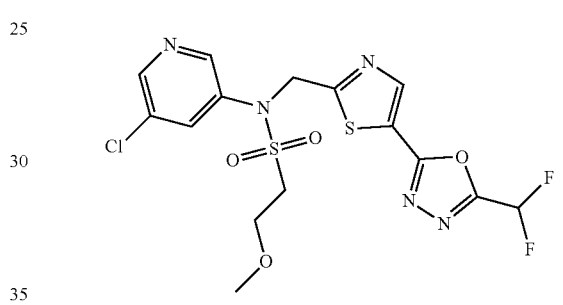
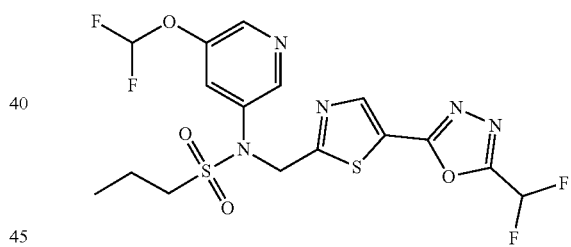
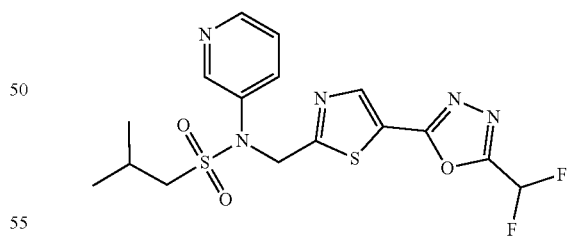
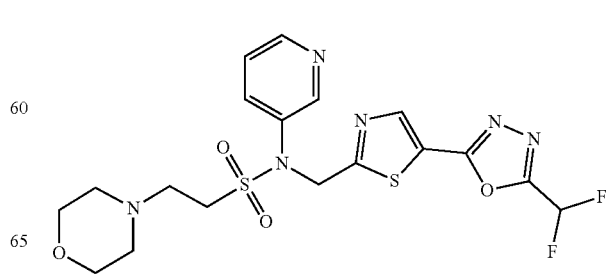

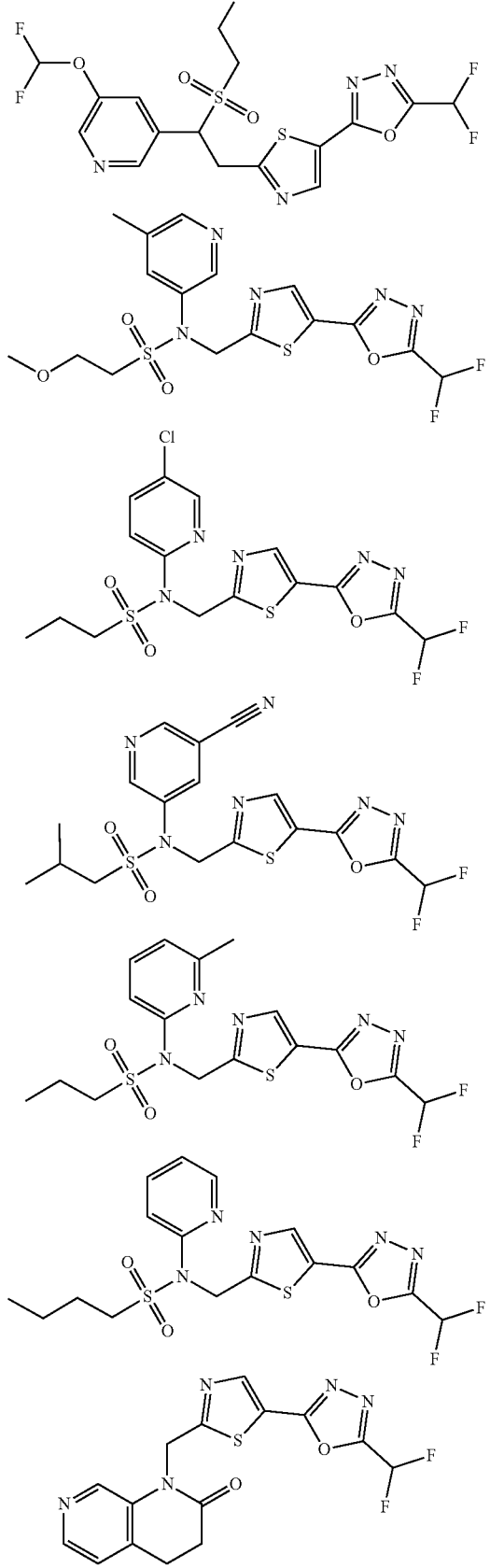

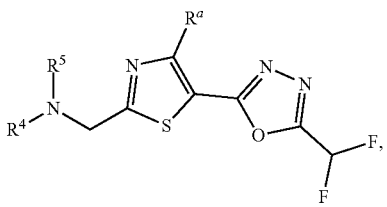

and

In some embodiments, the present disclosure provides a compound of Formula (Ic) or a pharmaceutically acceptable salt thereof:

$$\text{(Ic)}$$

wherein:
$R^a$ is H, Me, or F; and
$R^4$ and $R^5$ are as defined above in Formula (I).

In some embodiments of Formula (Ic), $R^a$ is H. In some embodiments, $R^a$ is F. In some embodiments, $R^a$ is Me.

In some embodiments of Formula (Ic), $R^4$ is selected from the group consisting of alkylenealkoxy, alkyleneheterocyclyl, —S(O)$_2$ alkyl, —S(O)$_2$ cycloalkyl, —S(O)$_2$ alkylenecycloalkyl, —S(O)$_2$ alkyleneheterocyclyl, —S(O)$_2$N(H)alkyleneheterocyclyl, —C(O)alkyl, —C(O)cycloalkyl, —C(O)alkylenecycloalkyl, —C(O)alkyleneheterocyclyl, and —C(O)N(H)alkyleneheterocyclyl. In some embodiments, $R^4$ is selected from the group consisting of alkyleneheterocyclyl, —S(O)$_2$ alkyl, —S(O)$_2$ cycloalkyl, —S(O)$_2$ alkyleneheterocyclyl, —C(O)alkyleneheterocyclyl, and —C(O)N(H)alkyleneheterocyclyl. In some embodiments, $R^4$ is selected from the group consisting of —S(O)$_2$ alkyl, —S(O)$_2$ cycloalkyl, and —S(O)$_2$ alkyleneheterocyclyl. In some embodiments, $R^4$ is —S(O)$_2$ alkyl. In some embodiments, $R^4$ is —S(O)$_2$ cycloalkyl. In some embodiments, $R^4$ is —S(O)$_2$N(H)alkyleneheterocyclyl. In some embodiments, the alkylene is a $C_{1-5}$ alkylene and the heterocyclyl is an optionally substituted 4- to 10-membered heterocyclyl having 1, 2, or 3 heteroatoms selected from the group consisting of N, O, and S. In some embodiments, the alkylene is a $C_{1-5}$ alkylene and the heterocyclyl is an optionally substituted 4- to 7-membered heterocyclyl having 1, 2, or 3 heteroatoms selected from the group consisting of N, O, and S. In some embodiments, the alkylene is a $C_{2-4}$ alkylene and the heterocyclyl is an optionally substituted 6-membered heterocyclyl having 1, 2, or 3 heteroatoms selected from the group consisting of N, O, and S. In some embodiments, the heterocyclyl is selected from the group consisting of piperidine, morpholine, thiomorpholine, thiomorpholine 1-oxide, thiomorpholine 1,1-dioxide, and piperizine, each of which is optionally substituted. In some embodiments, the optional substituent is selected from the group consisting of alkyl, haloalkyl, alkoxy, acyl, sulfonyl, heteroaryl, and heterocyclyl.

In some embodiments of Formula (Ic), $R^5$ is selected from the group consisting of:

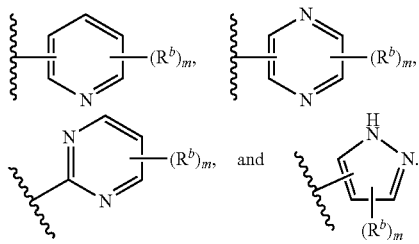

In some embodiments, $R^5$ is

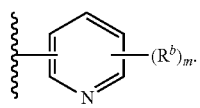

In some embodiments, $R^5$ is

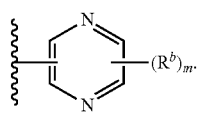

In some embodiments, $R^5$ is

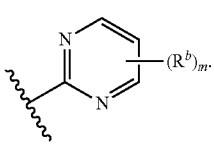

In some embodiments, $R^5$ is

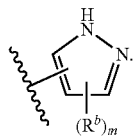

In some embodiments, $R^b$ is selected from the group consisting of halogen, haloalkyl, alkyl, Oalkyl, Ohaloalkyl, alkylene-Ohaloalkyl, cycloalkyl, heterocyclyl aryl, heteroaryl, alkylnitrile, or CN. In some embodiments, $R^b$ is selected from the group consisting of halo, alkyl, haloalkyl, alkoxy, haloalkoxy, acyl, sulfonyl, cycloalkyl, heteroaryl, and heterocyclyl. In some embodiments, the haloalkyl is selected from $CF_3$, $CF_2CH_3$, $CHF_2$, or $CH_2F$. In some embodiments, the alkyl is a $-C_{1-5}$ alkyl. In some embodiments, $-C_{1-5}$ alkyl is methyl, ethyl, propyl, i-propyl, butyl, or t-butyl. In some embodiments, methyl, ethyl, propyl, i-propyl, butyl, or t-butyl is optionally substituted with OH. In some embodiments, the cycloalkyl is a $C_{3-6}$ cycloalkyl. In some embodiments, the aryl is a phenyl. In some embodiments, the heteroaryl is 5- or 6-membered heteroaryl having 1, 2, or 3 heteroatoms selected from N, O, and S. In some embodiments, the heterocyclyl is a 4- to 7-member heterocyclyl with 1 or 2 heteroatoms selected from N, O, and S. In some embodiments, the Ohaloalkyl is selected from $OCF_3$, $OCHF_2$, or $OCH_2F$. In some embodiments, the Oalkyl is O-methyl, O-ethyl, O-propyl, O-i-propyl, O-butyl, or O-t-butyl. In some embodiments, $R^b$ is selected from the group consisting of F, Cl, $-CH_3$, $-CH_2CH_3$, $-CF_3$, $-CHF_2$, $-CF_2CH_3$, $-CN$, $-OCH_3$, $-OCH_2CH_3$, $-OCH(CH_3)_2$, $-OCHF_2$, $-OCH_2CF_2H$, and cyclopropyl. In some embodiments, m is 0, 1, or 2. In some embodiments, m is 0 or 1. In some embodiments, m is 0. In some embodiments, m is 1. In some embodiments, m is 2.

In some embodiments, the present disclosure provides a compound of Formula (Id) or a pharmaceutically acceptable salt thereof:

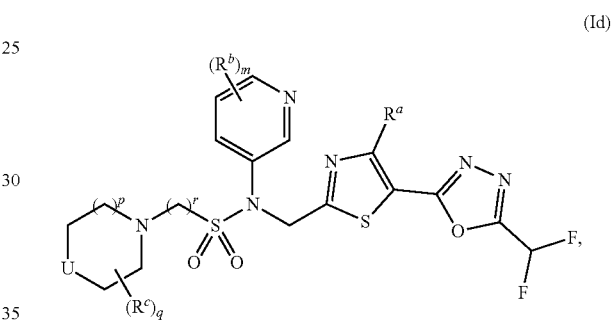

wherein:

U is $NR^d$, O, S, S(O), $S(O)_2$, $CH_2$, CHF, or $CF_2$;

$R^a$ is H, Me, or F;

$R^b$ is each independently halo, alkyl, haloalkyl, alkoxy, haloalkoxy, $-C(O)R^e$, $-C(O)OR^e$, $-C(O)N(R^e)(R^{e'})$, $-S(O_2)R^e$, cycloalkyl, heteroaryl, or heterocyclyl;

$R^c$ is each independently F, alkyl, haloalkyl, alkoxy, haloalkoxy, $-C(O)R^e$, $-C(O)OR^e$, $-C(O)N(R^e)(R^{e'})$, $-S(O_2)R^e$, heteroaryl, or heterocyclyl, and/or two $R^c$ groups taken together with the carbon atoms to which they are attached form a bridged or fused $C_{3-7}$ cycloalkyl, a bridged or fused 4- to 7-membered heterocyclyl; or a 5- or 6-membered heteroaryl, each of which is optionally substituted;

$R^d$ is H, alkyl, acyl, sulfonyl, cycloalkyl, aryl, or heteroaryl;

$R^e$ and $R^{e'}$ is each independently H, alkyl, cycloalkyl, heterocyclyl, aryl, heteroaryl, $-CH_2$ cycloalkyl, $-CH_2$ heterocyclyl, $-CH_2$ aryl, or $-CH_2$ heteroaryl;

m is 0, 1, 2, or 3;

p is 0, 1, 2, or 3;

q is 0, 1, or 2; and r is 1, 2, 3, or 4.

In some embodiments, the present disclosure provides a compound of Formula (Ie) or a pharmaceutically acceptable salt thereof:

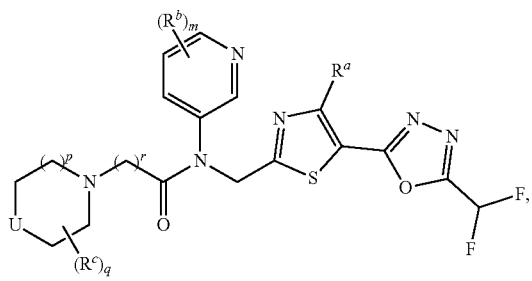

(Ie)

wherein:
U is NR$^d$, O, S, S(O), S(O)$_2$, CH$_2$, CHF, or CF$_2$;
R$^a$ is H, Me, or F;
R$^b$ is each independently halo, alkyl, haloalkyl, alkoxy, haloalkoxy, —C(O)R$^e$, —C(O)OR$^e$, —C(O)N(R$^e$)(R$^{e'}$), sulfonyl, cycloalkyl, heteroaryl, or heterocyclyl;
R$^c$ is each independently F, alkyl, haloalkyl, alkoxy, haloalkoxy, —C(O)R$^e$, —C(O)OR$^e$, —C(O)N(R$^e$)(R$^{e'}$), —S(O$_2$)R$^e$, heteroaryl, or heterocyclyl, and/or two R$^c$ groups taken together with the carbon atoms to which they are attached form a bridged or fused C$_{3-7}$ cycloalkyl, a bridged or fused 4- to 6-membered heterocyclyl; or a 5- or 6-membered heteroaryl, each of which is optionally substituted;
R$^d$ is H, alkyl, acyl, sulfonyl, cycloalkyl, aryl, or heteroaryl;
R$^e$ and R$^{e'}$ is each independently H, alkyl, cycloalkyl, heterocyclyl, aryl, heteroaryl, —CH$_2$ cycloalkyl, —CH$_2$ heterocyclyl, —CH$_2$ aryl, or —CH$_2$ heteroaryl;
m is 0, 1, 2, or 3;
p is 0, 1, 2, or 3;
q is 0, 1, or 2; and
r is 1, 2, 3, or 4.

In some embodiments, the present disclosure provides a compound of Formula (If) or a pharmaceutically acceptable salt thereof:

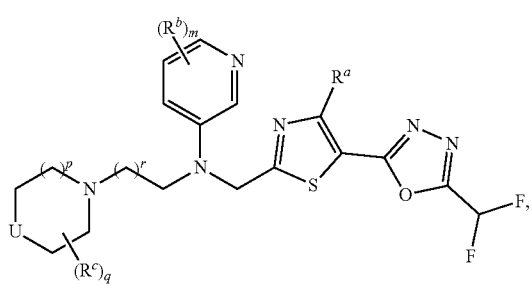

(If)

wherein:
U is NR$^d$, O, S, S(O), S(O)$_2$, CH$_2$, CHF, or CF$_2$;
R$^a$ is H, Me, or F;
R$^b$ is each independently halo, alkyl, haloalkyl, alkoxy, haloalkoxy, —C(O)R$^e$, —C(O)OR$^e$, —C(O)N(R$^e$)(R$^{e'}$), sulfonyl, cycloalkyl, heteroaryl, or heterocyclyl;
R$^c$ is each independently F, alkyl, haloalkyl, alkoxy, haloalkoxy, —C(O)R$^e$, —C(O)OR$^e$, —C(O)N(R$^e$)(R$^{e'}$), —S(O$_2$)R$^e$, heteroaryl, or heterocyclyl, and/or two R$^c$ groups taken together with the carbon atoms to which they are attached form a bridged or fused C$_{3-7}$ cycloalkyl, a bridged or fused 4- to 7-membered heterocyclyl; or a 5- or 6-membered heteroaryl, each of which is optionally substituted;
R$^d$ is H, alkyl, acyl, sulfonyl, cycloalkyl, aryl, or heteroaryl;
R$^e$ and R$^{e'}$ is each independently H, alkyl, cycloalkyl, heterocyclyl, aryl, heteroaryl, —CH$_2$ cycloalkyl, —CH$_2$ heterocyclyl, —CH$_2$ aryl, or —CH$_2$ heteroaryl;
m is 0, 1, 2, or 3;
p is 0, 1, 2, or 3;
q is 0, 1, or 2; and
r is 1, 2, 3, or 4.

In some embodiments, the present disclosure provides a compound of Formula (Ig) or a pharmaceutically acceptable salt thereof:

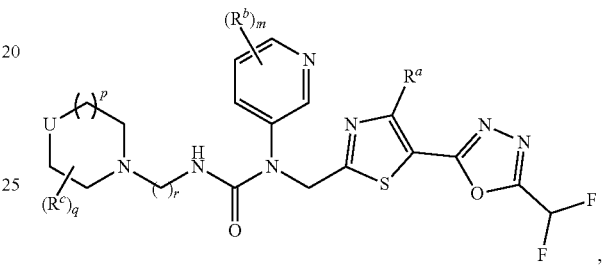

(Ig)

wherein:
U is NR$^d$, O, S, S(O), S(O)$_2$, CH$_2$, CHF, or CF$_2$;
R$^a$ is H, Me, or F;
R$^b$ is each independently halo, alkyl, haloalkyl, alkoxy, haloalkoxy, —C(O)R$^e$, —C(O)OR$^e$, —C(O)N(R$^e$)(R$^{e'}$), sulfonyl, cycloalkyl, heteroaryl, or heterocyclyl;
R$^c$ is each independently F, alkyl, haloalkyl, alkoxy, haloalkoxy, —C(O)R$^e$, —C(O)OR$^e$, —C(O)N(R$^e$)(R$^{e'}$), —S(O$_2$)R$^e$, heteroaryl, or heterocyclyl, and/or two R' groups taken together with the carbon atoms to which they are attached form a bridged or fused C$_{3-7}$ cycloalkyl, a bridged or fused 4- to 7-membered heterocyclyl; or a 5- or 6-membered heteroaryl, each of which is optionally substituted;
R$^d$ is H, alkyl, acyl, sulfonyl, cycloalkyl, aryl, or heteroaryl;
R$^e$ and R$^{e'}$ is each independently H, alkyl, cycloalkyl, heterocyclyl, aryl, heteroaryl, —CH$_2$ cycloalkyl, —CH$_2$ heterocyclyl, —CH$_2$ aryl, or —CH$_2$ heteroaryl;
m is 0, 1, 2, or 3;
p is 0, 1, 2, or 3;
q is 0, 1, or 2; and
r is 1, 2, 3, or 4.

In some embodiments, the compound has the formula:

(Id-1)

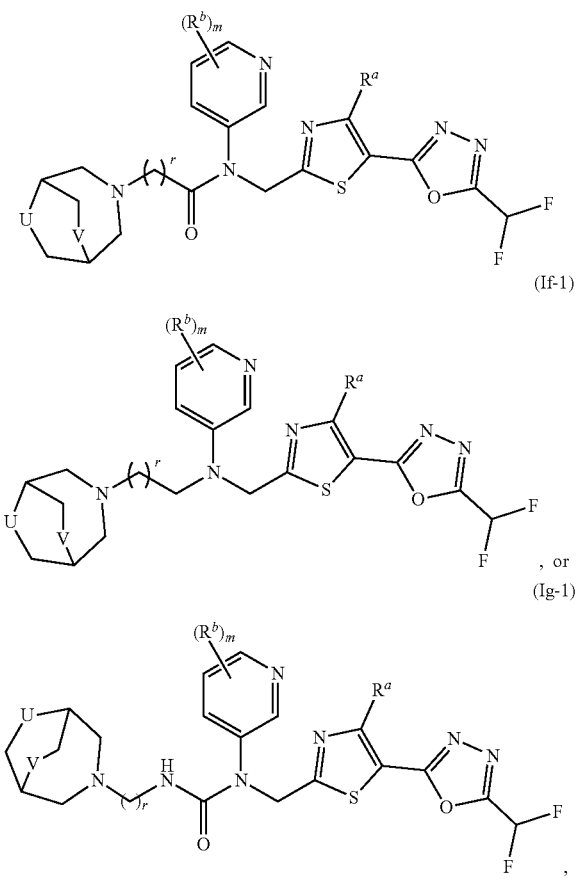

wherein:
U, $R^a$, $R^b$, m, and r are as defined above in Formulas (Id), (Ie), (If), and (Ig); and
V is O or $NR^d$.

In some embodiments of Formulas (Id)-(Ig) and (Id-1)-(Ig-1), U is $NR^d$, O, or S and V is O. In some embodiments, U is N, O, or S and V is $NR^d$. In some embodiments, U is NR d and V is $NR^d$. In some embodiments, U is O and V is $NR^d$. In some embodiments, U is S and V is $NR^d$. In some embodiments, U is $NR^d$ and V is O. In some embodiments, U is O and V is O. In some embodiments, U is S and V is O.

In some embodiments of Formulas (Id)-(Ig) and (Id-1)-(Ig-1), U is O, S, $S(O)_2$, $CH_2$, or $NR^d$. In some embodiments, U is O, S, $CH_2$, or $NR^d$. In some embodiments, U is O, S, or $NR^d$. In some embodiments, U is O or $CH_2$. In some embodiments, U is O. In some embodiments, U is S. In some embodiments, U is $NR^d$. In some embodiments, U is $S(O)_2$.

In some embodiments of Formulas (Id)-(Ig) and (Id-1)-(Ig-1), $R^a$ is H. In some embodiments, $R^a$ is F. In some embodiments, $R^a$ is Me.

In some embodiments of Formulas (Id)-(Ig) and (Id-1)-(Ig-1), $R^b$ is halo, alkyl, haloalkyl, alkyl, haloalkoxy, cycloalkyl, heterocyclyl, heteroaryl, or nitrile. In some embodiments, $R^b$ is halo, alkyl, haloalkyl, alkyl, haloalkoxy, cycloalkyl, or nitrile. In some embodiments, the haloalkyl is selected from $CF_3$, $CF_2CH_3$, $CHF_2$, or $CH_2F$. In some embodiments, the alkyl is a $-C_{1-5}$ alkyl. In some embodiments, $-C_{1-5}$ alkyl is methyl, ethyl, propyl, i-propyl, butyl, or t-butyl. In some embodiments, the cycloalkyl is a $C_{3-6}$ cycloalkyl. In some embodiments, the heteroaryl is 5- or 6-membered heteroaryl having 1, 2, or 3 heteroatoms selected from N, O, and S. In some embodiments, the heterocyclyl is a 4- to 7-member heterocyclyl with 1 or 2 heteroatoms selected from N, O, and S. In some embodiments, the haloalkoxy is selected from $OCF_3$, $OCHF_2$, or $OCH_2F$. In some embodiments, the alkoxy is O-ethyl, O-propyl, O-i-propyl, O-butyl, or O-t-butyl. In some embodiments, $R^b$ is $-C(O)R^e$, $-C(O)OR^e$, $-C(O)N(R^e)(R^{e'})$.

In some embodiments of Formulas (Id)-(Ig), $R^c$ is F, $C_{1-5}$ alkyl, haloalkyl, $C_{1-5}$ alkoxy, haloalkoxy, acyl, sulfonyl, 5- or 6-membered heteroaryl, or $C_{3-6}$ heterocyclyl. In some embodiments, $R^c$ is $-C(O)R^e$, $-C(O)OR^e$, $-C(O)N(R^e)(R^{e'})$. In some embodiments, two $R^c$ groups taken together with the carbon atoms to which they are attached form a bridged or fused $C_{3-7}$ cycloalkyl, a bridged or fused 5- or 6-membered heterocyclyl, or a 5- or 6-membered heteroaryl, each of which is optionally substituted. In some embodiments, two $R^e$ groups taken together with the carbon atoms to which they are attached form an optionally substituted bridged or fused $C_{3-7}$ cycloalkyl. In some embodiments, two $R^c$ groups taken together with the carbon atoms to which they are attached form an optionally substituted bridged or fused 5- or 6-membered heterocyclyl. In some embodiments, two $R^c$ groups taken together with the carbon atoms to which they are attached form an alkoxy or aminoalkyl bridge. In some embodiments, the optional substituent is one or more $R^b$, as defined above. In some embodiments, the optional substituent is selected from the group consisting of F, $C_{1-5}$ alkyl, $C_{1-5}$ alkoxy, $CF_3$, $CF_2H$, $CFH_2$, $-OCF_3$, $-OCF_2H$, $-OCFH_2$, $-C(O)R^e$, $-C(O)OR^e$, $-C(O)N(R^e)(R^{e'})$, and $-SO_2R^e$. In some embodiments, the optional substituent is selected from the group consisting of F, $C_{1-5}$ alkyl, $C_{1-5}$ alkoxy, $CF_3$, $CF_2H$, $CFH_2$, $-OCF_3$, $-OCF_2H$, and $-OCFH_2$. In some embodiments, the optional substituent is F or $C_{1-5}$ alkyl. In some embodiments, the optional substituent is F. In some embodiments, the optional substituent is $C_{1-5}$ alkyl. In some embodiments, the $C_{1-5}$ alkyl is methyl. In some embodiments, the $C_{1-5}$ alkyl is ethyl. In some embodiments, the $C_{1-5}$ alkyl is propyl. In some embodiments, the $C_{1-5}$ alkyl is isopropyl.

In some embodiments of Formulas (Id)-(Ig) and (Id-1)-(Ig-1), $R^e$ and $R^{e'}$ is each independently H, alkyl, cycloalkyl, or $-CH_2$ cycloalkyl. In some embodiments, the alkyl is a $-C_{1-5}$ alkyl. In some embodiments, $-C_{1-5}$ alkyl is methyl, ethyl, propyl, i-propyl, butyl, or t-butyl. In some embodiments, the cycloalkyl is a $C_{3-6}$ cycloalkyl. In some embodiments, the cycloalkyl is cyclopropyl. In some embodiments, $R^e$ and $R^{e'}$ are H.

In some embodiments of Formulas (Id)-(Ig) and (Id-1)-(Ig-1), m is 0, 1, or 2. In some embodiments, m is 0 or 1. In some embodiments, m is 0. In some embodiments, m is 1. In some embodiments, m is 2.

In some embodiments of Formulas (Id)-(Ig), p is 0, 1, or 2. In some embodiments, p is or 1. In some embodiments, p is 1 or 2. In some embodiments, p is 0. In some embodiments, p is 1. In some embodiments, p is 2.

In some embodiments of Formulas (Id)-(Ig) and (Id-1)-(Ig-1), r is 1, 2, or 3. In some embodiments, r is 1 or 2. In some embodiments, r is 2 or 3. In some embodiments, r is 1. In some embodiments, r is 2. In some embodiments, r is 3. In some embodiments, r is 4.

In some embodiments of Formulas (Id)-(Ig), q is 0 or 1. In some embodiments, q is 0. In some embodiments, q is 1. In some embodiments, q is 2.

In some embodiments of Formulas (Id)-(Ig), r is 1 and p is 1. In some embodiments, r is 2 and p is 1. In some embodiments, r is 3 and p is 1.

In some embodiments, the present disclosure provides a compound of Formula (Ih) or a pharmaceutically acceptable salt thereof:

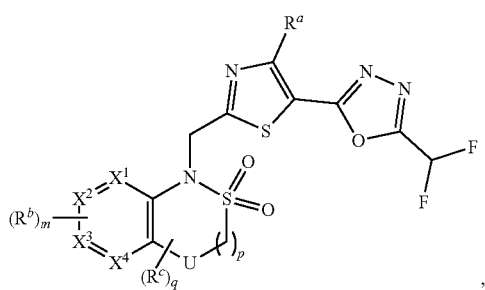
(Ih)

wherein:
U is $NR^d$, O, S, S(O), $S(O)_2$, $CH_2$, CHF, or $CF_2$;
$X^1$, $X^2$, $X^3$, and $X^4$ is each independently CH or N;
$R^a$ is H, Me, or F;
$R^b$ is each independently halo, alkyl, haloalkyl, alkoxy, haloalkoxy, —$C(O)R^e$, —$C(O)OR^e$, —$C(O)N(R^e)(R^{e'})$, —$SO_2R^e$, cycloalkyl, heteroaryl, or heterocyclyl;
$R^c$ is each independently F, alkyl, haloalkyl, alkoxy, or haloalkoxy, and/or two $R^e$ groups taken together with the atoms to which they are attached form an optionally substituted $C_{3-7}$ cycloalkyl;
$R^d$ is H, alkyl, acyl, sulfonyl, cycloalkyl, aryl, or heteroaryl;
$R^e$ and $R^{e'}$ is each independently H, alkyl, cycloalkyl, heterocyclyl, aryl, heteroaryl, —$CH_2$ cycloalkyl, —$CH_2$ heterocyclyl, —$CH_2$ aryl, or —$CH_2$ heteroaryl;
m is 0, 1, 2, or 3;
p is 0, 1, 2, or 3; and
q is 0, 1, or 2.

In some embodiments, the present disclosure provides a compound of Formula (Ii) or a pharmaceutically acceptable salt thereof:

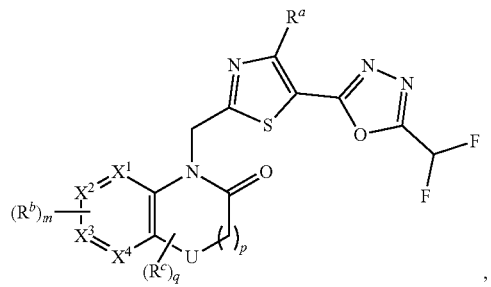
(Ii)

wherein:
U is $NR^d$, O, S, S(O), $S(O)_2$, $CH_2$, CHF, or $CF_2$;
$X^1$, $X^2$, $X^3$, and $X^4$ is each independently CH or N;
$R^a$ is H, Me, or F;
$R^b$ is each independently halo, alkyl, haloalkyl, alkoxy, haloalkoxy, —$C(O)R^e$, —$C(O)OR^e$, —$C(O)N(R^e)(R^{e'})$, —$SO_2R^e$, cycloalkyl, heteroaryl, or heterocyclyl;
$R^c$ is each independently F, alkyl, haloalkyl, alkoxy, or haloalkoxy, and/or two $R^e$ groups taken together with the atoms to which they are attached form an optionally substituted $C_{3-7}$ cycloalkyl;
$R^d$ is H, alkyl, —$C(O)R^e$, sulfonyl, cycloalkyl, aryl, or heteroaryl;
$R^e$ and $R^{e'}$ is each independently H, alkyl, cycloalkyl, heterocyclyl, aryl, heteroaryl, —$CH_2$ cycloalkyl, —$CH_2$ heterocyclyl, —$CH_2$ aryl, or —$CH_2$ heteroaryl;
m is 0, 1, 2, or 3;
p is 0, 1, 2, or 3; and
q is 0, 1, or 2.

In some embodiments, the present disclosure provides a compound of Formula (Ij) or a pharmaceutically acceptable salt thereof:

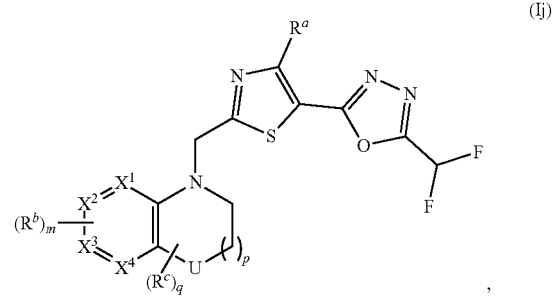
(Ij)

wherein:
U is $NR^d$, O, S, S(O), $S(O)_2$, $CH_2$, CHF, or $CF_2$;
$X^1$, $X^2$, $X^3$, and $X^4$ is each independently CH or N;
$R^a$ is H, Me, or F;
$R^b$ is each independently halo, alkyl, haloalkyl, alkoxy, haloalkoxy, —$C(O)R^e$, —$C(O)OR^e$, —$C(O)N(R^e)(R^{e'})$, —$SO_2R^e$, cycloalkyl, heteroaryl, or heterocyclyl;
$R^c$ is each independently F, alkyl, haloalkyl, alkoxy, or haloalkoxy, and/or two $R^c$ groups taken together with the atoms to which they are attached form an optionally substituted $C_{3-7}$ cycloalkyl;
$R^d$ is H, alkyl, —$C(O)R^e$, sulfonyl, cycloalkyl, aryl, or heteroaryl;
$R^e$ and $R^{e'}$ is each independently H, alkyl, cycloalkyl, heterocyclyl, aryl, heteroaryl, —$CH_2$ cycloalkyl, —$CH_2$ heterocyclyl, —$CH_2$ aryl, or —$CH_2$ heteroaryl;
m is 0, 1, 2, or 3;
p is 0, 1, 2, or 3; and
q is 0, 1, or 2.

In some embodiments of Formulas (Ih)-(Ij), $NR^d$, O, S, $S(O)_2$, or $CH_2$. In some embodiments, U is $NR^d$, O, S, or $CH_2$. In some embodiments, U is O or $CH_2$. In some embodiments, U is O. In some embodiments, U is $CH_2$. In some embodiments, U is S. In some embodiments, U is $S(O)_2$. In some embodiments, U is $NR^d$.

In some embodiments of Formulas (Ih)-(Ij), each of $X^1$, $X^2$, $X^3$, and $X^4$ is CH. In some embodiments, one of $X^1$, $X^2$, $X^3$, and $X^4$ is N. In some embodiments, two of $X^1$, $X^2$, $X^3$, and $X^4$ are N. In some embodiments, $X^1$ is N and each of $X^2$, $X^3$, and $X^4$ is CH. In some embodiments, $X^2$ is N and each of $X^1$, $X^3$, and $X^4$ is CH. In some embodiments, $X^3$ is N and each of $X^1$, $X^2$, and $X^4$ is CH. In some embodiments, $X^4$ is N and each of $X^1$, $X^2$, and $X^3$ is CH.

In some embodiments of Formulas (Ih)-(Ij), U is $CH_2$ and one of $X^1$, $X^2$, $X^3$, and $X^4$ is N. In some embodiments, U is $CH_2$, $X^1$ is N and each of $X^2$, $X^3$, and $X^4$ is CH. In some embodiments, U is $CH_2$, $X^2$ is N and each of $X^1$, $X^3$, and $X^4$ is CH. In some embodiments, U is $CH_2$, $X^3$ is N and each of $X^1$, $X^2$, and $X^4$ is CH. In some embodiments, U is $CH_2$, $X^4$ is N and each of $X^1$, $X^2$, and $X^3$ is CH. In some embodiments, p is 0. In some embodiments, p is 1.

In some embodiments of Formulas (Ih)-(Ij), U is O and one of $X^1$, $X^2$, $X^3$, and $X^4$ is N. In some embodiments, U is O, $X^1$ is N and each of $X^2$, $X^3$, and $X^4$ is CH. In some embodiments, U is O, $X^2$ is N and each of $X^1$, $X^3$, and $X^4$ is CH. In some embodiments, U is O, $X^3$ is N and each of $X^1$, $X^2$, and $X^4$ is CH. In some embodiments, U is O, $X^4$ is N and each of $X^1$, $X^2$, and $X^3$ is CH.

In some embodiments of Formulas (Ih)-(Ij), $R^a$ is H. In some embodiments, $R^a$ is F. In some embodiments, $R^a$ is Me.

In some embodiments of Formulas (Ih)-(Ij), $R^b$ is halo, alkyl, haloalkyl, alkyl, haloalkoxy, cycloalkyl, heterocyclyl, heteroaryl, or nitrile. In some embodiments, $R^b$ is halo, alkyl, haloalkyl, alkyl, haloalkoxy, cycloalkyl, or nitrile. In some embodiments, the haloalkyl is selected from $CF_3$, $CF_2CH_3$, $CHF_2$, or $CH_2F$. In some embodiments, the alkyl is a —$C_{1-5}$ alkyl. In some embodiments, —$C_{1-5}$ alkyl is methyl, ethyl, propyl, i-propyl, butyl, or t-butyl. In some embodiments, the cycloalkyl is a $C_{3-6}$ cycloalkyl. In some embodiments, the heteroaryl is 5- or 6-membered heteroaryl having 1, 2, or 3 heteroatoms selected from N, O, and S. In some embodiments, the heterocyclyl is a 4- to 7-member heterocyclyl with 1 or 2 heteroatoms selected from N, O, and S. In some embodiments, the haloalkoxy is selected from $OCF_3$, $OCHF_2$, or $OCH_2F$. In some embodiments, the alkoxy is O-methyl, O-ethyl, O-propyl, O-i-propyl, O-butyl, or O-t-butyl.

In some embodiments of Formulas (Ih)-(Ij), $R^c$ is F, $C_{1-5}$ alkyl, haloalkyl, $C_{1-5}$ alkoxy, haloalkoxy, acyl, sulfonyl, 5- or 6-membered heteroaryl, or $C_{3-6}$ heterocyclyl. In some embodiments, $R^c$ is F, $C_{1-5}$ alkyl, haloalkyl, $C_{1-5}$ alkoxy, or haloalkoxy. In some embodiments, $R^c$ is F or $C_{1-5}$ alkyl. In some embodiments, $R^c$ is F or methyl. In some embodiments, $R^c$ is F. In some embodiments, $R^c$ is methyl. In some embodiments, the two $R^c$ groups are attached to the same carbon atom, which can also be referred to as germinal substitution. In some embodiments, two $R^c$ groups taken together with the atoms to which they are attached form an optionally substituted $C_{3-6}$ cycloalkyl. In some embodiments, two $R^c$ groups taken together with the atoms to which they are attached form an optionally substituted cyclopropyl. In some embodiments, the optional substituent is one or more $R^b$, as defined above. In some embodiments, the optional substituent is selected from the group consisting of F, $C_{1-5}$ alkyl, $C_{1-5}$ alkoxy, $CF_3$, $CF_2H$, $CFH_2$, —$OCF_3$, —$OCF_2H$, —$OCFH_2$, —$C(O)R^e$, —$C(O)OR^e$, —$C(O)N(R^e)(R^{e'})$, and —$SO_2R^e$. In some embodiments, the optional substituent is selected from the group consisting of F, $C_{1-5}$ alkyl, $C_{1-5}$ alkoxy, $CF_3$, $CF_2H$, $CFH_2$, —$OCF_3$, —$OCF_2H$, and —$OCFH_2$. In some embodiments, the optional substituent is F or $C_{1-5}$ alkyl. In some embodiments, the optional substituent is F. In some embodiments, the optional substituent is $C_{1-5}$ alkyl. In some embodiments, the $C_{1-5}$ alkyl is methyl. In some embodiments, the $C_{1-5}$ alkyl is ethyl. In some embodiments, the $C_{1-5}$ alkyl is propyl. In some embodiments, the $C_{1-5}$ alkyl is isopropyl. In some embodiments, two optional substituents are attached to the same carbon, which is also referred to as germinal substitution.

In some embodiments of Formulas (Ih)-(Ij), when U is $NR^d$, an $R^d$ and $R^c$ taken together with the atoms to which they are attached form a 5- to 7-membered heterocyclyl. In some embodiments, an $R^d$ and $R^c$ taken together with the atoms to which they are attached form a 6-membered heterocyclyl. In some embodiments, the heterocyclyl comprises 1 or 2 heteroatoms selected from N, O, and S.

In some embodiments, the present disclosure provides a compound of Formula (Ih-1), Formula (Ii-1), or Formula (Ij-1):

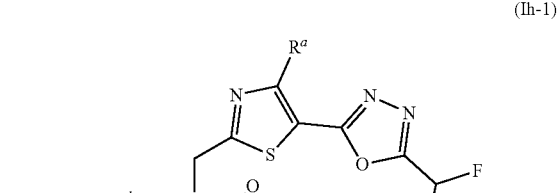

(Ih-1)

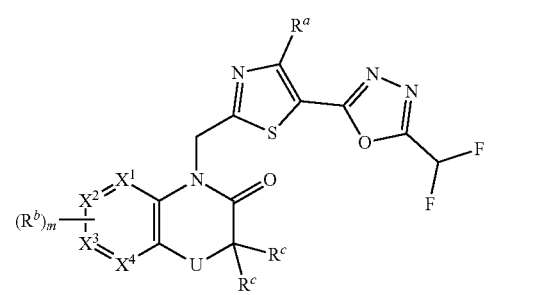

(Ii-1)

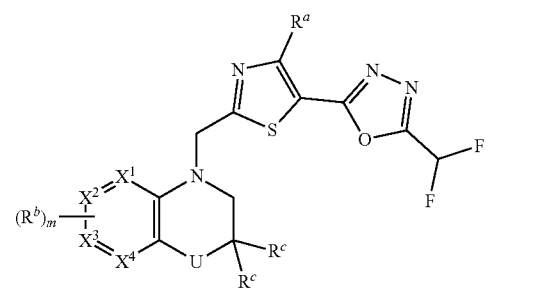

(Ij-1)

wherein $R^a$, $R^b$, $R^c$, $X^1$, $X^2$, $X^3$, $X^4$, U, and m are as defined above in Formula (Ih), Formula (Ii), and Formula (Ij).

In some embodiments of Formula (Ih-1), Formula (Ii-1), and Formula (Ij-1), each $R^c$ is F. In some embodiments, each $R^c$ is Me. In some embodiments, two $R^c$ groups taken together with the carbon atoms to which they are attached form an optionally substituted $C_{3-6}$ cycloalkyl. In some embodiments, two $R^c$ groups taken together with the carbon atoms to which they are attached form a cyclopropyl or cyclobutyl, each of which is optionally substituted. In some embodiments, two $R^c$ groups taken together with the carbon atoms to which they are attached form an optionally substituted cyclopropyl. In some embodiments, the optional substituent is F or $C_{1-5}$ alkyl. In some embodiments, the optional substituent is F. In some embodiments, the optional substituent is $C_{1-5}$ alkyl. In some embodiments, the $C_{1-5}$ alkyl is methyl. In some embodiments, the $C_{1-5}$ alkyl is ethyl. In some embodiments, the $C_{1-5}$ alkyl is propyl. In some embodiments, the $C_{1-5}$ alkyl is isopropyl. In some embodiments, two optional substituents are attached to the same carbon, which is also referred to as germinal substitution.

In some embodiments, $R^d$ is H, alkyl, or cycloalkyl. In some embodiments, $R^d$ is H. In some embodiments, $R^d$ is alkyl. In some embodiments, $R^d$ is cycloalkyl. In some embodiments, alkyl is methyl, ethyl, propyl, isopropyl, or t-butyl. In some embodiments, the cycloalkyl is cyclopropyl, cyclopentyl, or cyclohexyl.

In some embodiments, m is 0, 1, or 2. In some embodiments, m is 0 or 1. In some embodiments, m is 0. In some embodiments, m is 1. In some embodiments, m is 2.

In some embodiments, p is 0, 1, or 2. In some embodiments, p is 0 or 1. In some embodiments, p is 1 or 2. In some embodiments, p is 0. In some embodiments, p is 1. In some embodiments, p is 2.

In some embodiments, q is 0 or 1. In some embodiments, q is 0. In some embodiments, q is 1. In some embodiments, q is 2.

In some embodiments, the HDAC6 inhibitor has the formula:

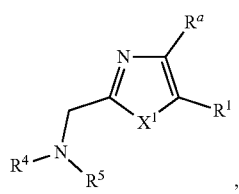

or a pharmaceutically acceptable salt thereof,
wherein:
 $X^1$ is S;
 $R^a$ is selected from the group consisting of H, halogen, and $C_{1-3}$ alkyl;
 $R^1$ is

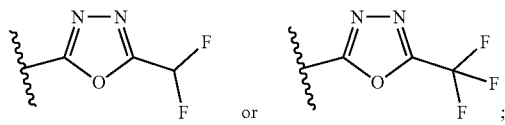 [SMILES: *c1nnc(C(F)F)o1 ; *c1nnc(C(F)(F)F)o1]

$R^2$ is selected from the group consisting of alkyl, alkoxy, and cycloalkyl, each of which is optionally substituted;
 $R^3$ is H or alkyl;
 $R^4$ is selected from the group consisting of alkyl, —(SO$_2$)R$^2$, —(SO$_2$)NR$^2$R$^3$, and —(CO)R$^2$; and
 $R^5$ is aryl or heteroaryl; or $R^4$ and $R^5$ together with the atom to which they are attached form a heterocyclyl, each of which is optionally substituted;
In some embodiments, $R^a$ is H.
In some embodiments, $R^1$ is

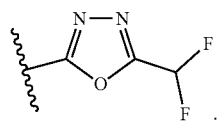 [SMILES: *c1nnc(C(F)F)o1]

In some embodiments, $R^4$ is —(SO$_2$)R$^2$.
In some embodiments, —(SO$_2$)R$^2$ is —(SO$_2$)alkyl, —(SO$_2$)alkyleneheterocyclyl, —(SO$_2$)haloalkyl, —(SO$_2$)haloalkoxy, or —(SO$_2$)cycloalkyl.
In some embodiments, $R^5$ is heteroaryl.
In some embodiments, the heteroaryl is a 5- to 6-membered heteroaryl In some embodiments, the 5- to 6-membered heteroaryl is selected from the group consisting of

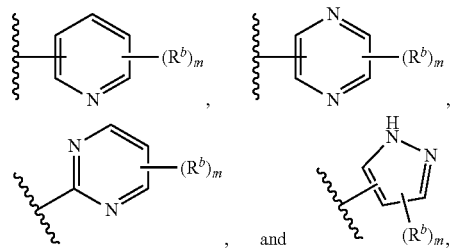

wherein $R^b$ is halogen, alkyl, alkoxy, cycloalkyl, —CN, haloalkyl, or haloalkoxy; and m is 0 or 1.

In some embodiments, $R^b$ is F, Cl, —CH$_3$, —CH$_2$CH$_3$, —CF$_3$, —CHF$_2$, —CF$_2$CH$_3$, —CN, —OCH$_3$, —OCH$_2$CH$_3$, —OCH(CH$_3$)$_2$, —OCF$_3$, —OCHF$_2$, —OCH$_2$CF$_2$H, and cyclopropyl.

In some embodiments, the aryl is selected from the group consisting of phenyl, 3-chlorophenyl, 3-chloro-4-fluorophenyl, 3-trifluoromethylphenyl, 3,4-difluorophenyl, and 2,6-difluorophenyl.

In some embodiments, the HDAC6 inhibitor has the Formula (Ik):

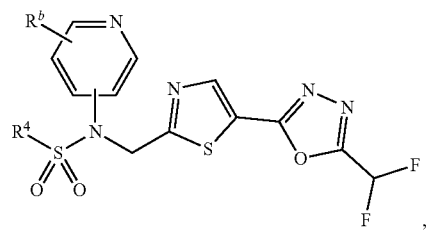

or a pharmaceutically acceptable salt thereof,
wherein:
 $R^b$ is H, halogen, alkyl, cycloalkyl, —CN, haloalkyl, or haloalkoxy; and
 $R^4$ is alkyl, alkoxy, haloalkyl, or cycloalkyl, each of which is optionally substituted.

In some embodiments, $R^b$ is H, halogen, haloalkyl, or haloalkoxy.

In some embodiments, $R^4$ is optionally substituted alkyl or cycloalkyl.

In some embodiments, the HDAC6 inhibitor has the structure:

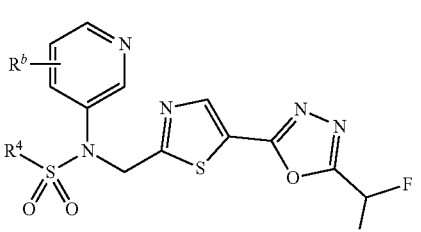

or a pharmaceutically acceptable salt thereof,
wherein:
 $R^b$ is H, halogen, alkyl, cycloalkyl, —CN, haloalkyl, or haloalkoxy; and $R^4$ is alkyl, alkoxy, haloalkyl, or cycloalkyl, each of which is optionally substituted.

In some embodiments, $R^b$ is H, halogen, haloalkyl, or haloalkoxy.

In some embodiments, $R^4$ is optionally substituted alkyl or cycloalkyl.

In some embodiments, $R^4$ is alkyl.

In some embodiments, the HDAC6 inhibitor has the structure:

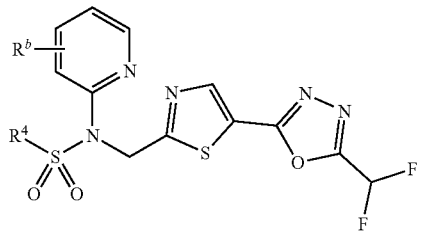

(Ik-2)

or a pharmaceutically acceptable salt thereof, wherein:

$R^b$ is H, halogen, alkyl, cycloalkyl, —CN, haloalkyl, or haloalkoxy; and $R^4$ is alkyl, alkoxy, haloalkyl, or cycloalkyl, each of which is optionally substituted.

In some embodiments, $R^b$ is H, halogen, haloalkyl, or haloalkoxy.

In some embodiments, $R^4$ is optionally substituted alkyl.

In some embodiments, the HDAC6 inhibitor is a compound having the formula:

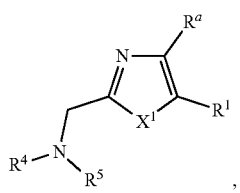

I(y)

or a pharmaceutically acceptable salt thereof, wherein:

$X^1$ is S;

$R^a$ is selected from the group consisting of H, halogen, and $C_{1-3}$ alkyl;

$R^1$ is

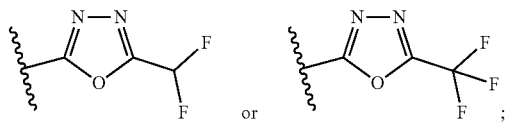 [SMILES: *c1nnc(C(F)F)o1 ; *c1nnc(C(F)(F)F)o1]

$R^2$ is selected from the group consisting of alkyl, alkoxy, and cycloalkyl, each of which is optionally substituted;

$R^3$ is H or alkyl;

$R^4$ is selected from the group consisting of alkyl, —(SO$_2$)R$^2$, —(SO$_2$)NR$^2$R$^3$, and —(CO)R$^2$; and $R^5$ is aryl or heteroaryl; or $R^4$ and $R^5$ together with the atom to which they are attached form a heterocyclyl, each of which is optionally substituted.

In some embodiments of Formula I(y), $R^a$ is H.

In some embodiments of Formula I(y), $R^1$ is

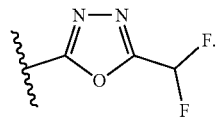 [SMILES: *c1nnc(C(F)F)o1]

In some embodiments of Formula I(y), $R^4$ is —(SO$_2$)R$^2$.

In some embodiments of Formula I(y), —(SO$_2$)R$^2$ is —(SO$_2$)alkyl, —(SO$_2$)alkyleneheterocyclyl, —(SO$_2$)haloalkyl, —(SO$_2$)haloalkoxy, or —(SO$_2$)cycloalkyl.

In some embodiments of Formula I(y), $R^5$ is heteroaryl.

In some embodiments of Formula I(y), the heteroaryl is a 5- to 6-membered heteroaryl.

In some embodiments of Formula I(y), the 5- to 6-membered heteroaryl is selected from the group consisting of

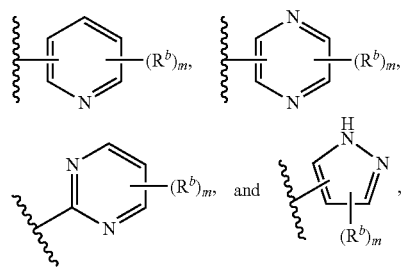

wherein $R^b$ is halogen, alkyl, alkoxy, cycloalkyl, —CN, haloalkyl, or haloalkoxy; and m is 0 or 1.

In some embodiments of Formula I(y), $R^b$ is F, Cl, —CH$_3$, —CH$_2$CH$_3$, —CF$_3$, —CHF$_2$, —CF$_2$CH$_3$, —CN, —OCH$_3$, —OCH$_2$CH$_3$, —OCH(CH$_3$)$_2$, —OCF$_3$, —OCHF$_2$, —OCH$_2$CF$_2$H, and cyclopropyl.

In some embodiments of Formula I(y), the aryl is selected from the group consisting of phenyl, 3-chlorophenyl, 3-chloro-4-fluorophenyl, 3-trifluoromethylphenyl, 3,4-difluorophenyl, and 2,6-difluorophenyl.

In some embodiments, the HDAC6 inhibitor has the structure:

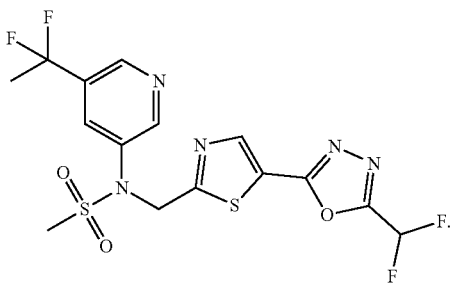 [SMILES: CC(F)(F)c1cncc(N(Cc2ncc(-c3nnc(C(F)F)o3)s2)S(C)(=O)=O)c1]

In some embodiments, the HDAC6 inhibitor has the structure:

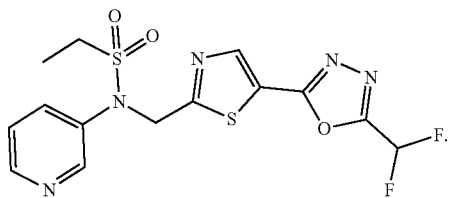 [SMILES: CCS(=O)(=O)N(Cc1ncc(-c2nnc(C(F)F)o2)s1)c1cccnc1]

In some embodiments, the HDAC6 inhibitor has the structure:

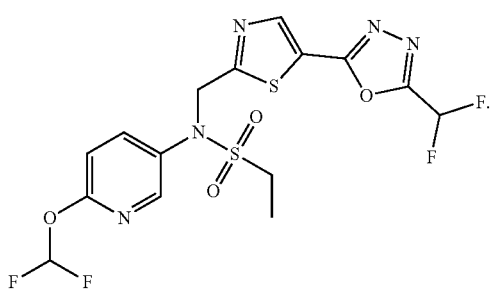 [SMILES: CCS(=O)(=O)N(Cc1ncc(-c2nnc(C(F)F)o2)s1)c1ccc(OC(F)F)nc1]

In some embodiments, the HDAC6 inhibitor has the structure:

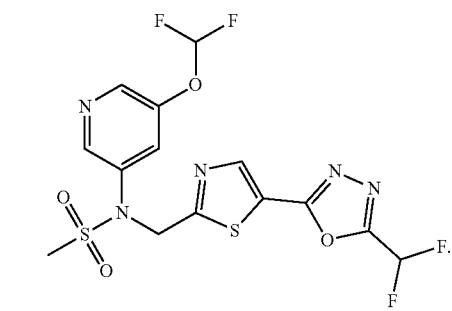 [SMILES: CS(=O)(=O)N(Cc1ncc(-c2nnc(C(F)F)o2)s1)c1cncc(OC(F)F)c1]

In some embodiments, the HDAC6 inhibitor has the structure:

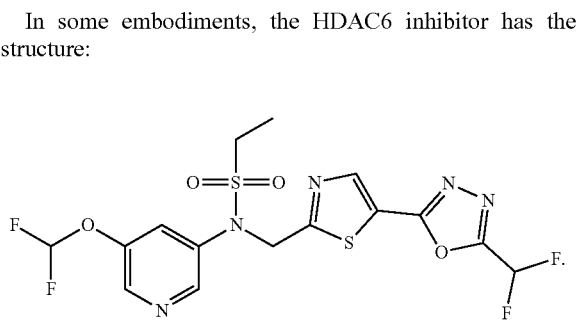

In some embodiments, the HDAC6 inhibitor has the structure:

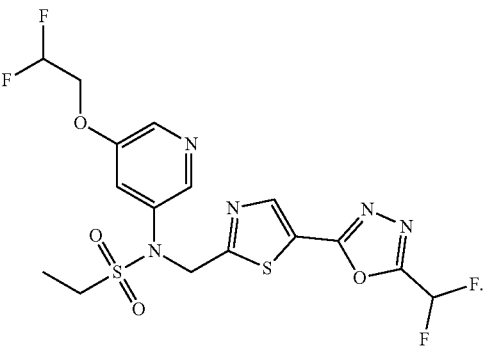 [SMILES: CCS(=O)(=O)N(Cc1ncc(-c2nnc(C(F)F)o2)s1)c1cncc(OCC(F)F)c1]

In some embodiments, the HDAC6 inhibitor has the structure:

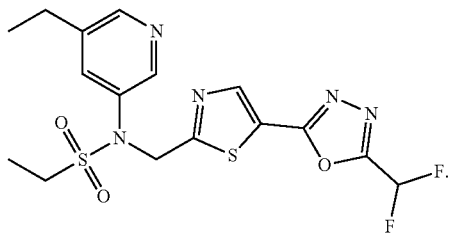 [SMILES: CCc1cncc(N(Cc2ncc(-c3nnc(C(F)F)o3)s2)S(=O)(=O)CC)c1]

In some embodiments, the HDAC6 inhibitor has the structure:

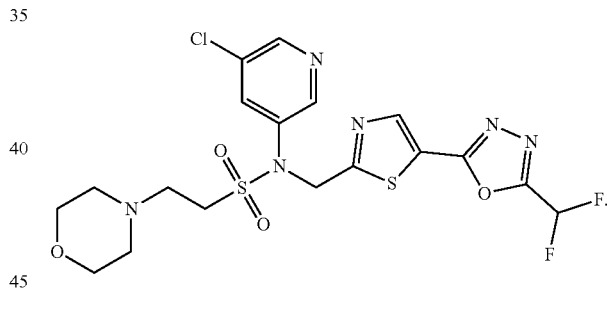

In some embodiments, the HDAC6 inhibitor has the structure:

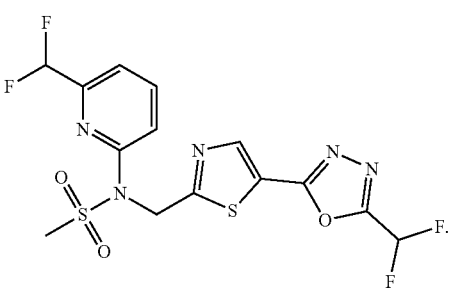 [SMILES: CS(=O)(=O)N(Cc1ncc(-c2nnc(C(F)F)o2)s1)c1cccc(C(F)F)n1]

In some embodiments, the HDAC6 inhibitor has the structure:

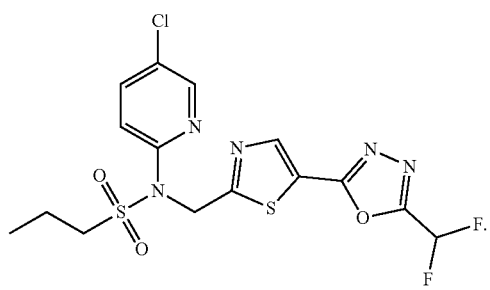 [SMILES: CCCS(=O)(=O)N(Cc1ncc(-c2nnc(C(F)F)o2)s1)c1ccc(Cl)cn1]
In some embodiments, the fluoroalkyl-oxadiazole derivative is TYA-018 or an analog thereof. The structure of TYA-018 is
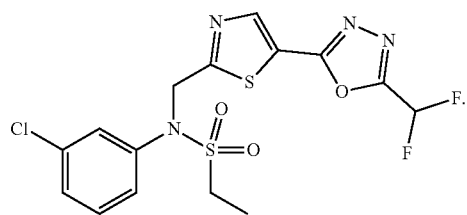 [SMILES: CCS(=O)(=O)N(Cc1ncc(-c2nnc(C(F)F)o2)s1)c1cccc(Cl)c1]
Analogs of TYA-018 include, without limitation, the compounds listed in Table 2.
TABLE 2
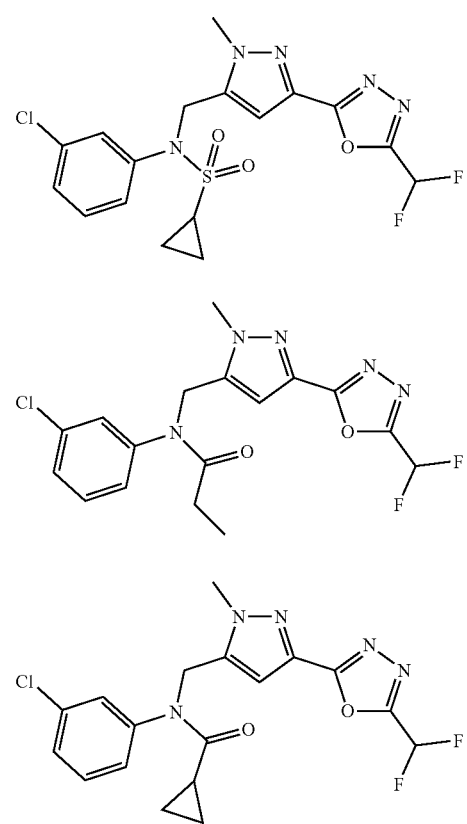
TABLE 2-continued
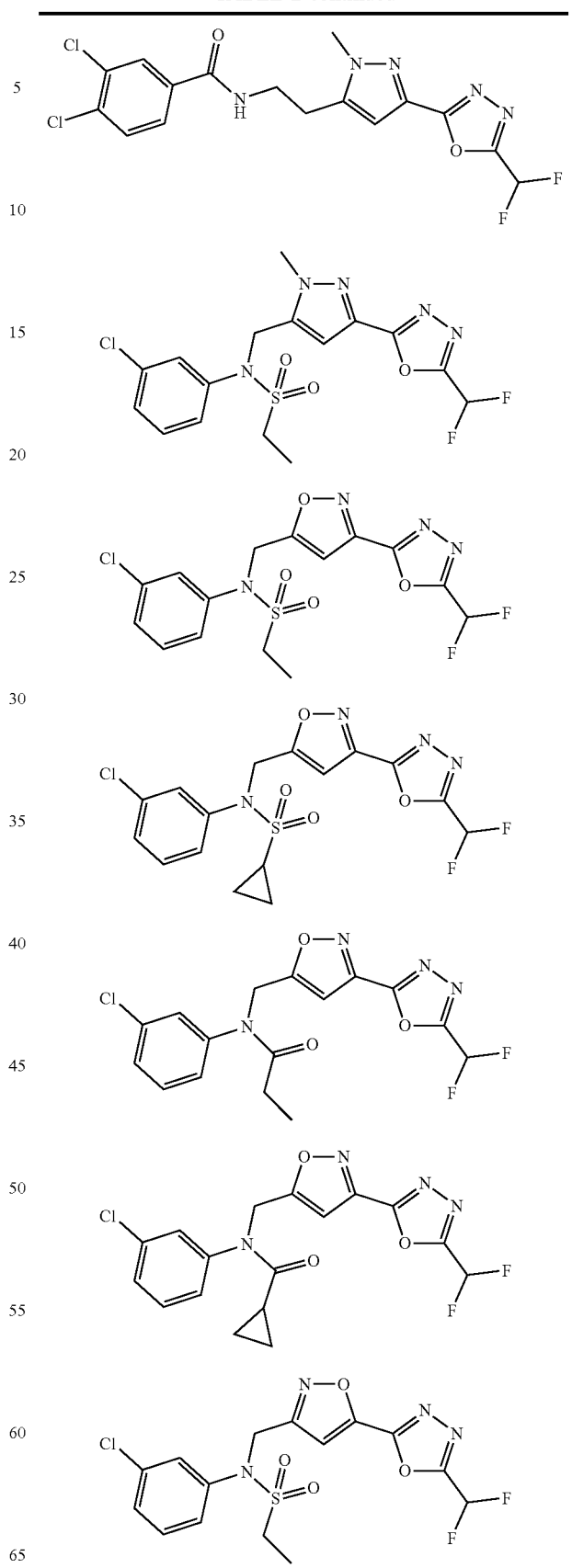

TABLE 2-continued
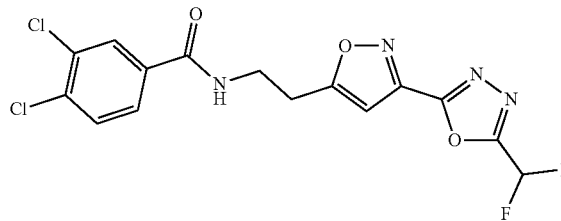
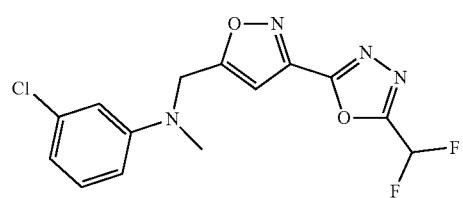 [SMILES: CN(Cc1cc(-c2nnc(C(F)F)o2)no1)c1cccc(Cl)c1]
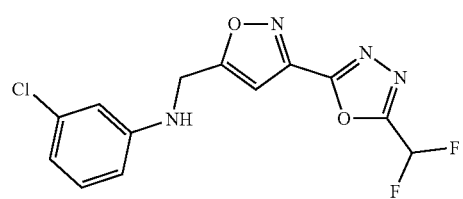 [SMILES: FC(F)c1nnc(-c2cc(CNc3cccc(Cl)c3)on2)o1]
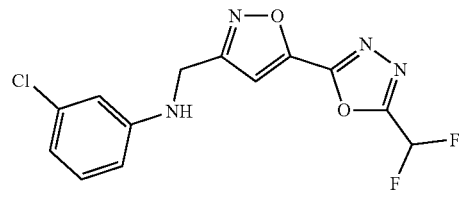 [SMILES: FC(F)c1nnc(-c2cc(CNc3cccc(Cl)c3)no2)o1]
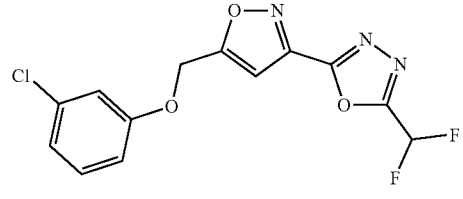 [SMILES: FC(F)c1nnc(-c2cc(COc3cccc(Cl)c3)on2)o1]
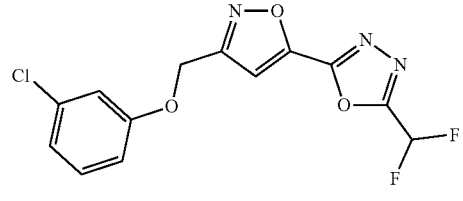 [SMILES: FC(F)c1nnc(-c2cc(COc3cccc(Cl)c3)no2)o1]
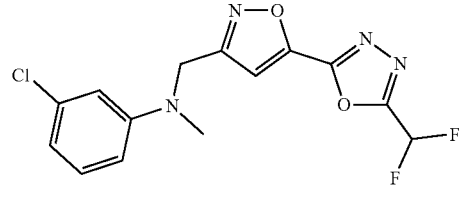 [SMILES: CN(Cc1cc(-c2nnc(C(F)F)o2)on1)c1cccc(Cl)c1]
TABLE 2-continued
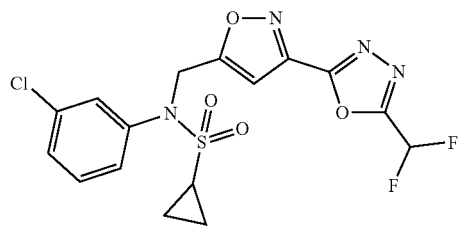 [SMILES: O=S(=O)(C1CC1)N(Cc1cc(-c2nnc(C(F)F)o2)no1)c1cccc(Cl)c1]
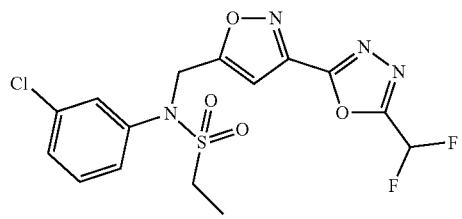 [SMILES: CCS(=O)(=O)N(Cc1cc(-c2nnc(C(F)F)o2)no1)c1cccc(Cl)c1]
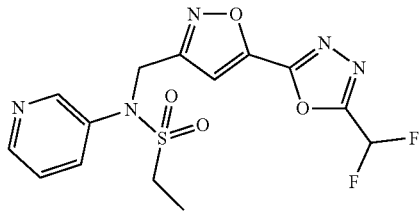 [SMILES: CCS(=O)(=O)N(Cc1cc(-c2nnc(C(F)F)o2)on1)c1cccnc1]
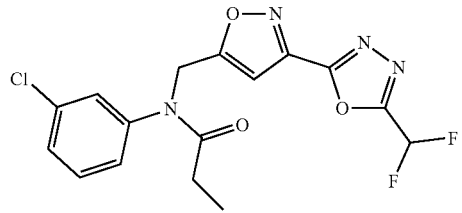 [SMILES: CCC(=O)N(Cc1cc(-c2nnc(C(F)F)o2)no1)c1cccc(Cl)c1]
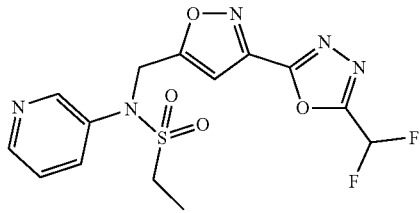 [SMILES: CCS(=O)(=O)N(Cc1cc(-c2nnc(C(F)F)o2)no1)c1cccnc1]
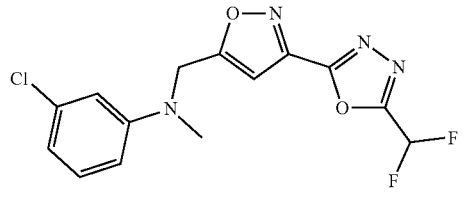 [SMILES: CN(Cc1cc(-c2nnc(C(F)F)o2)no1)c1cccc(Cl)c1]
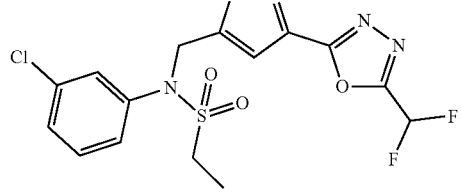

TABLE 2-continued

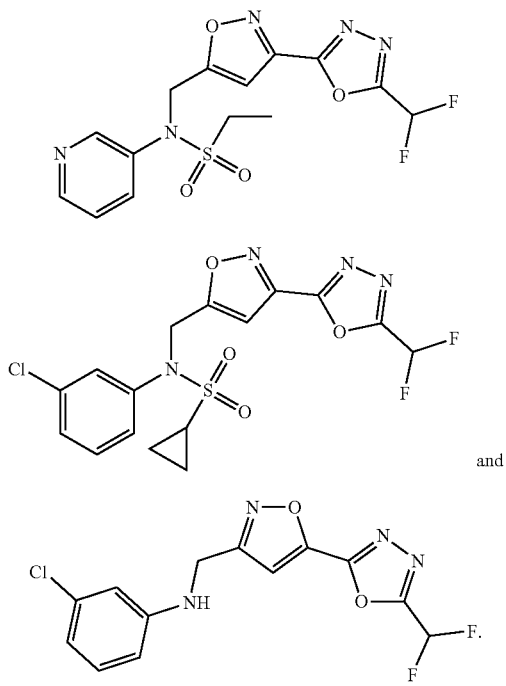

and

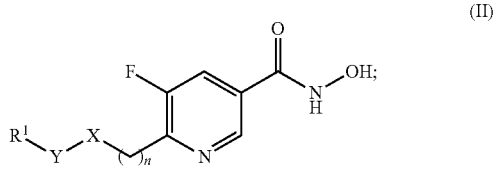

5-Fluoronicotinamide Derivatives

In some embodiments, the HDAC6 inhibitor is a 5-fluoronicotinamide derivative. Illustrative 5-fluoronicotinamide derivatives that may be used as HDAC6 inhibitors include those described herein and those described in Int'l Pat. Appl. Pub. No. PCT/US2020/054134, published as WO2021067859A1, the content of which is incorporated by reference herein in its entirety. PCT/US2020/054134, published as WO2021067859A1, also describes methods of synthesis of such compounds, which are specifically incorporated by reference herein.

In some embodiments, the HDAC6 inhibitor is a compound of Formula (II):

$$\underset{R^1\diagdown Y\diagdown X\diagdown(\phantom{.})_n\diagdown N}{\text{(II)}}$$

wherein n is 0 or 1;

X is O, $NR^4$, or $CR^4R^{4'}$;

Y is a bond, $CR^2R^3$ or $S(O)_2$; $R^1$ is selected from the group consisting of H, amido, carbocyclyl, heterocyclyl, aryl, and heteroaryl;

$R^2$ and $R^3$ are independently selected from the group consisting of H, halogen, alkyl, carbocyclyl, heterocyclyl, aryl, heteroaryl, —($CH_2$)-carbocyclyl, —($CH_2$)-heterocyclyl, —($CH_2$)-aryl, and —($CH_2$)-heteroaryl; or $R^1$ and $R^2$ taken together with the carbon atom to which they are attached form a carbocyclyl or heterocyclyl; or $R^2$ and $R^3$ taken together with the carbon atom to which they are attached form a carbocyclyl or heterocyclyl; and $R^4$ and $R^{4'}$ are each independently selected from the group consisting of H, alkyl, —$CO_2$-alkyl, carbocyclyl, heterocyclyl, aryl, heteroaryl, —($CH_2$)-carbocyclyl, —($CH_2$)-heterocyclyl, —($CH_2$)-aryl, and —($CH_2$)-heteroaryl; or $R^4$ and $R^{4'}$ taken together with the carbon atom to which they are attached form a carbocyclyl or heterocyclyl;

wherein each alkyl, carbocyclyl, heterocyclyl, aryl, and heteroaryl is independently optionally substituted with one or more substituents selected from the group consisting of halogen, haloalkyl, oxo, hydroxy, alkoxy, —$OCH_3$, —$CO_2CH_3$, —C(O)NH(OH), —$CH_3$, morpholine, and —C(O)N-cyclopropyl.

Pharmaceutical Compositions and Kits

In various embodiments of the present disclosure, pharmaceutical compositions comprising one or more HDAC6 inhibitors disclosed herein, or a pharmaceutically acceptable salt thereof, or a pharmaceutically acceptable solvate, hydrate, tautomer, N-oxide, or salt thereof, and a pharmaceutically acceptable excipient or adjuvant is provided. The pharmaceutically acceptable excipients and adjuvants are added to the composition or formulation for a variety of purposes. In some embodiments, a pharmaceutical composition comprising one or more compounds disclosed herein, or a pharmaceutically acceptable solvate, hydrate, tautomer, N-oxide, or salt thereof, further comprises a pharmaceutically acceptable carrier. In some embodiments, a pharmaceutically acceptable carrier includes a pharmaceutically acceptable excipient, binder, and/or diluent. In some embodiments, suitable pharmaceutically acceptable excipients include, but are not limited to, water, salt solutions, alcohol, polyethylene glycols (e.g., polyethylene glycol 300), gelatin, lactose, amylase, magnesium stearate, talc, silicic acid, viscous paraffin, hydroxymethylcellulose and polyvinylpyrrolidone.

In some embodiments, the HDAC6 inhibitor in the pharmaceutical composition described herein is one or more compounds of Formula (I), Formula (Ia), Formula (Ib), Formula (Ic), Formula (Id), Formula (Id-1), Formula (Id-2), Formula (Id-3), Formula (Id-4), Formula (Ie), Formula (Ie-1), Formula (If), Formula (If-1), Formula (Ig), Formula (Ig-1), Formula (Ih), Formula (Ih-1), Formula (Ti), Formula (Ii-1), Formula (Ij), Formula (Ij-1), Formula (Ik), Formula (Ik-1), Formula (Ik-2), Formula (Ik-3), Formula I(y), or Formula (II). In some embodiments, the HDAC6 inhibitor in the pharmaceutical composition described herein is a compound of Formula (I). In some embodiments, the HDAC6 inhibitor in the pharmaceutical composition described herein is a compound of Formula (Ic). In some embodiments, the HDAC6 inhibitor in the pharmaceutical composition described herein is a compound of Formula (Ik). In some embodiments, the HDAC6 inhibitor in the pharmaceutical composition described herein is a compound of Formula I(y) (which may also be referenced herein as Formula (Iy)).

In another aspect, the disclosure provides an HDAC6 inhibitor for use in a method for treating metabolic disease.

In another aspect, the disclosure provides a kit, comprising an HDAC6 inhibitor, or pharmaceutical composition thereof, and instructions for use in a method for treating metabolic disease.

In another aspect, the disclosure provides use of an HDAC6 inhibitor in treating metabolic disease.

In another aspect, the disclosure provides an HDAC6 inhibitor for use in a method for treating HFpEF.

In another aspect, the disclosure provides a kit, comprising an HDAC6 inhibitor, or pharmaceutical composition thereof, and instructions for use in a method for treating HFpEF.

In another aspect, the disclosure provides use of an HDAC6 inhibitor in treating HFpEF.

Methods of Administration

The HDAC6 inhibitors described herein (and pharmaceutical compositions comprising such HDAC6 inhibitors) can be administered to a subject by any suitable means disclosed herein or known in the art.

In some embodiments, the administration of an HDAC6 inhibitor is oral administration. In some embodiments, the method comprises orally administering to a subject an HDAC6 inhibitor of Formula (I), Formula (Ia), Formula (Ib), Formula (Ic), Formula (Id), Formula (Id-1), Formula (Id-2), Formula (Id-3), Formula (Id-4), Formula (Ie), Formula (Ie-1), Formula (If), Formula (If-1), Formula (Ig), Formula (Ig-1), Formula (Ih), Formula (Ih-1), Formula (Ii), Formula (Ii-1), Formula (Ij), Formula (Ij-1), Formula (Ik), Formula (Ik-1), Formula (Ik-2), Formula (Ik-3), Formula I(y), or Formula (II). In some embodiments, the method comprises orally administering to a subject an HDAC6 inhibitor of Formula (I). In some embodiments, the method comprises orally administering to a subject an HDAC6 inhibitor of Formula (Ic). In some embodiments, the method comprises orally administering to a subject an HDAC6 inhibitor of Formula (Ik). In some embodiments, the method comprises orally administering to a subject an HDAC6 inhibitor of Formula I(y). In some embodiments, the method comprises orally administering to a subject an HDAC6 inhibitor of Formula (II). In some embodiments, oral administration is by means of a tablet or capsule. In some embodiments, a human is orally administered an HDAC6 inhibitor described herein (or a pharmaceutical composition thereof).

Various dosing schedules of the HDAC6 inhibitors described herein (and pharmaceutical compositions comprising such HDAC6 inhibitors) are contemplated including single administration or multiple administrations over a period of time.

In some embodiments, an HDAC6 inhibitor described herein (or a pharmaceutical composition comprising the inhibitor) is administered twice a day, once a day, once in two days, once in three days, once a week, once in two weeks, once in three weeks or once a month. In some embodiments, an HDAC6 inhibitor described herein (or a pharmaceutical composition comprising the inhibitor) is administered once a day.

In some embodiments, an HDAC6 inhibitor described herein (or a pharmaceutical composition comprising the inhibitor) is administered a single time. In some embodiments, an HDAC6 inhibitor described herein (or a pharmaceutical composition comprising the inhibitor) is administered over a period of time, for example, for (or longer than) 1 week, 2 weeks, 3 weeks, 4 weeks, 5 weeks, 6 weeks, 7 weeks, 8 weeks, 9 weeks, 10 weeks, 11 weeks, 3 months, 4 months, 5 months, 6 months, 7 months, 8 months, 9 months, 10 months, 11 months, 1 year. In some embodiments, the subject being treated is administered an HDAC6 inhibitor described herein (or a pharmaceutical composition comprising the inhibitor) for at least 1 month, at least 6 weeks, at least 2 months, at least 3 months, or at least 6 months. In some embodiments, the subject being treated is administered an HDAC6 inhibitor described herein (or a pharmaceutical composition comprising the inhibitor) for less than 1 month, 6 weeks, 2 months, 3 months, or 6 months.

The appropriate dosage of an HDAC6 inhibitor described herein for use in the methods described herein will depend on the type of inhibitor used, the condition of the subject (e.g., age, body weight, health), the responsiveness of the subject, other medications used by the subject, and other factors to be considered at the discretion of the medical practitioner performing the treatment.

In some embodiments, an HDAC6 inhibitor described herein is administered to the subject in the amount in the range from 1 mg to 500 mg per day. In some embodiments, an HDAC6 inhibitor described herein is administered to a human orally in the amount in the range from 1 mg to 500 mg per day. In some embodiments, an HDAC6 inhibitor described herein is administered to a human orally in a single dose in the amount in the range from 1 mg to 500 mg. In some embodiments, an HDAC6 inhibitor described herein is administered to a human orally in the amount in the range from 1 mg to 500 mg once a day, e.g., over a course of treatment (e.g., for 1 week, 2 weeks, 3 weeks, 4 weeks, 5 weeks, 6 weeks, 7 weeks, 8 weeks, 9 weeks, 10 weeks, 11 weeks, 3 months, 4 months, 5 months, 6 months, 7 months, 8 months, 9 months, 10 months, 11 months, 1 year, or longer). In some embodiments, an HDAC6 inhibitor described herein is administered to a human subject in a starting dose between 0.5 and 3 mg/day (e.g., 1 mg/day). In some embodiments, an HDAC6 inhibitor described herein is administered to a human subject in a starting dose of 0.5 mg/day. In some embodiments, an HDAC6 inhibitor described herein is administered to a human subject in a starting dose of 1 mg/day. In some embodiments, an HDAC6 inhibitor described herein is administered to a human subject in a starting dose of 1.5 mg. In some embodiments, an HDAC6 inhibitor described herein is administered to a human subject in a starting dose of 3 mg. This dose may be escalated or remain the same depending on subject's responsiveness to the treatment. An HDAC6 inhibitor may be administered in an amount that is deemed to be therapeutically effective.

Combination Treatments and Kits

In some embodiments, the HDAC6 inhibitors described herein (and pharmaceutical compositions comprising such HDAC6 inhibitors) can be administered to a subject in combination with another medication or therapy. In some embodiments, two or three different HDAC6 inhibitors (e.g., out of those described herein) can be administered to a subject.

In some embodiments, one or more of the HDAC6 inhibitors described herein (and pharmaceutical compositions comprising such HDAC6 inhibitors) can be administered to a subject in combination with one or more therapy different from said one or more HDAC6 inhibitor(s), where the therapy is a cardioprotective therapy, an anti-hypertensive therapy, a hypoglycemic therapy, a therapy for a heart condition (e.g., heart failure), a therapy for HFpEF, or a therapy for metabolic disease. The additional therapy can be any such therapy known in the art. In some embodiments of metabolic disease treatments, an HDAC6 inhibitor described herein (or a pharmaceutical composition comprising such HDAC6 inhibitor) is administered to a subject in combination with another metabolic disease therapy (such as an agent used to treat metabolic disease). In some embodiments of HFpEF treatments, an HDAC6 inhibitor described herein (or a pharmaceutical composition comprising such HDAC6 inhibitor) is administered to a subject in combination with another HFpEF therapy (such as an agent used to treat HFpEF). In some embodiments, an HDAC6 inhibitor described herein (or a pharmaceutical composition comprising such HDAC6 inhibitor) is administered to a subject in combination with a hypoglycemic therapy (such as an agent used to treat hypoglycemia). In some embodiments, an HDAC6 inhibitor described herein (or a pharmaceutical composition comprising such HDAC6 inhibitor) is administered to a subject in combination with an anti-hypertensive therapy (such as an agent used to treat hypertension).

In some embodiments, an HDAC6 inhibitor described herein (or a pharmaceutical composition comprising such HDAC6 inhibitor) is administered to a subject in combination with an anti-hypertensive agent. For example, and without limitation, any of the following anti-hypertensive agents can be used in combination with HDAC6 inhibitors: thiazide diuretics (e.g., Capozide, Dyazide, Hyzaar, Lopressor HCT, Maxzide, Prinzide, Clorpres, Tenoretic, or Thalitone), calcium channel blockers (e.g., Amlodipine, Diltiazem, Felodipine, Isradipine, Nicardipine, Nifedipine, Nisoldipine, or Verapamil), ACE inhibitors (e.g., Benazepril, Captopril, Enalapril, Fosinopril, Lisinopril, Moexipril, Perindopril, Quinapril, Ramipril, or Trandolapril), angiotensin II receptor antagonists (ARB) (e.g., Azilsartan, Candesartan, Eprosartan, Irbesartan, Losartan, Olmesartan, Telmisartan, or Valsartan), and beta blockers (e.g., Acebutolol, Atenolol, Bisoprolol, Metoprolol, Nadolol, Nebivolol, or Propranolol).

In some embodiments, an HDAC6 inhibitor described herein (or a pharmaceutical composition comprising such HDAC6 inhibitor) is administered to a subject in combination with an ACE inhibitor. In some embodiments, an HDAC6 inhibitor described herein (or a pharmaceutical composition comprising such HDAC6 inhibitor) is administered to a subject in combination with a beta blocker. In some embodiments, an HDAC6 inhibitor described herein (or a pharmaceutical composition comprising such HDAC6 inhibitor) is administered to a subject in combination with a thiazide diuretic. In some embodiments, an HDAC6 inhibitor described herein (or a pharmaceutical composition comprising such HDAC6 inhibitor) is administered to a subject in combination with a calcium channel blocker. In some embodiments, an HDAC6 inhibitor described herein (or a pharmaceutical composition comprising such HDAC6 inhibitor) is administered to a subject in combination with an angiotensin II receptor antagonist (ARB).

In some embodiments, an HDAC6 inhibitor described herein (or a pharmaceutical composition comprising such HDAC6 inhibitor) is administered to a subject in combination with an aldosterone receptor agonist (e.g., spironolactone). In some embodiments, an HDAC6 inhibitor described herein (or a pharmaceutical composition comprising such HDAC6 inhibitor) is administered to a subject in combination with spironolactone.

In some embodiments, an HDAC6 inhibitor described herein (or a pharmaceutical composition comprising such HDAC6 inhibitor) is administered to a subject in combination with an angiotensin and neprilysin receptor agonist (e.g., sacubitril-valsartan). In some embodiments, an HDAC6 inhibitor described herein (or a pharmaceutical composition comprising such HDAC6 inhibitor) is administered to a subject in combination with angiotensin receptor-neprilysin inhibitor (ARNi). In some embodiments, an HDAC6 inhibitor described herein (or a pharmaceutical composition comprising such HDAC6 inhibitor) is administered to a subject in combination with sacubitril and/or valsartan.

In some embodiments, an HDAC6 inhibitor described herein (or a pharmaceutical composition comprising such HDAC6 inhibitor) is administered to a subject in combination with a hypoglycemic agent that lowers the level of blood glucose (e.g., an oral hypoglycemic therapy used to treat Type 2 diabetes). For example, and without limitation, any of the following hypoglycemic agents (or classes of agents) can be used in combination with HDAC6 inhibitors: sulfonylureas, meglitinides, biguanides (metformin), thiazolidinediones, alpha-glucosidase inhibitors, DPP4 inhibitors, cycloset, and SGLT2 inhibitors. In some embodiments, an HDAC6 inhibitor described herein (or a pharmaceutical composition comprising such HDAC6 inhibitor) is administered to a subject in combination with an oral hypoglycemic agent (e.g., which is used to treat Type 2 diabetes).

In some embodiments, an HDAC6 inhibitor described herein (or a pharmaceutical composition comprising such HDAC6 inhibitor) is administered to a subject in combination with a sodium-glucose co-transporter 2 (SLGT2) inhibitor (e.g., empagliflozin).

In some embodiments, an HDAC6 inhibitor described herein (or a pharmaceutical composition comprising such HDAC6 inhibitor) is administered to a subject before, at the same time, or after the additional therapy. In some embodiments, any HDAC6 inhibitor is administered to a subject in a therapeutically effective amount, and any additional therapy described herein is administered to a subject in a therapeutically effective amount.

In some embodiments, the subject being treated in accordance with the methods described herein has not received an anti-hypertensive therapy. In some embodiments, the subject being treated in accordance with the methods described herein has not received a hypoglycemic therapy. In some embodiments, the subject being treated in accordance with the methods described herein has not received metabolic disease therapy. In some embodiments, the subject being treated in accordance with the methods described herein has not received HFpEF therapy. In some embodiments, the subject being treated in accordance with the methods described herein has not received a cardioprotective therapy and/or a heart condition (e.g., heart failure) therapy. In some embodiments, the subject being treated in accordance with the methods described herein has not received an SGLT2 inhibitor.

In some embodiments provided herein are kits comprising an HDAC6 inhibitor described herein (or a pharmaceutical composition comprising the same) and one or more additional agents (e.g., an additional agent for the treatment of metabolic disease, an additional agent for the treatment of HFpEF, an anti-hypertensive agent, and/or a hypoglycemic agent). In some embodiments, provided herein are kits comprising (i) an HDAC6 inhibitor (e.g., in a therapeutically effective amount), and (ii) one or more additional agents (such as any additional agents described herein, e.g., without limitation, a thiazide diuretic, a calcium channel blocker, an ACE inhibitor, an angiotensin II receptor antagonist (ARB), an SGLT2 inhibitor (e.g., empagliflozin), or a beta blocker (e.g., in a therapeutically effective amount)).

Patient Populations to be Treated

In some embodiments, the subject is a human. In some embodiments, the human is an adult human. In some embodiments, the human is 60 years of age or older. In some embodiments, the human is over 60 years of age. In some embodiments, the human is 65 years of age or older. In some embodiments, the human is over 65 years of age. In some embodiments, the human is 70 years of age or older. In some embodiments, the human is over years of age. In some embodiments, the subject is a male (e.g., a male at least or older than 65 or 70 years of age). In some embodiments, the subject is a female (e.g., a female at least or older than 60, 65 or 70 years of age).

In some embodiments, the subject being treated is obese (e.g., has BMI of 30 or higher). In some embodiments, the subject is at risk for obesity (e.g., has BMI of 25 or higher). In some embodiments, the subject being treated has a metabolic disease. In some embodiments, the subject is at risk for metabolic disease. In some embodiments, the subject has (or is at risk for) diabetes. In some embodiments, the subject has (or is at risk for) diabetes mellitus. In some embodiments, the subject has (or is at risk for) pre-diabetes. In some embodiments, the subject has (or is at risk for) diabetic cardiomyopathy. In some embodiments, the subject has (or is at risk for) metabolic syndrome. In some embodiments, the subject has (or is at risk for) hypertension. In some embodiments, the subject has (or is at risk for) hypertriglyceridemia. In some embodiments, the subject has (or is at risk for) dyslipidemia.

In some embodiments, the subject being treated is not obese (e.g., has BMI of less than 30). In some embodiments, the subject has BMI of less than 25. In some embodiments, the subject being treated does not have a metabolic disease. In some embodiments, the subject being treated does not have diabetes (e.g., does not have diabetes mellitus). In some embodiments, the subject does not have pre-diabetes. In some embodiments, the subject does not have diabetic cardiomyopathy. In some embodiments, the subject does not have metabolic syndrome. In some embodiments, the subject does not have hypertension. In some embodiments, the subject does not have hypertriglyceridemia. In some embodiments, the subject does not have dyslipidemia. For example, a subject with HFpEF being treated in accordance with the methods described herein may have or not have these conditions.

In some embodiments, the subject being treated has HFpEF. In some embodiments, the subject being treated is at risk for HFpEF. In some embodiments, the subject has (or is at risk for) cardiac fibrosis. In some embodiments, the subject has (or is at risk for) diastolic dysfunction.

In some embodiments, the subject has (or is at risk for) coronary artery disease (CAD). In some embodiments, the subject has (or is at risk for) valvular heart disease. In some embodiments, the subject has (or is at risk for) atrial fibrillation.

NUMBERED EMBODIMENTS OF THE INVENTION (I)

1. A method of treating or preventing metabolic disease in a subject in need thereof, comprising administering to the subject a HDAC6 inhibitor.
2. The method of embodiment 1, wherein the subject is obese or at risk for obesity.
3. The method of embodiment 1 or embodiment 2, wherein the metabolic disease is a metabolic disease associated with obesity, optionally diet-induced obesity.
4. The method of any one of embodiments 1-3, wherein the metabolic disease is a diabetes (e.g., diabetes mellitus), pre-diabetes, diabetic cardiomyopathy, metabolic syndrome, hypertension, hypertriglyceridemia, or dyslipidemia.
5. The method of embodiment 4, wherein the metabolic disease is diabetes mellitus.
6. The method of embodiment 4, wherein the metabolic disease is metabolic syndrome.
7. A method of treating obesity in a subject in need thereof, comprising administering a to the subject a HDAC6 inhibitor.
8. The method of embodiments 1-7, wherein the HDAC6 inhibitor is fluoroalkyl-oxadiazole derivative.
9. The method of embodiment 8, wherein the HDAC6 inhibitor is fluoroalkyl-oxadiazole derivative according to the following Formula:

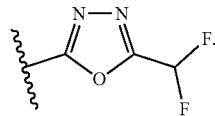 [SMILES: *c1nnc(C(F)F)o1]

10. The method of embodiments 1-9, wherein the HDAC6 inhibitor is a compound according to Formula (I):

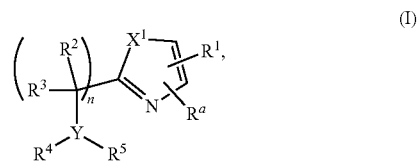

(I)

or pharmaceutically acceptable salt thereof, wherein $R^1$ is selected from the group consisting of:

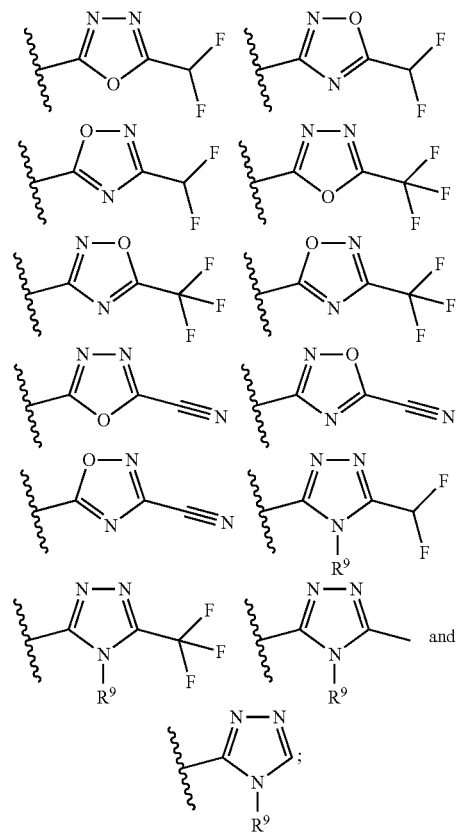

$R^a$ is selected from the group consisting of H, halo, $C_{1-3}$ alkyl, cycloalkyl, haloalkyl, and alkoxy;

R² and R³ are independently selected from the group consisting of H, halogen, alkoxy, haloalkyl, aryl, heteroaryl, alkyl, and cycloalkyl each of which is optionally substituted, or R² and R³ together with the atom to which they are attached form a cycloalkyl or heterocyclyl;

R⁴ and R⁵ are independently selected from the group consisting of H, —(SO₂)R², —(SO₂)NR²R³, —(CO)R², —(CONR²R³), aryl, arylheteroaryl, alkylenearyl, heteroaryl, cycloalkyl, heterocyclyl, alkyl, haloalkyl, and alkoxy, each of which is optionally substituted, or R⁴ and R⁵ together with the atom to which they are attached form a cycloalkyl or heterocyclyl, each of which is optionally substituted;

R⁹ is selected from the group consisting of H, C₁-C₆ alkyl, haloalkyl, cycloalkyl and heterocyclyl;

X¹ is selected from the group consisting of S, O, NH and NR⁶, wherein R⁶ is selected from the group consisting of C₁-C₆ alkyl, alkoxy, haloalkyl, cycloalkyl and heterocyclyl;

Y is selected from the group consisting of CR², O, N, S, SO, and SO₂, wherein when Y is O, S, SO, or SO₂, R⁵ is not present and when R⁴ and R⁵ together with the atom to which they are attached form a cycloalkyl or heterocyclyl, Y is CR² or N; and n is selected from 0, 1, and 2.

11. The method of embodiment 10, wherein the HDAC6 inhibitor is selected from the group consisting of:

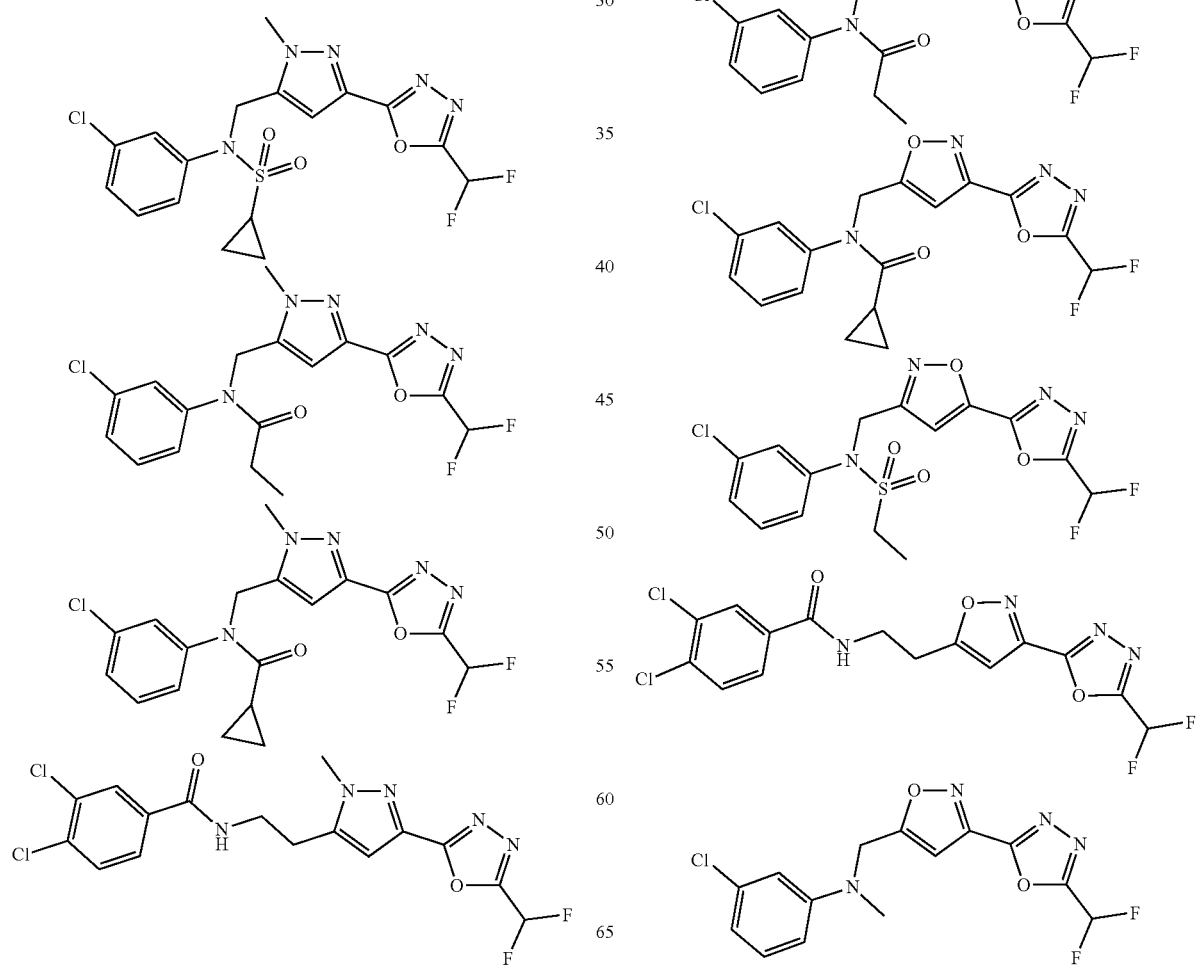

-continued

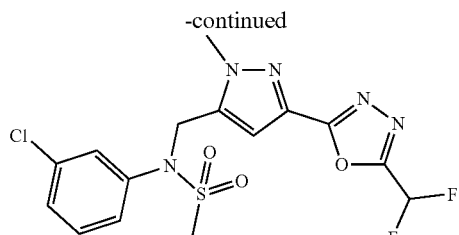
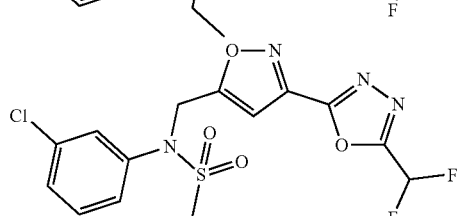
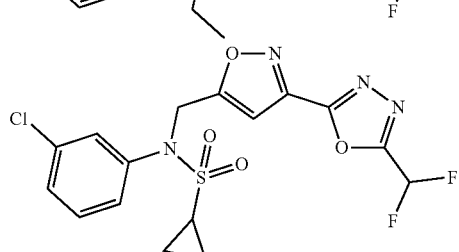
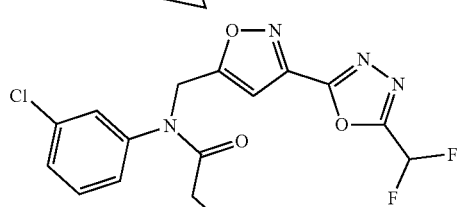
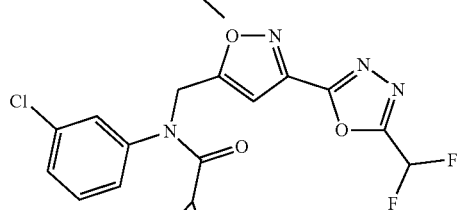
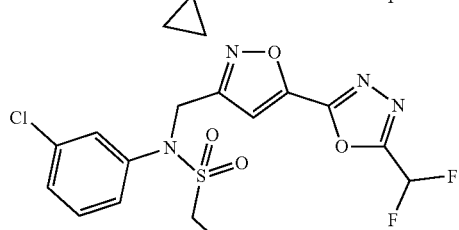
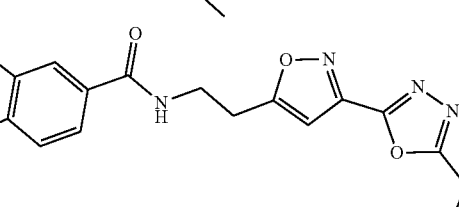
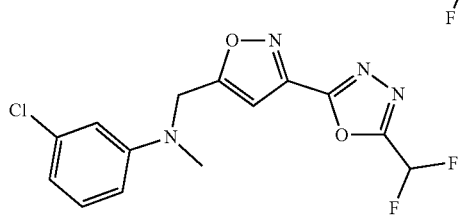

-continued
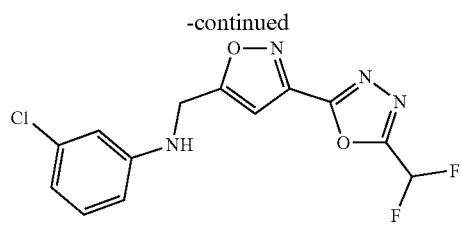
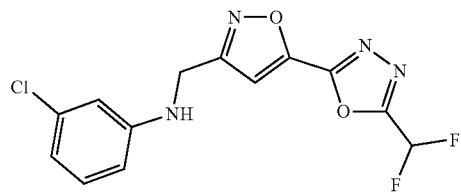
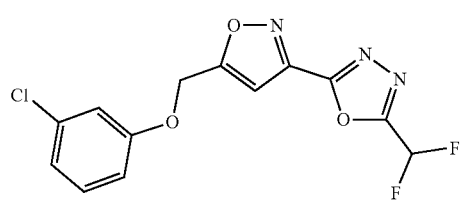
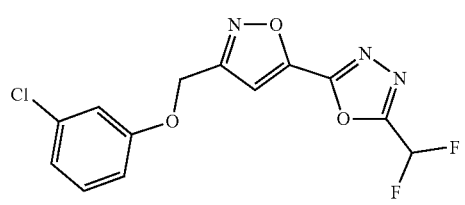
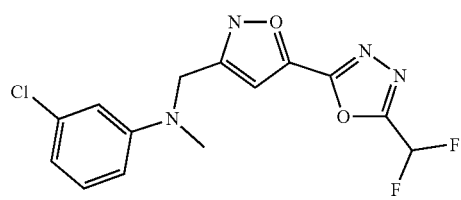
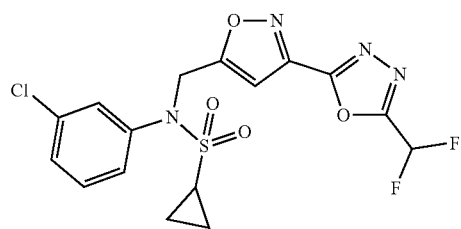
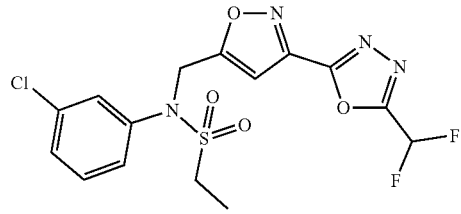
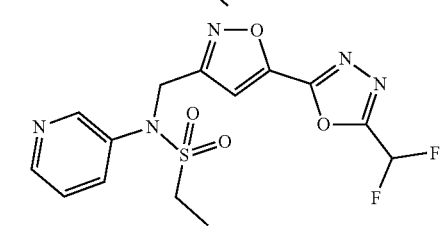
-continued
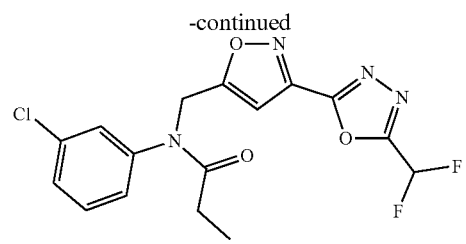
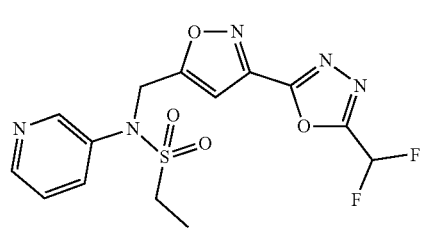
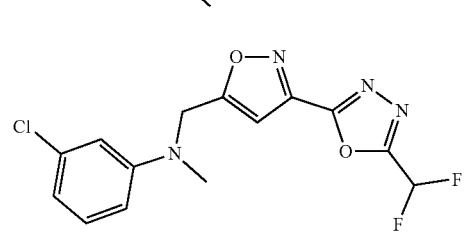
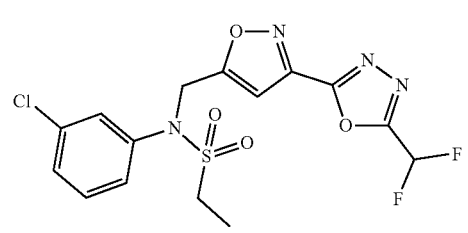
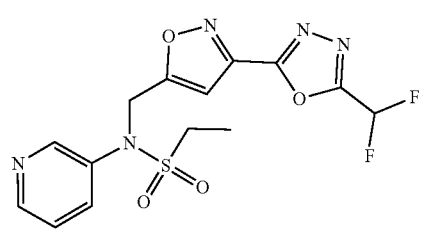
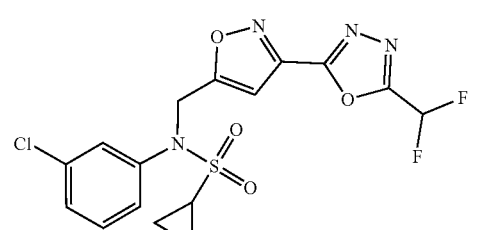
and
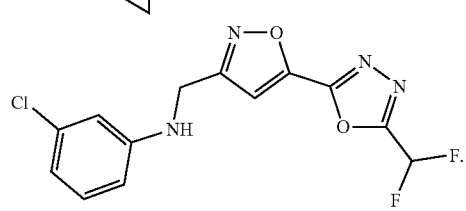
12. The method of embodiment 10, wherein the HDAC6 inhibitor is

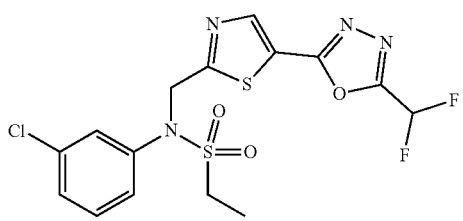 [SMILES: CCS(=O)(=O)N(Cc1ncc(-c2nnc(C(F)F)o2)s1)c1cccc(Cl)c1]

or an analog thereof.

13. The method of embodiment 10, wherein the HDAC6 inhibitor is

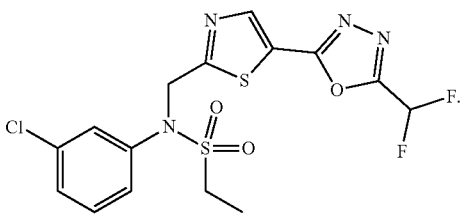

14. The method of embodiment 10, wherein the HDAC6 inhibitor is selected from any HDAC6 inhibitor in Table 13 (in Example 7).

The method of embodiment 14, wherein the HDAC6 inhibitor is any HDAC6 inhibitor in Table 13 which has an $IC_{50}$ equal to or less than 0.03 μM.

16. The method of embodiment 10, wherein the HDAC6 inhibitor is a compound having the

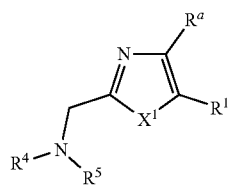

or a pharmaceutically acceptable salt thereof,
wherein:
$X^1$ is S;
$R^a$ is selected from the group consisting of H, halogen, and $C_{1-3}$ alkyl;
$R^1$ is

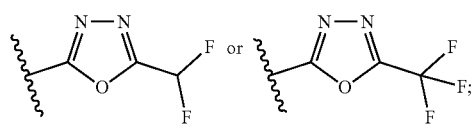 [SMILES: *c1nnc(C(F)F)o1 ; *c1nnc(C(F)(F)F)o1]

$R^2$ is selected from the group consisting of alkyl, alkoxy, and cycloalkyl, each of which is optionally substituted;
$R^3$ is H or alkyl;
$R^4$ is selected from the group consisting of alkyl, —($SO_2$)$R^2$, —($SO_2$)$NR^2R^3$, and —(CO)$R^2$; and
$R^5$ is aryl or heteroaryl; or $R^4$ and $R^5$ together with the atom to which they are attached form a heterocyclyl, each of which is optionally substituted.

17. The method of embodiment 16, wherein $R^a$ is H.
18. The method of embodiment 16 or 17, wherein $R^1$ is

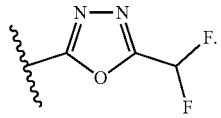 [SMILES: *c1nnc(C(F)F)o1]

19. The method of any one of embodiments 16-18, wherein $R^4$ is —($SO_2$)$R^2$.
20. The method of embodiment 19, wherein —($SO_2$)$R^2$ is —($SO_2$)alkyl, —($SO_2$)alkyleneheterocyclyl, —($SO_2$)haloalkyl, —($SO_2$)haloalkoxy, or —($SO_2$)cycloalkyl.
21. The method of any one of embodiments 16-20, wherein $R^5$ is heteroaryl.
22. The method of embodiment 21, wherein the heteroaryl is a 5- to 6-membered heteroaryl
23. The method of embodiment 22, wherein the 5- to 6-membered heteroaryl is selected from the group consisting of

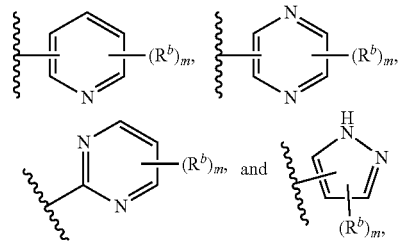

wherein $R^b$ is halogen, alkyl, alkoxy, cycloalkyl, —CN, haloalkyl, or haloalkoxy; and m is 0 or 1.
24. The method of embodiment 23, wherein $R^b$ is F, Cl, —$CH_3$, —$CH_2CH_3$, —$CF_3$, —$CHF_2$, —$CF_2CH_3$, —CN, —$OCH_3$, —$OCH_2CH_3$, —$OCH(CH_3)_2$, —$OCF_3$, —$OCHF_2$, —$OCH_2CF_2H$, and cyclopropyl.
25. The method of any one of embodiments 16-24, wherein the aryl is selected from the group consisting of phenyl, 3-chlorophenyl, 3-chloro-4-fluorophenyl, 3-trifluoromethylphenyl, 3,4-difluorophenyl, and 2,6-difluorophenyl.
26. The method of embodiment 10, wherein the HDAC6 inhibitor is a compound having Formula (Ik):

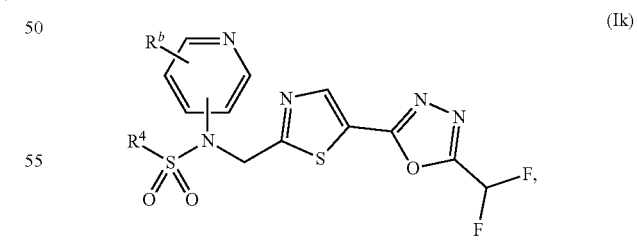

or a pharmaceutically acceptable salt thereof,
wherein:
$R^b$ is H, halogen, alkyl, cycloalkyl, —CN, haloalkyl, or haloalkoxy; and
$R^4$ is alkyl, alkoxy, haloalkyl, or cycloalkyl, each of which is optionally substituted.
27. The method of embodiment 26, wherein $R^b$ is H, halogen, haloalkyl, or haloalkoxy.

28. The method of embodiment 26 or 27, wherein $R^4$ is optionally substituted alkyl or cycloalkyl.

29. The method of embodiment 26, wherein the HDAC6 inhibitor is a compound having the

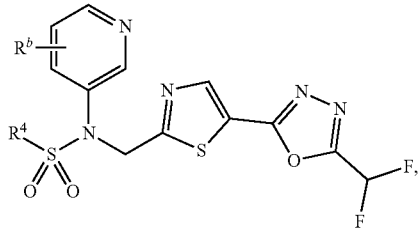
(Ik-1)

or a pharmaceutically acceptable salt thereof,
wherein:
$R^b$ is H, halogen, alkyl, cycloalkyl, —CN, haloalkyl, or haloalkoxy; and
$R^4$ is alkyl, alkoxy, haloalkyl, or cycloalkyl, each of which is optionally substituted.

30. The method of embodiment 29, wherein $R^b$ is H, halogen, haloalkyl, or haloalkoxy.

31. The method of embodiment 29 or 30, wherein $R^4$ is optionally substituted alkyl or cycloalkyl.

32. The method of embodiment 29, wherein $R^4$ is alkyl.

33. The method of embodiment 26, wherein the HDAC6 inhibitor is a compound having the structure:

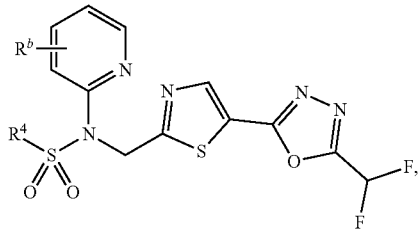
(Ik-2)

or a pharmaceutically acceptable salt thereof,
wherein:
$R^b$ is H, halogen, alkyl, cycloalkyl, —CN, haloalkyl, or haloalkoxy; and
$R^4$ is alkyl, alkoxy, haloalkyl, or cycloalkyl, each of which is optionally substituted.

34. The method of embodiment 33, wherein $R^b$ is H, halogen, haloalkyl, or haloalkoxy.

35. The method of embodiment 33 or 34, wherein $R^4$ is optionally substituted alkyl.

36. The method of embodiment 16, wherein the HDAC6 inhibitor is a compound of Formula:

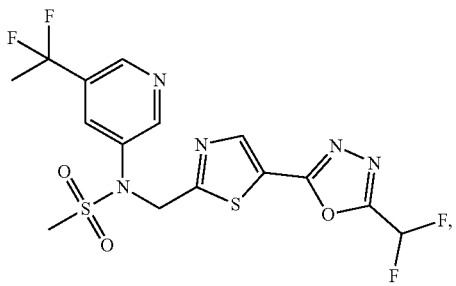

or a pharmaceutically acceptable salt thereof.

37. The method of embodiment 16, wherein the HDAC6 inhibitor is a compound of Formula:

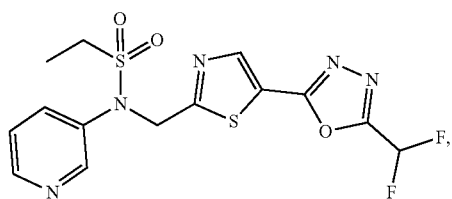 [SMILES: CCS(=O)(=O)N(Cc1ncc(-c2nnc(C(F)F)o2)s1)c1cccnc1]

or a pharmaceutically acceptable salt thereof.

38. The method of embodiment 16, wherein the HDAC6 inhibitor is a compound of Formula:

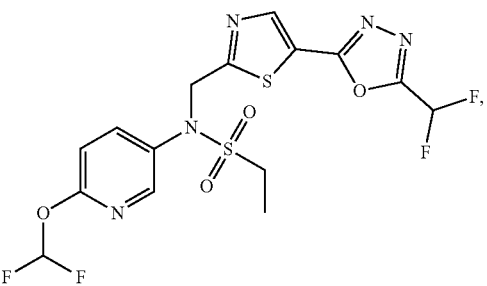 [SMILES: CCS(=O)(=O)N(Cc1ncc(-c2nnc(C(F)F)o2)s1)c1ccc(OC(F)F)nc1]

or a pharmaceutically acceptable salt thereof.

39. The method of embodiment 16, wherein the HDAC6 inhibitor is a compound of Formula:

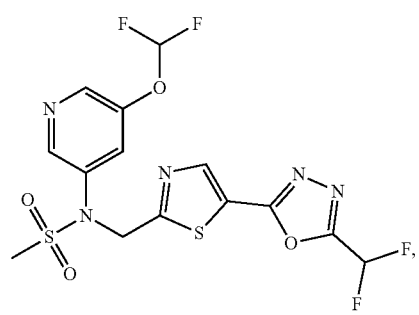 [SMILES: CS(=O)(=O)N(Cc1ncc(-c2nnc(C(F)F)o2)s1)c1cncc(OC(F)F)c1]

or a pharmaceutically acceptable salt thereof.

40. The method of embodiment 16, wherein the HDAC6 inhibitor is a compound of Formula:

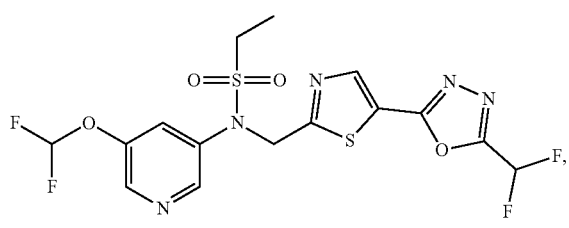 [SMILES: CCS(=O)(=O)N(Cc1ncc(-c2nnc(C(F)F)o2)s1)c1cncc(OC(F)F)c1]

or a pharmaceutically acceptable salt thereof.

41. The method of embodiment 16, wherein the HDAC6 inhibitor is a compound of Formula:

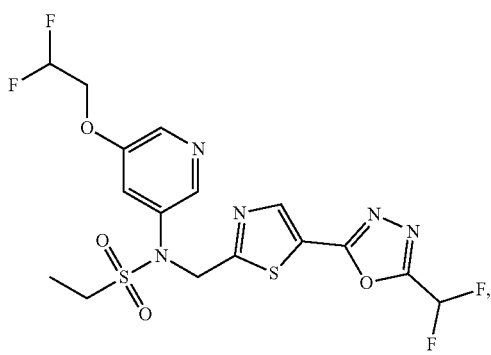 [SMILES: CCS(=O)(=O)N(Cc1ncc(-c2nnc(C(F)F)o2)s1)c1cncc(OCC(F)F)c1]

or a pharmaceutically acceptable salt thereof.

42. The method of embodiment 16, wherein the HDAC6 inhibitor is a compound of Formula:

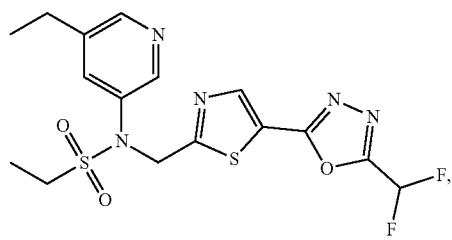 [SMILES: CCc1cncc(N(Cc2ncc(-c3nnc(C(F)F)o3)s2)S(=O)(=O)CC)c1]

or a pharmaceutically acceptable salt thereof.

43. The method of embodiment 16, wherein the HDAC6 inhibitor is a compound of Formula:

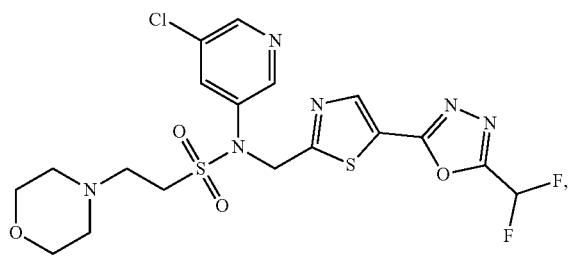 [SMILES: O=S(=O)(CCN1CCOCC1)N(Cc1ncc(-c2nnc(C(F)F)o2)s1)c1cncc(Cl)c1]

or a pharmaceutically acceptable salt thereof.

44. The method of embodiment 16, wherein the HDAC6 inhibitor is a compound of Formula:

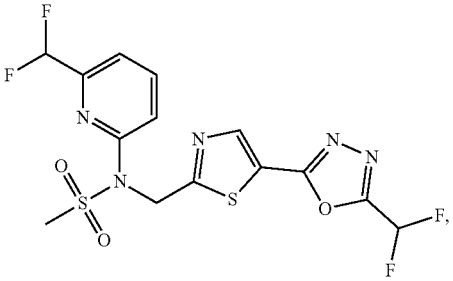

or a pharmaceutically acceptable salt thereof.

45. The method of embodiment 16, wherein the HDAC6 inhibitor is a compound of Formula:

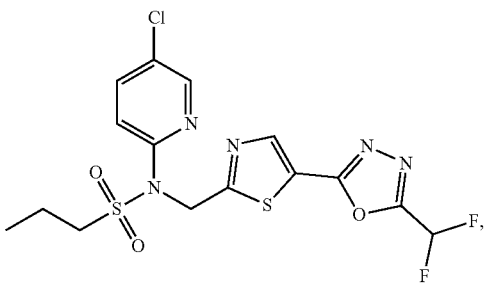 [SMILES: CCCS(=O)(=O)N(Cc1ncc(-c2nnc(C(F)F)o2)s1)c1ccc(Cl)cn1]

or a pharmaceutically acceptable salt thereof.

46. The method of embodiment 16, wherein the HDAC6 inhibitor is a compound of Formula:

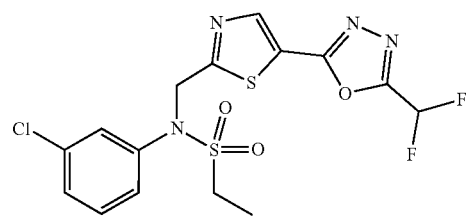 [SMILES: CCS(=O)(=O)N(CC1=NCC=C(c2nnc(C(F)F)o2)S1)c1cccc(Cl)c1]

or a pharmaceutically acceptable salt thereof.

47. The method of any one of embodiments 1-7, wherein the HDAC6 inhibitor is a compound of Formula (II):

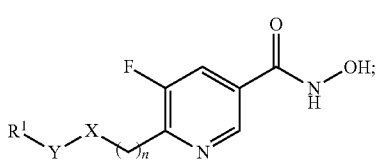

wherein
n is 0 or 1;
X is O, $NR^4$, or $CR^4R^{4'}$;
Y is a bond, $CR^2R^3$ or $S(O)_2$;
$R^1$ is selected from the group consisting of H, amido, carbocyclyl, heterocyclyl, aryl, and heteroaryl;
$R^2$ and $R^3$ are independently selected from the group consisting of H, halogen, alkyl, carbocyclyl, heterocyclyl, aryl, heteroaryl, —(CH$_2$)-carbocyclyl, —(CH$_2$)-heterocyclyl, —(CH$_2$)-aryl, and —(CH$_2$)-heteroaryl; or R¹ and R² taken together with the carbon atom to which they are attached form a carbocyclyl or heterocyclyl; or R² and R³ taken together with the carbon atom to which they are attached form a carbocyclyl or heterocyclyl; and R⁴ and R⁴' are each independently selected from the group consisting of H, alkyl, —CO₂-alkyl, carbocyclyl, heterocyclyl, aryl, heteroaryl, —(CH₂)-carbocyclyl, —(CH₂)-heterocyclyl, —(CH₂)-aryl, and —(CH₂)-heteroaryl; or R⁴ and R⁴' taken together with the carbon atom to which they are attached form a carbocyclyl or heterocyclyl;

wherein each alkyl, carbocyclyl, heterocyclyl, aryl, and heteroaryl is independently optionally substituted with one or more substituents selected from the group consisting of halogen, haloalkyl, oxo, hydroxy, alkoxy, —OCH₃, —CO₂CH₃, —C(O)NH(OH), —CH₃, morpholine, and —C(O)N-cyclopropyl.

48. The method of any one of embodiments 1-7, wherein the HDAC6 inhibitor is CAY10603, tubacin, rocilinostat (ACY-1215), citarinostat (ACY-241), ACY-738, QTX-125, CKD-506, nexturastat A, tubastatin A, or HPOB.

49. The method of any one of the preceding embodiments, wherein the compound is the compound and not the pharmaceutically acceptable salt thereof.

50. The method of any one of embodiments 1-49, wherein the HDAC6 inhibitor is at least 100-fold selective against HDAC6 compared to all other isozymes of HDAC.

51. The method of any one of embodiments 1-50, wherein the administering is oral.

52. The method of any one of embodiments 1-51, wherein the subject is a human.

53. The method of any one of embodiments 1-52, wherein the subject has or is at risk for hypertension.

54. The method of any one of embodiments 1-53, wherein the subject has or is at risk for diabetes mellitus.

55. The method of any one of embodiments 1-54, wherein the subject has or is at risk for diabetic cardiomyopathy.

56. The method of any one of embodiments 1-55, wherein the subject has or is at risk for metabolic syndrome.

57. The method of any one of embodiments 1-56, wherein the subject has or is at risk for hyperglyceridemia or dyslipidemia.

58. The method of any one of embodiments 1-57, wherein the subject is at least 65 years old human.

59. The method of embodiments 58 wherein the subject is at least 70 years old human.

60. The method of any one of embodiments 1-59, wherein the method treats or prevents at least one symptom of metabolic disease.

61. The method of any one of embodiments 1-60, wherein the method improves glucose tolerance.

62. The method of any one of embodiments 1-61, wherein the method improves insulin resistance.

63. The method of any one of embodiments 1-62, wherein the method reduces glucose level.

64. The method of any one of embodiments 1-63, wherein the method inhibits inflammatory genes in adipose tissue.

65. The method of any one of embodiments 1-64, wherein the method prevents heart failure in the subject.

66. An HDAC6 inhibitor for use in a method for treating metabolic disease.

67. The HDAC6 inhibitor of embodiment 66, wherein the HDAC6 inhibitor is any one described in embodiments 8-50.

68. A pharmaceutical composition for use in a method for treating metabolic disease, comprising an HDAC6 inhibitor.

69. The pharmaceutical composition of embodiment 68, wherein the HDAC6 inhibitor is any one described in embodiments 8-50.

70. A kit, comprising an HDAC6 inhibitor and instructions for use in a method for treating metabolic disease.

71. The kit of embodiment 70, wherein the HDAC6 inhibitor is any one described in embodiments 8-50.

72. Use of an HDAC6 inhibitor in treating metabolic disease.

73. The use of embodiment 72, wherein the HDAC6 inhibitor is any one described in embodiments 8-50.

NUMBERED EMBODIMENTS OF THE INVENTION (II)

1. A method of treating or preventing heart failure with preserved ejection fraction (HFpEF) in a subject in need thereof, comprising administering to the subject a HDAC6 inhibitor.

2. A method of treating or preventing diastolic disfunction (e.g., associated with HFpEF) in a subject in need thereof, comprising administering to the subject a HDAC6 inhibitor.

3. A method of treating or preventing cardiac fibrosis (e.g., associated with HFpEF) in a subject in need thereof, comprising administering to the subject a HDAC6 inhibitor.

4. The method of any one of embodiments 1-3, wherein the administering is oral.

5. The method of any one of embodiments 1-4, wherein the subject is a human.

6. The method of embodiment 5, wherein the subject is at least 65 years old.

7. The method of embodiment 5, wherein the subject is at least 70 years old.

8. The method of embodiments 1-7, wherein the HDAC6 inhibitor is fluoroalkyl-oxadiazole derivative.

9. The method of embodiment 8, wherein the HDAC6 inhibitor is fluoroalkyl-oxadiazole derivative according to the following Formula:

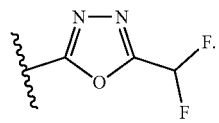 [SMILES: *c1nnc(C(F)F)o1]

10. The method of embodiments 1-9, wherein the HDAC6 inhibitor is a compound according to Formula (I):

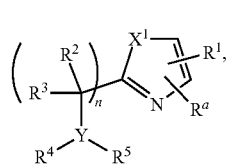

(I)

or pharmaceutically acceptable salt thereof, wherein
R¹ is selected from the group consisting of:

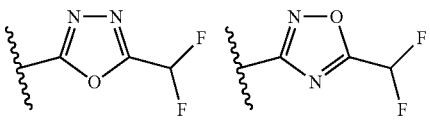

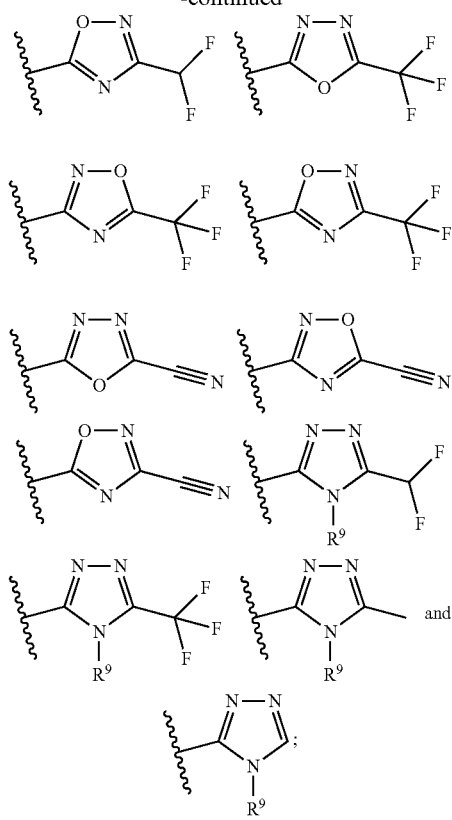

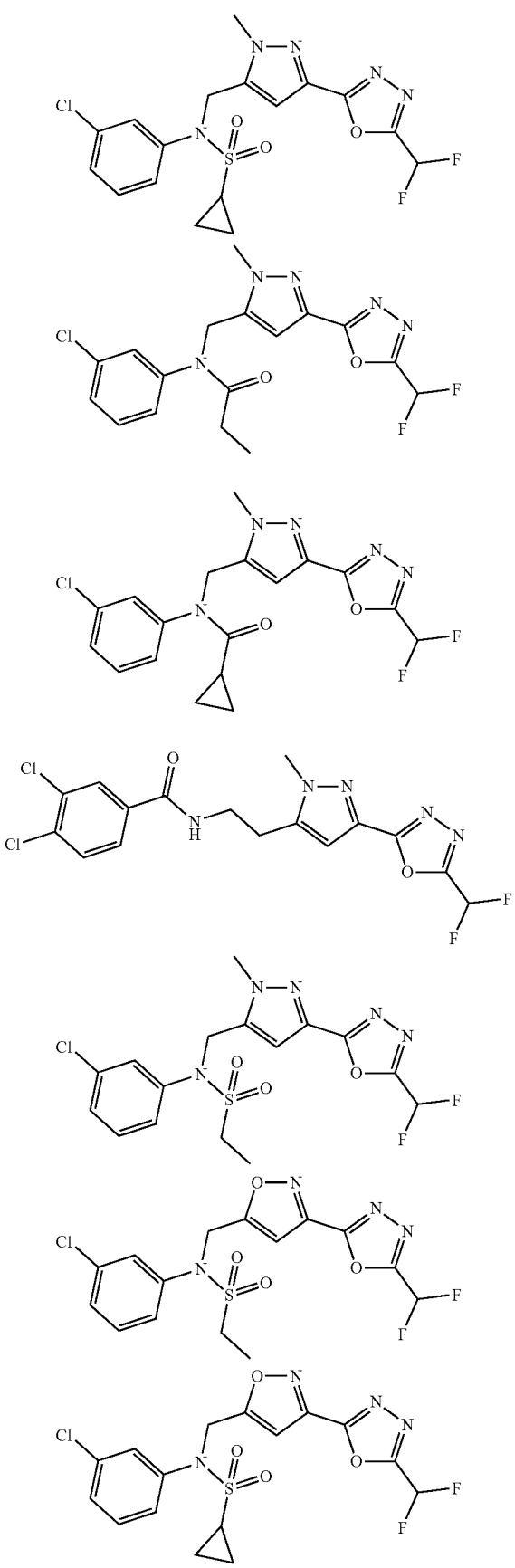

- $R^a$ is selected from the group consisting of H, halo, $C_{1-3}$ alkyl, cycloalkyl, haloalkyl, and alkoxy;
- $R^2$ and $R^3$ are independently selected from the group consisting of H, halogen, alkoxy, haloalkyl, aryl, heteroaryl, alkyl, and cycloalkyl each of which is optionally substituted, or $R^2$ and $R^3$ together with the atom to which they are attached form a cycloalkyl or heterocyclyl;
- $R^4$ and $R^5$ are independently selected from the group consisting of H, —($SO_2$)$R^2$, —($SO_2$)$NR^2R^3$, —(CO)$R^2$, —(CO$NR^2R^3$), aryl, arylheteroaryl, alkylenearyl, heteroaryl, cycloalkyl, heterocyclyl, alkyl, haloalkyl, and alkoxy, each of which is optionally substituted, or $R^4$ and $R^5$ together with the atom to which they are attached form a cycloalkyl or heterocyclyl, each of which is optionally substituted;
- $R^9$ is selected from the group consisting of H, $C_1$-$C_6$ alkyl, haloalkyl, cycloalkyl and heterocyclyl;
- $X^1$ is selected from the group consisting of S, O, NH and $NR^6$, wherein $R^6$ is selected from the group consisting of $C_1$-$C_6$ alkyl, alkoxy, haloalkyl, cycloalkyl and heterocyclyl;
- Y is selected from the group consisting of $CR^2$, O, N, S, SO, and $SO_2$, wherein when Y is O, S, SO, or $SO_2$, $R^5$ is not present and when $R^4$ and $R^5$ together with the atom to which they are attached form a cycloalkyl or heterocyclyl, Y is $CR^2$ or N; and
- n is selected from 0, 1, and 2.

11. The method of embodiment 10, wherein the HDAC6 inhibitor is selected from the group consisting of:

-continued
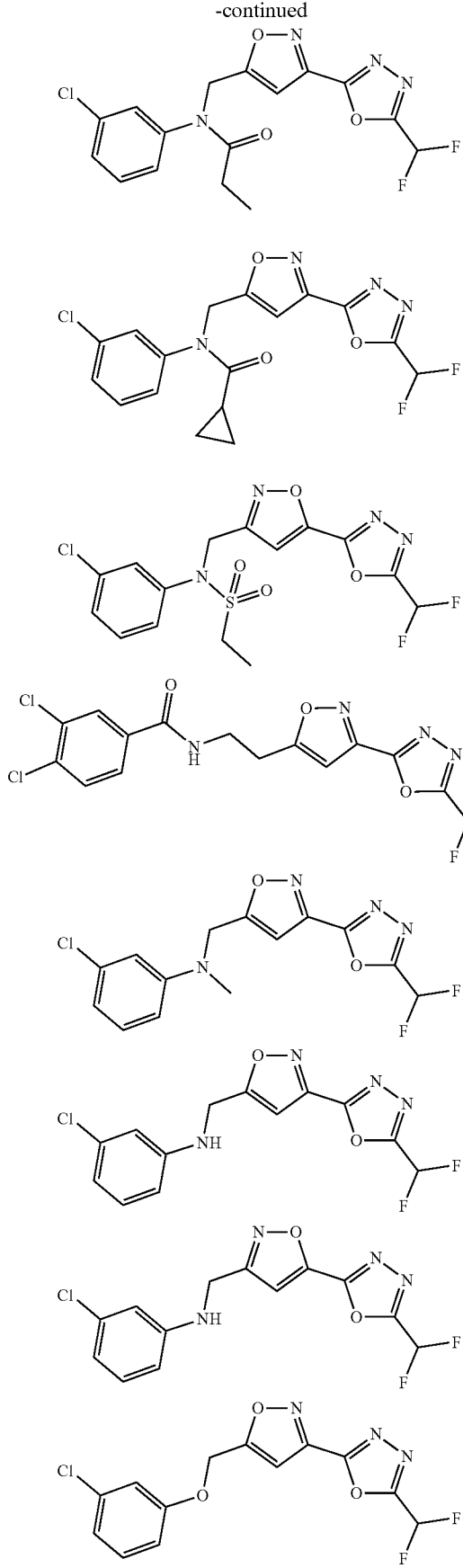
-continued
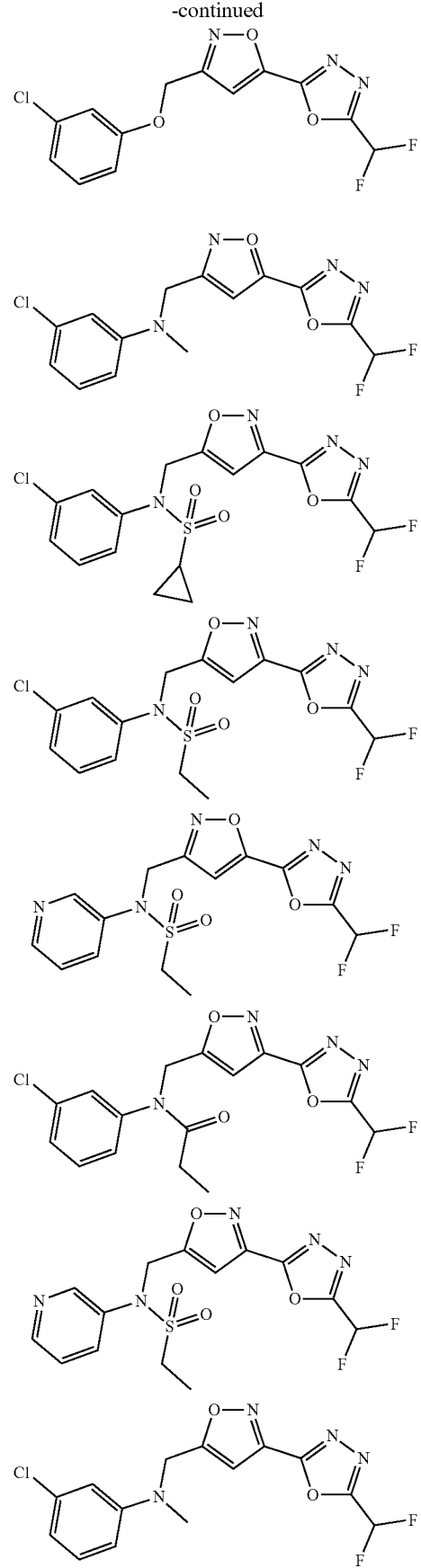

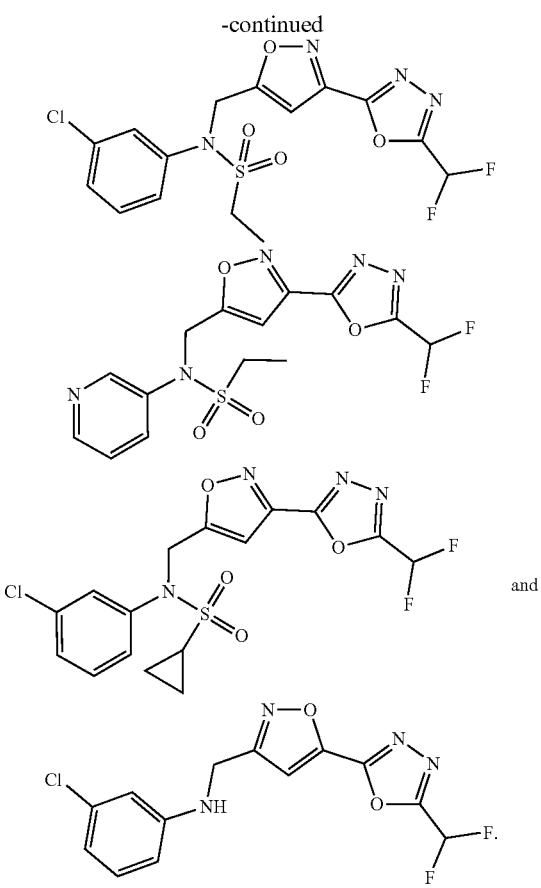

12. The method of embodiment 10, wherein the HDAC6 inhibitor is

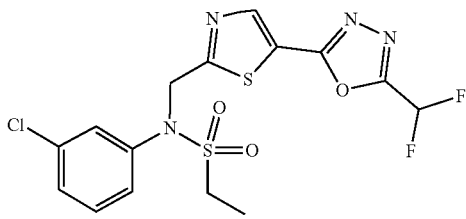 [SMILES: CCS(=O)(=O)N(CC1=NCC=C(c2nnc(C(F)F)o2)S1)c1cccc(Cl)c1]

or an analog thereof.

13. The method of embodiment 10, wherein the HDAC6 inhibitor is

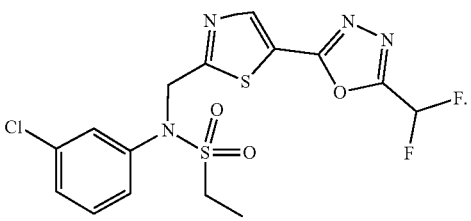 [SMILES: CCS(=O)(=O)N(CC1=NCC=C(c2nnc(C(F)F)o2)S1)c1cccc(Cl)c1]

14. The method of embodiment 10, wherein the HDAC6 inhibitor is selected from any HDAC6 inhibitor in Table 13 (in Example 7).

15. The method of embodiment 14, wherein the HDAC6 inhibitor is any HDAC6 inhibitor in Table 13 which has an $IC_{50}$ equal to or less than 0.03 μM.

16. The method of embodiment 10, wherein the HDAC6 inhibitor is a compound having the

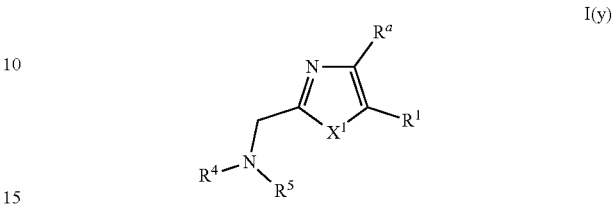

I(y)

or a pharmaceutically acceptable salt thereof,
wherein:
$X^1$ is S;
$R^a$ is selected from the group consisting of H, halogen, and $C_{1-3}$ alkyl;
$R^1$ is

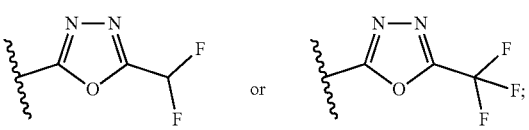 [SMILES: *c1nnc(C(F)F)o1 ; "or" ; *c1nnc(C(F)(F)F)o1]

$R^2$ is selected from the group consisting of alkyl, alkoxy, and cycloalkyl, each of which is optionally substituted;
$R^3$ is H or alkyl;
$R^4$ is selected from the group consisting of alkyl, —(SO$_2$)R$^2$, —(SO$_2$)NR$^2$R$^3$, and —(CO)R$^2$; and
$R^5$ is aryl or heteroaryl; or $R^4$ and $R^5$ together with the atom to which they are attached form a heterocyclyl, each of which is optionally substituted.

17. The method of embodiment 16, wherein $R^a$ is H.

18. The method of embodiment 16 or 17, wherein $R^1$ is

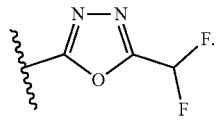 [SMILES: *c1nnc(C(F)F)o1]

19. The method of any one of embodiments 16-18, wherein $R^4$ is —(SO$_2$)R$^2$.

20. The method of embodiment 19, wherein —(SO$_2$)R$^2$ is —(SO$_2$)alkyl, —(SO$_2$)alkyleneheterocyclyl, —(SO$_2$)haloalkyl, —(SO$_2$)haloalkoxy, or —(SO$_2$)cycloalkyl.

21. The method of any one of embodiments 16-20, wherein $R^5$ is heteroaryl.

22. The method of embodiment 21, wherein the heteroaryl is a 5- to 6-membered heteroaryl 23. The method of embodiment 22, wherein the 5- to 6-membered heteroaryl is selected from the group consisting of

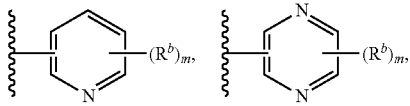

-continued

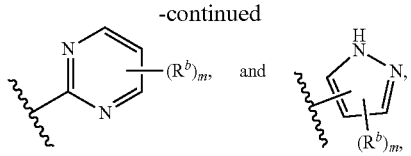

wherein $R^b$ is halogen, alkyl, alkoxy, cycloalkyl, —CN, haloalkyl, or haloalkoxy; and m is 0 or 1.

24. The method of embodiment 23, wherein $R^b$ is F, Cl, —CH$_3$, —CH$_2$CH$_3$, —CF$_3$, —CHF$_2$, —CF$_2$CH$_3$, —CN, —OCH$_3$, —OCH$_2$CH$_3$, —OCH(CH$_3$)$_2$, —OCF$_3$, —OCHF$_2$, —OCH$_2$CF$_2$H, and cyclopropyl.

25. The method of any one of embodiments 16-24, wherein the aryl is selected from the group consisting of phenyl, 3-chlorophenyl, 3-chloro-4-fluorophenyl, 3-trifluoromethylphenyl, 3,4-difluorophenyl, and 2,6-difluorophenyl.

26. The method of embodiment 10, wherein the HDAC6 inhibitor is a compound having Formula (Ik):

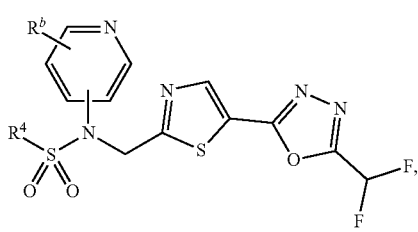

or a pharmaceutically acceptable salt thereof,
wherein:
$R^b$ is H, halogen, alkyl, cycloalkyl, —CN, haloalkyl, or haloalkoxy; and
$R^4$ is alkyl, alkoxy, haloalkyl, or cycloalkyl, each of which is optionally substituted.

27. The method of embodiment 26, wherein $R^b$ is H, halogen, haloalkyl, or haloalkoxy.

28. The method of embodiment 26 or 27, wherein $R^4$ is optionally substituted alkyl or cycloalkyl.

29. The method of embodiment 26, wherein the HDAC6 inhibitor is a compound having the

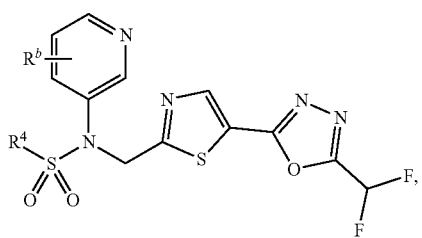

or a pharmaceutically acceptable salt thereof,
wherein:
$R^b$ is H, halogen, alkyl, cycloalkyl, —CN, haloalkyl, or haloalkoxy; and
$R^4$ is alkyl, alkoxy, haloalkyl, or cycloalkyl, each of which is optionally substituted.

30. The method of embodiment 29, wherein $R^b$ is H, halogen, haloalkyl, or haloalkoxy.

31. The method of embodiment 29 or 30, wherein $R^4$ is optionally substituted alkyl or cycloalkyl.

32. The method of embodiment 29, wherein $R^4$ is alkyl.

33. The method of embodiment 26, wherein the HDAC6 inhibitor is a compound having the structure:

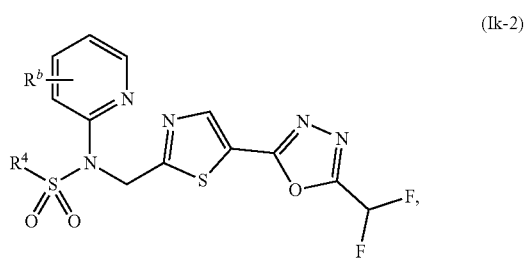

or a pharmaceutically acceptable salt thereof,
wherein:
$R^b$ is H, halogen, alkyl, cycloalkyl, —CN, haloalkyl, or haloalkoxy; and
$R^4$ is alkyl, alkoxy, haloalkyl, or cycloalkyl, each of which is optionally substituted.

34. The method of embodiment 33, wherein $R^b$ is H, halogen, haloalkyl, or haloalkoxy.

35. The method of embodiment 33 or 34, wherein $R^4$ is optionally substituted alkyl.

36. The method of embodiment 16, wherein the HDAC6 inhibitor is a compound of Formula:

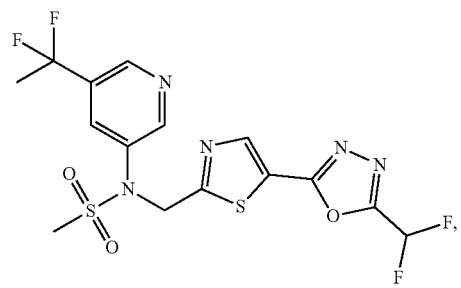

or a pharmaceutically acceptable salt thereof.

37. The method of embodiment 16, wherein the HDAC6 inhibitor is a compound of Formula:

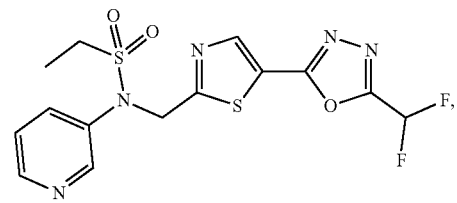 [SMILES: CCS(=O)(=O)N(Cc1ncc(-c2nnc(C(F)F)o2)s1)c1cccnc1]

or a pharmaceutically acceptable salt thereof.

38. The method of embodiment 16, wherein the HDAC6 inhibitor is a compound of Formula:

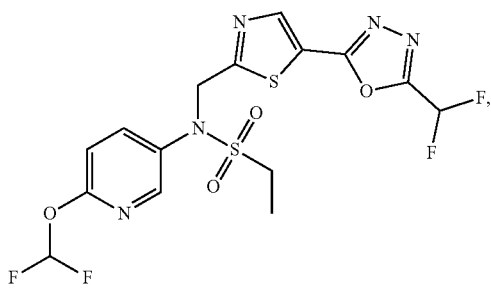 [SMILES: CCS(=O)(=O)N(Cc1ncc(-c2nnc(C(F)F)o2)s1)c1ccc(OC(F)F)nc1]

or a pharmaceutically acceptable salt thereof.

39. The method of embodiment 16, wherein the HDAC6 inhibitor is a compound of Formula:

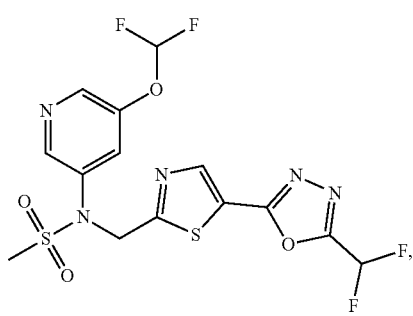 [SMILES: CS(=O)(=O)N(Cc1ncc(-c2nnc(C(F)F)o2)s1)c1cncc(OC(F)F)c1]

or a pharmaceutically acceptable salt thereof.

40. The method of embodiment 16, wherein the HDAC6 inhibitor is a compound of Formula:

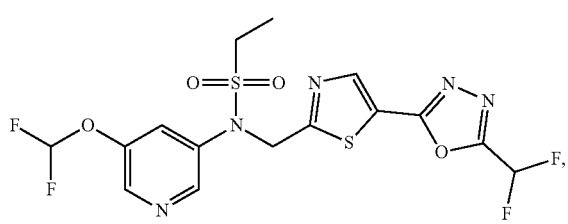 [SMILES: CCS(=O)(=O)N(Cc1ncc(-c2nnc(C(F)F)o2)s1)c1cncc(OC(F)F)c1]

or a pharmaceutically acceptable salt thereof.

41. The method of embodiment 16, wherein the HDAC6 inhibitor is a compound of Formula:

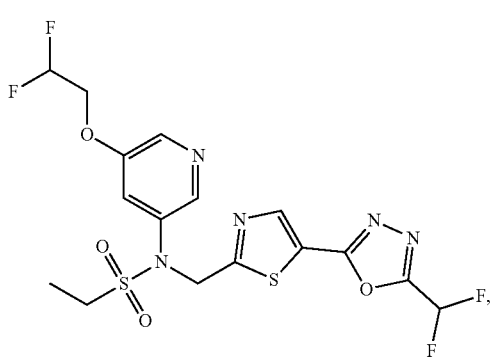 [SMILES: CCS(=O)(=O)N(Cc1ncc(-c2nnc(C(F)F)o2)s1)c1cncc(OCC(F)F)c1]

or a pharmaceutically acceptable salt thereof.

42. The method of embodiment 16, wherein the HDAC6 inhibitor is a compound of Formula:

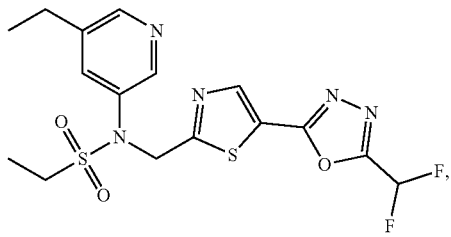 [SMILES: CCc1cncc(N(Cc2ncc(-c3nnc(C(F)F)o3)s2)S(=O)(=O)CC)c1]

or a pharmaceutically acceptable salt thereof.

43. The method of embodiment 16, wherein the HDAC6 inhibitor is a compound of Formula:

or a pharmaceutically acceptable salt thereof.

44. The method of embodiment 16, wherein the HDAC6 inhibitor is a compound of Formula:

or a pharmaceutically acceptable salt thereof.

45. The method of embodiment 16, wherein the HDAC6 inhibitor is a compound of Formula:

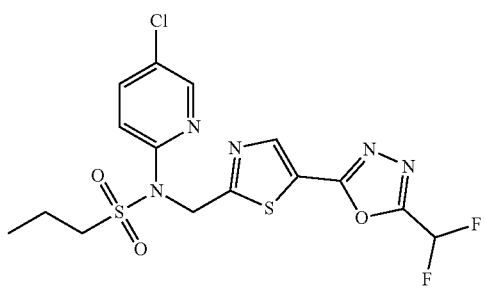

or a pharmaceutically acceptable salt thereof.

46. The method of embodiment 16, wherein the HDAC6 inhibitor is a compound of Formula:

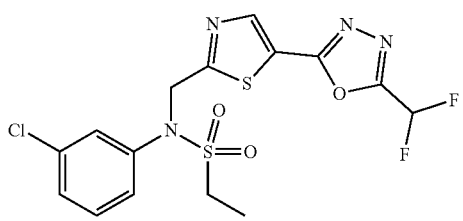 [SMILES: CCS(=O)(=O)N(Cc1ncc(-c2nnc(C(F)F)o2)s1)c1cccc(Cl)c1]

or a pharmaceutically acceptable salt thereof.

47. The method of any one of embodiments 1-7, wherein the HDAC6 inhibitor is a compound of Formula (II):

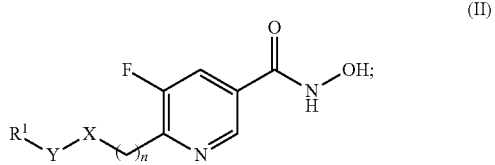

(II)

wherein
n is 0 or 1;
X is O, NR⁴, or CR⁴R⁴';
Y is a bond, CR²R³ or S(O)₂;
R¹ is selected from the group consisting of H, amido, carbocyclyl, heterocyclyl, aryl, and heteroaryl;
R² and R³ are independently selected from the group consisting of H, halogen, alkyl, carbocyclyl, heterocyclyl, aryl, heteroaryl, —(CH₂)-carbocyclyl, —(CH₂)-heterocyclyl, —(CH₂)-aryl, and —(CH₂)-heteroaryl; or
R¹ and R² taken together with the carbon atom to which they are attached form a carbocyclyl or heterocyclyl; or
R² and R³ taken together with the carbon atom to which they are attached form a carbocyclyl or heterocyclyl; and
R⁴ and R⁴' are each independently selected from the group consisting of H, alkyl, —CO₂-alkyl, carbocyclyl, heterocyclyl, aryl, heteroaryl, —(CH₂)-carbocyclyl, —(CH₂)-heterocyclyl, —(CH₂)-aryl, and —(CH₂)-heteroaryl; or
R⁴ and R⁴' taken together with the carbon atom to which they are attached form a carbocyclyl or heterocyclyl;
wherein each alkyl, carbocyclyl, heterocyclyl, aryl, and heteroaryl is independently optionally substituted with one or more substituents selected from the group consisting of halogen, haloalkyl, oxo, hydroxy, alkoxy, —OCH₃, —CO₂CH₃, —C(O)NH(OH), —CH₃, morpholine, and —C(O)N-cyclopropyl.

48. The method of any one of embodiments 1-7, wherein the HDAC6 inhibitor is CAY10603, tubacin, rocilinostat (ACY-1215), citarinostat (ACY-241), ACY-738, QTX-125, CKD-506, nexturastat A, tubastatin A, or HPOB.

49. The method of any one of the preceding embodiments, wherein the compound is the compound and not the pharmaceutically acceptable salt thereof.

50. The method of any one of embodiments 1-49, wherein the HDAC6 inhibitor is at least 100-fold selective against HDAC6 compared to all other isozymes of HDAC.

51. The method of any one of embodiments 1-50, wherein the subject has or is at risk for hypertension.

52. The method of any one of embodiments 1-51, wherein the subject has or is at risk for diabetes mellitus.

53. The method of any one of embodiments 1-52, wherein the subject has or is at risk for coronary artery disease (CAD).

54. The method of any one of embodiments 1-53, wherein the subject has or is at risk for valvular heart disease.

55. The method of any one of embodiments 1-54, wherein the subject has or is at risk for atrial fibrillation.

56. The method of any one of embodiments 1-55, wherein the method treats or prevents at least one symptom of HFpEF.

57. The method of any one of embodiments 1-56, wherein the method reduces left ventricular (LV) mass.

58. The method of any one of embodiments 1-57, wherein the method reduces LV wall thickness.

59. The method of any one of embodiments 1-58, wherein the method improves LV relaxation.

60. The method of any one of embodiments 1-59, wherein the method improves LV filling pressure.

61. The method of any one of embodiments 1-60, wherein the method prevents heart failure in the subject.

62. An HDAC6 inhibitor for use in a method for treating heart failure with preserved ejection fraction.

63. The HDAC6 inhibitor of embodiment 62, wherein the HDAC6 inhibitor is any one described in embodiments 8-50.

64. A pharmaceutical composition for use in a method for treating heart failure with preserved ejection fraction, comprising an HDAC6 inhibitor.

65. The pharmaceutical composition of embodiment 64, wherein the HDAC6 inhibitor is any one described in embodiments 8-50.

66. A kit, comprising an HDAC6 inhibitor and instructions for use in a method for treating heart failure with preserved ejection fraction.

67. The kit of embodiment 66, wherein the HDAC6 inhibitor is any one described in embodiments 8-50.

68. Use of an HDAC6 inhibitor in treating heart failure with preserved ejection fraction.

69. The use of embodiment 68, wherein the HDAC6 inhibitor is any one described in embodiments 8-50.

EXAMPLES

The invention is further illustrated by the following examples. The examples below are non-limiting are merely representative of various aspects of the invention.

Example 1: HDAC6 Selective Inhibitors Improve Glucose Tolerance and Insulin Resistance in a Diet-Induced Obesity Mouse Model This example demonstrates that histone deacetylase 6 (HDAC6) selective inhibitors improve glucose tolerance and insulin resistance in a diet induced obese mouse model. The diet-induced obesity model closely mimics high-fat/high-density foods that contribute to obesity in humans. (Reviewed in Wang et al. *Methods Mol Biol.* 821:421-433 (2012).)

FIGS. 1A-1L show that HDAC6 inhibition with TYA-11631 improves glucose tolerance and insulin resistance in a diet induced obese mouse model. TYA-11631 is a compound within Formula (I), as well as within, for example, Formula (Ic), Formula (Ik) and Formula I(y).

16-weeks old male Diet-Induced Obese (DIO) C57BL/6J (Cat. 380050) mice and age/gender matched controls (Cat. 000664) were purchased from the Jackson Laboratory®. DIO mice (n=40) were fed a rodent diet with 60 kcal % fat (D12492) and control mice were fed a rodent diet with 10 kcal % fat (D12450B) starting from 6-weeks of age.

Figure 1A:
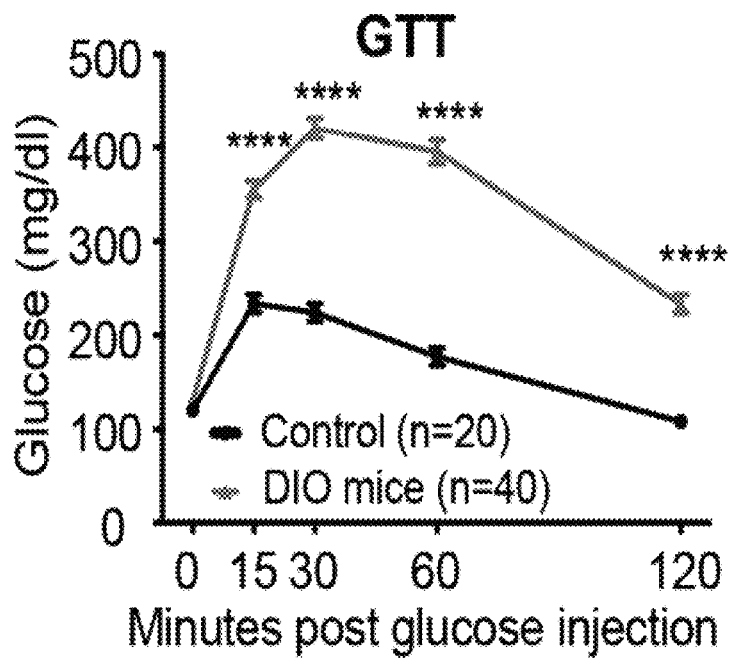
FIGS. 1A-1L show that HDAC6 inhibition with TYA-11631 improves glucose tolerance and insulin resistance in diet induced obese mouse model.
Figure 1B:
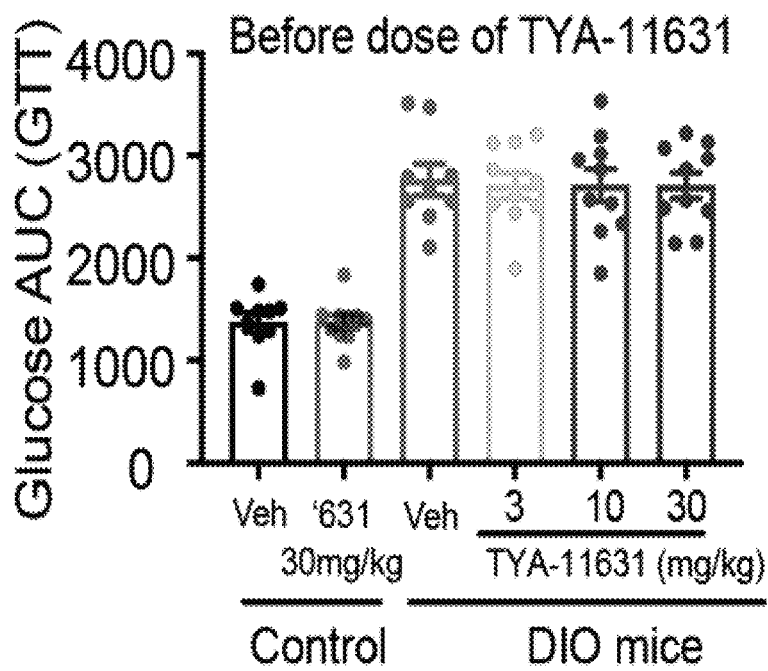

Intraperitoneal glucose-tolerance tests (GTT) were performed by injection of glucose (2 g/kg in saline) after 6 hours fasting. Tail blood glucose levels (mg/dl) were measured with a glucometer before (0 min) and at 15, 30, 45, 60 and 120 min after glucose administration. DIO mice at 16 weeks of age developed severe glucose intolerance compared to controls. (FIG. 1A, FIG. 1B).

Figure 1C:
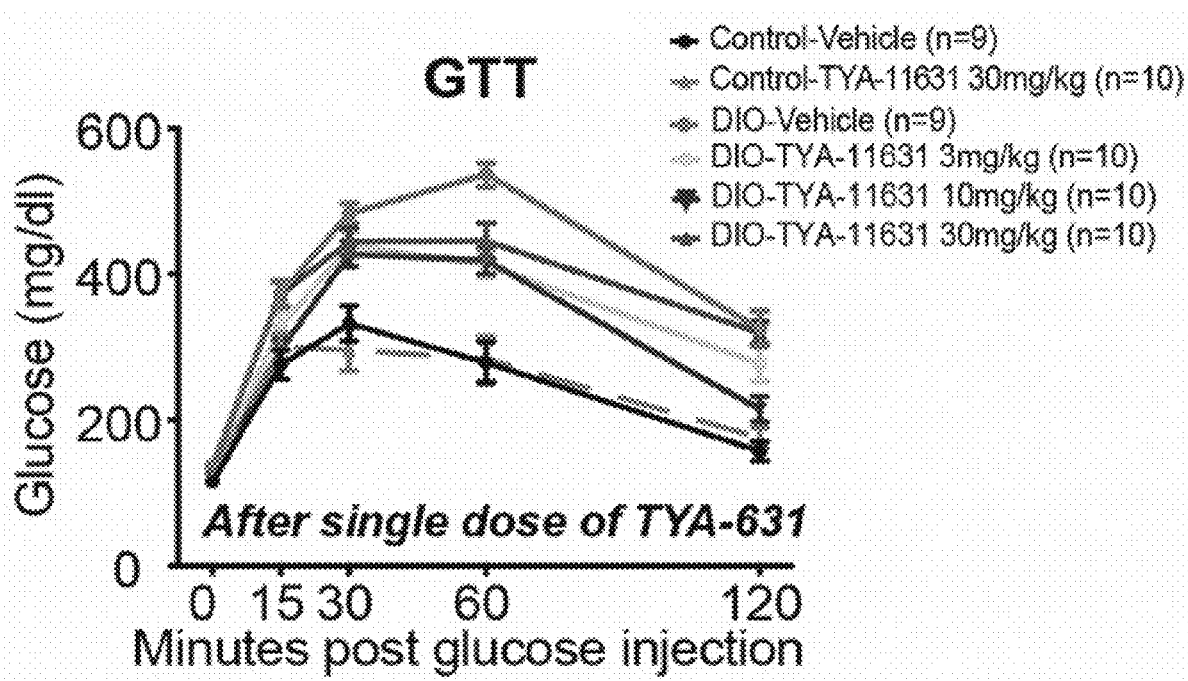
Figure 1D:
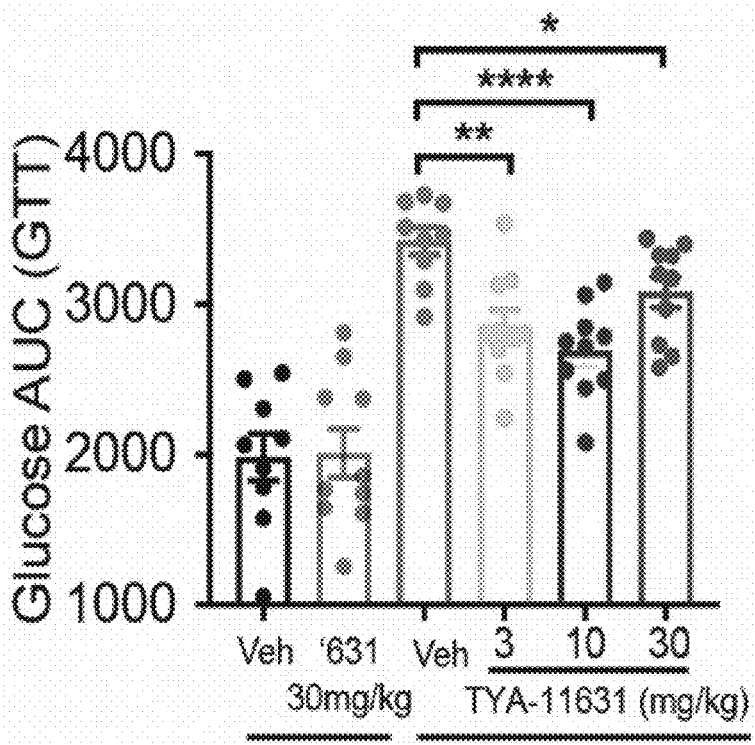
Figure 1E:
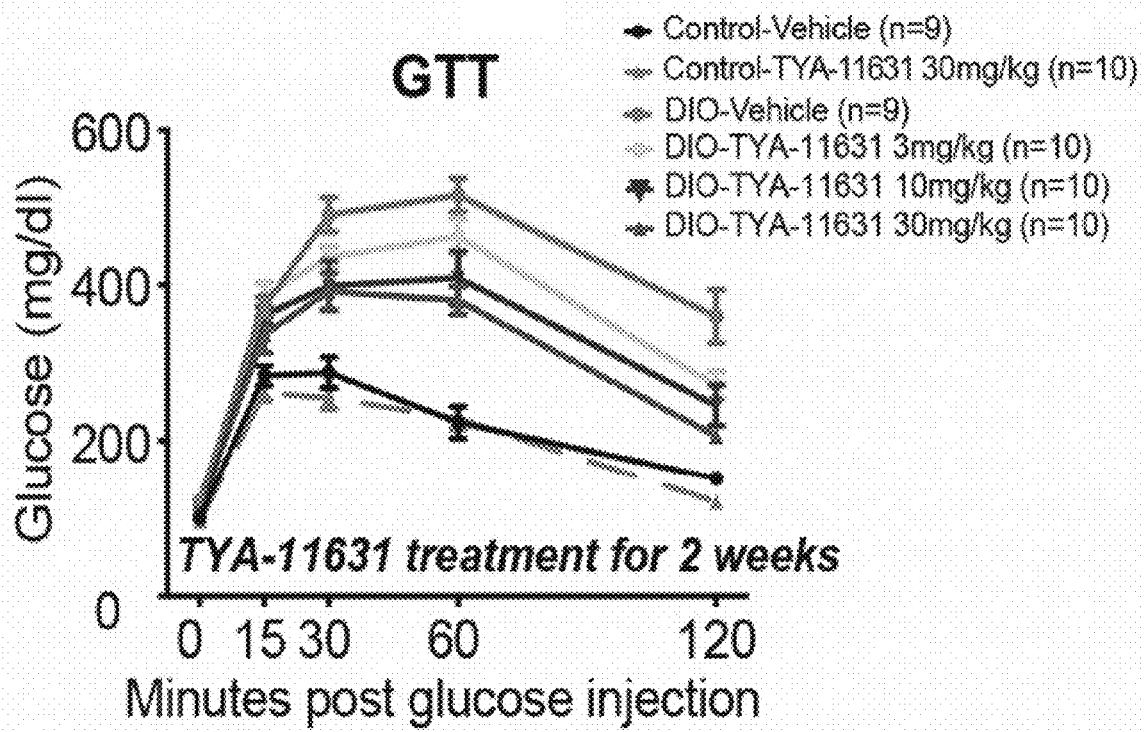
Figure 1F:
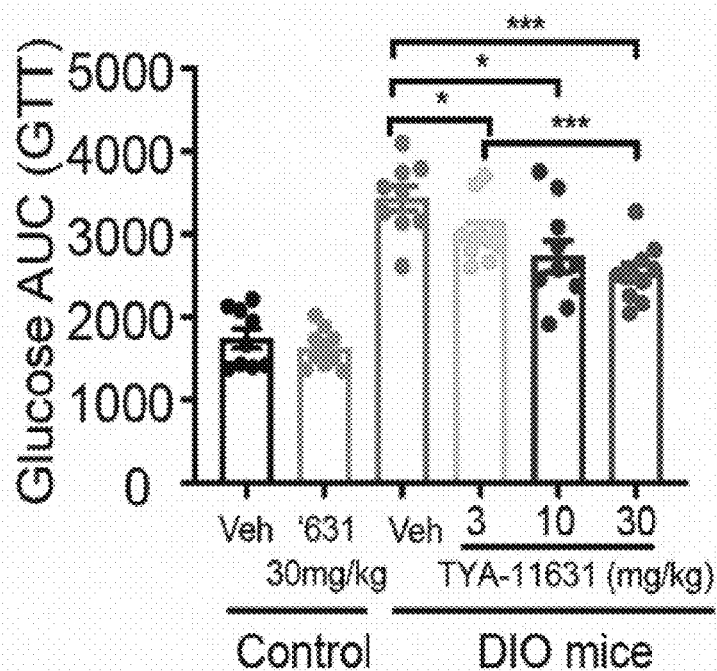

Based on glucose AUC level, DIO mice were evenly randomized into four treatment groups to receive Vehicle (n=9) or TYA-11631 at three dosages 3, 10, 30 mg/kg (n=10 each). Control mice were also divided to dose orally with vehicle (n=10) or 30 mg/kg TYA-11631 (n=10). To assess the acute response of TYA-11631 on glucose metabolism, GTT was performed at 6 h after $1^{st}$ dose. Strikingly, single dose of TYA-11631 at all three test dosages significantly reduced glucose level. (FIG. 1C, FIG. 1D). TYA-11631 treatment for 2 weeks led to pronounced improvements in glucose tolerance in dose-dependent manner. (FIG. 1E, FIG. 1F).

Figure 1G:
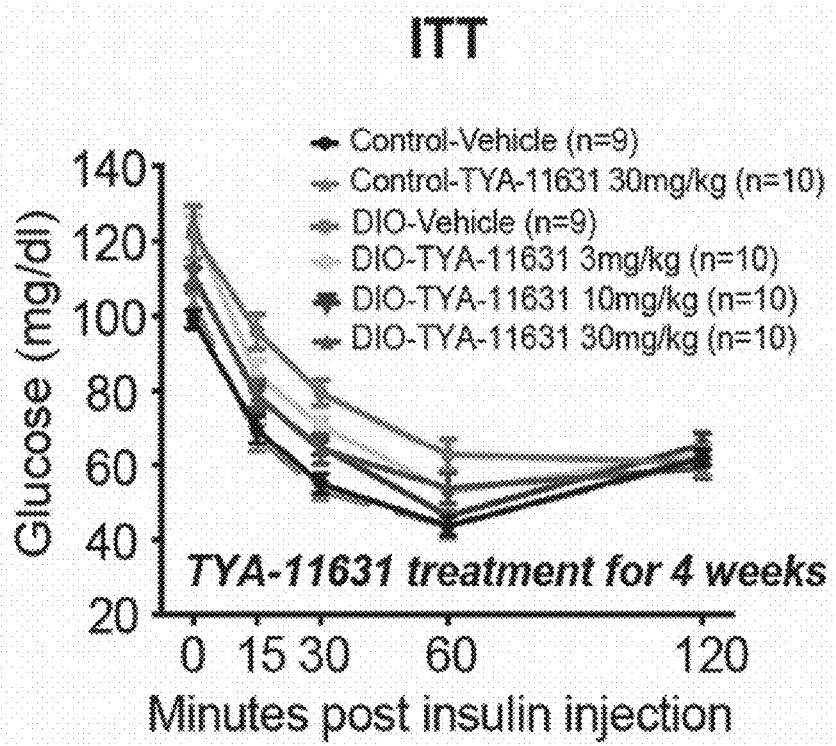
Figure 1H:
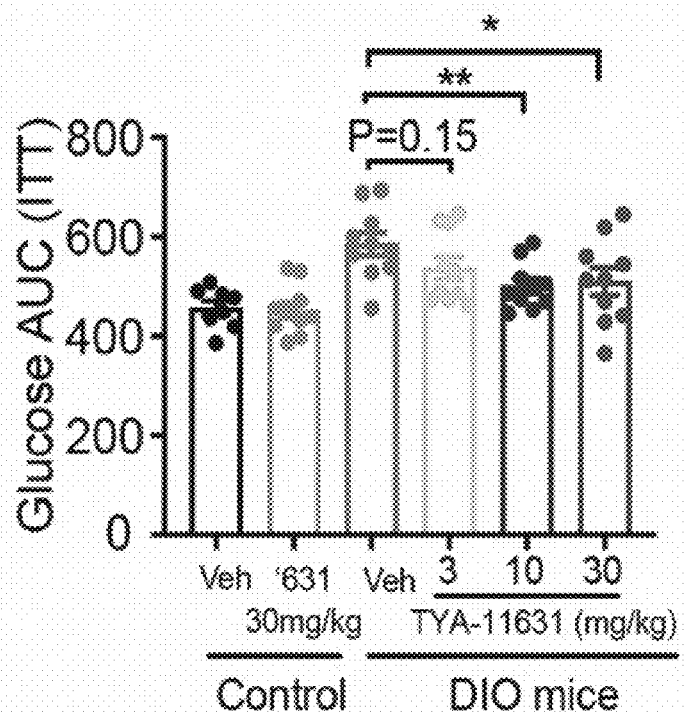

To evaluate the effects of TYA-11631 on insulin resistance, intraperitoneal insulin-tolerance test (ITT) was performed by injection of insulin (1 U/kg) after 6 hours fasting. Tail blood glucose levels (mg/dl) were measured with a glucometer before (0 min) and at 15, 30, 60 and 120 min after insulin administration. HDAC6 inhibitor (TYA-11631) treatment for 4 weeks improved insulin resistance in DIO mice. 10 and 30 mg/kg were significantly reduced glucose AUC (ITT) with comparable activities, 3 mg/kg showed a trend of reduction. (FIG. 1G, FIG. 1H)

Figure 1I:
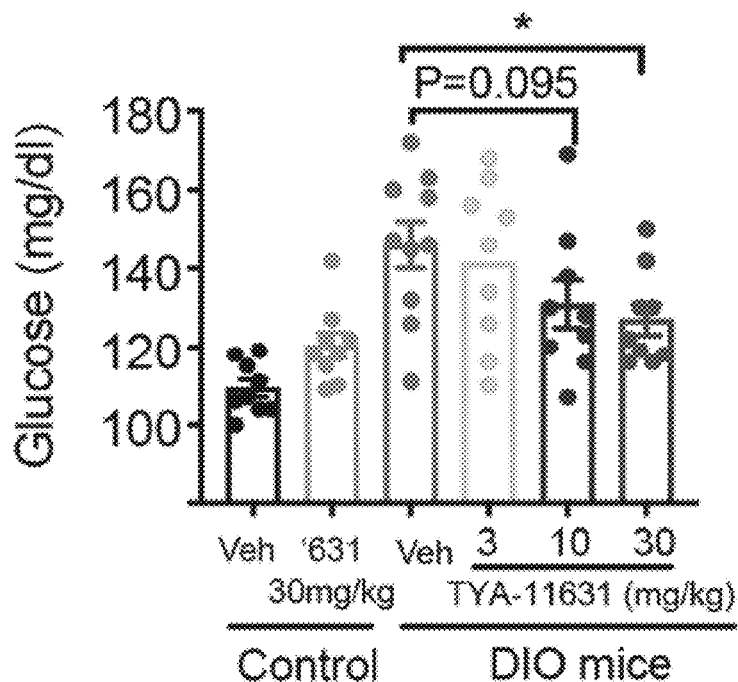
Figure 1J:
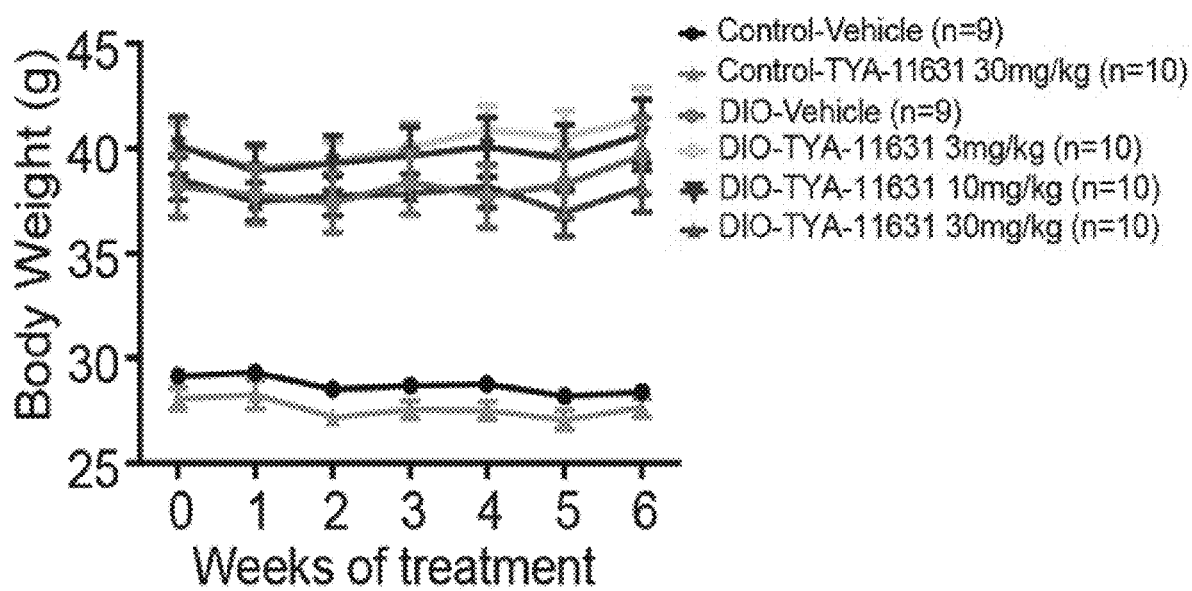
Figure 1K:
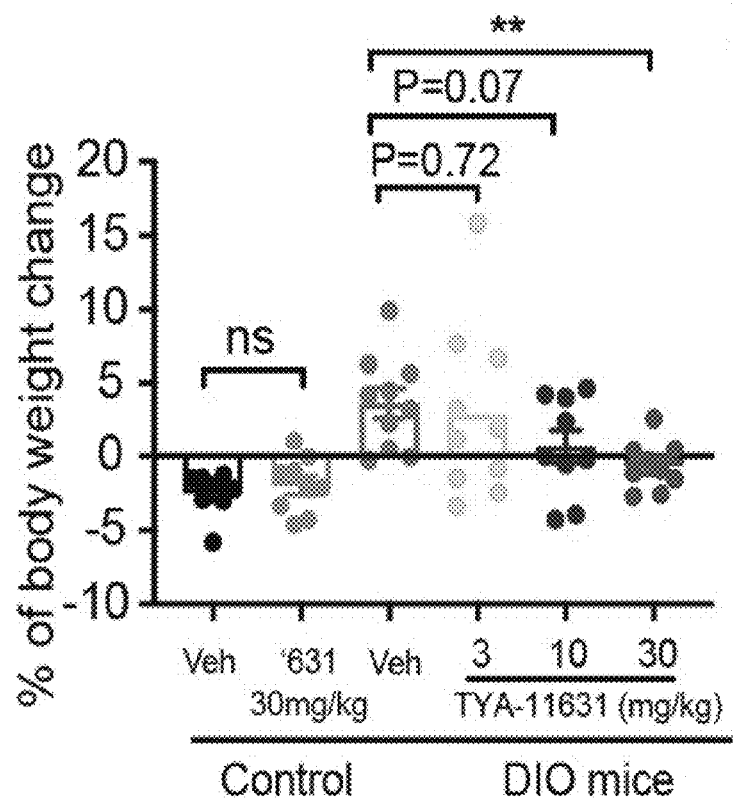
Figure 1L:
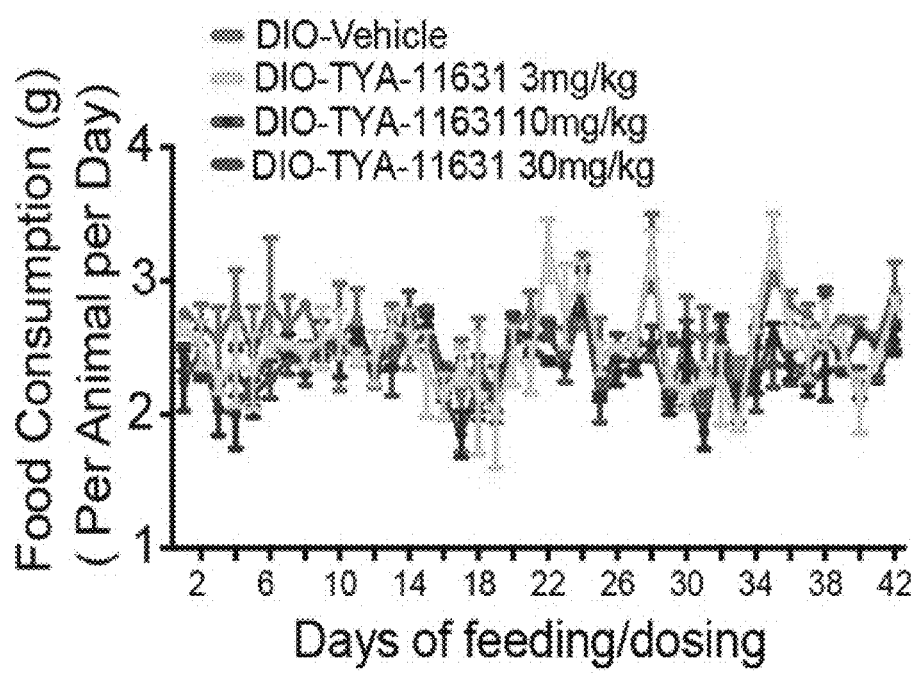

Effects of TYA-11631 on blood glucose were also assessed in non-fasting mice. Tail blood samples were collected in the morning and measured with a glucometer. TYA-11631 treatment for 6 wks led to a dose-dependent reduction of non-fasting glucose, consistent with the data of glucose tolerant test after fasting. (FIG. 1I)

Treatment with TYA-11631 caused a dose dependent reduction of body weight in DIO mice. (See FIG. 1J, FIG. 1K, FIG. 1L) No differences of food consumption were observed between groups. Notably, control mice dosed with TYA-11631 30 mg/kg for 6 wks did not show changes on blood glucose levels and body weights. Bars and error bars show means and SEM. *P<0.05, P<0.01, *P<0.001, ****P<0.0001.

Figures 2A, 2B, 2C:
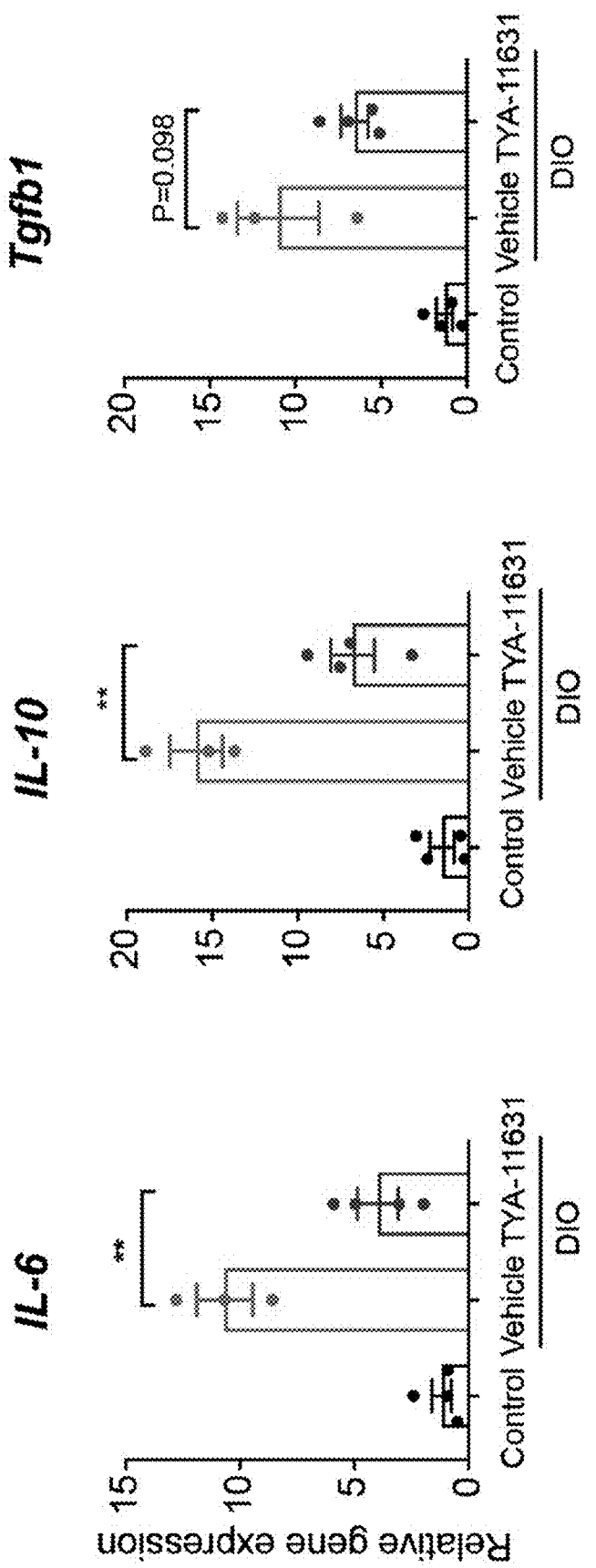
FIG. 2A, FIG. 2B and FIG. 2C show HDAC 6 inhibition with TYA-11631 inhibits inflammatory genes in adipose tissue in diet induce obese mouse model. White adipose tissue (epididymal) was dissected from DIO mice after 6 hours of single dose 30 mg/kg TYA-11631. Realtime q-PCR data showed that TYA-11631 remarkably inhibited upregulation of pro-inflammatory genes—IL-6 (FIG. 2A), IL-10 (FIG. 2B) and TGFb1 (FIG. 2C) in white adipose tissue.

FIGS. 2A-C show HDAC 6 inhibition with TYA-11631 inhibits inflammatory genes in adipose tissue in a diet induced obese mouse model.

White adipose tissue (epididymal) was dissected from DIO mice after 6 hours of single dose 30 mg/kg TYA-11631. Realtime q-PCR data showed that TYA-11631 remarkably inhibited upregulation of pro-inflammatory genes—IL-6 (FIG. 2A), IL-10 (FIG. 2B) and TGFb1 (FIG. 2C) in white adipose tissue. Inhibition or ablation of these genes have been shown to protect mice from diet-induced obesity with improvement of glucose tolerance and insulin sensitivity (Han et al., PNAS 2020; Rajbhandari et al., *Cell* 2018).

Taken together, these data show that histone deacetylase 6 (HDAC6) selective inhibitors improve glucose tolerance and insulin resistance in a diet induced obese mouse model, and suggest a potential molecular mechanism underlying the effect on systemic glucose metabolism.

Example 2: HDAC6 Inhibitors Improve Glucose Metabolism and Symptoms of Metabolic Disease in a Diabetes Mouse Model This example demonstrates that histone deacetylase 6 (HDAC6) selective inhibitors improve glucose metabolism and symptoms of metabolic disease in a mouse model of diabetes (independent of high fat diet).

Materials and Methods

An HDAC6 inhibitor, TYA-11018, was used in this example. TYA-11018 is a compound within Formula (I), as well as within, for example, Formula (Ic) and Formula I(y). Vehicle contained 5% DMSO+45% PEG-300 in purified water.

Test System:

8-week old male db/db (Cat. 000697, homozygous Lep-$r^{db}$) mice and age/gender matched wild type controls (Cat. 000664) were purchased from the Jackson Laboratory (Bar Harbor, ME). Animals were fed with normal chow (LabDiet 5053, 10 kcal % fat diet, St Louis, MO), and housed in an animal research facility in accordance with the National Research Council of the National Academies guidelines for the care and use of laboratory animals. All mice were used for experiments after 1 week of acclimation period.

Baseline Glucose and Animal Randomization:

Blood samples in the fed state (before administration of TYA-11018 or vehicle alone) were taken from the tail vein for determination of baseline glucose. Based on both body weights and blood glucose levels, db/db mice were randomized to three groups to orally receive vehicle or TYA-11018 at two dosages—1.5 or 15 mg/kg. Wild type mice were dosed orally with vehicle for control.

Single Oral Administration and Blood Glucose Test:

After single administration of TYA-11018 or vehicle via a stomach tube at a volume of ml/kg, animals were transferred to clean cage and wire top with water bottles for fasting. Blood samples in the fasting state were taken from the tail vein at 0.5, 1, 2, 4 and 6 h after the single dose of TYA-11018 or vehicle for determination of glucose. Blood glucose levels (mg/dL) were measured by AimStrip Plus blood glucose strips used with the AimStrip Plus blood glucose monitoring system (Germaine Laboratories, San Antonio, TX).

Results

Animal Enrollment and Randomization:

The animals were randomized and enrolled for the single administration study based on body weights and baseline glucose. Body weight and tail blood glucose levels (mg/dL) were measured at fed state, just before TYA-11018 or vehicle administration. db/db mice at 9 weeks of age developed severe obesity with hyperglycemia compared to controls. Animals were randomized and evenly distributed into three groups to receive vehicle (n=8) or TYA-11018 of two dosages 1.5 (n=8) and 15 mg/kg (n=9). Controls (age and sex matched wild type mice) were dosed orally with vehicle (n=8) (Table).

TABLE 3

Animal randomization and group information

| Group | Test Article | Dose/QD | Number |
|---|---|---|---|
| Control | Vehicle | n/a | 8 |
| db/db diabetic Model | Vehicle | n/a | 8 |
| | TYA-11018 | 1.5 mg/kg | 8 |
| | TYA-11018 | 15 mg/kg | 9 |

Figure 3A:
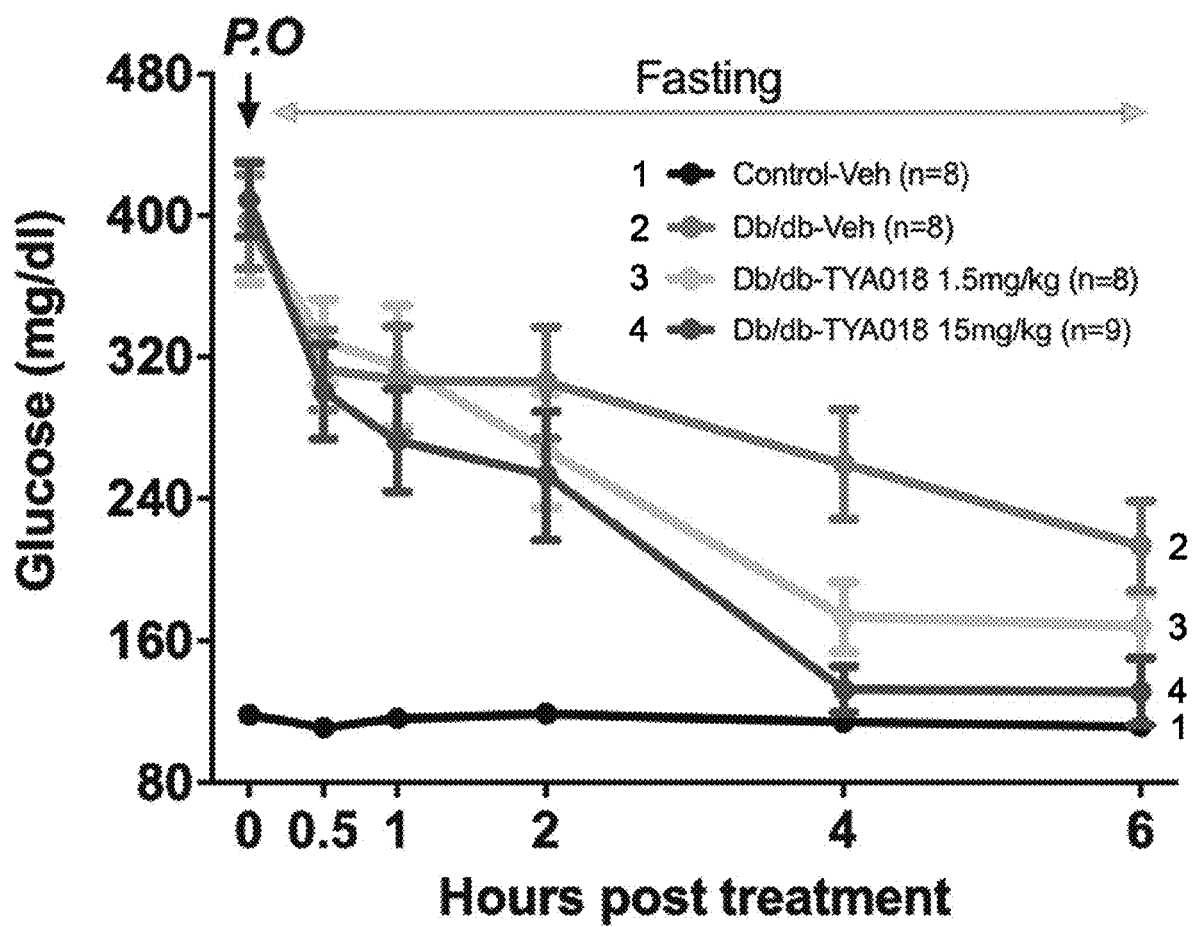
FIGS. 3A-3C show TYA-11018 effects in db/db diabetic mice.
Figure 3B:
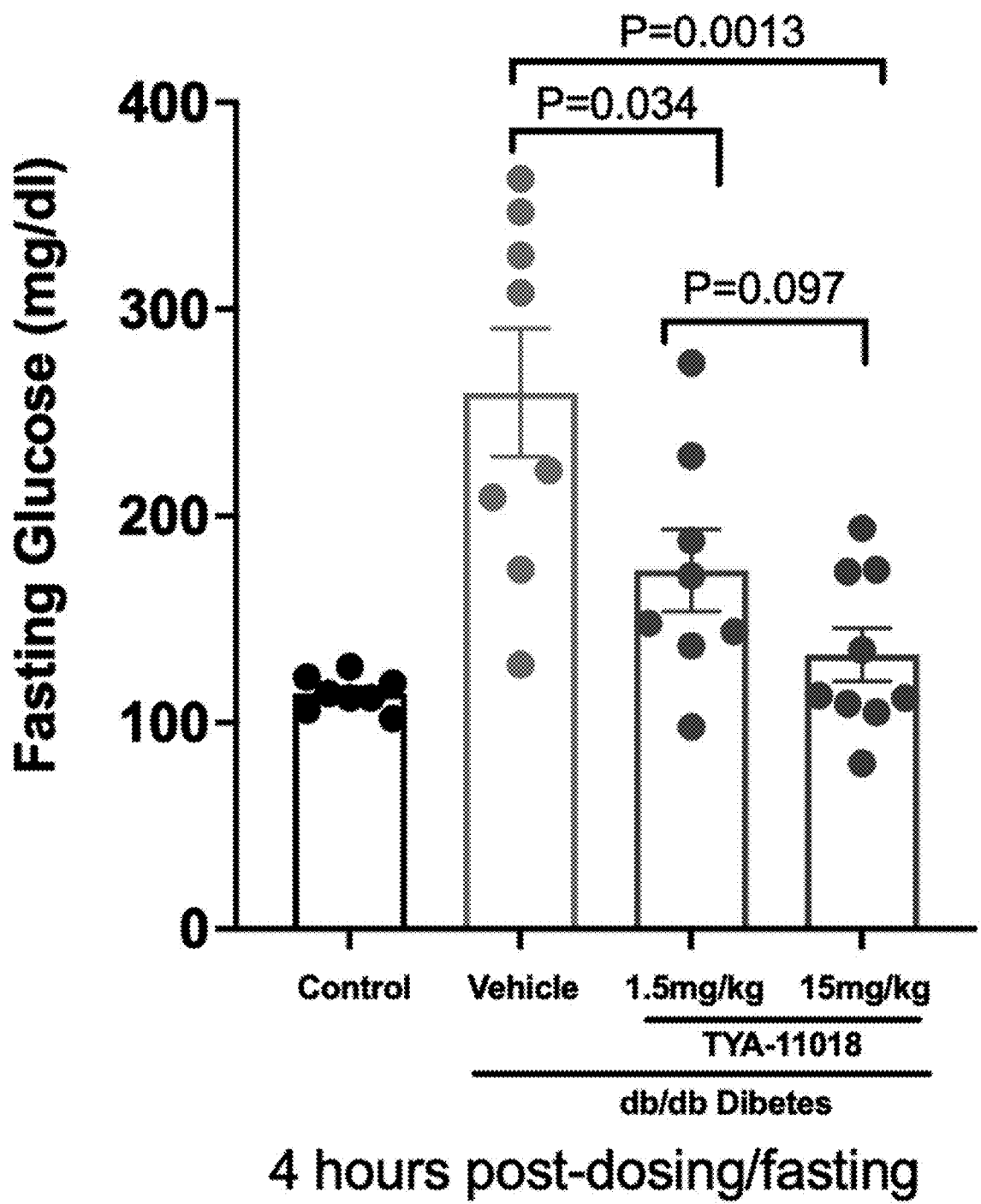
Figure 3C:
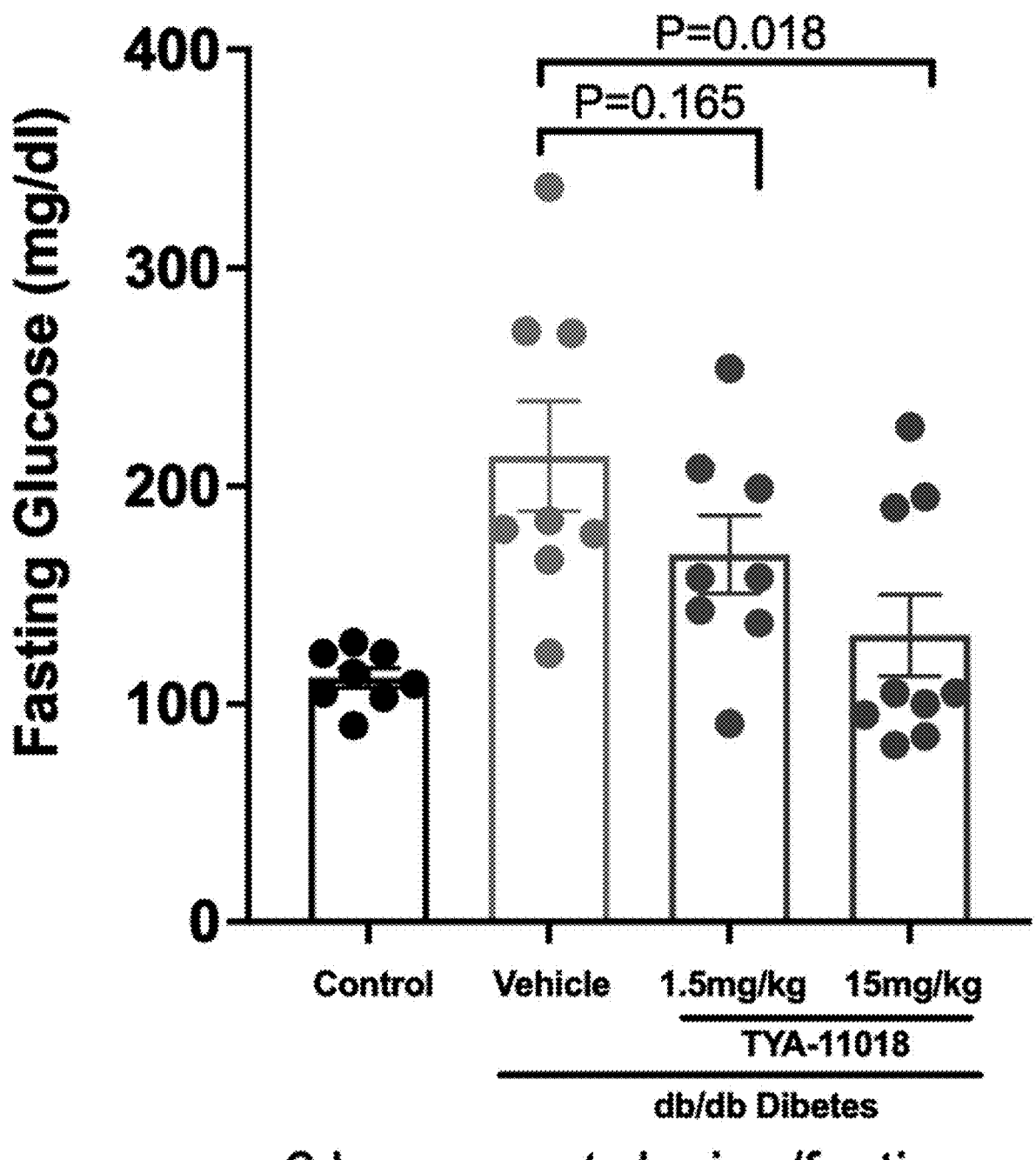

Single Administration of TYA-11018 Dose-Dependently Reduced Fasting Glucose in db/db Diabetic Mice:

To assess the acute response of TYA-11018 on glucose metabolism, blood glucose was measured at 0.5, 1, 2, 4 and 6 h after the single dose. As shown in FIG. 3A-3C, treatment with TYA-11018 showed a dose-dependent effect on reducing fasting glucose. Four hours after dosing/fasting, both 1.5 and 15 mg/kg significantly decreased blood glucose compared to vehicle treated db/db diabetic mice. Of note, single administration of 15 mg/kg TYA-11018 normalized fasting glucose in 4 hours. These data support the utility of HDAC6 selective inhibitors in improving glucose metabolism and symptoms of metabolic disease.

Example 3: HDAC6 Selective Inhibitors Improve Cardiac Structure and Heart Function in a HFpEF Mouse Model This example demonstrates that histone deacetylase 6 (HDAC6) selective inhibitors improve cardiac structure and heart function in a mouse model of heart failure with preserved ejection fraction (HFpEF).

First, an animal model of HFpEF was established: Surgically applying moderate transaortic constriction (mTAC) in wild type C57BL6 mice fed on high fat diet (HFD) was found to induce a cardio-metabolic heart failure phenotype that recapitulates systemic and cardiovascular features of HFpEF in human (FIGS. 4A-4H).

HFpEF model animals were dosed orally with 30 mg/kg HDAC6 inhibitor (TYA-11631) or vehicle once per day for six weeks. HDAC6 inhibitor effectively treated HFpEF. The HDAC6 inhibitor treatment regimen significantly reduced left ventricular (LV) mass (FIG. 5E) and LV wall thickness (FIG. 5F) measured by echocardiograph; and HDAC6 inhibitor treatment improved glucose tolerance (FIG. 5A). In addition, TYA-11631 treatment sustained improved LV relaxation and LV filling pressures as shown by decreased prolongation of isovolumetric relaxation time (FIG. 5H); lower E/A (FIG. 5I) and E/e' ratios (FIG. 5L); improved e' velocity (FIG. 5K); and reduced end diastolic pressure (FIG. 5M). Each of these efficacy parameters were normalized to control levels.

Furthermore, HFD/mTAC mice treated with TYA-11631 showed a trending decrease in lung weight (FIG. 5O), indicating improved pulmonary congestion, consistent with reduced filling pressure. No treatment related adverse events or toxicities were observed in the animals in the study.

At molecular level, the HDAC6 inhibitor significantly inhibited upregulation of genes commonly associated with fibrosis (Postn, Col1a1, Col3a1, Col5a2), cardiac stress (Nppb), and inflammation (Tnfα) in heart tissue of HFD/mTAC mice (FIGS. 6A-6H).

The results demonstrate that selectively inhibiting HDAC6 reverses a number of adverse pathophysiological processes in HFpEF.

Example 4: HDAC6 Selective Inhibitors Improve Cardiac Structure and Heart Function in a Second HFpEF Mouse Model This example demonstrates that histone deacetylase 6 (HDAC6) selective inhibitors improve cardiac structure and heart function in a second mouse model of heart failure with preserved ejection fraction (HFpEF), which recapitulates the vast majority of the clinical features of the syndrome: high-fat diet (HFD) coupled with inhibition of constitutive nitric oxide synthases (NOS) with N[w]-nitro-1-arginine methyl ester (L-NAME). (Schiattarella et al. *Nature* 568 (7752): 351-356 (2019)).

First, the mouse model was validated. HFD/L-NAME treatment significantly induced body weight increase (FIG. 7B), hypertension (FIG. 7C) and glucose intolerance (FIG. 7D) compared to the control mice. Echocardiographic evaluation revealed persistent preservation of the left ventricular ejection fraction (LVEF) (FIG. 7E). Significant concentric left ventricular (LV) hypertrophy was present in HFD/L-NAME mice, as indicated by increases in LV mass (FIG. 7F) and LV wall thickness at diastole (FIG. 7G), without LV chamber dilatation (FIG. 7H). In addition, mice concomitantly exposed to HFD/L-NAME exhibited signs of LV diastolic dysfunction with impaired relaxation and increased left ventricular filling pressure, as evidenced by prolonged IVRT (FIG. 7I), decreased e' velocity (FIG. 7J), and increased ratios of E/e'(FIG. 7K), E/A (FIG. 7L), measured by noninvasive Doppler imaging.

Second, treatment with an HDAC6 inhibitor, TYA-11631, was shown to improve glucose tolerance and diastolic dysfunction in the HFD/L-NAME model.

Animals were randomized to dose orally with 30 mg/kg TYA-11631 (n=8) or vehicle (n=12) once per day for nine weeks, respectively. In control groups, 6 mice were received vehicle and 8 mice were dosed with 30 mg/kg TYA-11631. As shown in FIG. 8A and FIG. 8B, Glucose tolerance test (GTT) was performed after 5 weeks of dosing.

Treatment with TYA-11631 markedly improved glucose tolerance in HFD/L-NAME mice, but no changes in control animals. (FIG. 8B) Plasma insulin level during GTT at the indicated time points (0 and 30 minutes after glucose injection) was measured by a sensitive mouse insulin detection kit (Cat. 80-INSMS-E01, ALPCO). TYA-11631 treatment led to decreased insulin secretion, suggesting that the improved glucose tolerance might be due to improved insulin action/sensitivity. (FIG. 8C) Treatment with TYA-11631 caused a significant reduction of body weight, but no difference of food consumption in mice fed with HFD/L-NAME. (FIG. 8D, FIG. 8E) TYA-11631 did not affect systolic blood pressure in HFD/L-NAME mice measured by non-invasive tail cuff method. (FIG. 5F) Echocardiography showed that TYA-11631 treatment preserved ejection fraction (FIG. 8G), however significantly reduced left ventricular mass (FIG. 8H) and LV wall thickness (FIG. 8I).

Noninvasive Doppler imaging and terminal invasive catheterization analysis revealed that treatment with TYA-11631 for 9 wks decreased prolongation of isovolumetric relaxation time (FIG. 8J), E/A (FIG. 8K) and E/e' ratios (FIG. 8L), increased e' velocity (FIG. 8M), and reduced end diastolic pressure (FIG. 8N), indicating the improved LV relaxation and filling pressure. In addition, HFD/L-NAME mice treated with TYA-11631 showed a trending decrease in lung weight (FIG. 8O), suggesting an improved pulmonary congestion, consistent with the reduction of filling pressure.

Notably, no adverse effects related to TYA-11631 have been observed. Control animals dosed with TYA-11631 has no changes on each of LV structural and functional parameters, as well as ECG signals—QT, QRS, PR intervals and R amplitude (FIG. 8P, FIG. 8Q, FIG. 8R and FIG. 8S), further supports an overall favorable safety profile of the compound.

Example 5: HDAC6 Inhibitors Reduce Cardiac Fibrosis and Enhance Mitochondrial Function in a Mouse Model of HFpEF This example demonstrates that histone deacetylase 6 (HDAC6) selective inhibitors reduce cardiac fibrosis and enhance mitochondrial function in a mouse model of HFpEF. In particular, this example demonstrates that HDAC6 selective inhibitors (i) correct dysregulated fibrosis and oxidative phosphorylation gene expression in HFpEF model, (ii) increase mitochondrial membrane potential and spare respiratory capacity in human iPSC-CMs, and (iii) prevent fibroblast activation from TGF-beta in primary human cardiac fibroblasts.

As described below, transcriptional analysis was performed on cardiac tissue from mice with HFpEF using RNA sequencing and qPCR. RNA-Seq data presented here show reduced expression of gene sets associated with hypertrophy, fibrosis, and PDGFR signaling in HFpEF mice treated with TYA-11631. qPCR data further confirmed reduced expression of fibrotic genes which correlated with improved diastolic function. Additionally, RNA-Seq data presented here show that gene sets associated with mitochondrial energy production were enriched in TYA-11631 treated HFpEF mice. The increased expression of mitochondrial genes correlated with improved diastolic function. TYA-11631 was further tested to determine whether it has a direct effect on metabolism in an in-vitro model using human induced pluripotent stem cell-derived cardiomyocytes. The data presented here show enhanced reserve respiratory capacity, indicating improved ATP production in response to stress in TYA-11631 treated human iPSC-derived CMs.

Materials and Methods

HFpEF was induced surgically by moderate transaortic constriction in high fat diet-fed mice for 12 weeks (mTAC/HFD). After HFpEF phenotypes were established, mice received TYA-11631 (30 mg/kg) or vehicle orally once daily for 6 weeks. TYA-11631 treated mice showed improved cardiac function as measured by reduced left ventricular posterior wall thickness (LVPWd), isovolumic relaxation time (IVRT) and mitral valve E/e' (MV E/e'). TYA-11631 is a compound within Formula (I), as well as within, for example, Formula (Ic), Formula (Ik) and Formula I(y).

Test System

Twelve-week-old male C57Bl/6NJ mice were purchased from Jackson Laboratories. Mice were maintained under specific pathogen-free conditions and provided with sterile food and water ad libitum. Animals were housed in an animal research facility in accordance with the National Research Council of the National Academies guidelines for the care and use of laboratory animals. Animals were allowed to acclimate for 3 days prior to experiment.

Induced pluripotent stem cell derived cardiomyocytes (iPSC-derived cardiomyocyte): iCell Cardiomyocyte$^2$ were purchased from Cellular Dynamics (Madison, WI). Cells were cultured in a low-glucose and lipid rich medium to enhance cellular maturation for one week prior to treatment.

RNA Extraction and mRNA Sequencing (RNA-Seq) Method and Analysis

RNA was extracted from mouse heart tissues (control mice, vehicle-treated n=3, HFpEF mice, vehicle-treated, n=5, and HFpEF mice, TYA-11631-treated, n=6) using the polyA-tail-specific protocol from Illumina (San Diego, CA, Cat. #20020594). RNA library preparation and ribosomal RNA removal was performed on 100 ng RNA using the TruSeq Stranded mRNA kit (Illumina, San Diego, CA, Cat. #20020594) following the manufacturer's instructions. Libraries were sequenced as 100 bp single end reads using Illumina NovaSeq SP with an average of 45.7 million reads per sample. Raw RNA-seq reads in FASTQ format were aligned directly to GENCODE (version M25) for reference transcript assembly (GRCm38.p6 and ensemble 101). Next, a script using tximport was used to generate an expression matrix normalized to transcripts per million (TPM). In this analysis, only genes detected in at least 90% of all samples were used. Protein-coding genes were determined using Ensembl release Mus musculus annotations (GRCm38, April 2020) and extracted by biomaRt (version 2.46.3). Non-protein-coding and mitochondrial genes were omitted, followed by renormalization to TPM. The generated expression matrix (16,499 genes) was $\log_2$-transformed after adding 1 as the pseudo-count.

To evaluate functional perturbations, pre-ranked Gene Set Enrichment Analysis was performed using GSEA developed by Broad institute (version 4.1.0). GSEA assesses whether differences in expression of gene sets between two phenotypes are statistically significant (Subramanian, 2005). Prior to analysis, a ranked list was calculated with each gene assigned a score and direction ("+" or "−") based on the t-statistics values. Gene sets were only considered statistically significant if the false discovery rate (FDR) was less than 0.25 as determined by the multiple hypothesis testing correction method (Benjamini, 1995). The normalized enrichment score (NES), which reflects the degree to which a gene set is over-represented in the ranked list and normalized for gene set size, was used to select significantly altered gene sets. The Pearson correlation coefficient was used to calculate correlation between genes of interest and cardiac diastolic function parameters.

RNA Extraction and TaqMan qPCR Analysis Method

Fifteen to thirty milligrams (15-30 mg) of mouse cardiac tissue (control mice, vehicle-treated n=3, HFpEF mice, vehicle-treated, n=5, and HFpEF mice, TYA-11631-treated, n=6) was placed directly into 500 µL of Tri-Reagent (Zymo research, Irvine, CA, Cat. #R2050-1-200) and snap frozen at −80° C. Samples were thawed and homogenized by Bullet Blender Tissue Homogenizer (Storm Pro BT24M, Next Advance, Troy) for 15 minutes at 4° C. RNA was extracted using the Direct-Zol RNA Miniprep Plus Kit (Zymo research, Irvine, CA, Cat. #R2070) according to manufacturer instruction. Upon collecting RNA, the concentration was determined by NanoDrop (ThermoScientific, Waltham, MA). cDNA was reverse transcribed from 750 ng of RNA through random hexamers using the SuperScriptIII kit (Invitrogen, Waltham, MA, Cat. #18080051). cDNA samples were diluted 6-fold in nuclease free water. Real-Time qPCR reactions were performed using the Standard TaqMan Universal PCR Master Mix (Applied Biosystems, Waltham, MA, Cat. #43-181-57) with the listed TaqMan probes (Life Technologies, San Diego, CA) in Table 4.

TABLE 4

TaqMan Probes Used in qPCR Analysis

| Gene Probe | Gene ID | Exon Boundary | Amplicon Length (bp) |
| --- | --- | --- | --- |
| Col1a1 | Mm00801666_g1 | 49-50 | 89 |
| Col3a1 | Mm01254476_m1 | 50-51 | 136 |
| Postn | Mm00450111_m1 | 3-4 | 79 |
| Gapdh | Mm99999915_g1 | 2-3 | 107 |

Real-Time qPCR reactions were performed using the QuantStudio7 Flex Real-Time PCR Systems (Life Technologies, San Diego, CA) with thermal cycling parameters of a 2-minute UNG incubation at 50° C., a 10-minute polymerase activation at 95° C., and 40 PCR cycles consisting of a denaturation for 15 seconds at 95° C. and a 1 minute anneal/extension at 60° C. Gene expression was normalized to Gapdh as a housekeeping gene. Four technical replicates were analysed for each sample. Relative gene expression was determined using the $2^{-\Delta\Delta C}T$ method. Statistical analysis was performed in Prism Version 9 (GraphPad Software, San Diego, CA) using an unpaired t-test.

Metabolic Measurements Using Seahorse Oximetry

The Seahorse Xfe96 Analyzer (Agilent, Santa Clara, CA), which measures oxygen consumption rate (OCR) of live cells in a multi-well plate, was used to assess metabolic activity of human induced pluripotent stem cell-derived cardiomyocytes (iPSC-derived CMs). Seahorse XF96 V3 PS Cell Culture Microplates (Cat. #101085-004) were coated with 100 µL of Matrigel (Corning, Corning, NY, Cat. #356231) in phenol-free DMEM medium at a dilution of 1/100 overnight. The following day, the Matrigel was removed and 25 µL of Plating Medium (Cellular Dynamics, Madison, WI, Cat. #R1151) was added to each well of the Seahorse XF96 V3 PS Cell Culture Microplates. One vial of iCell Cardiomyocytes 2 (~6 million cells, Cellular Dynamics, Madison, WI, Cat. #01434) was thawed in a 37° C. water bath for 2 minutes. Cells were seeded directly onto the Seahorse XF96 V3 PS Cell Culture Microplates for a final density of 15,000 cells per well in Plating Medium. The corner wells were excluded for background recordings. Cells were allowed to rest at room temperature for 10 minutes to allow for even distribution of seeding, then placed in a 37° C. incubator. Five hours following cell seeding, the medium was changed to Maintenance Medium (Cellular Dynamics, Madison, WI, Cat. #R1151) for 3 days for recovery. Once beating monolayers were observed, the medium was changed to fatty acid enriched Maturation Medium (Feyen, 2020) for one week to increase metabolic maturity of iPSC-derived CMs. Cells were replenished with fresh medium every 3 days. The day of the assay, cells were incubated in starvation medium containing 2 mM glutamine in DMEM (Agilent, Santa Clara, CA, Cat. #103575-100) for one hour. Cells were then treated with DMSO (0.1%) or TYA-11631 (3 µM) in Mercola Medium for 6 hours. Cells were washed and incubated for 1 hour prior to the assay with Seahorse XF DMEM Basal Medium supplemented with 2 mM glutamine, 2 mM pyruvate, and 3 mM glucose. The Seahorse Xfe96 cartridge was prepared according to manufacturer's guidelines. Oxygen consumption rates (OCR) were measured followed by the Mito Stress Test (Agilent, Santa Clara, CA, Cat. #103015-100) with inhibitors injected in the following order: oligomycin (2.5 µM), FCCP (1 µM), rotenone and antimycin A (0.5 µM). OCR was normalized to total nuclear count as measured by Hoechst staining. Basal respiration was calculated as: (last rate measurement before first oligomycin injection)−(minimum rate measurement after rotenone/antimycin). Reserve respiratory capacity (RRC) was calculated as: (Maximal Respiration after the addition of FFCP)−(Basal Respiration). Statistical analysis was performed in Prism Version 9 (GraphPad Software, San Diego, CA) using an unpaired t-test.

Results

Transcriptional Analysis of TYA-11631 Effects on HFpEF Mouse Model by RNA-Seq

Comprehensive transcriptional profiling of protein coding genes in heart tissue from control mice and HFpEF mice (mTAC/HFD) was performed using RNA sequencing. To evaluate functional perturbations, unbiased gene set enrichment analysis was performed on two comparisons: 1) vehicle-treated HFpEF mouse tissue relative to vehicle-treated control mouse tissue, 2) TYA-11631-treated versus vehicle-treated HFpEF mouse tissue.

Gene sets associated with muscle hypertrophy and contraction, fibrosis (transforming growth factor β receptor signaling, type I collagen synthesis, extracellular matrix structural constituent), and platelet-derived growth factor receptor (PDGFR) signaling were enriched in vehicle-treated HFpEF animals relative to control and were reversed in HFpEF mice treated with TYA-11631 (FIG. 9 and FIG. 10). Gene sets associated with mitochondrial function including electron transport chain, oxidative phosphorylation, and complex I were significantly depleted in HFpEF mice treated with vehicle relative to control (FIG. 9 and FIG. 10). These mitochondrial gene sets were significantly enriched in HFpEF mice treated with TYA-11631 (FIG. 9, FIG. 10 and Table 5).

TABLE 5

GSEA Categories Altered (FDR <0.25) in HFpEF Mice Treated with Vehicle or TYA-11631

| Gene set name | Gene set size | Healthy vs HFpEF (+vehicle) | | HFpEF (+vehicle vs +TYA-11631) | |
|---|---|---|---|---|---|
| | | NES | FDR | NES | FDR |
| Muscle hypertrophy in response to stress | 20 | −1.25 | 0.34 | 1.98 | 0.09 |
| Regulation of cardiac muscle contraction by calcium ion signaling | 23 | −1.43 | 0.21 | 1.98 | 0.17 |
| TGFβ receptor signaling in skeletal dysplasias | 56 | −1.86 | 0.04 | 1.68 | 0.19 |
| Type I collagen synthesis in the context of osteogenesis imperfecta | 28 | −1.76 | 0.05 | 1.64 | 0.23 |
| Extracellular matrix structural constituent conferring tensile strength | 38 | −1.72 | 0.13 | 1.77 | 0.09 |
| Platelet derived growth factor receptor signaling pathway | 52 | −1.52 | 0.15 | 1.86 | 0.22 |
| Electron transport chain OXPHOS system in mitochondria | 85 | 2.43 | 0.00 | −1.79 | 0.13 |
| Mitochondrial complex I assembly model OXPHOS (oxidative phosphorylation) system | 46 | 1.94 | 0.021 | −2.02 | 0.05 |

Pearson correlation coefficient analysis was performed between the expression of genes identified by GSEA analysis and different parameters of LV structure and cardiac diastolic function, including Left ventricular posterior wall thickness at end diastole (LVPWd), and isovolumic relaxation time (IVRT), or mitral valve E/e' (MV E/e'). The expression levels of several genes associated with fibrosis (Col1a2, Col3a1, Fbn1, Postn, Cilp) were significantly increased in vehicle-treated HFpEF animals with impaired diastolic function as shown by increased LVPWd and IVRT. TYA-11631 treatment resulted in reduced expression of fibrosis-associated genes in HFpEF mice with improved diastolic function (FIGS. 12A-12J, Table 6 and Table 7).

TABLE 6

Echocardiogram Data and the Expression Level of Fibrotic Genes

| Groups | | LV structure/Diastolic function parameters | | Fibrotic genes | | | | |
|---|---|---|---|---|---|---|---|---|
| | | LVPW (mm) | IVRT (ms) | Gene symbol | | | | |
| | | | | Col1a2 | Col3a1 | Fbn1 | Postn | Cilp |
| Healthy + vehicle | Replicate 1 | 0.61 | 13.64 | 3.98 | 5.40 | 2.71 | 5.44 | 1.76 |
| | Replicate 2 | 0.70 | 14.72 | 4.20 | 6.07 | 2.37 | 5.58 | 1.54 |
| | Replicate 3 | 0.76 | 14.04 | 3.98 | 4.95 | 2.49 | 5.82 | 1.79 |
| HFpEF + vehicle | Replicate 1 | 0.87 | 17.53 | 4.29 | 6.60 | 2.95 | 5.82 | 2.29 |
| | Replicate 2 | 0.92 | 15.06 | 4.00 | 5.51 | 2.65 | 5.77 | 1.58 |
| | Replicate 3 | 0.89 | 15.40 | 4.54 | 6.04 | 2.98 | 6.68 | 2.61 |
| | Replicate 4 | 0.79 | 17.29 | 4.51 | 6.39 | 3.12 | 6.21 | 2.39 |
| | Replicate 5 | 0.78 | 13.57 | 4.30 | 5.80 | 2.67 | 6.22 | 2.48 |
| HFpEF + TYA-11631 | Replicate 1 | 0.70 | 13.33 | 4.29 | 5.54 | 2.39 | 6.23 | 2.09 |
| | Replicate 2 | 0.66 | 12.92 | 4.11 | 5.17 | 2.77 | 4.69 | 1.46 |
| | Replicate 3 | 0.63 | 12.78 | 3.74 | 4.50 | 1.86 | 5.58 | 1.43 |
| | Replicate 3 | 0.66 | 12.86 | 4.08 | 5.23 | 2.41 | 6.00 | 1.57 |
| | Replicate 5 | 0.63 | 14.93 | 3.91 | 5.20 | 2.26 | 5.72 | 1.26 |
| | Replicate 6 | 0.63 | 12.64 | 4.10 | 5.36 | 2.53 | 4.95 | 1.26 |

Vehicle treated healthy animals were used as control.

TABLE 7

Pearson Correlation Coefficient (r Value) and Statistical Significance (p-Value) Between Echocardiogram Data and Genes Associated with Fibrosis

| | LV structure/Diastolic function parameters | Fibrotic genes | | | | |
|---|---|---|---|---|---|---|
| | | Col1a2 | Col3a1 | Fbn1 | Postn | Cilp |
| r value | LVPWd (mm) | 0.55 | 0.61 | 0.60 | 0.56 | 0.65 |
| | IVRT (ms) | 0.53 | 0.79 | 0.62 | 0.43 | 0.54 |
| p-value | LVPWd (mm) | 0.04 | 0.02 | 0.02 | 0.04 | 0.01 |
| | IVRT (ms) | 0.05 | 0.00 | 0.02 | 0.12 | 0.05 |

The expression level of genes associated with different subunits of the mitochondrial respiratory electron transport chain, (NADH:Ubiquinone Oxidoreductase subunits; Ndufa13, Ndufa13, Ndufa5, Ndufs7, Ndufa1, Ndufa8) were significantly reduced in vehicle-treated HFpEF animals with impaired diastolic function as shown by increased LVPWd and MV E/e'. In response to TYA-11631 treatment, the expression level of mitochondrial genes increased in HFpEF mice and was positively correlated with improved diastolic function (FIGS. 11A-11F, Table 8 and Table 9).

TABLE 8

Echocardiogram Data and the Expression Level of Mitochondrial Genes

| Groups | | LV structure/Diastolic function parameters | | Mitochondrial related genes | | | | |
|---|---|---|---|---|---|---|---|---|
| | | LVPWd (mm) | MV E/E' | Gene symbol | | | | |
| | | | | Ndufa13 | Ndufa5 | Ndufs7 | Ndufa1 | Ndufa8 |
| Healthy + vehicle | Rep 1 | 0.61 | 24.29 | 8.44 | 11.36 | 10.43 | 10.30 | 9.90 |
| | Rep 2 | 0.70 | 26.70 | 8.16 | 11.16 | 10.24 | 10.16 | 9.84 |
| | Rep 3 | 0.76 | 19.74 | 8.65 | 11.46 | 10.49 | 10.56 | 10.02 |
| HFpEF + vehicle | Rep 1 | 0.87 | 36.25 | 8.08 | 10.93 | 10.21 | 10.20 | 9.78 |
| | Rep 2 | 0.92 | 36.51 | 8.21 | 11.07 | 10.27 | 9.95 | 9.85 |
| | Rep 3 | 0.89 | 30.17 | 8.35 | 11.35 | 10.31 | 10.64 | 9.93 |
| | Rep 4 | 0.79 | 25.34 | 8.55 | 11.64 | 10.56 | 10.62 | 10.05 |
| | Rep 5 | 0.78 | 35.66 | 8.41 | 11.14 | 10.54 | 10.38 | 9.87 |
| HFpEF + TYA-11631 | Rep 1 | 0.70 | 21.77 | 8.89 | 11.66 | 10.70 | 10.97 | 10.01 |
| | Rep 2 | 0.66 | 28.59 | 8.46 | 11.33 | 10.67 | 10.62 | 9.95 |
| | Rep 3 | 0.63 | 26.70 | 9.01 | 11.68 | 10.99 | 10.80 | 10.26 |
| | Rep 3 | 0.66 | 28.79 | 8.90 | 11.53 | 10.57 | 10.54 | 9.97 |
| | Rep 5 | 0.63 | 21.91 | 8.79 | 11.60 | 10.81 | 10.92 | 10.06 |
| | Rep 6 | 0.63 | 22.71 | 8.56 | 11.36 | 10.60 | 10.58 | 9.92 |

Healthy animals treated with vehicle were used as control.

TABLE 9

Pearson Correlation Coefficient (r) And Statistical Significance (p-Value) Between Echocardiogram Data and Genes Associated with Mitochondria

| LV structure/ Diastolic function parameters | | Mitochondrial related genes | | | | |
|---|---|---|---|---|---|---|
| | | Ndufa13 | Ndufa5 | Ndufs7 | Ndufa1 | Ndufa8 |
| r value | LVPWd (mm) | −0.61 | −0.55 | −0.67 | −0.47 | −0.45 |
| | MV E/E' | −0.59 | −0.74 | −0.48 | −0.64 | −0.54 |
| p value | LVPWd (mm) | 0.02 | 0.04 | 0.01 | 0.09 | 0.10 |
| | MV E/E' | 0.03 | 0.00 | 0.08 | 0.01 | 0.05 |

Effects of TYA-11631 on Fibrosis Genes in HFpEF Mouse Model by q-PCR

Fibrotic markers periostin (encoded by the Postn gene), collagen 3A1 (encoded by the Col3a1 gene), and collagen 1A1 (encoded by the Col1a1 gene), showed a trend in increased expression in HFpEF mouse hearts as measured by qPCR. TYA-11631 treatment significantly reduced the expression of fibrotic genes to near healthy control levels (Table).

TABLE 10 mRNA Expression Levels Measured by qPCR

RNA Relative Expression Level (Normalized to GAPDH)

| | | Gene Symbol | | |
|---|---|---|---|---|
| | | Postn | Col3a1 | Col1a1 |
| Healthy + vehicle (control) | Rep 1 | 0.83 | 0.68 | 0.6 |
| | Rep 2 | 1.15 | 1.61 | 1.55 |
| | Rep 3 | 1.02 | 0.7 | 0.85 |
| | Average | 1.00 | 1.00 | 1.00 |
| | SEM | 0.09 | 0.31 | 0.28 |
| HFpEF + vehicle | Rep 1 | 1.57 | 1.07 | 1.14 |
| | Rep 2 | 1.81 | 1.46 | 1.58 |
| | Rep 3 | 3.25 | 3.94 | 1.89 |
| | Rep 4 | 2.47 | 1.95 | 1.87 |
| | Rep 5 | 2.55 | 2.27 | 1.15 |
| | Average | 2.33 | 2.14 | 1.53 |
| | SEM | 0.30 | 0.49 | 0.16 |
| HFpEF + TYA-11631 | Rep 1 | 1.91 | 1.23 | 1.28 |
| | Rep 2 | 1.02 | 0.91 | 1.26 |
| | Rep 3 | 0.14 | 0.34 | 0.62 |
| | Rep 4 | 1.17 | 1.16 | 1.32 |
| | Rep 5 | 1.17 | 1.03 | 0.9 |
| | Average | 1.08 | 0.93 | 1.08 |
| | SEM | 0.28 | 0.16 | 0.14 |

RNA Expression Level (Raw CT values)

| | | Gene Symbol | | | |
|---|---|---|---|---|---|
| | | Postn | Col3a1 | Col1a1 | GAPDH |
| Healthy + vehicle (control) | Rep 1 | 33.52 | 33.66 | 31.41 | 24.05 |
| | Rep 2 | 31.43 | 30.79 | 28.42 | 22.43 |
| | Rep 3 | 31.77 | 32.16 | 29.46 | 22.6 |
| | Average | 32.24 | 32.20 | 29.76 | 23.03 |
| | SEM | 0.65 | 0.83 | 0.88 | 0.51 |
| HFpEF + vehicle | Rep 1 | 31.43 | 31.83 | 29.31 | 22.88 |
| | Rep 2 | 31.05 | 31.22 | 28.67 | 22.71 |
| | Rep 3 | 32.48 | 32.06 | 30.68 | 24.99 |
| | Rep 4 | 30.5 | 30.69 | 28.32 | 22.61 |
| | Rep 5 | 33.23 | 33.25 | 31.8 | 25.38 |
| | Average | 31.74 | 31.81 | 29.76 | 23.71 |
| | SEM | 0.49 | 0.43 | 0.65 | 0.61 |
| HFpEF + TYA-11631 | Rep 1 | 30.38 | 30.86 | 28.37 | 22.11 |
| | Rep 2 | 31.17 | 31.19 | 28.29 | 22.01 |
| | Rep 3 | 37.09 | 35.71 | 32.39 | 25.09 |
| | Rep 4 | 31.51 | 31.38 | 28.76 | 22.54 |
| | Rep 5 | 32.12 | 32.15 | 29.91 | 23.14 |
| | Average | 32.45 | 32.26 | 29.54 | 22.98 |
| | SEM | 1.19 | 0.89 | 0.77 | 0.56 |

Rep indicates replicate.

Effects of TYA-11631 on iPSC-CM Metabolic Status

The metabolic status was compared of human iPSC-derived CMs treated with TYA-11631 (3 µM) to vehicle-treated cells (DMSO). Measurements of basal respiration and reserve respiratory capacity were collected using Seahorse oximetry. While both groups had similar basal respiration rate, TYA-11631-treated human iPSC-derived CMs had higher membrane potential and reserve respiratory capacity, demonstrating greater ATP production, the cells' ability to respond to energetic stress, and a direct effect on cardiomyocytes (FIGS. 11G and 11H and Table 10).

TABLE 11

Metabolic Parameters in Human iPSC-derived CMs.

| Group | | Basal Respiration | Reserve Respiratory Capacity |
|---|---|---|---|
| DMSO | Replicate 1 | 89.95 | 432.70 |
| | Replicate 2 | 95.31 | 415.93 |
| | Replicate 3 | 63.19 | 233.20 |
| | Replicate 4 | 87.07 | 486.64 |
| | Replicate 5 | 65.76 | 289.69 |
| | Replicate 6 | 69.80 | 306.20 |
| | Replicate 7 | 123.48 | 334.96 |
| | Replicate 8 | 138.68 | 497.42 |
| | Replicate 9 | 82.01 | 423.78 |
| | Replicate 10 | 106.12 | 379.22 |
| | Replicate 11 | 103.52 | 469.37 |
| | Average | 93.17 | 388.1 |
| | SEM | 7.159 | 26.21 |
| TYA-11631 | Replicate 1 | 118.83 | 552.00 |
| | Replicate 2 | 78.80 | 544.68 |
| | Replicate 3 | 99.26 | 519.90 |
| | Replicate 4 | 79.73 | 443.36 |
| | Replicate 5 | 105.14 | 507.14 |
| | Replicate 6 | 134.13 | 628.19 |
| | Average | 102.6 | 532.5 |
| | SEM | 8.878 | 24.79 |

Accordingly, TYA-11631 treatment was shown to reduce pathogenic transcriptional signatures activated in a mouse model of HFpEF (gene sets include hypertrophy, fibrosis, and platelet-derived growth factor receptor signaling). Targeted gene expression analysis using qPCR confirmed reduced expression of fibrotic genes which correlated with improved diastolic function. Also, based on RNA-Seq data, TYA-11631 enriched gene sets associated with mitochondrial energy production in HFpEF mice. The increased expression of mitochondrial genes correlated with an improved HFpEF phenotype. In order to functionally assess the metabolic effects of TYA-11631 in vitro, iPSC-derived CMs were used. The data showed increased reserve respiratory capacity in TYA-11631 treated human iPSC-derived CMs, indicating improved ATP production in response to metabolic demand.

Taken together, these results show that HDAC6 selective inhibitors reverse preexisting diastolic dysfunction through multiple pathways in the heart associated with fibrosis and mitochondrial dysfunction, which both contribute to HFpEF pathogenesis. These results also confirm that HDAC6 selective inhibitors have a direct benefit on the heart in HFpEF models, and that the improvements seen are due to multimodal mechanisms in the heart and are not only as a result of improvement in systemic metabolism and inflammation.

Example 6: Efficacy of HDAC6 Selective Inhibitor and Empagliflozin in a HFpEF Mouse Model The study was designed to side-by-side compare efficacy between TYA-11018 (a selective HDAC6 inhibitor) and Empagliflozin (a selective SGLT2 inhibitor, MedChemExpress LLC), in a mouse model of heart failure with preserved ejection fraction (HFpEF) induced by a combination of high fat diet and inhibition of constitutive nitric oxide synthase using $N^{\omega}$-nitrol-arginine methyl ester (L-NAME). After HFpEF phenotypes were established, mice received 15 mg/kg TYA-11018 or 10 mg/kg Empagliflozin, or vehicle orally once daily for 9 weeks. Health monitoring was performed weekly with body weights recorded. Glucose tolerance test was performed after $1^{st}$ dose. Cardiac function was recorded by echocardiography after treatment for 9 weeks. End diastolic pressure (EDP) was measured by PV-Loop at terminal at 9 weeks after dosing.

Test System

Animals: Cohort of mice with established HFpEF phenotypes and age/sex matched wild type controls were used for dosing study. HFpEF model preparation was accomplished as previously described (Schiattarella, G. G. et al., Nature 568, 351-356 (2019)). In brief, 10-week old male C57BL/6J (Cat. 000664) mice were purchased from the Jackson Laboratory (Bar Harbor, ME). After acclimation for 1 week, one group of mice was fed with high fat diet containing 0.07% L-NAME (LabDiet 5G5V, St Louis, MO) for 15 weeks. The control group of mice were fed with normal chow (LabDiet 5053, St Louis, MO). Echocardiography was performed to prove the HFpEF onset before the animals were enrolled in efficacy study. Animals were housed in an animal research facility in accordance with the National Research Council of the National Academies guidelines for the care and use of laboratory animals.

HFpEF Model Induction

Ten (10) week old male C57BL/6J (Cat. 000664) mice were purchased from the Jackson Laboratory (Bar Harbor, ME). After acclimation for 1 week, one group of mice was fed a high fat diet containing 0.07% $N^{\omega}$-nitrol-arginine methyl ester (L-NAME) for 15 weeks (modified from the reference by Schiattarella, G. G. et al., Nature 568, 351-356 (2019)). A second group of mice was fed with standard chow for controls.

Conventional Echocardiography and Doppler Imaging

Transthoracic echocardiography was performed using a VisualSonics Vevo 2100 system equipped with MS400 transducer (Visual Sonics, Toronto, ON). LVEF and other indices of systolic function were obtained from short-axis M-mode scans at the midventricular level, as indicated by the presence of papillary muscles, in conscious, gently restrained mice. Apical four-chamber views were obtained in anaesthetized mice for diastolic function measurements using pulsed-wave and tissue Doppler imaging at the level of the mitral valve. Anesthesia was induced by 5% isoflurane and confirmed by lack of response to firm pressure on one of the hind paws. During echocardiogram acquisition—under body-temperature-controlled conditions—isoflurane was reduced to 1.0-1.5% and adjusted to maintain a heart rate in the range of 450-500 beats per minute. Parameters collected include: left ventricular ejection fraction (LVEF), left ventricular mass (LV mass), left ventricular end-diastolic posterior wall (LVPWd), peak Doppler blood inflow velocity across the mitral valve during early diastole (E wave), peak Doppler blood inflow velocity across the mitral valve during late diastole (e'), isovolumic relaxation time (IVRT). At the end of the procedures all mice recovered from anesthesia without difficulties.

Intraperitoneal Glucose-Tolerance Test (IP-GTT)

Intraperitoneal glucose-tolerance tests were performed by injection of glucose (2 g/kg in saline) after 6 hour fasting (from 7 a.m. to 1 p.m.). Tail blood glucose levels (mg/dL) were measured by AimStrip Plus blood glucose strips used with the AimStrip Plus blood glucose monitoring system (Germaine Laboratories, San Antonio, TX) at 0 (baseline, before glucose dose), 15, 30, 45, 60 and 120 minutes after glucose administration.

Animal Enrollment and Randomization in Efficacy Test

After the HFpEF phenotypes were established, with balanced parameters of echocardiography, animals on HFD/L-NAME or control diet were randomized to two groups to receive dosing orally with 30 mg/kg TYA-11631 or vehicle once per day for nine weeks, respectively. TYA-11631 was formulated in the vehicle 5% DMSO+45% PEG-300+50% purified water. Body weights and food consumption were monitored daily during study.

Pressure—Volume Analysis

The trachea was exposed by a midline incision from the base of the throat to just above the clavicle. The mice were intubated with a piece of polyethylene-90 tube. After the tube was secured in place by using a 6-0 silk suture, 100% oxygen was gently blown across the opening. The mice receiving ventilation were placed on a warmed (37° C.) pad. The right carotid artery was then isolated. Care was taken to prevent damage to the vagal nerve. The mice were lightly anaesthetized with isoflurane maintaining their heart rates at 450-550 beats per minute. A 1.2F Pressure-Volume Catheter (FTE-1212B-4518, Transonic, Inc, Ithaca, NY) was inserted into the right carotid artery and then advanced into the left ventricle. The transducer was securely tied into place, after it was advanced to the ventricular chamber as evidenced by a change in pressure curves. The hemodynamic parameters were then recorded in close-chest mode.

Animal Randomization

Mice with established HFpEF phenotypes were randomized to dose orally with mg/kg TYA-11018 or 10 mg/kg Empagliflozin or vehicle (n=12 each group) once per day for nine weeks. In control (non HFpEF) group, 9 mice received vehicle.

TABLE 12

Animal enrollment and randomization

| Group | Diet | Test Article | Dose/QD | Number |
|---|---|---|---|---|
| Control | Chow | Vehicle | n/a | 9 |
| HFpEF | HFD/0.07% L-NAME | Vehicle | n/a | 12 |
| | | TYA-11018 | 15 mg/kg | 12 |
| | | Empagliflozin | 10 mg/kg | 12 |

Results

Single Dose of TYA-11018 Improves Fasting Glucose and Glucose Tolerance to Similar Levels as Empagliflozin A glucose tolerance test (IP-GTT) was performed after 6 hours of the $1^{st}$ dose. Animals were on fasting during the 6 hours. Single oral dose 15 mg/kg TYA-11018 markedly reduced fasting glucose and improved glucose tolerance to similar levels as Empagliflozin in the established mouse HFpEF model (FIG. 14A).

TYA-11018 Treatment for 9 Weeks Demonstrates Comparable Efficacy Compared to Empagliflozin in HFpEF Model Echocardiography was used to measure LV structure and function after 9 weeks of treatment. M-Mode echocardiography showed that TYA-11018 treatment preserved ejection fraction and significantly reduced left ventricular mass, similar to that of Empagliflozin. Noninvasive Doppler imaging and terminal invasive catheterization analysis revealed that treatment with both compounds for 9 weeks decreased E/A, E/e' ratios, and reduced end diastolic pressure, indicating the improved LV relaxation and filling pressure. Of note, a superior reduction of E/e' was observed with TYA-11018 compared to Empagliflozin (FIGS. 14B-14F).

TYA-11018 Inhibits Upregulation of Marker Genes of Cardia Stress and Fibrosis in Heart Tissue Heart tissues were collected and processed for gene expression analyses after 9 weeks of treatment. Total RNA was extracted from mouse heart tissues using TRIzol reagent (Invitrogen, Waltham, MA). A total of 500 ng RNA was used for reverse transcription using SuperScript™ III First-Strand Synthesis System (Invitrogen, Waltham, MA). Real-time PCR was performed in duplicate using TaqMan Gene Expression Assay probes with specific primers for Nppb and Col3a1 gene sequences. The 2−ΔΔCt relative quantification method, using Gapdh for normalization, was used to estimate the amount of target mRNA in samples, and fold ratios were calculated relative to mRNA expressions levels from control samples.

TYA-11018 remarkably inhibited up-regulation of Nppb and Col3a1, the two marker genes commonly used to reveal cardiac stress and fibrosis in heart tissue respectively. The gene expression changes in heart tissue were consistent with the improvements of cardiac structure and function. Notably, this selective HDAC6 inhibitor demonstrated superior effects on the inhibition of these genes compared to Empagliflozin. The dramatic effect of the selective HDAC6 inhibitor on pro-fibrotic gene-Col3a1 also suggest a potential mechanism underlying the effects of HDAC6 inhibition that distinct to SGLT2 inhibition.

In summary, the comparable efficacy observed in HFpEF model with HDAC6 inhibition and an SGLT2 inhibitor provides evidence of translatability of these findings to clinical development.

Example 7

Biochemical Activity and Potency of Various HDAC6 Inhibitors of Formula (I)

The compounds disclosed herein, in particular those of Formula (I), were synthesized according to methods disclosed in PCT/US2020/066439, published as WO2021127643A1, which is incorporated herein by reference in its entirety. These compounds were tested for potency against HDAC6 and selectivity against HDAC1 in a biochemical assay. A biochemical assay was adopted using a luminescent HDAC-Glo I/II assay (Promega) and measured the relative activity of HDAC6 and HDAC1 recombinant proteins. Compounds were first incubated in the presence of HDAC6 or HDAC1 separately, followed by addition of the luminescent substrate. The data was acquired using a plate reader and the biochemical $IC_{50}$ were calculated from the data accordingly. Data is tabulated in Table 13. From these studies, it was determined that the compounds of the present disclosure are selective inhibitors of HDAC6 over HDAC1, providing selectivity ratios from about 5 to about 30,0000.

TABLE 13

Characterization Data and HDAC6 Activity for Compounds of Formula (I).

| Cmpd | Structure/Name | $^1$H NMR MS (m/z) (RT) | HDAC6 $IC_{50}$ (µM) |
|---|---|---|---|
| I-1 | 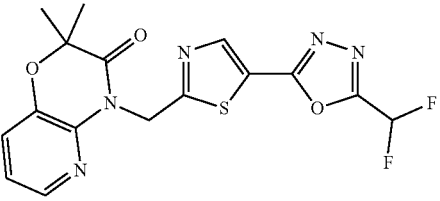 [SMILES: CC1(C)Oc2cccnc2N(Cc2ncc(-c3nnc(C(F)F)o3)s2)C1=O]<br>4-((5-(5-(difluoromethyl)-1,3,4-oxadiazol-2-yl)thiazol-2-yl)methyl)-2,2-dimethyl-2H-pyrido[3,2-b][1,4]oxazin-3(4H)-one | $^1$H NMR (400 MHz, CDCl$_3$) δ 8.39 (s, 1H), 8.01-8.05 (m, 1H), 7.29 (dd, J = 8.1, 1.5 Hz, 1H), 7.01 (dd, J = 8.1, 1.5 Hz, 1H), 6.89 (t, J = 51.6 Hz, 1H), 5.70 (s, 2H) LCMS: RT = 5.00 min, m/z = 394.0 | 0.107 |
| I-2 | 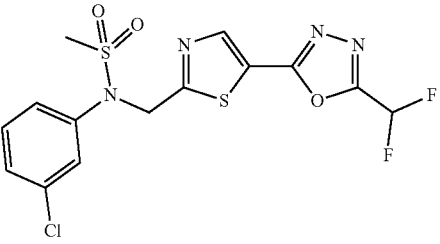 [SMILES: CS(=O)(=O)N(Cc1ncc(-c2nnc(C(F)F)o2)s1)c1cccc(Cl)c1]<br>N-(3-chlorophenyl)-N-((5-(5-(difluoromethyl)-1,3,4-oxadiazol-2-yl)thiazol-2-yl)methyl)methanesulfonamide | $^1$H NMR (400 MHz, CDCl$_3$) δ 8.39 (s, 1H), 7.48 (s, 1H), 7.32-7.40 (m, 3H), 6.91 (t, J = 51.6 Hz, 1H), 5.25 (s, 2H), 3.07 (s, 3H) LCMS: RT = 4.83 min, m/z = 421.0 | 0.021 |

TABLE 13-continued

Characterization Data and HDAC6 Activity for Compounds of Formula (I).

| Cmpd | Structure/Name | ¹H NMR MS (m/z) (RT) | HDAC6 IC$_{50}$ (μM) |
|---|---|---|---|
| I-3 | 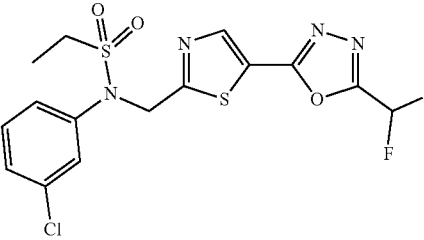<br>N-(3-chlorophenyl)-N-((5-(5-(difluoromethyl)-1,3,4-oxadiazol-2-yl)thiazol-2-yl)methyl)ethanesulfonamide | ¹H NMR (400 MHz, CDCl$_3$) δ 8.37 (s, 1H), 7.48 (s, 1H), 7.25-7.40 (m, 3H), 6.19 (t, J = 51.6 Hz, 1H), 5.28 (s, 2H), 3.18 (q, J = 7.6 Hz, 2H), 1.44 (t, J = 7.2 Hz, 3H)<br>LCMS: RT = 4.90 min, m/z = 435.0 | 0.0044 |
| I-4 | 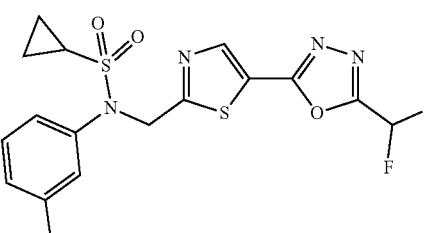<br>N-(3-chlorophenyl)-N-((5-(5-(difluoromethyl)-1,3,4-oxadiazol-2-yl)thiazol-2-yl)methyl)cyclopropanesulfonamide | ¹H NMR (400 MHz, DMSO-d$_6$) δ 8.53 (s, 1H), 7.40-7.70 (m, 5H), 5.43 (s, 2H), 2.95-3.00 (m, 1H), 1.00-1.05 (m, 2H), 0.90-0.95 (m, 2H)<br>LCMS: RT = 5.10 min, m/z = 447.0 | 0.0042 |
| I-5 | 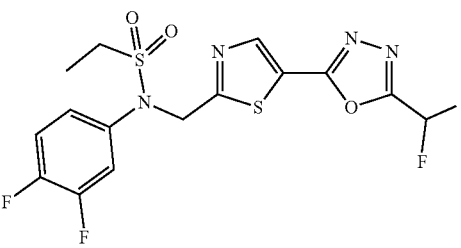<br>N-((5-(5-(difluoromethyl)-1,3,4-oxadiazol-2-yl)thiazol-2-yl)methyl)-N-(3,4-difluorophenyl)ethanesulfonamide | ¹H NMR (400 MHz, DMSO-d$_6$) δ 8.38 (s, 1H), 7.30-7.40 (m, 1H), 7.15-7.25 (m, 2H), 6.91 (t, J = 51.2 Hz, 1H), 5.24 (s, 2H), 3.17 (q, J = 7.6 Hz, 2H), 1.44 (t, J = 5.7 Hz, 3H)<br>LCMS: RT = 4.92 min, m/z = 437.0 | 0.016 |
| I-6 | 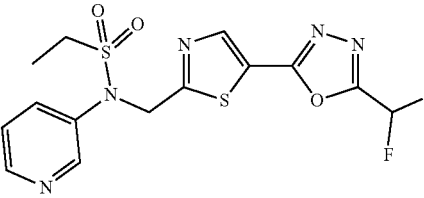<br>N-((5-(5-(difluoromethyl)-1,3,4-oxadiazol-2-yl)thiazol-2-yl)methyl)-N-(pyridin-3-yl)ethanesulfonamide | ¹H NMR (400 MHz, CDCl$_3$) δ 8.71 (br s, 1H), 8.58 (br s, 1H), 8.38 (s, 1H), 7.80-7.85 (m, 1H), 7.31-7.35 (m 1H), 6.91 (t, J = 51.6 Hz, 1H), 5.30 (s, 2H), 3.21 (q, J = 7.2 Hz, 2H), 1.46 (t, J = 7.6 Hz, 1H)<br>LCMS: RT = 3.39 min, m/z = 402.0 | 0.029 |

TABLE 13-continued

Characterization Data and HDAC6 Activity for Compounds of Formula (I).

| Cmpd | Structure/Name | ¹H NMR MS (m/z) (RT) | HDAC6 IC$_{50}$ (μM) |
|---|---|---|---|
| I-7 | 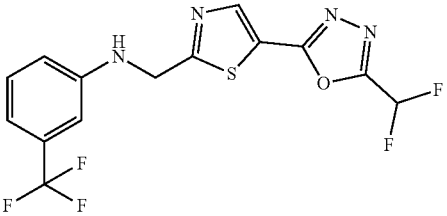 [SMILES: FC(F)c1nnc(-c2cnc(CNc3cccc(C(F)(F)F)c3)s2)o1]<br>N-((5-(5-(difluoromethyl)-1,3,4-oxadiazol-2-yl)thiazol-2-yl)methyl)-3-(trifluoromethyl)aniline | ¹H NMR (400 MHz, CDCl$_3$) δ 8.58 (s, 1H) 7.52 (t, J = 51.2 Hz, 1H) 7.22-7.35 (m, 2H) 6.89-6.87 (m, 3H) 4.80 (d, J = 6.1 Hz, 2H) LCMS: RT 5.20 min, m/z = 377.0 | 0.222 |
| I-8 | 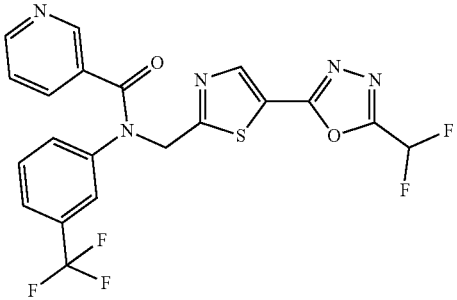 [SMILES: O=C(c1cccnc1)N(Cc1ncc(-c2nnc(C(F)F)o2)s1)c1cccc(C(F)(F)F)c1]<br>N-((5-(5-(difluoromethyl)-1,3,4-oxadiazol-2-yl)thiazol-2-yl)methyl)-N-(3-(trifluoromethyl)phenyl)nicotinamide | ¹H NMR (400 MHz, CDCl$_3$) δ 8.50-8.60 (m, 1H) 8.41 (s, 1H) 7.71 (d, J = 7.8 Hz, 1H), 7.50 (d, J = 7.8 Hz, 1H), 7.35-7.45 (m, 2H), 7.25-7.30 (m, 1H) 7.20-7.25 (m, 1H) 6.91 (t, J = 51.6 Hz, 1H) 5.46 (s, 2H) LCMS: RT = 4.22 min, m/z = 482.0 | 0.088 |
| I-9 | 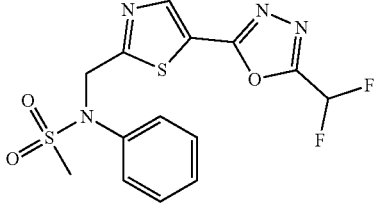 [SMILES: CS(=O)(=O)N(Cc1ncc(-c2nnc(C(F)F)o2)s1)c1ccccc1]<br>N-((5-(5-(difluoromethyl)-1,3,4-oxadiazol-2-yl)thiazol-2-yl)methyl)-N-phenylmethanesulfonamide | ¹H NMR (400 MHz, CDCl$_3$) δ = 8.37 (s, 1H), 7.33-7.49 (m, 5H), 6.90 (t, 1H, J = 51.6 Hz) 5.27 (s, 2H), 3.05 (s, 3H) ppm LCMS: RT = 4.42 min, m/z = 387.0 | 0.051 |
| I-10 | 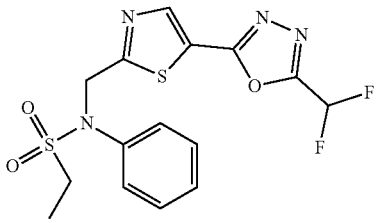 [SMILES: CCS(=O)(=O)N(Cc1ncc(-c2nnc(C(F)F)o2)s1)c1ccccc1]<br>N-((5-(5-(difluoromethyl)-1,3,4-oxadiazol-2-yl)thiazol-2-yl)methyl)-N-phenylethanesulfonamide | ¹H NMR (400 MHz, CDCl$_3$) δ 8.35 (s, 1H), 7.29-7.53 (m, 5H), 6.90 (t, 1H, J = 51.5 Hz), 5.30 (s, 2H), 3.17 (q, J = 7.34 Hz, 2H), 1.45 (t, J = 7.46 Hz, 4H) ppm LCMS: RT = 4.65 min, m/z = 401.0 | 0.026 |

TABLE 13-continued

Characterization Data and HDAC6 Activity for Compounds of Formula (I).

| Cmpd | Structure/Name | ¹H NMR<br>MS (m/z) (RT) | HDAC6<br>IC$_{50}$<br>(µM) |
|---|---|---|---|
| I-12 | 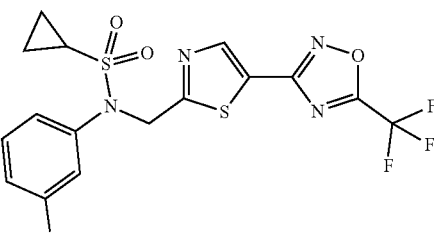<br>N-(3-chlorophenyl)-N-((5-(5-(trifluoromethyl)-1,2,4-oxadiazol-3-yl)thiazol-2-yl)methyl)cyclopropanesulfonamide | ¹H NMR (400 MHz, chloroform-d) δ ppm 8.39 (s, 1H) 7.51 (s, 1H) 7.41 (br s, 1H) 7.32 (br d, J = 3.91 Hz, 2H) 5.27 (s, 2H) 2.48-2.59 (m, 1H) 1.10-1.17 (m, 2H) 0.99-1.09 (m, 2H)<br>LCMS: RT = 5.84 min, m/z = 465 | 0.869 |
| I-13 | 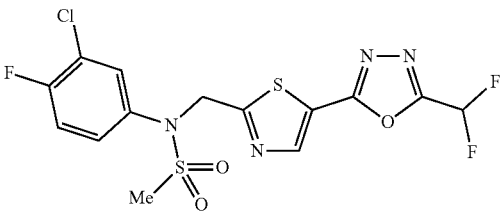 [SMILES: CS(=O)(=O)N(Cc1ncc(-c2nnc(C(F)F)o2)s1)c1ccc(F)c(Cl)c1]<br>N-(3-chloro-4-fluorophenyl)-N-((5-(5-(difluoromethyl)-1,3,4-oxadiazol-2-yl)thiazol-2-yl)methyl)methanesulfonamide | ¹H NMR (400 MHz, CDCl$_3$) δ 8.40 (s, 1H) 7.56 (dd, J = 6.36, 2.69 Hz, 1H) 7.32-7.41 (m, 1H) 7.18 (t, J = 8.56 Hz, 1H) 6.76-7.08 (m, 1H) 5.22 (s, 2H) 3.07 (s, 3H)<br>LCMS: RT = 4.93 min, m/z = 438.9 | 0.021 |
| I-14 | 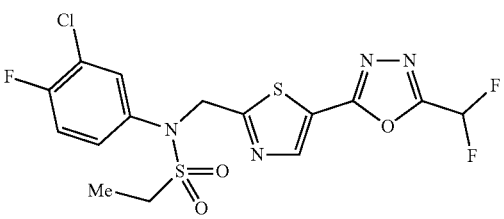 [SMILES: CCS(=O)(=O)N(Cc1ncc(-c2nnc(C(F)F)o2)s1)c1ccc(F)c(Cl)c1]<br>N-(3-chloro-4-fluorophenyl)-N-((5-(5-(difluoromethyl)-1,3,4-oxadiazol-2-yl)thiazol-2-yl)methyl)ethanesulfonamide | ¹H NMR (400 MHz, CDCl$_3$) δ 8.38 (s, 1H) 7.54 (dd, J = 6.24, 2.32 Hz, 1H) 7.33-7.40 (m, 1H) 7.16 (t, J = 8.68 Hz, 1H) 6.76-7.06 (m, 1H) 5.23 (s, 2H) 3.18 (q, J = 7.34 Hz, 2H) 1.45 (t, J = 7.34 Hz, 3H)<br>LCMS: RT = 5.11 min, m/z = 453 | 0.014 |
| I-15 | 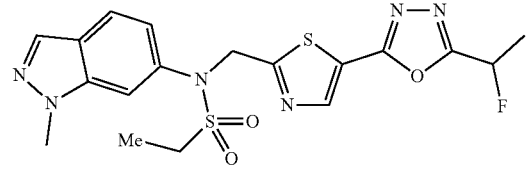<br>N-((5-(5-(difluoromethyl)-1,3,4-oxadiazol-2-yl)thiazol-2-yl)methyl)-N-(1-methyl-1H-indazol-6-yl)ethanesulfonamide | ¹H NMR (400 MHz, CDCl$_3$) δ 8.36 (s, 1H) 7.98 (d, J = 0.98 Hz, 1H) 7.75 (d, J = 8.56 Hz, 1H) 7.60 (s, 1H) 7.18 (d, J = 8.31 Hz, 1H) 6.75-7.05 (m, 1H) 5.39 (s, 2H) 4.09 (s, 3H) 3.19 (q, J = 7.17 Hz, 2H) 1.46 (t, J = 7.46 Hz, 3H)<br>LCMS: RT = 4.43 min, m/z = 455.0. | 0.014 |

TABLE 13-continued

Characterization Data and HDAC6 Activity for Compounds of Formula (I).

| Cmpd | Structure/Name | ¹H NMR<br>MS (m/z) (RT) | HDAC6<br>IC$_{50}$<br>(μM) |
|---|---|---|---|
| I-16 | 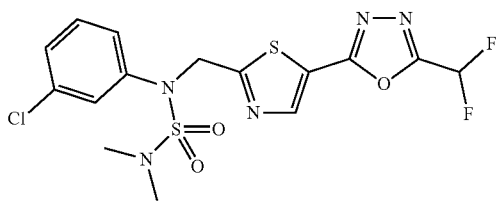 [SMILES: CN(C)S(=O)(=O)N(Cc1ncc(-c2nnc(C(F)F)o2)s1)c1cccc(Cl)c1]<br>[(3-chlorophenyl)({5-[5-(difluoromethyl)-1,3,4-oxadiazol-2-yl]-1,3-thiazol-2-yl}methyl)sulfamoyl]dimethylamine | ¹H NMR (400 MHz, CDCl$_3$) δ 8.36 (s, 1H) 7.49 (s, 1H) 7.28-7.42 (m, 3H) 6.76-6.06 (m, 1H) 5.17 (s, 2H) 2.82 (s, 6H)<br>LCMS: RT = 5.18 min, m/z = 450.0 | 0.012 |
| I-17 | 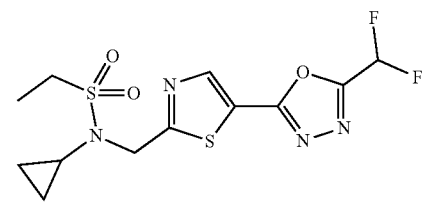 [SMILES: CCS(=O)(=O)N(Cc1ncc(-c2nnc(C(F)F)o2)s1)C1CC1]<br>N-cyclopropyl-N-((5-(5-(difluoromethyl)-1,3,4-oxadiazol-2-yl)thiazol-2-yl)methyl)ethanesulfonamide | ¹H NMR (400 MHz, chloroform-d) δ ppm 8.42 (s, 1H) 6.74-7.07 (m, 1H) 4.83 (s, 2H) 3.21 (q, J = 7.50 Hz, 2H) 2.70 (br s, 1H) 1.41 (t, J = 7.46 Hz, 3H) 0.83-0.95 (m, 4H)<br>LCMS: RT = 4.34 min, m/z = 365.0 | 1.23 |
| I-18 | 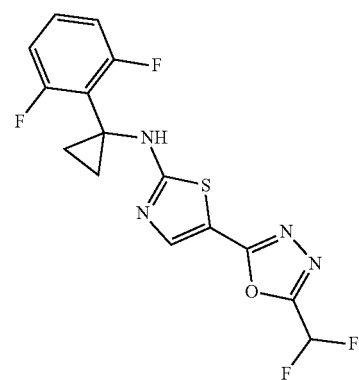 [SMILES: Fc1cccc(F)c1C1(Nc2ncc(-c3nnc(C(F)F)o3)s2)CC1]<br>5-(5-(difluoromethyl)-1,3,4-oxadiazol-2-yl)-N-(1-(2,6-difluorophenyl)cyclopropyl)thiazol-2-amine | ¹H NMR (400 MHz, DMSO-d$_6$) δ ppm 9.62 (br s, 1H) 7.95 (br s, 1H) 7.29-7.67 (overlapping m, 2H) 7.02-7.18 (m, 2H) 1.35 (d, J = 26.80 Hz, 4H)<br>LCMS: RT = 4.87 min, m/z = 371.1 | 1.95 |

TABLE 13-continued

Characterization Data and HDAC6 Activity for Compounds of Formula (I).

| Cmpd | Structure/Name | $^1$H NMR MS (m/z) (RT) | HDAC6 IC$_{50}$ (μM) |
|---|---|---|---|
| I-19 | 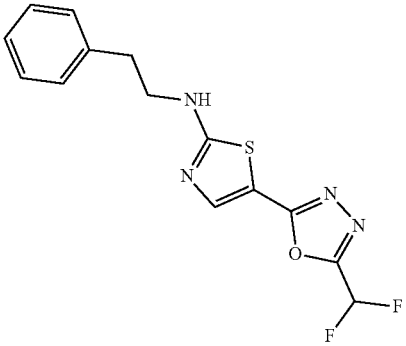 [SMILES: FC(F)c1nnc(-c2cnc(NCCc3ccccc3)s2)o1]<br>5-(5-(difluoromethyl)-1,3,4-oxadiazol-2-yl)-N-phenethylthiazol-2-amine | $^1$H NMR (400 MHz, chloroform-d) δ ppm 7.86 (s, 1H) 7.16-7.46 (m, 5 Hz) 6.68-7.03 (m, 1H) 5.75 (br s, 1H) 3.64 (br d, J = 6.11 Hz, 2H) 3.02 (br t, J = 6.85 Hz, 2H) LCMS: RT = 4.73 min, m/z = 323.0. | 13.6 |
| I-20 | 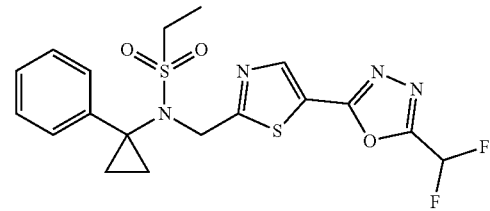 [SMILES: CCS(=O)(=O)N(Cc1ncc(-c2nnc(C(F)F)o2)s1)C1(c2ccccc2)CC1]<br>N-((5-(5-(difluoromethyl)-1,3,4-oxadiazol-2-yl)thiazol-2-yl)methyl)-N-(1-phenylcyclopropyl)ethanesulfonamide | $^1$H NMR (400 MHz, CDCl$_3$-d$_3$) δ 8.78 (s, 1H), 8.40 (s, 1H), 7.50 (d, J = 7.34 Hz, 2H), 7.26-7.38 (m, 4H), 7.04 (s, 0.25 Hz), 6.91 (s, 0.5H), 6.78 (s, 0.25 Hz), 4.94 (s, 2H), 2.81 (q, J = 7.58 Hz, 2H), 1.47 (m, 2H), 1.31-1.22 (m, 5 Hz). LCMS: RT = 6.12, m/z = 441.1 | 4.14 |
| I-21 | 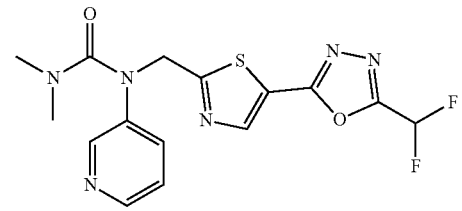 [SMILES: CN(C)C(=O)N(Cc1ncc(-c2nnc(C(F)F)o2)s1)c1cccnc1]<br>1-((5-(5-(difluoromethyl)-1,3,4-oxadiazol-2-yl)thiazol-2-yl)methyl)-3,3-dimethyl-1-(pyridin-3-yl)urea | $^1$H NMR (400 MHz, METHANOL-d4) δ ppm 9.55 (s, 1H) 8.78 (br d, J = 5.62 Hz, 1H) 8.52-8.59 (m, 2H) 8.06 (br d, J = 7.83 Hz, 1H) 7.26 (t, J = 51.2 Hz, 1H) 6.33 (s, 2H) 3.09 (s, 6H). LCMS RT = 2.85 min, m/z = 381.1 | 1.2 |

TABLE 13-continued

Characterization Data and HDAC6 Activity for Compounds of Formula (I).

| Cmpd | Structure/Name | $^1$H NMR<br>MS (m/z) (RT) | HDAC6<br>IC$_{50}$<br>(μM) |
|---|---|---|---|
| I-22 | 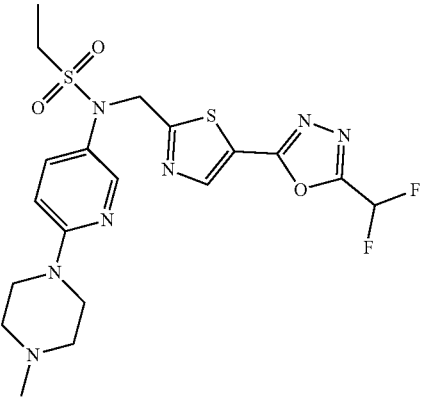 [SMILES: CCS(=O)(=O)N(Cc1ncc(-c2nnc(C(F)F)o2)s1)c1ccc(N2CCN(C)CC2)nc1]<br>N-((5-(5-(difluoromethyl)-1,3,4-oxadiazol-2-yl)thiazol-2-yl)methyl)-N-(6-(4-methylpiperazin-1-yl)pyridin-3-yl)ethanesulfonamide | $^1$H NMR (400 MHz, CD3OD) δ 8.40 (s, 1H), 8.15 (s, 1H), 7.63 (m, 1H), 7.21 (t, J = 51.2 Hz, 1H), 6.79 (m, 1H), 5.24 (s, 2H), 3.56 (m, 4H), 3.25 (q, J = 7.2 Hz, 2H), 2.51 (m, 4H), 2.32 (s, 3H), 1.40 (t, J = 7.2 Hz, 3H).<br>m/z = 500.1 | 0.143 |
| I-23 | 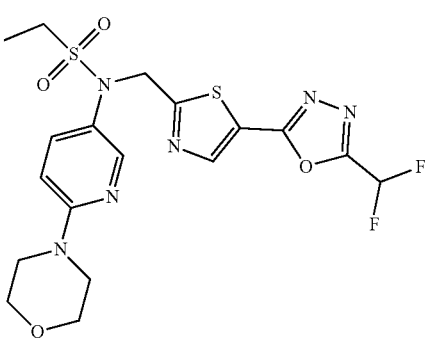 [SMILES: CCS(=O)(=O)N(Cc1ncc(-c2nnc(C(F)F)o2)s1)c1ccc(N2CCOCC2)nc1]<br>N-((5-(5-(difluoromethyl)-1,3,4-oxadiazol-2-yl)thiazol-2-yl)methyl)-N-(6-morpholinopyridin-3-yl)ethanesulfonamide | $^1$H NMR (400 MHz, DMSO-d6) δ 8.51 (s, 1H), 8.18 (s, 1H), 7.69 (m, 1H), 7.54 (t, J = 51.2 Hz, 1H), 6.83 (m, 1H), 5.28 (s, 1H), 3.66 (m, 4H), 3.44 (m, 4H), 3.30 (q, J = 6.8 Hz, 2H), 1.29 (t, J = 6.8 Hz, 3H).<br>m/z = 487.1 | 0.417 |
| I-24 | 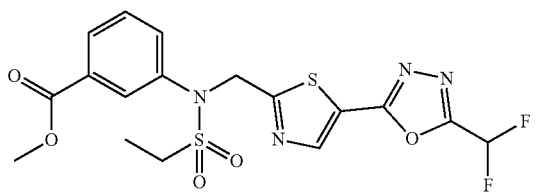 [SMILES: CCS(=O)(=O)N(Cc1ncc(-c2nnc(C(F)F)o2)s1)c1cccc(C(=O)OC)c1]<br>methyl 3-(N-((5-(5-(difluoromethyl)-1,3,4-oxadiazol-2-yl)thiazol-2-yl)methyl)ethylsulfonamido)benzoate | $^1$H NMR (400 MHz, DMSO-d$_6$) δ 8.50 (s, 1H), 8.08 (s, 1H), 7.95-7.83 (m, 2H), 7.67-7.39 (m, 2H), 5.43 (s, 2H), 3.86 (s, 3H), 3.45-3.33 (m, 2H), 1.28 (t, J = 7.21 Hz, 3H).<br>LCMS RT = 4.73 min, m/z = 459.1 | 0.031 |

TABLE 13-continued

Characterization Data and HDAC6 Activity for Compounds of Formula (I).

| Cmpd | Structure/Name | $^1$H NMR MS (m/z) (RT) | HDAC6 IC$_{50}$ (μM) |
| --- | --- | --- | --- |
| I-25 | tert-butyl 4-(N-((5-(5-(difluoromethyl)-1,3,4-oxadiazol-2-yl)thiazol-2-yl)methyl)ethylsulfonamido)benzoate | $^1$H NMR (400 MHz, CDCl$_3$) δ 8.36 (s, 1H), 8.01 (m, 2H), 7.53 (m, 2H), 6.91 (t, J = 51.6 Hz, 1H), 5.34 (s, 2H), 3.21 (q, J = 7.2 Hz, 2H), 1.57 (s, 9H), 1.43 (t, J = 7.2 Hz, 3H). m/z = 501.1 | 0.101 |
| I-26 | methyl ((5-(5-(difluoromethyl)-1,3,4-oxadiazol-2-yl)thiazol-2-yl)methyl)(pyridin-3-yl)carbamate | $^1$H NMR (400 MHz, METHANOL-d4) δ ppm 9.55 (s, 1H) 8.85 (br d, J = 5.87 Hz, 1H) 8.57 (s, 1H) 8.45 (br d, J = 8.80 Hz, 1H) 8.06-8.13 (m, 1H) 7.26 (t, J = 51.2 Hz, 1H) 3.86 (s, 3H). LCMS RT = 2.97 min, m/z = 368.0 | 2.5 |
| I-27 | N-((5-(5-(difluoromethyl)-1,3,4-oxadiazol-2-yl)thiazol-2-yl)methyl)-N-(pyrimidin-5-yl)ethanesulfonamide | $^1$H NMR (400 MHz, DMSO-d$_6$) δ 9.12 (s, 1H), 9.00 (s, 2H), 8.53 (s, 1H), 7.70-7.30 (m, 1H), 5.50 (s, 2H), 3.55-3.40 (m, 2H), 1.31 (t, −7.34 Hz, 3H). LCMS RT = 3.84 min, m/z = 403.0 | 0.050 |
| I-28 | N-((5-(5-(difluoromethyl)-1,3,4-oxadiazol-2-yl)thiazol-2-yl)methyl)pyridin-3-amine | $^1$H NMR (400 MHz, METHANOL-d4) δ ppm 8.58 (s, 1H) 8.22-8.32 (m, 2H) 7.69-7.78 (m, 2H) 7.26 (t, J = 51.2 Hz, 1H) 6.17 (s, 2H). LCMS RT = 1.24 min, m/z = 310.1 | 1.5 |

TABLE 13-continued

Characterization Data and HDAC6 Activity for Compounds of Formula (I).

| Cmpd | Structure/Name | ¹H NMR MS (m/z) (RT) | HDAC6 IC$_{50}$ (μM) |
|---|---|---|---|
| I-29 | 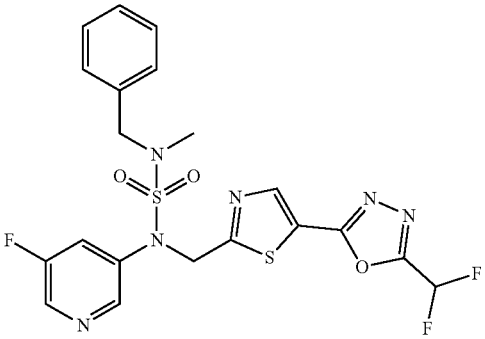 [SMILES: CN(Cc1ccccc1)S(=O)(=O)N(Cc1ncc(-c2nnc(C(F)F)o2)s1)c1cncc(F)c1] | ¹H NMR (400 MHz, CDCl$_3$-d$_3$) δ 8.55 (s, 1H), 8.47 (s, 1H), 8.39 (s, 1H), 7.67 (d, J = 9.05 Hz, 1H), 7.36-7.28 (m, 2H), 7.19 (d, J = 6.60 Hz, 2H), 7.04-6.77 (m, 1H), 5.22 (s, 2H), 4.25 (s, 2H), 2.74 (s, 3H). LCMS RT = 5.23 min, m/z = 511.1 | 0.041 |
| I-30 | 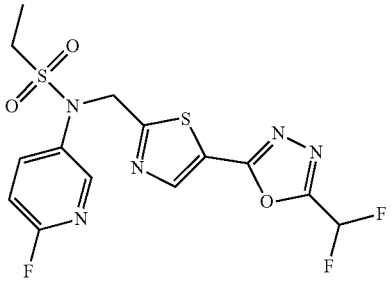 [SMILES: CCS(=O)(=O)N(Cc1ncc(-c2nnc(C(F)F)o2)s1)c1ccc(F)nc1]<br>N-((5-(5-(difluoromethyl)-1,3,4-oxadiazol-2-yl)thiazol-2-yl)methyl)-N-(6-fluoropyridin-3-yl)ethanesulfonamide | ¹H NMR (400 MHz, CDCl$_3$) δ 8.39 (s, 1H), 8.31 (s, 1H), 7.94 (m, 1H), 7.02 (m, 1H), 6.91 (t, J = 51.6 Hz, 1H), 5.25 (s, 2H), 3.21 (q, J = 7.2 Hz, 2H), 1.21 (t, J = 7.2 Hz, 3H). m/z = 420.0 | 0.011 |
| I-31 | 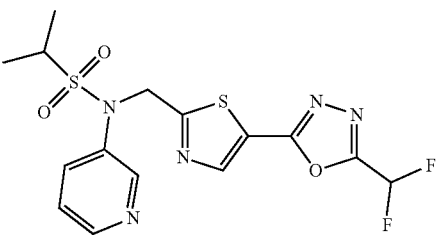 [SMILES: CC(C)S(=O)(=O)N(Cc1ncc(-c2nnc(C(F)F)o2)s1)c1cccnc1]<br>N-((5-(5-(difluoromethyl)-1,3,4-oxadiazol-2-yl)thiazol-2-yl)methyl)-N-(pyridin-3-yl)propane-2-sulfonamide | ¹H NMR (400 MHz, DMSO-d6) δ 8.72 (s, 1H), 8.50 (m, 2H), 8.02 (m, 1H), 7.40-7.66 (m, 2H), 5.46 (s, 2H), 3.60 (m, 1H), 1.34 (d, J = 6.8 Hz, 6H). m/z = 416.1 | 0.042 |
| I-32 | 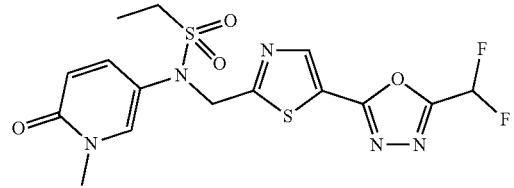 [SMILES: CCS(=O)(=O)N(Cc1ncc(-c2nnc(C(F)F)o2)s1)c1ccc(=O)n(C)c1]<br>N-((5-(5-(difluoromethyl)-1,3,4-oxadiazol-2-yl)thiazol-2-yl)methyl)-N-(1-methyl-6-oxo-1,6-dihydropyridin-3-yl)ethanesulfonamide | ¹H NMR (400 MHz, Methanol-d$_4$) δ 8.47 (s, 1H), 7.96 (s, 1H), 7.66 (d, J = 9.54 Hz, 1H), 7.35 (s, 0.25 Hz), 7.22 (s, 0.5 Hz), 7.09 (s, 0.25 Hz), 6.53 (d, J = 9.54 Hz, 1H), 5.22 (s, 2H), 3.56 (s, 3H), 3.35-3.30 (m, 2H), 1.43 (t, J = 7.34 Hz, 3H). LCMS RT = 3.53 min, m/z = 432.1 | 0.411 |

TABLE 13-continued

Characterization Data and HDAC6 Activity for Compounds of Formula (I).

| Cmpd | Structure/Name | ¹H NMR MS (m/z) (RT) | HDAC6 IC$_{50}$ (μM) |
|---|---|---|---|
| I-33 | 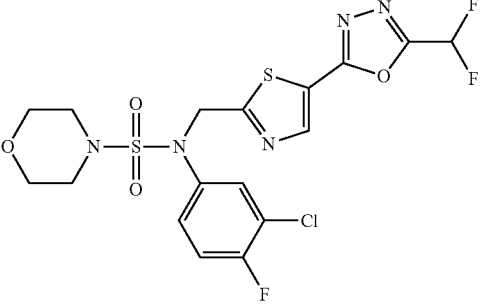 [SMILES: O=S(=O)(N1CCOCC1)N(Cc1ncc(-c2nnc(C(F)F)o2)s1)c1ccc(F)c(Cl)c1]<br>N-(3-chloro-4-fluorophenyl)-N-((5-(5-(difluoromethyl)-1,3,4-oxadiazol-2-yl)thiazol-2-yl)methyl)morpholine-4-sulfonamide | ¹H NMR (400 MHz, DMSO-d6) δ 8.52 (s, 1H), 7.86-7.95 (m, 1H), 7.35-7.69 (m, 3H), 5.36 (s, 2H), 3.58 (m, 4H), 3.20 (m, 4H). m/z = 510.0 | 0.047 |
| I-34 | 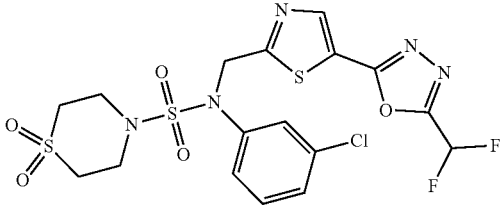 [SMILES: O=S1(=O)CCN(S(=O)(=O)N(Cc2ncc(-c3nnc(C(F)F)o3)s2)c2cccc(Cl)c2)CC1]<br>N-(3-chlorophenyl)-N-((5-(5-(difluoromethyl)-1,3,4-oxadiazol-2-yl)thiazol-2-yl)methyl)thiomorpholine-4-sulfonamide 1,1-dioxide | ¹H NMR (400 MHz, CHLOROFORM-d) δ ppm 8.41 (s, 1H) 7.48 (s, 1H) 7.30-7.40 (m, 3H) 6.91 (t, J = 52.4 Hz, 1H) 5.15 (s, 2H) 3.73-3.82 (m, 4H) 3.05-3.13 (m, 4H). LCMS RT = 4.83 min, m/z = 540.0 | 0.022 |
| I-35 | 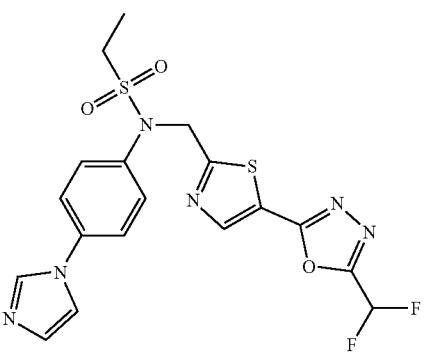 [SMILES: CCS(=O)(=O)N(Cc1ncc(-c2nnc(C(F)F)o2)s1)c1ccc(-n2ccnc2)cc1]<br>N-(4-(1H-imidazol-1-yl)phenyl)-N-((5-(5-(difluoromethyl)-1,3,4-oxadiazol-2-yl)thiazol-2-yl)methyl)ethanesulfonamide | ¹H NMR (400 MHz, DMSO-d6) δ 8.51 (s, 1H), 8.27 (s, 1H), 7.69-7.76 (m, 5 Hz), 7.3 (t, J = 51.2 Hz, 1H), 7.10 (s, 1H), 5.41 (s, 2H), 3.37 (q, J = 6.8 Hz, 2H), 1.30 (t, J = 6.8 Hz, 3H). m/z = 467.0 | 0.008 |

TABLE 13-continued

Characterization Data and HDAC6 Activity for Compounds of Formula (I).

| Cmpd | Structure/Name | ¹H NMR<br>MS (m/z) (RT) | HDAC6<br>IC$_{50}$<br>(μM) |
|---|---|---|---|
| I-36 | 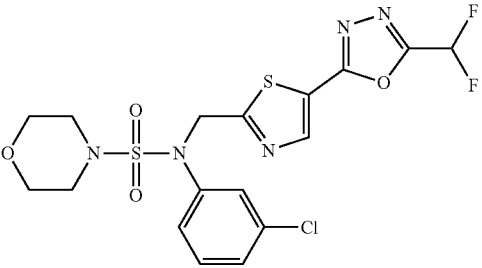 [SMILES: O=S(=O)(N1CCOCC1)N(Cc1ncc(-c2nnc(C(F)F)o2)s1)c1cccc(Cl)c1]<br>N-(3-chlorophenyl)-N-((5-(5-(difluoromethyl)-1,3,4-oxadiazol-2-yl)thiazol-2-yl)methyl)morpholine-4-sulfonamide | ¹H NMR (400 MHz, DMSO-d6)<br>δ 8.52 (s, 1H), 7.73 (m, 1H),<br>7.54-7.58 (m, 2H), 7.36-7.44 (m,<br>2H), 5.38 (s, 2H), 3.59 (m, 4H),<br>3.18 (m, 4H).<br>m/z = 492.1 | 0.005 |
| I-37 | 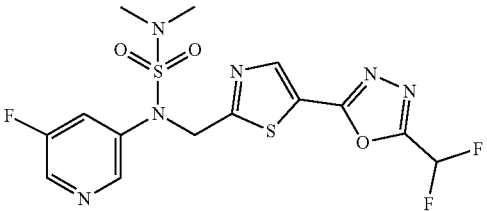 [SMILES: CN(C)S(=O)(=O)N(Cc1ncc(-c2nnc(C(F)F)o2)s1)c1cncc(F)c1] | ¹H NMR (400 MHz, DMSO-d$_6$) δ<br>8.63 (s, 1H), 8.54 (d, J = 9. Hz, 2H),<br>8.10 (d, J = 10.0 Hz, 1H),<br>7.65-7.39 (m, 1H), 5.41 (s, 2H),<br>2.83 (s, 6H).<br>LCMS RT = 4.39 min, m/z = 435.1 | 0.013 |
| I-38 | 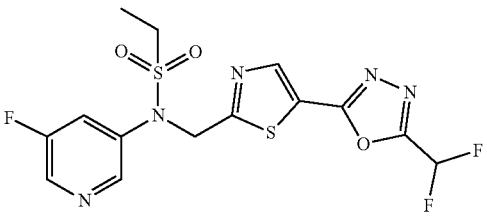 [SMILES: CCS(=O)(=O)N(Cc1ncc(-c2nnc(C(F)F)o2)s1)c1cncc(F)c1]<br>N-((5-(5-(difluoromethyl)-1,3,4-oxadiazol-2-yl)thiazol-2-yl)methyl)-N-(5-fluoropyridin-3-yl)ethanesulfonamide | ¹H NMR (400 MHz, DMSO-d$_6$) δ<br>8.62-8.52 (m, H), 8.13-8.09 (m, 1H),<br>7.65-7.39 (m, 1H), 5.46 (s, 2H),<br>3.55-3.45 (m, 2H), 1.30 (t,<br>J = 7.34 Hz, 3H).<br>LCMS RT = 4.32 min, m/z = 420.0 | 0.019 |
| I-39 | 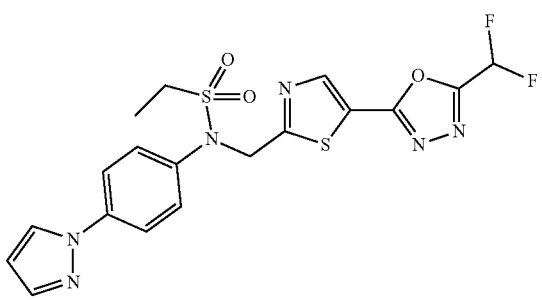 [SMILES: CCS(=O)(=O)N(Cc1ncc(-c2nnc(C(F)F)o2)s1)c1ccc(-n2cccn2)cc1]<br>N-(4-(1H-pyrazol-1-yl)phenyl)-N-((5-(5-(difluoromethyl)-1,3,4-oxadiazol-2-yl)thiazol-2-yl)methyl)ethanesulfonamide | ¹H NMR (400 MHz,<br>CHLOROFORM-d) δ ppm 8.36<br>(s, 1H) 7.90 (s, 1H) 7.69-7.77<br>(m, 3H) 7.55 (d, J = 8.31 Hz, 2H)<br>6.90 (t, J = 52.0 Hz, 1H) 6.48 (s, 1H)<br>5.31 (s, 2H) 3.19 (d, J = 7.34<br>Hz, 2H) 1.46 (t, J = 7.46 Hz, 3H).<br>LCMS RT = 4.67 min, m/z = 467.0 | 0.010 |

TABLE 13-continued

Characterization Data and HDAC6 Activity for Compounds of Formula (I).

| Cmpd | Structure/Name | ¹H NMR MS (m/z) (RT) | HDAC6 IC$_{50}$ (µM) |
|---|---|---|---|
| I-40 | 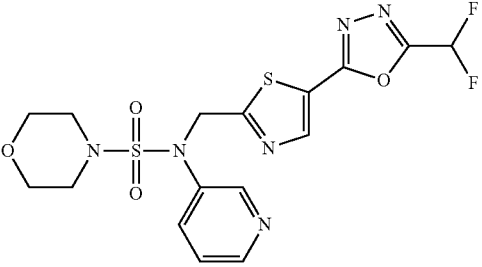 [SMILES: O=S(=O)(N1CCOCC1)N(Cc1ncc(-c2nnc(C(F)F)o2)s1)c1cccnc1]<br>N-((5-(5-(difluoromethyl)-1,3,4-oxadiazol-2-yl)thiazol-2-yl)methyl)-N-(pyridin-3-yl)morpholine-4-sulfonamide | ¹H NMR (400 MHz, CD3OD) δ 8.57 (s, 1H), 8.45 (s, 1H), 8.27 (m, 1H), 7.97 (m, 1H), 7.73 (m, 1H), 7.22 (t, J = 51.6 Hz, 1H), 4.88 (s, 2H), 3.36 (m, 4H), 3.10 (m, 4H).<br>m/z = 459.1 | 4.22 |
| I-43 | 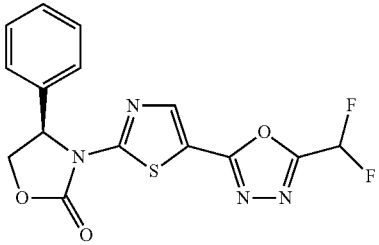 [SMILES: O=C1OC[C@@H](c2ccccc2)N1c1ncc(-c2nnc(C(F)F)o2)s1]<br>(R)-3-(5-(5-(difluoromethyl)-1,3,4-oxadiazol-2-yl)thiazol-2-yl)-4-phenyloxazolidin-2-one | ¹H NMR (400 MHz, METHANOL-d4) δ = 8.07 (s, 1H) 7.40 (s, 5 Hz) 7.19 (t, 1H, J = 51.6 Hz) 5.84 (dd, J = 8.80, 3.67 Hz, 1H) 5.03 (t, J = 8.80 Hz, 1H) 4.48 (dd, J = 8.93, 4.03 Hz, 1H) ppm<br>LCMS: RT = 4.67 min, m/z = 365.1 | 0.085 |
| I-44 | 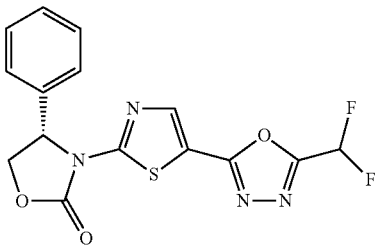 [SMILES: O=C1OC[C@H](c2ccccc2)N1c1ncc(-c2nnc(C(F)F)o2)s1]<br>(S)-3-(5-(5-(difluoromethyl)-1,3,4-oxadiazol-2-yl)thiazol-2-yl)-4-phenyloxazolidin-2-one | 1H NMR (400 MHz, METHANOL-d4) δ = 8.07 (s, 1H), 7.40 (s, 4H), 7.33-7.38 (m, 1H), 7.19 (t, 1H, J = 5.6 Hz), 5.84 (dd, J = 8.56, 3.91 Hz, 1H), 5.03 (t, J = 8.93 Hz, 1H), 4.43-4.51 (m, 1H) ppm<br>LCMS: RT = 4.95 min, m/z = 365.1 | 8.97 |
| I-45 | 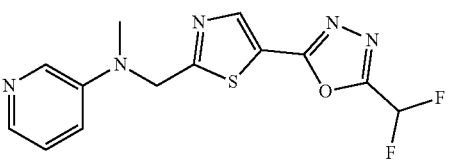 [SMILES: CN(Cc1ncc(-c2nnc(C(F)F)o2)s1)c1cccnc1]<br>N-(1-(cyclopropylmethyl)-1H-pyrazol-4-yl)-N-((5-(5-(difluoromethyl)-1,3,4-oxadiazol-2-yl)thiazol-2-yl)methyl)ethanesulfonamide | 1H NMR (400 MHz, CD3OD) δ ppm 8.55 (s, 1H), 8.27-8.24 (m, 2H), 7.78-7.67 (m, 2H), 7.23 (t, J = 51.6 Hz, 1H), 6.15 (s, 2H), 2.90 (s, 3H).<br>LCMS RT = 2.431 min, m/z = 324.0 | 1.3 |

TABLE 13-continued

Characterization Data and HDAC6 Activity for Compounds of Formula (I).

| Cmpd | Structure/Name | ¹H NMR MS (m/z) (RT) | HDAC6 IC$_{50}$ (μM) |
|---|---|---|---|
| I-46 | 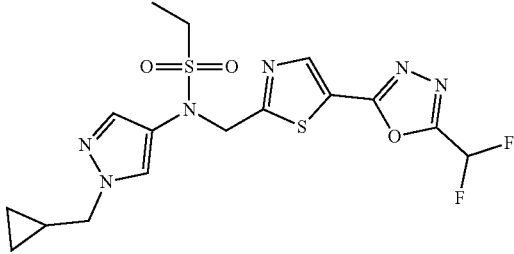 [SMILES: CCS(=O)(=O)N(Cc1ncc(-c2nnc(C(F)F)o2)s1)c1cnn(CC2CC2)c1]<br>N-(1-(cyclopropylmethyl)-1H-pyrazol-4-yl)-N-((5-(5-(difluoromethyl)-1,3,4-oxadiazol-2-yl)thiazol-2-yl)methyl)ethanesulfonamide | 1H NMR (400 MHz, CDCl3) δ ppm 8.40 (s, 1H), 7.69 (s, 1H), 7.49 (s, 1H), 6.91 (t, J = 51.6 Hz, 1H), 5.17 (s, 2H), 3.93 (d, J = 7.2 Hz, 2H), 3.18 (q, J = 7.6 Hz, 2H), 1.42 (t, J = 7.6 Hz, 3H), 1.31-1.22 (m, 1H), 0.70-0.62 (m, 2H), 0.38-0.32 (m, 2H). LCMS RT = 2.417 min, m/z = 444.9 | 0.077 |
| I-47 | 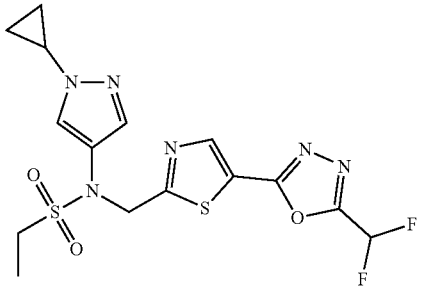 [SMILES: CCS(=O)(=O)N(Cc1ncc(-c2nnc(C(F)F)o2)s1)c1cnn(C2CC2)c1]<br>N-(1-cyclopropyl-1H-pyrazol-4-yl)-N-((5-(5-(difluoromethyl)-1,3,4-oxadiazol-2-yl)thiazol-2-yl)methyl)ethanesulfonamide | 1H NMR (400 MHz, CDCl3) δ ppm 8.40 (s, 1H), 7.65 (s, 1H), 7.46 (s, 1H), 6.91 (t, J = 51.6 Hz, 1H), 5.14 (s, 2H), 3.58-3.52 (m, 1H), 3.16 (q, J = 8.0 Hz, 2H), 1.42 (t, J = 8.0 Hz, 3H), 1.13-1.00 (m, 4H). LCMS RT = 1.223 min, m/z = 430.9 | 0.070 |
| I-48 | 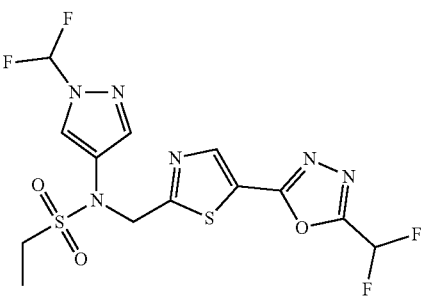 [SMILES: CCS(=O)(=O)N(Cc1ncc(-c2nnc(C(F)F)o2)s1)c1cnn(C(F)F)c1]<br>N-((5-(5-(difluoromethyl)-1,3,4-oxadiazol-2-yl)thiazol-2-yl)methyl)-N-(1-(difluoromethyl)-1H-pyrazol-4-yl)ethanesulfonamide | 1H NMR (400 MHz, CDCl3) δ ppm 8.35 (s, 1H), 7.92 (s, 1H), 7.66 (s, 1H), 6.96 (t, J = 60.4 Hz, 1H), 6.84 (t, J = 45.2 Hz, 1H), 5.11 (s, 2H), 3.10 (q, J = 7.2 Hz, 2H), 1.33 (t, J = 7.6 Hz, 3H). LCMS RT = 3.543 min, m/z = 441.1 | 0.262 |

TABLE 13-continued

Characterization Data and HDAC6 Activity for Compounds of Formula (I).

| Cmpd | Structure/Name | ¹H NMR<br>MS (m/z) (RT) | HDAC6 IC$_{50}$ (μM) |
|---|---|---|---|
| I-49 | 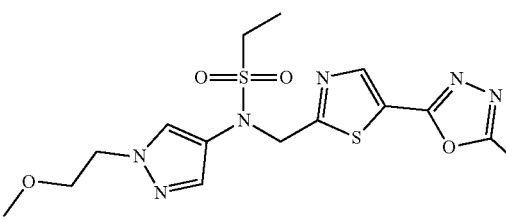<br>N-((5-(5-(difluoromethyl)-1,3,4-oxadiazol-2-yl)thiazol-2-yl)methyl)-N-(1-(2-methoxyethyl)-1H-pyrazol-4-yl)ethanesulfonamide | 1H NMR (400 MHz, CDCl3) δ ppm 8.40 (s, 1H), 7.65 (s, 1H), 7.51 (s, 1H), 6.91 (t, J = 51.6 Hz, 1H), 5.15 (s, 2H), 4.22 (t, J = 4.8 Hz, 2H), 3.70 (t, J = 5.2 Hz, 2H), 3.30 (s, 3H), 3.17 (q, J = 7.6 Hz, 2H), 1.41 (t, J = 7.2 Hz, 3H). LCMS RT = 3.093 min, m/z = 448.9 | 0.134 |
| I-50 | 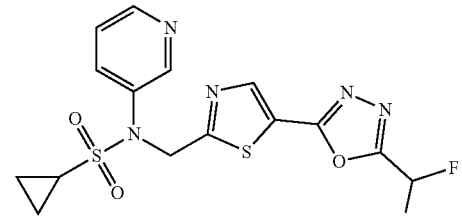<br>N-((5-(5-(difluoromethyl)-1,3,4-oxadiazol-2-yl)thiazol-2-yl)methyl)-N-(pyridin-3-yl)cyclopropanesulfonamide | 1H NMR (400 MHz, CDCl3) δ ppm 8.69 (d, J = 2.0 Hz, 1H), 8.53-8.50 (m, 1H), 8.30 (s, 1H), 7.79-7.76 (m, 1H), 7.30-7.26 (m, 1H), 6.83 (t, J = 51.6 Hz, 1H), 5.23 (s, 2H), 2.53-2.46 (m, 1H), 1.06-0.95 (m, 4H). LCMS RT = 2.897 min, m/z = 414.1 | 0.036 |
| I-51 | 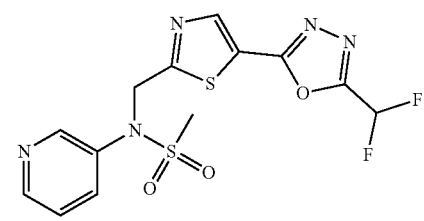 [SMILES: CS(=O)(=O)N(Cc1ncc(-c2nnc(C(F)F)o2)s1)c1cccnc1]<br>N-((5-(5-(difluoromethyl)-1,3,4-oxadiazol-2-yl)thiazol-2-yl)methyl)-N-(pyridin-3-yl)methanesulfonamide | 1H NMR (400 MHz, CDCl3) δ ppm 8.54 (s, 1H), 8.50 (s, 1H), 7.93-7.90 (m, 1H), 7.68 (d, J = 8.0 Hz, 1H), 7.49-7.44 (m, 1H), 6.92 (t, J = 51.6 Hz, 1H), 5.84 (s, 2H), 3.00 (s, 3H). LCMS RT = 1.096 min, m/z = 387.9 | 0.676 |
| I-52 | 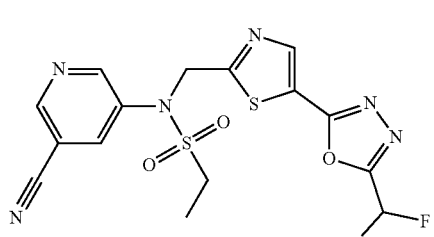<br>N-(5-cyanopyridin-3-yl)-N-((5-(5-(difluoromethyl)-1,3,4-oxadiazol-2-yl)thiazol-2-yl)methyl)ethanesulfonamide | 1H NMR (400 MHz, CDCl3) δ ppm 8.96 (d, J = 2.8 Hz, 1H), 8.82 (s, 1H), 8.42 (s, 1H), 8.18-8.17 (m, 1H), 6.92 (t, J = 51.6 Hz, 1H), 5.30 (s, 2H), 3.21 (q, J = 7.6 Hz, 2H), 1.44 (t, J = 7.6 Hz, 3H). LCMS RT = 0.752 min, m/z = 427.1 | 0.022 |

TABLE 13-continued

Characterization Data and HDAC6 Activity for Compounds of Formula (I).

| Cmpd | Structure/Name | ¹H NMR MS (m/z) (RT) | HDAC6 IC$_{50}$ (μM) |
|---|---|---|---|
| I-53 | 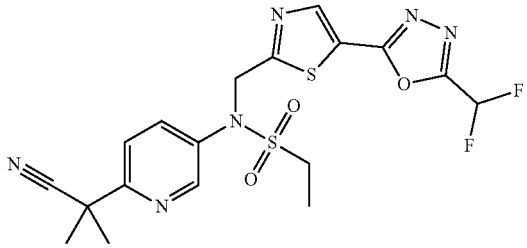 [SMILES: CCS(=O)(=O)N(Cc1ncc(-c2nnc(C(F)F)o2)s1)c1ccc(C(C)(C)C#N)nc1]<br>N-(6-(2-cyanopropan-2-yl)pyridin-3-yl)-N-((5-(5-(difluoromethyl)-1,3,4-oxadiazol-2-yl)thiazol-2-yl)methyl)ethanesulfonamide | 1H NMR (400 MHz, CDCl3) δ ppm 8.70 (d, J = 2.8 Hz, 1H), 8.40 (s, 1H), 7.86 (d, J = 8.4 Hz, 1H), 7.63 (d, J = 8.4 Hz, 1H), 6.91 (t, J = 51.6 Hz, 1H), 5.29 (s, 2H), 3.22 (q, J = 7.6 Hz, 2H), 1.75 (s, 6H), 1.47 (t, J = 7.2 Hz, 3H). LCMS RT = 0.828 min, m/z = 469.2 | 0.317 |
| I-54 | 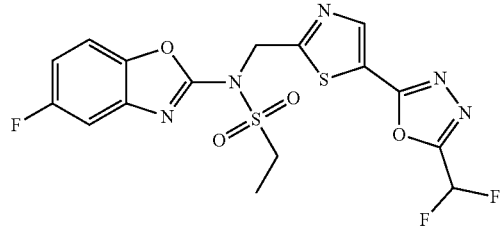 [SMILES: CCS(=O)(=O)N(Cc1ncc(-c2nnc(C(F)F)o2)s1)c1nc2cc(F)ccc2o1]<br>N-((5-(5-(difluoromethyl)-1,3,4-oxadiazol-2-yl)thiazol-2-yl)methyl)-N-(5-fluorobenzo[d]oxazol-2-yl)ethanesulfonamide | 1H NMR (400 MHz, CDCl3) δ ppm 8.45 (s, 1H), 7.40-7.38 (m, 1H), 7.10-6.91 (m, 3H), 5.40 (s, 2H), 3.29 (q, J = 7.2 Hz, 2H), 1.52 (t, J = 7.2 Hz, 3H). LCMS RT = 3.800 min, m/z = 460.0 | 0.104 |
| I-55 | 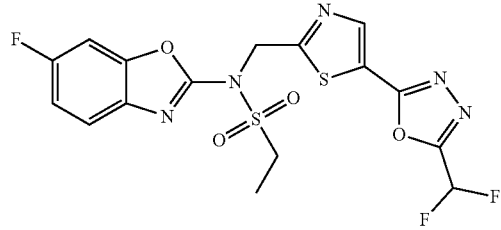 [SMILES: CCS(=O)(=O)N(Cc1ncc(-c2nnc(C(F)F)o2)s1)c1nc2ccc(F)cc2o1]<br>N-((5-(5-(difluoromethyl)-1,3,4-oxadiazol-2-yl)thiazol-2-yl)methyl)-N-(6-fluorobenzo[d]oxazol-2-yl)ethanesulfonamide | 1H NMR (400 MHz, CDCl3) δ ppm 8.44 (s, 1H), 7.29-7.21 (m, 2H), 7.10-7.04 (m, 1H), 6.91 (t, J = 51.6 Hz, 1H), 5.42 (s, 2H), 3.29 (q, J = 7.2 Hz, 2H), 1.52 (t, J = 7.2 Hz, 3H). LCMS RT = 0.863 min, m/z = 459.7 | 0.124 |
| I-56 | 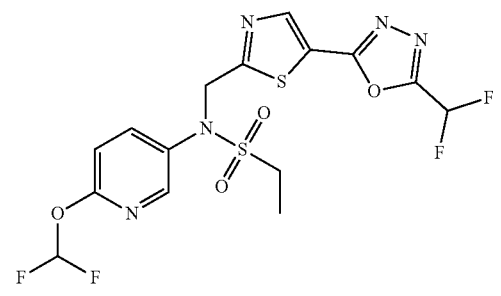 [SMILES: CCS(=O)(=O)N(Cc1ncc(-c2nnc(C(F)F)o2)s1)c1ccc(OC(F)F)nc1]<br>N-(6-(difluoromethoxy)pyridin-3-yl)-N-((5-(5-(difluoromethyl)-1,3,4-oxadiazol-2-yl)thiazol-2-yl)methyl)ethanesulfonamide | 1H NMR (400 MHz, CDCl3) δ ppm 8.39 (s, 1H), 8.28 (d, J = 2.8 Hz, 1H), 7.85 (d, J = 8.8 Hz, 1H), 7.41 (t, J = 51.6 Hz, 1H), 7.06-6.76 (m, 2H), 5.24 (s, 2H), 3.20 (q, J = 7.2 Hz, 2H), 1.47 (t, J = 7.6 Hz, 3H). LCMS RT = 0.886 min, m/z = 468.1 | 0.050 |

TABLE 13-continued

Characterization Data and HDAC6 Activity for Compounds of Formula (I).

| Cmpd | Structure/Name | ¹H NMR MS (m/z) (RT) | HDAC6 IC$_{50}$ (µM) |
|---|---|---|---|
| I-57 | 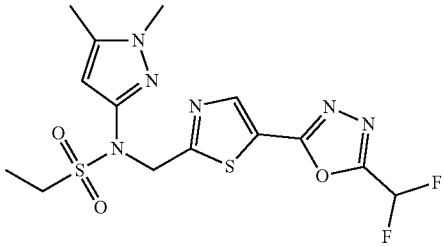 [SMILES: CCS(=O)(=O)N(Cc1ncc(-c2nnc(C(F)F)o2)s1)c1cc(C)n(C)n1]<br>N-((5-(5-(difluoromethyl)-1,3,4-oxadiazol-2-yl)thiazol-2-yl)methyl)-N-(1,5-dimethyl-1H-pyrazol-3-yl)ethanesulfonamide | 1H NMR (400 MHz, CDCl3) δ ppm 8.40 (s, 1H), 6.91 (t, J = 51.6 Hz, 1H), 6.13 (s, 1H), 5.37 (s, 2H), 3.70 (s, 3H), 3.27 (q, J = 7.6 Hz, 2H), 2.24 (s, 3H), 1.42 (t, J = 7.2 Hz, 3H).<br>LCMS RT = 3.486 min, m/z = 418.9 | 0.117 |
| I-58 | 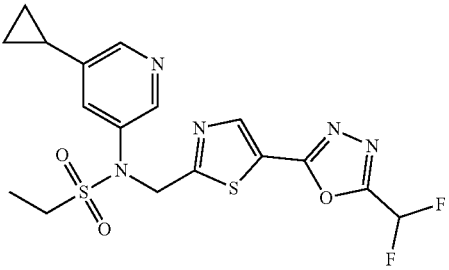 [SMILES: CCS(=O)(=O)N(Cc1ncc(-c2nnc(C(F)F)o2)s1)c1cncc(C2CC2)c1]<br>N-(5-cyclopropylpyridin-3-yl)-N-((5-(5-(difluoromethyl)-1,3,4-oxadiazol-2-yl)thiazol-2-yl)methyl)ethanesulfonamide | 1H NMR (400 MHz, CDCl3) δ ppm 8.45 (s, 1H), 8.41 (s, 1H), 8.35 (s, 1H), 7.46 (s, 1H), 6.91 (t, J = 51.6 Hz, 1H), 5.27 (s, 2H), 3.19 (q, J = 8.0 Hz, 2H), 1.92-1.89 (m, 1H), 1.45 (t, J = 7.2 Hz, 3H), 1.11-1.05 (m, 2H), 0.76-0.74 (m, 2H).<br>LCMS RT = 0.992 min, m/z = 442.3 | 0.025 |
| I-59 | 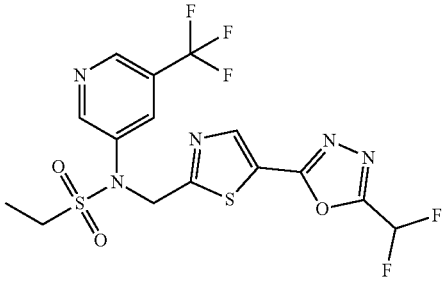 [SMILES: CCS(=O)(=O)N(Cc1ncc(-c2nnc(C(F)F)o2)s1)c1cncc(C(F)(F)F)c1]<br>N-((5-(5-(difluoromethyl)-1,3,4-oxadiazol-2-yl)thiazol-2-yl)methyl)-N-(5-(trifluoromethyl)pyridin-3-yl)ethanesulfonamide | 1H NMR (400 MHz, CDCl3) δ ppm 8.93 (d, J = 2.0 Hz, 1H), 8.83 (s, 1H), 8.41 (s, 1H), 8.10 (s, 1H), 6.91 (t, J = 51.6 Hz, 1H), 5.31 (s, 2H), 3.22 (q, J = 7.6 Hz, 2H), 1.45 (t, J = 7.6 Hz, 3H).<br>LCMS RT = 1.190 min, m/z = 469.8 | 0.030 |
| I-60 | 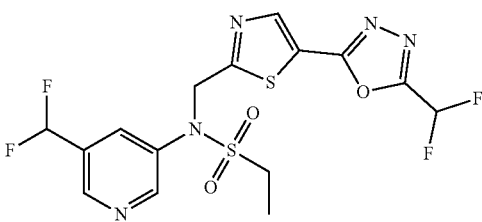 [SMILES: CCS(=O)(=O)N(Cc1ncc(-c2nnc(C(F)F)o2)s1)c1cncc(C(F)F)c1]<br>N-((5-(5-(difluoromethyl)-1,3,4-oxadiazol-2-yl)thiazol-2-yl)methyl)-N-(5-(difluoromethyl)pyridin-3-yl)ethanesulfonamide | 1H NMR (400 MHz, CDCl3) δ ppm 8.85 (s, 1H), 8.73 (s, 1H), 8.40 (s, 1H), 7.99 (s, 1H), 6.91 (t, J = 52.0 Hz, 1H), 6.74 (t, J = 56.0 Hz, 1H), 5.31 (s, 2H), 3.22 (q, J = 4.0 Hz, 2H), 1.46 (t, J = 8.0 Hz, 3H).<br>LCMS RT = 2.508 min, m/z = 452.1 | 0.070 |

TABLE 13-continued

Characterization Data and HDAC6 Activity for Compounds of Formula (I).

| Cmpd | Structure/Name | $^1$H NMR MS (m/z) (RT) | HDAC6 IC$_{50}$ (μM) |
|---|---|---|---|
| I-61 | N-((5-(5-(difluoromethyl)-1,3,4-oxadiazol-2-yl)thiazol-2-yl)methyl)-N-(6-isopropylpyridin-3-yl)ethanesulfonamide | 1H NMR (400 MHz, CDCl3) δ ppm 8.59 (d, J = 2.4 Hz, 1H), 8.38 (s, 1H), 7.75-7.71 (m, 1H), 7.22 (d, J = 8.0 Hz, 1H), 6.91 (t, J = 51.6 Hz, 1H), 5.27 (s, 2H), 3.20 (q, J = 7.2 Hz, 2H), 3.11-3.03 (m, 1H), 1.47 (t, J = 7.2 Hz, 3H), 1.29 (d, J = 7.2 Hz, 6H). LCMS RT = 0.757 min, m/z = 444.2 | 0.073 |
| I-62 | N-((5-(5-(difluoromethyl)-1,3,4-oxadiazol-2-yl)thiazol-2-yl)methyl)-N-(6-(difluoromethyl)pyridin-2-yl)ethanesulfonamide | 1H NMR (400 MHz, CDCl3) δ ppm 8.30 (s, 1H), 7.85-7.69 (m, 2H), 7.39 (d, J = 7.6 Hz, 1H), 6.81 (t, J = 51.6 Hz, 1H), 6.47 (t, J = 79.2 Hz, 1H), 5.54 (s, 2H), 3.29 (q, J = 7.6 Hz, 2H), 1.33 (t, J = 7.6 Hz, 3H). LCMS RT = 2.238 min, m/z = 452.1 | 0.0206 |
| I-63 | N-((5-(5-(difluoromethyl)-1,3,4-oxadiazol-2-yl)thiazol-2-yl)methyl)-N-(4,6-dimethylpyrimidin-2-yl)ethanesulfonamide | 1H NMR (400 MHz, CDCl3) δ ppm 8.40 (s, 1H), 6.89 (t, J = 51.6 Hz, 1H), 6.77 (s, 1H), 5.65 (s, 2H), 3.95 (q, J = 7.6 Hz, 2H), 2.44 (s, 6H), 1.39 (t, J = 7.6 Hz, 3H). LCMS RT = 3.758 min, m/z = 431.2 | 0.018 |
| I-64 | N-((5-(5-(difluoromethyl)-1,3,4-oxadiazol-2-yl)thiazol-2-yl)methyl)-N-(1-ethyl-1H-pyrazol-4-yl)ethanesulfonamide | 1H NMR (400 MHz, CDCl3) δ ppm 8.40 (s, 1H), 7.60 (s, 1H), 7.49 (s, 1H), 6.91 (t, J = 51.6 Hz, 1H), 5.16 (s, 2H), 4.12 (q, J = 7.2 Hz, 2H), 3.17 (q, J = 7.6 Hz, 2H), 1.50-1.40 (m, 6H). LCMS RT = 1.418 min, m/z = 418.9 | 0.065 |

TABLE 13-continued

Characterization Data and HDAC6 Activity for Compounds of Formula (I).

| Cmpd | Structure/Name | ¹H NMR MS (m/z) (RT) | HDAC6 IC$_{50}$ (μM) |
|---|---|---|---|
| I-65 | 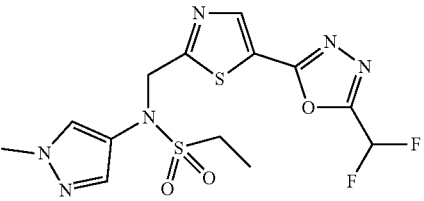 [SMILES: CCS(=O)(=O)N(Cc1ncc(-c2nnc(C(F)F)o2)s1)c1cnn(C)c1]<br>N-((5-(5-(difluoromethyl)-1,3,4-oxadiazol-2-yl)thiazol-2-yl)methyl)-N-(1-methyl-1H-pyrazol-4-yl)ethanesulfonamide | 1H NMR (400 MHz, CD3OD) δ ppm 8.33 (s, 1H), 7.71 (s, 1H), 7.48 (s, 1H), 7.11 (t, J = 51.6 Hz, 1H), 5.10 (s, 2H), 3.74 (s, 3H), 3.14 (q, J = 7.2 Hz, 2H), 1.28 (t, J = 7.2 Hz, 3H).<br>LCMS RT = 2.950 min, m/z = 404.9 | 0.022 |
| I-66 | 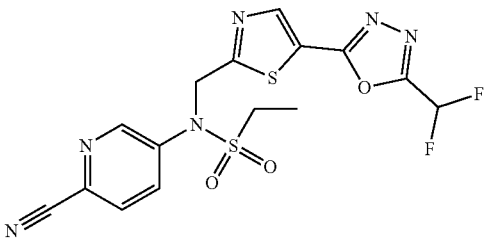 [SMILES: CCS(=O)(=O)N(Cc1ncc(-c2nnc(C(F)F)o2)s1)c1ccc(C#N)nc1]<br>N-(6-cyanopyridin-3-yl)-N-((5-(5-(difluoromethyl)-1,3,4-oxadiazol-2-yl)thiazol-2-yl)methyl)ethanesulfonamide | 1H NMR (400 MHz, CDCl3) δ ppm 8.87 (s, 1H), 8.40 (s, 1H), 8.04 (d, J = 8.4 Hz, 1H), 7.74 (d, J = 8.4 Hz, 1H), 6.91 (t, J = 51.6 Hz, 1H), 5.35 (s, 2H), 3.23 (q, J = 7.2 Hz, 2H), 1.43 (t, J = 7.2 Hz, 3H).<br>LCMS RT = 1.030 min, m/z = 426.8 | 0.029 |
| I-67 | 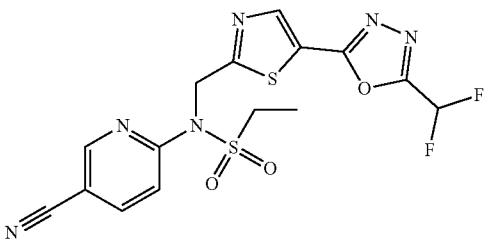 [SMILES: CCS(=O)(=O)N(Cc1ncc(-c2nnc(C(F)F)o2)s1)c1ccc(C#N)cn1]<br>N-(5-cyanopyridin-2-yl)-N-((5-(5-(difluoromethyl)-1,3,4-oxadiazol-2-yl)thiazol-2-yl)methyl)ethanesulfonamide | 1H NMR (400 MHz, CDCl3) δ ppm 8.66 (s, 1H), 8.39 (s, 1H), 7.96-7.78 (m, 2H), 6.90 (t, J = 51.6 Hz, 1H), 5.63 (s, 2H), 3.48 (q, J = 7.6 Hz, 2H), 1.43 (t, J = 7.6 Hz, 3H).<br>LCMS RT = 2.180 min, m/z = 427.1 | 0.037 |
| I-68 | 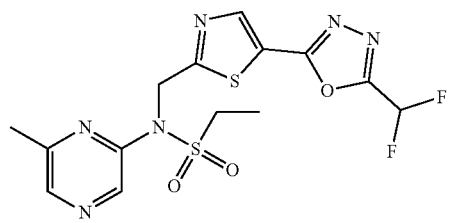 [SMILES: CCS(=O)(=O)N(Cc1ncc(-c2nnc(C(F)F)o2)s1)c1cncc(C)n1]<br>N-((5-(5-(difluoromethyl)-1,3,4-oxadiazol-2-yl)thiazol-2-yl)methyl)-N-(6-methylpyrazin-2-yl)ethanesulfonamide | 1H NMR (400 MHz, CDCl3) δ ppm 8.80 (s, 1H), 8.39 (s, 1H), 8.29 (s, 1H), 6.90 (t, J = 51.6 Hz, 1H), 5.58 (s, 2H), 3.38 (q, J = 7.2 Hz, 2H), 2.55 (s, 3H), 1.42 (t, J = 7.6 Hz, 3H).<br>LCMS RT = 1.657 min, m/z = 417.1 | 0.100 |

TABLE 13-continued

Characterization Data and HDAC6 Activity for Compounds of Formula (I).

| Cmpd | Structure/Name | ¹H NMR<br>MS (m/z) (RT) | HDAC6 IC$_{50}$ (μM) |
|---|---|---|---|
| I-69 | 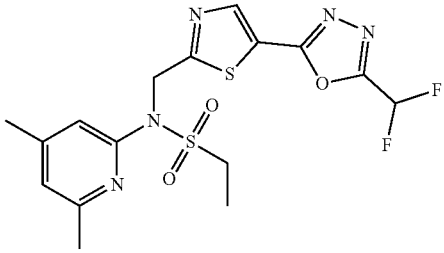 [SMILES: CCS(=O)(=O)N(Cc1ncc(-c2nnc(C(F)F)o2)s1)c1cc(C)cc(C)n1]<br>N-((5-(5-(difluoromethyl)-1,3,4-oxadiazol-2-yl)thiazol-2-yl)methyl)-N-(4,6-dimethylpyridin-2-yl)ethanesulfonamide | 1H NMR (400 MHz, CDCl3) δ ppm 8.38 (s, 1H), 7.27 (s, 1H), 7.02-6.72 (m, 2H), 5.58 (s, 2H), 3.24 (q, J = 7.6 Hz, 2H), 2.47 (s, 3H), 2.33 (s, 3H), 1.36 (t, J = 7.4 Hz, 3H).<br>LCMS RT = 3.082 min, m/z = 429.9 | 0.071 |
| I-70 | 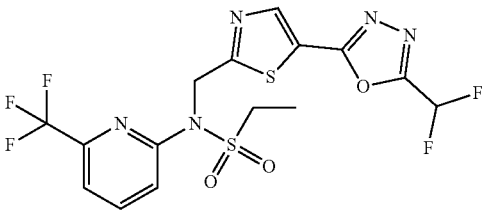 [SMILES: CCS(=O)(=O)N(Cc1ncc(-c2nnc(C(F)F)o2)s1)c1cccc(C(F)(F)F)n1]<br>N-((5-(5-(difluoromethyl)-1,3,4-oxadiazol-2-yl)thiazol-2-yl)methyl)-N-(6-(trifluoromethyl)pyridin-2-yl)ethanesulfonamide | 1H NMR (400 MHz, CD3OD) δ ppm 8.42 (s, 1H), 8.07-8.02 (m, 1H), 7.92-7.89 (m, 1H), 7.61-7.58 (m, 1H), 7.19 (t, J = 51.6 Hz, 1H), 5.62 (s, 2H), 3.57 (q, J = 7.2 Hz, 2H), 1.38 (t, J = 7.2 Hz, 3H).<br>LCMS RT = 2.965 min, m/z = 470.1 | 0.0281 |
| I-71 | 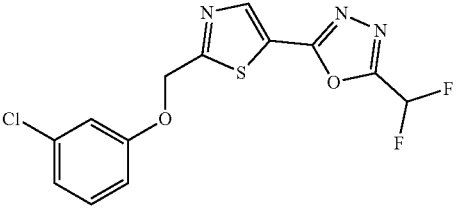 [SMILES: FC(F)c1nnc(-c2cnc(COc3cccc(Cl)c3)s2)o1]<br>2-(2-((3-chlorophenoxy)methyl)thiazol-5-yl)-5-(difluoromethyl)-1,3,4-oxadiazole | 1H NMR (400 MHz, CDCl3) δ ppm 8.49 (s, 1H), 7.29-7.24 (m, 1H), 7.06-7.04 (m, 2H), 6.94-6.78 (m, 2H), 5.43 (s, 2H).<br>LCMS RT = 1.840 min, m/z = 344.1 | 0.251 |
| I-72 | 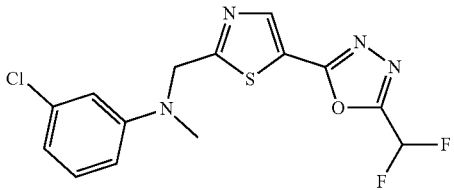 [SMILES: CN(Cc1ncc(-c2nnc(C(F)F)o2)s1)c1cccc(Cl)c1]<br>3-chloro-N-((5-(5-(difluoromethyl)-1,3,4-oxadiazol-2-yl)thiazol-2-yl)methyl)-N-methylaniline | 1H NMR (400 MHz, CDCl3) δ ppm 8.55 (s, 1H), 7.43-6.70 (m, 5 Hz), 4.93 (s, 2H), 3.26 (s, 3H).<br>LCMS RT = 3.547 min, m/z = 356.8 | 0.034 |

TABLE 13-continued

Characterization Data and HDAC6 Activity for Compounds of Formula (I).

| Cmpd | Structure/Name | ¹H NMR<br>MS (m/z) (RT) | HDAC6<br>IC$_{50}$<br>(μM) |
|---|---|---|---|
| I-73 | 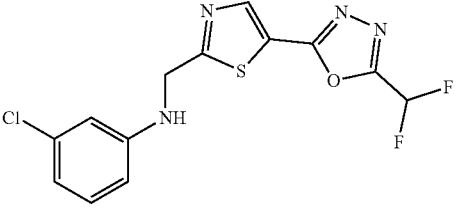 [SMILES: FC(F)c1nnc(-c2cnc(CNc3cccc(Cl)c3)s2)o1]<br>3-chloro-N-((5-(5-(difluoromethyl)-1,3,4-oxadiazol-2-yl)thiazol-2-yl)methyl)aniline | 1H NMR (400 MHz, CDCl3) δ ppm 8.37 (s, 1H), 7.06-6.44 (m, 5 Hz), 4.66 (s, 3H).<br>LCMS RT = 2.368 min, m/z = 343.1 | 0.046 |
| I-74 | 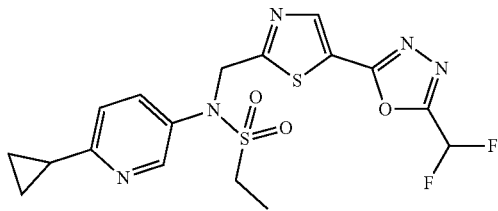 [SMILES: CCS(=O)(=O)N(Cc1ncc(-c2nnc(C(F)F)o2)s1)c1ccc(C2CC2)nc1]<br>N-(6-cyclopropylpyridin-3-yl)-N-((5-(5-(difluoromethyl)-1,3,4-oxadiazol-2-yl)thiazol-2-yl)methyl)ethanesulfonamide | 1H NMR (400 MHz, CD3OD) δ ppm 8.46 (d, J = 2.4 Hz, 1H), 8.41 (s, 1H), 7.80 (dd, J = 8.4, 2.8 Hz, 1H), 7.33-7.07 (m, 2H), 5.33 (s, 2H), 3.31-3.27 (m, 2H), 2.11-2.08 (m, 1H), 1.40 (t, J = 7.2 Hz, 3H), 1.04-0.94 (m, 4H).<br>LCMS RT = 5.273 min, m/z = 441.9 | 0.016 |
| I-75 | 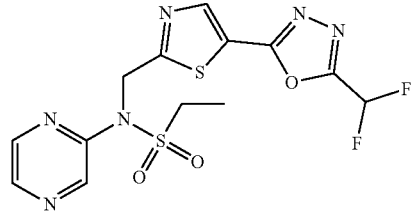 [SMILES: CCS(=O)(=O)N(Cc1ncc(-c2nnc(C(F)F)o2)s1)c1cnccn1]<br>N-((5-(5-(difluoromethyl)-1,3,4-oxadiazol-2-yl)thiazol-2-yl)methyl)-N-(pyrazin-2-yl)ethanesulfonamide | 1H NMR (400 MHz, CDCl3) δ ppm 9.00 (s, 1H), 8.43 (d, J = 2.8 Hz, 1H), 8.39-8.35 (m, 2H), 6.89 (t, J = 51.6 Hz, 1H), 5.58 (s, 2H), 3.41 (q, J = 7.6 Hz, 2H), 1.43 (t, J = 7.2 Hz, 3H).<br>LCMS RT = 2.823 min, m/z = 403.1 | 0.023 |
| I-76 | 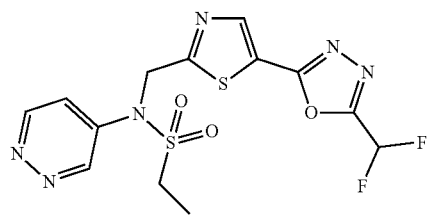 [SMILES: CCS(=O)(=O)N(Cc1ncc(-c2nnc(C(F)F)o2)s1)c1ccnnc1]<br>N-((5-(5-(difluoromethyl)-1,3,4-oxadiazol-2-yl)thiazol-2-yl)methyl)-N-(pyridazin-4-yl)ethanesulfonamide | 1H NMR (400 MHz, CD3OD) δ ppm 8.57 (d, J = 7.6 Hz, 1H), 8.53 (s, 1H), 8.23 (s, 1H), 7.42-7.40 (m, 1H), 7.22 (t, J = 51.6 Hz, 1H), 5.85 (s, 2H), 3.10 (q, J = 7.6 Hz, 2H), 1.36 (t, J = 7.2 Hz, 3H).<br>LCMS RT = 3.671 min, m/z = 402.9 | 0.097 |

TABLE 13-continued

Characterization Data and HDAC6 Activity for Compounds of Formula (I).

| Cmpd | Structure/Name | ¹H NMR MS (m/z) (RT) | HDAC6 IC$_{50}$ (μM) |
|---|---|---|---|
| I-77 | N-((5-(5-(difluoromethyl)-1,3,4-oxadiazol-2-yl)thiazol-2-yl)methyl)-N-(2-(trifluoromethyl)pyrimidin-5-yl)ethanesulfonamide | 1H NMR (400 MHz, CDCl3) δ ppm 9.10 (s, 2H), 8.43 (s, 1H), 6.92 (t, J = 51.6 Hz, 1H), 5.32 (d, J = 12 Hz, 2H), 3.25 (q, J = 7.2 Hz, 2H), 1.44 (t, J = 7.2 Hz, 3H). LCMS RT = 2.594 min, m/z = 471.1 | 0.155 |
| I-78 | N-((5-(5-(difluoromethyl)-1,3,4-oxadiazol-2-yl)thiazol-2-yl)methyl)-N-(6-(trifluoromethyl)pyridin-3-yl)ethanesulfonamide | 1H NMR (400 MHz, CDCl3) δ ppm 8.86 (s, 1H), 8.40 (s, 1H), 8.10 (d, J = 8.4 Hz, 1H), 7.74 (d, J = 8.4 Hz, 1H), 6.91 (t, J = 51.6 Hz, 1H), 5.34 (s, 2H), 3.23 (q, J = 7.2 Hz, 2H), 1.45 (t, J = 7.2 Hz, 3H). LCMS RT = 0.882 min, m/z = 470.1 | 0.059 |
| I-79 | N-((5-(5-(difluoromethyl)-1,3,4-oxadiazol-2-yl)thiazol-2-yl)methyl)-N-(6-methylpyridin-3-yl)ethanesulfonamide | 1H NMR (400 MHz, CDCl3) δ ppm 8.55 (s, 1H), 8.37 (s, 1H), 7.73-7.68 (m, 1H), 7.20 (d, J = 7.6 Hz, 1H), 6.91 (t, J = 51.6 Hz, 1H), 5.27 (s, 2H), 3.20 (q, J = 7.2 Hz, 2H), 2.56 (s, 3H), 1.46 (t, J = 7.2 Hz, 3H). LCMS RT = 0.616 min, m/z = 416.2 | 0.073 |
| I-80 | N-((5-(5-(difluoromethyl)-1,3,4-oxadiazol-2-yl)thiazol-2-yl)methyl)-N-(5-fluoropyridin-2-yl)ethanesulfonamide | 1H NMR (400 MHz, CDCl3) δ ppm 8.37 (s, 1H), 8.28 (s, 1H), 7.70-7.60 (m, 1H), 7.50-7.40 (m, 1H), 6.89 (t, J = 51.6 Hz, 1H), 5.54 (s, 2H), 3.25 (q, J = 7.2 Hz, 2H), 1.40 (t, J = 7.6 Hz, 3H). LCMS RT = 2.661 min, m/z = 419.9 | 0.0265 |

TABLE 13-continued

Characterization Data and HDAC6 Activity for Compounds of Formula (I).

| Cmpd | Structure/Name | $^1$H NMR MS (m/z) (RT) | HDAC6 IC$_{50}$ (μM) |
|---|---|---|---|
| I-81 | 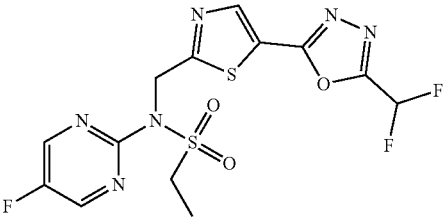 [SMILES: CCS(=O)(=O)N(Cc1ncc(-c2nnc(C(F)F)o2)s1)c1ncc(F)cn1]<br>N-((5-(5-(difluoromethyl)-1,3,4-oxadiazol-2-yl)thiazol-2-yl)methyl)-N-(5-fluoropyrimidin-2-yl)ethanesulfonamide | 1H NMR (400 MHz, CDCl3) δ ppm 8.49 (s, 2H), 8.40 (s, 1H), 6.90 (t, J = 51.6 Hz, 1H), 5.65 (s, 2H), 3.91 (q, J = 7.6 Hz, 2H), 1.45 (t, J = 7.6 Hz, 3H). LCMS RT = 1.977 min, m/z = 421.1 | 0.116 |
| I-82 | 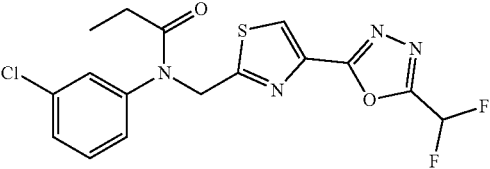 [SMILES: CCC(=O)N(Cc1nc(-c2nnc(C(F)F)o2)cs1)c1cccc(Cl)c1]<br>N-(3-chlorophenyl)-N-((4-(5-(difluoromethyl)-1,3,4-oxadiazol-2-yl)thiazol-2-yl)methyl)propionamide | 1H NMR (400 MHz, CDCl3) δ ppm 8.28 (s, 1H), 7.37-7.32 (m, 2H), 7.25-7.23 (m, 1H), 7.10-7.07 (m, 1H), 6.91 (t, J = 51.6 Hz, 1H), 5.22 (s, 2H), 2.19 (q, J = 7.2 Hz, 2H), 1.21 (t, J = 7.2 Hz, 3H). LCMS RT = 0.931 min, m/z = 399.1 | 4.1 |
| I-83 | 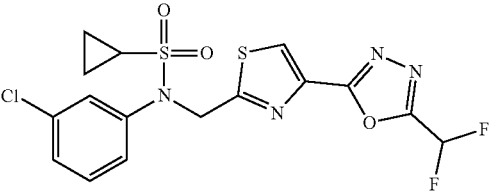 [SMILES: O=S(=O)(C1CC1)N(Cc1nc(-c2nnc(C(F)F)o2)cs1)c1cccc(Cl)c1]<br>N-(3-chlorophenyl)-N-((4-(5-(difluoromethyl)-1,3,4-oxadiazol-2-yl)thiazol-2-yl)methyl)cyclopropanesulfonamide | 1H NMR (400 MHz, CDCl3) δ ppm 8.26 (s, 1H), 7.51 (s, 1H), 7.41-7.30 (m, 3H), 6.91 (t, J = 51.6 Hz, 1H), 5.32 (s, 2H), 2.59-2.52 (m, 1H), 1.18-1.13 (m, 2H), 1.08-1.04 (m, 2H). LCMS RT = 0.944 min, m/z = 447.1 | 0.759 |
| I-84 | 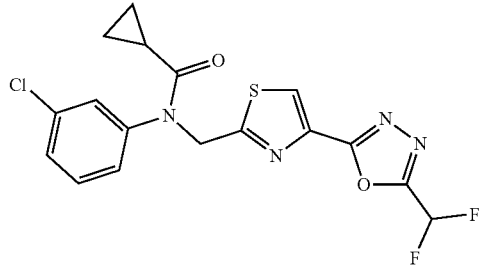 [SMILES: O=C(C1CC1)N(Cc1nc(-c2nnc(C(F)F)o2)cs1)c1cccc(Cl)c1]<br>N-(3-chlorophenyl)-N-((4-(5-(difluoromethyl)-1,3,4-oxadiazol-2-yl)thiazol-2-yl)methyl)cyclopropanecarboxamide | 1H NMR (400 MHz, CDCl3) δ ppm 8.27 (s, 1H), 7.40-7.20 (m, 4H), 6.91 (t, J = 51.6 Hz, 1H), 5.25 (s, 2H), 1.50-1.40 (m, 1H), 1.18-1.09 (m, 2H), 0.83-0.74 (m, 2H). LCMS RT = 1.163 min, m/z = 410.8 | 7.5 |

TABLE 13-continued

Characterization Data and HDAC6 Activity for Compounds of Formula (I).

| Cmpd | Structure/Name | $^1$H NMR<br>MS (m/z) (RT) | HDAC6<br>IC$_{50}$<br>(µM) |
|---|---|---|---|
| I-85 | 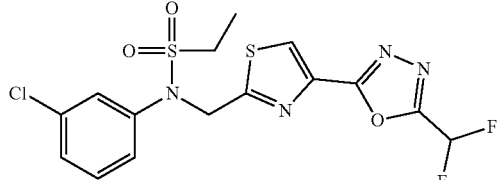<br>N-(3-chlorophenyl)-N-((4-(5-(difluoromethyl)-1,3,4-oxadiazol-2-yl)thiazol-2-yl)methyl)ethanesulfonamide | 1H NMR (400 MHz, CDCl3) δ ppm 8.26 (s, 1H), 7.48 (s, 1H), 7.37-7.31 (m, 3H), 6.91 (t, J = 51.6 Hz, 1H), 5.32 (s, 2H), 3.19 (q, J = 7.2 Hz, 2H), 1.46 (t, J = 7.2 Hz, 3H).<br>LCMS RT = 0.922 min, m/z = 435.0 | 0.584 |
| I-86 | 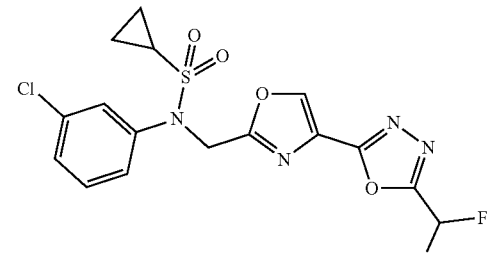<br>N-(3-chlorophenyl)-N-((4-(5-(difluoromethyl)-1,3,4-oxadiazol-2-yl)oxazol-2-yl)methyl)cyclopropanesulfonamide | 1H NMR (400 MHz, CDCl3) δ ppm 8.36 (s, 1H), 7.50 (s, 1H), 7.39-7.37 (m, 1H), 7.33-7.30 (m, 2H), 6.91 (t, J = 51.6 Hz, 1H), 5.03 (s, 2H), 2.69-2.65 (m, 1H), 1.09-0.90 (m, 4H).<br>LCMS RT = 3.210 min, m/z = 431.1 | 8.0 |
| I-87 | 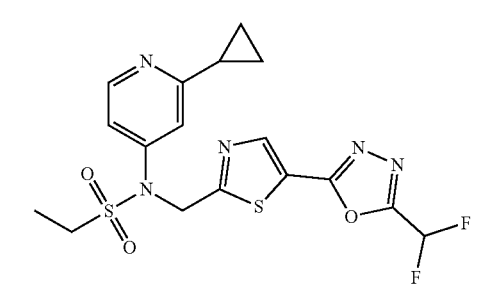 [SMILES: CCS(=O)(=O)N(Cc1ncc(-c2nnc(C(F)F)o2)s1)c1ccnc(C2CC2)c1]<br>N-(2-cyclopropylpyridin-4-yl)-N-((5-(5-(difluoromethyl)-1,3,4-oxadiazol-2-yl)thiazol-2-yl)methyl)ethanesulfonamide | 1H NMR (400 MHz, CDCl3) δ 8.42-8.36 (m, 2H), 7.31 (s, 1H), 7.18-7.14 (m, 1H), 6.90 (t, J = 51.6 Hz, 1H), 5.37 (s, 2H), 3.26 (q, J = 7.6 Hz, 2H), 2.04-1.95 (m, 1H), 1.42 (t, J = 7.2 Hz, 3H), 1.05-1.00 (m, 4H).<br>LCMS RT = 1.094 min, m/z = 441.9 | 0.039 |
| I-88 | 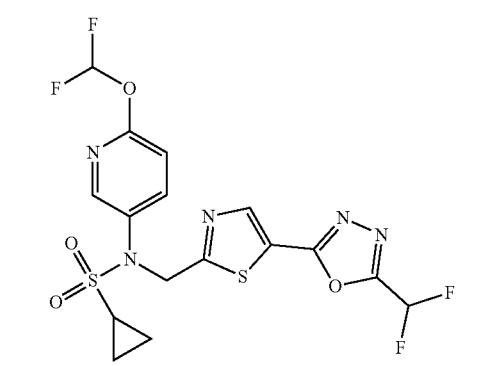 [SMILES: O=S(=O)(C1CC1)N(Cc1ncc(-c2nnc(C(F)F)o2)s1)c1ccc(OC(F)F)nc1]<br>N-(6-(difluoromethoxy)pyridin-3-yl)-N-((5-(5-(difluoromethyl)-1,3,4-oxadiazol-2-yl)thiazol-2-yl)methyl)cyclopropanesulfonamide | 1H NMR (400 MHz, CDCl3) δ 8.39 (s, 1H), 8.33 (d, J = 2.8 Hz, 1H), 7.87 (dd, J = 2.8, 8.8 Hz, 1H), 7.42 (t, J = 72.0 Hz, 1H), 7.06-6.77 (m, 2H), 5.26 (s, 2H), 2.64-2.48 (m, 1H), 1.21-0.98 (m, 4H).<br>LCMS RT = 0.957 min, m/z = 479.9 | 0.048 |

TABLE 13-continued

Characterization Data and HDAC6 Activity for Compounds of Formula (I).

| Cmpd | Structure/Name | ¹H NMR<br>MS (m/z) (RT) | HDAC6 IC$_{50}$ (µM) |
|---|---|---|---|
| I-89 | 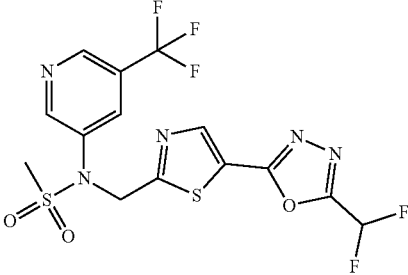 [SMILES: CS(=O)(=O)N(Cc1ncc(-c2nnc(C(F)F)o2)s1)c1cncc(C(F)(F)F)c1]<br>N-((5-(5-(difluoromethyl)-1,3,4-oxadiazol-2-yl)thiazol-2-yl)methyl)-N-(5-(trifluoromethyl)pyridin-3-yl)methanesulfonamide | 1H NMR (400 MHz, CDCl3) δ 8.95 (d, J = 2.4 Hz, 1H), 8.87 (d, J = 2.4 Hz, 1H), 8.44 (s, 1H), 8.13 (s, 1H), 6.92 (t, J = 51.6 Hz, 1H), 5.31 (s, 2H), 3.12 (s, 3H).<br>LCMS RT = 0.878 min, m/z = 455.9 | 0.049 |
| I-90 | 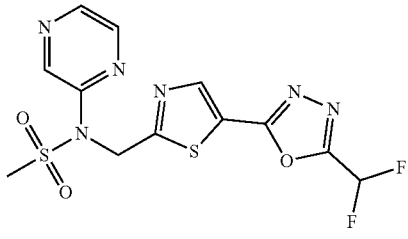 [SMILES: CS(=O)(=O)N(Cc1ncc(-c2nnc(C(F)F)o2)s1)c1cnccn1]<br>N-((5-(5-(difluoromethyl)-1,3,4-oxadiazol-2-yl)thiazol-2-yl)methyl)-N-(pyrazin-2-yl)methanesulfonamide | 1H NMR (400 MHz, CDCl3) δ 9.00 (s, 1H), 8.47-8.36 (m, 3H), 6.91 (t, J = 51.2 Hz, 1H), 5.58 (s, 2H), 3.27 (s, 3H).<br>LCMS RT = 0.943 min, m/z = 389.1 | 0.041 |
| I-91 | 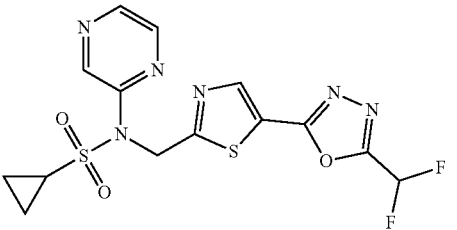 [SMILES: O=S(=O)(C1CC1)N(Cc1ncc(-c2nnc(C(F)F)o2)s1)c1cnccn1]<br>N-((5-(5-(difluoromethyl)-1,3,4-oxadiazol-2-yl)thiazol-2-yl)methyl)-N-(pyrazin-2-yl)cyclopropanesulfonamide | 1H NMR (400 MHz, CDCl3) δ 9.02 (d, J = 1.2 Hz, 1H), 8.46-8.35 (m, 3H), 6.91 (t, J = 51.6 Hz, 1H), 5.58 (s, 2H), 2.72-2.61 (m, 1H), 1.27-1.21 (m, 2H), 1.11-1.01 (m, 2H).<br>LCMS RT = 1.031 min, m/z = 415.1 | 0.018 |
| I-92 | 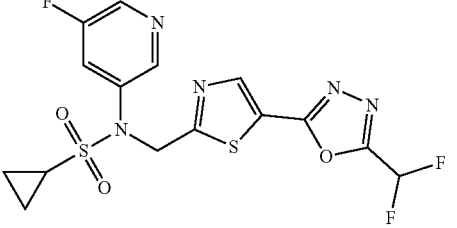<br>N-((5-(5-(difluoromethyl)-1,3,4-oxadiazol-2-yl)thiazol-2-yl)methyl)-N-(5-fluoropyridin-3-yl)cyclopropanesulfonamide | 1H NMR (400 MHz, CDCl3) δ 8.61 (s, 1H), 8.47 (d, J = 4.0 Hz, 1H), 8.40 (s, 1H), 7.68-7.62 (m, 1H), 6.91 (t, J = 51.6 Hz, 1H), 5.31 (s, 2H), 2.63-2.52 (m, 1H), 1.17-1.02 (m, 4H).<br>LCMS RT = 2.295 min, m/z = 431.9 | 0.014 |

TABLE 13-continued

Characterization Data and HDAC6 Activity for Compounds of Formula (I).

| Cmpd | Structure/Name | ¹H NMR<br>MS (m/z) (RT) | HDAC6<br>IC$_{50}$<br>(µM) |
|---|---|---|---|
| I-93 | N-((5-(5-(difluoromethyl)-1,3,4-oxadiazol-2-yl)thiazol-2-yl)methyl)-N-(5-methylpyridin-3-yl)methanesulfonamide | 1H NMR (400 MHz, CDCl3) δ 8.52-8.43 (m, 2H), 8.40 (s, 1H), 7.65 (s, 1H), 6.91 (t, J = 51.6 Hz, 1H), 5.27 (s, 2H), 3.10 (s, 3H), 2.39 (s, 3H).<br>LCMS RT = 0.828 min, m/z = 401.9 | 0.055 |
| I-94 | N-((5-(5-(difluoromethyl)-1,3,4-oxadiazol-2-yl)thiazol-2-yl)methyl)-N-(5-fluoropyridin-3-yl)methanesulfonamide | 1H NMR (400 MHz, CDCl3) δ 8.58 (s, 1H), 8.49 (s, 1H), 8.43 (s, 1H), 7.68-7.65 (m, 1H), 6.92 (t, J = 51.6 Hz, 1H), 5.29 (s, 2H), 3.12 (s, 3H).<br>LCMS RT = 1.877 min, m/z = 406.1 | 0.025 |
| I-95 | N-(5-chloropyridin-3-yl)-N-((5-(5-(difluoromethyl)-1,3,4-oxadiazol-2-yl)thiazol-2-yl)methyl)methanesulfonamide | 1H NMR (400 MHz, CDCl3) δ 8.62 (d, J = 2.4 Hz, 1H), 8.57 (d, J = 2.4 Hz, 1H), 8.43 (s, 1H), 7.90 (s, 1H), 6.92 (t, J = 51.6 Hz, 1H), 5.27 (s, 2H), 3.11 (s, 3H).<br>LCMS RT = 2.188 min, m/z = 421.8 | 0.0235 |
| I-96 | N-(5-(difluoromethoxy)pyridin-3-yl)-N-((5-(5-(difluoromethyl)-1,3,4-oxadiazol-2-yl)thiazol-2-yl)methyl)ethanesulfonamide | 1H NMR (400 MHz, CDCl3) δ 8.63 (s, 1H), 8.46 (s, 1H), 8.39 (s, 1H), 7.68 (s, 1H), 6.91 (t, J = 51.6 Hz, 1H), 6.58 (t, J = 51.6 Hz, 1H), 5.29 (s, 2H), 3.22 (q, J = 7.2 Hz, 2H), 1.44 (t, J = 7.6 Hz, 3H).<br>LCMS RT = 0.907 min, m/z = 467.8 | 0.010 |

TABLE 13-continued

Characterization Data and HDAC6 Activity for Compounds of Formula (I).

| Cmpd | Structure/Name | ¹H NMR MS (m/z) (RT) | HDAC6 IC$_{50}$ (μM) |
|---|---|---|---|
| I-97 | 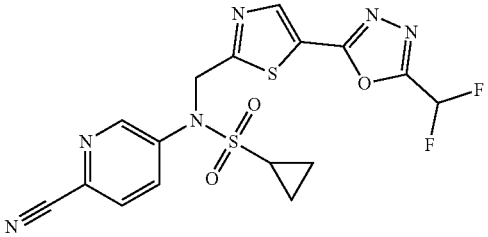 [SMILES: N#Cc1ccc(N(Cc2ncc(-c3nnc(C(F)F)o3)s2)S(=O)(=O)C2CC2)cn1]<br>N-(6-cyanopyridin-3-yl)-N-((5-(5-(difluoromethyl)-1,3,4-oxadiazol-2-yl)thiazol-2-yl)methyl)cyclopropanesulfonamide | 1H NMR (400 MHz, CDCl3) δ 8.89 (d, J = 2.4 Hz, 1H), 8.39 (s, 1H), 8.05 (d, J = 8.4 Hz, 1H), 7.74 (d, J = 8.8 Hz, 1H), 6.91 (t, J = 51.6 Hz, 1H), 5.35 (s, 2H), 2.59-2.53 (m, 1H), 1.16-1.07 (m, 4H).<br>LCMS RT = 0.859 min, m/z = 439.0 | 0.010 |
| I-98 | 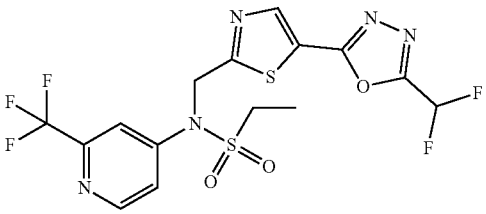 [SMILES: CCS(=O)(=O)N(Cc1ncc(-c2nnc(C(F)F)o2)s1)c1ccnc(C(F)(F)F)c1]<br>N-((5-(5-(difluoromethyl)-1,3,4-oxadiazol-2-yl)thiazol-2-yl)methyl)-N-(2-(trifluoromethyl)pyridin-4-yl)ethanesulfonamide | 1H NMR (400 MHz, CDCl3) δ 8.59 (d, J = 5.6 Hz, 1H), 8.39 (s, 1H), 7.81 (s, 1H), 7.61-7.53 (m, 1H), 6.83 (t, J = 51.6 Hz, 1H), 5.35 (s, 2H), 3.24 (q, J = 7.2 Hz, 2H), 1.35 (t, J = 7.2 Hz, 3H).<br>LCMS RT = 0.956 min, m/z = 469.9 | 0.069 |
| I-99 | 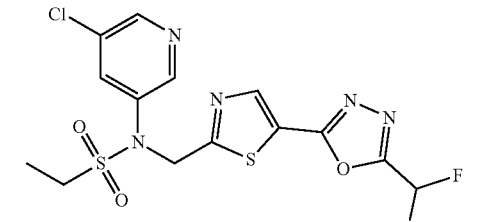<br>N-(5-chloropyridin-3-yl)-N-((5-(5-(difluoromethyl)-1,3,4-oxadiazol-2-yl)thiazol-2-yl)methyl)ethanesulfonamide | 1H NMR (400 MHz, CDCl3) δ 8.61 (d, J = 2.0 Hz, 1H), 8.55 (d, J = 2.0 Hz, 1H), 8.41 (s, 1H), 7.89 (t, J = 2.2 Hz, 1H), 6.92 (t, J = 51.6 Hz, 1H), 5.28 (s, 2H), 3.22 (q, J = 7.2 Hz, 2H), 1.46 (t, J = 7.6 Hz, 3H).<br>LCMS RT = 2.461 min, m/z = 435.9 | 0.0189 |
| I-100 | 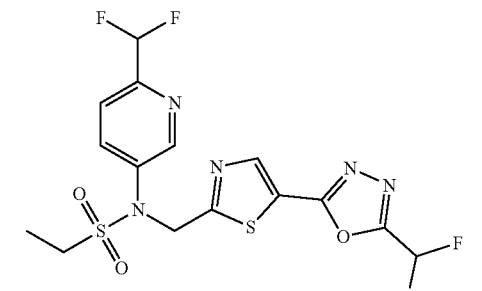<br>N-((5-(5-(difluoromethyl)-1,3,4-oxadiazol-2-yl)thiazol-2-yl)methyl)-N-(6-(difluoromethyl)pyridin-3-yl)ethanesulfonamide | 1H NMR (400 MHz, CDCl3) δ 8.77 (d, J = 2.4 Hz, 1H), 8.47 (s, 1H), 8.01 (dd, J = 2.4, 8.4 Hz, 1H), 7.69 (d, J = 8.4 Hz, 1H), 6.91 (t, J = 51.6 Hz, 1H), 6.63 (t, J = 55.2 Hz, 1H), 5.32 (s, 2H), 3.21 (q, J = 7.2 Hz, 2H), 1.45 (t, J = 7.6 Hz, 3H).<br>LCMS RT = 2.547 min, m/z = 452.1 | 0.065 |

TABLE 13-continued

Characterization Data and HDAC6 Activity for Compounds of Formula (I).

| Cmpd | Structure/Name | ¹H NMR<br>MS (m/z) (RT) | HDAC6<br>IC$_{50}$<br>(μM) |
|---|---|---|---|
| I-101 | 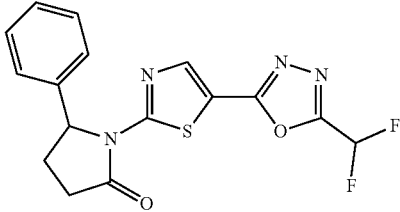 [SMILES: O=C1CCC(c2ccccc2)N1c1ncc(-c2nnc(C(F)F)o2)s1]<br>1-(5-(5-(difluoromethyl)-1,3,4-oxadiazol-2-yl)thiazol-2-yl)-5-phenylpyrrolidin-2-one | 1H NMR (400 MHz, CDCl3) δ 8.08 (s, 1H), 7.38-7.30 (m, 3H), 7.18 (d, J = 7.2 Hz, 2H), 6.88 (t, J = 51.6 Hz, 1H), 5.80 (d, J = 7.6 Hz, 1H), 2.93-2.74 (m, 3H), 2.25-2.20 (m, 1H).<br>LCMS RT = 2.937 min, m/z = 362.9 | 0.171 |
| I-102 | 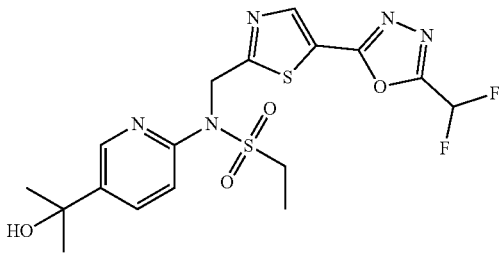 [SMILES: CCS(=O)(=O)N(Cc1ncc(-c2nnc(C(F)F)o2)s1)c1ccc(C(C)(C)O)cn1]<br>N-((5-(5-(difluoromethyl)-1,3,4-oxadiazol-2-yl)thiazol-2-yl)methyl)-N-(5-(2-hydroxypropan-2-yl)pyridin-2-yl)ethanesulfonamide | 1H NMR (400 MHz, CDCl3) δ 8.55 (d, J = 2.0 Hz, 1H), 8.38 (s, 1H), 7.86 (d, J = 6.8 Hz, 1H), 7.60 (d, J = 8.8 Hz, 1H), 6.89 (t, J = 51.6 Hz, 1H), 5.58 (s, 2H), 3.29 (q, J = 7.6 Hz , 2H), 1.61 (s, 6H), 1.39 (t, J = 7.6 Hz, 3H).<br>LCMS RT = 1.017 min, m/z = 459.9 | 0.137 |
| I-103 | 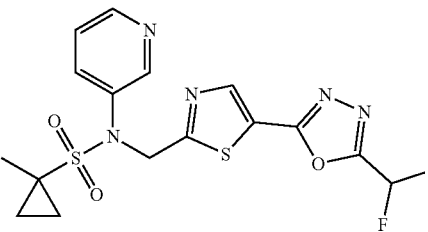<br>N-((5-(5-(difluoromethyl)-1,3,4-oxadiazol-2-yl)thiazol-2-yl)methyl)-1-methyl-N-(pyridin-3-yl)cyclopropane-1-sulfonamide | 1H NMR (400 MHz, CDCl3) δ 8.74 (d, J = 2.4 Hz, 1H), 8.58 (d, J = 3.6 Hz, 1H), 8.35 (s, 1H), 7.87-7.81 (m, 1H), 7.38-7.31 (m, 1H), 6.90 (t, J = 51.6 Hz, 1H), 5.35 (s, 2H), 1.59 (s, 3H), 1.22-1.15 (m, 2H), 0.79-0.72 (m, 2H).<br>LCMS RT = 0.956 min, m/z = 427.9 | 0.013 |
| I-104 | 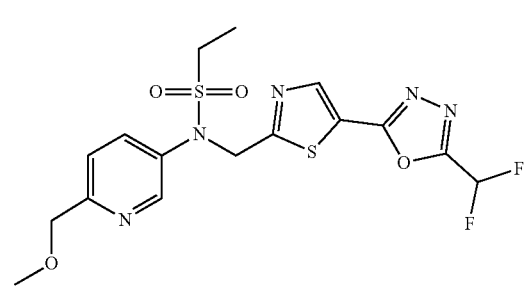 [SMILES: CCS(=O)(=O)N(Cc1ncc(-c2nnc(C(F)F)o2)s1)c1ccc(COC)nc1]<br>N-((5-(5-(difluoromethyl)-1,3,4-oxadiazol-2-yl)thiazol-2-yl)methyl)-N-(6-(methoxymethyl)pyridin-3-yl)ethanesulfonamide | 1H NMR (400 MHz, CDCl3) δ 8.63 (d, J = 2.4 Hz, 1H), 8.38 (s, 1H), 7.83 (dd, J = 2.4, 8.0 Hz, 1H), 7.48 (d, J = 8.4 Hz, 1H), 6.91 (t, J = 51.6 Hz, 1H), 5.29 (s, 2H), 4.57 (s, 2H), 3.49 (s, 3H), 3.20 (q, J = 7.6 Hz, 2H), 1.46 (t, J = 7.6 Hz, 3H).<br>LCMS RT = 0.789 min, m/z = 446.2 | 0.051 |

TABLE 13-continued

Characterization Data and HDAC6 Activity for Compounds of Formula (I).

| Cmpd | Structure/Name | ¹H NMR<br>MS (m/z) (RT) | HDAC6 IC$_{50}$ (μM) |
|---|---|---|---|
| I-105 | 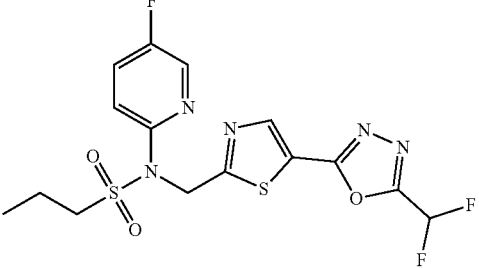<br>N-({5-[5-(difluoromethyl)-1,3,4-oxadiazol-2-yl]-1,3-thiazol-2-yl}methyl)-N-(5-fluoropyridin-2-yl)propane-1-sulfonamide | ¹H NMR (400 MHz, CDCl$_3$) δ 8.37 (s, 1H), 8.28 (d, J = 3.2 Hz, 1H), 7.69-7.63 (m, 1H), 7.51-7.43 (m, 1H), 6.89 (t, J = 51.6 Hz, 1H), 5.52 (s, 2H), 3.20-3.14 (m, 2H), 1.91-1.83 (m, 2H), 1.05 (t, J = 7.6 Hz, 3H).<br>LCMS R$_T$ = 0.684 min, m/z = 433.9 | 0.0268 |
| I-106 | 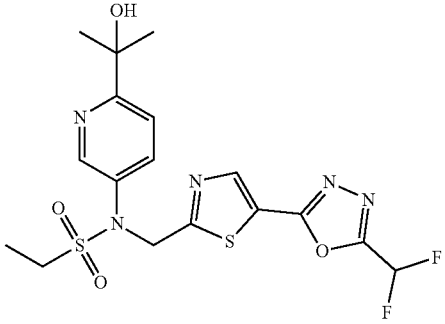 [SMILES: CCS(=O)(=O)N(Cc1ncc(-c2nnc(C(F)F)o2)s1)c1ccc(C(C)(C)O)nc1]<br>N-({5-[5-(difluoromethyl)-1,3,4-oxadiazol-2-yl]-1,3-thiazol-2-yl}methyl)-N-[6-(2-hydroxypropan-2-yl)pyridin-3-yl]ethane-1-sulfonamide | ¹H NMR (400 MHz, CDCl$_3$) δ 8.55 (s, 1H), 8.38 (s, 1H), 7.85 (d, J = 8.8 Hz, 1H), 7.60 (d, J = 8.4 Hz, 1H), 6.89 (t, J = 52.0 Hz, 1H), 5.58 (s, 2H), 3.30 (q, J = 7.2 Hz, 2H), 2.63 (s, 1H), 1.39 (t, J = 7.6 Hz, 3H), 1.30-1.23 (m, 6H).<br>LCMS R$_T$ = 1.467 min, m/z = 460.2 | 0.480 |
| I-107 | 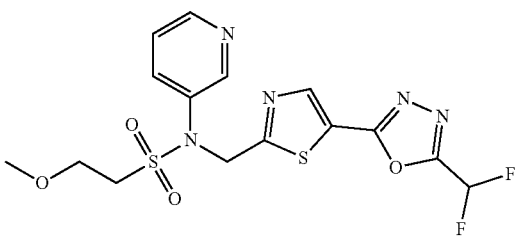 [SMILES: COCCS(=O)(=O)N(Cc1ncc(-c2nnc(C(F)F)o2)s1)c1cccnc1]<br>N-({5-[5-(difluoromethyl)-1,3,4-oxadiazol-2-yl]-1,3-thiazol-2-yl}methyl)-2-methoxy-N-(pyridin-3-yl)ethane-1-sulfonamide | ¹H NMR (400 MHz, CDCl$_3$) δ 8.80 (s, 1H), 8.57 (d, J = 3.6 Hz, 1H), 8.34 (s, 1H), 7.91-7.88 (m, 1H), 7.36-7.33 (m, 1H), 6.90 (t, J = 51.6 Hz, 1H), 5.24 (s, 2H), 3.87 (t, J = 5.2 Hz, 2H), 3.51 (s, 3H), 3.35 (t, J = 5.2 Hz, 2H).<br>LCMS R$_T$ = 1.284 min, m/z = 431.9 | 0.0212 |

TABLE 13-continued

Characterization Data and HDAC6 Activity for Compounds of Formula (I).

| Cmpd | Structure/Name | $^1$H NMR<br>MS (m/z) (RT) | HDAC6<br>IC$_{50}$<br>(µM) |
|---|---|---|---|
| I-108 | N-({5-[5-(difluoromethyl)-1,3,4-oxadiazol-2-yl]-1,3-thiazol-2-yl}methyl)-N-(5-ethoxypyridin-3-yl)ethane-1-sulfonamide | $^1$H NMR (400 MHz, CDCl$_3$) δ 8.40 (s, 1H), 8.32-8.27 (m, 2H), 7.42-7.38 (m, 1H), 6.92 (t, J = 51.6 Hz, 1H), 5.31 (s, 2H), 4.10 (q, J = 6.8 Hz, 2H), 3.22 (q, J = 7.2 Hz, 2H), 1.49-1.43 (m, 6H). LCMS R$_T$ = 0.604 min, m/z = 446.0 | 0.0138 |
| I-109 | N-(5-chloropyridin-3-yl)-N-({5-[5-(difluoromethyl)-1,3,4-oxadiazol-2-yl]-1,3-thiazol-2-yl}methyl)propane-1-sulfonamide | $^1$H NMR (400 MHz, CDCl$_3$) δ 8.60 (d, J = 2.0 Hz, 1H), 8.54 (s, 1H), 8.40 (s, 1H), 7.88 (t, J = 2.4 Hz, 1H), 6.91 (t, J = 51.6 Hz, 1H), 5.27 (s, 2H), 3.22-3.00 (m, 2H), 1.99-1.70 (m, 2H), 1.09 (t, J = 7.6 Hz, 3H). LCMS R$_T$ = 0.668 min, m/z = 449.9 | 0.00392 |
| I-110 | N-({5-[5-(difluoromethyl)-1,3,4-oxadiazol-2-yl]-1,3-thiazol-2-yl}methyl)-N-(5-fluoropyridin-3-yl)propane-1-sulfonamide | $^1$H NMR (400 MHz, CDCl$_3$) δ 8.56 (s, 1H), 8.46 (d, J = 2.4 Hz, 1H), 8.40 (s, 1H), 7.67-7.61 (m, 1H), 6.91 (t, J = 51.6 Hz, 1H), 5.29 (s, 2H), 3.19-3.09 (m, 2H), 1.97-1.85 (m, 2H), 1.08 (t, J = 7.2 Hz, 3H). LCMS R$_T$ = 2.144 min, m/z = 434.2 | 0.0104 |
| I-111 | N-(5-cyanopyridin-3-yl)-N-({5-[5-(difluoromethyl)-1,3,4-oxadiazol-2-yl]-1,3-thiazol-2-yl}methyl)methanesulfonamide | $^1$H NMR (400 MHz, CDCl$_3$) δ 8.98 (d, J = 2.4 Hz, 1H), 8.84 (s, 1H), 8.45 (s, 1H), 8.20 (s, 1H), 6.93 (t, J = 51.2 Hz, 1H), 5.29 (s, 2H), 3.11 (s, 3H). LCMS R$_T$ = 1.456 min, m/z = 412.8 | 0.0374 |

TABLE 13-continued

Characterization Data and HDAC6 Activity for Compounds of Formula (I).

| Cmpd | Structure/Name | $^1$H NMR<br>MS (m/z) (RT) | HDAC6<br>IC$_{50}$<br>(μM) |
|---|---|---|---|
| I-112 | N-[5-(1,1-difluoroethyl)pyridin-3-yl]-N-({5-[5-(difluoromethyl)-1,3,4-oxadiazol-2-yl]-1,3-thiazol-2-yl}methyl)ethane-1-sulfonamide | $^1$H NMR (400 MHz, CDCl$_3$) δ 8.79 (s, 1H), 8.72 (s, 1H), 8.40 (s, 1H), 7.96 (s, 1H), 6.91 (t, J = 52.0 Hz, 1H), 5.30 (s, 2H), 3.21 (q, J = 7.2 Hz, 2H), 1.97 (t, J = 18.4 Hz, 3H), 1.46 (t, J = 7.6 Hz, 3H).<br>LCMS R$_T$ = 1.138 min, m/z = 466.2 | 0.0101 |
| I-113 | N-(5-cyanopyridin-3-yl)-N-({5-[5-(difluoromethyl)-1,3,4-oxadiazol-2-yl]-1,3-thiazol-2-yl}methyl)propane-1-sulfonamide | $^1$H NMR (400 MHz, CDCl$_3$) δ 8.95 (d, J = 2.4 Hz, 1H), 8.82 (d, J = 2.0 Hz, 1H), 8.42 (s, 1H), 8.20-8.12 (m, 1H), 6.92 (t, J = 51.6 Hz, 1H), 5.29 (s, 2H), 3.19-3.08 (m, 2H), 1.98-1.85 (m, 2H), 1.09 (t, J = 7.6 Hz, 3H).<br>LCMS R$_T$ = 1.560 min, m/z = 441.2 | 0.0429 |
| I-114 | N-phenyl-N-({5-[5-(trifluoromethyl)-1,3,4-oxadiazol-2-yl]-1,3-thiazol-2-yl}methyl)methanesulfonamide | $^1$H NMR (400 MHz, CDCl$_3$) δ 8.39 (s, 1H), 7.48-7.38 (m, 5H), 5.28 (s, 2H), 3.06 (s, 3H).<br>LCMS R$_T$ = 2.568 min, m/z = 404.8 | 0.354 |
| I-115 | N-(5-fluoropyridin-3-yl)-N-({5-[5-(trifluoromethyl)-1,3,4-oxadiazol-2-yl]-1,3-thiazol-2-yl}methyl)ethane-1-sulfonamide | $^1$H NMR (400 MHz, CDCl$_3$) δ 8.57 (s, 1H), 8.47 (d, J = 2.4 Hz, 1H), 8.42 (s, 1H), 7.68-7.63 (m, 1H), 5.31 (s, 2H), 3.22 (q, J = 7.2 Hz, 2H), 1.46 (t, J = 7.2 Hz, 3H).<br>LCMS R$_T$ = 0.904 min, m/z = 437.9 | 0.022 |

TABLE 13-continued

Characterization Data and HDAC6 Activity for Compounds of Formula (I).

| Cmpd | Structure/Name | $^1$H NMR<br>MS (m/z) (RT) | HDAC6 IC$_{50}$ (μM) |
|---|---|---|---|
| I-116 | 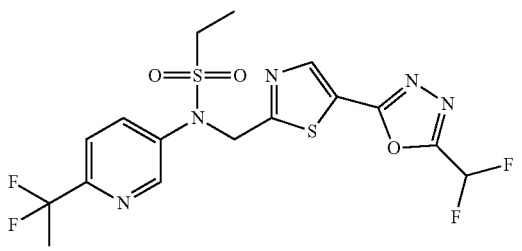 [SMILES: CCS(=O)(=O)N(Cc1ncc(-c2nnc(C(F)F)o2)s1)c1ccc(C(C)(F)F)nc1]<br>N-[6-(1,1-difluoroethyl)pyridin-3-yl]-N-({5-[5-(difluoromethyl)-1,3,4-oxadiazol-2-yl]-1,3-thiazol-2-yl}methyl)ethane-1-sulfonamide | $^1$H NMR (400 MHz, CDCl$_3$) δ 8.74 (d, J = 2.4 Hz, 1H), 8.39 (s, 1H), 7.98-7.92 (m, 1H), 7.70 (d, J = 8.4 Hz, 1H), 6.91 (t, J = 51.6 Hz, 1H), 5.32 (s, 2H), 3.22 (q, J = 7.6 Hz, 2H), 2.01 (t, J = 18.8 Hz, 3H), 1.46 (t, J = 7.6 Hz, 3H).<br>LCMS R$_T$ = 0.908 min, m/z = 465.9 | 0.0514 |
| I-117 | 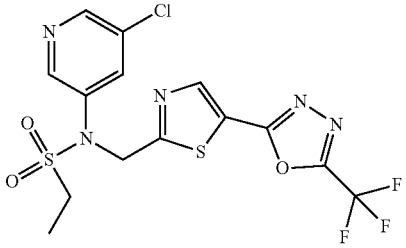 [SMILES: CCS(=O)(=O)N(Cc1ncc(-c2nnc(C(F)(F)F)o2)s1)c1cncc(Cl)c1]<br>N-(5-chloropyridin-3-yl)-N-({5-[5-(trifluoromethyl)-1,3,4-oxadiazol-2-yl]-1,3-thiazol-2-yl}methyl)ethane-1-sulfonamide | $^1$H NMR (400 MHz, CDCl$_3$) δ 8.61 (d, J = 2.4 Hz, 1H), 8.55 (d, J = 2.4 Hz, 1H), 8.42 (s, 1H), 7.88 (t, J = 2.0 Hz, 1H), 5.29 (s, 2H), 3.21 (q, J = 4.0 Hz, 2H), 1.46 (t, J = 8.0 Hz, 3H).<br>LCMS R$_T$ = 2.591 min, m/z = 453.8 | 0.0245 |
| I-118 | 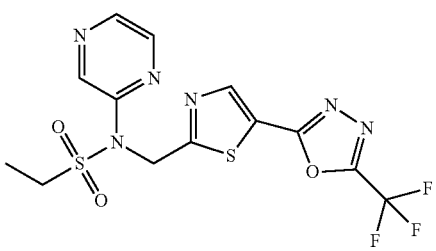 [SMILES: CCS(=O)(=O)N(Cc1ncc(-c2nnc(C(F)(F)F)o2)s1)c1cnccn1]<br>N-(pyrazin-2-yl)-N-({5-[5-(trifluoromethyl)-1,3,4-oxadiazol-2-yl]-1,3-thiazol-2-yl}methyl)ethane-1-sulfonamide | $^1$H NMR (400 MHz, CDCl$_3$) δ 9.00 (s, 1H), 8.44-8.37 (m, 3H), 5.58 (s, 2H), 3.41 (d, J = 6.8 Hz, 2H), 1.43 (t, J = 6.8 Hz, 3H).<br>LCMS R$_T$ = 0.895 min, m/z = 420.9 | 0.0278 |
| I-119 | 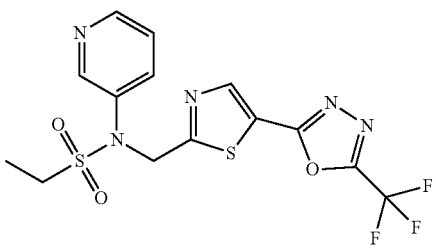 [SMILES: CCS(=O)(=O)N(Cc1ncc(-c2nnc(C(F)(F)F)o2)s1)c1cccnc1]<br>N-(pyridin-3-yl)-N-({5-[5-(trifluoromethyl)-1,3,4-oxadiazol-2-yl]-1,3-thiazol-2-yl}methyl)ethane-1-sulfonamide | $^1$H NMR (400 MHz, CDCl$_3$) δ 8.73 (s, 1H), 8.62-8.60 (m, 1H), 8.41 (s, 1H), 7.86 (d, J = 8.0 Hz, 1H), 7.40-7.35 (m, 1H), 5.32 (s, 2H), 3.22 (q, J = 6.8 Hz, 2H), 1.48 (t, J = 7.2 Hz, 3H).<br>LCMS R$_T$ = 1.897 min, m/z = 420.1 | 0.042 |

TABLE 13-continued

Characterization Data and HDAC6 Activity for Compounds of Formula (I).

| Cmpd | Structure/Name | $^1$H NMR<br>MS (m/z) (RT) | HDAC6<br>IC$_{50}$<br>(μM) |
|---|---|---|---|
| I-120 | 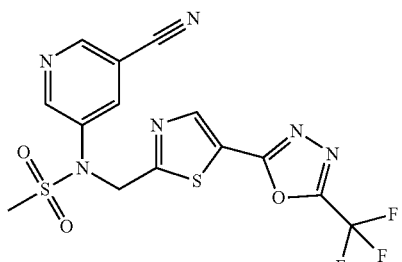<br>N-(5-cyanopyridin-3-yl)-N-({5-[5-(trifluoromethyl)-1,3,4-oxadiazol-2-yl]-1,3-thiazol-2-yl}methyl)methanesulfonamide | $^1$H NMR (400 MHz, CDCl$_3$) δ 8.98 (d, J = 2.8 Hz, 1H), 8.85 (s, 1H), 8.46 (s, 1H), 8.20 (t, J = 2.0 Hz, 1H), 5.30 (s, 2H), 3.11 (s, 3H).<br>LCMS R$_T$ = 2.105 min, m/z = 431.1 | 0.111 |
| I-121 | 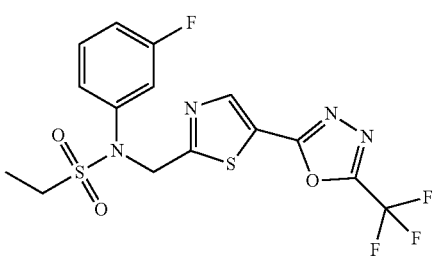 [SMILES: CCS(=O)(=O)N(Cc1ncc(-c2nnc(C(F)(F)F)o2)s1)c1cccc(F)c1]<br>N-(3-fluorophenyl)-N-({5-[5-(trifluoromethyl)-1,3,4-oxadiazol-2-yl]-1,3-thiazol-2-yl}methyl)ethane-1-sulfonamide | $^1$H NMR (400 MHz, CDCl$_3$) δ 8.40 (s, 1H), 7.41-7.36 (m, 1H), 7.28 (s, 1H), 7.25-7.22 (m, 1H), 7.09-7.04 (m, 1H), 5.30 (s, 2H), 3.19 (q, J = 7.6 Hz, 2H), 1.45 (t, J = 7.2 Hz, 3H).<br>LCMS R$_T$ = 1.978 min, m/z = 437.1 | 0.0839 |
| I-122 | 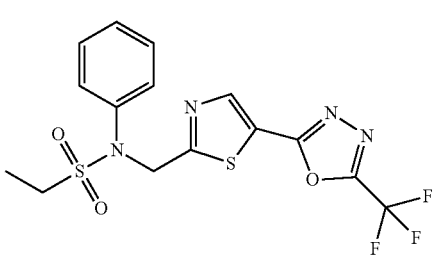 [SMILES: CCS(=O)(=O)N(Cc1ncc(-c2nnc(C(F)(F)F)o2)s1)c1ccccc1]<br>N-phenyl-N-({5-[5-(trifluoromethyl)-1,3,4-oxadiazol-2-yl]-1,3-thiazol-2-yl}methyl)ethane-1-sulfonamide | $^1$H NMR (400 MHz, CDCl$_3$) δ 8.38 (s, 1H), 7.50-7.30 (m, 5H), 5.31 (s, 2H), 3.17 (q, J = 7.2 Hz, 2H), 1.45 (t, J = 7.2 Hz, 3H).<br>LCMS R$_T$ = 0.973 min, m/z = 419.0 | 0.0249 |
| I-123 | 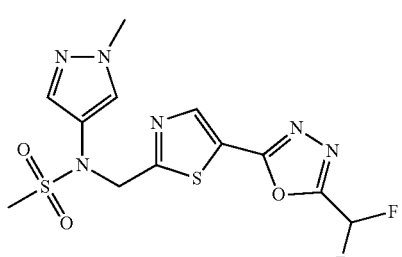<br>N-({5-[5-(difluoromethyl)-1,3,4-oxadiazol-2-yl]-1,3-thiazol-2-yl}methyl)-N-(1-methyl-1H-pyrazol-4-yl)methanesulfonamide | $^1$H NMR (400 MHz, CDCl$_3$) δ 8.42 (s, 1H), 7.57 (s, 1H), 7.48 (s, 1H), 6.91 (t, J = 51.6 Hz, 1H), 5.14 (s, 2H), 3.88 (s, 3H), 3.03 (s, 3H).<br>LCMS R$_T$ = 1.057 min, m/z = 390.9 | 0.0388 |

TABLE 13-continued

Characterization Data and HDAC6 Activity for Compounds of Formula (I).

| Cmpd | Structure/Name | ¹H NMR<br>MS (m/z) (RT) | HDAC6<br>IC$_{50}$<br>(μM) |
|---|---|---|---|
| I-124 | 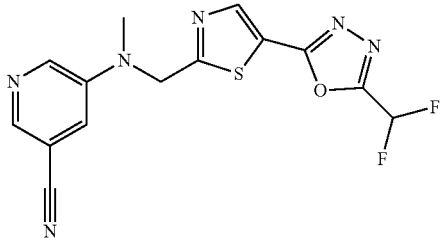 [SMILES: CN(Cc1ncc(-c2nnc(C(F)F)o2)s1)c1cncc(C#N)c1]<br>5-[({5-[5-(difluoromethyl)-1,3,4-oxadiazol-2-yl]-1,3-thiazol-2-yl}methyl)(methyl)amino]pyridine-3-carbonitrile | ¹H NMR (400 MHz, CDCl$_3$) δ 8.46 (s, 1H), 8.41 (s, 1H), 8.33 (s, 1H), 7.25 (s, 1H), 6.90 (t, J = 51.6 Hz, 1H), 4.92 (s, 2H), 3.27 (s, 3H).<br>LCMS R$_T$ = 0.971 min, m/z = 349.0 | 0.0636 |
| I-125 | 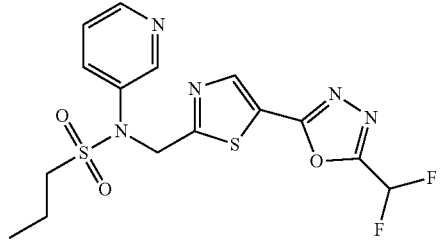 [SMILES: CCCS(=O)(=O)N(Cc1ncc(-c2nnc(C(F)F)o2)s1)c1cccnc1]<br>N-({5-[5-(difluoromethyl)-1,3,4-oxadiazol-2-yl]-1,3-thiazol-2-yl}methyl)-N-(pyridin-3-yl)propane-1-sulfonamide | ¹H NMR (400 MHz, CDCl$_3$) δ 8.71 (d, J = 2.4 Hz, 1H), 8.60-8.56 (m, 1H), 8.38 (s, 1H), 7.85-7.82 (m, 1H), 7.39-7.32 (m, 1H), 6.91 (t, J = 51.6 Hz, 1H), 5.29 (s, 2H), 3.18-3.11 (m, 2H), 1.98-1.89 (m, 2H), 1.09 (t, J = 7.2 Hz, 3H).<br>LCMS R$_T$ = 0.776 min, m/z = 416.1 | 0.0599 |
| I-126 | 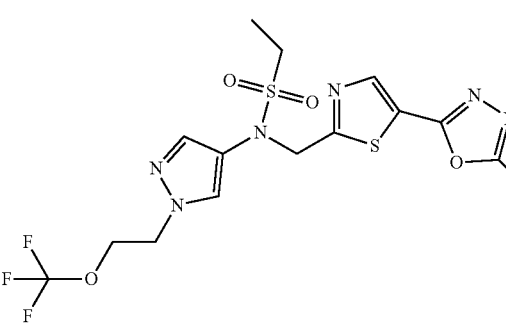<br>N-({5-[5-(difluoromethyl)-1,3,4-oxadiazol-2-yl]-1,3-thiazol-2-yl}methyl)-N-{1-[2-(trifluoromethoxy)ethyl]-1H-pyrazol-4-yl}ethane-1-sulfonamide | ¹H NMR (400 MHz, CDCl$_3$) δ 8.39 (s, 1H), 7.64 (s, 1H), 7.57 (s, 1H), 6.91 (t, J = 51.6 Hz, 1H), 5.16 (s, 2H), 4.36-4.33 (m, 2H), 4.30-4.23 (m, 2H), 3.15 (q, J = 7.6 Hz, 2H), 1.40 (t, J = 7.2 Hz, 3H).<br>LCMS R$_T$ = 1.043 min, m/z = 502.9 | 0.134 |

TABLE 13-continued

Characterization Data and HDAC6 Activity for Compounds of Formula (I).

| Cmpd | Structure/Name | ¹H NMR MS (m/z) (RT) | HDAC6 IC$_{50}$ (µM) |
|---|---|---|---|
| I-127 | 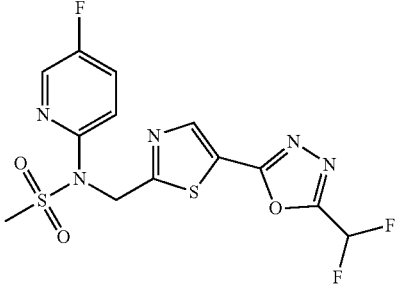 [SMILES: CS(=O)(=O)N(Cc1ncc(-c2nnc(C(F)F)o2)s1)c1ccc(F)cn1]<br>N-({5-[5-(difluoromethyl)-1,3,4-oxadiazol-2-yl]-1,3-thiazol-2-yl}methyl)-N-(5-fluoropyridin-2-yl)methanesulfonamide | ¹H NMR (400 MHz, CDCl$_3$) δ 8.37 (s, 1H), 8.29 (d, J = 3.2 Hz, 1H), 7.67-7.61 (m, 1H), 7.53-7.46 (m, 1H), 6.90 (t, J = 51.6 Hz, 1H), 5.50 (s, 2H), 3.10 (s, 3H).<br>LCMS R$_T$ = 0.854 min, m/z = 406.1 | 0.0215 |
| I-128 | 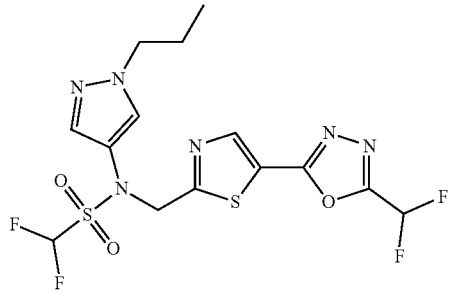 [SMILES: CCCn1cc(N(Cc2ncc(-c3nnc(C(F)F)o3)s2)S(=O)(=O)C(F)F)cn1]<br>N-({5-[5-(difluoromethyl)-1,3,4-oxadiazol-2-yl]-1,3-thiazol-2-yl}methyl)-1,1-difluoro-N-(1-propyl-1H-pyrazol-4-yl)methanesulfonamide | ¹H NMR (400 MHz, CDCl$_3$) δ 8.42 (s, 1H), 7.49 (d, J = 4.4 Hz, 2H), 6.92 (t, J = 51.6 Hz, 1H), 6.44 (t, J = 53.2 Hz, 1H), 5.21 (s, 2H), 4.02 (t, J = 7.2 Hz, 2H), 1.94-1.78 (m, 2H), 0.88 (t, J = 7.6 Hz, 3H).<br>LCMS R$_T$ = 0.901 min, m/z = 455.1 | 0.251 |
| I-129 | 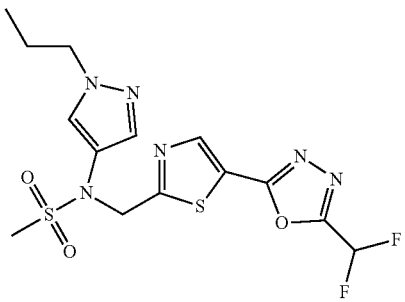 [SMILES: CCCn1cc(N(Cc2ncc(-c3nnc(C(F)F)o3)s2)S(C)(=O)=O)cn1]<br>N-({5-[5-(difluoromethyl)-1,3,4-oxadiazol-2-yl]-1,3-thiazol-2-yl}methyl)-N-(1-propyl-1H-pyrazol-4-yl)methanesulfonamide | ¹H NMR (400 MHz, CDCl$_3$) δ 8.41 (s, 1H), 7.58 (s, 1H), 7.49 (s, 1H), 6.91 (t, J = 51.6 Hz, 1H), 5.14 (s, 2H), 4.03 (t, J = 7.2 Hz, 2H), 3.03 (s, 3H), 1.92-1.81 (m, 2H), 0.90 (t, J = 7.2 Hz, 3H).<br>LCMS R$_T$ = 0.795 min, m/z = 418.9 | 0.118 |

TABLE 13-continued

Characterization Data and HDAC6 Activity for Compounds of Formula (I).

| Cmpd | Structure/Name | ¹H NMR<br>MS (m/z) (RT) | HDAC6<br>IC$_{50}$<br>(μM) |
|---|---|---|---|
| I-130 | 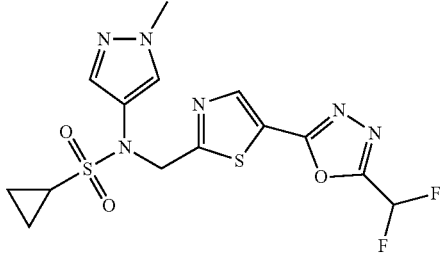 [SMILES: Cn1cc(N(Cc2ncc(-c3nnc(C(F)F)o3)s2)S(=O)(=O)C2CC2)cn1]<br>N-({5-[5-(difluoromethyl)-1,3,4-oxadiazol-2-yl]-1,3-thiazol-2-yl}methyl)-N-(1-methyl-1H-pyrazol-4-yl)cyclopropanesulfonamide | ¹H NMR (400 MHz, CDCl$_3$) δ 8.39 (s, 1H), 7.56 (s, 1H), 7.52 (s, 1H), 6.91 (t, J = 51.6 Hz, 1H), 5.15 (s, 2H), 3.87 (s, 3H), 2.58-2.50 (m, 1H), 1.20-1.15 (m, 2H), 1.07-1.01 (m, 2H).<br>LCMS R$_T$ = 1.320 min, m/z = 416.8 | 0.0348 |
| I-131 | 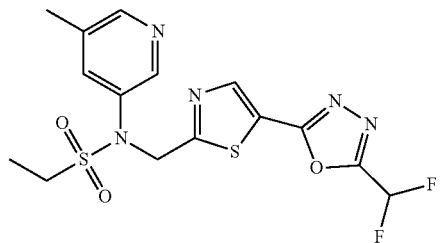 [SMILES: CCS(=O)(=O)N(Cc1ncc(-c2nnc(C(F)F)o2)s1)c1cncc(C)c1]<br>N-({5-[5-(difluoromethyl)-1,3,4-oxadiazol-2-yl]-1,3-thiazol-2-yl}methyl)-N-(5-methylpyridin-3-yl)ethane-1-sulfonamide | ¹H NMR (400 MHz, CDCl$_3$) δ 8.50 (d, J = 2.4 Hz, 1H), 8.41 (s, 1H), 8.38 (s, 1H), 7.65 (s, 1H), 6.91 (t, J = 51.6 Hz, 1H), 5.29 (s, 2H), 3.20 (q, J = 7.6 Hz, 2H), 2.37 (s, 3H), 1.47 (t, J = 7.6 Hz, 3H).<br>LCMS R$_T$ = 0.714 min, m/z = 416.2 | 0.013 |
| I-132 | 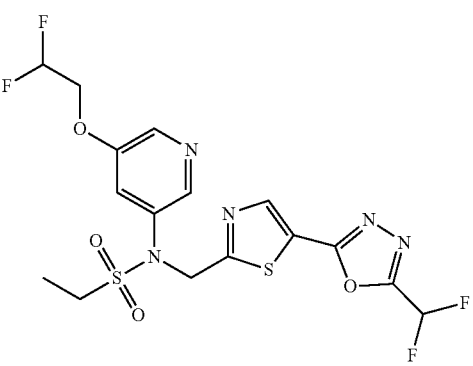 [SMILES: CCS(=O)(=O)N(Cc1ncc(-c2nnc(C(F)F)o2)s1)c1cncc(OCC(F)F)c1]<br>N-[5-(2,2-difluoroethoxy)pyridin-3-yl]-N-({5-[5-(difluoromethyl)-1,3,4-oxadiazol-2-yl]-1,3-thiazol-2-yl}methyl)ethane-1-sulfonamide | ¹H NMR (400 MHz, CDCl$_3$) δ 8.40 (s, 2H), 8.32 (d, J = 2.4 Hz, 1H), 7.45 (t, J = 2.4 Hz, 1H), 6.91 (t, J = 51.6 Hz, 1H), 6.25-5.96 (m, 1H), 5.30 (s, 2H), 4.30-4.20 (m, 2H), 3.21 (q, J = 7.2 Hz, 2H), 1.46 (t, J = 7.6 Hz, 3H).<br>LCMS R$_T$ = 0.857 min, m/z = 482.2 | 0.00964 |

TABLE 13-continued

Characterization Data and HDAC6 Activity for Compounds of Formula (I).

| Cmpd | Structure/Name | ¹H NMR<br>MS (m/z) (RT) | HDAC6<br>IC$_{50}$<br>(µM) |
|---|---|---|---|
| I-133 | N-({5-[5-(difluoromethyl)-1,3,4-oxadiazol-2-yl]-1,3-thiazol-2-yl}methyl)-1,1-difluoro-N-(5-fluoropyridin-2-yl)methanesulfonamide | ¹H NMR (400 MHz, CDCl$_3$) δ 8.39 (s, 1H), 8.30 (d, J = 2.8 Hz, 1H), 7.58-7.55 (m, 1H), 7.54-7.48 (m, 1H), 7.03 (t, J = 51.6 Hz, 1H), 6.33 (t, J = 53.6 Hz, 1H), 5.55 (s, 2H).<br>LCMS R$_T$ = 0.954 min, m/z = 441.9 | 0.0857 |
| I-134 | N-[1-(1-cyano-1-methylethyl)-1H-pyrazol-4-yl]-N-({5-[5-(difluoromethyl)-1,3,4-oxadiazol-2-yl]-1,3-thiazol-2-yl}methyl)ethane-1-sulfonamide | ¹H NMR (400 MHz, CDCl$_3$) δ 8.42 (s, 1H), 7.83 (s, 1H), 7.63 (s, 1H), 6.91 (t, J = 51.6 Hz, 1H), 5.17 (s, 2H), 3.17 (q, J = 7.2 Hz, 2H), 1.99 (s, 6H), 1.42 (t, J = 7.2 Hz, 3H).<br>LCMS R$_T$ = 1.012 min, m/z = 458.1 | 0.121 |
| I-135 | 3-chloro-N-({5-[5-(difluoromethyl)-1,3,4-oxadiazol-2-yl]-1,3-thiazol-2-yl}methyl)-N-ethylaniline | ¹H NMR (400 MHz, CDCl$_3$) δ 8.45 (s, 1H), 7.14 (t, J = 8.0 Hz, 1H), 6.88 (t, J = 51.6 Hz, 1H), 6.76-6.74 (m, 2H), 6.64-6.60 (m, 1H), 4.79 (s, 2H), 3.58 (q, J = 7.2 Hz, 2H), 1.30 (t, J = 7.2 Hz, 3H).<br>LCMS R$_T$ = 1.098 min, m/z = 370.9 | 0.0531 |
| I-136 | N-(5-cyclopropylpyridin-3-yl)-N-({5-[5-(difluoromethyl)-1,3,4-oxadiazol-2-yl]-1,3-thiazol-2-yl}methyl)methanesulfonamide | ¹H NMR (400 MHz, CDCl$_3$) δ 8.46 (s, 1H), 8.41 (s, 1H), 8.37 (s, 1H), 7.46 (s, 1H), 6.91 (t, J = 51.6 Hz, 1H), 5.25 (s, 2H), 3.09 (s, 3H), 1.96-1.89 (m, 1H), 1.14-1.06 (m, 2H), 0.79-0.71 (m, 2H).<br>LCMS R$_T$ = 0.743 min, m/z = 427.9 | 0.013 |

TABLE 13-continued

Characterization Data and HDAC6 Activity for Compounds of Formula (I).

| Cmpd | Structure/Name | $^1$H NMR<br>MS (m/z) (RT) | HDAC6 IC$_{50}$ (μM) |
|---|---|---|---|
| I-137 | 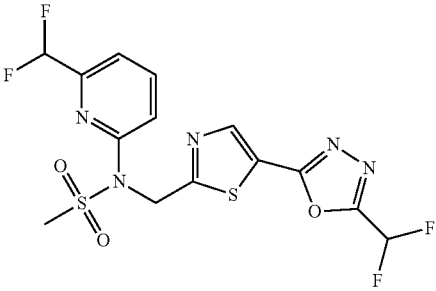 [SMILES: CS(=O)(=O)N(Cc1ncc(-c2nnc(C(F)F)o2)s1)c1cccc(C(F)F)n1]<br>N-({5-[5-(difluoromethyl)-1,3,4-oxadiazol-2-yl]-1,3-thiazol-2-yl}methyl)-N-[6-(difluoromethyl)pyridin-2-yl]methanesulfonamide | $^1$H NMR (400 MHz, CDCl$_3$) δ 8.38 (s, 1H), 7.90 (t, J = 8.0 Hz, 1H), 7.77 (d, J = 8.4 Hz, 1H), 7.48 (d, J = 7.6 Hz, 1H), 6.89 (t, J = 51.6 Hz, 1H), 6.54 (t, J = 55.2 Hz, 1H), 5.59 (s, 2H), 3.23 (s, 3H).<br>LCMS R$_T$ = 0.899 min, m/z = 437.9 | 0.0107 |
| I-138 | 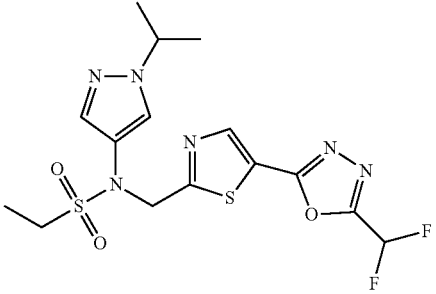 [SMILES: CCS(=O)(=O)N(Cc1ncc(-c2nnc(C(F)F)o2)s1)c1cnn(C(C)C)c1]<br>N-({5-[5-(difluoromethyl)-1,3,4-oxadiazol-2-yl]-1,3-thiazol-2-yl}methyl)-N-[1-(propan-2-yl)-1H-pyrazol-4-yl]ethane-1-sulfonamide | $^1$H NMR (400 MHz, CDCl$_3$) δ 8.37 (s, 1H), 7.57 (s, 1H), 7.46 (s, 1H), 6.87 (t, J = 51.2 Hz, 1H), 5.12 (s, 2H), 4.44-4.34 (m, 1H), 3.13 (q, J = 7.2 Hz, 2H), 1.45 (d, J = 6.8 Hz, 6H), 1.39 (t, J = 7.2 Hz, 3H).<br>LCMS R$_T$ = 1.141 min, m/z = 433.2 | 0.043 |
| I-139 | 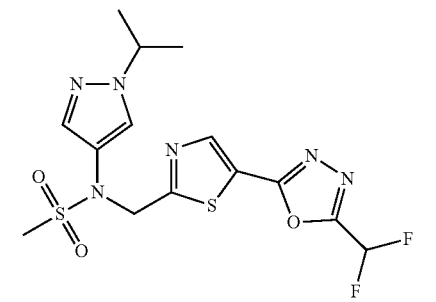 [SMILES: CC(C)n1cc(N(Cc2ncc(-c3nnc(C(F)F)o3)s2)S(C)(=O)=O)cn1]<br>N-({5-[5-(difluoromethyl)-1,3,4-oxadiazol-2-yl]-1,3-thiazol-2-yl}methyl)-N-[1-(propan-2-yl)-1H-pyrazol-4-yl]methanesulfonamide | $^1$H NMR (400 MHz, CDCl$_3$) δ 8.39 (s, 1H), 7.58 (s, 1H), 7.46 (s, 1H), 6.88 (t, J = 51.6 Hz, 1H), 5.11 (s, 2H), 4.45-4.35 (m, 1H), 3.00 (s, 3H), 1.46 (d, J = 6.8 Hz, 6H).<br>LCMS R$_T$ = 0.997 min, m/z = 419.2 | 0.118 |

TABLE 13-continued

Characterization Data and HDAC6 Activity for Compounds of Formula (I).

| Cmpd | Structure/Name | $^1$H NMR<br>MS (m/z) (RT) | HDAC6<br>IC$_{50}$<br>(μM) |
|---|---|---|---|
| I-140 | 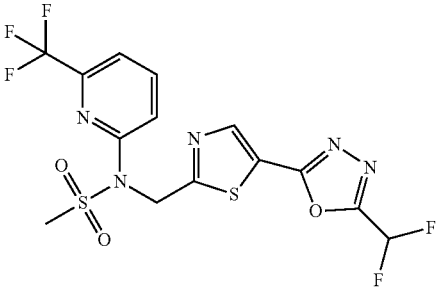 [SMILES: CS(=O)(=O)N(Cc1ncc(-c2nnc(C(F)F)o2)s1)c1cccc(C(F)(F)F)n1]<br>N-({5-[5-(difluoromethyl)-1,3,4-oxadiazol-2-yl]-1,3-thiazol-2-yl}methyl)-N-[6-(trifluoromethyl)pyridin-2-yl]methanesulfonamide | $^1$H NMR (400 MHz, CDCl$_3$) δ 8.37 (s, 1H), 7.95-7.85 (m, 2H), 7.51 (d, J = 7.2 Hz, 1H), 6.90 (t, J = 51.6 Hz, 1H), 5.61 (s, 2H), 3.29 (s, 3H).<br>LCMS R$_T$ = 1.112 min, m/z = 455.8 | 0.0576 |
| I-141 | 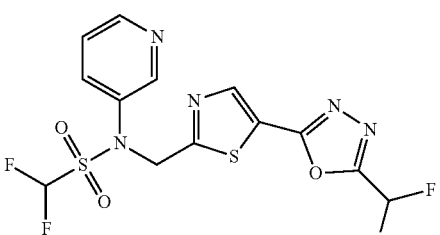<br>N-({5-[5-(difluoromethyl)-1,3,4-oxadiazol-2-yl]-1,3-thiazol-2-yl}methyl)-1,1-difluoro-N-(pyridin-3-yl)methanesulfonamide | $^1$H NMR (400 MHz, CDCl$_3$) δ 8.70-8.60 (m, 2H), 8.39 (s, 1H), 7.75 (d, J = 6.8 Hz, 1H), 7.39-7.36 (m, 1H), 6.92 (t, J = 51.6 Hz, 1H), 6.49 (t, J = 53.2 Hz, 1H), 5.35 (s, 2H).<br>LCMS R$_T$ = 0.965 min, m/z = 423.8 | 0.0655 |
| I-142 | 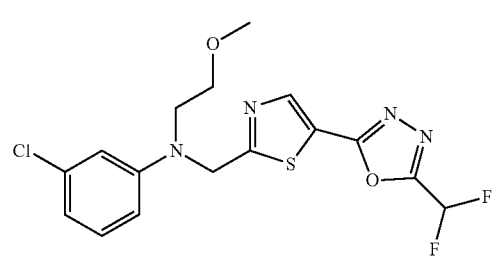 [SMILES: COCCN(Cc1ncc(-c2nnc(C(F)F)o2)s1)c1cccc(Cl)c1]<br>3-chloro-N-({5-[5-(difluoromethyl)-1,3,4-oxadiazol-2-yl]-1,3-thiazol-2-yl}methyl)-N-(2-methoxyethyl)aniline | $^1$H NMR (400 MHz, CDCl$_3$) δ 8.44 (s, 1H), 7.13 (t, J = 8.0 Hz, 1H), 6.88 (t, J = 89.2 Hz, 1H), 6.80-6.70 (m, 2H), 6.68-6.55 (m, 1H), 4.94 (s, 2H), 3.74-3.71 (m, 2H), 3.70-3.65 (m, 2H), 3.38 (s, 3H).<br>LCMS R$_T$ = 1.055 min, m/z = 400.9 | 0.0245 |
| I-143 | 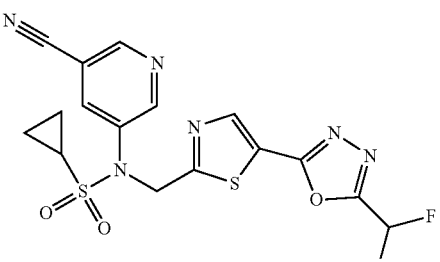<br>N-(5-cyanopyridin-3-yl)-N-({5-[5-(difluoromethyl)-1,3,4-oxadiazol-2-yl]-1,3-thiazol-2-yl}methyl)cyclopropanesulfonamide | $^1$H NMR (400 MHz, CDCl$_3$) δ 8.99 (d, J = 2.0 Hz, 1H), 8.83 (s, 1H), 8.41 (s, 1H), 8.18 (t, J = 2.0 Hz, 1H), 6.92 (t, J = 51.6 Hz, 1H), 5.31 (s, 2H), 2.59-2.50 (m, 1H), 1.13-1.08 (m, 4H).<br>LCMS R$_T$ = 0.834 min, m/z = 439.1 | 0.0153 |

TABLE 13-continued

Characterization Data and HDAC6 Activity for Compounds of Formula (I).

| Cmpd | Structure/Name | ¹H NMR<br>MS (m/z) (RT) | HDAC6 IC$_{50}$ (μM) |
|---|---|---|---|
| I-144 | 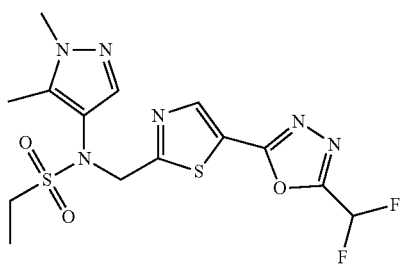 [SMILES: CCS(=O)(=O)N(Cc1ncc(-c2nnc(C(F)F)o2)s1)c1cnn(C)c1C]<br>N-({5-[5-(difluoromethyl)-1,3,4-oxadiazol-2-yl]-1,3-thiazol-2-yl}methyl)-N-(1,5-dimethyl-1H-pyrazol-4-yl)ethane-1-sulfonamide | ¹H NMR (400 MHz, CDCl$_3$) δ 8.39 (s, 1H), 7.38 (s, 1H), 6.91 (t, J = 51.6 Hz, 1H), 5.11 (s, 2H), 3.76 (s, 3H), 3.20 (q, J = 7.2 Hz, 2H), 2.25 (s, 3H), 1.47 (t, J = 7.4 Hz, 3H).<br>LCMS R$_T$ = 0.751 min, m/z = 419.0 | 0.102 |
| I-145 | 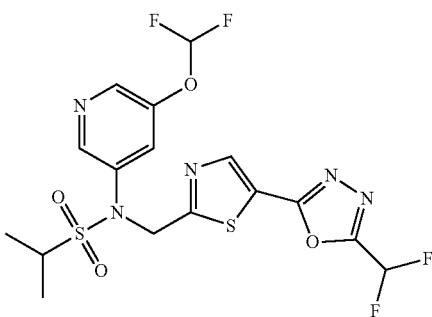 [SMILES: CC(C)S(=O)(=O)N(Cc1ncc(-c2nnc(C(F)F)o2)s1)c1cncc(OC(F)F)c1]<br>N-[5-(difluoromethoxy)pyridin-3-yl]-N-({5-[5-(difluoromethyl)-1,3,4-oxadiazol-2-yl]-1,3-thiazol-2-yl}methyl)propane-2-sulfonamide | 1H NMR (400 MHz, CDCl3) δ 8.61 (d, J = 2.0 Hz, 1H), 8.45 (d, J = 2.4 Hz, 1H), 8.38 (s, 1H), 7.68 (t, J = 2.0 Hz, 1H), 6.91 (t, J = 51.6 Hz, 1H), 6.58 (t, J = 72.0 Hz, 1H), 5.31 (s, 2H), 3.40-3.29 (m, 1H), 1.45 (d, J = 6.8 Hz, 6H).<br>LCMS RT = 1.625 min, m/z = 482.2 | 0.0102 |
| I-146 | 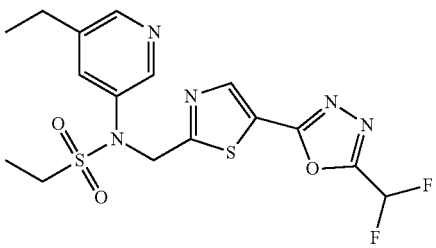 [SMILES: CCc1cncc(N(Cc2ncc(-c3nnc(C(F)F)o3)s2)S(=O)(=O)CC)c1]<br>N-({5-[5-(difluoromethyl)-1,3,4-oxadiazol-2-yl]-1,3-thiazol-2-yl}methyl)-N-(5-ethylpyridin-3-yl)ethane-1-sulfonamide | 1H NMR (400 MHz, CD3OD) δ 8.59 (s, 1H), 8.40 (s, 2H), 8.02 (s, 1H), 7.19 (t, J = 51.2 Hz, 1H), 5.40 (s, 2H), 3.40-3.30 (m, 2H), 2.73 (q, J = 7.6 Hz, 2H), 1.39 (t, J = 7.6 Hz, 3H), 1.25 (t, J = 7.6 Hz, 3H).<br>LCMS RT = 1.215 min, m/z = 430.2 | 0.0162 |

TABLE 13-continued

Characterization Data and HDAC6 Activity for Compounds of Formula (I).

| Cmpd | Structure/Name | ¹H NMR MS (m/z) (RT) | HDAC6 IC$_{50}$ (μM) |
|---|---|---|---|
| I-147 | 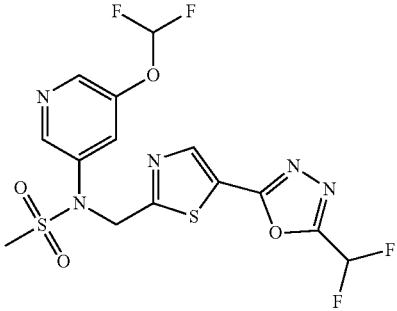 [SMILES: CS(=O)(=O)N(Cc1ncc(-c2nnc(C(F)F)o2)s1)c1cncc(OC(F)F)c1]<br>N-[5-(difluoromethoxy)pyridin-3-yl]-N-({5-[5-(difluoromethyl)-1,3,4-oxadiazol-2-yl]-1,3-thiazol-2-yl}methyl)methanesulfonamide | 1H NMR (400 MHz, CDCl3) δ 8.62 (s, 1H), 8.49 (s, 1H), 8.43 (s, 1H), 7.69 (s, 1H), 6.92 (t, J = 51.6 Hz, 1H), 6.59 (t, J = 72.0 Hz, 1H), 5.28 (s, 2H), 3.12 (s, 3H). LCMS RT = 1.512 min, m/z = 453.8 | 0.019 |
| I-148 | 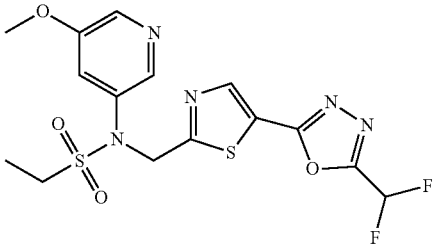 [SMILES: CCS(=O)(=O)N(Cc1ncc(-c2nnc(C(F)F)o2)s1)c1cncc(OC)c1]<br>N-({5-[5-(difluoromethyl)-1,3,4-oxadiazol-2-yl]-1,3-thiazol-2-yl}methyl)-N-(5-methoxypyridin-3-yl)ethane-1-sulfonamide | 1H NMR (400 MHz, CDCl3) δ ppm 8.39 (s, 1H), 8.30-8.28 (m, 2H), 7.38 (s, 1H), 6.91 (t, J = 51.6 Hz, 1H), 5.30 (s, 2H), 3.87 (s, 3H), 3.21 (q, J = 7.6 Hz, 2H), 1.46 (t, J = 7.6 Hz, 3H). LCMS RT = 1.360 min, m/z = 431.9 [M + H]+ | 0.0192 |
| I-149 | 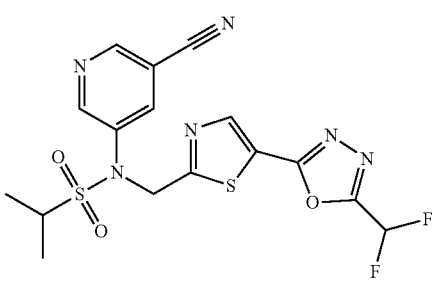 [SMILES: CC(C)S(=O)(=O)N(Cc1ncc(-c2nnc(C(F)F)o2)s1)c1cncc(C#N)c1]<br>N-(5-cyanopyridin-3-yl)-N-({5-[5-(difluoromethyl)-1,3,4-oxadiazol-2-yl]-1,3-thiazol-2-yl}methyl)propane-2-sulfonamide | 1H NMR (400 MHz, CDCl3) δ 8.95 (d, J = 2.8 Hz, 1H), 8.80 (s, 1H), 8.39 (s, 1H), 8.16 (s, 1H), 6.92 (t, J = 51.6 Hz, 1H), 5.30 (s, 2H), 3.39-3.25 (m, 1H), 1.45 (d, J = 6.8 Hz, 6H). LCMS RT = 1.584 min, m/z = 440.9 | 0.0231 |

TABLE 13-continued

Characterization Data and HDAC6 Activity for Compounds of Formula (I).

| Cmpd | Structure/Name | ¹H NMR<br>MS (m/z) (RT) | HDAC6<br>IC$_{50}$<br>(µM) |
|---|---|---|---|
| I-150 | 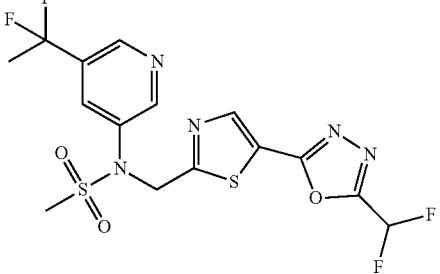<br>N-[5-(1,1-difluoroethyl)pyridin-3-yl]-N-({5-[5-(difluoromethyl)-1,3,4-oxadiazol-2-yl]-1,3-thiazol-2-yl}methyl)methanesulfonamide | 1H NMR (400 MHz, CDCl3) δ 8.80 (s, 1H), 8.75 (s, 1H), 8.43 (s, 1H), 7.98 (s, 1H), 6.92 (t, J = 51.6 Hz, 1H), 5.29 (s, 2H), 3.12 (s, 3H), 1.98 (t, J = 18.0 Hz, 3H).<br>LCMS RT = 1.554 min, m/z = 451.8 | 0.0255 |
| I-151 | 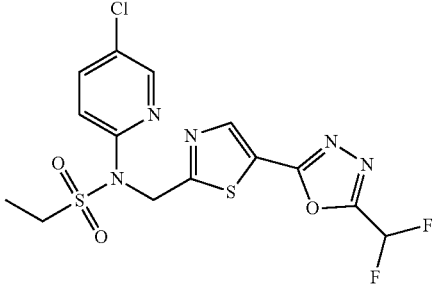 [SMILES: CCS(=O)(=O)N(Cc1ncc(-c2nnc(C(F)F)o2)s1)c1ccc(Cl)cn1]<br>N-(5-chloropyridin-2-yl)-N-({5-[5-(difluoromethyl)-1,3,4-oxadiazol-2-yl]-1,3-thiazol-2-yl}methyl)ethane-1-sulfonamide | 1H NMR (400 MHz, CDCl3) δ 8.37 (d, J = 4.0 Hz, 2H), 7.74-7.67 (m, 2H), 6.90 (t, J = 51.6 Hz, 1H), 5.56 (s, 2H), 3.29 (q, J = 7.2 Hz, 2H), 1.39 (t, J = 7.2 Hz, 3H).<br>LCMS RT = 1.826 min, m/z = 436.1 | 0.0315 |
| I-152 | 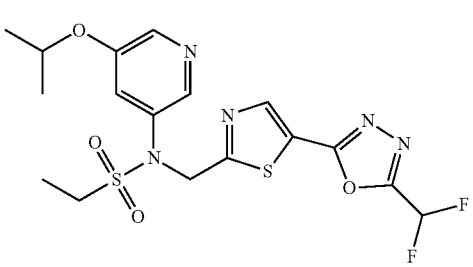 [SMILES: CCS(=O)(=O)N(Cc1ncc(-c2nnc(C(F)F)o2)s1)c1cncc(OC(C)C)c1]<br>N-({5-[5-(difluoromethyl)-1,3,4-oxadiazol-2-yl]-1,3-thiazol-2-yl}methyl)-N-[5-(propan-2-yloxy)pyridin-3-yl]ethane-1-sulfonamide | 1H NMR (400 MHz, CDCl3) δ 8.39 (s, 1H), 8.25 (s, 2H), 7.35 (s, 1H), 6.91 (t, J = 51.6 Hz, 1H), 5.29 (s, 2H), 4.61-4.55 (m, 1H), 3.25-3.18 (m, 2H), 1.61 (s, 3H), 1.36 (d, J = 4.4 Hz, 6H).<br>LCMS RT = 1.666 min, m/z = 459.9 | 0.0429 |

TABLE 13-continued

Characterization Data and HDAC6 Activity for Compounds of Formula (I).

| Cmpd | Structure/Name | ¹H NMR<br>MS (m/z) (RT) | HDAC6 IC$_{50}$ (μM) |
|---|---|---|---|
| I-153 | 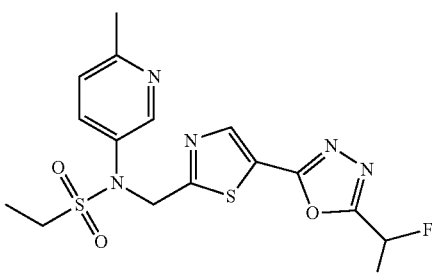<br>N-({5-[5-(difluoromethyl)-1,3,4-oxadiazol-2-yl]-1,3-thiazol-2-yl}methyl)-N-(5-methylpyridin-2-yl)ethane-1-sulfonamide | 1H NMR (400 MHz, CDCl3) δ 8.22 (s, 1H), 8.10 (s, 1H), 7.40 (s, 2H), 6.75 (t, J = 51.6 Hz, 1H), 5.42 (s, 2H), 3.09 (q, J = 7.6 Hz, 2H), 2.18 (s, 3H), 1.23 (t, J = 7.2 Hz, 3H).<br>LCMS RT = 1.666 min, m/z = 416.2 | 0.043 |
| I-155 | 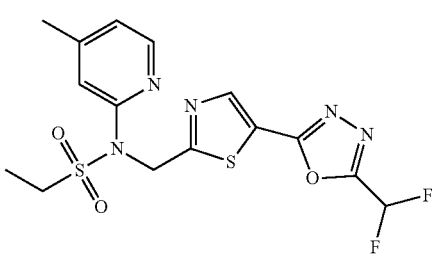 [SMILES: CCS(=O)(=O)N(Cc1ncc(-c2nnc(C(F)F)o2)s1)c1cc(C)ccn1]<br>N-({5-[5-(difluoromethyl)-1,3,4-oxadiazol-2-yl]-1,3-thiazol-2-yl}methyl)-N-(4-methylpyridin-2-yl)ethane-1-sulfonamide | 1H NMR (400 MHz, CDCl3) δ 8.39 (s, 1H), 8.29 (d, J = 4.8 Hz, 1H), 7.47 (s, 1H), 7.01 (d, J = 4.8 Hz, 1H), 6.90 (t, J = 51.6 Hz, 1H), 5.60 (s, 2H), 3.28 (q, J = 7.6 Hz, 2H), 2.40 (s, 3H), 1.39 (t, J = 7.2 Hz, 3H).<br>LCMS RT = 1.635 min, m/z = 416.2 | 0.0528 |
| I-156 | 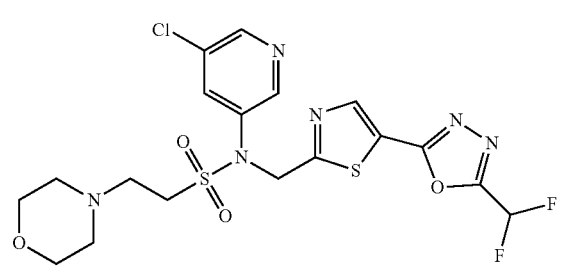 [SMILES: O=S(=O)(CCN1CCOCC1)N(Cc1ncc(-c2nnc(C(F)F)o2)s1)c1cncc(Cl)c1]<br>N-(5-chloropyridin-3-yl)-N-({5-[5-(difluoromethyl)-1,3,4-oxadiazol-2-yl]-1,3-thiazol-2-yl}methyl)-2-(morpholin-4-yl)ethane-1-sulfonamide | 1H NMR (400 MHz, CD3OD) δ ppm 8.68 (d, J = 2.4 Hz, 1H), 8.52 (d, J = 2.0 Hz, 1H), 8.44 (s, 1H), 8.17 (t, J = 2.0 Hz, 1H), 7.22 (t, J = 52.0 Hz, 1H), 5.45 (s, 2H), 3.73-3.70 (m, 4H), 3.58 (t, J = 7.6 Hz, 2H), 2.89 (t, J = 6.8 Hz, 2H), 2.58-2.51 (m, 4H).<br>LCMS RT = 0.992 min, m/z = 521.2 | 0.00253 |

TABLE 13-continued

Characterization Data and HDAC6 Activity for Compounds of Formula (I).

| Cmpd | Structure/Name | ¹H NMR MS (m/z) (RT) | HDAC6 IC$_{50}$ (µM) |
|---|---|---|---|
| I-157 | 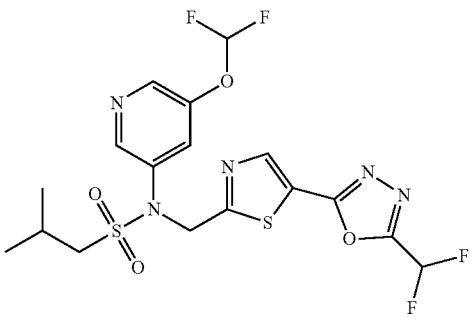 [SMILES: CC(C)CS(=O)(=O)N(Cc1ncc(-c2nnc(C(F)F)o2)s1)c1cncc(OC(F)F)c1]<br>N-[5-(difluoromethoxy)pyridin-3-yl]-N-({5-[5-(difluoromethyl)-1,3,4-oxadiazol-2-yl]-1,3-thiazol-2-yl}methyl)-2-methylpropane-1-sulfonamide | 1H NMR (400 MHz, CDCl3) δ 8.59 (d, J = 2.0 Hz, 1H), 8.47 (d, J = 2.0 Hz, 1H), 8.40 (s, 1H), 7.67 (t, J = 2.4 Hz, 1H), 6.91 (t, J = 51.6 Hz, 1H), 6.59 (t, J = 72.0 Hz, 1H), 5.28 (s, 2H), 3.05 (d, J = 8.0 Hz, 2H), 2.40-2.30 (m, 1H), 1.12 (d, J = 6.8 Hz, 6H). LCMS RT = 0.644 min, m/z = 496.1 | 0.00693 |
| I-158 | 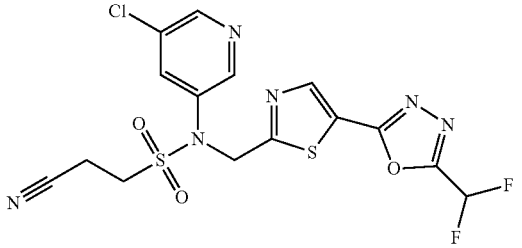 [SMILES: N#CCCS(=O)(=O)N(Cc1ncc(-c2nnc(C(F)F)o2)s1)c1cncc(Cl)c1]<br>N-(5-chloropyridin-3-yl)-2-cyano-N-({5-[5-(difluoromethyl)-1,3,4-oxadiazol-2-yl]-1,3-thiazol-2-yl}methyl)ethane-1-sulfonamide | 1H NMR (400 MHz, CDCl3) δ ppm 8.63 (d, J = 2.4 Hz, 1H), 8.60 (d, J = 2.0 Hz, 1H), 8.46 (s, 1H), 7.91 (t, J = 2.4 Hz, 1H), 6.93 (t, J = 51.6 Hz, 1H), 5.30 (s, 2H), 3.54 (t, J = 7.2 Hz, 2H), 2.98 (t, J = 7.2 Hz, 2H). LCMS RT = 0.576 min, m/z = 461.1 | 0.00722 |
| I-159 | 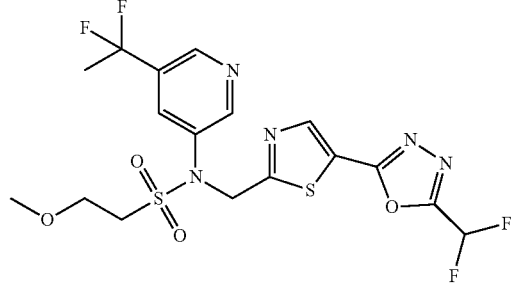 [SMILES: COCCS(=O)(=O)N(Cc1ncc(-c2nnc(C(F)F)o2)s1)c1cncc(C(C)(F)F)c1]<br>N-[5-(1,1-difluoroethyl)pyridin-3-yl]-N-({5-[5-(difluoromethyl)-1,3,4-oxadiazol-2-yl]-1,3-thiazol-2-yl}methyl)-2-methoxyethane-1-sulfonamide | 1H NMR (400 MHz, CDCl3) δ 8.85 (s, 1H), 8.56 (s, 1H), 8.72 (s, 1H), 8.35 (s, 1H), 8.01 (s, 1H), 6.91 (t, J = 51.6 Hz, 1H), 5.26 (s, 2H), 3.87 (t, J = 5.2 Hz, 2H), 3.50 (s, 3H), 3.36 (t, J = 5.2 Hz, 2H), 1.97 (t, J = 18.4 Hz, 3H). LCMS RT = 1.701 min, m/z = 495.9 | 0.00994 |

TABLE 13-continued

Characterization Data and HDAC6 Activity for Compounds of Formula (I).

| Cmpd | Structure/Name | ¹H NMR MS (m/z) (RT) | HDAC6 IC$_{50}$ (μM) |
|---|---|---|---|
| I-160 | N-({5-[5-(difluoromethyl)-1,3,4-oxadiazol-2-yl]-1,3-thiazol-2-yl}methyl)-N-(5-methylpyridin-3-yl)propane-1-sulfonamide | 1H NMR (400 MHz, CDCl3) δ 8.49 (d, J = 2.4 Hz, 1H), 8.41 (s, 1H), 8.38 (s, 1H), 7.65 (s, 1H), 6.91 (t, J = 51.6 Hz, 1H), 5.27 (s, 2H), 3.16-3.08 (m, 2H), 2.37 (s, 3H), 1.99-1.85 (m, 2H), 1.09 (t, J = 7.2 Hz, 3H). LCMS RT = 1.815 min, m/z = 430.2 | 0.0109 |
| I-161 | N-(5-chloropyridin-3-yl)-N-({5-[5-(difluoromethyl)-1,3,4-oxadiazol-2-yl]-1,3-thiazol-2-yl}methyl)-2-methoxyethane-1-sulfonamide | 1H NMR (400 MHz, CDCl3) δ 8.67 (s, 1H), 8.53 (s, 1H), 8.35 (s, 1H), 7.90 (t, J = 2.0 Hz, 1H), 6.90 (t, J = 51.6 Hz, 1H), 5.22 (s, 2H), 3.86 (t, J = 5.6 Hz, 2H), 3.49 (s, 3H), 3.36 (t, J = 5.6 Hz, 2H). LCMS RT = 1.529 min, m/z = 466.1 | 0.012 |
| I-162 | N-[5-(difluoromethoxy)pyridin-3-yl]-N-({5-[5-(difluoromethyl)-1,3,4-oxadiazol-2-yl]-1,3-thiazol-2-yl}methyl)propane-1-sulfonamide | 1H NMR (400 MHz, CDCl3) δ 8.60 (s, 1H), 8.47 (s, 1H), 8.40 (s, 1H), 7.67 (s, 1H), 6.91 (t, J = 51.6 Hz, 1H), 6.59 (t, J = 72.0 Hz, 1H), 5.29 (s, 2H), 3.19-3.11 (m, 2H), 1.99-1.86 (m, 2H), 1.09 (t, J = 7.2 Hz, 3H). LCMS RT = 1.794 min, m/z = 481.9 | 0.0144 |
| I-163 | N-({5-[5-(difluoromethyl)-1,3,4-oxadiazol-2-yl]-1,3-thiazol-2-yl}methyl)-2-methyl-N-(pyridin-3-yl)propane-1-sulfonamide | 1H NMR (400 MHz, CDCl3) δ 8.70 (d, J = 2.4 Hz, 1H), 8.60-8.55 (m, 1H), 8.41 (s, 1H), 8.07-8.01 (m, 1H), 7.53-7.47 (m, 1H), 7.20 (t, J = 51.6 Hz, 1H), 5.37 (s, 2H), 3.20 (d, J = 6.4 Hz, 2H), 2.34-2.22 (m, 1H), 1.10 (d, J = 6.4 Hz, 6H). LCMS RT = 1.423 min, m/z = 430.2 | 0.0161 |

TABLE 13-continued

Characterization Data and HDAC6 Activity for Compounds of Formula (I).

| Cmpd | Structure/Name | ¹H NMR<br>MS (m/z) (RT) | HDAC6<br>IC$_{50}$<br>(µM) |
|---|---|---|---|
| I-164 | 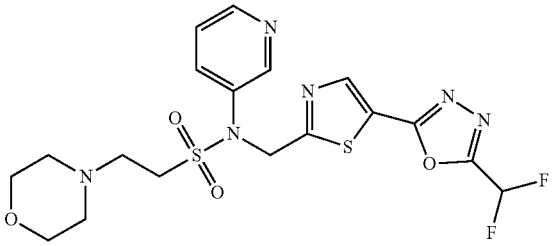 [SMILES: O=S(=O)(CCN1CCOCC1)N(Cc1ncc(-c2nnc(C(F)F)o2)s1)c1cccnc1]<br>N-({5-[5-(difluoromethyl)-1,3,4-oxadiazol-2-yl]-1,3-thiazol-2-yl}methyl)-2-(morpholin-4-yl)-N-(pyridin-3-yl)ethane-1-sulfonamide | 1H NMR (400 MHz, CDCl3) δ ppm 8.73 (d, J = 2.4 Hz, 1H), 8.60-8.55 (m, 1H), 8.38 (s, 1H), 7.87-7.81 (m, 1H), 7.38-7.33 (m, 1H), 6.91 (t, J = 51.6 Hz, 1H), 5.32 (s, 2H), 3.76-3.72 (m, 4H), 3.37 (t, J = 7.2 Hz, 2H), 2.90 (t, J = 6.8 Hz, 2H), 2.52-2.50 (m, 4H).<br>LCMS RT = 0.430 min, m/z = 487.2 | 0.0173 |
| I-165 | 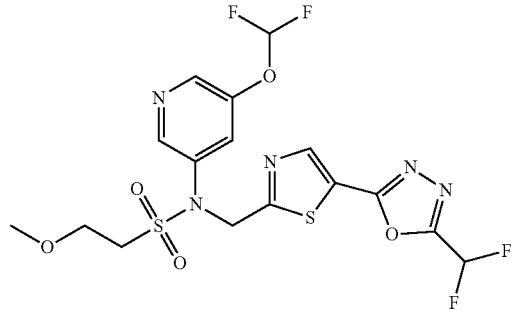 [SMILES: COCCS(=O)(=O)N(Cc1ncc(-c2nnc(C(F)F)o2)s1)c1cncc(OC(F)F)c1]<br>N-[5-(difluoromethoxy)pyridin-3-yl]-N-({5-[5-(difluoromethyl)-1,3,4-oxadiazol-2-yl]-1,3-thiazol-2-yl}methyl)-2-methoxyethane-1-sulfonamide | 1H NMR (400 MHz, CD3OD) δ 8.59 (s, 1H), 8.40 (s, 2H), 7.87 (d, J = 2.4 Hz, 1H), 7.19 (t, J = 51.6 Hz, 1H), 6.97 (t, J = 72.8 Hz, 1H), 5.34 (s, 2H), 3.83 (t, J = 5.2 Hz, 2H), 3.52 (t, J = 5.6 Hz, 2H), 3.30 (t, J = 1.6 Hz, 3H).<br>LCMS RT = 1.533 min, m/z = 498.2 | 0.0196 |
| I-166 | 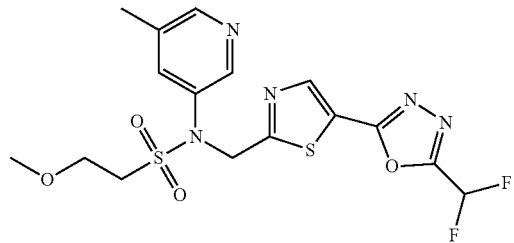 [SMILES: COCCS(=O)(=O)N(Cc1ncc(-c2nnc(C(F)F)o2)s1)c1cncc(C)c1]<br>N-({5-[5-(difluoromethyl)-1,3,4-oxadiazol-2-yl]-1,3-thiazol-2-yl}methyl)-2-methoxy-N-(5-methylpyridin-3-yl)ethane-1-sulfonamide | 1H NMR (400 MHz, CD3OD) δ 8.49 (s, 1H), 8.39 (s, 1H), 8.34 (s, 1H), 7.87 (s, 1H), 7.20 (t, J = 51.6 Hz, 1H), 5.31 (s, 2H), 3.83 (t, J = 5.2 Hz, 2H), 3.49 (t, J = 5.6 Hz, 2H), 3.43 (s, 3H), 2.38 (s, 3H).<br>LCMS RT = 2.329 min, m/z = 446.5 | 0.0266 |

TABLE 13-continued

Characterization Data and HDAC6 Activity for Compounds of Formula (I).

| Cmpd | Structure/Name | ¹H NMR MS (m/z) (RT) | HDAC6 IC$_{50}$ (µM) |
|---|---|---|---|
| I-167 | 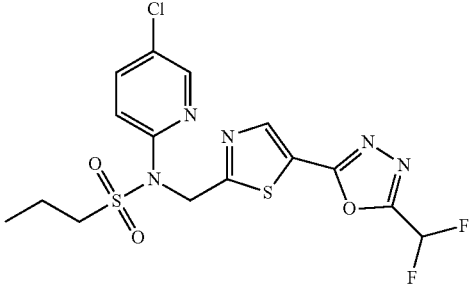 [SMILES: CCCS(=O)(=O)N(Cc1ncc(-c2nnc(C(F)F)o2)s1)c1ccc(Cl)cn1]<br>N-(5-chloropyridin-2-yl)-N-({5-[5-(difluoromethyl)-1,3,4-oxadiazol-2-yl]-1,3-thiazol-2-yl}methyl)propane-1-sulfonamide | 1H NMR (400 MHz, CDCl3) δ 8.40-8.35 (m, 2H), 7.73-7.68 (m, 1H), 7.66-7.60 (m, 1H), 6.89 (t, J = 51.6 Hz, 1H), 5.55 (s, 2H), 3.26-3.17 (m, 2H), 1.93-1.81 (m, 2H), 1.05 (t, J = 7.4 Hz, 3H). LCMS RT = 2.072 min, m/z = 449.8 | 0.0266 |
| I-168 | 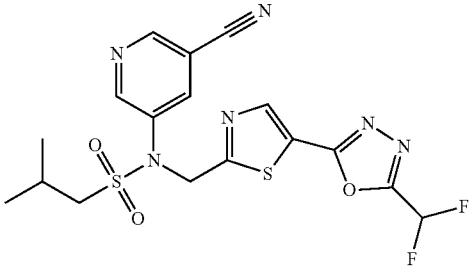 [SMILES: CC(C)CS(=O)(=O)N(Cc1ncc(-c2nnc(C(F)F)o2)s1)c1cncc(C#N)c1]<br>N-(5-cyanopyridin-3-yl)-N-({5-[5-(difluoromethyl)-1,3,4-oxadiazol-2-yl]-1,3-thiazol-2-yl}methyl)-2-methylpropane-1-sulfonamide | 1H NMR (400 MHz, CDCl3) δ 8.95 (d, J = 2.4 Hz, 1H), 8.82 (s, 1H), 8.42 (s, 1H), 8.16 (s, 1H), 6.92 (t, J = 52.0 Hz, 1H), 5.28 (s, 2H), 3.03 (d, J = 6.4 Hz, 2H), 2.42-2.28 (m, 1H), 1.12 (d, J = 6.8 Hz, 6H). LCMS RT = 1.690 min, m/z = 455.2 | 0.0305 |
| I-169 | 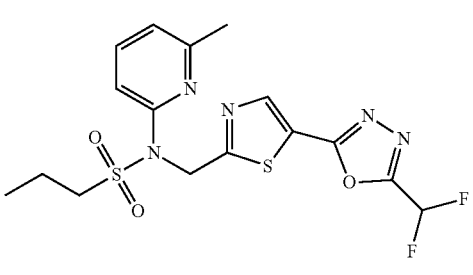 [SMILES: CCCS(=O)(=O)N(Cc1ncc(-c2nnc(C(F)F)o2)s1)c1cccc(C)n1]<br>N-({5-[5-(difluoromethyl)-1,3,4-oxadiazol-2-yl]-1,3-thiazol-2-yl}methyl)-N-(6-methylpyridin-2-yl)propane-1-sulfonamide | 1H NMR (400 MHz, CDCl3) δ 8.38 (s, 1H), 7.61 (t, J = 7.6 Hz, 1H), 7.45 (d, J = 8.4 Hz, 1H), 7.02-6.75 (m, 2H), 5.59 (s, 2H), 3.22-3.15 (m, 2H), 2.52 (s, 3H), 1.93-1.80 (m, 2H), 1.03 (t, J = 7.6 Hz, 3H). LCMS RT = 1.942 min, m/z = 429.9 | 0.0309 |
| I-170 | 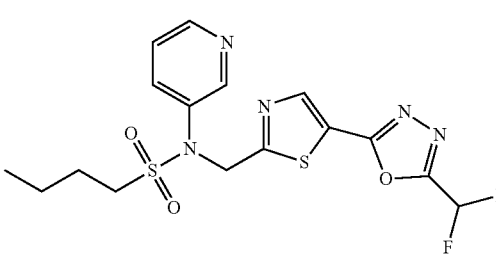<br>N-({5-[5-(difluoromethyl)-1,3,4-oxadiazol-2-yl]-1,3-thiazol-2-yl}methyl)-N-(pyridin-3-yl)butane-1-sulfonamide | 1H NMR (400 MHz, CDCl3) δ 8.70 (s, 1H), 8.58 (d, J = 4.8 Hz, 1H), 8.38 (s, 1H), 7.90-7.80 (m, 1H), 7.45-7.31 (m, 1H), 6.91 (t, J = 51.2 Hz, 1H), 5.29 (s, 2H), 3.21-3.06 (m, 2H), 1.92-1.83 (m, 2H), 1.52-1.43 (m, 2H), 0.96 (t, J = 7.2 Hz, 3H). LCMS RT = 0.623 min, m/z = 429.9 | 0.0264 |

TABLE 13-continued

Characterization Data and HDAC6 Activity for Compounds of Formula (I).

| Cmpd | Structure/Name | $^1$H NMR<br>MS (m/z) (RT) | HDAC6<br>IC$_{50}$<br>(μM) |
|---|---|---|---|
| I-171 | 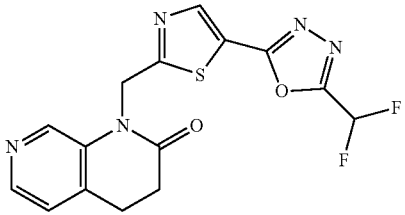 [SMILES: O=C1CCc2ccncc2N1Cc1ncc(-c2nnc(C(F)F)o2)s1]<br>1-({5-[5-(difluoromethyl)-1,3,4-oxadiazol-2-yl]-1,3-thiazol-2-yl}methyl)-1,2,3,4-tetrahydro-1,7-naphthyridin-2-one | 1H NMR (400 MHz, CDCl3) δ 8.55 (s, 1H), 8.42 (s, 1H), 8.31 (d, J = 3.6 Hz, 1H), 7.16 (d, J = 4.4 Hz, 1H), 6.89 (t, J = 51.6 Hz, 1H), 5.52 (s, 2H), 3.04 (t, J = 6.8 Hz, 2H), 2.81 (t, J = 8.0 Hz, 2H). LCMS RT = 1.398 min, m/z = 363.9 | 0.0215 |
| I-172 | 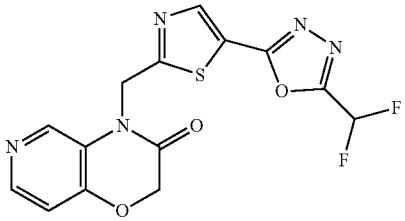 [SMILES: O=C1COc2ccncc2N1Cc1ncc(-c2nnc(C(F)F)o2)s1]<br>4-({5-[5-(difluoromethyl)-1,3,4-oxadiazol-2-yl]-1,3-thiazol-2-yl}methyl)-2H,3H,4H-pyrido[4,3-b][1,4]oxazin-3-one | 1H NMR (400 MHz, CDCl3) δ 8.52 (s, 1H), 8.43 (s, 1H), 8.27 (d, J = 5.6 Hz, 1H), 6.96 (d, J = 5.2 Hz, 1H), 6.90 (t, J = 51.6 Hz, 1H), 5.52 (s, 2H), 4.85 (s, 2H). LCMS RT = 0.418 min, m/z = 366.0 | 0.025 |
| I-173 | 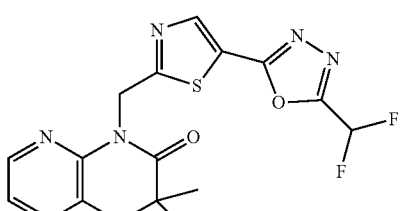<br>4-((5-(5-(difluoromethyl)-1,3,4-oxadiazol-2-yl)thiazol-2-yl)methyl)-2,2-dimethyl-2H-pyrido[3,2-b][1,4]oxazin-3(4H)-one | $^1$H NMR (400 MHz, CDCl$_3$) δ 8.39 (s, 1H), 8.01-8.05 (m, 1H), 7.29 (dd, J = 8.1, 1.5 Hz, 1H), 7.01 (dd, J = 8.1, 1.5 Hz, 1H), 6.89 (t, J = 51.6 Hz, 1H), 5.70 (s, 2H) LCMS: RT = 5.00 min, m/z = 394.0 | 0.108 |
| I-174 | 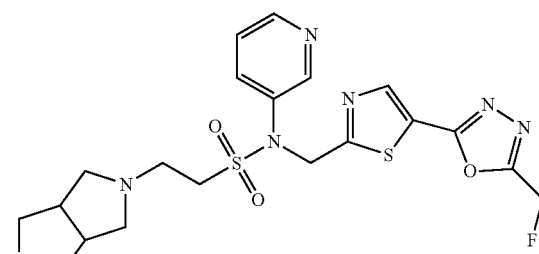<br>N-((5-(5-(difluoromethyl)-1,3,4-oxadiazol-2-yl)thiazol-2-yl)methyl)-N-(pyridin-3-yl)-2-(tetrahydro-1H-furo[3,4-c]pyrrol-5(3H)-yl)ethane-1-sulfonamide | 1H NMR (400 MHz, CDCl3) δ 8.76 (s, 1H), 8.58 (d, J = 4.4 Hz, 1H), 8.39 (s, 1H), 7.89 (d, J = 8.4 Hz, 1H), 7.40-7.35 (m, 1H), 6.91 (t, J = 51.6 Hz, 1H), 5.33 (s, 2H), 3.75-3.70 (m, 4H), 3.49 (t, J = 6.8 Hz, 2H), 3.07 (t, J = 6.8 Hz, 2H), 2.99-2.96 (m, 4H), 2.49 (d, J = 6.0 Hz, 2H). LCMS RT = 1.435 min, m/z = 513.0 | 0.022 |

TABLE 13-continued

Characterization Data and HDAC6 Activity for Compounds of Formula (I).

| Cmpd | Structure/Name | $^1$H NMR<br>MS (m/z) (RT) | HDAC6<br>IC$_{50}$<br>(µM) |
|---|---|---|---|
| I-175 | N-({5-[5-(difluoromethyl)-1,3,4-oxadiazol-2-yl]-1,3-thiazol-2-yl}methyl)-N-(5-fluoropyridin-3-yl)-3-(morpholin-4-yl)propanamide | 1H NMR (400 MHz, CDCl3) δ 8.55 (d, J = 2.0 Hz, 1H), 8.43-8.36 (m, 2H), 7.50-7.44 (m, 1 H), 6.92 (t, J = 51.6 Hz, 1H), 5.20 (s, 2H), 3.71-3.66 (m, 4H), 2.81 (t, J = 6.8 Hz, 2H), 2.50-2.22 (m, 6H).<br>LCMS RT = 0.400 min, m/z = 469.2 | 0.496 |
| I-176 | 1-({5-[5-(difluoromethyl)-1,3,4-oxadiazol-2-yl]-1,3-thiazol-2-yl}methyl)-1H,2H,3H-pyrido[3,4-b][1,4]oxazin-2-one | 1H NMR (400 MHz, CD3OD) δ 8.54-8.53 (m, 1H), 8.13-8.10 (m, 1H), 7.22 (t, J = 51.6 Hz, 1H), 6.97-6.89 (m, 1H), 5.84-5.78 (m, 1H), 4.72-4.45 (m, 4H).<br>LCMS RT = 1.091 min, m/z = 365.8 | 2.52 |
| I-177 | N-[5-(difluoromethoxy)pyridin-3-yl]-N-({5-[5-(difluoromethyl)-1,3,4-oxadiazol-2-yl]-1,3-thiazol-2-yl}methyl)butane-2-sulfonamide | 1H NMR (400 MHz, CDCl3) δ 8.59 (d, J = 2.0 Hz, 1H), 8.45 (d, J = 2.4 Hz, 1H), 8.37 (s, 1H), 7.67 (t, J = 2.4 Hz, 1H), 6.91 (t, J = 51.6 Hz, 1H), 6.58 (t, J = 72.0 Hz, 1H), 5.38-5.20 (m, 2H), 3.15-3.07 (m, 1H), 2.13-2.02 (m, 1H), 1.73-1.60 (m, 1H), 1.43 (d, J = 6.8 Hz, 3H), 1.05 (t, J = 7.2 Hz, 3H).<br>LCMS RT = 1.580 min, m/z = 496.2 | 0.006 |
| I-178 | N-({5-[5-(difluoromethyl)-1,3,4-oxadiazol-2-yl]-1,3-thiazol-2-yl}methyl)-N-[(pyridin-3-yl)methyl]ethane-1-sulfonamide | 1H NMR (400 MHz, CDCl3) δ 8.62-8.55 (m, 2H), 8.42 (s, 1H), 7.88-7.82 (m, 1H), 7.38-7.34 (m, 1H), 6.88 (t, J = 51.6 Hz, 1H), 4.71 (s, 2H), 4.60 (s, 2H), 3.19 (q, J = 7.6 Hz, 2H), 1.44 (t, J = 7.2 Hz, 3H).<br>LCMS RT = 1.031 min, m/z = 416.2 | 4.35 |

TABLE 13-continued

Characterization Data and HDAC6 Activity for Compounds of Formula (I).

| Cmpd | Structure/Name | ¹H NMR<br>MS (m/z) (RT) | HDAC6<br>IC$_{50}$<br>(µM) |
|---|---|---|---|
| I-179 | 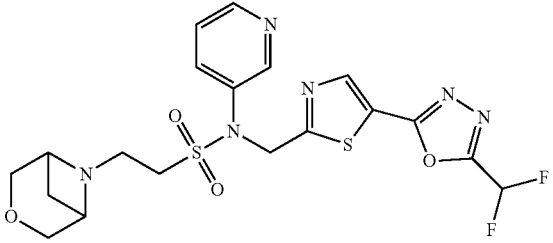 [SMILES: O=S(=O)(CCN1C2COCC1C2)N(Cc1ncc(-c2nnc(C(F)F)o2)s1)c1cccnc1]<br>N-({5-[5-(difluoromethyl)-1,3,4-oxadiazol-2-yl]-1,3-thiazol-2-yl}methyl)-2-{3-oxa-6-azabicyclo[3.1.1]heptan-6-yl}-N-(pyridin-3-yl)ethane-1-sulfonamide | 1H NMR (400 MHz, CDCl3) δ 8.76 (d, J = 2.4 Hz, 1H), 8.58 (d, J = 3.2 Hz, 1H), 8.38 (s, 1H), 7.89-7.86 (m, 1H), 7.39-7.35 (m, 1H), 6.91 (t, J = 51.6 Hz, 1H), 5.34 (s, 2H), 4.22 (d, J = 11.2 Hz, 2H), 3.81 (d, J = 11.6 Hz, 2H), 3.64 (d, J = 6.4 Hz, 2H), 3.36-3.20 (m, 4H), 2.74-2.69 (m, 1H), 1.91 (d, J = 8.8 Hz, 1H).<br>LCMS RT = 1.438 min, m/z = 499.0 | 0.013 |
| I-180 | 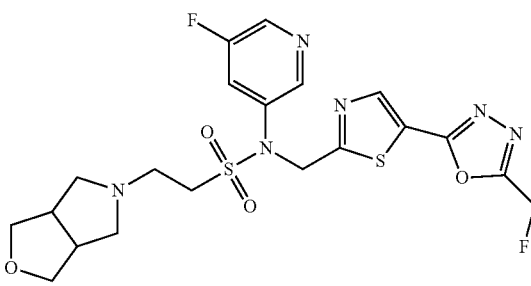<br>N-({5-[5-(difluoromethyl)-1,3,4-oxadiazol-2-yl]-1,3-thiazol-2-yl}methyl)-N-(5-fluoropyridin-3-yl)-2-{hexahydro-1H-furo[3,4-c]pyrrol-5-yl}ethane-1-sulfonamide | 1H NMR (400 MHz, CDCl3) δ 8.62 (s, 1H), 8.45 (d, J = 2.4 Hz, 1H), 8.38 (s, 1H), 7.75-7.70 (m, 1H), 6.91 (t, J = 51.6 Hz, 1H), 5.35 (s, 2H), 3.78-3.69 (m, 4H), 3.34 (t, J = 6.8 Hz, 2H), 2.94 (t, J = 6.4 Hz, 2H), 2.87-2.86 (m, 2H), 2.72-2.68 (m, 2H), 2.49-2.46 (m, 2H).<br>LCMS RT = 0.417 min, m/z = 531.2 | 0.010 |
| I-181 | 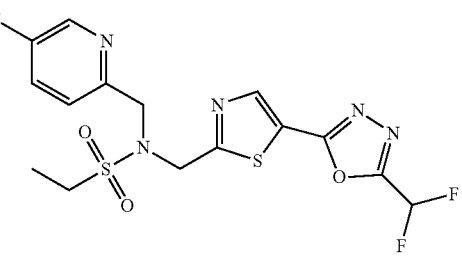<br>N-({5-[5-(difluoromethyl)-1,3,4-oxadiazol-2-yl]-1,3-thiazol-2-yl}methyl)-N-[(5-fluoropyridin-2-yl)methyl]ethane-1-sulfonamide | 1H NMR (400 MHz, CDCl3) δ 8.44 (t, J = 2.0 Hz, 1H), 8.41 (s, 1H), 7.44 (d, J = 2.4 Hz, 1H), 7.42 (s, 1H), 6.92 (t, J = 51.6 Hz, 1H), 4.86 (s, 2H), 4.65 (s, 2H), 3.23 (q, J = 7.2 Hz, 2H), 1.42 (t, J = 7.2 Hz, 3H).<br>LCMS RT = 1.338 min, m/z = 434.2 | 3.46 |

TABLE 13-continued

Characterization Data and HDAC6 Activity for Compounds of Formula (I).

| Cmpd | Structure/Name | ¹H NMR MS (m/z) (RT) | HDAC6 IC$_{50}$ (μM) |
|---|---|---|---|
| I-182 | N-({5-[5-(difluoromethyl)-1,3,4-oxadiazol-2-yl]-1,3-thiazol-2-yl}methyl)-N-(5-fluoropyridin-3-yl)-2-{3-oxa-6-azabicyclo[3.1.1]heptan-6-yl}ethane-1-sulfonamide | 1H NMR (400 MHz, CDCl3) δ 8.61 (s, 1H), 8.46 (d, J = 2.4 Hz, 1H), 8.39 (s, 1H), 7.72-7.65 (m, 1H), 6.91 (t, J = 51.6 Hz, 1H), 5.35 (s, 2H), 4.19 (d, J = 11.2 Hz, 2H), 3.78 (d, J = 11.2 Hz, 2H), 3.56 (d, J = 6.4 Hz, 2H), 3.29-3.25 (m, 2H), 3.21-3.18 (m, 2H), 2.70-2.65 (m, 1H), 1.89 (d, J = 8.4 Hz, 1H). LCMS RT = 0.844 min, m/z =517.3 | 0.018 |
| I-183 | N-({5-[5-(difluoromethyl)-1,3,4-oxadiazol-2-yl]-1,3-thiazol-2-yl}methyl)-N-[(pyridin-2-yl)methyl]ethane-1-sulfonamide | 1H NMR (400 MHz, CDCl3) δ 8.59 (d, J = 4.4 Hz, 1H), 8.40 (s, 1H), 7.76-7.69 (m, 1H), 7.39 (d, J = 7.6 Hz, 1H), 7.25 (s, 1H), 6.92 (t, J = 51.6 Hz, 1H), 4.89 (s, 2H), 4.68 (s, 2H), 3.25 (q, J = 7.2 Hz, 2H), 1.42 (t, J = 7.2 Hz, 3H). LCMS RT = 0.932 min, m/z = 416.2 | 2.54 |
| I-184 | N-({5-[5-(difluoromethyl)-1,3,4-oxadiazol-2-yl]-1,3-thiazol-2-yl}methyl)-2-{6-oxa-3-azabicyclo[3.1.1]heptan-3-yl}-N-(pyridin-3-yl)ethane-1-sulfonamide | 1H NMR (400 MHz, CDCl3) δ 8.73 (d, J = 2.4 Hz, 1H), 8.60 (d, J = 3.2 Hz, 1H), 8.39 (s, 1H), 7.89-7.82 (m, 1H), 7.40-7.33 (m, 1H), 6.91 (t, J = 51.6 Hz, 1H), 5.31 (s, 2H), 4.53 (d, J = 6.4 Hz, 2H), 3.46-3.42 (m, 2H), 3.21-3.02 (m, 5 Hz), 2.86 (d, J = 11.2 Hz, 2H), 2.29 (d, J = 8.4 Hz, 1H). LCMS RT = 1.352 min, m/z = 498.9 | 0.014 |
| I-185 | N-({5-[5-(difluoromethyl)-1,3,4-oxadiazol-2-yl]-1,3-thiazol-2-yl}methyl)-3-(morpholin-4-yl)-N-(pyridin-3-yl)propanamide | 1H NMR (400 MHz, CDCl3) δ 8.65 (d, J = 4.4 Hz, 1H), 8.55 (d, J = 2.4 Hz, 1H), 8.38 (s, 1H), 7.63 (d, J = 8.0 Hz, 1H), 7.43-7.39 (m, 1H), 6.92 (t, J = 51.6 Hz, 1H), 5.21 (s, 2H), 3.65 (t, J = 4.4 Hz, 4H), 2.73 (t, J = 7.2 Hz, 2H), 2.38-2.33 (m, 6H). LCMS RT = 0.411 min, m/z = 451.2 | 0.516 |

TABLE 13-continued

Characterization Data and HDAC6 Activity for Compounds of Formula (I).

| Cmpd | Structure/Name | $^1$H NMR<br>MS (m/z) (RT) | HDAC6<br>IC$_{50}$<br>(μM) |
|---|---|---|---|
| I-186 | N-({5-[5-(difluoromethyl)-1,3,4-oxadiazol-2-yl]-1,3-thiazol-2-yl}methyl)-N-(5-fluoropyridin-3-yl)-2-(1,4-oxazepan-4-yl)ethane-1-sulfonamide | 1H NMR (400 MHz, CDCl3) δ 8.58 (s, 1H), 8.47 (d, J = 2.4 Hz, 1H), 8.40 (s, 1H), 7.70-7.67 (m, 1H), 6.91 (t, J = 51.6 Hz, 1H), 5.32 (s, 2H), 3.81 (t, J = 6.4 Hz, 2H), 3.75 (t, J = 4.8 Hz, 2H), 3.41 (t, J = 7.2 Hz, 2H), 3.12 (t, J = 7.6 Hz, 2H), 2.84-2.76 (m, 4H), 1.97-1.92 (m, 2H).<br>LCMS RT = 0.414 min, m/z = 519.2 | 0.0276 |
| I-187 | N-({5-[5-(difluoromethyl)-1,3,4-oxadiazol-2-yl]-1,3-thiazol-2-yl}methyl)-2-[(1S,4S)-2-oxa-5-azabicyclo[2.2.1]heptan-5-yl]-N-(pyridin-3-yl)ethane-1-sulfonamide | 1H NMR (400 MHz, CDCl3) δ 8.74 (d, J = 2.4 Hz, 1H), 8.60-8.57 (m, 1H), 8.38 (s, 1H), 7.88-7.85 (m, 1H), 7.40-7.26 (m, 1H), 6.91 (t, J = 51.6 Hz, 1H), 5.37-5.25 (m, 2H), 4.47 (s, 1H), 4.02 (d, J = 8.4 Hz, 1H), 3.70-3.55 (m, 1H), 3.58 (s, 1H), 3.36 (t, J = 6.8 Hz, 2H), 3.22-3.09 (m, 2H), 3.00-2.92 (m, 1H), 2.60 (d, J = 9.6 Hz, 1H), 1.86-1.80 (m, 2H).<br>LCMS RT = 0.429 min, m/z = 499.2 | 0.0247 |
| I-188 | N-({5-[5-(difluoromethyl)-1,3,4-oxadiazol-2-yl]-1,3-thiazol-2-yl}methyl)-N-(5-fluoropyridin-3-yl)-2-[(1R,4R)-2-oxa-5-azabicyclo[2.2.1]heptan-5-yl]ethane-1-sulfonamide | 1H NMR (400 MHz, CDCl3) δ 8.58 (s, 1H), 8.47 (d, J = 2.4 Hz, 1H), 8.39 (s, 1H), 7.69-7.66 (m, 1H), 6.91 (t, J = 51.6 Hz, 1 H), 5.37-5.27 (m, 2H), 4.47 (s, 1H), 4.02 (d, J = 8.0 Hz, 1H), 3.68 (dd, J = 8.4, 1.6 Hz, 1H), 3.58 (s, 1H), 3.38 (t, J = 6.8 Hz, 2H), 3.22-3.09 (m, 2H), 2.98-2.96 (m, 1H), 2.60 (d, J = 10.0 Hz, 1H), 1.85-1.83 (m, 2H).<br>LCMS RT = 0.457 min, m/z = 517.2 | 0.0151 |
| I-189 | N-({5-[5-(difluoromethyl)-1,3,4-oxadiazol-2-yl]-1,3-thiazol-2-yl}methyl)-2-[(2S)-2-methylmorpholin-4-yl]-N-(pyridin-3-yl)ethane-1-sulfonamide | 1H NMR (400 MHz, CDCl3) δ 8.73 (d, J = 2.4 Hz, 1H), 8.59 (d, J = 3.6 Hz, 1H), 8.38 (s, 1H), 7.88-7.85 (m, 1H), 7.39-7.35 (m, 1H), 6.91 (t, J = 51.6 Hz, 1H), 5.32 (s, 2H), 3.91-3.88 (m, 1H), 3.71-3.62 (m, 2H), 3.38 (t, J = 6.8 Hz, 2H), 2.90 (t, J = 7.2 Hz, 2H), 2.76-2.69 (m, 2H), 2.28-2.21 (m, 1H), 1.93 (t, J = 10.8 Hz, 1H), 1.17 (d, J = 6.0 Hz, 3H).<br>LCMS RT = 1.427 min, m/z = 500.9 | 0.0363 |

TABLE 13-continued

Characterization Data and HDAC6 Activity for Compounds of Formula (I).

| Cmpd | Structure/Name | ¹H NMR MS (m/z) (RT) | HDAC6 IC$_{50}$ (µM) |
|---|---|---|---|
| I-190 | 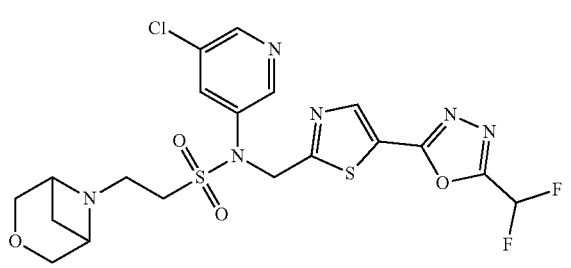 [SMILES: O=S(=O)(CCN1C2COCC1C2)N(Cc1ncc(-c2nnc(C(F)F)o2)s1)c1cncc(Cl)c1]<br>N-(5-chloropyridin-3-yl)-N-({5-[5-(difluoromethyl)-1,3,4-oxadiazol-2-yl]-1,3-thiazol-2-yl}methyl)-2-{3-oxa-6-azabicyclo[3.1.1]heptan-6-yl}ethane-1-sulfonamide | 1H NMR (400 MHz, CDCl3) δ 8.65 (d, J = 2.4 Hz, 1H), 8.54 (d, J = 2.4 Hz, 1H), 8.39 (s, 1H), 7.95 (t, J = 2.4 Hz, 1H), 6.91 (t, J = 51.6 Hz, 1H), 5.34 (s, 2H), 4.21 (d, J = 11.6 Hz, 2H), 3.80 (d, J = 11.2 Hz, 2H), 3.60 (d, J = 6.0 Hz, 2H), 3.32-3.25 (m, 2H), 3.24-3.17 (m, 2H), 2.77-2.63 (m, 1H), 1.91 (d, J = 8.4 Hz, 1H). LCMS RT = 0.968 min, m/z = 533.2 | 0.016 |
| I-191 | 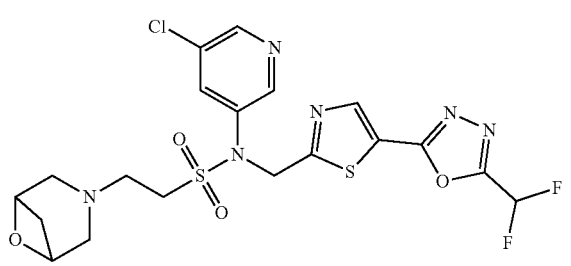 [SMILES: O=S(=O)(CCN1CC2CC(C1)O2)N(Cc1ncc(-c2nnc(C(F)F)o2)s1)c1cncc(Cl)c1]<br>N-(5-chloropyridin-3-yl)-N-({5-[5-(difluoromethyl)-1,3,4-oxadiazol-2-yl]-1,3-thiazol-2-yl}methyl)-2-{6-oxa-3-azabicyclo[3.1.1]heptan-3-yl}ethane-1-sulfonamide | 1H NMR (400 MHz, CDCl3) δ 8.62 (d, J = 2.0 Hz, 1H), 8.55 (d, J = 2.0 Hz, 1H), 8.41 (s, 1H), 7.90 (t, J = 2.4 Hz, 1H), 6.91 (t, J = 51.2 Hz, 1H), 5.29 (s, 2H), 4.52 (d, J = 6.4 Hz, 2H), 3.43 (t, J = 6.8 Hz, 2H), 3.18 (t, J = 7.2 Hz, 2H), 3.10 (d, J = 10.8 Hz, 2H), 3.06-2.80 (m, 3H), 2.28 (d, J = 8.0 Hz, 1H). LCMS RT = 0.482 min, m/z = 533.2 | 0.0124 |
| I-192 | 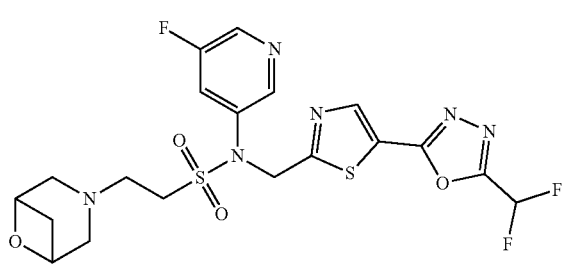 [SMILES: O=S(=O)(CCN1CC2CC(C1)O2)N(Cc1ncc(-c2nnc(C(F)F)o2)s1)c1cncc(F)c1]<br>N-({5-[5-(difluoromethyl)-1,3,4-oxadiazol-2-yl]-1,3-thiazol-2-yl}methyl)-N-(5-fluoropyridin-3-yl)-2-{6-oxa-3-azabicyclo[3.1.1]heptan-3-yl}ethane-1-sulfonamide | 1H NMR (400 MHz, CDCl3) δ 8.57 (s, 1H), 8.46 (d, J = 2.4 Hz, 1H), 8.40 (s, 1H), 7.73-7.61 (m, 1H), 6.92 (t, J = 51.2 Hz, 1H), 5.31 (s, 2H), 4.52 (d, J = 6.0 Hz, 2H), 3.46 (t, J = 6.8 Hz, 2H), 3.18 (t, J = 7.6 Hz, 2H), 3.12 (d, J = 11.0 Hz, 2H), 3.08-3.01 (m, 1H), 2.86 (d, J = 11.2 Hz, 2H), 2.27 (d, J = 8.0 Hz, 1H). LCMS RT = 1.368 min, m/z = 517.2 | 0.0168 |
| I-193 | 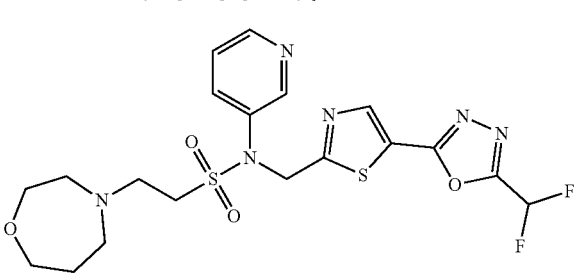<br>N-({5-[5-(difluoromethyl)-1,3,4-oxadiazol-2-yl]-1,3-thiazol-2-yl}methyl)-2-(1,4-oxazepan-4-yl)-N-(pyridin-3-yl)ethane-1-sulfonamide | 1H NMR (400 MHz, CDCl3) δ ppm 8.73 (d, J = 2.4 Hz, 1H), 8.58 (d, J = 4.0 Hz, 1H), 8.38 (s, 1H), 7.86 (d, J = 8.0 Hz, 1H), 7.39-7.35 (m, 1H), 6.92 (t, J = 51.6 Hz, 1H), 5.32 (s, 2H), 3.80 (t, J = 6.0 Hz, 2H), 3.75-3.73 (m, 2H), 3.37 (t, J = 7.6 Hz, 2H), 3.10 (t, J = 6.4 Hz, 2H), 2.79-2.75 (m, 4H), 1.95-1.91 (m, 2H). LCMS RT = 0.429 min, m/z = 501.2 | 0.0203 |

TABLE 13-continued

Characterization Data and HDAC6 Activity for Compounds of Formula (I).

| Cmpd | Structure/Name | $^1$H NMR MS (m/z) (RT) | HDAC6 IC$_{50}$ (µM) |
|---|---|---|---|
| I-194 | N-({5-[5-(difluoromethyl)-1,3,4-oxadiazol-2-yl]-1,3-thiazol-2-yl}methyl)-2-[(2R)-2-methylmorpholin-4-yl]-N-(pyridin-3-yl)ethane-1-sulfonamide | 1H NMR (400 MHz, CDCl3) δ ppm 8.73 (s, 1H), 8.59 (d, J = 4.4 Hz, 1H), 8.38 (s, 1H), 7.86-7.83 (m, 1H), 7.38-7.35 (m, 1H), 6.91 (t, J = 51.2 Hz, 1H), 5.31 (s, 2H), 3.87-3.67 (m, 1H), 3.66-3.64 (m, 2H), 3.64 (t, J = 6.8 Hz, 2H), 2.89 (t, J = 6.8 Hz, 2H), 2.74-2.67 (m, 2H), 2.24-2.23 (m, 1H), 1.92 (t, J = 6.8 Hz, 1H), 1.17 (d, J = 6.8 Hz, 3H). LCMS RT = 0.748 min, m/z = 501.2 | 0.0267 |
| I-195 | N-(5-chloropyridin-3-yl)-N-({5-[5-(difluoromethyl)-1,3,4-oxadiazol-2-yl]-1,3-thiazol-2-yl}methyl)-3-(morpholin-4-yl)propanamide | 1H NMR (400 MHz, CDCl3) δ ppm 8.62 (s, 1H), 8.44 (s, 1H), 8.39 (s, 1H), 7.72 (s, 1H), 6.92 (t, J = 51.6 Hz, 1H), 5.18 (s, 2H), 3.17-3.69 (m, δ H), 2.86-2.83 (m, 2H), 2.44-2.41 (m, 2H). LCMS RT = 1.381 min, m/z = 485.3 | 0.312 |
| I-196 | N-({5-[5-(difluoromethyl)-1,3,4-oxadiazol-2-yl]-1,3-thiazol-2-yl}methyl)-2-[(1R,4R)-2-oxa-5-azabicyclo[2.2.1]heptan-5-yl]-N-(pyridin-3-yl)ethane-1-sulfonamide | 1H NMR (400 MHz, CDCl3) δ 8.74 (s, 1H), 8.59 (d, J = 4.0 Hz, 1H), 8.39 (s, 1H), 7.87 (d, J = 8.4 Hz, 1H), 7.39-7.35 (m, 1H), 6.91 (t, J = 51.6 Hz, 1H), 5.36-5.27 (m, 2H), 4.48 (s, 1H), 4.05 (d, J = 8.4 Hz, 1H), 3.70-3.66 (m, 2H), 3.43 (t, J = 6.8 Hz, 2H), 3.26-3.13 (m, 2H), 3.03 (d, J = 10.0 Hz, 1H), 2.66 (d, J = 10.4 Hz, 1H), 1.95-1.85 (m, 2H). LCMS RT = 1.117 min, m/z = 499.2 | 0.0497 |

TABLE 13-continued

Characterization Data and HDAC6 Activity for Compounds of Formula (I).

| Cmpd | Structure/Name | ¹H NMR<br>MS (m/z) (RT) | HDAC6 IC$_{50}$ (μM) |
|---|---|---|---|
| I-197 | N-(5-chloropyridin-3-yl)-N-({5-[5-(difluoromethyl)-1,3,4-oxadiazol-2-yl]-1,3-thiazol-2-yl}methyl)-2-[(2R)-2-methylmorpholin-4-yl]ethane-1-sulfonamide | 1H NMR (400 MHz, CDCl3) δ 8.63 (d, J = 2.0 Hz, 1H), 8.54 (d, J = 2.0 Hz, 1H), 8.39 (s, 1H), 7.91 (t, J = 2.0 Hz, 1H), 6.91 (t, J = 51.6 Hz, 1H), 5.30 (s, 2H), 3.93-3.85 (m, 1H), 3.72-3.60 (m, 2H), 3.36 (t, J = 6.8 Hz, 2H), 2.88 (t, J = 6.8 Hz, 2H), 2.75-2.65 (m, 2H), 2.28-2.17 (m, 1H), 1.91 (t, J = 10.8 Hz, 1H), 1.17 (d, J = 6.4 Hz, 3H).<br>LCMS RT = 1.558 min, m/z = 535.2 | 0.0472 |
| I-198 | N-(5-chloropyridin-3-yl)-N-({5-[5-(difluoromethyl)-1,3,4-oxadiazol-2-yl]-1,3-thiazol-2-yl}methyl)propanamide | 1H NMR (400 MHz, CDCl3) δ 8.62 (s, 1H), 8.44-8.35 (m, 2H), 7.67 (t, J = 2.0 Hz, 1H), 6.92 (t, J = 51.6 Hz, 1H), 5.18 (s, 2H), 2.18 (q, J = 7.2 Hz, 2H), 1.13 (t, J = 7.6 Hz, 3H).<br>LCMS RT = 1.929 min, m/z = 400.2 | 0.299 |
| I-199 | N-({5-[5-(difluoromethyl)-1,3,4-oxadiazol-2-yl]-1,3-thiazol-2-yl}methyl)-N-(pyridin-3-yl)propanamide | 1H NMR (400 MHz, CDCl3) δ 8.64 (d, J = 4.0 Hz, 1H), 8.53 (s, 1H), 8.37 (s, 1H), 7.61 (d, J = 8.0 Hz, 1H), 7.42-7.36 (m, 1H), 6.91 (t, J = 51.6 Hz, 1H), 5.20 (s, 2H), 2.15 (q, J = 7.2 Hz, 2H), 1.12 (t, J = 7.2 Hz, 3H).<br>LCMS RT = 1.372 min, m/z = 366.2 | 0.355 |
| I-200 | 1-({5-[5-(difluoromethyl)-1,3,4-oxadiazol-2-yl]-1,3-thiazol-2-yl}methyl)-1H,2H,3H,4H,5H-pyrido[4,3-b]azepin-2-one | 1H NMR (400 MHz, CDCl3) δ 8.56 (d, J = 5.2 Hz, 1H), 8.46 (s, 1H), 8.39 (s, 1H), 7.36 (d, J = 5.6 Hz, 1H), 6.91 (t, J = 51.6 Hz, 1H), 5.33 (s, 2H), 2.80 (t, J = 7.2 Hz, 2H), 2.44 (t, J = 7.2 Hz, 2H), 2.36-2.24 (m, 2H).<br>LCMS RT = 0.993 min, m/z = 378.2 | 0.125 |

TABLE 13-continued

Characterization Data and HDAC6 Activity for Compounds of Formula (I).

| Cmpd | Structure/Name | $^1$H NMR<br>MS (m/z) (RT) | HDAC6 IC$_{50}$ (µM) |
|---|---|---|---|
| I-201 | 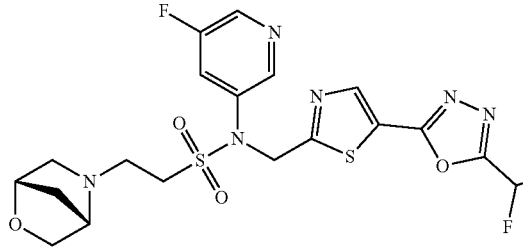<br>N-({5-[5-(difluoromethyl)-1,3,4-oxadiazol-2-yl]-1,3-thiazol-2-yl}methyl)-N-(5-fluoropyridin-3-yl)-2-[(1S,4S)-2-oxa-5-azabicyclo[2.2.1]heptan-5-yl]ethane-1-sulfonamide | 1H NMR (400 MHz, CDCl3) δ 8.57 (s, 1H), 8.46 (d, J = 2.4 Hz, 1H), 8.39 (s, 1H), 7.70-7.62 (m, 1H), 6.91 (t, J = 51.6 Hz, 1H), 5.39-5.25 (m, 2H), 4.46 (s, 1H), 4.00 (d, J = 8.0 Hz, 1H), 3.69-3.64 (m, 1H), 3.52 (s, 1H), 3.34 (t, J = 6.8 Hz, 2H), 3.19-3.07 (m, 2H), 2.94 (d, J = 10.0 Hz, 1H), 2.56 (d, J = 10.0 Hz, 1H), 1.89-1.79 (m, 2H).<br>LCMS RT = 0.459 min, m/z = 517.2 | 0.0207 |
| I-202 | 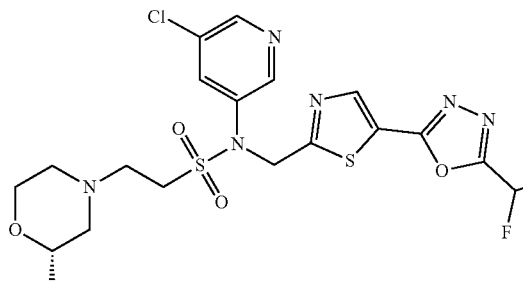<br>N-(5-chloropyridin-3-yl)-N-({5-[5-(difluoromethyl)-1,3,4-oxadiazol-2-yl]-1,3-thiazol-2-yl}methyl)-2-[(2S)-2-methylmorpholin-4-yl]ethane-1-sulfonamide | 1H NMR (400 MHz, CDCl3) δ 8.63 (s, 1H), 8.54 (s, 1H), 8.39 (s, 1H), 7.91 (s, 1H), 6.91 (t, J = 51.2 Hz, 1H), 5.30 (s, 2H), 3.94-3.85 (m, 1H), 3.74-3.62 (m, 2H), 3.43 (t, J = 6.8 Hz, 2H), 2.88 (t, J = 6.8 Hz, 2H), 2.72 (t, J = 12.8 Hz, 2H), 2.28-2.17 (m, 1H), 1.92 (t, J = 9.6 Hz, 1H), 1.17 (d, J = 6.0 Hz, 3H).<br>LCMS RT = 1.561 min, m/z = 535.2 | 0.0127 |
| I-203 | 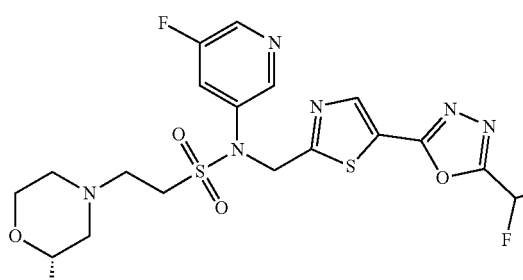<br>N-({5-[5-(difluoromethyl)-1,3,4-oxadiazol-2-yl]-1,3-thiazol-2-yl}methyl)-N-(5-fluoropyridin-3-yl)-2-[(2S)-2-methylmorpholin-4-yl]ethane-1-sulfonamide | 1H NMR (400 MHz, CDCl3) δ 8.58 (s, 1H), 8.47 (d, J = 2.4 Hz, 1H), 8.40 (s, 1H), 7.68 (d, J = 9.2 Hz, 1H), 6.92 (t, J = 51.2 Hz, 1H), 5.32 (s, 2H), 3.91-3.71 (m, 1H), 3.72-3.64 (m, 2H), 3.41 (t, J = 6.8 Hz, 2H), 2.91 (t, J = 7.2 Hz, 2H), 2.73 (t, J = 12.8 Hz, 2H), 2.29-2.22 (m, 1H), 1.96-1.94 (m, 1H), 1.17 (d, J = 6.4 Hz, 3H).<br>LCMS RT = 1.660 min, m/z = 519.0 | 0.0254 |

TABLE 13-continued

Characterization Data and HDAC6 Activity for Compounds of Formula (I).

| Cmpd | Structure/Name | ¹H NMR MS (m/z) (RT) | HDAC6 IC$_{50}$ (μM) |
|---|---|---|---|
| I-204 | N-({5-[5-(difluoromethyl)-1,3,4-oxadiazol-2-yl]-1,3-thiazol-2-yl}methyl)-N-(5-fluoropyridin-3-yl)-2-[(2R)-2-methylmorpholin-4-yl]ethane-1-sulfonamide | 1H NMR (400 MHz, CDCl3) δ 8.58 (s, 1H), 8.47 (s, 1H), 8.40 (s, 1H), 7.70-7.66 (m, 1H), 6.91 (t, J = 51.6 Hz, 1H), 5.32 (s, 2H), 3.89 (d, J = 9.6 Hz, 1H), 3.70-3.60 (m, 2H), 3.37 (t, J = 6.8 Hz, 2H), 2.88 (t, J = 6.8 Hz, 2H), 2.72-2.65 (m, 2H), 2.26-2.20 (m, 1H), 1.91 (t, J = 10.4 Hz, 1H), 1.17 (d, J = 6.0 Hz, 3H). LCMS RT = 1.664 min, m/z = 518.9 | 0.0336 |
| I-205 | N-(5-chloropyridin-3-yl)-N-({5-[5-(difluoromethyl)-1,3,4-oxadiazol-2-yl]-1,3-thiazol-2-yl}methyl)-2-[(1R,4R)-2-oxa-5-azabicyclo[2.2.1]heptan-5-yl]ethane-1-sulfonamide | 1H NMR (400 MHz, CDCl3) δ 8.62 (d, J = 2.0 Hz, 1H), 8.54 (d, J = 2.0 Hz, 1H), 8.40 (s, 1H), 7.91 (t, J = 2.0 Hz, 1H), 6.91 (t, J = 51.6 Hz, 1H), 5.40-5.21 (m, 2H), 4.47 (s, 1H), 4.02 (d, J = 8.0 Hz, 1H), 3.68-3.63 (m, 1H), 3.56 (s, 1H), 3.35 (t, J = 6.8 Hz, 2H), 3.25-3.05 (m, 2H), 3.01-2.90 (m, 1H), 2.59 (d, J = 10.0 Hz, 1H), 1.93-1.80 (m, 2H). LCMS RT = 0.919 min, m/z = 533.2 | 0.0159 |
| I-206 | N-(5-chloropyridin-3-yl)-N-({5-[5-(difluoromethyl)-1,3,4-oxadiazol-2-yl]-1,3-thiazol-2-yl}methyl)-2-[(1S,4S)-2-oxa-5-azabicyclo[2.2.1]heptan-5-yl]ethane-1-sulfonamide | 1H NMR (400 MHz, CDCl3) δ 8.62 (d, J = 2.0 Hz, 1H), 8.54 (d, J = 2.0 Hz, 1H), 8.39 (s, 1H), 7.91 (t, J = 2.0 Hz, 1H), 6.91 (t, J = 51.6 Hz, 1H), 5.37-5.25 (m, 2H), 4.46 (s, 1H), 4.01 (d, J = 8.4 Hz, 1H), 3.69-3.62 (m, 1H), 3.51 (s, 1H), 3.31 (t, J = 6.8 Hz, 2H), 3.18-3.07 (m, 2H), 2.93 (d, J = 10.0 Hz, 1H), 2.56 (d, J = 9.6 Hz, 1H), 1.89-1.84 (q, J = 7.2 Hz, 2H). LCMS RT = 0.472 min, m/z = 533.2 | 0.0162 |

TABLE 13-continued

Characterization Data and HDAC6 Activity for Compounds of Formula (I).

| Cmpd | Structure/Name | ¹H NMR MS (m/z) (RT) | HDAC6 IC$_{50}$ (μM) |
|---|---|---|---|
| I-207 | 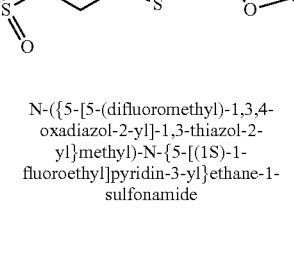<br>N-({5-[5-(difluoromethyl)-1,3,4-oxadiazol-2-yl]-1,3-thiazol-2-yl}methyl)-N-{5-[(1S)-1-fluoroethyl]pyridin-3-yl}ethane-1-sulfonamide | 1H NMR (400 MHz, CDCl3) δ 8.67 (d, J = 2.4 Hz, 1H), 8.56 (s, 1H), 8.39 (s, 1H), 7.83 (s, 1H), 6.91 (t, J = 51.6 Hz, 1H), 5.79-5.60 (m, 1H), 5.30 (s, 2H), 3.21 (q, J = 7.2 Hz, 2H), 1.69-1.55 (m, 3H), 1.46 (t, J = 7.6 Hz, 3H). LCMS RT = 1.500 min, m/z = 447.8 | 0.0137 |
| I-208 | 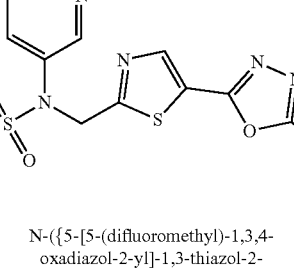<br>N-({5-[5-(difluoromethyl)-1,3,4-oxadiazol-2-yl]-1,3-thiazol-2-yl}methyl)-N-{5-[(1R)-1-fluoroethyl]pyridin-3-yl}ethane-1-sulfonamide | 1H NMR (400 MHz, CDCl3) δ 8.67 (d, J = 2.0 Hz, 1H), 8.56 (s, 1H), 8.39 (s, 1H), 7.83 (s, 1H), 6.91 (t, J = 52.0 Hz, 1H), 5.78-5.62 (m, 1H), 5.30 (s, 2H), 3.21 (q, J = 7.2 Hz, 2H), 1.74-1.62 (m, 3H), 1.46 (t, J = 7.6 Hz, 3H). LCMS RT = 1.503 min, m/z = 447.8 | 0.027 |
| I-209 | 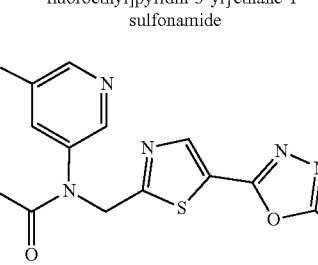<br>N-({5-[5-(difluoromethyl)-1,3,4-oxadiazol-2-yl]-1,3-thiazol-2-yl}methyl)-N-(5-fluoropyridin-3-yl)propanamide | 1H NMR (400 MHz, CDCl3) δ 8.54 (d, J = 2.4 Hz, 1H), 8.39-8.35 (m, 2H), 7.44-7.40 (m, 1H), 6.92 (t, J = 51.6 Hz, 1H), 5.19 (s, 2H), 2.19 (q, J = 6.8 Hz, 2H), 1.13 (t, J = 7.6 Hz, 3H). LCMS RT = 1.755 min, m/z = 384.2 | 0.284 |
| I-210 | 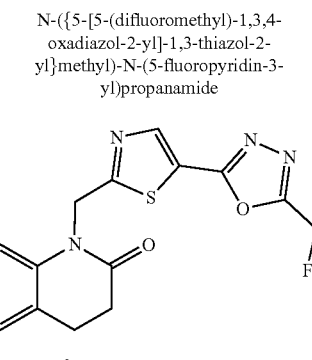<br>1-({5-[5-(difluoromethyl)-1,3,4-oxadiazol-2-yl]-1,3-thiazol-2-yl}methyl)-1,2,3,4-tetrahydro-1,6-naphthyridin-2-one | 1H NMR (400 MHz, CDCl3) δ 8.49-8.37 (m, 3H), 7.19 (d, J = 5.6 Hz, 1H), 6.89 (t, J = 51.6 Hz, 1H), 5.46 (s, 2H), 3.10-3.01 (m, 2H), 2.91-2.80 (m, 2H). LCMS RT = 0.971 min, m/z = 364.2 | 0.0487 |

TABLE 13-continued

Characterization Data and HDAC6 Activity for Compounds of Formula (I).

| Cmpd | Structure/Name | $^1$H NMR<br>MS (m/z) (RT) | HDAC6 IC$_{50}$ (μM) |
|---|---|---|---|
| I-211 | 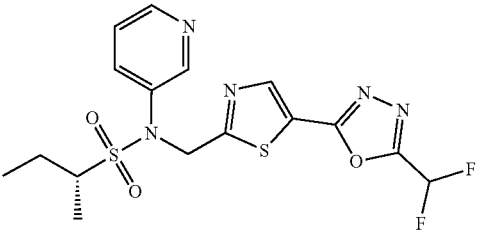 [SMILES: CC[C@@H](C)S(=O)(=O)N(Cc1ncc(-c2nnc(C(F)F)o2)s1)c1cccnc1]<br>(2R)-N-({5-[5-(difluoromethyl)-1,3,4-oxadiazol-2-yl]-1,3-thiazol-2-yl}methyl)-N-(pyridin-3-yl)butane-2-sulfonamide | 1H NMR (400 MHz, CDCl3) δ 8.70 (s, 1H), 8.57-8.55 (m, 1H), 8.35 (s, 1H), 7.87-7.82 (m, 1H), 7.38-7.32 (m, 1H), 6.91 (t, J = 51.6 Hz, 1H), 5.38-5.20 (m, 2H), 3.14-3.06 (m, 1H), 2.13-2.05 (m, 1H), 1.72-1.65 (m, 1H), 1.45 (d, J = 6.8 Hz, 3H), 1.04 (t, J = 7.6 Hz, 3H). LCMS RT = 0.563 min, m/z = 430.1 | 0.0137 |
| I-212 | 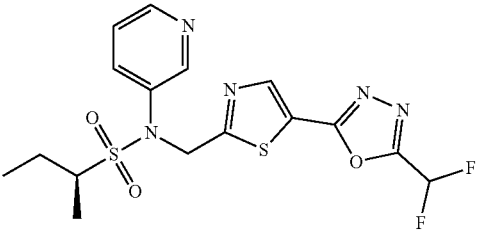 [SMILES: CC[C@H](C)S(=O)(=O)N(Cc1ncc(-c2nnc(C(F)F)o2)s1)c1cccnc1]<br>(2S)-N-({5-[5-(difluoromethyl)-1,3,4-oxadiazol-2-yl]-1,3-thiazol-2-yl}methyl)-N-(pyridin-3-yl)butane-2-sulfonamide | 1H NMR (400 MHz, CDCl3) δ 8.70 (s, 1H), 8.58-8.55 (m, 1H), 8.35 (s, 1H), 7.89-7.86 (m, 1H), 7.34 (q, J = 4.8 Hz, 1H), 6.91 (t, J = 51.6 Hz, 1H), 5.39-5.23 (m, 2H), 3.14-3.06 (m, 1H), 2.14-2.04 (m, 1H), 1.74-1.65 (m, 1H), 1.45 (d, J = 6.8 Hz, 3H), 1.04 (t, J = 7.6 Hz, 3H). LCMS RT = 0.563 min, m/z = 430.1 | 0.0105 |
| I-213 | 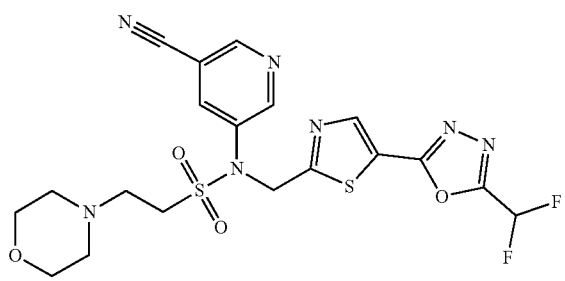 [SMILES: N#Cc1cncc(N(Cc2ncc(-c3nnc(C(F)F)o3)s2)S(=O)(=O)CCN2CCOCC2)c1]<br>N-(5-cyanopyridin-3-yl)-N-({5-[5-(difluoromethyl)-1,3,4-oxadiazol-2-yl]-1,3-thiazol-2-yl}methyl)-2-(morpholin-4-yl)ethane-1-sulfonamide | 1H NMR (400 MHz, CDCl3) δ 8.96 (d, J = 2.4 Hz, 1H), 8.82 (s, 1H), 8.41 (s, 1H), 8.19 (s, 1H), 6.92 (t, J = 51.6 Hz, 1H), 5.33 (s, 2H), 3.74 (t, J = 4.8 Hz, 4H), 3.38 (t, J = 6.8 Hz, 2H), 2.89 (t, J = 7.2 Hz, 2H), 2.50 (t, J = 4.8 Hz, 4H). LCMS RT = 1.295 min, m/z = 512.2 | 0.0902 |
| I-214 | 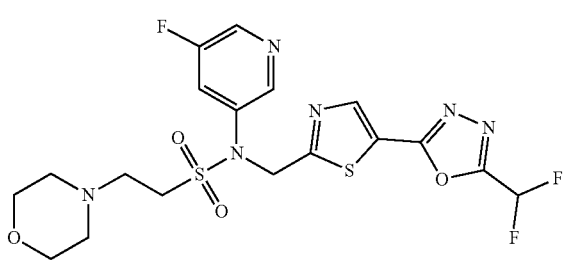 [SMILES: O=S(=O)(CCN1CCOCC1)N(Cc1ncc(-c2nnc(C(F)F)o2)s1)c1cncc(F)c1]<br>N-({5-[5-(difluoromethyl)-1,3,4-oxadiazol-2-yl]-1,3-thiazol-2-yl}methyl)-N-(5-fluoropyridin-3-yl)-2-(morpholin-4-yl)ethane-1-sulfonamide | 1H NMR (400 MHz, CDCl3) δ ppm 8.59 (s, 1H), 8.47 (d, J = 2.4 Hz, 1H), 8.40 (s, 1H), 7.71-7.67 (m, 1H), 6.93 (t, J = 51.6 Hz, 1H), 5.33 (s, 2H), 3.78-3.72 (m, 4H), 3.40 (t, J = 6.8 Hz, 2H), 2.91 (t, J = 6.8 Hz, 2H), 2.53-2.51 (m, 4H). LCMS RT = 0.908 min, m/z = 505.2 | 0.0154 |

TABLE 13-continued

Characterization Data and HDAC6 Activity for Compounds of Formula (I).

| Cmpd | Structure/Name | ¹H NMR MS (m/z) (RT) | HDAC6 IC$_{50}$ (μM) |
|---|---|---|---|
| I-215 | 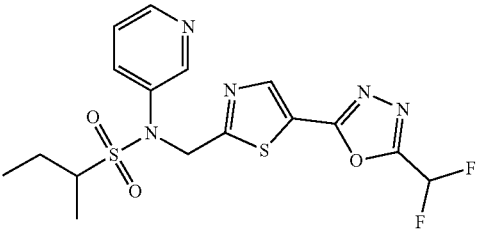 [SMILES: CCC(C)S(=O)(=O)N(Cc1ncc(-c2nnc(C(F)F)o2)s1)c1cccnc1]<br>N-({5-[5-(difluoromethyl)-1,3,4-oxadiazol-2-yl]-1,3-thiazol-2-yl}methyl)-N-(pyridin-3-yl)butane-2-sulfonamide | 1H NMR (400 MHz, CDCl3) δ 8.72 (d, J = 2.8 Hz, 1H), 8.58-8.56 (m, 1H), 8.35 (s, 1H), 7.89-7.86 (m, 1H), 7.36 (q, J = 4.8 Hz, 1H), 6.91 (t, J = 51.6 Hz, 1H), 5.37-5.26 (m, 2H), 3.14-3.05 (m, 1H), 2.12-2.06 (m, 1H), 1.75-1.69 (m, 1H), 1.45 (d, J = 6.8 Hz, 3H), 1.04 (t, J = 7.6 Hz, 3H). LCMS RT = 0.560 min, m/z = 430.1 | 0.00675 |
| I-216 | 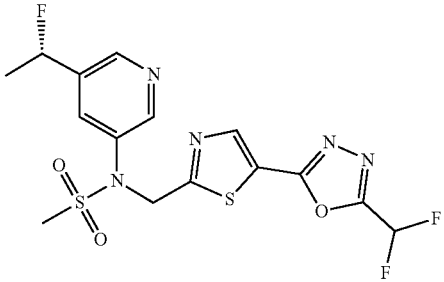 [SMILES: C[C@H](F)c1cncc(N(Cc2ncc(-c3nnc(C(F)F)o3)s2)S(C)(=O)=O)c1]<br>N-({5-[5-(difluoromethyl)-1,3,4-oxadiazol-2-yl]-1,3-thiazol-2-yl}methyl)-N-{5-[(1S)-1-fluoroethyl]pyridin-3-yl}methanesulfonamide | 1H NMR (400 MHz, CDCl3) δ 8.68 (s, 1H), 8.58 (s, 1H), 8.42 (s, 1H), 7.84 (s, 1H), 6.92 (t, J = 51.6 Hz, 1H), 5.80-5.61 (m, 1H), 5.29 (s, 2H), 3.11 (s, 3H), 1.75-1.55 (m, 3H). LCMS RT = 0.550 min, m/z = 434.1 | 0.0119 |
| I-217 | 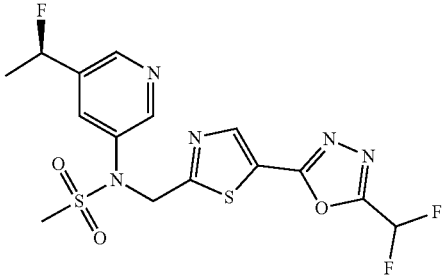 [SMILES: C[C@@H](F)c1cncc(N(Cc2ncc(-c3nnc(C(F)F)o3)s2)S(C)(=O)=O)c1]<br>N-({5-[5-(difluoromethyl)-1,3,4-oxadiazol-2-yl]-1,3-thiazol-2-yl}methyl)-N-{5-[(1R)-1-fluoroethyl]pyridin-3-yl}methanesulfonamide | 1H NMR (400 MHz, CDCl3) δ 8.70 (s, 1H), 8.58 (s, 1H), 8.42 (s, 1H), 7.86 (s, 1H), 6.92 (t, J = 51.6 Hz, 1H), 5.81-5.60 (m, 1H), 5.29 (s, 2H), 3.11 (s, 3H), 1.75-1.55 (m, 3H). LCMS RT = 0.551 min, m/z = 434.1 | 0.0236 |

TABLE 13-continued

Characterization Data and HDAC6 Activity for Compounds of Formula (I).

| Cmpd | Structure/Name | ¹H NMR MS (m/z) (RT) | HDAC6 IC$_{50}$ (µM) |
|---|---|---|---|
| I-218 | 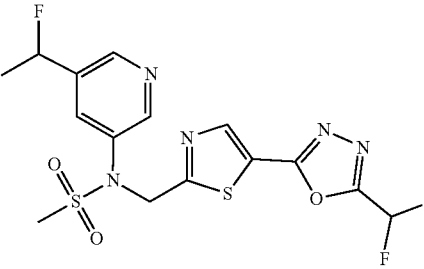<br>N-({5-[5-(difluoromethyl)-1,3,4-oxadiazol-2-yl]-1,3-thiazol-2-yl}methyl)-N-[5-(1-fluoroethyl)pyridin-3-yl]methanesulfonamide | 1H NMR (400 MHz, CDCl3) δ 8.68 (d, J = 2.4 Hz, 1H), 8.57 (s, 1H), 8.41 (s, 1H), 7.84 (s, 1H), 6.91 (t, J = 51.2 Hz, 1H), 5.79-5.62 (m, 1H), 5.28 (s, 2H), 3.11 (s, 3H), 1.75-1.55 (m, 3H). LCMS RT = 0.545 min, m/z = 434.1 | 0.0369 |
| I-219 | 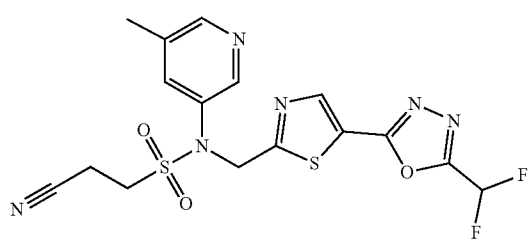 [SMILES: Cc1cncc(N(Cc2ncc(-c3nnc(C(F)F)o3)s2)S(=O)(=O)CCC#N)c1]<br>2-cyano-N-({5-[5-(difluoromethyl)-1,3,4-oxadiazol-2-yl]-1,3-thiazol-2-yl}methyl)-N-(5-methylpyridin-3-yl)ethane-1-sulfonamide | 1H NMR (400 MHz, CDCl3) δ 8.52 (d, J = 2.0 Hz, 1H), 8.47 (s, 1H), 8.45 (s, 1H), 7.65 (s, 1H), 6.92 (t, J = 51.6 Hz, 1H), 5.28 (s, 2H), 3.53 (t, J = 7.6 Hz, 2H), 2.98 (t, J = 7.2 Hz, 2H), 2.39 (s, 3H). LCMS RT = 0.507 min, m/z = 441.1 | 0.0202 |
| I-220 | 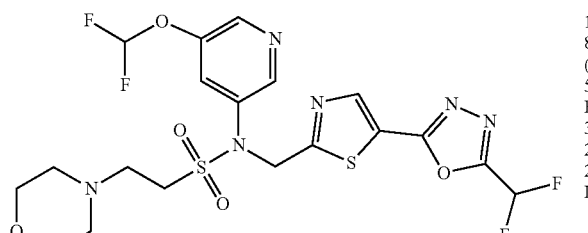<br>N-[5-(difluoromethoxy)pyridin-3-yl]-N-({5-[5-(difluoromethyl)-1,3,4-oxadiazol-2-yl]-1,3-thiazol-2-yl}methyl)-2-(morpholin-4-yl)ethane-1-sulfonamide | 1H NMR (400 MHz, CDCl3) δ 8.61 (s, 1H), 8.46 (s, 1H), 8.39 (s, 1H), 7.70 (s, 1H), 6.91 (t, J = 51.6 Hz, 1H), 6.59 (t, J = 72.0 Hz, 1H), 5.31 (s, 2H), 3.77-3.69 (m, 4H), 3.38 (t, J = 6.8 Hz, 2H), 2.89 (t, J = 7.2 Hz, 2H), 2.54-2.46 (m, 4H). LCMS RT = 1.504 min, m/z = 553.2 | 0.0184 |
| I-221 | 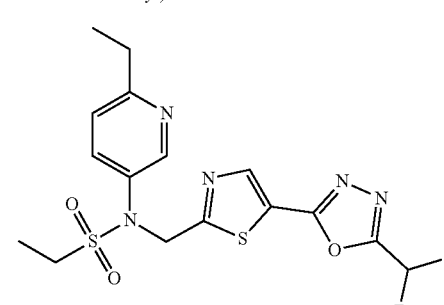<br>N-({5-[5-(difluoromethyl)-1,3,4-oxadiazol-2-yl]-1,3-thiazol-2-yl}methyl)-N-(6-ethylpyridin-3- | 1H NMR (400 MHz, CDCl3) δ 8.58 (d, J = 2.4 Hz, 1H), 8.37 (s, 1H), 7.75-7.70 (m, 1H), 7.22 (d, J = 8.4 Hz, 1H), 6.91 (t, J = 51.6 Hz, 1H), 5.7 (s, 2H), 3.20 (q, J = 7.6 Hz, 2H), 2.83 (q, J = 7.6 Hz, 2H), 1.46 (t, J = 7.2 Hz, 3H), 1.30 (t, J = 7.6 Hz, 3H). LCMS RT = 1.134 min, m/z = 430.2 | 0.033 |

TABLE 13-continued

Characterization Data and HDAC6 Activity for Compounds of Formula (I).

| Cmpd | Structure/Name | $^1$H NMR<br>MS (m/z) (RT) | HDAC6 IC$_{50}$ (μM) |
|---|---|---|---|
| | yl)ethane-1-sulfonamide | | |
| I-222 | 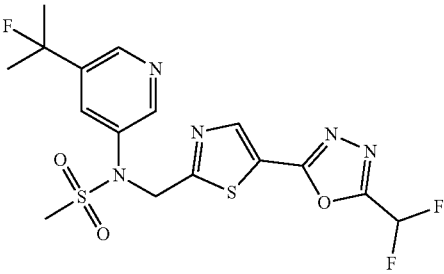 [SMILES: CC(C)(F)c1cncc(N(Cc2ncc(-c3nnc(C(F)F)o3)s2)S(C)(=O)=O)c1]<br>N-({5-[5-(difluoromethyl)-1,3,4-oxadiazol-2-yl]-1,3-thiazol-2-yl}methyl)-N-[5-(2-fluoropropan-2-yl)pyridin-3-yl]methanesulfonamide | 1H NMR (400 MHz, CDCl3) δ 8.64 (d, J = 2.0 Hz, 1H), 8.60 (s, 1H), 8.42 (s, 1H), 7.86 (t, J = 2.0 Hz, 1H), 6.92 (t, J = 51.6 Hz, 1H), 5.28 (s, 2H), 3.11 (s, 3H), 1.75 (s, 3H), 1.69 (s, 3H).<br>LCMS RT = 1.499 min, m/z = 447.9 | 0.0376 |
| I-223 | 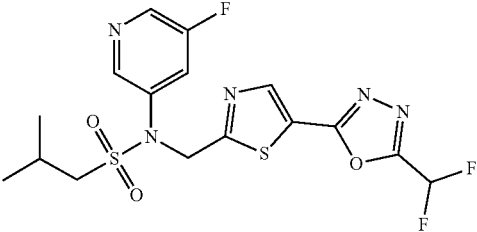 [SMILES: CC(C)CS(=O)(=O)N(Cc1ncc(-c2nnc(C(F)F)o2)s1)c1cncc(F)c1]<br>N-({5-[5-(difluoromethyl)-1,3,4-oxadiazol-2-yl]-1,3-thiazol-2-yl}methyl)-N-(5-fluoropyridin-3-yl)-2-methylpropane-1-sulfonamide | 1H NMR (400 MHz, CDCl3) δ 8.58 (s, 1H), 8.47 (d, J = 2.8 Hz, 1H), 8.40 (s, 1H), 7.68-7.62 (m, 1H), 6.91 (t, J = 51.6 Hz, 1H), 5.29 (s, 2H), 3.05 (d, J = 2.0 Hz, 2H), 2.40-2.30 (m, 1H), 1.12 (d, J = 6.8 Hz, 6H).<br>LCMS RT = 1.790 min, m/z = 447.9 | 0.00563 |
| I-224 | 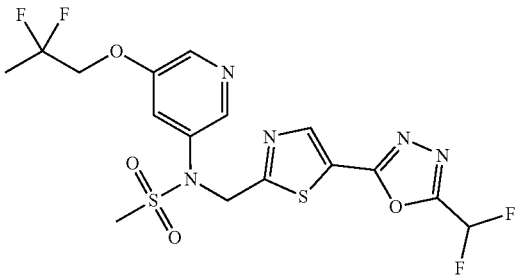 [SMILES: CC(F)(F)COc1cncc(N(Cc2ncc(-c3nnc(C(F)F)o3)s2)S(C)(=O)=O)c1]<br>N-({5-[5-(difluoromethyl)-1,3,4-oxadiazol-2-yl]-1,3-thiazol-2-yl}methyl)-N-[5-(2,2-difluoropropoxy)pyridin-3-yl]methanesulfonamide | 1H NMR (400 MHz, CDCl3) δ 8.42 (s, 1H), 8.39-8.33 (m, 2H), 7.48-7.41 (m, 1H), 6.92 (t, J = 51.6 Hz, 1H), 5.28 (s, 2H), 4.18 (t, J = 11.2 Hz, 2H), 3.11 (s, 3H), 1.79 (t, J = 18.8 Hz, 3H).<br>LCMS RT = 1.492 min, m/z = 482.2 | 0.0204 |

TABLE 13-continued

Characterization Data and HDAC6 Activity for Compounds of Formula (I).

| Cmpd | Structure/Name | ¹H NMR<br>MS (m/z) (RT) | HDAC6<br>IC$_{50}$<br>(μM) |
|---|---|---|---|
| I-225 | 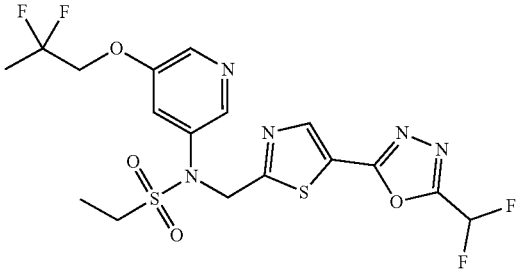 [SMILES: CCS(=O)(=O)N(Cc1ncc(-c2nnc(C(F)F)o2)s1)c1cncc(OCC(C)(F)F)c1]<br>N-({5-[5-(difluoromethyl)-1,3,4-oxadiazol-2-yl]-1,3-thiazol-2-yl}methyl)-N-[5-(2,2-difluoropropoxy)pyridin-3-yl]ethane-1-sulfonamide | 1H NMR (400 MHz, CDCl3) δ 8.42-8.36 (m, 2H), 8.33 (s, 1H), 7.45 (s, 1H), 6.91 (t, J = 51.6 Hz, 1H), 5.30 (s, 2H), 4.17 (t, J = 11.2 Hz, 2H), 3.21 (q, J = 7.6 Hz, 2H), 1.79 (t, J = 18.8 Hz, 3H), 1.46 (t, J = 7.6 Hz, 3H).<br>LCMS RT = 1.559 min, m/z = 496.2 | 0.00601 |
| I-226 | 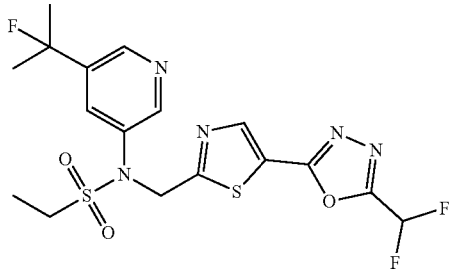 [SMILES: CCS(=O)(=O)N(Cc1ncc(-c2nnc(C(F)F)o2)s1)c1cncc(C(C)(C)F)c1]<br>N-({5-[5-(difluoromethyl)-1,3,4-oxadiazol-2-yl]-1,3-thiazol-2-yl}methyl)-N-[5-(2-fluoropropan-2-yl)pyridin-3-yl]ethane-1-sulfonamide | 1H NMR (400 MHz, CDCl3) δ 8.66 (d, J = 2.4 Hz, 1H), 8.59 (d, J = 1.2 Hz, 1H), 8.40 (s, 1H), 7.91-7.86 (m, 1H), 6.91 (t, J = 51.6 Hz, 1H), 5.30 (s, 2H), 3.21 (q, J = 6.8 Hz, 2H), 1.75 (s, 3H), 1.69 (s, 3H), 1.47 (t, J = 6.4 Hz, 3H).<br>LCMS RT = 1.510 min, m/z = 462.2 | 0.0319 |
| I-227 | 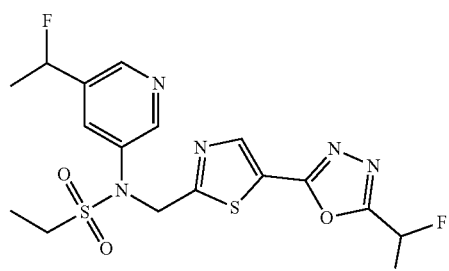<br>N-({5-[5-(difluoromethyl)-1,3,4-oxadiazol-2-yl]-1,3-thiazol-2-yl}methyl)-N-[5-(1-fluoroethyl)pyridin-3-yl]ethane-1-sulfonamide | 1H NMR (400 MHz, CDCl3) δ 8.67 (d, J = 2.4 Hz, 1H), 8.56 (s, 1H), 8.39 (s, 1H), 7.83 (s, 1H), 6.91 (t, J = 51.6 Hz, 1H), 5.79-5.62 (m, 1H), 5.30 (s, 2H), 3.21 (q, J = 7.2 Hz, 2H), 1.74-1.56 (m, 3H), 1.47 (t, J = 7.2 Hz, 3H).<br>LCMS RT = 1.518 min, m/z = 447.9 | 0.0123 |

TABLE 13-continued

Characterization Data and HDAC6 Activity for Compounds of Formula (I).

| Cmpd | Structure/Name | ¹H NMR<br>MS (m/z) (RT) | HDAC6 IC$_{50}$ (μM) |
|---|---|---|---|
| I-228 | 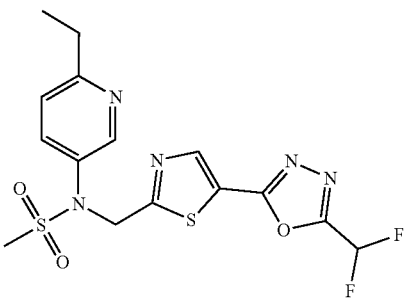 [SMILES: CCc1ccc(N(Cc2ncc(-c3nnc(C(F)F)o3)s2)S(C)(=O)=O)cn1]<br>N-({5-[5-(difluoromethyl)-1,3,4-oxadiazol-2-yl]-1,3-thiazol-2-yl}methyl)-N-(6-ethylpyridin-3-yl)methanesulfonamide | 1H NMR (400 MHz, CD3OD) δ 8.54 (d, J = 2.4 Hz, 1H), 8.39 (s, 1H), 7.93-7.88 (m, 1H), 7.35 (d, J = 8.4 Hz, 1H), 7.17 (t, J = 51.6 Hz, 1H), 5.31 (s, 2H), 3.12 (s, 3H), 2.78 (q, J = 7.6 Hz, 2H), 1.24 (t, J = 7.6 Hz, 3H).<br>LCMS RT = 0.981 min, m/z = 416.2 | 0.0435 |
| I-229 | 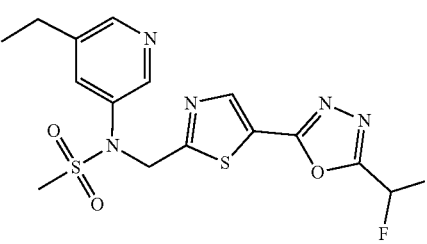<br>N-({5-[5-(difluoromethyl)-1,3,4-oxadiazol-2-yl]-1,3-thiazol-2-yl}methyl)-N-(5-ethylpyridin-3-yl)methanesulfonamide | 1H NMR (400 MHz, CD3OD) δ 8.51 (s, 1H), 8.42 (s, 1H), 8.40 (s, 1H), 7.89 (s, 1H), 7.18 (t, J = 51.6 Hz, 1H), 5.35 (s, 2H), 3.14 (s, 3H), 2.69 (q, J = 7.2 Hz, 2H), 1.25 (t, J = 7.6 Hz, 3H).<br>LCMS RT = 1.099 min, m/z = 416.2 | 0.0248 |
| I-230 | 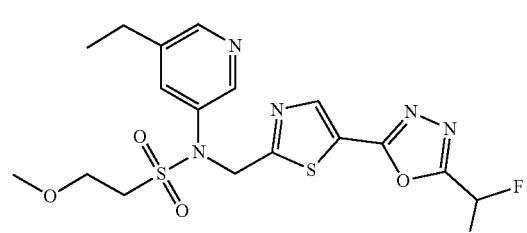<br>N-({5-[5-(difluoromethyl)-1,3,4-oxadiazol-2-yl]-1,3-thiazol-2-yl}methyl)-N-(5-ethylpyridin-3-yl)-2-methoxyethane-1-sulfonamide | 1H NMR (400 MHz, CD3OD) δ 8.50 (d, J = 2.4 Hz, 1H), 8.38 (s, 1H), 8.35 (s, 1H), 7.88 (s, 1H), 7.18 (t, J = 51.6 Hz, 1H), 5.31 (s, 2H), 3.82 (t, J = 5.6 Hz, 2H), 3.48 (t, J = 5.2 Hz, 2H), 3.43 (s, 3H), 2.69 (q, J = 5.2 Hz, 2H), 1.24 (t, J = 7.6 Hz, 3H).<br>LCMS RT = 1.752 min, m/z = 460.2 | 0.033 |
| I-231 | 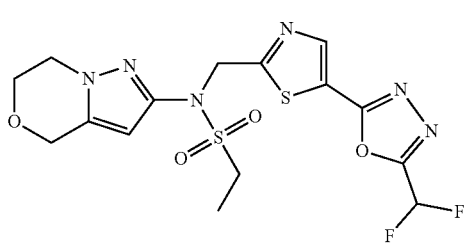<br>N-({5-[5-(difluoromethyl)-1,3,4-oxadiazol-2-yl]-1,3-thiazol-2-yl}methyl)-N-{4H,6H,7H-pyrazolo[3,2-c][1,4]oxazin-2-yl}ethane-1-sulfonamide | 1H NMR (400 MHz, CDCl3) δ 8.39 (s, 1H), 6.90 (t, J = 51.6 Hz, 1H), 6.12 (s, 1H), 5.38 (s, 2H), 4.77 (s, 2H), 4.12-4.06 (m, 4H), 3.27 (q, J = 7.2 Hz, 2H), 1.42 (t, J = 7.6 Hz, 3H).<br>LCMS RT = 0.552 min, m/z = 447.1 | 0.0924 |

TABLE 13-continued

Characterization Data and HDAC6 Activity for Compounds of Formula (I).

| Cmpd | Structure/Name | $^1$H NMR MS (m/z) (RT) | HDAC6 IC$_{50}$ (μM) |
|---|---|---|---|
| I-232 | N-[5-(difluoromethoxy)pyridin-3-yl]-N-({5-[5-(trifluoromethyl)-1,3,4-oxadiazol-2-yl]-1,3-thiazol-2-yl}methyl)methanesulfonamide | 1H NMR (400 MHz, CDCl3) δ 8.63 (d, J = 2.0 Hz, 1H), 8.51 (d, J = 2.4 Hz, 1H), 8.46 (s, 1H), 7.70 (s, 1H), 6.61 (t, J = 71.6 Hz, 1H), 5.30 (s, 2H), 3.13 (s, 3H). LCMS RT = 1.766 min, m/z = 471.8 | 0.0342 |
| I-233 | N-[5-(difluoromethoxy)pyridin-3-yl]-N-({5-[5-(trifluoromethyl)-1,3,4-oxadiazol-2-yl]-1,3-thiazol-2-yl}methyl)propane-1-sulfonamide | 1H NMR (400 MHz, CDCl3) δ 8.59 (d, J = 2.0 Hz, 1H), 8.47 (d, J = 2.4 Hz, 1H), 8.42 (s, 1H), 7.67 (t, J = 2.4 Hz, 1H), 6.59 (t, J = 72.0 Hz, 1H), 5.29 (s, 2H), 3.19-3.11 (m, 2H), 1.97-1.88 (m, 2H), 1.08 (t, J = 7.6 Hz, 3H). LCMS RT = 2.013 min, m/z = 499.9 | 0.0606 |
| I-234 | N-(5-cyanopyridin-3-yl)-N-({5-[5-(trifluoromethyl)-1,3,4-oxadiazol-2-yl]-1,3-thiazol-2-yl}methyl)propane-1-sulfonamide | 1H NMR (400 MHz, CDCl3) δ 8.95 (d, J = 2.4 Hz, 1H), 8.82 (s, 1H), 8.44 (s, 1H), 8.16 (d, J = 2.4 Hz, 1H), 5.29 (s, 2H), 3.18-3.11 (m, 2H), 2.00-1.80 (m, 2H), 1.09 (t, J = 7.2 Hz, 3H). LCMS RT = 1.811 min, m/z = 459.2 | 0.184 |
| I-235 | N-({5-[5-(difluoromethyl)-1,3,4-oxadiazol-2-yl]-1,3-thiazol-2-yl}methyl)-N-(1H-imidazol-5-yl)ethane-1-sulfonamide | 1H NMR (400 MHz, CD3OD) δ 8.43 (s, 1H), 7.99 (s, 1H), 7.39-7.03 (m, 2H), 5.30 (s, 2H), 3.39-3.28 (m, 2H), 1.40 (t, J = 7.2 Hz, 3H). LCMS RT = 1.848 min, m/z = 390.8 | 0.323 |

TABLE 13-continued

Characterization Data and HDAC6 Activity for Compounds of Formula (I).

| Cmpd | Structure/Name | $^1$H NMR<br>MS (m/z) (RT) | HDAC6<br>IC$_{50}$<br>(μM) |
|---|---|---|---|
| I-236 | N-({5-[5-(difluoromethyl)-1,3,4-oxadiazol-2-yl]-1,3-thiazol-2-yl}methyl)-N-(6-methylpyridin-2-yl)ethane-1-sulfonamide | 1H NMR (400 MHz, CDCl3) δ 8.39 (s, 1H), 7.61 (t, J = 8.0 Hz, 1H), 7.45 (d, J = 8.4 Hz, 1H), 7.01 (s, 1H), 6.89 (t, J = 51.6 Hz, 1H), 5.60 (s, 2H), 3.27 (q, J = 7.6 Hz, 2H), 2.52 (s, 3H), 1.37 (t, J = 7.4 Hz, 3H).<br>LCMS RT = 1.704 min, m/z = 416.2 | 0.0592 |
| I-237 | N-(3-fluorophenyl)-N-({5-[5-(trifluoromethyl)-1,3,4-oxadiazol-2-yl]-1,3-thiazol-2-yl}methyl)methanesulfonamide | 1H NMR (400 MHz, CDCl3) δ 8.41 (s, 1H), 7.44-7.36 (m, 1H), 7.30-7.27 (m, 1H), 7.24-7.20 (m, 1H), 7.12-7.05 (m, 1H), 5.27 (s, 2H), 3.07 (s, 3H).<br>LCMS RT = 1.912 min, m/z = 422.8 | 0.0992 |
| I-238 | N-({5-[5-(trifluoromethyl)-1,3,4-oxadiazol-2-yl]-1,3-thiazol-2-yl}methyl)-N-[5-(trifluoromethyl)pyridin-3-yl]methanesulfonamide | 1H NMR (400 MHz, CDCl3) δ 8.95 (d, J = 2.0 Hz, 1H), 8.87 (s, 1H), 8.46 (s, 1H), 8.12 (t, J = 2.0 Hz, 1H), 5.31 (s, 2H), 3.12 (s, 3H).<br>LCMS RT = 1.905 min, m/z = 473.8 | 0.256 |
| I-239 | N-(5-cyclopropylpyridin-3-yl)-N-({5-[5-(trifluoromethyl)-1,3,4-oxadiazol-2-yl]-1,3-thiazol-2-yl}methyl)methanesulfonamide | 1H NMR (400 MHz, CDCl3) δ 8.46 (s, 1H), 8.42 (s, 1H), 8.37 (s, 1H), 7.45 (t, J = 2.4 Hz, 1H), 5.26 (s, 2H), 3.09 (s, 3H), 2.00-1.90 (m, 1H), 1.11-1.08 (m, 2H), 0.78-0.75 (m, 2H).<br>LCMS RT = 1.621 min, m/z = 445.9 | 0.085 |

TABLE 13-continued

Characterization Data and HDAC6 Activity for Compounds of Formula (I).

| Cmpd | Structure/Name | ¹H NMR MS (m/z) (RT) | HDAC6 IC$_{50}$ (μM) |
|---|---|---|---|
| I-240 | 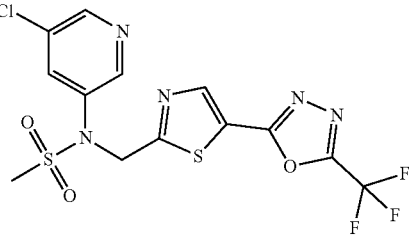<br>N-(5-chloropyridin-3-yl)-N-({5-[5-(trifluoromethyl)-1,3,4-oxadiazol-2-yl]-1,3-thiazol-2-yl}methyl)methanesulfonamide | 1H NMR (400 MHz, CDCl3) δ 8.62 (s, 1H), 8.57 (s, 1H), 7.89 (s, 1H), 5.28 (s, 2H), 3.11 (s, 3H). LCMS RT = 2.259 min, m/z = 440.1 | 0.062 |
| I-241 | 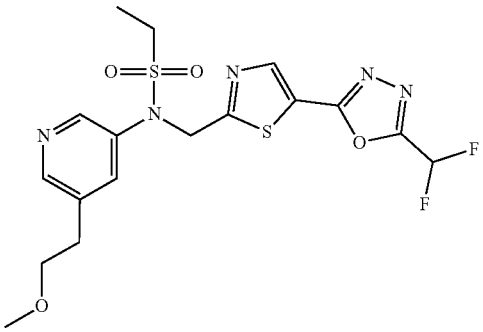 [SMILES: CCS(=O)(=O)N(Cc1ncc(-c2nnc(C(F)F)o2)s1)c1cncc(CCOC)c1]<br>N-({5-[5-(difluoromethyl)-1,3,4-oxadiazol-2-yl]-1,3-thiazol-2-yl}methyl)-N-[5-(2-methoxyethyl)pyridin-3-yl]ethane-1-sulfonamide | 1H NMR (400 MHz, CDCl3) δ 8.50 (s, 1H), 8.48 (s, 1H), 7.80 (s, 1H), 7.65 (s, 1H), 6.92 (t, J = 51.6 Hz, 1H), 5.80 (s, 2H), 3.60 (t, J = 6.0 Hz, 2H), 3.33 (s, 3H), 3.08 (q, J = 7.2 Hz, 2H), 2.85 (t, J = 6.0 Hz, 2H), 1.40 (t, J = 7.6 Hz, 3H). LCMS RT = 0.718 min, m/z = 460.2 | 0.994 |
| I-242 | 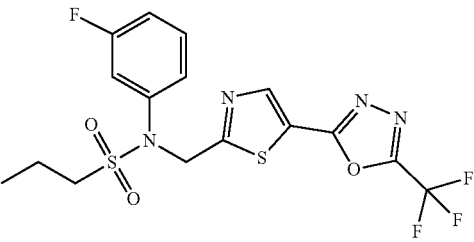 [SMILES: CCCS(=O)(=O)N(Cc1ncc(-c2nnc(C(F)(F)F)o2)s1)c1cccc(F)c1]<br>N-(3-fluorophenyl)-N-({5-[5-(trifluoromethyl)-1,3,4-oxadiazol-2-yl]-1,3-thiazol-2-yl}methyl)propane-1-sulfonamide | 1H NMR (400 MHz, CDCl3) δ 8.41 (s, 1H), 7.43-7.37 (m, 1H), 7.27-7.26 (m, 1H), 7.25-7.22 (m, 1H), 7.10-7.05 (m, 1H), 5.30 (s, 2H), 3.15-3.10 (m, 2H), 1.97-1.89 (m, 2H), 1.09 (t, J = 7.2 Hz, 3H). LCMS RT = 2.207 min, m/z = 450.8 | 0.053 |
| I-243 | 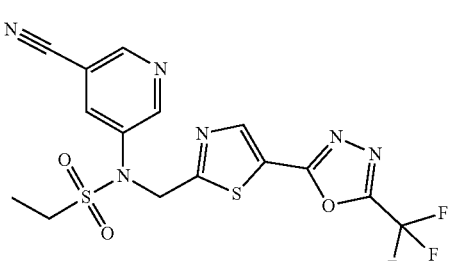<br>N-(5-cyanopyridin-3-yl)-N-({5-[5-(trifluoromethyl)-1,3,4-oxadiazol-2-yl]-1,3-thiazol-2-yl}methyl)ethane-1-sulfonamide | 1H NMR (400 MHz, CDCl3) δ 8.96 (d, J = 2.4 Hz, 1H), 8.82 (d, J = 2.0 Hz, 1H), 8.44 (s, 1H), 8.17 (t, J = 2.0 Hz, 1H), 5.30 (s, 2H), 3.21 (q, J = 7.2 Hz, 2H), 1.45 (t, J = 7.2 Hz, 3H). LCMS RT = 1.718 min, m/z = 444.8 | 0.129 |

TABLE 13-continued

Characterization Data and HDAC6 Activity for Compounds of Formula (I).

| Cmpd | Structure/Name | $^1$H NMR MS (m/z) (RT) | HDAC6 IC$_{50}$ (μM) |
|---|---|---|---|
| I-244 | 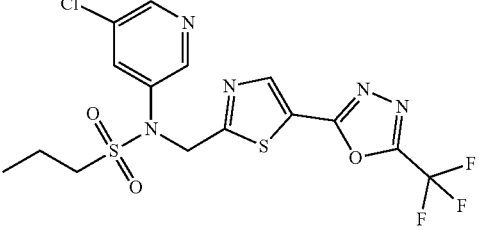<br>N-(5-chloropyridin-3-yl)-N-({5-[5-(trifluoromethyl)-1,3,4-oxadiazol-2-yl]-1,3-thiazol-2-yl}methyl)propane-1-sulfonamide | 1H NMR (400 MHz, CDCl3) δ 8.61 (d, J = 2.4 Hz, 1H), 8.55 (d, J = 2.4 Hz, 1H), 8.42 (s, 1H), 7.88 (t, J = 2.0 Hz, 1H), 5.28 (s, 2H), 3.19-3.11 (m, 2H), 1.97-1.82 (m, 2H), 1.09 (t, J = 7.6 Hz, 3H). LCMS RT = 2.027 min, m/z = 467.8 | 0.0872 |
| I-245 | 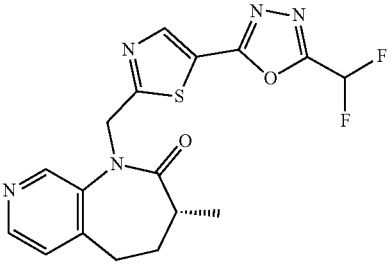 [SMILES: C[C@@H]1CCc2ccncc2N(Cc2ncc(-c3nnc(C(F)F)o3)s2)C1=O]<br>(3R)-1-({5-[5-(difluoromethyl)-1,3,4-oxadiazol-2-yl]-1,3-thiazol-2-yl}methyl)-3-methyl-1H,2H,3H,4H,5H-pyrido[3,4-b]azepin-2-one | 1H NMR (400 MHz, CDCl3) δ 8.96 (s, 1H), 8.52 (d, J = 5.2 Hz, 1H), 8.38 (s, 1H), 7.52 (d, J = 5.2 Hz, 1H), 6.91 (t, J = 51.6 Hz, 1H), 5.47-5.27 (m, 2H), 3.09-3.04 (m, 1H), 2.83-2.78 (m, 1H), 2.51-2.47 (m, 1H), 2.26-2.21 (m, 1H), 2.18-2.11 (m, 1H), 1.16 (d, J = 6.4 Hz, 3H) LCMS RT = 1.250 min, m/z = 392.3. | 1.42 |
| I-246 | 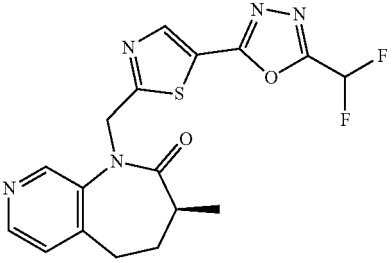 [SMILES: C[C@H]1CCc2ccncc2N(Cc2ncc(-c3nnc(C(F)F)o3)s2)C1=O]<br>(3S)-1-({5-[5-(difluoromethyl)-1,3,4-oxadiazol-2-yl]-1,3-thiazol-2-yl}methyl)-3-methyl-1H,2H,3H,4H,5H-pyrido[3,4-b]azepin-2-one | 1H NMR (400 MHz, CDCl3) δ 8.91 (s, 1H), 8.50 (d, J = 5.2 Hz, 1H), 8.37 (s, 1H), 7.47 (d, J = 5.2 Hz, 1H), 6.91 (t, J = 51.6 Hz, 1H), 5.46-5.28 (m, 2H), 3.11-2.85 (m, 1H), 2.84-2.71 (m, 1H), 2.548-2.45 (m, 1H), 2.29-2.14 (m, 1H), 2.18-2.07 (m, 1H), 1.16 (d, J = 6.4 Hz, 3H) LCMS RT = 1.251 min, m/z = 392.3. | 0.039 |
| I-247 | 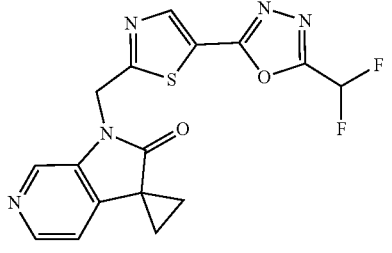 [SMILES: O=C1N(Cc2ncc(-c3nnc(C(F)F)o3)s2)c2cnccc2C12CC2]<br>1'-({5-[5-(difluoromethyl)-1,3,4-oxadiazol-2-yl]-1,3-thiazol-2-yl}methyl)-1',2'-dihydrospiro[cyclopropane-1,3'-pyrrolo[2,3-c]pyridin]-2'-one | 1H NMR (400 MHz, CDCl3) δ 8.47 (s, 1H), 8.44-8.40 (m, 2 H), 7.07 (d, J = 5.2 Hz, 1H), 6.90 (t, J = 51.6 Hz, 1H), 5.43 (s, 2H), 2.17-2.10 (m, 2H), 1.93-1.86 (m, 2H) LCMS RT = 0.970 min, m/z = 376.2. | 0.158 |

TABLE 13-continued

Characterization Data and HDAC6 Activity for Compounds of Formula (I).

| Cmpd | Structure/Name | ¹H NMR MS (m/z) (RT) | HDAC6 IC$_{50}$ (μM) |
|---|---|---|---|
| I-248 | 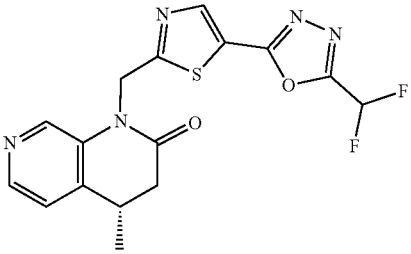 [SMILES: C[C@H]1CC(=O)N(Cc2ncc(-c3nnc(C(F)F)o3)s2)c2cnccc21]<br>(4S)-1-({5-[5-(difluoromethyl)-1,3,4-oxadiazol-2-yl]-1,3-thiazol-2-yl}methyl)-4-methyl-1,2,3,4-tetrahydro-1,7-naphthyridin-2-one | 1H NMR (400 MHz, CDCl3) δ 8.54 (s, 1H), 8.41 (s, 1H), 8.35 (d, J = 4.8 Hz, 1H), 7.19 (d, J = 4.8 Hz, 1H), 6.89 (t, J = 51.6 Hz, 1H), 5.62-5.46 (m, 2H), 3.23-3.16 (m, 1H), 2.92-2.84 (m, 1H), 2.66-2.55 (m, 1H), 1.38 (d, J = 6.8 Hz, 3H)<br>LCMS RT = 1.098 min, m/z = 378.3. | 0.034 |
| I-249 | 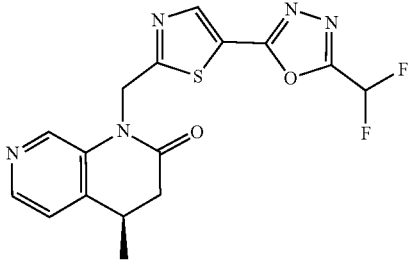 [SMILES: C[C@@H]1CC(=O)N(Cc2ncc(-c3nnc(C(F)F)o3)s2)c2cnccc21]<br>(4R)-1-({5-[5-(difluoromethyl)-1,3,4-oxadiazol-2-yl]-1,3-thiazol-2-yl}methyl)-4-methyl-1,2,3,4-tetrahydro-1,7-naphthyridin-2-one | 1H NMR (400 MHz, CDCl3) δ 8.53 (s, 1H), 8.40 (s, 1H), 8.34 (d, J = 4.8 Hz, 1H), 7.18 (d, J = 4.8 Hz, 1H), 6.90 (t, J = 51.6 Hz, 1H), 5.60-5.46 (m, 2H), 3.23-3.15 (m, 1H), 2.90-2.81 (m, 1H), 2.64-2.55 (m, 1H), 1.38 (d, J = 6.8 Hz, 3H)<br>LCMS RT = 1.028 min, m/z = 378.2. | 0.089 |
| I-250 | 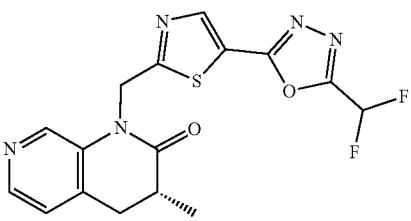 [SMILES: C[C@@H]1Cc2ccncc2N(Cc2ncc(-c3nnc(C(F)F)o3)s2)C1=O]<br>(3R)-1-({5-[5-(difluoromethyl)-1,3,4-oxadiazol-2-yl]-1,3-thiazol-2-yl}methyl)-3-methyl-1,2,3,4-tetrahydro-1,7-naphthyridin-2-one | 1H NMR (400 MHz, CDCl3) δ 8.54 (s, 1H), 8.41 (s, 1H), 8.31 (d, J = 3.6 Hz, 1H), 7.18 (d, J = 4.4 Hz, 1H), 6.89 (t, J = 51.6 Hz, 1H), 5.62-5.36 (m, 2H), 3.09-3.02 (m, 1H), 2.89-2.79 (m, 2H), 1.35 (d, J = 6.8 Hz, 3H).<br>LCMS RT = 0.684 min, m/z = 378.2. | 0.041 |
| I-251 | 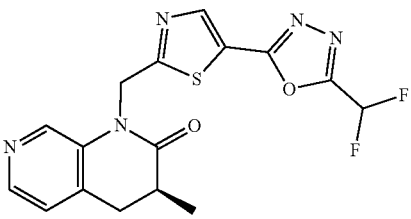 [SMILES: C[C@H]1Cc2ccncc2N(Cc2ncc(-c3nnc(C(F)F)o3)s2)C1=O]<br>(3S)-1-({5-[5-(difluoromethyl)-1,3,4-oxadiazol-2-yl]-1,3-thiazol-2-yl}methyl)-3-methyl-1,2,3,4-tetrahydro-1,7-naphthyridin-2-one | 1H NMR (400 MHz, CDCl3) δ 8.52 (s, 1H), 8.41 (s, 1H), 8.30 (d, J = 4.4 Hz, 1H), 7.17 (d, J = 4.8 Hz, 1H), 6.89 (t, J = 51.6 Hz, 1H), 5.62-5.36 (m, 2H), 3.09-3.02 (m, 1H), 2.89-2.79 (m, 2H), 1.34 (d, J = 6.8 Hz, 3H).<br>LCMS RT = 0.521 min, m/z = 378.2. | 0.034 |

TABLE 13-continued

Characterization Data and HDAC6 Activity for Compounds of Formula (I).

| Cmpd | Structure/Name | $^1$H NMR<br>MS (m/z) (RT) | HDAC6 IC$_{50}$ (μM) |
|---|---|---|---|
| I-252 | 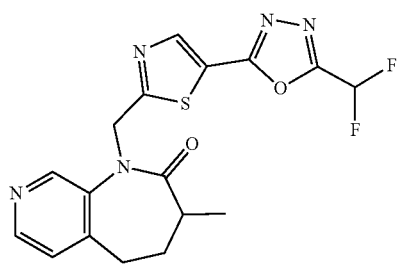 [SMILES: CC1CCc2ccncc2N(Cc2ncc(-c3nnc(C(F)F)o3)s2)C1=O]<br>1-({5-[5-(difluoromethyl)-1,3,4-oxadiazol-2-yl]-1,3-thiazol-2-yl}methyl)-3-methyl-1H,2H,3H,4H,5H-pyrido[3,4-b]azepin-2-one | 1H NMR (400 MHz, CDCl3) δ 8.77 (s, 1H), 8.46 (d, J = 4.8 Hz, 1H), 8.37 (s, 1H), 7.30 (d, J = 4.4 Hz, 1H), 6.90 (t, J = 51.6 Hz, 1H), 5.37 (s, 2H), 2.99-2.90 (m, 1H), 2.70-2.66 (m, 1H), 2.55-2.49 (m, 1H), 2.23-2.14 (m, 1H), 2.18-2.04 (m, 1H), 1.16 (d, J = 6.4 Hz, 3H).<br>LCMS RT = 1.229 min, m/z = 392.3. | 0.073 |
| I-253 | 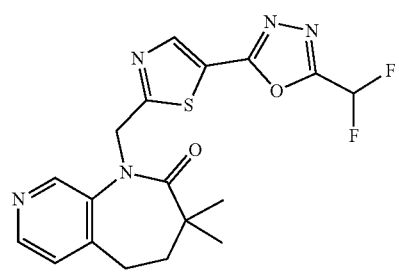 [SMILES: CC1(C)CCc2ccncc2N(Cc2ncc(-c3nnc(C(F)F)o3)s2)C1=O]<br>1-({5-[5-(difluoromethyl)-1,3,4-oxadiazol-2-yl]-1,3-thiazol-2-yl}methyl)-3,3-dimethyl-1H,2H,3H,4H,5H-pyrido[3,4-b]azepin-2-one | 1H NMR (400 MHz, CDCl3) δ 8.84 (s, 1H), 8.47 (s, 1H), 8.40 (s, 1H), 7.42 (s, 1H), 6.91 (t, J = 51.6 Hz, 1H), 5.37 (s, 2H), 2.91 (t, J = 6.0 Hz, 2H), 2.18 (t, J = 6.4 Hz, 2H), 1.04 (s, 6H)<br>LCMS RT = 1.946 min, m/z = 405.9. | 0.035 |
| I-254 | 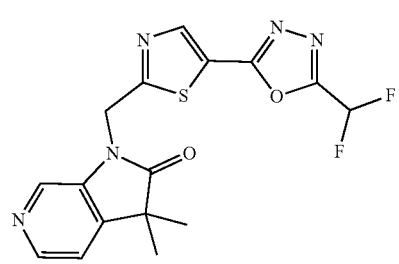 [SMILES: CC1(C)C(=O)N(Cc2ncc(-c3nnc(C(F)F)o3)s2)c2cnccc21]<br>1-({5-[5-(difluoromethyl)-1,3,4-oxadiazol-2-yl]-1,3-thiazol-2-yl}methyl)-3,3-dimethyl-1H,2H,3H-pyrrolo[2,3-c]pyridin-2-one | 1H NMR (400 MHz, CDCl3) δ 8.45-8.43 (m, 2H), 8.29 (s, 1H), 7.24 (d, J = 4.8 Hz, 1H), 6.89 (t, J = 51.6 Hz, 1H), 5.33 (s, 2H), 1.49 (s, 6H)<br>LCMS RT = 0.408 min, m/z = 378.1. | 0.149 |
| I-255 | 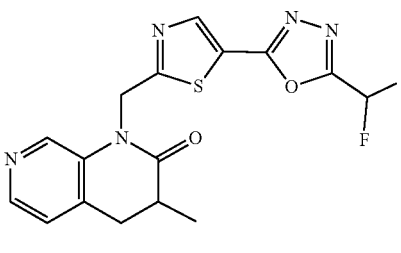<br>1-({5-[5-(difluoromethyl)-1,3,4-oxadiazol-2-yl]-1,3-thiazol-2-yl}methyl)-3-methyl-1,2,3,4-tetrahydro-1,7-naphthyridin-2-one | 1H NMR (400 MHz, CDCl3) δ 8.59 (s, 1H), 8.42 (s, 1H), 8.34 (d, J = 4.8 Hz, 1H), 7.26 (d, J = 4.8 Hz, 1H), 6.90 (t, J = 51.6 Hz, 1H), 5.63-5.37 (m, 2H), 3.13-3.06 (m, 1H), 2.92-2.80 (m, 2H), 1.36 (d, J = 6.4 Hz, 3H)<br>LCMS RT = 0.583 min, m/z = 378.2. | 0.036 |

TABLE 13-continued

Characterization Data and HDAC6 Activity for Compounds of Formula (I).

| Cmpd | Structure/Name | $^1$H NMR<br>MS (m/z) (RT) | HDAC6<br>IC$_{50}$<br>(μM) |
|---|---|---|---|
| I-256 | 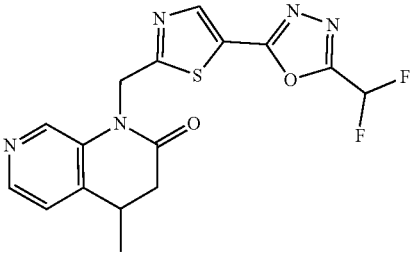 [SMILES: CC1CC(=O)N(Cc2ncc(-c3nnc(C(F)F)o3)s2)c2cnccc21]<br>1-({5-[5-(difluoromethyl)-1,3,4-oxadiazol-2-yl]-1,3-thiazol-2-yl}methyl)-4-methyl-1,2,3,4-tetrahydro-1,7-naphthyridin-2-one | 1H NMR (400 MHz, CDCl3) δ 8.58 (s, 1H), 8.45-8.34 (m, 2H), 7.25 (d, J = 4.8 Hz, 1H), 6.89 (t, J = 51.6 Hz, 1H), 5.62-5.47 (m, 2H), 3.27-3.20 (m, 1H), 2.94-2.82 (m, 1H), 2.67-2.56 (m, 1H), 1.40 (d, J = 6.8 Hz, 3H) LCMS RT = 0.580 min, m/z = 378.2. | 0.057 |
| I-257 | 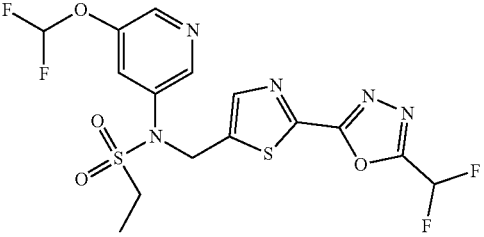 [SMILES: CCS(=O)(=O)N(Cc1cnc(-c2nnc(C(F)F)o2)s1)c1cncc(OC(F)F)c1]<br>N-[5-(difluoromethoxy)pyridin-3-yl]-N-({2-[5-(difluoromethyl)-1,3,4-oxadiazol-2-yl]-1,3-thiazol-5-yl}methyl)ethane-1-sulfonamide | 1H NMR (400 MHz, CD3OD) δ 8.48 (d, J = 2.4 Hz, 1H), 8.40 (d, J = 2.4 Hz, 1H), 7.90 (s, 1H), 7.77 (t, J = 2.4 Hz, 1H), 7.23 (t, J = 51.6 Hz, 1H), 6.97 (t, J = 72.8 Hz, 1H), 5.35 (s, 2H), 3.31 (q, J = 7.6 Hz, 2H), 1.41 (t, J = 7.6 Hz, 3H) LCMS RT = 1.251 min, m/z = 468.2. | 0.231 |
| I-258 | 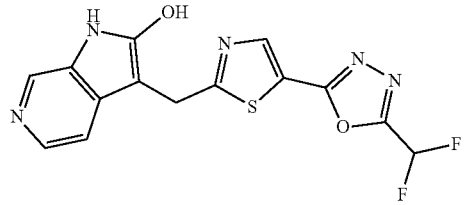 [SMILES: Oc1[nH]c2cnccc2c1Cc1ncc(-c2nnc(C(F)F)o2)s1]<br>3-({5-[5-(difluoromethyl)-1,3,4-oxadiazol-2-yl]-1,3-thiazol-2-yl}methyl)-1H-pyrrolo[2,3-c]pyridin-2-ol | 1H NMR (400 MHz, CD3OD) δ 8.40 (s, 1H), 7.65 (s, 1H), 7.50 (d, J = 6.8 Hz, 1H), 7.17 (t, J = 51.6 Hz, 1H), 6.94 (d, J = 6.8 Hz, 1H), 4.27 (s, 2H) LCMS RT = 0.778 min, m/z = 350.2. | 0.069 |
| I-259 | 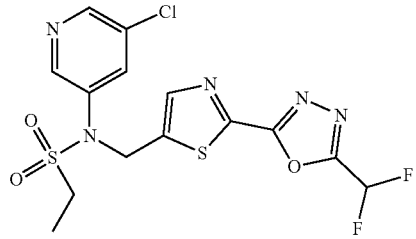 [SMILES: CCS(=O)(=O)N(Cc1cnc(-c2nnc(C(F)F)o2)s1)c1cncc(Cl)c1]<br>N-(5-chloropyridin-3-yl)-N-({2-[5-(difluoromethyl)-1,3,4-oxadiazol-2-yl]-1,3-thiazol-5-yl}methyl)ethane-1-sulfonamide | 1H NMR (400 MHz, CD3OD) δ 8.55-8.51 (m, 2H), 8.05 (t, J = 2.4 Hz, 1H), 7.92 (s, 1H), 7.25 (t, J = 51.6 Hz, 1H), 5.36 (s, 2H), 3.34 (q, J = 7.2 Hz, 2H), 1.42 (t, J = 7.6 Hz, 3H) LCMS RT = 1.273 min, m/z = 436.2. | 0.121 |

TABLE 13-continued

Characterization Data and HDAC6 Activity for Compounds of Formula (I).

| Cmpd | Structure/Name | $^1$H NMR MS (m/z) (RT) | HDAC6 IC$_{50}$ (μM) |
|---|---|---|---|
| I-260 | 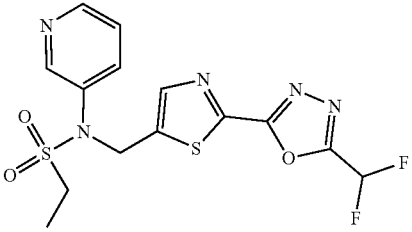 [SMILES: CCS(=O)(=O)N(Cc1cnc(-c2nnc(C(F)F)o2)s1)c1cccnc1]<br>N-({2-[5-(difluoromethyl)-1,3,4-oxadiazol-2-yl]-1,3-thiazol-5-yl}methyl)-N-(pyridin-3-yl)ethane-1-sulfonamide | 1H NMR (400 MHz, CDCl3) δ 8.58 (d, J = 2.4 Hz, 1H), 8.52-8.48 (m, 1H), 7.98 (s, 1H), 7.87-7.66 (m, 1H), 7.56 (t, J = 51.2 Hz, 1H), 7.45-7.42 (m, 1H), 5.34 (s, 2H), 3.37 (q, J = 7.2 Hz, 2H), 1.30 (t, J = 7.2 Hz, 3H) LCMS RT = 0.821 min, m/z = 402.2. | 0.333 |
| I-261 | 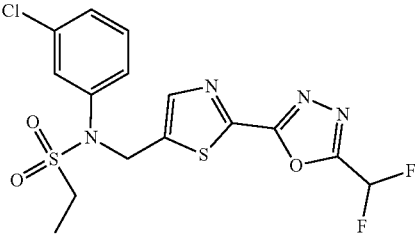 [SMILES: CCS(=O)(=O)N(Cc1cnc(-c2nnc(C(F)F)o2)s1)c1cccc(Cl)c1]<br>N-(3-chlorophenyl)-N-({2-[5-(difluoromethyl)-1,3,4-oxadiazol-2-yl]-1,3-thiazol-5-yl}methyl)ethane-1-sulfonamide | 1H NMR (400 MHz, CDCl3) δ 8.00 (s, 1H), 7.56 (t, J = 51.2 Hz, 1H), 7.41-7.36 (m, 4H), 5.32 (s, 2H), 3.36 (q, J = 7.2 Hz, 2H), 1.29 (t, J = 8.0 Hz, 3H) LCMS RT = 1.554 min, m/z = 435.1. | 0.089 |
| I-262 | 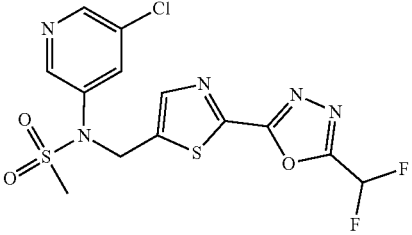 [SMILES: CS(=O)(=O)N(Cc1cnc(-c2nnc(C(F)F)o2)s1)c1cncc(Cl)c1]<br>N-(5-chloropyridin-3-yl)-N-({2-[5-(difluoromethyl)-1,3,4-oxadiazol-2-yl]-1,3-thiazol-5-yl}methyl)methanesulfonamide | 1H NMR (400 MHz, CD3OD) δ 8.61-8.47 (m, 2H), 8.05 (t, J = 2.4 Hz, 1H), 7.93 (s, 1H), 7.23 (t, J = 51.6 Hz, 1H), 5.32 (s, 2H), 3.16 (s, 3H) LCMS RT = 1.643 min, m/z = 422.1. | 0.110 |
| I-263 | 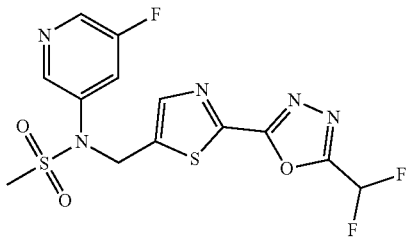 [SMILES: CS(=O)(=O)N(Cc1cnc(-c2nnc(C(F)F)o2)s1)c1cncc(F)c1]<br>N-({2-[5-(difluoromethyl)-1,3,4-oxadiazol-2-yl]-1,3-thiazol-5-yl}methyl)-N-(5-fluoropyridin-3-yl)methanesulfonamide | 1H NMR (400 MHz, CD3OD) δ 8.48 (s, 1H), 8.46 (d, J = 2.4 Hz, 1H), 7.93 (s, 1H), 7.88-7.82 (m, 1H), 7.23 (t, J = 51.6 Hz, 1H), 5.33 (s, 2H), 3.16 (s, 3H) LCMS RT = 1.478 min, m/z = 406.1. | 0.108 |

TABLE 13-continued

Characterization Data and HDAC6 Activity for Compounds of Formula (I).

| Cmpd | Structure/Name | $^1$H NMR MS (m/z) (RT) | HDAC6 IC$_{50}$ (µM) |
|---|---|---|---|
| I-264 | 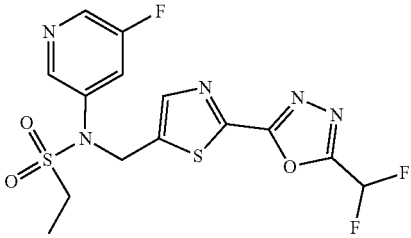 [SMILES: CCS(=O)(=O)N(Cc1cnc(-c2nnc(C(F)F)o2)s1)c1cncc(F)c1]<br>N-({2-[5-(difluoromethyl)-1,3,4-oxadiazol-2-yl]-1,3-thiazol-5-yl}methyl)-N-(5-fluoropyridin-3-yl)ethane-1-sulfonamide | 1H NMR (400 MHz, CD3OD) δ 8.48 (s, 1H), 8.45 (d, J = 2.8 Hz, 1H), 7.91 (s, 1H), 7.86-7.80 (m, 1H), 7.24 (t, J = 51.6 Hz, 1H), 5.35 (s, 2H), 3.31 (q, J = 7.2 Hz, 2H), 1.41 (t, J = 7.6 Hz, 3H). LCMS RT = 1.618 min, m/z = 420.2. | 0.087 |
| I-265 | 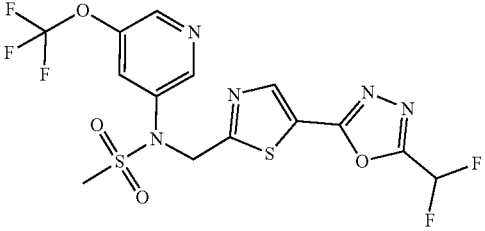 [SMILES: CS(=O)(=O)N(Cc1ncc(-c2nnc(C(F)F)o2)s1)c1cncc(OC(F)(F)F)c1]<br>N-({5-[5-(difluoromethyl)-1,3,4-oxadiazol-2-yl]-1,3-thiazol-2-yl}methyl)-N-[5-(trifluoromethoxy)pyridin-3-yl]methanesulfonamide | 1H NMR (400 MHz, CDCl3) δ 8.72 (d, J = 2.0 Hz, 1H), 8.56 (s, 1H), 8.44 (s, 1H), 7.80 (s, 1H), 6.92 (t, J = 51.6 Hz, 1H), 5.30 (s, 2H), 3.11 (s, 3H) LCMS RT = 1.950 min, m/z = 472.1. | 0.048 |
| I-266 | 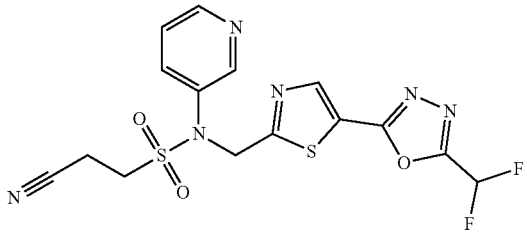 [SMILES: N#CCCS(=O)(=O)N(Cc1ncc(-c2nnc(C(F)F)o2)s1)c1cccnc1]<br>2-cyano-N-({5-[5-(difluoromethyl)-1,3,4-oxadiazol-2-yl]-1,3-thiazol-2-yl}methyl)-N-(pyridin-3-yl)ethane-1-sulfonamide | 1H NMR (400 MHz, CD3OD) δ 8.70 (d, J = 2.8 Hz, 1H), 8.52 (d, J = 3.6 Hz, 1H), 8.44 (s, 1H), 8.07-8.01 (m, 1H), 7.54-7.49 (m, 1H), 7.21 (t, J = 51.6 Hz, 1H), 5.41 (s, 2H), 3.72 (t, J = 7.2 Hz, 2H), 3.05 (t, J = 7.2 Hz, 2H). LCMS RT = 1.287 min, m/z = 426.8. | 0.042 |
| I-267 | 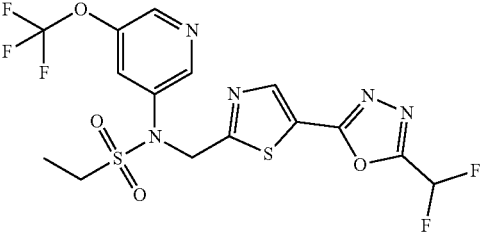 [SMILES: CCS(=O)(=O)N(Cc1ncc(-c2nnc(C(F)F)o2)s1)c1cncc(OC(F)(F)F)c1]<br>N-({5-[5-(difluoromethyl)-1,3,4-oxadiazol-2-yl]-1,3-thiazol-2-yl}methyl)-N-[5-(trifluoromethoxy)pyridin-3-yl]ethane-1-sulfonamide | 1H NMR (400 MHz, CDCl3) δ 8.71 (s, 1H), 8.54 (s, 1H), 8.41 (s, 1H), 7.79 (s, 1H), 6.92 (t, J = 51.6 Hz, 1H), 5.30 (s, 2H), 3.22 (q, J = 7.6 Hz, 2H), 1.45 (t, J = 7.6 Hz, 3H) LCMS RT = 0.328 min, m/z = 486.1 | 0.044 |

TABLE 13-continued

Characterization Data and HDAC6 Activity for Compounds of Formula (I).

| Cmpd | Structure/Name | 1H NMR MS (m/z) (RT) | HDAC6 IC$_{50}$ (µM) |
|---|---|---|---|
| I-268 | 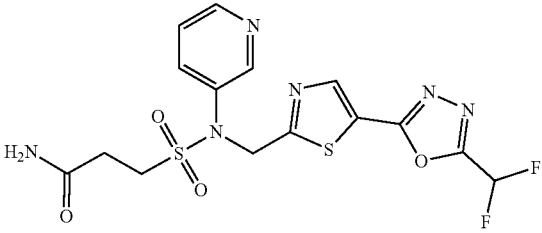 [SMILES: NC(=O)CCS(=O)(=O)N(Cc1ncc(-c2nnc(C(F)F)o2)s1)c1cccnc1]<br>3-[({5-[5-(difluoromethyl)-1,3,4-oxadiazol-2-yl]-1,3-thiazol-2-yl}methyl)(pyridin-3-yl)sulfamoyl]propanamide | 1H NMR (400 MHz, CDCl3) δ 8.75 (d, J = 2.4 Hz, 1H), 8.62-8.55 (m, 1H), 8.39 (s, 1H), 7.90-7.84 (m, 1H), 7.40-7.33 (m, 1H), 6.91 (t, J = 52.0 Hz, 1H), 5.27 (s, 2H), 3.58 (t, J = 7.2 Hz, 2H), 2.81 (t, J = 7.2 Hz, 2H). LCMS RT = 0.783 min, m/z = 444.9. | 0.013 |
| I-269 | 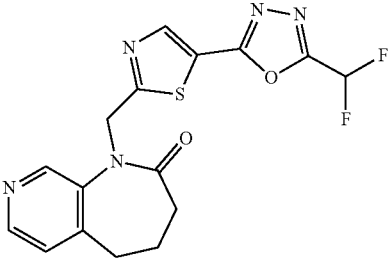 [SMILES: O=C1CCCc2ccncc2N1Cc1ncc(-c2nnc(C(F)F)o2)s1]<br>1-({5-[5-(difluoromethyl)-1,3,4-oxadiazol-2-yl]-1,3-thiazol-2-yl}methyl)-1H,2H,3H,4H,5H-pyrido[3,4-b]azepin-2-one | 1H NMR (400 MHz, CDCl3) δ 8.77 (s, 1H), 8.46 (s, 1H), 8.38 (s, 1H), 7.28 (s, 1H), 6.91 (t, J = 51.6 Hz, 1H), 5.36 (s, 2H), 2.84 (t, J = 6.8 Hz, 2H), 2.49-2.37 (m, 2H), 2.37-2.23 (m, 2H). LCMS RT = 1.043 min, m/z = 378.2 | 0.018 |
| I-270 | 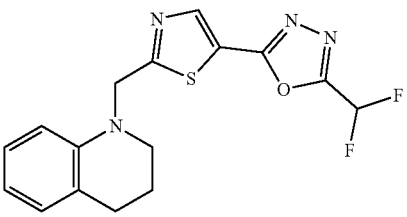 [SMILES: FC(F)c1nnc(-c2cnc(CN3CCCc4ccccc43)s2)o1]<br>1-({5-[5-(difluoromethyl)-1,3,4-oxadiazol-2-yl]-1,3-thiazol-2-yl}methyl)-1,2,3,4-tetrahydroquinoline | 1H NMR (400 MHz, DMSO-d6) δ 8.57 (s, 1H), 7.51 (t, J = 51.2 Hz, 1H), 7.00-6.90 (m, 2H), 6.60-6.55 (m, 2H), 4.86 (s, 2H), 3.47 (t, J = 5.6 Hz, 2H), 2.75 (t, J = 6.0 Hz, 2H), 2.02-1.92 (m, 2H) LCMS RT = 1.769 min, m/z = 349.2 | 0.539 |

Example 8

Biochemical Activity and Potency of Various HDAC6 Inhibitors of Formula (II)

The compounds disclosed herein, in particular those of Formula (II), were synthesized according to methods disclosed in WO2021067859, which is incorporated herein by reference in its entirety. These compounds were tested for potency against HDAC6 and selectivity against HDAC1 in a biochemical assay. A biochemical assay was adopted using a luminescent HDAC-Glo I/II assay (Promega) and measured the relative activity of HDAC6 and HDAC1 recombinant proteins. Compounds were first incubated in the presence of HDAC6 or HDAC1 separately, followed by addition of the luminescent substrate. The data was acquired using a plate reader and the biochemical IC$_{50}$ were calculated from the data accordingly. Data is tabulated in Table 14. From these studies, it was determined that the compounds of the present disclosure are selective inhibitors of HDAC6 over HDAC1, providing selectivity ratios from about 5 to about 300,000.

TABLE 14

Evaluation of HDAC6 Activity and Selectivity for Disclosed Compounds.

| Compound ID | HDAC6 IC50 (nM) |
|---|---|
| 1 | 136 |
| I-1 | 12.5 |
| I-6 | 1.61 |
| I-4 | 16.7 |
| I-24 | 146 |
| I-5 | 6.68 |
| I-7A | 1.5 |
| I-7B | 4.13 |
| I-2 | 104 |
| I-10 | 76.6 |

TABLE 14-continued

Evaluation of HDAC6 Activity and Selectivity for Disclosed Compounds.

| Compound ID | HDAC6 IC50 (nM) |
|---|---|
| I-3 | 73 |
| IV-1 | 8.26 |
| IV-4 | 1.8 |
| I-9A | 0.351 |
| IV-2 | 0.677 |
| IV-3 | 3.35 |
| I-9B | 0.791 |
| I-11 | 0.639 |
| I-19 | 0.425 |
| I-18 | 1.68 |
| I-16 | 1.61 |
| I-8B | 0.275 |
| I-13 | 73 |
| I-14 | 28.3 |
| I-17 | 1.12 |
| 4 | 1.2 |
| I-25 | 0.669 |
| IV-9 | 0.595 |
| I-21 | 0.601 |
| I-22 | 3.36 |
| I-23 | 1.59 |
| III-1 | 1.79 |
| IV-5 | 2.04 |
| I-12B | 0.809 |
| IV-10 | 2.3 |
| IV-7 | 1.1 |
| IV-6 | 4.06 |
| IV-8 | 10.3 |
| I-15 | 2.64 |
| I-20 | 3.78 |
| I-8A | 1.65 |
| 5 | 1.49 |
| I-26A | 4.57 |
| I-26B | 2.23 |
| 6 | 2.54 |
| I-27 | 1.13 |
| I-28A | 1.81 |
| I-29 | 13.2 |
| I-30A | 1.36 |
| I-30B | 7.91 |
| I-31 | 13.8 |
| I-32 | 13 |
| I-33 | 27.9 |
| I-34 | 2.32 |
| I-35 | 21.7 |
| I-36 | 5.22 |

The structures, chemical names and additional biochemical properties of the compounds described in this example are provided below.

| Aldehyde/ Organometallic | Compound | Characterization Data |
|---|---|---|
| cyclobutanone/ 2-bromopyridine, and n-BuLi | I-37 | ¹H NMR (400 MHz, MeOH-d4) δ 8.52 (d, J = 6.03 Hz, 1 H), 8.03 (s, 1 H), 7.70 (t, J = 7.70 Hz, 1 H), 7.58 (d, J = 12.2 Hz, 1 H), 7.51 (d, J = 8.07 Hz, 1 H), 7.22 (t, J = 6.03 Hz, 1 H), 2.89-2.80 (m, 2 H), 2.62-2.52 (m, 2 H), 2.20-2.15 (m, 1 H), 2.12-2.06 (m, 1H). LC-MS $t_R$ (min) 1.24 (20-100% ACN with 0.1% TFA 6 min), m/z [M + H]⁺ $C_{15}H_{15}FN_4O_2$ requires: 302.3, found: 303.1 HPLC $t_R$ (min) 3.68, 95% (20-100% ACN with 0.1% TFA 10 min. |

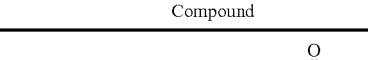

| Amine | Compound | Characterization Data |
|---|---|---|
| 2-amino-N, 2-dimethyl propanamide | I-33 | ¹H NMR (400 MHz, MeOH-d4) δ 8.24 (s, 1 H), 7.62 (s, 1 H), 7.59 (s, 1 H), 2.69-2.65 (m, 3 H), 1.59 (s, 6 H). LC-MS $t_R$ (min) 1.32 (20-100% ACN with 0.1% TFA 6 min), m/z [M + H]⁺ $C_{11}H_{15}FN_4O_2$ requires: 270.3, found: 271.1 HPLC $t_R$ (min) 1.57, 95% (20-100% ACN with 0.1% TFA 10 min.) |
| 3-amino-1-methyl-piperidin-2-one | I-35 | ¹H NMR (400 MHz, DMSO-d6) δ 11.1-10.9 (br, s, 1 H), 8.98 (s, 1 H), 8.25 (s, 1 H), 7.73-7.53 (m, 1 H), 7.29-7.04 (m, 1 H), 4.80-4.50 (m, 1 H), 3.33-3.28 (m, 2 H), 2.83 (s, 3 H), 2.16-2.00 (m, 1 H), 1.90 (br, s, 3 H). LC-MS: tR (min) 1.28 (20-100% ACN with 0.1% TFA 6 min), m/z [M + H]⁺ $C_{12}H_{15}FN_4O_2$ requires: 282.3, found: 283.1 HPLC tR (min) 3.66, 95% (20-100% ACN with 0.1% TFA 10 min.) |

-continued

| Amine | Compound | Characterization Data |
|---|---|---|
| (S)-1-cyclopropylethan-1-amine | 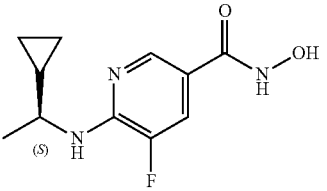<br>I-26A | ¹H NMR (400 MHz, MeOH-d4) δ 7.98 (s, 1 H), 7.32 (d, J = 1.71 Hz, 1 H), 7.29 (d, J = 1.71 Hz, 1 H), 3.45-3.35 (m, 1 H), 1.07 (d, J = 6.60 Hz, 3 H), 0.86-0.74 (m, 1 H), 0.33-0.01 (m, 4 H).<br>LC-MS: $t_R$ (min) 2.03 (20-100% ACN with 0.1% TFA 6 min), m/z [M + H]⁺ $C_{11}H_{12}FN_3O_2$ requires: 239.3, found: 240.1<br>HPLC $t_R$ (min) 4.37, 95% (20-100% ACN with 0.1% TFA 10 min.) |
| (R)-1-cyclopropylethan-1-amine | 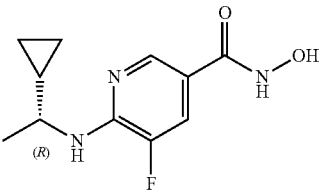<br>I-26B | ¹H NMR (400 MHz, MeOH-d4) δ 7.98 (s, 1 H), 7.32 (d, J = 1.71 Hz, 1 H), 7.29 (d, J = 1.47 Hz, 1 H), 3.10-3.07 (m, 1 H), 1.07 (d, J = 6.60 Hz, 3 H), 0.90-0.70 (m, 1 H), 0.33-0.00 (m, 4 H).<br>LC-MS: $t_R$ (min) 2.03 (20-100% ACN with 0.1% TFA 6 min), m/z [M + H]⁺ $C_{11}H_{12}FN_3O_2$ requires: 239.3, found: 240.1<br>HPLC $t_R$ (min) 3.74, 95% (20-100% ACN with 0.1% TFA 10 min.) |
| (R)-1-phenylpropan-1-amine | 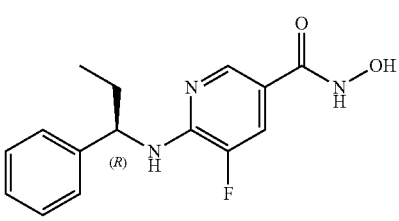<br>I-28A | ¹H NMR (400 MHz, MeOH-d4) δ 8.20 (s, 1 H), 7.56 (d, J = 11.7 Hz, 1 H), 7.39 (d, J = 7.58 Hz, 2 H), 7.29 (t, J = 7.46 Hz, 2 H), 7.24-7.11 (m, 1 H), 5.15-5.02 (m, 1 H), 2.00-1.75 (m, 2 H), 1.02-0.90 (m, 3 H).<br>LC-MS: $t_R$ (min) 3.70 (20-100% ACN with 0.1% TFA 6 min), m/z [M + H]⁺ $C_{13}H_{15}FN_3O_2$ requires: 289.3, found: 290.1<br>HPLC $t_R$ (min) 5.23, 98% (20-100% ACN with 0.1% TFA 10 min.) |
| (R)-1-cyclohexylethylamine | 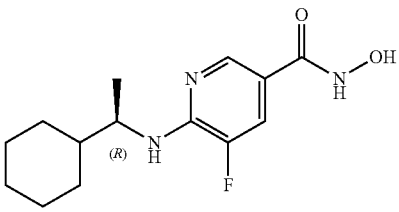<br>I-30A | ¹H NMR (400 MHz, MeOH-d4) δ 8.24 (s, 1H), 7.56 (s, 1 H), 7.53 (s, 1 H), 4.63 (s, 2 H), 4.09 (t, J = 6.72 Hz, 1 H), 1.88-1.65 (m, 5 H), 1.55-1.45 (m, 1 H), 1.31-1.22 (m, 3 H), 1.22-1.15 (m, 3 H), 1.10-0.90 (m, 2 H).<br>LC-MS: $t_R$ (min) 3.37 (20-100% ACN with 0.1% TFA 6 min), m/z [M + H]⁺ $C_{14}H_{20}FN_3O_2$ requires: 281.3, found: 282.2<br>HPLC $t_R$ (min) 4.84, 97% (20-100% ACN with 0.1% TFA 10 min.) |
| (S)-1-cyclohexylethylamine | 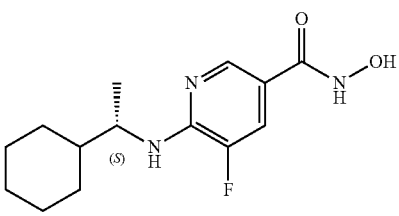<br>I-30B | ¹H NMR (400 MHz, MeOH-d4) δ 8.24 (s, 1H), 7.56 (s, 1 H), 7.53 (s, 1 H), 4.63 (s, 2 H), 4.09 (t, J = 6.97 Hz, 1 H), 1.88-1.65 (m, 5 H), 1.51 (s, 1 H), 1.31-1.20 (m, 3 H), 1.22-1.18 (m, 3 H), 1.10-0.90 (m, 2 H).<br>LC-MS: $t_R$ (min) 3.50 (20-100% ACN with 0.1% TFA 6 min), m/z [M + H]⁺ $C_{14}H_{20}FN_3O_2$ requires: 281.3, found: 282.1<br>HPLC $t_R$ (min) 5.10, 98% (20-100% ACN with 0.1% TFA 10 min.) |
| (1S, 2S)-2-methoxycyclopentylamine | 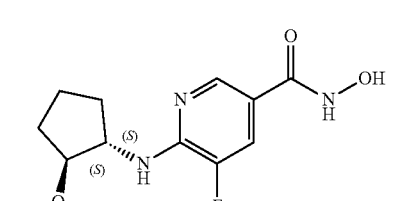<br>I-36 | ¹H NMR (400 MHz, CDCl3-d) δ 8.27 (s, 1 H), 7.58-7.39 (m, 1 H), 5.06 (br, s, 1 H), 4.31 (br, s, 1 H), 3.68 (br, s, 1 H), 3.34 (s, 3 H), 2.25- 2.15 (m, 1 H), 1.93-1.88 (m, 1 H), 1.85-1.75 (m, 3 H), 1.50-1.40 (m, 1 H).<br>LC-MS: $t_R$ (min) 1.93 (20-100% ACN with 0.1% TFA 6 min), m/z [M + H]⁺ $C_{12}H_{16}FN_3O_2$ requires: 269.3, found: 270.1<br>HPLC $t_R$ (min) 3.71, 97% (20-100% ACN with 0.1% TFA 10 min.) |

-continued

| Amine | Compound | Characterization Data |
|---|---|---|
| (3S, 4R)-4-methoxy-tetrahydrofuran-3-yl)amine | 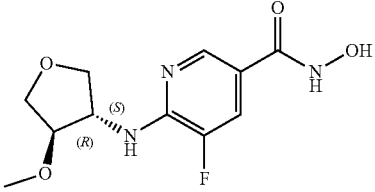<br>I-38 | $^1$H NMR (400 MHz, MeOH-d4) δ 8.33 (s, 1 H), 7.60 (d, J = 11.98 Hz, 1 H), 4.60 (br, s, 1 H), 4.20-4.05 (m, 2 H), 4.00-3.90 (m, 1 H), 3.85-3.75 (m, 2 H), 3.48 (s, 3 H).<br>LC-MS: $t_R$ (min) 1.39 (20-100% ACN with 0.1% TFA 6 min), m/z [M + H]$^+$ C$_{11}$H$_{14}$FN$_3$O$_2$ requires: 271.3, found: 272.1<br>HPLC $t_R$ (min) 2.97, 97% (20-100% ACN with 0.1% TFA 10 min.) |
| 3,3-difluoro-1-(methoxymethyl)cyclobutan-1-amine | 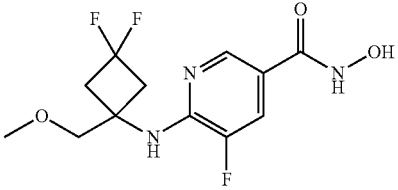 [SMILES: COCC1(Nc2ncc(C(=O)NO)cc2F)CC(F)(F)C1]<br>I-39 | $^1$H NMR (400 MHz, MeOH-d4) δ 8.16 (s, 1 H), 7.48 (d, J = 12.2 Hz, 1 H), 4.52 (s, 2 H), 3.63 (s, 2 H), 3.26-3.23 (m, 3 H), 2.82-2.72 (m, 4H).<br>LC-MS: $t_R$ (min) 3.00 (20-100% ACN with 0.1% TFA 6 min), m/z [M + H]$^+$ C$_{12}$H$_{14}$F$_3$N$_3$O$_3$ requires: 305.3, found: 306.1<br>HPLC $t_R$ (min) 5.02, 93% (20-100% ACN with 0.1% TFA 10 min.) |
| 3-ethyl-oxetan-3-amine | 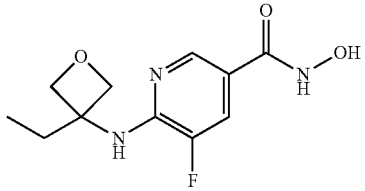 [SMILES: CCC1(Nc2ncc(C(=O)NO)cc2F)COC1]<br>I-40 | $^1$H NMR (400 MHz, MeOH-d4) δ 8.22 (s, 1 H), 7.59 (d, J = 11.98 Hz, 1 H), 4.80 (br, s, 2 H), 4.60 (br, s, 2 H), 2.22 (q, J = 6.93 Hz, 2 H), 0.92 (t, J = 6.95 Hz, 3 H).<br>LC-MS: $t_R$ (min) 1.10 (20-100% ACN with 0.1% TFA 6 min), m/z [M + H]$^+$ C$_{11}$H$_{13}$FN$_3$O$_3$ requires: 255.2, found: 256.1<br>HPLC tR (min) 3.80, 99% (20-100% ACN with 0.1% TFA 10 min.) |
| 1,1'-bi(cyclopropan)-1-amine | 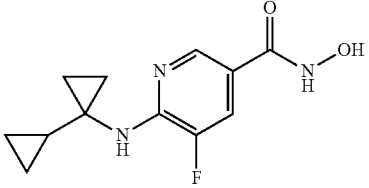 [SMILES: O=C(NO)c1cnc(NC2(C3CC3)CC2)c(F)c1]<br>I-41 | $^1$H NMR (400 MHz, MeOH-d4) δ 8.07 (s, 1 H), 7.32 (d, J = 11.98 Hz, 1 H), 4.40 (br, s, 1 H), 3.08 (s, 1 H), 1.35-1.25 (m, 1 H), 0.48 (d, J = 5.38 Hz, 4 H), 0.38-0.42 (m, 2 H), 0.01 (s, 2 H).<br>LC-MS: $t_R$ (min) 1.20 (20-100% ACN with 0.1% TFA 6 min), m/z [M + H]$^+$ C$_{11}$H$_{13}$FN$_3$O$_3$ requires: 251.3, found: 252.1<br>HPLC $t_R$ (min) 3.17, 96% (20-100% ACN with 0.1% TFA 10 min.) |
| (S)-1-methyl-2-oxopyrrolidin-3-amine | 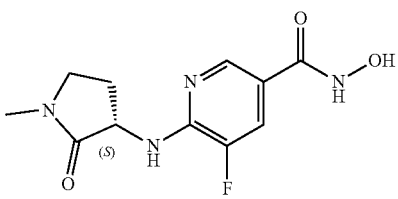<br>I-42A | $^1$H NMR (400 MHz, DMSO-d6) δ 11.05 (br, s, 1 H), 9.00 (br, s, 1 H), 8.50 (br, s, 1 H), 7.65 (d, J = 12.0 Hz, 1 H), 7.45 (d, J = 8.80 Hz, 1 H), 4.90-4.80 (m, 1 H), 3.45-3.40 (m, 2 H), 2.76 (s, 3 H), 2.30-2.20 (m, 1 H), 1.90-2.00 (m, 1 H).<br>LC-MS: $t_R$ (min) 1.10 (20-100% ACN with 0.1% TFA 6 min), m/z [M + H]$^+$ C$_{11}$H$_{13}$FN$_3$O$_3$ requires: 268.3, found: 269.1<br>HPLC $t_R$ (min) 1.54, 96% (20-100% ACN with 0.1% TFA 10 min.) |
| (S)-2-oxopyrrolidin-3-amine | 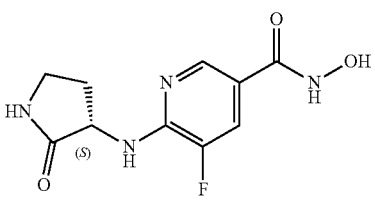<br>I-43A | $^1$H NMR (400 MHz, DMSO-d6) δ 11.05 (br, s, 1 H), 8.95 (br, s, 1 H), 8.25 (br, s, 1 H), 7.83 (s, 1 H), 7.65 (d, J = 12.0 Hz, 1 H), 7.45 (d, J = 8.80 Hz, 1 H), 4.70-4.85 (m, 1 H), 3.23 (d, J = 6.34 Hz, 2 H), 2.40-2.30 (m, 1 H), 2.15-2.05 (m, 1 H).<br>LC-MS: $t_R$ (min) 1.10 (20-100% ACN with 0.1% TFA 6 min), m/z [M + H]$^+$ C$_{12}$H$_{16}$FN$_3$O$_3$ requires: 254.2, found: 255.1<br>HPLC $t_R$ (min) 1.71, 96% (20-100% ACN with 0.1% TFA 10 min.) |

| Amine | Compound | Characterization Data |
|---|---|---|
| (R)-1-methyl-2-oxopyrrolidin-3-amine | 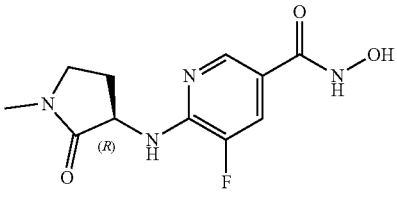<br>I-42B | ¹H NMR (400 MHz, DMSO-d6) δ 11.05 (br, s, 1 H), 8.99 (br, s, 1 H), 8.25 (s, 1 H), 7.65 (d, J = 12.2 Hz, 1 H), 7.42 (d, d, J = 8.07 Hz, 1 H), 4.82 (d, J = 9.05 Hz, 1 H), 3.34-3.27 (m, 2 H), 2.76 (s, 3 H), 2.40-2.26 (m, 1 H), 2.03-1.92 (m, 1 H).<br>LC-MS: $t_R$ (min) 1.20 (20-100% ACN with 0.1% TFA 6 min), m/z [M + H]⁺ $C_{12}H_{16}FN_3O3$ requires: 268.3, found: 269.1<br>HPLC $t_R$ (min) 1.75, 99% (20-100% ACN with 0.1% TFA 10 min.) |
| (R)-2-oxopyrrolidin-3-amine | 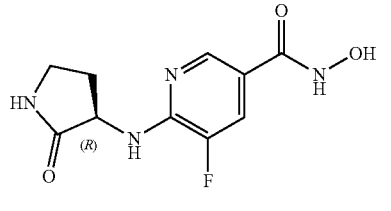<br>I-43B | ¹H NMR (400 MHz, DMSO-d6) δ 11.0 (br, s, 1 H), 9.05 (br, s, 1 H), 8.45 (s, 1 H), 7.84 (s, 1 H), 7.65 (d, J = 12.0 Hz, 1 H), 7.34 (d, J = 8.80 Hz, 1 H), 4.77 (d, J = 9.29 Hz, 1 H), 3.18-3.28 (m, 2 H), 2.30-2.40 (m, 1 H), 2.15-2.05 (m, 1 H).<br>LC-MS: tR (min) 1.15 (20-100% ACN with 0.1% TFA 6 min), m/z [M + H]⁺ $C_{12}H_{16}FN_3O_3$ requires: 254.2, found: 255.1<br>HPLC tR (min) 1.55, 93% (20-100% ACN with 0.1% TFA 10 min.) |
| 1-(2-methoxyethyl)cyclopropyl)amine | 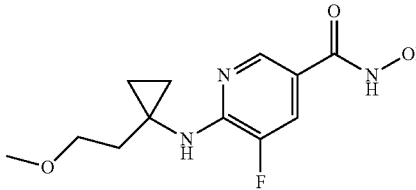<br>I-44 | ¹H NMR (400 MHz, MeOH-d4) δ 8.32 (s, 1 H), 7.57 (d, J = 11.98 Hz, 1 H), 3.55 (t, J = 6.85, 2 H), 3.30 (s, 3 H), 1.96 (t, J = 6.85 Hz, 2 H), 0.80 (s, 4 H).<br>LC-MS: $t_R$ (min) 1.20 (20-100% ACN with 0.1% TFA 6 min), m/z [M + H]⁺ $C_{12}H_{16}FN_3O_3$ requires: 269.3, found: 270.1<br>HPLC $t_R$ (min) 2.07, 99% (20-100% ACN with 0.1% TFA 10 min.) |
| 3-phenyl-oxetan-3-amine | 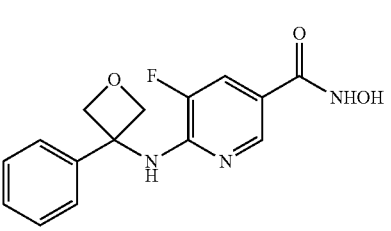<br>I-27 | ¹H NMR (400 MHz, DMSO-d6) δ 10.95 (br s, 1 H), 8.97 (s, 1 H), 8.38 (m, 1 H), 8.02 (m, 1 H), 7.69 (m, 1 H), 7.53 (m, 2 H), 7.34 (m, 2 H), 7.24 (m, 1 H), 4.99 (m, 2 H), 4.78 (m, 2 H).<br>LC-MS: m/z [M + H]⁺ $C_{15}H_{14}FN_3O_3$ requires: 303.2, found: 304.1<br>HPLC $t_R$ (min) 4.81, 95% (10-100% ACN with 0.1% TFA 10 min.) |
| 3-(pyridin-2-yl)oxetan-3-amine | 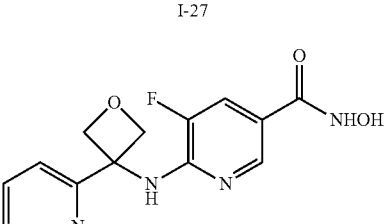<br>I-56 | ¹H NMR (400 MHz, DMSO-d6) δ 10.97 (br s, 1 H), 8.97 (s, 1 H), 8.63 (m, 1 H), 8.46 (m, 1 H), 7.99 (m, 1 H), 7.71-7.66 (m, 1 H), 7.31-7.15 (m, 2 H), 5.01 (m, 2 H), 4.87 (m, 2 H).<br>LC-MS: m/z [M + H]⁺ $C_{14}H_{13}FN_4O_3$ requires: 304.2, found: 305.1<br>HPLC $t_R$ (min) 1.27, 93% (10-100% ACN with 0.1% TFA 10 min.) |

| Amine | Compound | Characterization Data |
|---|---|---|
| 1H-pyrrolo[2,3-b]pyridine | 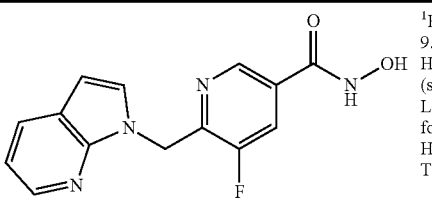 | ¹H NMR (400 MHz, DMSO-d6) δ 11.41 (br s, 1 H), 9.31 (s, 1 H), 8.57 (m, 1 H), 8.18 (m, 1 H), 7.98 (m, 2 H), 7.60 (m, 1 H), 7.08 (m, 1 H), 6.52 (m, 1 H), 5.71 (s, 2 H).<br>LC-MS: m/z [M + H]⁺ $C_{14}H_{11}FN_4O_2$ requires: 286.2, found: 287.1<br>HPLC $t_R$ (min) 3.21, 98% (20-100% ACN with 0.1% TFA 10 min.) |

| Amine | Compound | Characterization Data |
|---|---|---|
| 2-(difluoromethyl)-1H-benzo[d]imidazole | 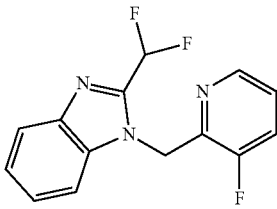<br>6 | $^1$H NMR (400 MHz, DMSO-d6) δ 11.41 (br s, 1 H), 9.32 (s, 1 H), 8.51 (s, 1 H), 8.01 (m, 1 H), 7.63 (m, 1 H), 7.62 (m, 1 H), 7.53-7.27 (m, 3 H), 5.92 (s, 2 H).<br>LC-MS: m/z [M + H]$^+$ C$_{15}$H$_{11}$F$_3$N$_4$O$_2$ requires: 336.2.1, found: 337.1<br>HPLC t$_R$ (min) 4.87, 97% (10-100% ACN with 0.1% TFA 10 min.) |
| 2,2-dimethyl-2H-pyrido[3,2-b][1,4]oxazin-3(4H)-one | 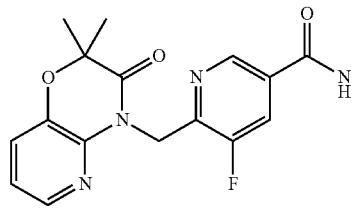<br>I-34 | $^1$H NMR (400 MHz, DMSO-d6) δ 11.37 (br s, 1 H), 9.30 (s, 1 H), 8.52 (s, 1 H), 7.97 (m, 1 H), 7.88 (m, 1 H), 7.44 (m, 1 H), 7.03 (m, 1 H), 5.42 (s, 2 H), 1.51 (s, 6 H).<br>LC-MS: m/z [M + H]$^+$ C$_{16}$H$_{15}$FN$_4$O$_4$ requires: 346.3, found: 347.1<br>HPLC t$_R$ (min) 5.04, 100% (10-100% ACN with 0.1% TFA 10 min.) |
| 3-methyl-3,4-dihydroquinazolin-2(1H)-one | 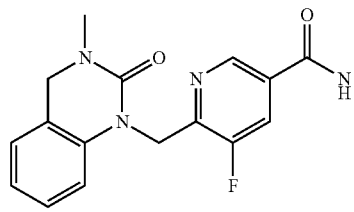<br>I-47 | $^1$H NMR (400 MHz, DMSO-d6) δ 11.40 (br s, 1 H), 9.30 (s, 1 H), 8.55 (s, 1 H), 7.94 (m, 1 H), 7.15-7.11 (m, 2 H), 6.93 (m, 1 H), 6.74 (m, 1 H), 5.22 (s, 2 H), 4.40 (s, 2 H), 2.90 (s, 3 H).<br>LC-MS: m/z [M + H]$^+$ C$_{16}$H$_{15}$FN$_4$O$_3$ requires: 330.3, found: 331.1<br>HPLC t$_R$ (min) 4.93, 100% (10-100% ACN with 0.1% TFA 10 min.) |
| 3,4-dihydro-2H-thieno[3,2-b]indole 1,1-dioxide | 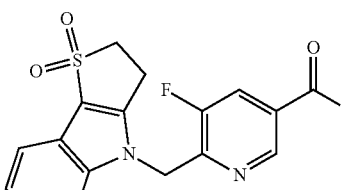<br>I-48 | $^1$H NMR (400 MHz, DMSO-d6) δ 8.62 (s, 1 H), 8.02 (m, 1 H), 7.56 (m, 2 H), 7.27 (m, 2 H), 5.68 (s, 2 H), 3.94 (m, 2 H), 3.46 (m, 2 H).<br>LC-MS: m/z [M + H]$^+$ C$_{17}$H$_{14}$FN$_3$O$_4$S requires: 375.3, found: 376.1<br>HPLC t$_R$ (min) 4.85, 96% (10-100% ACN with 0.1% TFA 10 min.) |
| 2-(trifluoromethyl)-1H-benzo[d]imidazole | 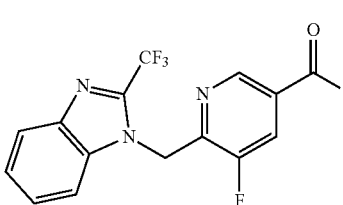<br>I-49 | $^1$H NMR (400 MHz, DMSO-d6) δ 11.41 (br s, 1 H), 9.33 (s, 1 H), 8.49 (s, 1 H), 8.04 (m, 1 H), 7.84 (m, 1 H), 7.72 (m, 1 H), 7.44 (m, 2 H), 5.95 (s, 2 H).<br>LC-MS: m/z [M + H]$^+$ C$_{15}$H$_{10}$F$_4$N$_4$O$_2$ requires: 354.2, found: 355.1<br>HPLC t$_R$ (min) 4.94, 98% (10-100% ACN with 0.1% TFA 10 min.) |
| 2-methyl-1H-pyrrolo[2,3-b]pyridine | 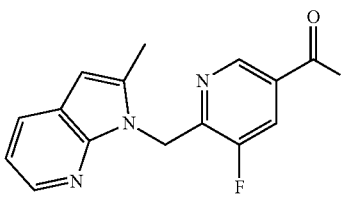<br>I-50 | $^1$H NMR (400 MHz, DMSO-d6) δ 11.39 (br s, 1 H), 9.31 (s, 1 H), 8.51 (s, 1 H), 8.06 (m, 1 H), 7.97 (m, 1 H), 7.84 (m, 1 H), 7.03 (m, 1 H), 6.29 (s, 1 H), 5.69 (s, 2 H), 2.40 (s, 3 H).<br>LC-MS: m/z [M + H]$^+$ C$_{15}$H$_{13}$FN$_4$O$_2$ requires: 300.2, found: 301.1<br>HPLC t$_R$ (min) 3.83, 100% (20-100% ACN with 0.1% TFA 10 min.) |

| Amine | Compound | Characterization Data |
|---|---|---|
| 2,3-dimethyl-1H-pyrrolo[2,3-b]pyridine | I-51 | ¹H NMR (400 MHz, DMSO-d6) δ 11.39 (br s, 1 H), 9.31 (s, 1 H), 8.51 (s, 1 H), 8.05 (m, 1 H), 7.95 (m, 1 H), 7.81 (m, 1 H), 7.01 (m, 1 H), 5.67 (s, 2 H), 2.31 (s, 3 H), 2.21 (s, 3 H).<br>LC-MS: m/z [M + H]⁺ C₁₆H₁₅FN₄O₂ requires: 314.3, found: 315.1<br>HPLC $t_R$ (min) 4.17, 100% (20-100% ACN with 0.1% TFA 10 min.) |
| oxazolo[4,5-b]pyridin-2(3H)-one | I-52 | ¹H NMR (400 MHz, CD₃OD-d₄) δ 8.70 (s, 1 H), 7.98 (m, 2 H), 7.47 (m, 1 H), 7.38 (m, 1 H), 5.06 (s, 2 H), 3.64 (s, 3 H).<br>LC-MS: m/z [M + H]⁺ C₁₄H₁₃FN₄O₅ requires: 336.2, found: 337.1<br>HPLC $t_R$ (min) 4.18, 96% (10-100% ACN with 0.1% TFA 10 min.) |
| 2-methyl-3H-imidazo[4,5-b]pyridine | I-53 | ¹H NMR (400 MHz, DMSO-d6) δ 11.30 (br s, 1 H), 9.27 (s, 1 H), 8.47 (s, 1 H), 8.12 (m, 1 H), 7.95 (m, 1 H), 7.88 (m, 1 H), 7.15 (m, 1 H), 5.68 (s, 2 H), 2.44 (s, 3 H).<br>LC-MS: m/z [M + H]⁺ C₁₄H₁₂FN₅O₂ requires: 301.2, found: 302.1<br>HPLC $t_R$ (min) 3.60, 98% (10-100% ACN with 0.1% TFA 10 min.) |
| 4-(1H-benzo[d]imidazol-2-yl)morpholine | I-54 | ¹H NMR (400 MHz, DMSO-d6) δ 11.45 (br s, 1 H), 9.34 (s, 1 H), 8.59 (s, 1 H), 8.03 (m, 1 H), 7.45 (m, 1 H), 7.15-7.03 (m, 3 H), 5.55 (s, 2 H), 3.67 (m, 4 H), 3.14 (m, 4 H).<br>LC-MS: m/z [M + H]⁺ C₁₈H₁₈FN₅O₃ requires: 371.3, found: 372.1<br>HPLC $t_R$ (min) 3.66, 95% (10-100% ACN with 0.1% TFA 10 min.) |
| 2-methyl-2,3,4,5-tetrahydro-1H-pyrido[4,3-b]indole | IV-10 | ¹H NMR (400 MHz, DMSO-d6) δ 11.40 (br s, 1 H), 9.36 (s, 1 H), 8.61 (s, 1 H), 7.95 (m, 1 H), 7.35 (m, 2 H), 7.03-6.94 (m, 2 H), 5.50 (s, 2 H), 3.52 (s, 2 H), 2.83 (m, 2 H), 2.72 (m, 2 H), 2.42 (s, 3 H).<br>LC-MS: m/z [M + H]⁺ C₁₉H₁₉FN₄O₂ requires: 354.3, found: 355.2<br>HPLC $t_R$ (min) 4.58, 99% (10-100% ACN with 0.1% TFA 10 min.) |

-continued

| Amine | Compound | Characterization Data |
|---|---|---|
| 1,3,4,5-tetrahydro-pyrano[4,3-b]indole | 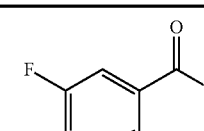<br>I-29 | ¹H NMR (400 MHz, DMSO-d6) δ 11.41 (br s, 1 H), 9.35 (s, 1 H), 8.61 (s, 1 H), 8.01 (m, 1 H), 7.40-7.32 (m, 2 H), 7.06-6.95 (m, 2 H), 5.54 (s, 2 H), 4.78 (s, 2 H), 3.95 (m, 2 H), 2.84 (m, 2 H).<br>LC-MS: m/z [M + H]⁺ $C_{18}H_{16}FN_3O_3$ requires: 341.3, found: 342.1<br>HPLC $t_R$ (min) 4.99, 94% (10-100% ACN with 0.1% TFA 10 min.) |

| Compound | Characterization Data |
|---|---|
| 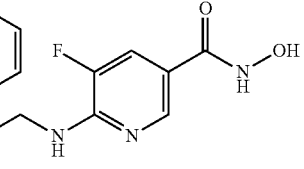<br>I-25 | ¹H NMR (400 MHz, Solvent) δ ppm 8.18 (s, 1 H) 7.50 (br d, J = 11.98 Hz, 1 H) 7.31-7.38 (m, 2 H) 7.23 (br t, J = 7.46 Hz, 2 H) 7.10-7.17 (m, 1 H) 3.74 (s, 2 H) 0.93-0.99 (m, 2 H) 0.80-0.86 (m, 2 H) |
| 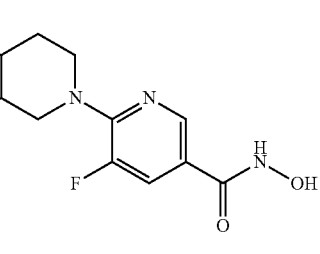<br>IV-9 | ¹H NMR (400 MHz, Solvent) δ ppm 8.39 (s, 1 H) 8.35 (d, J = 4.65 Hz, 1 H) 7.64-7.76 (m, 2 H) 7.27 (dd, J = 7.58, 5.14 Hz, 1 H) 4.86 (s, 2 H) 4.03 (t, J = 5.87 Hz, 2 H) 3.10 (t, J = 5.87 Hz, 2 H) |
| 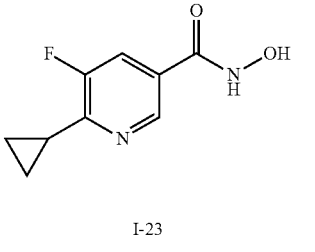<br>I-23 | ¹H NMR (400 MHz, METHANOL-d4) δ ppm 8.57 (s, 1 H) 7.77 (d, J = 10.27 Hz, 1 H) 2.31-2.46 (m, 1 H) 1.08-1.16 (m, 4 H)<br>LCMS $R_T$ = 2.79 min, m/z = 197.1 [M + H]⁺. |
| 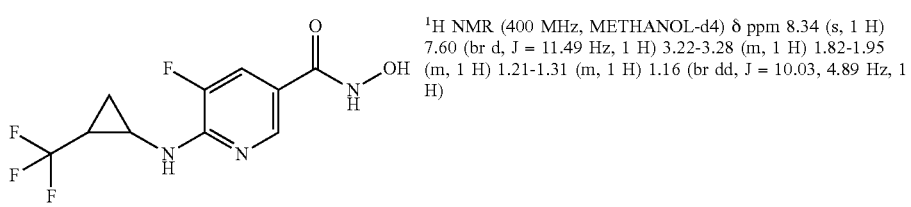<br>I-31 | ¹H NMR (400 MHz, METHANOL-d4) δ ppm 8.34 (s, 1 H) 7.60 (br d, J = 11.49 Hz, 1 H) 3.22-3.28 (m, 1 H) 1.82-1.95 (m, 1 H) 1.21-1.31 (m, 1 H) 1.16 (br dd, J = 10.03, 4.89 Hz, 1 H) |

| Compound | Characterization Data |
|---|---|
| <br>I-32 | $^1$H NMR (400 MHz, METHANOL-d4) δ ppm 8.30 (s, 1 H) 7.61 (br d, J = 11.74 Hz, 1 H) 4.32-4.47 (m, 1 H) 2.94-3.12 (m, 2 H) 2.54-2.76 (m, 2 H) |
| 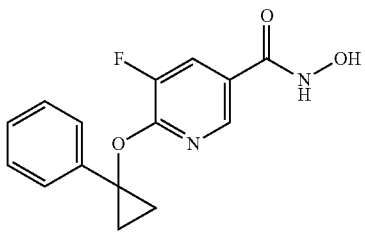 [SMILES: O=C(NO)c1cnc(OC2(c3ccccc3)CC2)c(F)c1]<br>III-1 | $^1$H NMR (400 MHz, METHANOL-d4) δ ppm 8.21 (s, 1 H) 7.82 (br d, J = 10.27 Hz, 1 H) 7.25-7.32 (m, 4 H) 7.15-7.23 (m, 1 H) 1.44-1.50 (m, 2 H) 1.36-1.43 (m, 2 H) |

REFERENCES

Cao, D. J., Wang, Z. V., Battiprolu, P. K., Jiang, N., Morales, C. R., Kong, Y., Rothermel, B. A., Gillette, T. G., Hill, J. A., 2011. Histone deacetylase (HDAC) inhibitors attenuate cardiac hypertrophy by suppressing autophagy. Proc. Natl. Acad. Sci. 108, 4123-4128. https://doi.org/10.1073/pnas.1015081108

Demos-Davies, K. M., Ferguson, B. S., Cavasin, M. A., Mahaffey, J. H., Williams, S. M., Spiltoir, J. I., Schuetze, K. B., Horn, T. R., Chen, B., Ferrara, C., Scellini, B., Piroddi, N., Tesi, C., Poggesi, C., Jeong, M. Y., McKinsey, T. A., 2014. HDAC6 contributes to pathological responses of heart and skeletal muscle to chronic angiotensin-II signaling. Am. J. Physiol.—Heart Circ. Physiol. 307, H252-H258. https://doi.org/10.1152/ajpheart.00149.2014

Haberland, M., Montgomery, R. L., Olson, E. N., 2009. The many roles of histone deacetylases in development and physiology: implications for disease and therapy. Nat. Rev. Genet. 10, 32-42. https://doi.org/10.1038/nrg2485

Hubbert, C., Guardiola, A., Shao, R., Kawaguchi, Y., Ito, A., Nixon, A., Yoshida, M., Wang, X. F., Yao, T. P., 2002. HDAC6 is a microtubule-associated deacetylase. Nature 417, 455-458. https://doi.org/10.1038/417455a Jeong, M. Y., Lin, Y. H., Wennersten, S. A., Demos-Davies, K. M., Cavasin, M. A., Mahaffey, J. H., Monzani, V., Saripalli, C., Mascagni, P., Reece, T. B., Ambardekar, A. V., Granzier, H. L., Dinarello, C. A., McKinsey, T. A., 2018. Histone deacetylase activity governs diastolic dysfunction through a nongenomic mechanism. Sci. Transl. Med. 10, eaao0144. https://doi.org/10.1126/scitranslmed.aao0144

McLendon, P. M., Ferguson, B. S., Osinska, H., Bhuiyan, M. S., James, J., McKinsey, T. A., Robbins, J., 2014. Tubulin hyperacetylation is adaptive in cardiac proteotoxicity by promoting autophagy. Proc. Natl. Acad. Sci. 111, E5178-E5186. https://doi.org/10.1073/pnas.1415589111

Nagata, S., Marunouchi, T., Tanonaka, K., 2019. Histone Deacetylase Inhibitor SAHA Treatment Prevents the Development of Heart Failure after Myocardial Infarction via an Induction of Heat-Shock Proteins in Rats. Biol. Pharm. Bull. 42, 453-461. https://doi.org/10.1248/bpb.b18-00785

Zhang, Y., Kwon, S., Yamaguchi, T., Cubizolles, F., Rousseaux, S., Kneissel, M., Cao, C., Li, N., Cheng, H. L., Chua, K., Lombard, D., Mizeracki, A., Matthias, G., Alt, F. W., Khochbin, S., Matthias, P., 2008. Mice Lacking Histone Deacetylase 6 Have Hyperacetylated Tubulin but Are Viable and Develop Normally. Mol. Cell. Biol. 28, 1688-1701. https://doi.org/10.1128/MCB.01154-06

Yoon S, Eom G H. HDAC and HDAC Inhibitor: From Cancer to Cardiovascular Diseases. Chonnam Med J. 2016 January; 52(1):1-11. https://doi.org/10.4068/cmj.2016.52.1.1

Schiattarella, G. G., Tong, D., Hill, J. A., 2020. Can HFpEF and HFrEF Coexist? Circulation 141, 709-711. https://doi.org/10.1161/CIRCULATIONAHA.119.045171

Kyle V. Butler, Jay Kalin, Camille Brochier, Guilio Vistoli, Brett Langley, and Alan P. Kozikowski. Rational Design and Simple Chemistry Yield a Superior, Neuroprotective HDAC6 Inhibitor, Tubastatin A. Journal of the American Chemical Society 2010 132 (31), 10842-10846 DOI: 10.1021/ja102758v Choi S Y, Kee H J, Jin L, Ryu Y, Sun S, Kim G R, Jeong M H. Inhibition of class IIa histone deacetylase activity by gallic acid, sulforaphane, TMP269, and panobinostat. Biomed Pharmacother. 2018 May; 101:145-154. doi: 10.1016/j.biopha.2018.02.071.

Krukowski K, Ma J, Golonzhka O, Laumet G O, Gutti T, van Duzer J H, Mazitschek R, Jarpe M B, Heijnen C J, Kavelaars A. HDAC6 inhibition effectively reverses chemotherapy-induced peripheral neuropathy. Pain. 2017 June; 158(6):1126-1137. doi: 10.1097/j.pain.0000000000000893.

Brindisi M, Saraswati A P, Brogi S, Gemma S, Butini S, Campiani G. Old but Gold: Tracking the New Guise of Histone Deacetylase 6 (HDAC6) Enzyme as a Biomarker and Therapeutic Target in Rare Diseases. J Med Chem. 2020 Jan. 9; 63(1):23-39. doi: medchem.9b00924.

Nebbioso A, Carafa V, Conte M, Tambaro F P, Abbondanza C, Martens J, Nees M, Benedetti R, Pallavicini I, Minucci S, Garcia-Manero G, Iovino F, Lania G, Ingenito C, Belsito Petrizzi V, Stunnenberg H G, Altucci L. c-Myc Modulation and Acetylation Is a Key HDAC Inhibitor Target in Cancer. Clin Cancer Res. 2017 May 15; 23(10): 2542-2555. doi:

Santo L, Hideshima T, Kung A L, Tseng J C, Tamang D, Yang M, Jarpe M, van Duzer J H, Mazitschek R, Ogier W C, Cirstea D, Rodig S, Eda H, Scullen T, Canavese M, Bradner J, Anderson K C, Jones S S, Raj e N. Preclinical activity, pharmacodynamic, and pharmacokinetic properties of a selective HDAC6 inhibitor, ACY-1215, in combination with bortezomib in multiple myeloma. Blood. 2012 Mar. 15; 119(11):2579-89. doi: 10.1182/blood-2011-10-387365.

Schiattarella, G. G., Tong, D., Hill, J. A., 2020. Can HFpEF and HFrEF Coexist? Circulation 141, 709-711.

Schiattarella et al. *Nature* 568(7752):351-356 (2019).

Aravind Subramanian, Pablo Tamayo, Vamsi K Mootha, Sayan Mukherjee, Benjamin L Ebert, et al. Gene set enrichment analysis: a knowledge-based approach for interpreting genome-wide expression profiles. Proc Natl Acad Sci USA. 2005 Oct. 25; 102(43):15545-50. doi: 10.1073/pnas.0506580102. Epub 2005 Sep. 30.

Carolyn S P Lam, Adriaan A Voors, Rudolf A de Boer, Scott D Solomon, Dirk J van Veldhuisen. Heart failure with preserved ejection fraction: from mechanisms to therapies. Eur Heart J. 2018 Aug. 7; 39(30):2780-2792. doi: 10.1093/eurheartj/ehy301.

Dries A M Feyen, Wesley L McKeithan, Arne A N Bruyneel, Sean Spiering, Larissa Hörmann, et al. Metabolic Maturation Media Improve Physiological Function of Human iPSC-Derived Cardiomyocytes. Cell Rep. 2020 Jul. 21; 32(3):107925. doi:

Yoav Benjamini and Yosef Hochberg. Controlling the False Discovery Rate: A Practical and Powerful Approach to Multiple Testing. Journal of the Royal Statistical Society. Series B (Methodological), Vol. 57, No. 1 (1995), pp. 289-300.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world.

What is claimed is:

1. A method of treating heart failure with preserved ejection fraction (HFpEF) in a subject in need thereof, comprising administering a therapeutically effective amount of an HDAC6 inhibitor to the subject, wherein the HDAC6 inhibitor is a compound according to Formula (Ic):

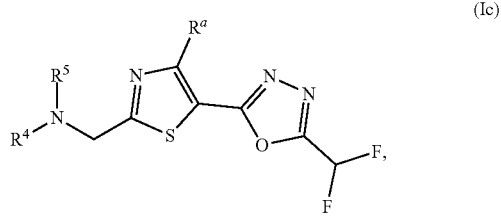

(Ic)

or a pharmaceutically acceptable salt thereof, wherein:
$R^a$ is H, Me, or F;
$R^2$ and $R^3$ are each independently selected from the group consisting of H, alkoxy, aryl, heteroaryl, alkyl, and cycloalkyl, or $R^2$ and $R^3$ together with the atom to which they are attached form a cycloalkyl or heterocyclyl;
$R^4$ is selected from the group consisting of $—(SO_2)R^2$, $—(SO_2)NR^2R^3$, and $—(CO)R^2$; and
$R^5$ is aryl or heteroaryl, or $R^4$ and $R^5$ together with the atom to which they are attached form a heterocyclyl.

2. The method of claim 1, wherein $R^a$ is H.

3. The method of claim 1, wherein $R^4$ is $—(SO_2)R^2$.

4. The method of claim 3, wherein $—(SO_2)R^2$ is $—(SO_2)$alkyl, $—(SO_2)$alkyleneheterocyclyl, $—(SO_2)$haloalkyl, $—(SO_2)$haloalkoxy, or $—(SO_2)$cycloalkyl.

5. The method of claim 1, wherein $R^5$ is heteroaryl.

6. The method of claim 5, wherein the heteroaryl is a 5- to 6-membered heteroaryl selected from the group consisting of

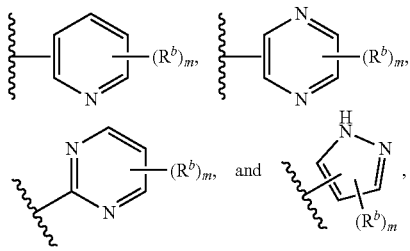

wherein $R^b$ is halogen, alkyl, alkoxy, cycloalkyl, —CN, haloalkyl, or haloalkoxy; and m is 0 or 1.

7. The method of claim 6, wherein $R^b$ is selected from the group consisting of F, Cl, $—CH_3$, $—CH_2CH_3$, $—CF_3$, $—CHF_2$, $—CF_2CH_3$, $—CN$, $—OCH_3$, $—OCH_2CH_3$, $—OCH(CH_3)_2$, $—OCF_3$, $—OCHF_2$, $—OCH_2CF_2H$, and cyclopropyl.

8. The method of claim 1, wherein the compound is:

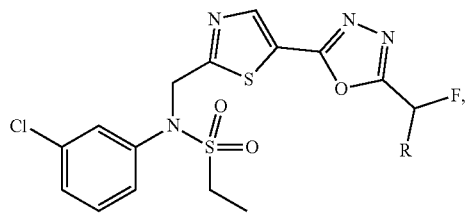

or a pharmaceutically acceptable salt thereof.

9. The method of claim 1, wherein the compound is:

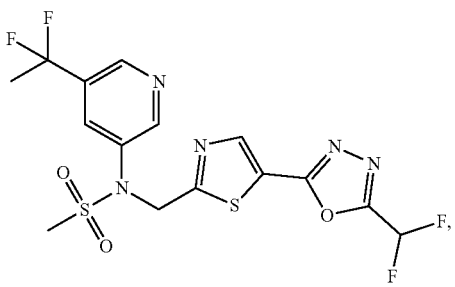

or a pharmaceutically acceptable salt thereof.

10. The method of claim 1, wherein the compound is:

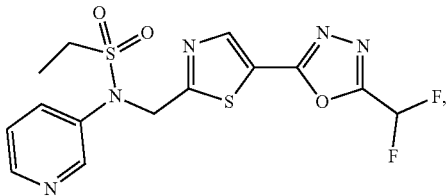 [SMILES: CCS(=O)(=O)N(Cc1ncc(-c2nnc(C(F)F)o2)s1)c1cccnc1]

or a pharmaceutically acceptable salt thereof.

11. The method of claim 1, wherein the compound is:

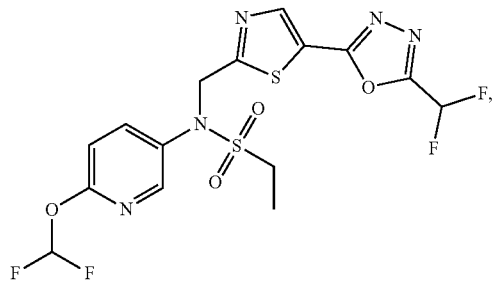 [SMILES: CCS(=O)(=O)N(Cc1ncc(-c2nnc(C(F)F)o2)s1)c1ccc(OC(F)F)nc1]

or a pharmaceutically acceptable salt thereof.

12. The method of claim 1, wherein the compound is:

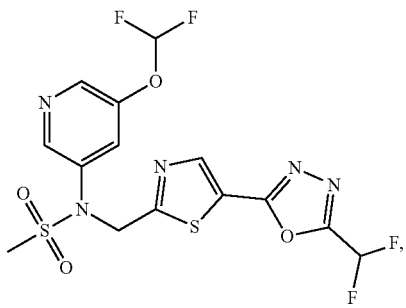 [SMILES: CS(=O)(=O)N(Cc1ncc(-c2nnc(C(F)F)o2)s1)c1cncc(OC(F)F)c1]

or a pharmaceutically acceptable salt thereof.

13. The method of claim 1, wherein the compound is:

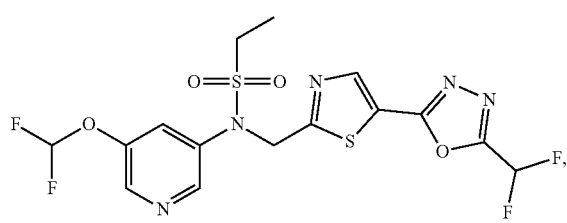 [SMILES: CCS(=O)(=O)N(Cc1ncc(-c2nnc(C(F)F)o2)s1)c1cncc(OC(F)F)c1]

or a pharmaceutically acceptable salt thereof.

14. The method of claim 1, wherein the compound is:

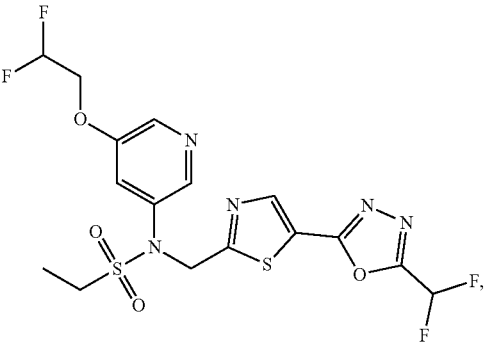

or a pharmaceutically acceptable salt thereof.

15. The method of claim 1, wherein the compound is:

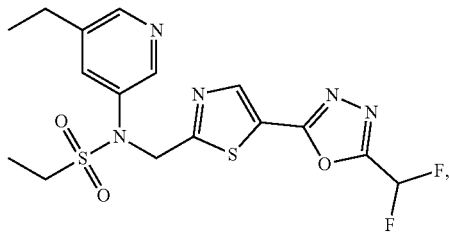 [SMILES: CCc1cncc(N(Cc2ncc(-c3nnc(C(F)F)o3)s2)S(=O)(=O)CC)c1]

or a pharmaceutically acceptable salt thereof.

16. The method of claim 1, wherein the compound is:

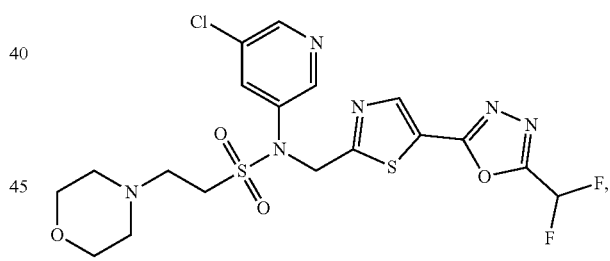

or a pharmaceutically acceptable salt thereof.

17. The method of claim 1, wherein the compound is:

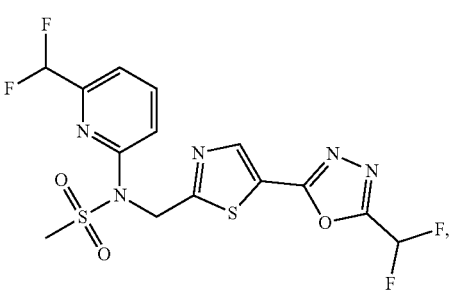

or a pharmaceutically acceptable salt thereof.

18. The method of claim 1, wherein the compound is:

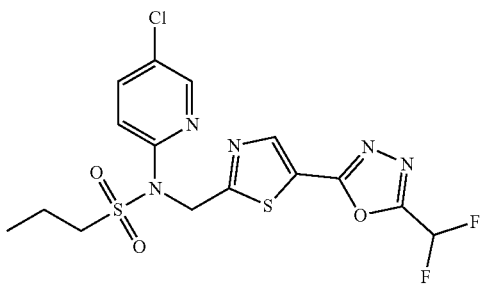 [SMILES: CCCS(=O)(=O)N(Cc1ncc(-c2nnc(C(F)F)o2)s1)c1ccc(Cl)cn1]

or a pharmaceutically acceptable salt thereof.

19. The method of claim 1, wherein the method reduces left ventricular (LV) mass.

20. The method of claim 1, wherein the method reduces LV wall thickness.

21. The method of claim 1, wherein the method improves LV relaxation.

22. The method of claim 1, wherein the method improves LV filling pressure.

23. The method of claim 1, wherein the method reduces cardiac fibrosis.

24. The method of claim 1, wherein the method reduces cardiac fibroblast activation in a cell.

25. The method of claim 1, wherein the method reduces the expression of one or more genes associated with fibrosis.

26. The method of claim 1, wherein the method reduces TGF-beta receptor signaling.

27. The method of claim 1, wherein the method reduces cardiac muscle hypertrophy.

28. The method of claim 1, wherein the HDAC6 inhibitor is a compound having the structure:

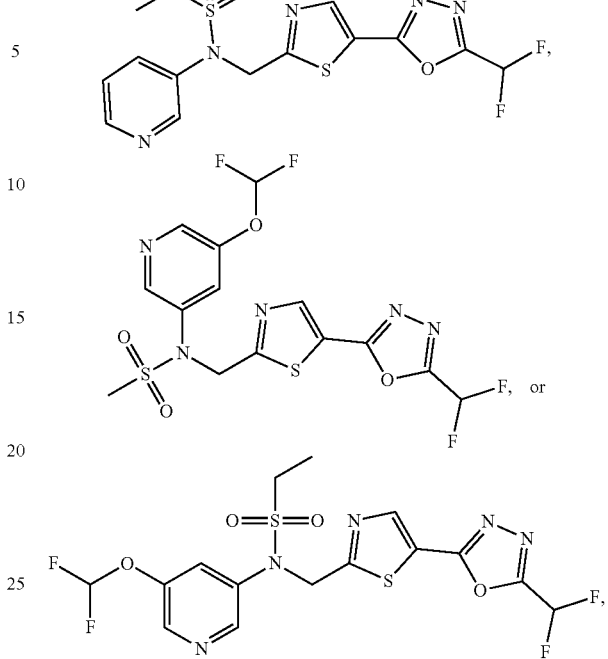

or a pharmaceutically acceptable salt thereof.

29. The method of claim 1, wherein $R^5$ is aryl and the aryl is phenyl, 3-chlorophenyl, 3-chloro-4-fluorophenyl, 3-trifluoromethylphenyl, 3,4-difluorophenyl, or 2,6-difluorophenyl.

* * * * *